United States Patent
Marx et al.

(10) Patent No.: US 11,220,509 B2
(45) Date of Patent: *Jan. 11, 2022

(54) SUBSTITUTED IMIDAZO[1,2-C]PYRIMIDINES AS PRC2 INHIBITORS

(71) Applicant: Mirati Therapeutics, Inc., San Diego, CA (US)

(72) Inventors: Matthew Arnold Marx, San Diego, CA (US); Matthew Randolph Lee, Del Mar, CA (US); Thomas P. Bobinski, San Diego, CA (US); Aaron Craig Burns, San Diego, CA (US); Nidhi Arora, San Diego, CA (US); James Gail Christensen, San Diego, CA (US); John Michael Ketcham, San Diego, CA (US)

(73) Assignee: MIRATI THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/219,379

(22) Filed: Mar. 31, 2021

(65) Prior Publication Data

US 2021/0230168 A1    Jul. 29, 2021

Related U.S. Application Data

(63) Continuation of application No. 17/116,270, filed on Dec. 9, 2020, now Pat. No. 11,091,495, which is a continuation of application No. 16/966,708, filed as application No. PCT/US2019/015677 on Jan. 29, 2019.

(60) Provisional application No. 62/747,736, filed on Oct. 19, 2018, provisional application No. 62/672,701, filed on May 17, 2018, provisional application No. 62/624,176, filed on Jan. 31, 2018.

(51) Int. Cl.
*C07D 487/04* (2006.01)

(52) U.S. Cl.
CPC .................................. *C07D 487/04* (2013.01)

(58) Field of Classification Search
CPC ................................................... C07D 487/04
USPC ......................................................... 544/282
See application file for complete search history.

(56) References Cited

U.S. PATENT DOCUMENTS

| | | | |
|---|---|---|---|
| 8,410,088 B2 | 4/2013 | Kuntz et al. | |
| 8,536,179 B2 | 9/2013 | Miller et al. | |
| 8,962,620 B2 | 2/2015 | Kuntz et al. | |
| 8,975,291 B2 | 3/2015 | Brackley, III et al. | |
| 9,006,242 B2 | 4/2015 | Kuntz et al. | |
| 9,040,515 B2 | 5/2015 | Edwards | |
| 9,382,234 B2 | 7/2016 | Knight et al. | |
| 9,409,865 B2 | 8/2016 | Albrecht et al. | |
| 9,469,646 B2 | 10/2016 | Albrecht et al. | |
| 9,481,666 B2 | 11/2016 | Kania et al. | |
| 9,505,745 B2 | 11/2016 | Blackledge, Jr. et al. | |
| 9,527,837 B2 | 12/2016 | Yu et al. | |
| 9,549,931 B2 | 1/2017 | Kuntz et al. | |
| 9,556,157 B2 | 1/2017 | Burgess et al. | |
| 9,562,041 B2 | 2/2017 | Burgess et al. | |
| 9,580,437 B2 | 2/2017 | Chan et al. | |
| 9,624,205 B2 | 4/2017 | Campbell | |
| 9,637,472 B2 | 5/2017 | Kuntz et al. | |
| 9,701,666 B2 | 7/2017 | Kuntz et al. | |

(Continued)

FOREIGN PATENT DOCUMENTS

| | | |
|---|---|---|
| CN | 110563722 A | 12/2019 |
| WO | WO-2010021381 A1 | 2/2010 |

(Continued)

OTHER PUBLICATIONS

Ansari et al. Novel 3-methylindoline inhibitors of EZH2: Design, synthesis and SAR. Bioog Med Chem Lett 27(2):217-222 (2016).

(Continued)

*Primary Examiner* — Douglas M Willis
(74) *Attorney, Agent, or Firm* — Wilson Sonsini Goodrich & Rosati

(57) ABSTRACT

The present disclosure relates to compounds of Formula (I), or pharmaceutically, acceptable salts thereof, that inhibit Polycomb Repressive Complex 2 (PRC2) activity. In particular, the present disclosure relates to compounds, or pharmaceutically acceptable salts thereof pharmaceutical compositions and methods of use, such as methods of treating cancer using the compounds of Formula (I), or pharmaceutically acceptable salts thereof, and pharmaceutical compositions comprising compounds of Formula (I), or pharmaceutically acceptable salts thereof.

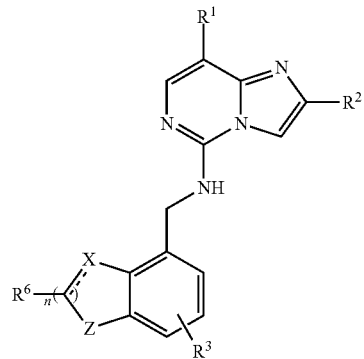

Formula (I)

27 Claims, No Drawings

(56) References Cited

U.S. PATENT DOCUMENTS

| | | |
|---|---|---|
| 9,718,838 B2 | 8/2017 | Guo et al. |
| 9,745,305 B2 | 8/2017 | Albrecht et al. |
| 9,776,996 B2 | 10/2017 | Campbell et al. |
| 9,822,103 B2 | 11/2017 | Seitz et al. |
| 10,266,542 B2 | 4/2019 | Marx et al. |
| 2013/0310379 A1 | 11/2013 | Albrecht et al. |
| 2014/0142083 A1 | 5/2014 | Kuntz et al. |
| 2014/0275081 A1 | 9/2014 | Kuntz et al. |
| 2014/0288123 A1 | 9/2014 | Albrecht et al. |
| 2014/0296283 A1 | 10/2014 | Campbell et al. |
| 2014/0303106 A1 | 10/2014 | Zheng et al. |
| 2014/0315945 A1 | 10/2014 | Campbell et al. |
| 2014/0315949 A1 | 10/2014 | Albrecht et al. |
| 2015/0011546 A1 | 1/2015 | Albrecht et al. |
| 2015/0239842 A1 | 8/2015 | Edwards et al. |
| 2015/0284370 A1 | 10/2015 | Kuntz et al. |
| 2015/0303106 A1 | 10/2015 | Wang et al. |
| 2015/0344427 A1 | 12/2015 | Kuntz et al. |
| 2015/0344459 A1 | 12/2015 | Kuntz et al. |
| 2015/0368229 A1 | 12/2015 | Albrecht et al. |
| 2016/0024081 A1 | 1/2016 | Campbell et al. |
| 2016/0031907 A1 | 2/2016 | Campbell et al. |
| 2016/0130261 A1 | 5/2016 | Burgess et al. |
| 2016/0159782 A1 | 6/2016 | Yu et al. |
| 2016/0176882 A1 | 6/2016 | Chan et al. |
| 2016/0185757 A1 | 6/2016 | Albrecht et al. |
| 2016/0297805 A1 | 10/2016 | Seitz et al. |
| 2016/0297806 A1 | 10/2016 | Kim et al. |
| 2016/0361309 A1 | 12/2016 | McCabe et al. |
| 2017/0015666 A1 | 1/2017 | Miller et al. |
| 2017/0066780 A1 | 3/2017 | Dominguez et al. |
| 2017/0073335 A1 | 3/2017 | Kanno et al. |
| 2017/0152239 A1 | 6/2017 | Edwards et al. |
| 2017/0320880 A1 | 11/2017 | Michaelides et al. |
| 2017/0348306 A1 | 12/2017 | Creasy et al. |
| 2018/0265517 A1 | 9/2018 | Marx et al. |
| 2019/0142837 A1 | 5/2019 | Chan et al. |
| 2019/0202828 A1 | 7/2019 | Chan et al. |
| 2021/0032252 A1 | 2/2021 | Marx et al. |

FOREIGN PATENT DOCUMENTS

| | | |
|---|---|---|
| WO | WO-2011140324 A1 | 11/2011 |
| WO | WO-2011140325 A1 | 11/2011 |
| WO | WO-2012082436 A2 | 6/2012 |
| WO | WO-2012142504 A1 | 10/2012 |
| WO | WO-2012154760 A1 | 11/2012 |
| WO | WO-2013155464 A1 | 10/2013 |
| WO | WO-2013173441 A2 | 11/2013 |
| WO | WO-2014049488 A1 | 4/2014 |
| WO | WO-2014062720 A2 | 4/2014 |
| WO | WO-2014097041 A1 | 6/2014 |
| WO | WO-2014124418 A1 | 8/2014 |
| WO | WO-2014151142 A1 | 9/2014 |
| WO | WO-2014177982 A1 | 11/2014 |
| WO | WO-2014195919 A1 | 12/2014 |
| WO | WO-2015004618 A1 | 1/2015 |
| WO | WO-2015010049 A1 | 1/2015 |
| WO | WO-2015010078 A2 | 1/2015 |
| WO | WO-2015023915 A1 | 2/2015 |
| WO | WO-2015077193 A1 | 5/2015 |
| WO | WO-2015077194 A1 | 5/2015 |
| WO | WO-2015193765 A1 | 12/2015 |
| WO | WO-2015193768 A1 | 12/2015 |
| WO | WO-2016066697 A1 | 5/2016 |
| WO | WO-2016073903 A1 | 5/2016 |
| WO | WO-2016073956 A1 | 5/2016 |
| WO | WO-2016102493 A1 | 6/2016 |
| WO | WO-2016103155 A1 | 6/2016 |
| WO | WO-2016103255 A1 | 6/2016 |
| WO | WO-2016123387 A1 | 8/2016 |
| WO | WO-2016130396 A1 | 8/2016 |
| WO | WO-2017084494 A1 | 5/2017 |
| WO | WO-2017100362 A2 | 6/2017 |
| WO | WO-2017174023 A1 | 10/2017 |
| WO | WO-2017184999 A1 | 10/2017 |
| WO | WO-2017191545 A1 | 11/2017 |
| WO | WO-2017210395 A1 | 12/2017 |
| WO | WO-2017218953 A1 | 12/2017 |
| WO | WO-2017219948 A1 | 12/2017 |
| WO | WO-2017221092 A1 | 12/2017 |
| WO | WO-2017221100 A1 | 12/2017 |
| WO | WO-2019062435 A1 | 4/2019 |
| WO | WO-2019120276 A1 | 6/2019 |
| WO | WO-2019152419 A1 | 8/2019 |
| WO | WO-2019158025 A1 | 8/2019 |
| WO | WO-2020219448 A1 | 10/2020 |
| WO | WO-2020247475 A1 | 12/2020 |

OTHER PUBLICATIONS

Antonysamy et al. Structural context of disease-associated mutations and putative mechanism of autoinhibition revealed by X-ray crystallographic analysis of the EZH2-SET domain. PLoS One 8(12):e84147 (2013).

Bradley et al. EZH2 inhibitor efficacy in non-Hodgkin's lymphoma does not require suppression of H3K27 monomethylation. Chem Biol 21 (11):1463-75 (2014).

Brooun et al. Polycomb repressive complex 2 structure with inhibitor reveals a mechanism of activation and drug resistance. Nat Commun 7:11384 (2016) (w/Supp Material).

Campbell et al. EPZ011989, A Potent, Orally-Available EZH2 Inhibitor with Robust in Vivo Activity. ACS Med Chem Lett 6(5):491-495 (2015).

Cao et al. Role of histone H3 lysine 27 methylation in Polycomb-group silencing. Science 298:1039-1043 (2002).

Copeland. Epigenetic Medicinal Chemistry. ACS Med Chem Lett 7(2):124-7 (2015).

Co-pending U.S. Appl. No. 16/966,708, Inventors Marx Matthew Arnold et al., filed Jul. 31, 2020.

Co-pending U.S. Appl. No. 17/116,270, inventors Marx; Matthew Arnold et al., filed Dec. 9, 2020.

Denisenko et al. Point mutations in the WD40 domain of Eed block its interaction with Ezh2. Mol. Cell Biol. 18:5634-5642 (1998).

Garapaty-Rao et al. Identification of EZH2 and EZH1 Small Molecule Inhibitors with Selective Impact on Diffuse Large B Cell Lymphoma Cell Growth. Chem Biol 20(11):1329-39 (2013).

Hackam, et al. Translation of research evidence from animals to humans. JAMA. Oct. 11, 2006;296(14):1731-2.

He et al. Erratum: The EED protein-protein interaction inhibitor A-395 inactivates the PRC2 complex. Nat Chem Biol. 13(8):922 (2017).

Helin et al. Chromatin proteins and modifications as drug targets. Nature 502:480-488 (2013).

Horiuchi et al. Assay development for histone methyltransferases. Assay Drug Dev Technol. 4:227-236 (2013).

Huang et al. Discovery of First-in-Class, Potent and Orally Bioavailable EED inhibitor with Robust Anti-cancer Efficacy. J Med Chem 60(6):2215-2226 (2017).

Jordan. Tamoxifen: A most unlikely pioneering medicine. Nature Reviews: Drug Discovery 2:205-213 (2003).

Kleer et al. EZH2 is a marker of aggressive breast cancer and promotes neoplastic transformation of breast epithelial cells. PNAS USA 100(20):11606-11611 (2003).

Knutson et al. Selective Inhibition of EZH2 by EPZ-6438 Leads to Potent Antitumor Activity in F7H2-Mutant Non-Hodgkin Lymphoma. Mol Cancer Ther 13(4):842-54 (2014) (w/Supp Material).

Kung et al. Design and Synthesis of Pyridone-Containing 3,4-Dihydroisoquinoline-1(2H)-ones as a Novel Class of Enhancer of Zeste Homolog 2 (EZH2) Inhibitors. J Med Chem 59(18):8306-25 (2016).

Kung et al. Optimization of Orally Bioavailable Enhancer of Zeste Homolog 2 (EZH2) Inhibitors Using Ligand and Property-Based Design Strategies: Identification of Development Candidate (R)-5,8-Dichloro-7-(methoxy(oxetan-3-yl)methyl)-2-((4-methoxy-6-methyl-2-oxo-1,2-dihydropyridin-3-yl)methyl)-3,4-dihydroisoquinolin-1(2H)-one (PF-06821497). J Med Chem 61(3):650-665 (2018).

(56) References Cited

OTHER PUBLICATIONS

Kuntz et al. The Importance of Being Me: Magic Methyls, Methyltransferase Inhibitors, and the Discovery of Tazemetostat. J Med Chem 59(4):1556-64 (2016) (w/Supp Material).

Li et al. Discovery and Molecular Basis of a Diverse Set of Polycomb Repressive Complex 2 Inhibitors Recognition by EED. PLoS One 12(1):e0169855 (2017).

Lingel et al. Structure-Guided Design of EED Binders Allosterically Inhibiting the Epigenetic Polycomb Repressive Complex 2 (PRC2) Methyltransferase. 60(1):415-427 (2017).

McCabe et al. EZH2 inhibition as a therapeutic strategy for lymphoma with EZH2-activating mutations. Nature 492:108-112 (2012).

Nasveschuk et al. Discovery and Optimization of Tetramethylpiperidinyl Benzamides as Inhibitors of EZH2. ACS Med Chem Lett 5(4):378-83 (2014).

Pasqualucci et al. Analysis of the coding genome of diffuse large B-cell lymphoma. Nature Genet. 43(9):830-837 (2011).

PCT/US2019/015677 International Search Report and Written Opinion dated May 24, 2019.

PCT/US2020/029118 International Search Report and Written Opinion dated Jul. 9, 2020.

PCT/US2020/035891 International Search Report and Written Opinion dated Aug. 28, 2020.

Qi et al. an allosteric prC2 inhibitor targeting the H3K27me3 binding pocket of EED. Nat Chem Biol 13(4):381-388 (2017).

Santiago et al. Druggability of methyl-lysine biding sites. J Comput Aided Mol Des 25:1171-1178 (2011).

Souroullas et al. An oncogenic Ezh2 mutation induces tumors through global redistribution of histone 3 lysine 27 trimethylation. Nat Med 22(6):632-40 (2016).

Stazi et al. EZH2 inhibitors: a patent review (2014-2016). Expert Opin Ther Pat 27(7):797-813 (2017).

U.S. Appl. No. 17/116,270 Office Action dated Feb. 5, 2021.

Varambally, S. et al., Genomic Loss of microRNA-101 Leads to Overexpression of Histone Methyltransferase EZH2 in Cancer, Science, 322:1695-1699 (2008).

Vaswani et al. Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1 H-indole-3-carboxamide (CPI-1205), a Potent and Selective Inhibitor of Histone Methyltransferase EZH2, Suitable for Phase I Clinical Trials for B-Cell Lymphomas. J Med Chem 59(21):9928-9941 (2016).

Wu et al. Identification of novel EZH2 inhibitors through pharmacophore-based virtual screening and biological assays. Bioog Med Chem Lett 26(15):3813-3817 (2016).

Yang et al. Allosteric Inactivation of Polycomb Repressive Complex 2 (PRC2) by Inhibiting Its Adapter Protein: Embryonic Ectodomain Development (EED). J Med Chem 60(6):2212-2214 (2017).

U.S. Appl. No. 17/116,270 Office Action dated Jun. 10, 2021.

SUBSTITUTED IMIDAZO[1,2-C]PYRIMIDINES AS PRC2 INHIBITORS

CROSS-REFERENCE TO RELATED APPLICATIONS

This application is a continuation of U.S. application Ser. No. 17/116,270, filed Dec. 9, 2020, which is a continuation of U.S. application Ser. No. 16/966,708, filed Jul. 31, 2020, which is a § 371 U.S. National Stage entry of International Application No. PCT/US2019/015677, filed Jan. 29, 2019, which claims the benefit of U.S. Provisional Application No. 62/747,736, filed Oct. 19, 2018; U.S. Provisional Application No. 62/672,701, filed May 17, 2018, and U.S. Provisional Application No. 62/624,176, filed Jan. 31, 2018, the entire content of each application is hereby incorporated by reference in their entirety.

FIELD OF THE INVENTION

The present invention relates to compounds that inhibit the Polycomb Repressive Complex 2 (PRC2). In particular, the present invention relates to compounds, pharmaceutical compositions comprising the compounds and methods for use therefor.

BACKGROUND OF THE INVENTION

The Polycomb Repressive Complex 2 (PRC2) is a multiprotein complex that contributes to the epigenetic silencing of target genes to regulate development and homeostasis. The PRC2 complex is comprised of three core subunits: enhancer of zeste homolog 2 (EZH2), embryonic ectoderm development protein (EED), and suppressor of zeste 12 (SUZ12). Two additional non-essential subunits, AEBP2, and RbAp48, function to promote the enzymatic activity of the PRC2 complex (e.g., see Cao et al., (2002) Science 298: 1039-1043).

EZH2, the catalytic subunit of the PRC2 complex, is a histone methyltransferase that functions to silence target genes by tri-methylating lysine 27 of histone H3 (H3K27me3). EED is partially responsible for the recognition of trimethylated histone H3 lysine 27 and serves as scaffold protein for the assembly of the PRC2 complex. The interaction between EZH2 and EED subunits is essential for PRC2 complex histone methyltransferase activity and function (e.g., see Denisenko et al., (1998) Mol. Cell Biol. 18:5634-5642).

Aberrant PRC2 expression has been reported in several cancers. EZH2 is overexpressed in aggressive solid tumors, including the prostate, breast, skin, bladder, liver, pancreas, and head and neck cancers. For instance, EZH2 transcript and protein were shown to be consistently elevated in invasive breast carcinoma compared with normal breast epithelia and were strongly associated with breast cancer aggressiveness. Overexpression of EZH2 in immortalized human mammary epithelial cell lines promotes anchorage-independent growth and cell invasion. EZH2-mediated cell invasion required an intact SET domain and histone deacetylase activity (Kleer et al., (2003) Proc. Natl Acad Sci USA 100(20):11606-11611). There also is a greater risk of recurrence after prostatectomy in tumors expressing high levels of EZH2 (Varambally et al, (2008) Science 322:1695-1699).

In addition to overexpression, somatic activating and inactivating mutations of the EZH2 subunit have been reported. Somatic activating mutations in EZH2 have been identified in follicular lymphoma and diffuse large B-cell lymphomas that result in increased levels of H3K27me3 (for a review, see Helin and Dhanak (2013) Nature 502:480-488; Pasqualucci et al., (2011) Nature Genet. 43(9):830-837). These mutations taken together with overexpression of EZH2 in various solid tumors suggests that mis-regulation of EZH2 can lead to silencing of genes by the PRC2 complex that are important to tumor growth and survival. Interestingly, however, inhibitors of the PRC2 complex that target non-catalytic subunits, e.g., EED, retain potent activity against cell lines harboring EZH2 activating mutations (e.g., He et al., (2017) Nat Chem Biol.: 13(8):922. doi: 10.1038/nchembio0817-922b).

SUMMARY OF THE INVENTION

We recognize that enhanced PRC2 activity contributes to undesired cellular proliferation and invasiveness of tumor cells, in part, through trimethylation of H3K27. Since increased H3K27me3 levels appear to contribute to cancer aggressiveness in many tumor types, the inhibition of PRC2 activity may provide therapeutic benefit for a wide range of cancers. The compounds of the present invention offer potential therapeutic benefit as inhibitors that bind to the EED subunit that may be useful for negatively modulating the activity of PRC2 in a cell or for treating various forms of cancer.

There is a need to develop new PRC2 inhibitors that retain potency against EZH2 activating mutations and that demonstrate improved cellular potency, efficacy, stability and safety compared to inhibitors targeting the SET domain of EZH2. The compounds and compositions of the present invention advantageously overcome one or more of these shortcomings by providing potent, selective and orally active compounds that bind to EED and inhibit PRC2 activity irrespective of EZH2 mutation status or expression levels.

In one aspect of the invention, compounds are provided represented by formula (I):

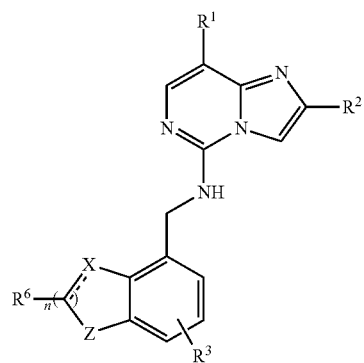

Formula (I)

or a pharmaceutically acceptable salt thereof:
wherein:
▬▬▬▬ represents a single or a double bond;
Z is O or S;
X is O, $CR^5$, $CR^5OH$, $C(R^5)_2$, wherein:
when X is O, ▬▬▬▬ is a single bond;
when X is $C(R^5)_2$, ▬▬▬▬ is a single bond:
when X is $CR^5OH$, ▬▬▬▬ is a single bond; or
when X is $CR^{5'}$ ▬▬▬▬ is a double bond;

R[1] is aryl, heteroaryl, L-cycloalkyl, or L-heterocyclyl, wherein the aryl, the heteroaryl or the cyclyl portion of the L-cycloalkyl or L-heterocyclyl may be optionally substituted with one or more R[4];

R[2] is cyano, —COOR[5], —C(O)N(R[5])$_2$ or —C(O)N(R[5])$_2$, wherein each R[5] taken together with the nitrogen atom to which they are attached form a 5-8 membered heterocyclic ring optionally substituted with one or more R[4]:

each R[3] is independently C1-C3 alkyl or halogen:

each R[4] is independently acyl, cyano, halogen, alkoxy, hydroxyalkyl, heteroalkyl, haloalkyl, Y[2]-haloalkyl; Y[1]—C1-C6 alkyl, Y[2]—C1-C6 alkyl, L-cycloalkyl, L-heteroaryl, L-heterocyclyl, Y[1]-heterocyclyl, -L-N(R[5])$_2$, —Y[1]—N(R[5])$_2$ or —Y[2]—N(R[5])$_2$ wherein the ring of the L-cycloalkyl, L-heteroaryl, L-heterocyclyl or Y[1]-heterocyclyl may be optionally substituted with one or more R[7];

L is a bond or C1-C4 alkylene;

Y[1] is a bond, —C(O)—, or —NHC(O)—:

Y[1] is a bond, —S—, —SO—, —SO$_2$—, or —NR[5]SO$_2$—, each R[5] is independently hydrogen or C1-C3 alkyl;

R[6] is hydrogen, C1-C3 alkyl, halogen, haloalkyl, hydroxyalkyl, or heteroalkyl;

each R[7] is independently oxo, cyano, hydroxyl, alkoxy, halogen, haloalkyl, hydroxyalkyl, heteroalkyl, cycloalkyl, -L-N(R[5])$_2$, C1-C6 alkyl or Y[1]-heterocyclyl, wherein the Y[1]-heterocyclyl may be optionally substituted with one or more R[7]; and n is 1 or 2.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods are provided for inhibiting PRC2 activity in a in a cell, comprising contacting the cell with a compound of Formula I. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of formula I, or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method for treating cancer in a patient in need thereof, the method comprising (a) determining that the cancer is associated with PRC2 mutation (e.g., a PRC2-associated cancer); and (b) administering to the patient a therapeutically effective amount of a compound of Formula I, or a pharmaceutically acceptable salt thereof, or a pharmaceutical composition thereof.

Also provided herein is a use of a compound of Formula I, or a pharmaceutically acceptable salt or solvate thereof, as defined herein in the manufacture of a medicament for the inhibition of activity of PRC2.

Also provided herein is the use of a compound of Formula I, or a pharmaceutically acceptable salt or solvate thereof, as defined herein, in the manufacture of a medicament for the treatment of a PRC2-associated disease or disorder.

DETAILED DESCRIPTION OF THE INVENTION

The present invention relates to PRC2 inhibitors. In particular, the present invention relates to compounds that bind to EED to inhibit PRC2 activity, pharmaceutical compositions comprising a therapeutically effective amount of the compounds, and methods of use therefor.

Definitions

Unless defined otherwise, all terms and ranges used herein have the same meaning as is commonly understood by one of skill in the art to which this invention belongs, unless expressly defined otherwise. All patents, patent applications, and publications referred to herein are incorporated by reference to the extent they are consistent with the present disclosure.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—CH—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

As used herein, "Polycomb Repressive Complex 2" or "PRC2 complex" refers to a mammalian multiprotein complex comprising three core subunits: enhancer of zeste homolog 2 (EZH2), embryonic ectoderm development protein (EED), and suppressor of zeste 12 (SUZ12) and two additional non-essential subunits, AEBP2, and RbAp48.

As used herein, "EED" refers to the embryonic ectoderm development protein subunit of the PRC2 complex.

As used herein, "EZH2" or "EZH2 enzyme" refers to a mammalian histone methyltransferase, which is the catalytic submit of the Polycomb Repressive Complex 2 (PRC2), and functions to silence target genes by tri-methylating lysine 27 of histone H3 (H3K27me3).

As used herein, an "PRC2 inhibitor" refers to compounds of the present invention that are represented by formula (I) as described herein. These compounds are capable of negatively modulating or inhibiting all or a portion of the enzymatic activity of the PRC2 complex. While not wanting to be bound by any theory, we theorize that the inhibitors of the present invention may inhibit PRC2 enzymatic activity by binding to EED to prevent assembly of the PRC2 complex on histone H3 tails thereby inhibiting its activity.

An "PRC2-associated disease or disorder" as used herein refers to diseases or disorders associated with or mediated by or having an activating EZH2 mutation and/or aberrant expression of PRC2. A non-limiting example of an PRC2-associated disease or disorder is a PRC2-associated cancer.

The term "amino" refers to —$NH_2$.

The term "acetyl" refers to "—$C(O)CH_3$.

As herein employed, the term "acyl" refers to an alkylcarbonyl or arylcarbonyl substituent wherein the alkyl and aryl portions are as defined herein.

The term "alkyl" as employed herein refers to straight and branded chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —OC1-C6 alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or $NR^x$, wherein $R^x$ is hydrogen or C1-C3 alkyl. Examples of heteroalkyl groups include methoxymethyl, methoxyethyl and methoxypropyl.

An "aryl" group is a $C_6$-$C_{14}$ aromatic moiety comprising one to three aromatic rings. As such, "aryl" includes $C_6$, $C_{10}$, $C_{11}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl.

An "aralkyl" or "arylalkyl" group comprises an aryl group covalently linked to an alkylene group wherein the moiety is linked to another group via the alkyl moiety. An exemplary aralkyl group is —(C1-C6)alkyl(C6-C10)aryl, including, without limitation, benzyl, phenethyl, and naphthylmethyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, N, $NR^5$, O, or S, and the remainder of the ring atoms are quaternary or carbonyl carbons. Examples of heterocyclic groups include, without limitation, epoxy, oxiranyl, oxetanyl, azetidinyl, aziridinyl, tetrahydrofuranyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

As used herein, "L-heterocyclyl" refers to a heterocyclyl group covalently linked to another group via an alkylene linker L, where L is C1-C4 alkylene.

As used herein, the term "heteroaryl" refers to a group having 5 to 14 ring atoms, preferably 5, 6, 10, 13 or 14 ring atoms; having 6, 10, or 14 n electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "L-heteroaryl", "heteroaralkyl" or "heteroarylalkyl" group comprises a heteroaryl group covalently linked to another group via an alkylene linker. Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylmethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is an bivalent aryl, heteroaryl, or heterocyclyl group, respectively, as defined hereinabove, that is positioned between and serves to connect two other chemical groups.

As employed herein, when a moiety (e.g., cycloalkyl, aryl, heteroaryl, heterocyclyl, urea, etc.) is described as "optionally substituted" without expressly stating the substituents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, chloromethyl, and fluoromethyl.

The term "hydroxyalkyl" refers to an alkyl chain, as defined herein, wherein at least on hydrogen of the alkyl chain has been replaced by hydroxyl.

As used herein, "an effective amount" of a compound is an amount that is sufficient to negatively modulate or inhibit the activity of PRC2 complex.

As used herein, a "therapeutically effective amount" of a compound is an amount that is sufficient to ameliorate or in some manner reduce a symptom or stop or reverse progression of a condition, or negatively modulate or inhibit the activity of PRC2 complex.

Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, "amelioration of the symptoms of a particular disorder by administration of a particular compound or pharmaceutical composition" refers to any lessening, whether permanent or temporary, lasting or transient, that can be attributed to or associated with administration of the composition.

Compounds

In one aspect of the invention, compounds are provided represented by formula (I):

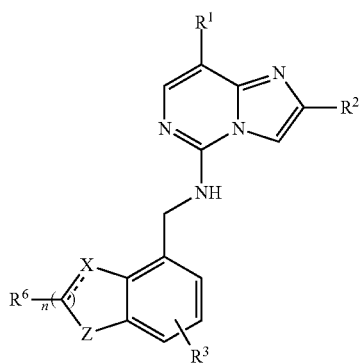

or a pharmaceutically acceptable salt thereof:
wherein:
═════ represents a single or a double bond:
Z is O or S:
X is O, $CR^5$, $CR^5OH$, $C(R^5)_2$, wherein:
when X is O, ═════ is a single bond:
when X is $C(R^5)_2$, ═════ is a single bond;
when X is $CR^5OH$, ═════ is a single bond; or
when X is $CR^{5'}$ ═════ is a double bond:
$R^1$ is aryl, heteroaryl, L-cycloalkyl, or L-heterocyclyl, wherein the aryl, the heteroaryl or the cyclyl portion of the L-cycloalkyl or L-heterocyclyl may be optionally substituted with one or more $R^4$;
$R^2$ is cyano, —$COOR^5$, —$C(O)N(R^5)_2$ or —$C(O)N(R^5)_2$ wherein each $R^5$ taken together with the nitrogen atom to which they are attached form a 5-8 membered heterocyclic ring optionally substituted with one or more $R^4$;
each $R^3$ is independently C1-C3 alkyl or halogen:
each $R^4$ is independently cyano, halogen, alkoxy, hydroxyalkyl, heteroalkyl, haloalkyl, $Y^2$-haloalkyl; $Y^1$—C1-C6 alkyl, $Y^2$—C1-C6 alkyl, L-cycloalkyl, L-heteroaryl, L-heterocyclyl, $Y^1$-heterocyclyl, -L-$N(R^5)_2$, —$Y^1$—$N(R^5)_2$ or —$Y^2$—$N(R^5)_2$ wherein the ring of the L-cycloalkyl, L-heteroaryl, L-heterocyclyl or $Y^1$-heterocyclyl may be optionally substituted with one or more $R^7$:
L is a bond or C1-C4 alkylene;
$Y^1$ is a bond, —C(O)—, or —NHC(O)—;
$Y^2$ is a bond, —S—, —SO—, —$SO_2$—, or —$NR^5SO_2$—,
each $R^5$ is independently hydrogen or C1-C3 alkyl:
$R^6$ is hydrogen, C1-C3 alkyl, halogen, haloalkyl, hydroxyalkyl, or heteroalkyl;
each $R^7$ is independently oxo, cyano, hydroxyl, alkoxy, halogen, haloalkyl, hydroxyalkyl, heteroalkyl, cycloalkyl, -L-$N(R^5)_2$, C1-C6 alkyl or $Y^1$-heterocyclyl, wherein the $Y^1$-heterocyclyl may be optionally substituted with one or more $R^7$; and
n is 1 or 2.

In one embodiment, Z is O or S. In one embodiment, X is O, $CR^5$, $CR^5OH$ or $C(R^5)_2$, wherein when X is O, ═════ is a single bond; when X is $C(R^5)_2$, ═════ is a single bond; when X is $CR^5OH$, ═════ is a single bond; or when X is $CR^5$, ═════ is a double bond. In one embodiment, n is one. In one embodiment, n is two.

In one embodiment, Z is O, X is O, n is one and ═════ is a single bond. In another embodiment, Z is O, X is $CR^5$ and ═════ is a double bond. In one embodiment, Z is O, X is $C(R^5)_2$, n is one, and ═════ is a single bond. In one embodiment, Z is O, X is $CR^5OH$, n is one, and ═════ is a single bond. In another embodiment. Z is O, X is $C(R^5)_2$ n is two, and ═════ is a single bond. In yet another embodiment, Z is S, X is $C(R^5)_2$ n is one, and ═════ is a single bond.

In one embodiment, $R^1$ is aryl, which may be optionally substituted with one or more $R^4$. In certain embodiments, the aryl is phenyl, which may be optionally substituted with one or more $R^4$.

In one embodiment, the aryl is substituted with a single $R^4$ group. In one embodiment, the aryl is substituted with two $R^4$ groups. In one embodiment, the aryl is substituted with three $R^4$ groups. Exemplary aryl $R^4$ groups include halogen, hydroxyl, haloalkyl, —$Y^1$—C1-C6 alkyl, $Y^2$—C1-C6 alkyl, -L-$N(R^5)_2$, —$Y^1$—$N(R')_2$, —$Y^2$—$N(R^5)_2$, $Y^2$-haloalkyl, L-heterocyclyl, or $Y^1$-heterocycyl, wherein the heterocyclyl portion of the L-heterocyclyl, or $Y^1$-heterocyclyl may be optionally substituted with one or more $R^7$.

In one embodiment, $R^1$ is phenyl substituted with —$Y^2$—C1-C6 alkyl. In one embodiment, Y is a bond and the C1-C6 alkyl is methyl, ethyl or isopropyl. In one embodiment, $R^1$ is phenyl substituted with the $Y^2$—C1-C6 alkyl, wherein $Y^2$ is —$SO^2$— and the $C_1$-$C_6$ alkyl is methyl. In one embodiment, $R^1$ is phenyl, which is disubstituted with methyl and $Y^2$—C1-C6 alkyl, wherein $Y^2$ is —$SO^2$— and the $C_1$-$C_6$ alkyl is methyl.

In one embodiment, $R^1$ is phenyl substituted one $R^4$, wherein $R^4$ is a cyano group.

In one embodiment, $R^1$ is phenyl substituted one $R^4$, wherein $R^4$ is L-heteroaryl. In certain embodiments, the L-heteroaryl is tetrazolyl. In one embodiment, $R^1$ is phenyl substituted one $R^4$, wherein $R^4$ is $PO_3(C1-C3\ alkyl)_2$. In one embodiment, $R^1$ is phenyl substituted one $R^4$, wherein $R^4$ is —$COOR^5$. In one embodiment, $R^1$ is phenyl substituted one $R^4$, wherein $R^4$ is —O-L-$N(R^5)_2$. In one embodiment, $R^5$ is phenyl substituted one $R^4$, wherein $R^4$ is aralkyl.

In one embodiment, $R^1$ is phenyl substituted with at least one $R^4$, wherein $R^4$ is -L-$N(R^5)_2$. In one embodiment, Lisa bond. In one embodiment, Lis methylene. In one embodiment, each $R^5$ is independently hydrogen. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, $R^5$ is phenyl substituted with -L-N($R^5$)$_2$ and further substituted with one or more halogen and/or C1-C6 alkyl.

In one embodiment, $R^1$ is phenyl substituted with one $R^4$, wherein $R^4$ is —$Y^1$—N($R^5$). In certain embodiments. $Y^1$ is —C(O)— and each $R^5$ is C1-C3 alkyl. In one embodiment, each C1-C3 alkyl is methyl. In one embodiment. $Y^1$ is —C(O)— and each $R^5$ is hydrogen. In one embodiment. $Y^1$ is —C(O)— and one $R^5$ is C1-C3 alkyl and the other is hydrogen. In one embodiment, the one C1-C3 alkyl is methyl. In one embodiment, $R^1$ is phenyl substituted with —$Y^1$—N($R^5$)$_2$ and further substituted with one or more halogen and/or C1-C6 alkyl.

In one embodiment, $R^1$ is phenyl substituted with the $Y^2$-haloalkyl, wherein $Y^2$ is —S— or —SO$^2$— and the haloalkyl is trifluoromethyl.

In one embodiment, $R^1$ is phenyl substituted with at least one -L-heterocyclyl or —$Y^1$-heterocyclyl, each heterocyclyl optionally substituted with one or more $R^7$. In one embodiment, $R^1$ is phenyl substituted with one $R^4$, wherein $R^4$ is —$Y^1$-heterocyclyl optionally substituted with one or more $R^7$. In one embodiment, $Y^1$ is —C(O)— and the heterocyclyl is piperazinyl optionally substituted with C1-C3 alkyl.

In certain embodiments, the $R^4$ group is L-heterocyclyl optionally substituted with one or more $R^7$. In one embodiment. L is methylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more $R^7$. Exemplary $R^7$ groups include oxo, halogen, hydroxyalkyl and C1-C3 alkyl.

In one embodiment, $R^1$ is phenyl substituted with Y-heterocyclyl optionally substituted with one or more $R^7$. In certain embodiments, $Y^1$ is —C(O)— and the heterocyyl is azetidinyl, pyrrolidinyl, piperdinyl, piperazinyl or 4-methyl-piperazinyl, each optionally further substituted with one or more halogen.

In one embodiment, $R^1$ is phenyl substituted with L-heteroaryl optionally substituted with one or more $R^7$. In certain embodiments, the L-heteroaryl is tetrazoyl.

In one embodiment, $R^1$ is phenyl substituted with PO$_3$(C$_1$-C$_3$ alkyl)$_2$. In another embodiment. $R^1$ is phenyl substituted with —COOR$^5$. In one embodiment, $R^1$ is phenyl substituted with hydroxyalkyl, —O-L-N($R^5$)$_2$ or aralkyl.

In one embodiment, $R^1$ is heteroaryl, which may be optionally substituted with one or more $R^4$. In certain embodiments, the heteroaryl is pyrazolyl, imidazolyl, oxazolyl, isoxazolyl, thiazolyl, triazinyl, pyridyl, pyridinyl-2-one, pyrazinyl, pyridazinyl, pyrimidinyl, or 5,6-dihydro-4H-pyrrolo[1,2-b]pyrazoyl, each of which may be optionally substituted with one or more $R^4$.

In one embodiment, the heteroaryl is substituted with a single $R^4$ group. In one embodiment, the heteroaryl is substituted with two $R^4$ groups. In one embodiment, the heteroaryl is substituted with three $R^4$ groups. Exemplary heteroaryl $R^4$ groups include amino, cyano, halogen, alkoxy, hydroxyalkyl, heteroalkyl, haloalkyl, $Y^2$-haloalkyl $Y^1$—C1-C6 alkyl, $Y^2$—C1-C6 alkyl, L-cycloalkyl, L-heteroaryl, L-heterocyclyl, $Y^1$-heterocyclyl, -L-N($R^5$)$_2$, or —$Y^1$—N($R^5$)$_2$, wherein the ring of the L-cycloalkyl, L-heteroaryl, L-heterocyclyl or $Y^1$-heterocyclyl may be optionally substituted with one or more $R^7$.

In one embodiment, $R^7$ is amino, hydroxyl, cyano, alkoxy, or halogen. In one embodiment, $R^7$ is C1-C3 alkyl. In one embodiment, $R^7$ is halogen, wherein the halogen is fluorine or chlorine. In one embodiment, $R^7$ is alkoxy, wherein the alkoxy is methoxy or ethoxy. In one embodiment, $R^7$ is cycloalkyl, wherein the cycloalkyl is cyclopropyl.

In another embodiment, $R^1$ is heteroaryl and each $R^4$ is independently hydroxyalkyl, heteroalkyl or haloalkyl. In certain embodiments, the hydroxyalkyl is hydroxymethyl, hydroxyethyl or 2-methyl, 2-hydroxypropyl. In certain embodiments, the heteroalkyl is methoxymethyl or methoxyethyl. In certain embodiments, the haloalkyl is fluoromethyl, difluoromethyl, trifluoromethyl, fluoroethyl, difluoroethyl, or trifluoroethyl.

In certain embodiments, $R^1$ is heteroaryl and $R^4$ is —$Y^1$—C1-C6 alkyl, wherein $Y^1$ is a bond and the C1-C6 alkyl is methyl, ethyl or isopropyl. In one embodiment, $R^4$ is —$Y^1$—C1-C6 alkyl, wherein $Y^1$ is a —C(O)— and the C1-C6 alkyl is methyl, ethyl or isopropyl. In other embodiments, $Y^1$ is —NHC(O)— and the C1-C6 alkyl portion is methyl.

In one embodiment, $R^1$ is heteroaryl and $R^4$ is —$Y^2$—C1-C6 alkyl, wherein $Y^2$ is —SO$_2$— and the C1-C6 alkyl is methyl. In another embodiment, $R^4$ is —$Y^1$—C1-C6 alkyl, wherein $Y^2$ is —S— and the C1-C6 alkyl is methyl.

In one embodiment, $R^1$ is heteroaryl and $R^4$ is —$Y^1$-heterocyclyl, which may be optionally substituted with one or more $R^7$. In one embodiment, $Y^1$ is a bond. In another embodiment, $Y^1$ is —C(O)—. In one embodiment, $Y^1$ is a bond and the heterocyclyl is azetidinyl, oxetanyl, tetrahydrofuranyl, tetrahydropyranyl, pyrrolidinyl, piperdinyl, piperazinyl or 4-methyl-piperazinyl. In one embodiment, $R^1$ is C1-C3 alkyl. In one embodiment, $R^7$ is halogen.

In one embodiment, the heteroaryl is substituted with at least one $R^4$ that is -L-heterocyclyl, which may be optionally substituted with one or more $R^7$. In one embodiment, L is ethylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more $R^7$.

In one embodiment, the $R^7$ is independently -L-N($R^5$)$_2$, hydroxyl, cyano, alkoxy, or halogen. In one embodiment, $R^7$ is C1-C3 alkyl. In one embodiment, $R^7$ is halogen, wherein the halogen is fluorine or chlorine. In one embodiment, $R^7$ is alkoxy, wherein the alkoxy is methoxy or ethoxy. In one embodiment, $R^7$ is cycloalkyl, wherein the cycloalkyl is cyclopropyl. In one embodiment, $R^1$ is -L-N($R^5$)$_2$. In one embodiment, L is a bond. In one embodiment, L is methylene. In one embodiment, each $R^5$ is independently hydrogen. In one embodiment, each $R^5$ is independently C1-C3 alkyl. In one embodiment, each C1-C3 alkyl is methyl. In one embodiment, one $R^7$ is C1-C3 alkyl and the other is hydrogen. In one embodiment, the one C1-C3 alkyl is methyl.

In one embodiment, $R^1$ is heteroaryl and $R^4$ is -L-N($R^5$)$_2$. In one embodiment, L is a bond. In one embodiment, L is methylene, ethylene or propylene. In one embodiment, each $R^7$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, each $R^5$ is independently hydrogen.

In one embodiment, $R^1$ is heteroaryl and $R^4$ is L-heteroaryl, which may be optionally substituted with one or more $R^7$. In one embodiment, L is a bond. In one embodiment, L is C1-C3 alkylene. In one embodiment, the C1-C3 alkylene is methylene. In certain embodiments, the heteroaryl of the L-heteroaryl is pyrazolyl, pyridyl, pyrimidinyl, pyrazinyl, triazinyl, thiazolyl or pyridazinyl. In one embodiment, the heteroaryl of the L-heteroaryl is pyridyl.

In one embodiment, $R^1$ is heteroaryl which is substituted with two $R^4$ groups independently selected from two —$Y^1$—C1-C6 alkyl groups: —$Y^1$—C1-C6 alkyl and alkoxy; —$Y^1$—C1-C6 alkyl and cycloalkyl; —$Y^1$—C1-C6 alkyl and haloalkyl; —$Y^1$—C1-C6 alkyl and amino; two alkoxy groups; alkoxy and halogen; alkoxy and cyano, and amino and haloalkyl. In certain embodiments, $R^4$ is —$Y^1$—C1-C6 alkyl, wherein each Y t is a bond and each C1-C6 alkyl is methyl, ethyl or isopropyl. In one embodiment, the cycloalkyl is cyclopropyl. In one embodiment, the alkoxy is methoxy. In one embodiment, the halogen is fluorine or chlorine. In one embodiment, the haloalkyl is trifluoromethyl or trifluoroethyl.

In one embodiment, $R^1$ is L-heterocyclyl optionally substituted with one or more $R^4$. In one embodiment, L is a bond and the heterocyclyl is tetrahydrofuranyl, piperdinyl, piperazinyl or morpholinyl. In one embodiment, Lis a methylene and the heterocyclyl is azetidinyl, pyrrolidinyl or $3\lambda^2$-azabicyclo[3.1.0]hexanyl. In certain embodiments, the heterocyclyl is substituted with one or more $R^4$ selected from oxo, halogen, alkoxy, hydroxyl and $Y^1$—C1-C6 alkyl, wherein Y is a bond or —C(O)—.

In one embodiment, $R^2$ is cyano. In one embodiment, $R^2$ is —$COOR^5$. In certain embodiments, the $R^5$ group is hydrogen.

In one embodiment, $R^2$ is —$C(O)N(R^5)_2$. In one embodiment, each $R^5$ is independently C1-C3 alkyl. In certain embodiments, each C1-C3 alkyl is methyl. In one embodiment, one $R^5$ is C1-C3 alkyl and the other is hydrogen. In certain embodiments, the one C1-C3 alkyl is methyl. In one embodiment, each $R^5$ is independently hydrogen. In one embodiment, each $R^5$ together with the nitrogen atom to which they are attached form a 5-8 membered heterocyclic ring optionally substituted with one or more $R^4$.

In one embodiment, n is zero. In one embodiment, n is one and $R^3$ is halogen. In certain embodiments, the halogen is fluorine or chlorine. In one embodiment, the halogen is fluorine.

In one embodiment, $R^6$ is hydrogen. C1-C3 alkyl, halogen, haloalkyl, hydroxyalkyl, or heteroalkyl. In certain embodiments, $R^6$ is hydrogen. In other embodiments, $R^6$ is methyl, ethyl or propyl.

In one embodiment, the cyclyl portion of $R^4$ group is substituted with one $R^7$ group. In certain embodiments, $R^7$ is oxo, hydroxyl, alkoxy, halogen, haloalkyl, hydroxyalkyl, heteroalkyl, cycloalkyl, -L-N($R^5$)$_2$ or C1-C3 alkyl. In certain embodiments, $R^7$ is C1-C3 alkyl, wherein the C1-C3 alkyl is methyl, ethyl or isopropyl. In certain embodiments, $R^7$ is halogen, wherein the halogen is fluorine or chlorine. In certain embodiments, $R^7$ is oxo.

In one embodiment, the cyclyl portion of $R^4$ group is substituted with two R groups. In certain embodiments, the two $R^1$ groups are each halogen, wherein each halogen is fluorine.

In one embodiment, the compound is:

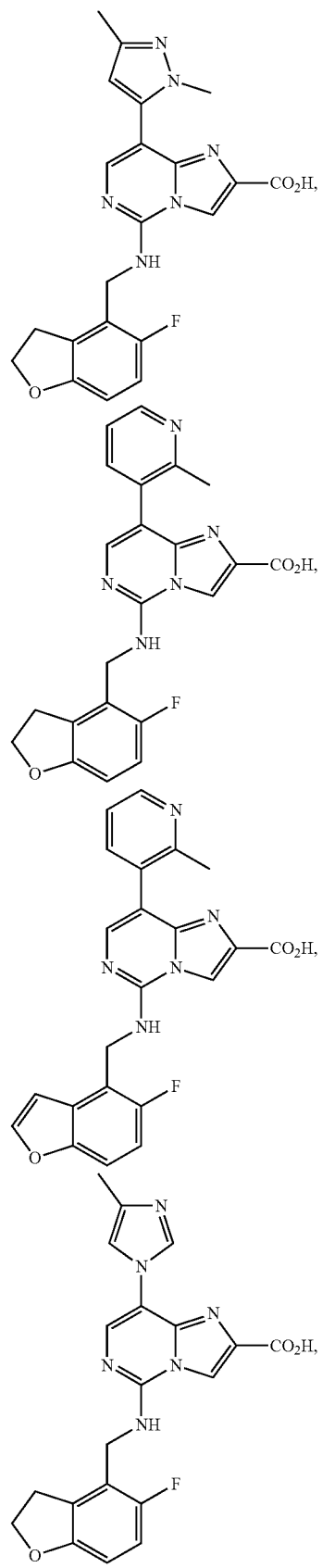

-continued
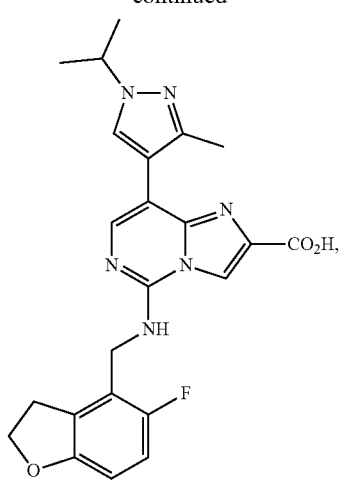
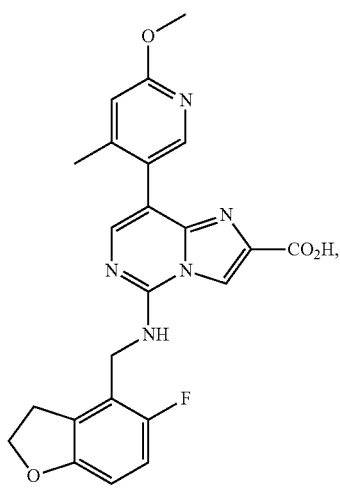
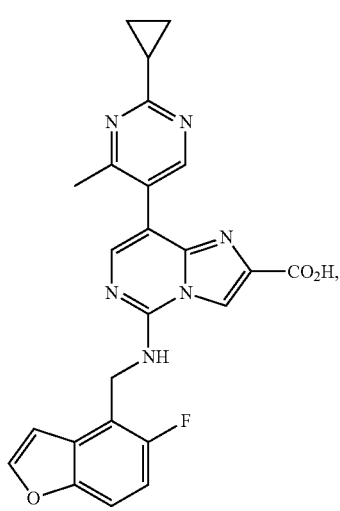
-continued
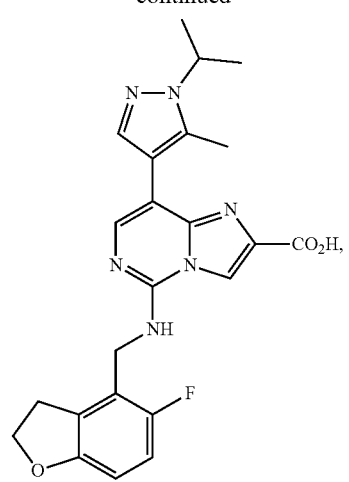
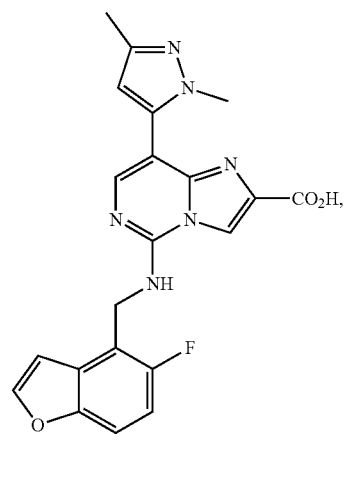
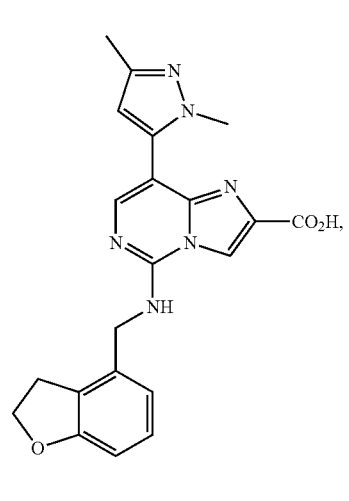

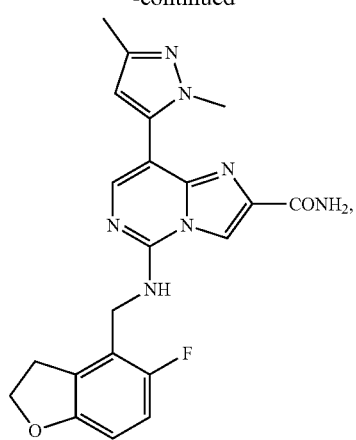
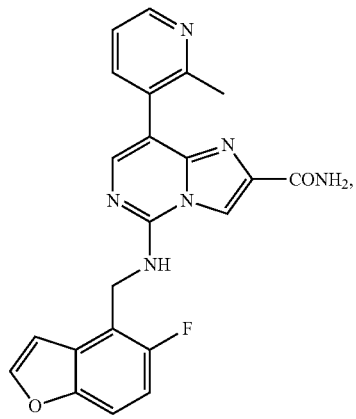
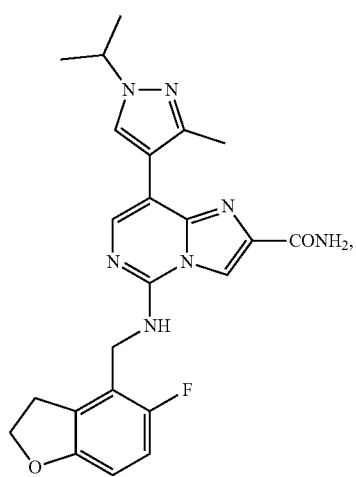
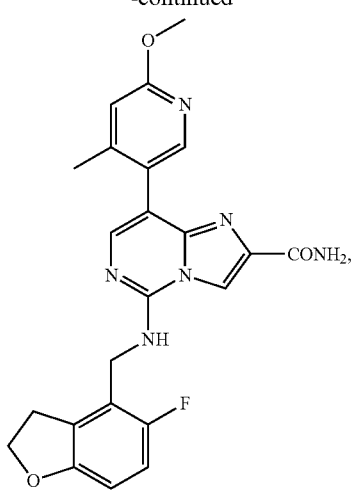
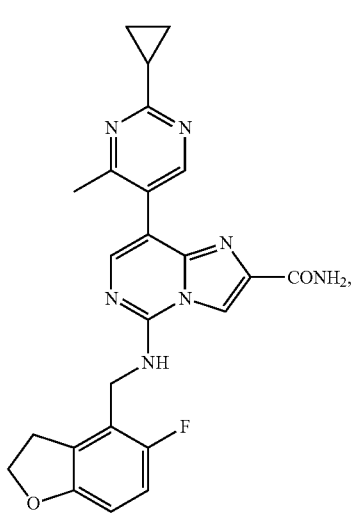
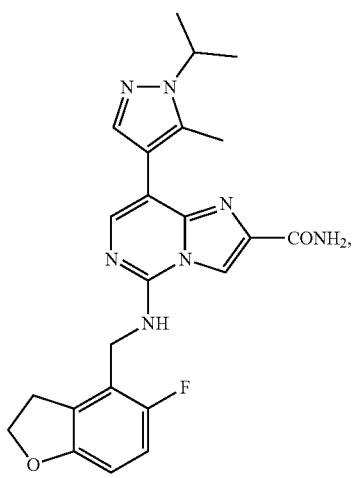

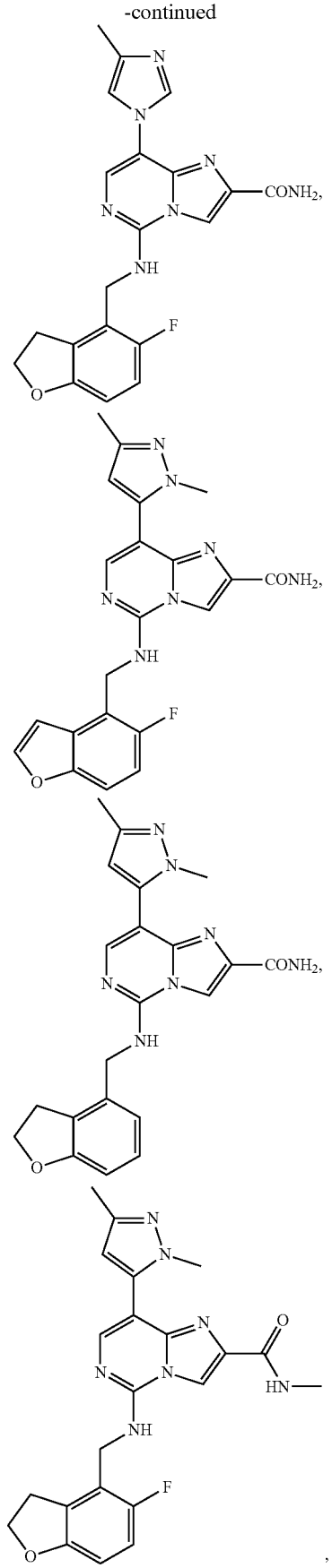
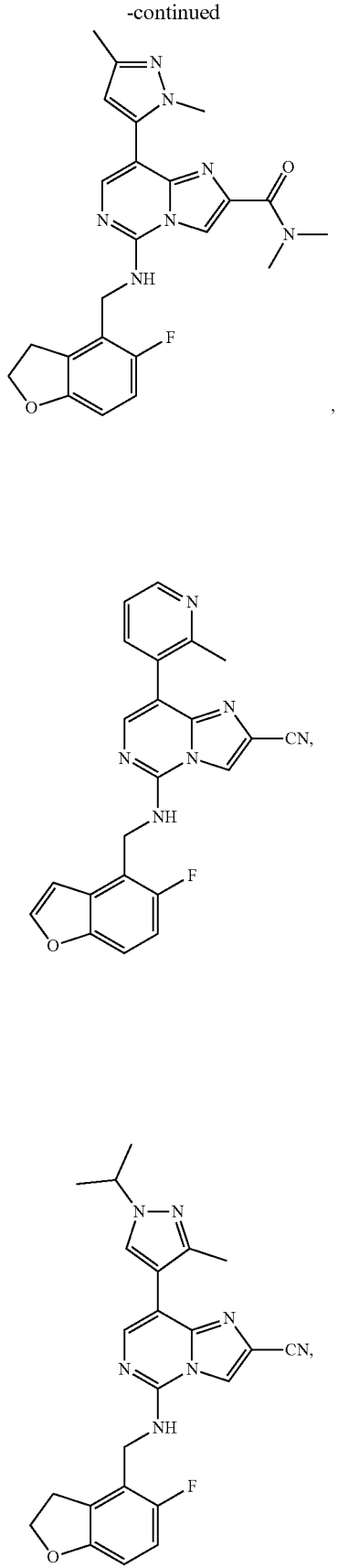

19
-continued
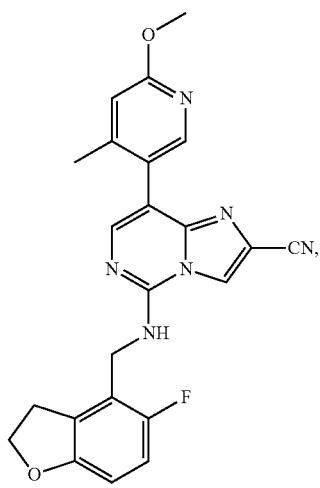
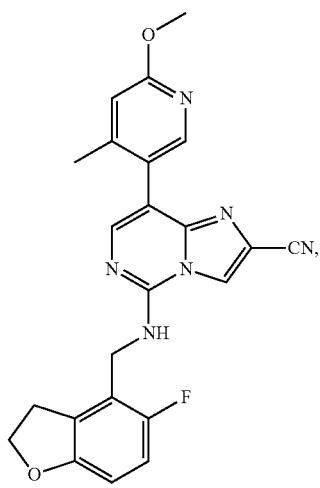
20
-continued
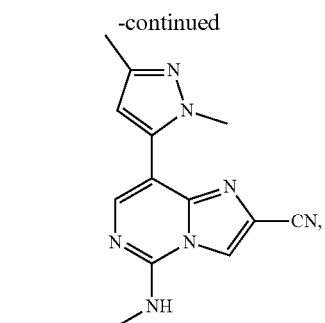
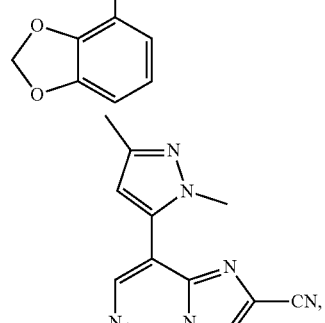
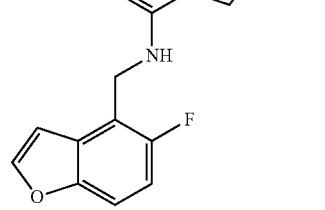
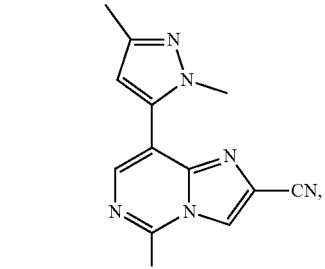
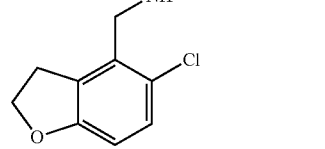
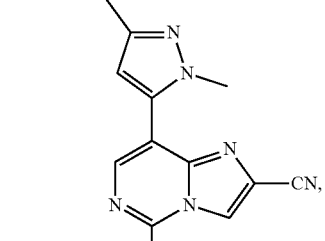
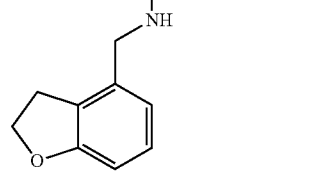

-continued
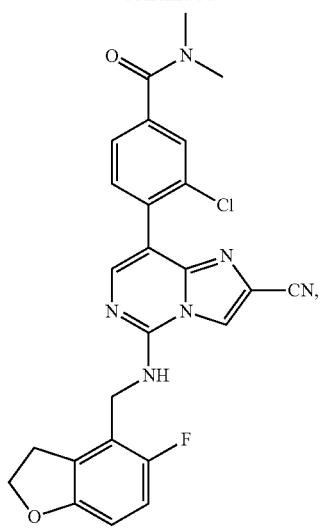
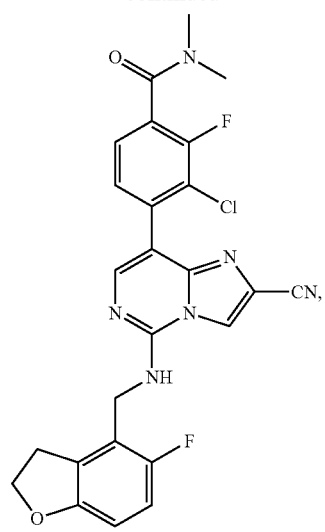
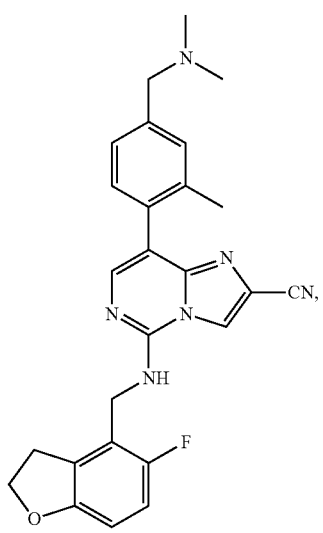
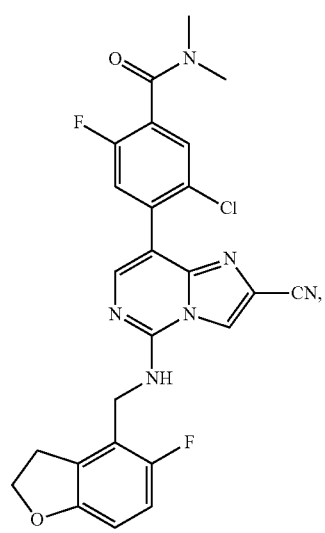
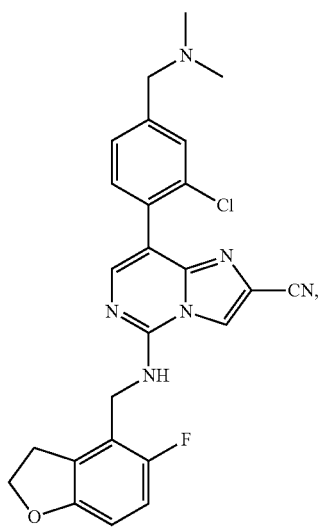
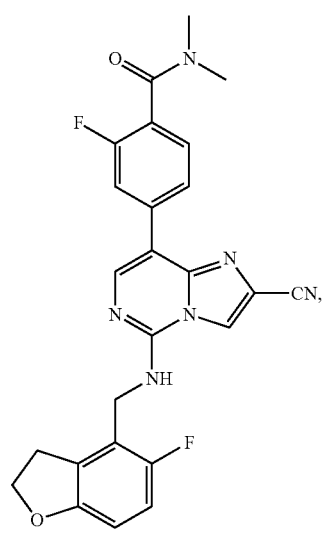

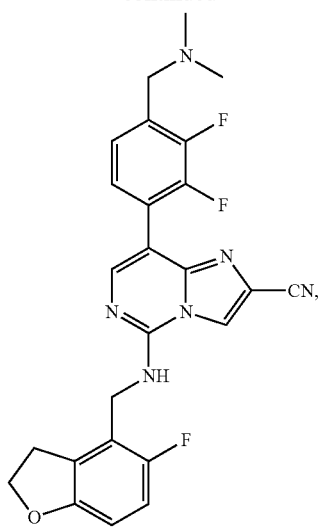
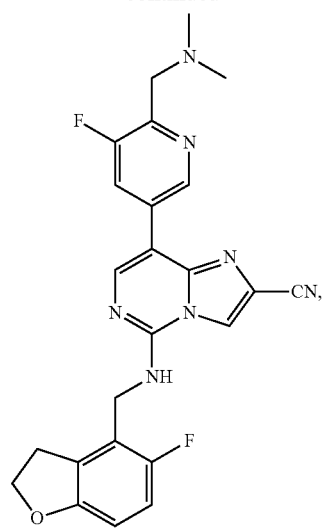
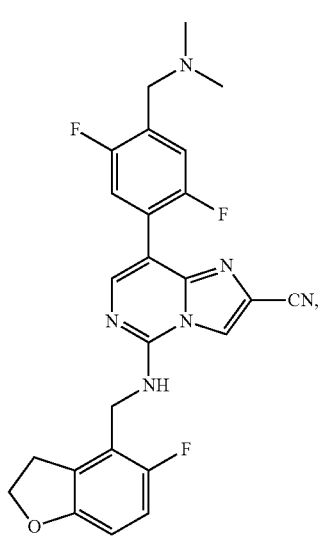
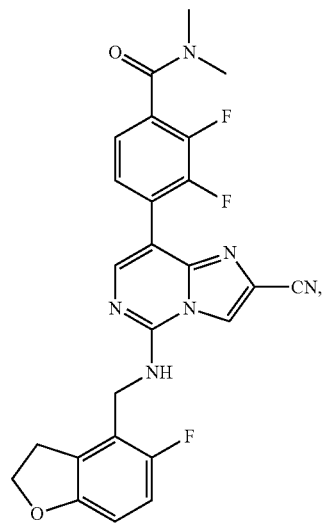

-continued
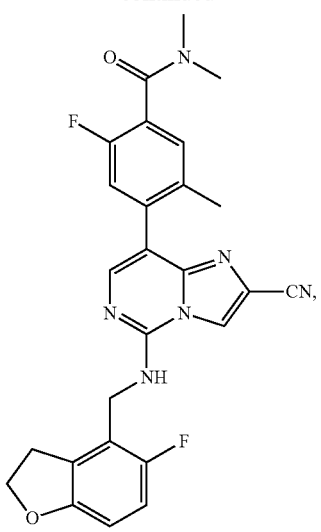
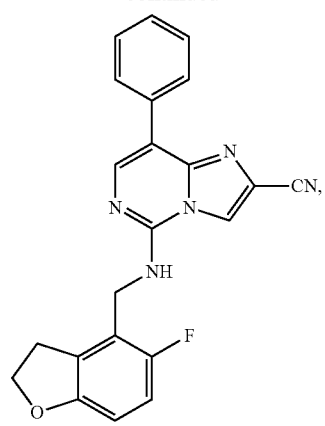
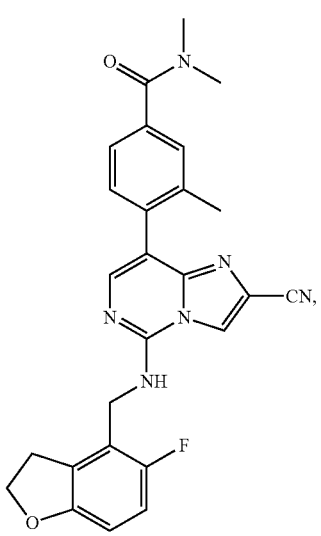
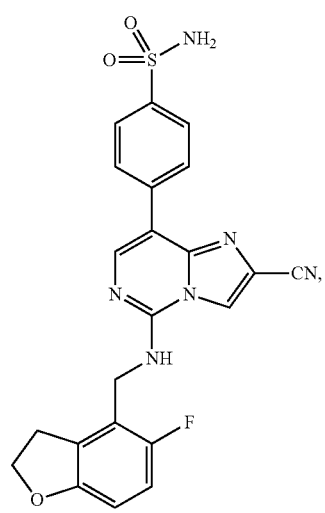
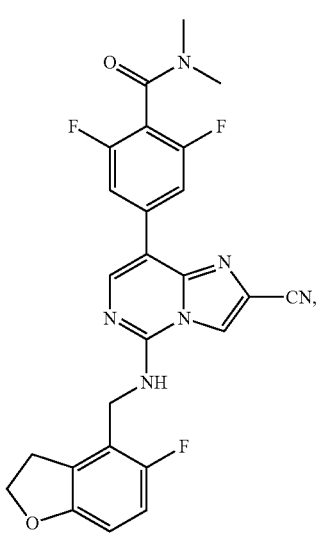
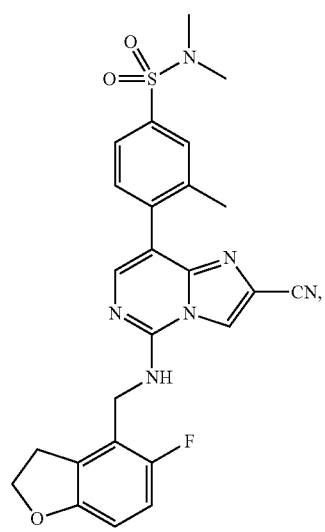

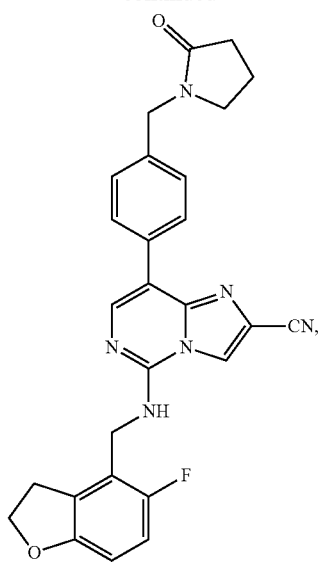
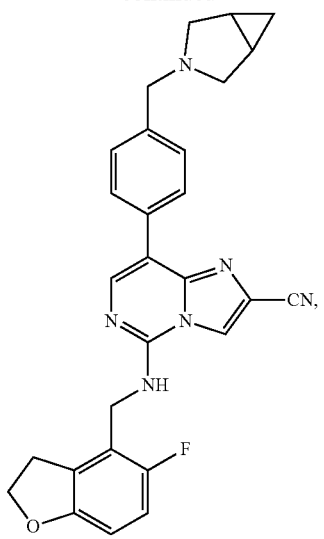

29
-continued
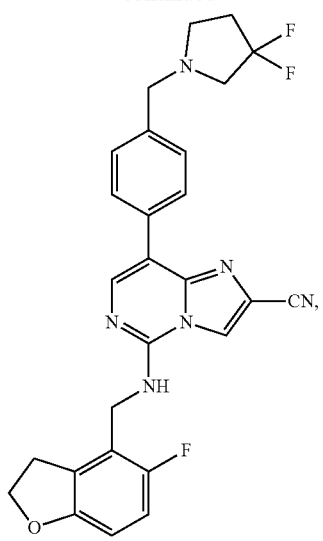
30
-continued
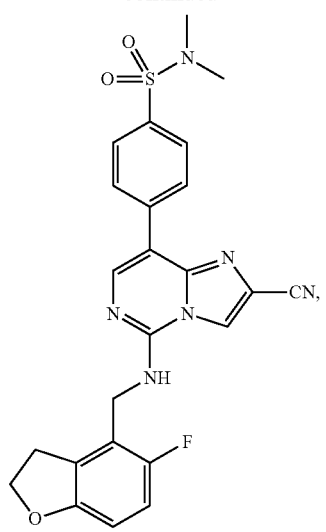
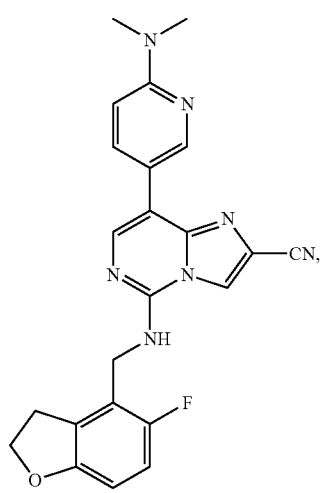

31
-continued
32
-continued
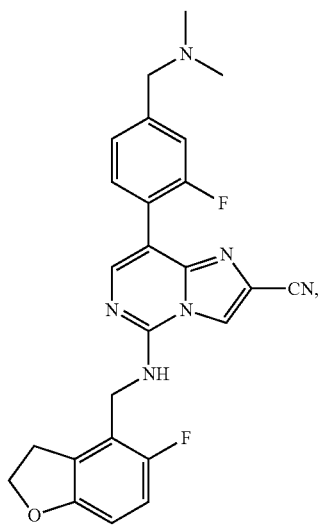
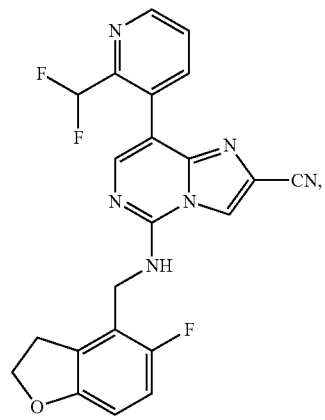

33
-continued
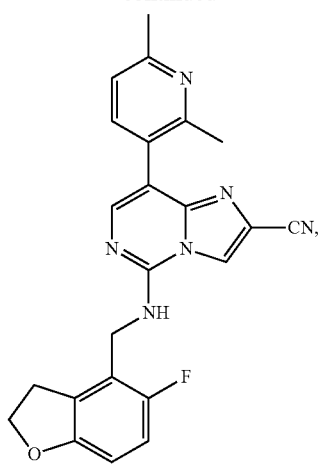
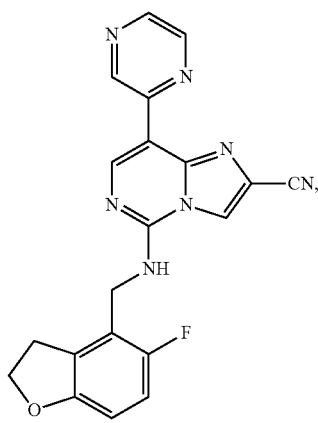
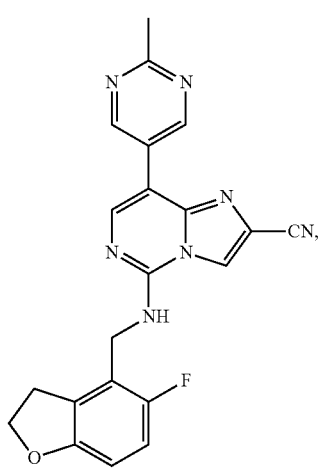
34
-continued
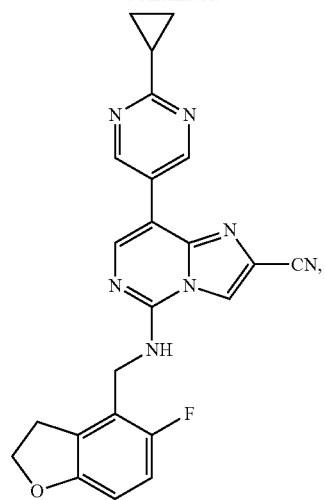
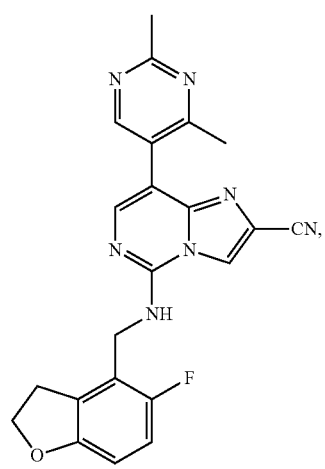
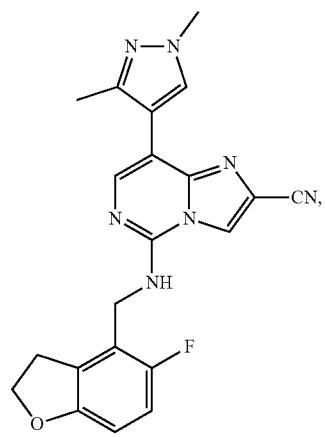

35
-continued
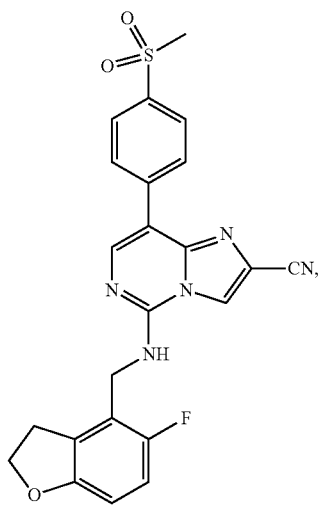
36
-continued
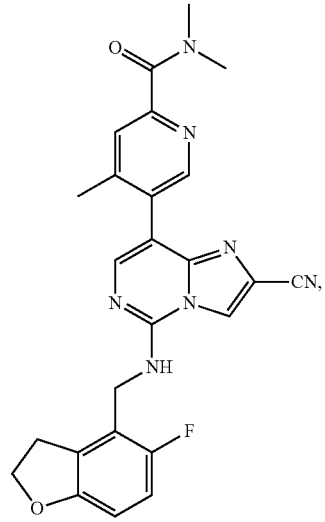
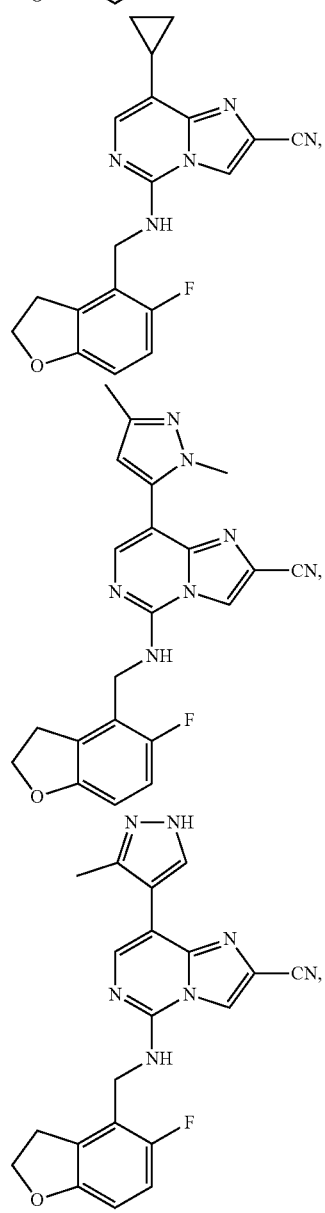

37
-continued
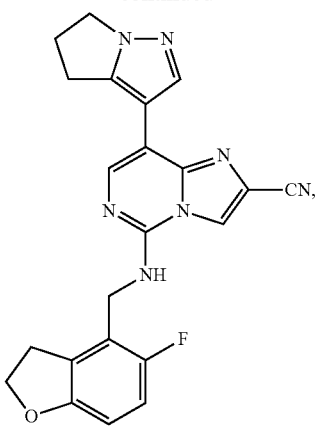
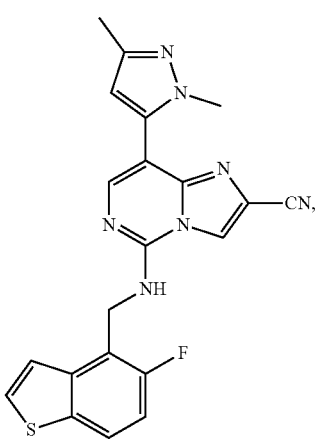
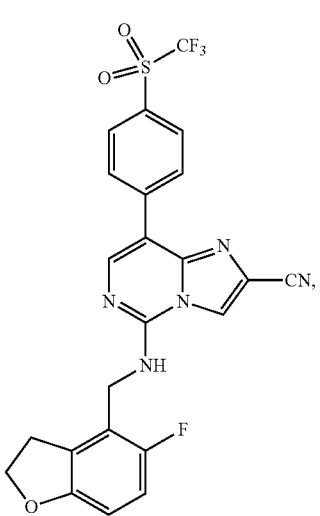
38
-continued
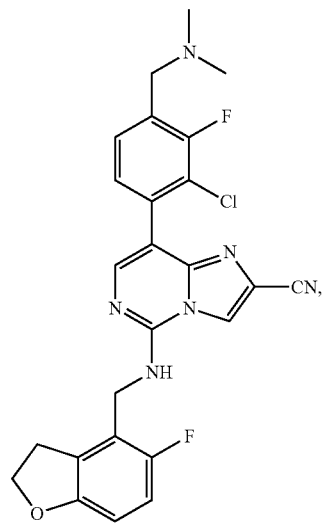
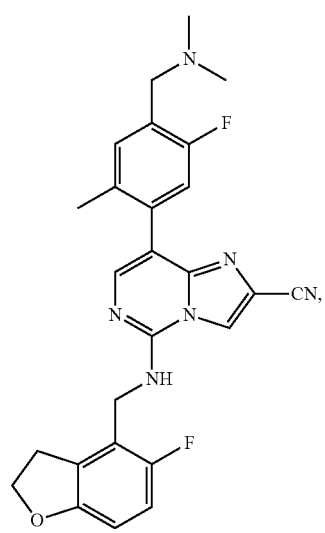
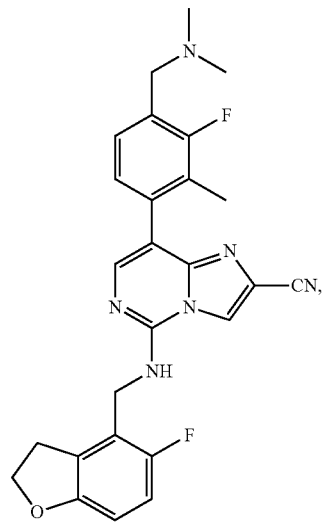

39
-continued
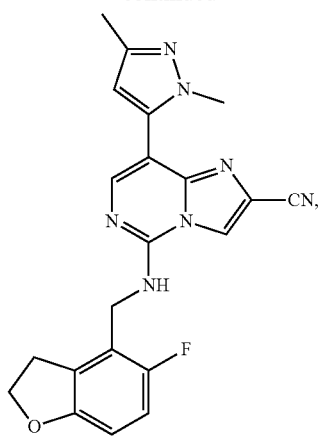
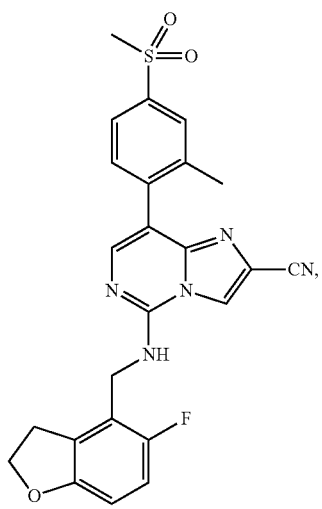
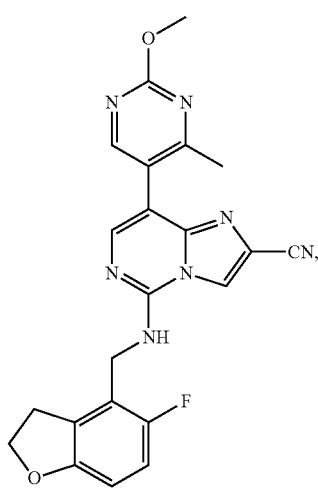
40
-continued
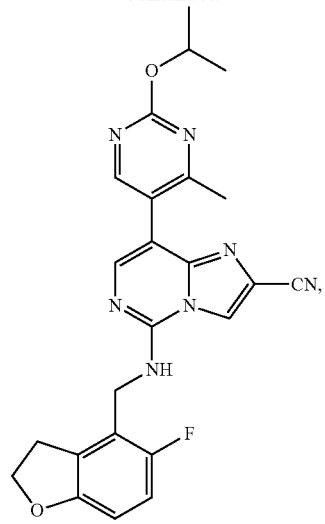
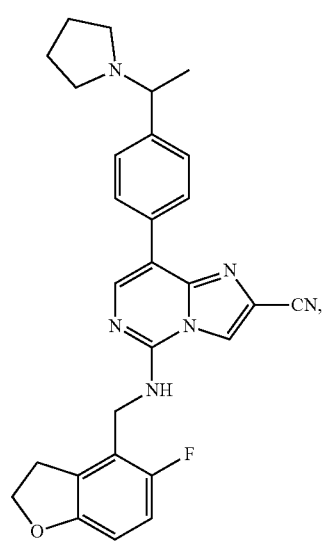
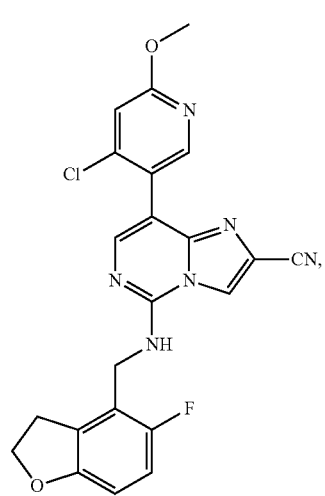

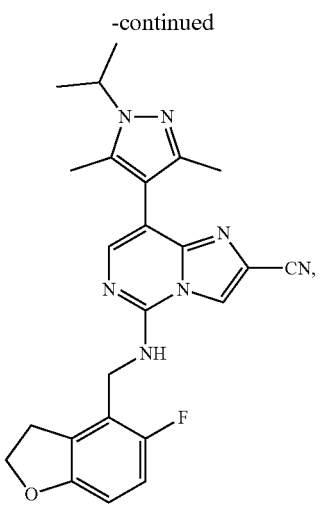
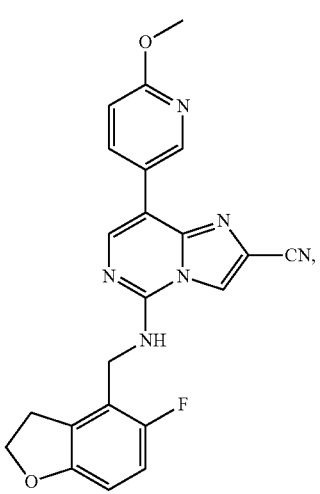
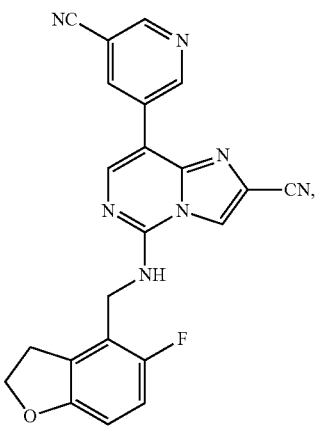
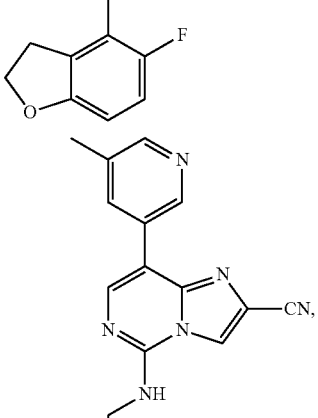
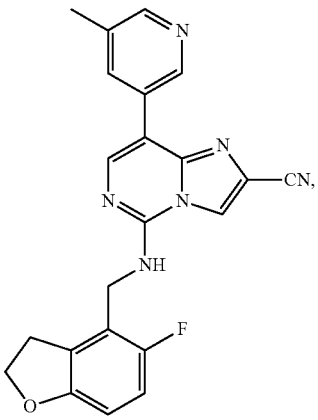
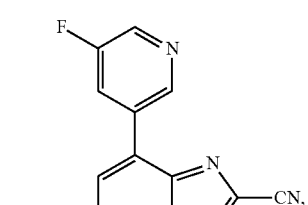
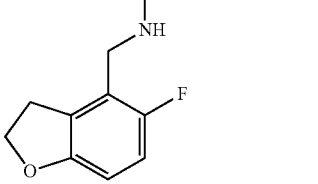
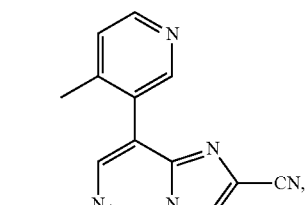
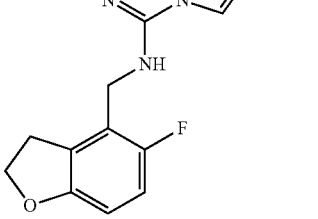

43
-continued
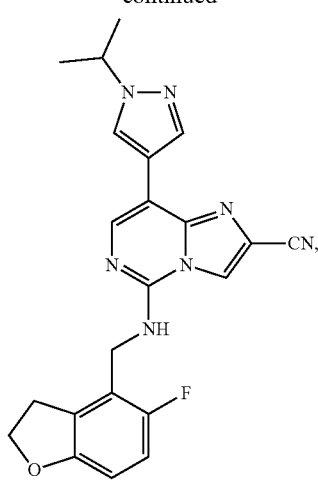
44
-continued
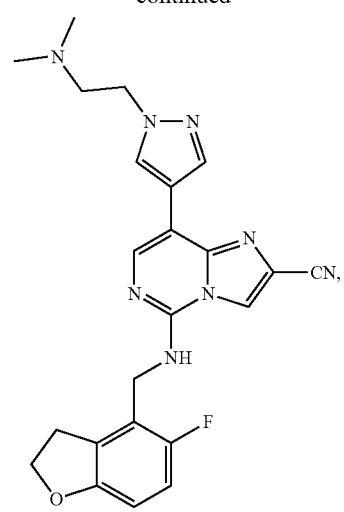
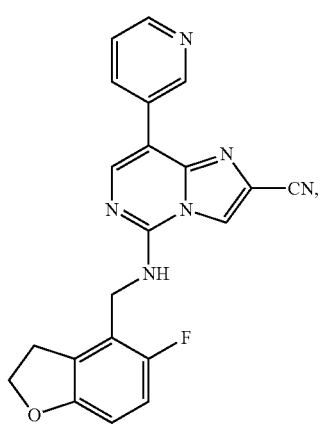
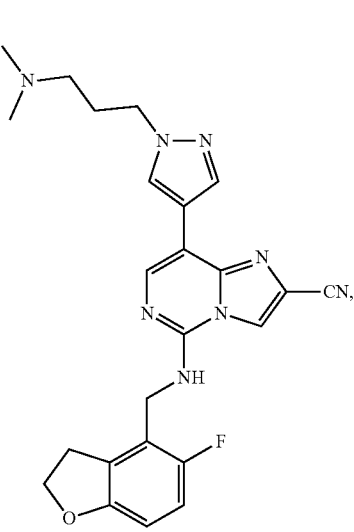
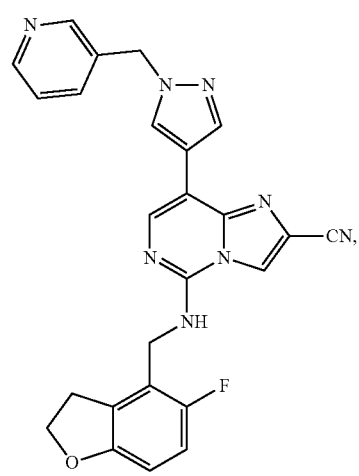
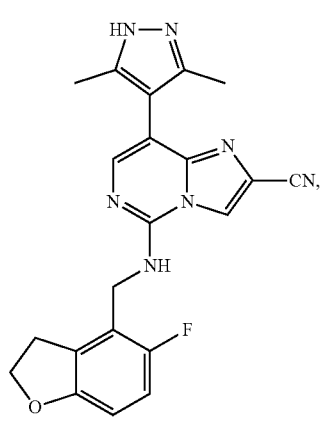

-continued
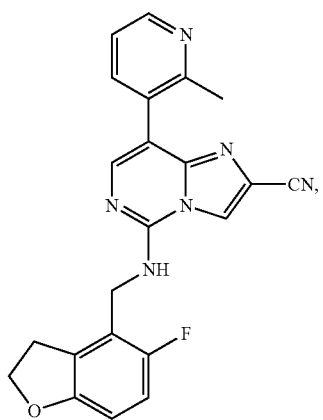
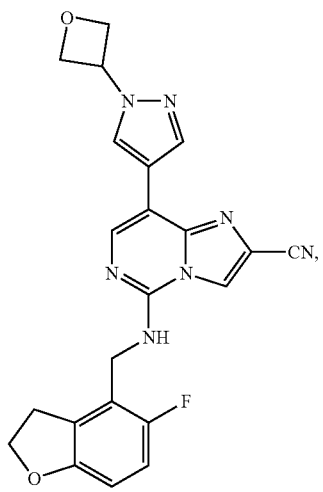
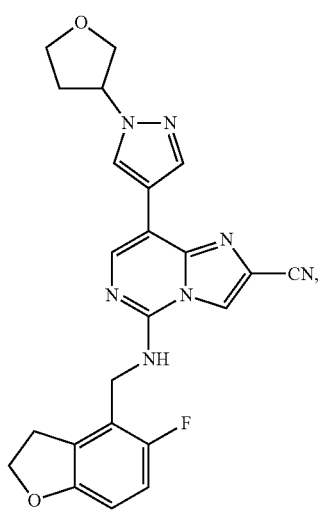
-continued
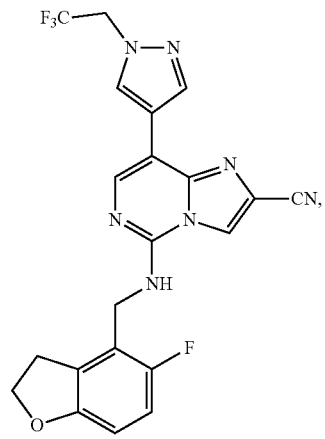
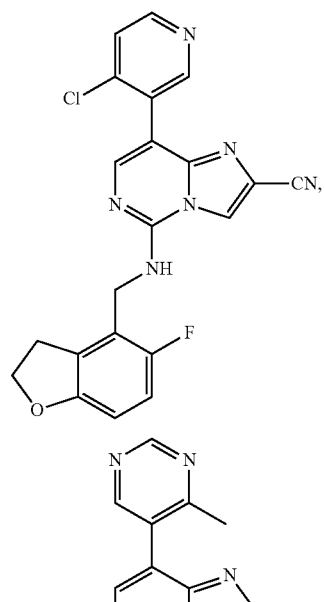
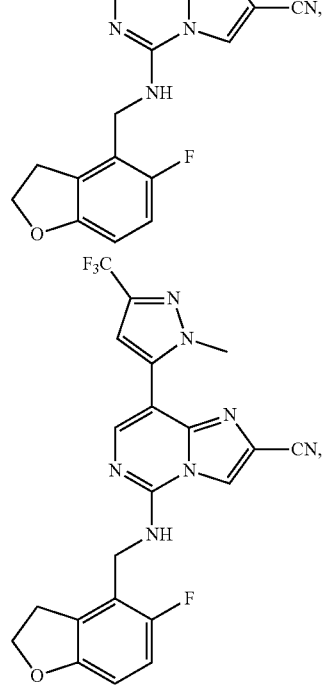

47
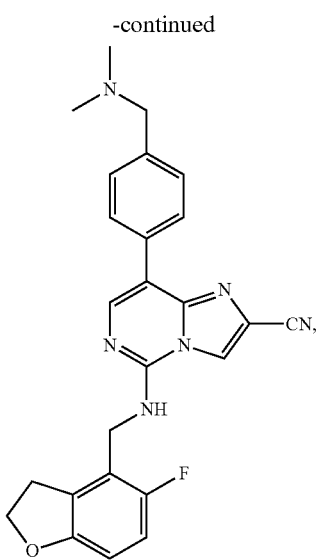
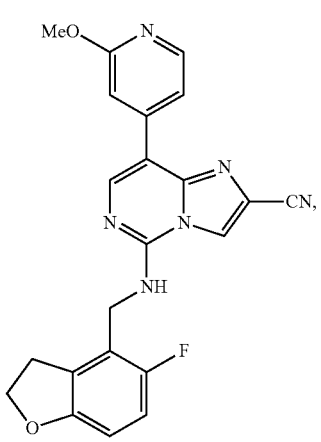
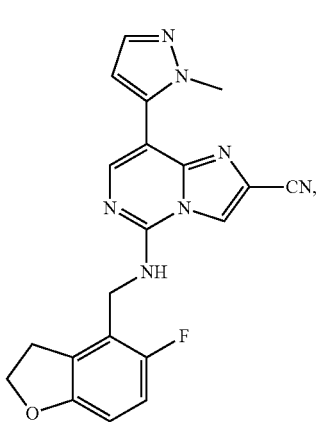
48
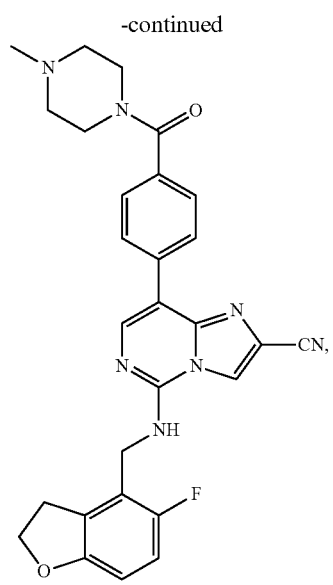
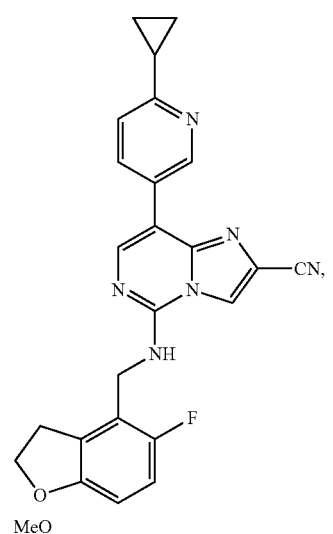

-continued
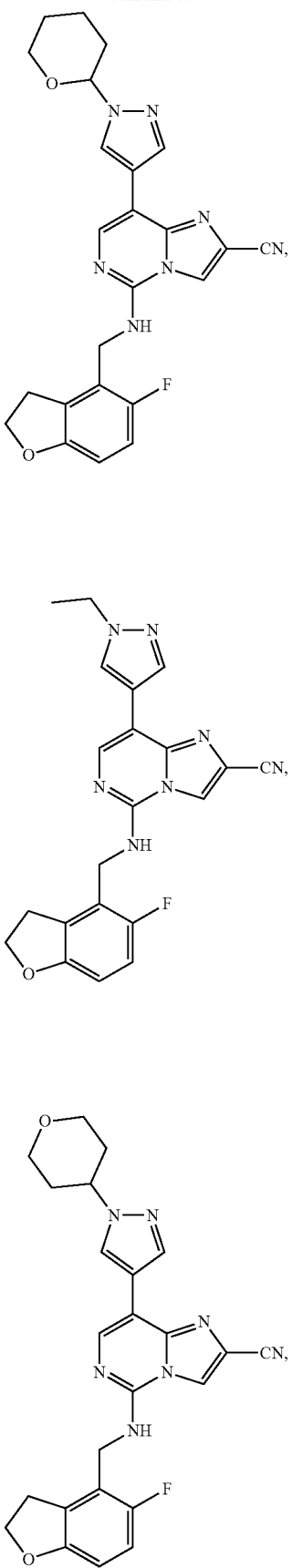
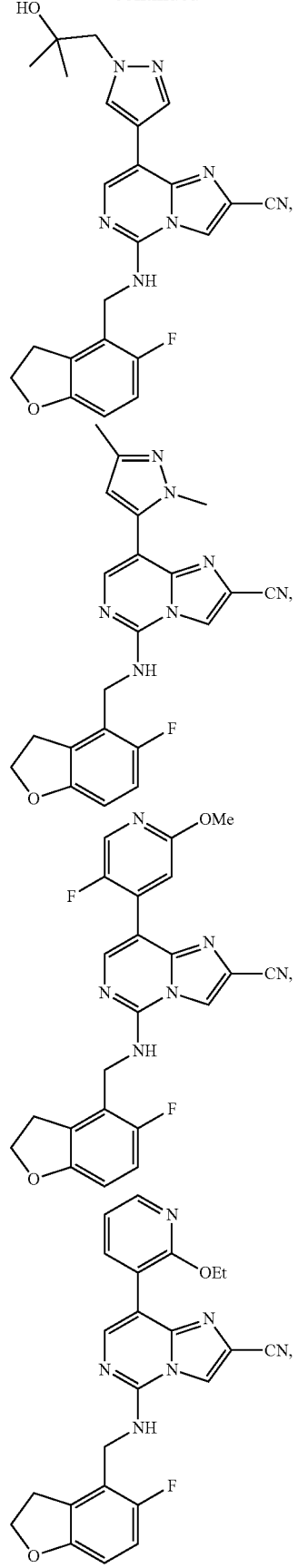

51
-continued
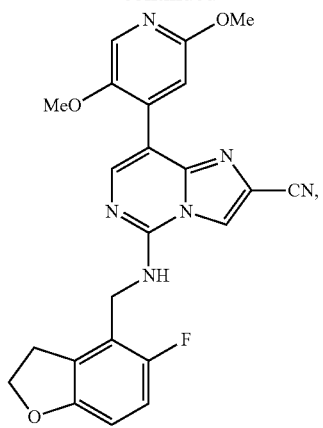
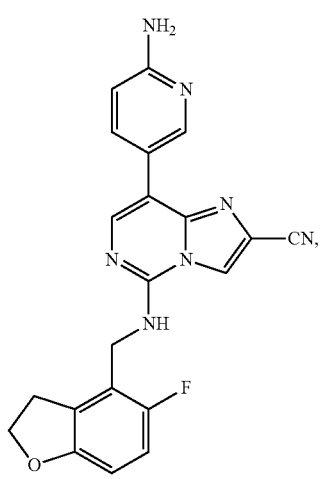
52
-continued
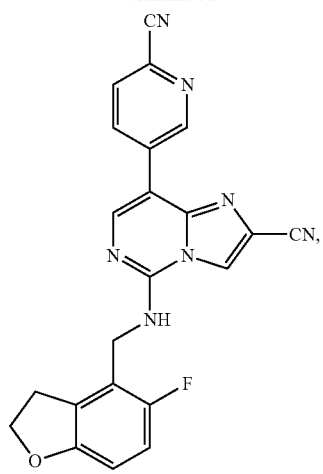
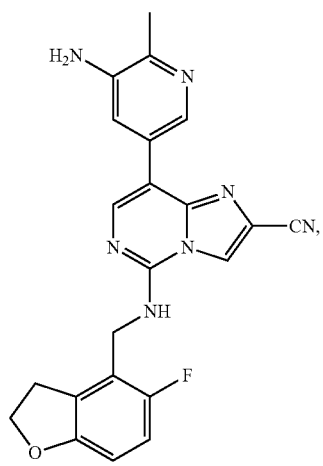

53
-continued
54
-continued
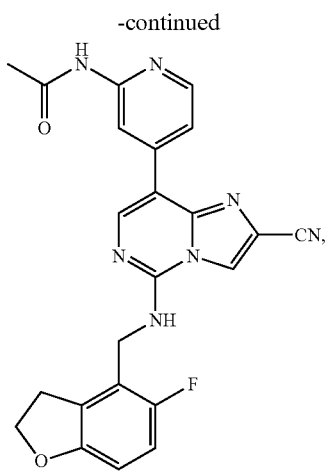
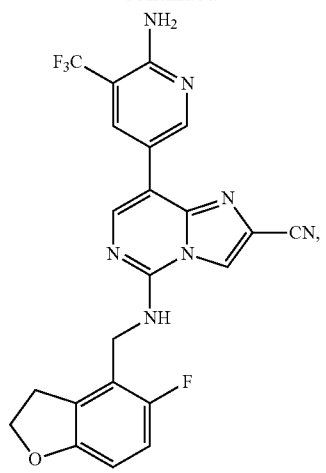

55
-continued
56
-continued
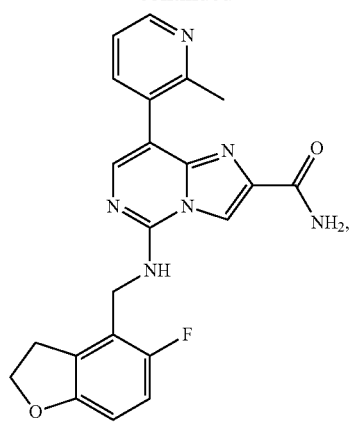
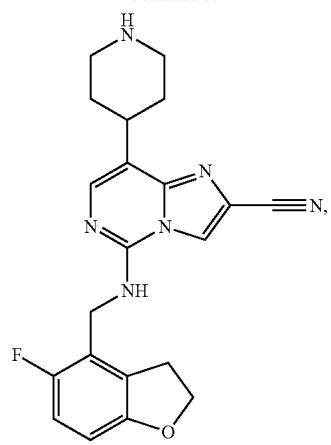

57
-continued
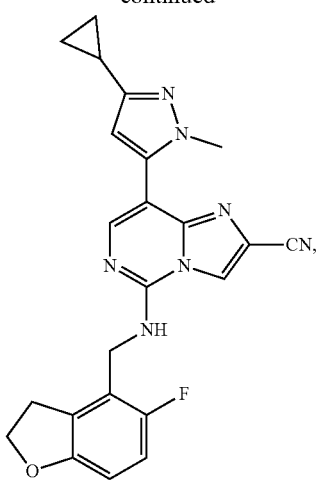
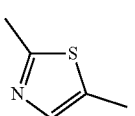
58
-continued
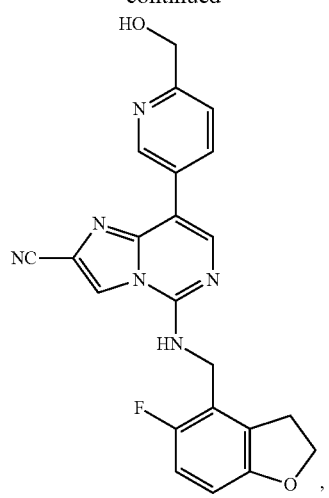
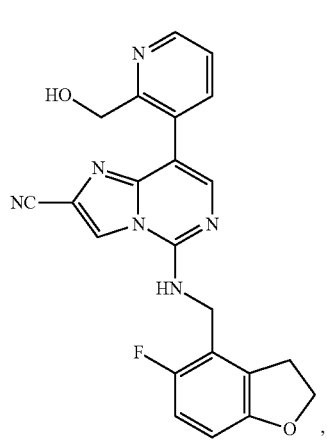
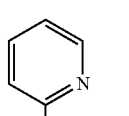
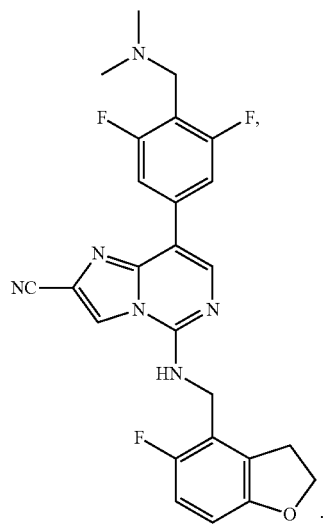 [SMILES: Cc1c(-c2cnc(NCc3c(F)ccc4c3CCO4)n3cc(C#N)nc23)cnc(CN(C)C)c1F]

59
-continued
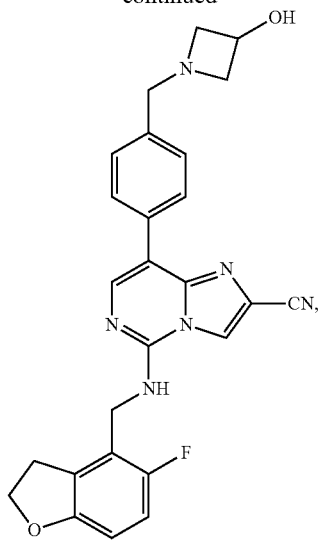
60
-continued
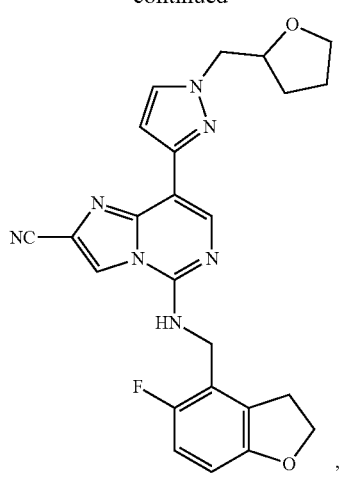
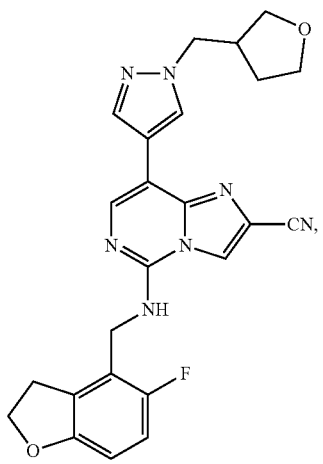
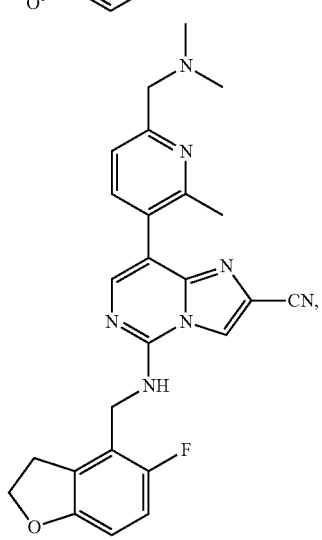
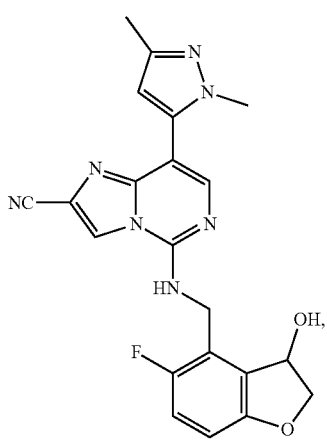

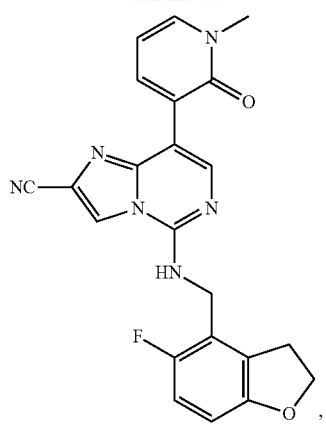
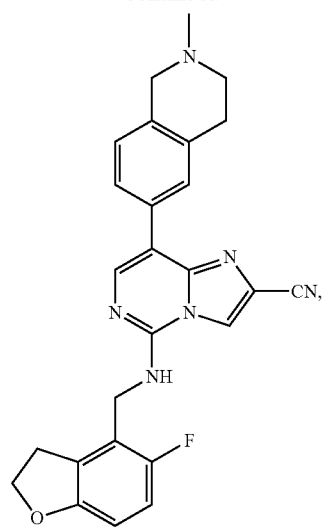
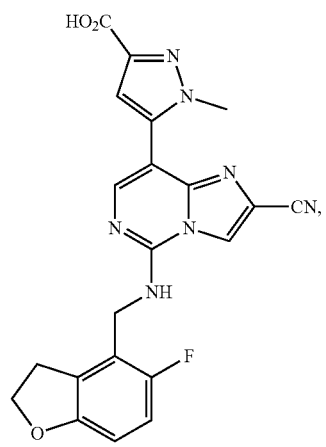
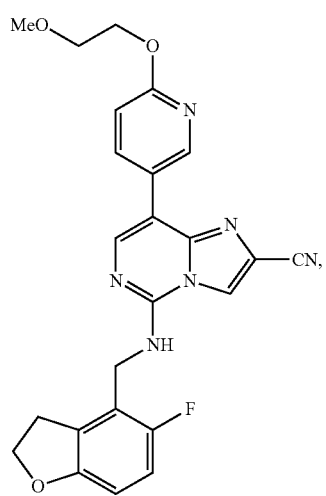

63
-continued
64
-continued
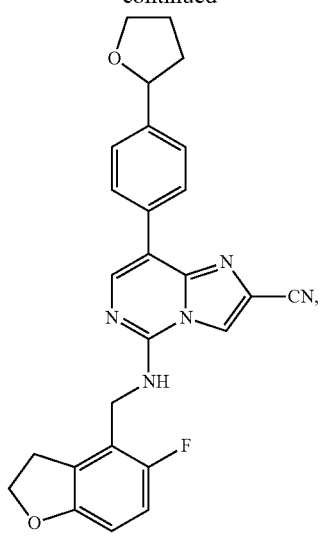
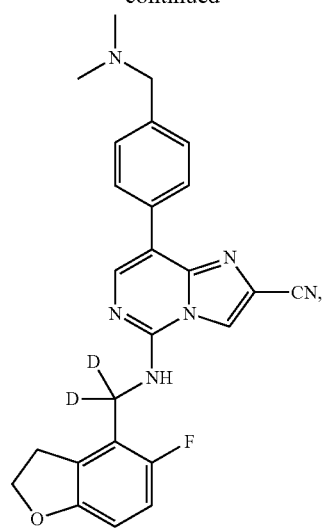
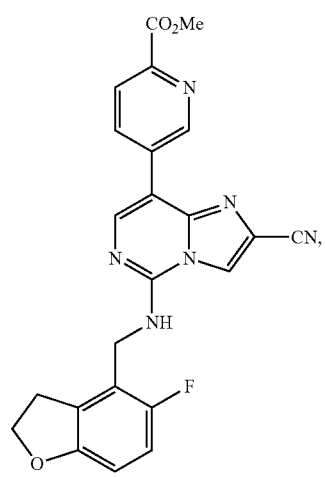
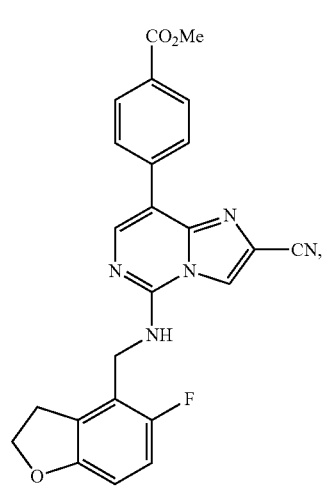

-continued
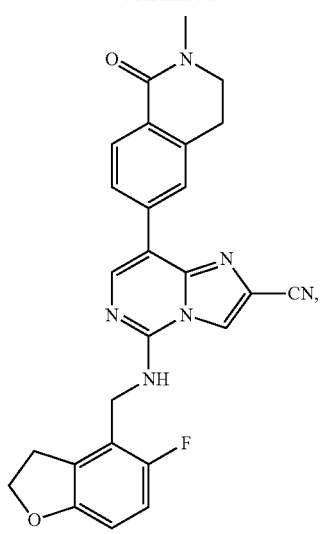
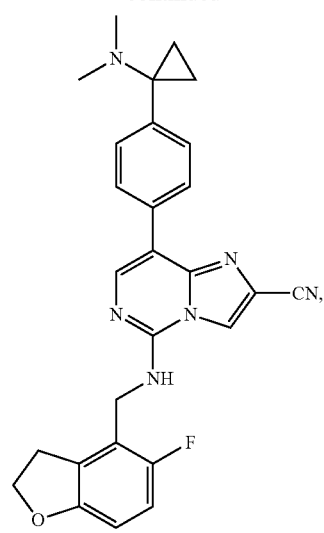
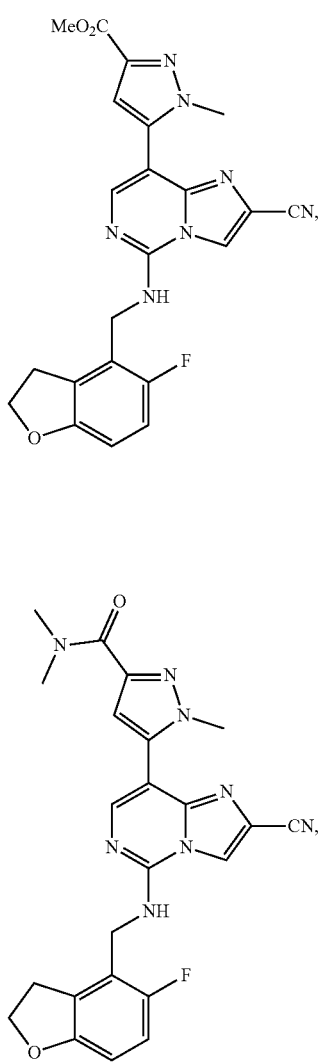
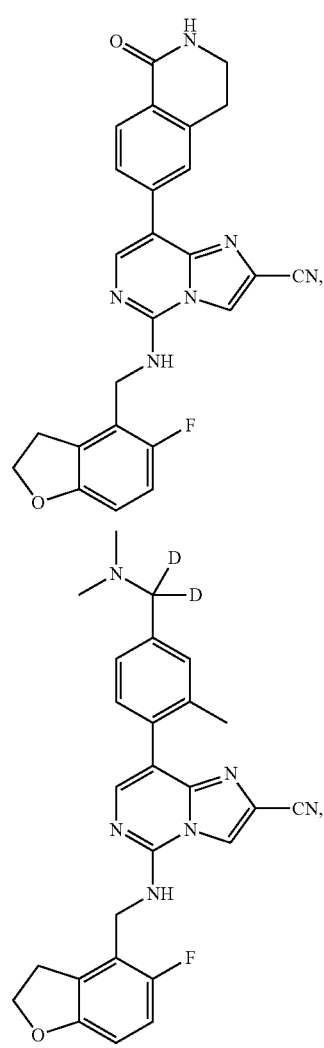

67
-continued
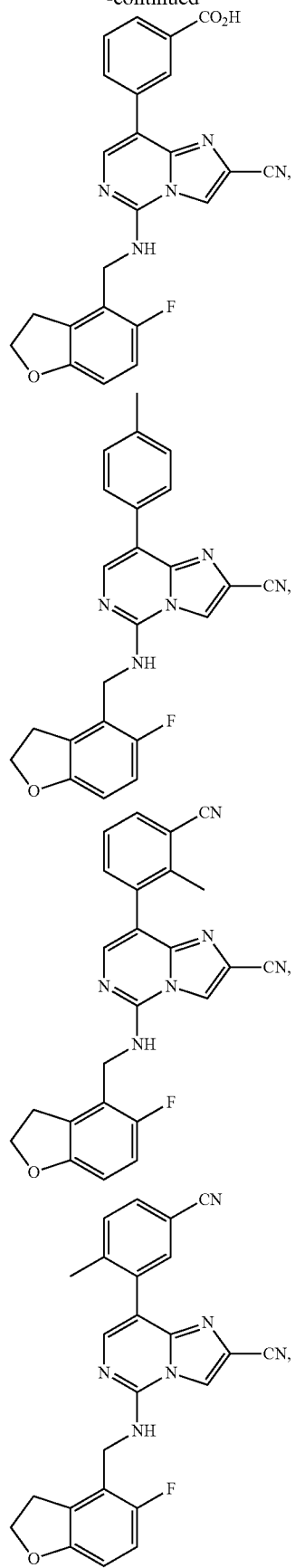
68
-continued
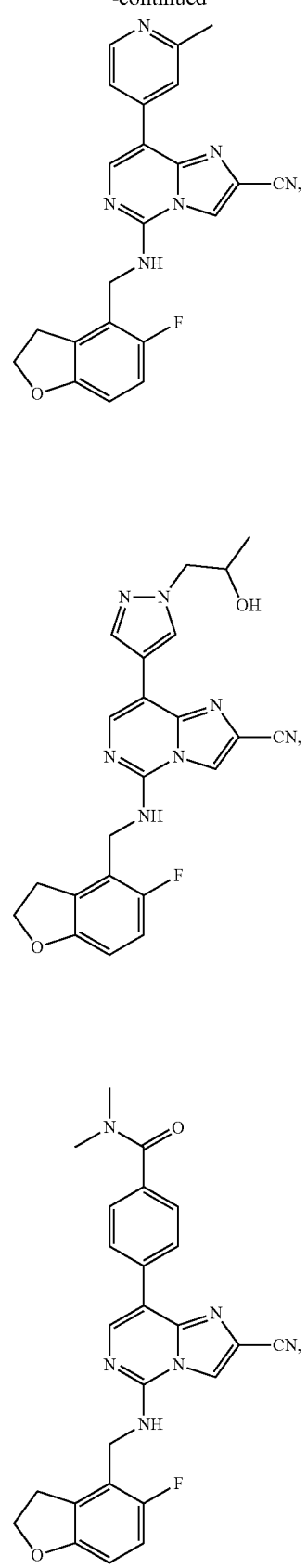

69
-continued
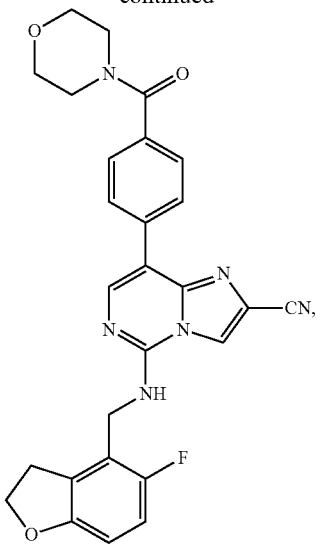
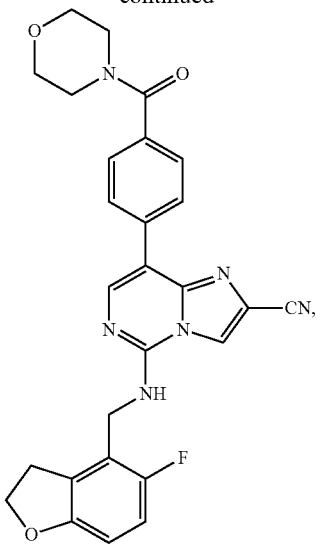
70
-continued
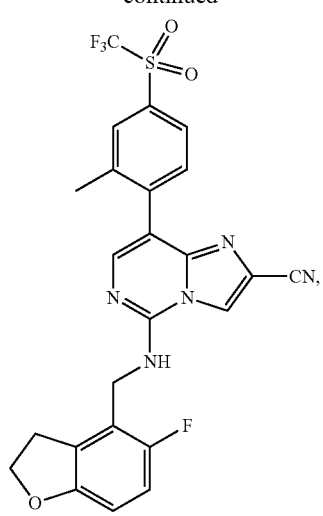
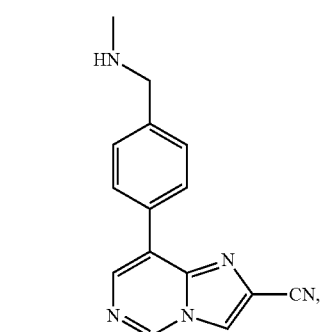
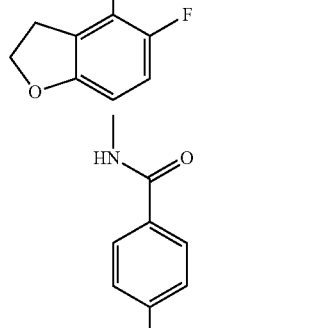
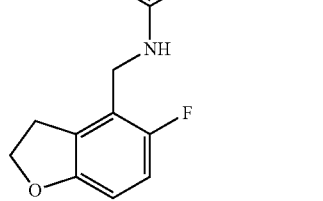

71
-continued
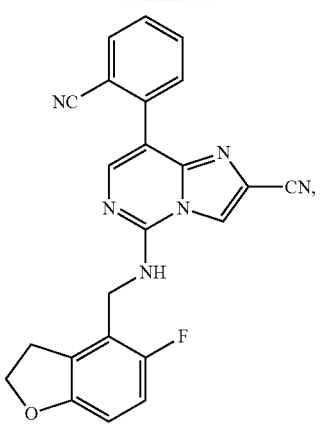
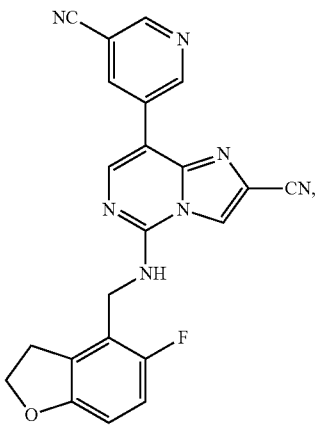
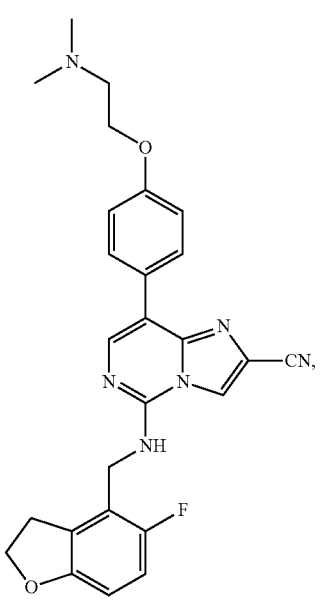
72
-continued
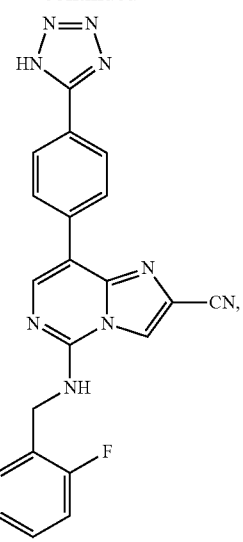
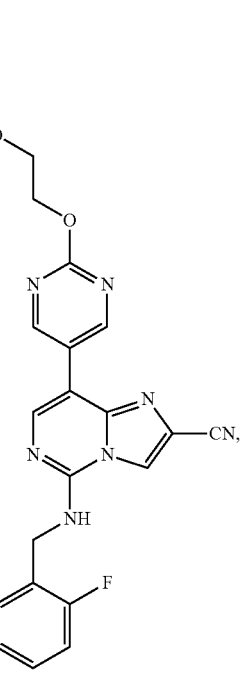
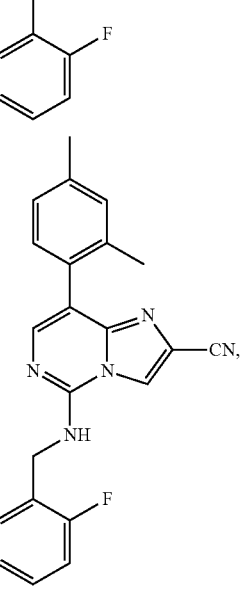

73
-continued
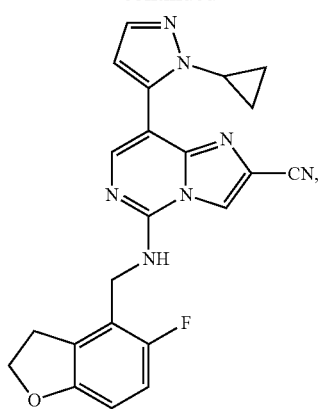
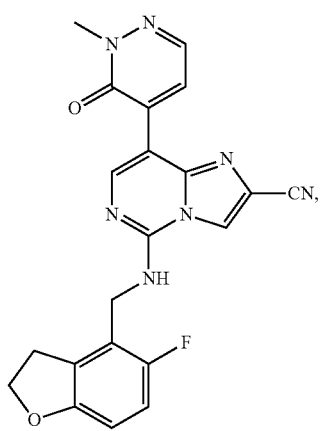
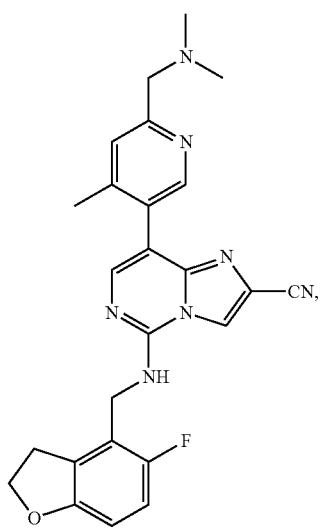
74
-continued
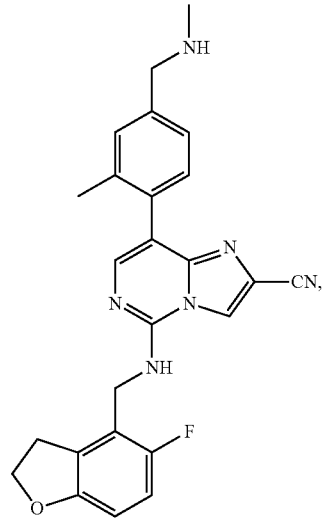
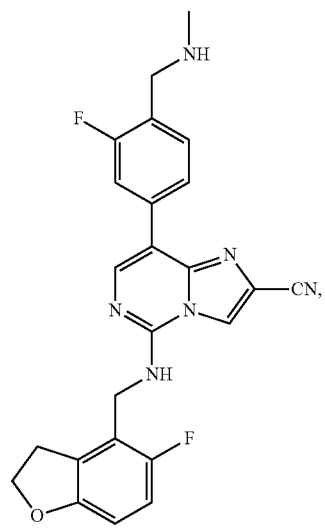
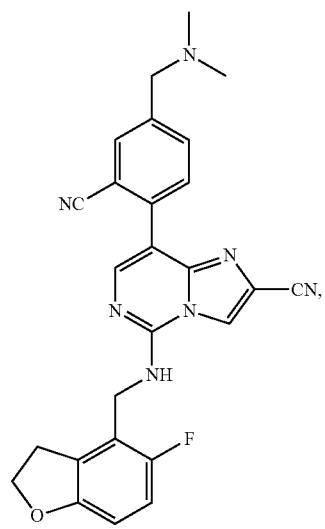

75
-continued
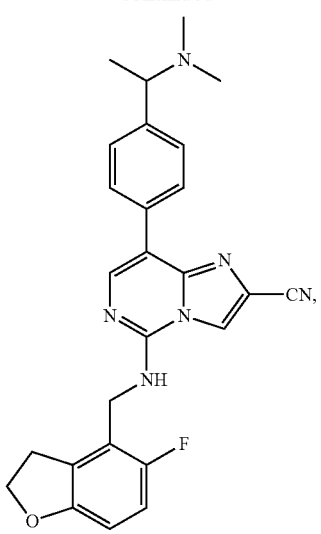
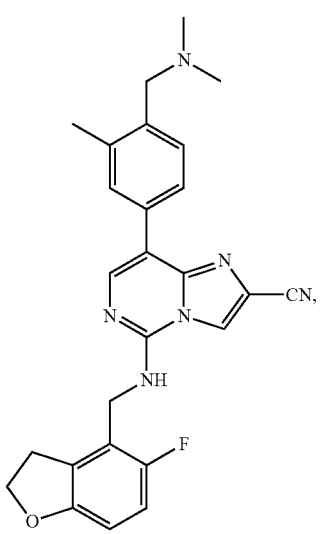
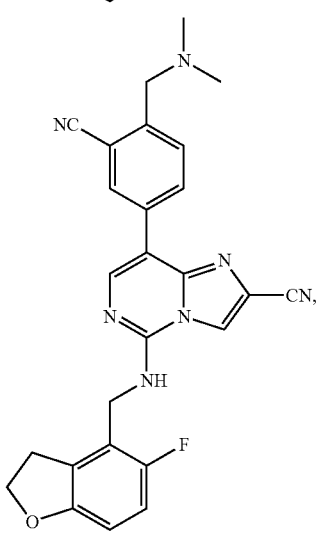
76
-continued
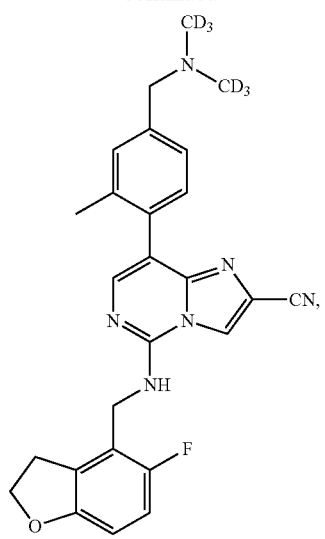
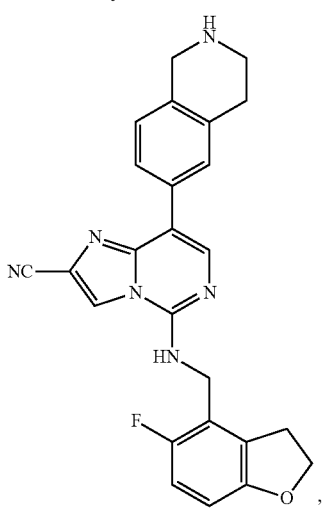
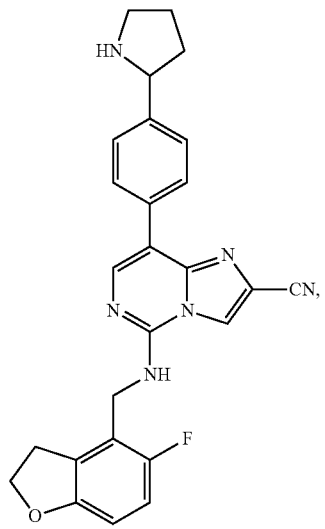

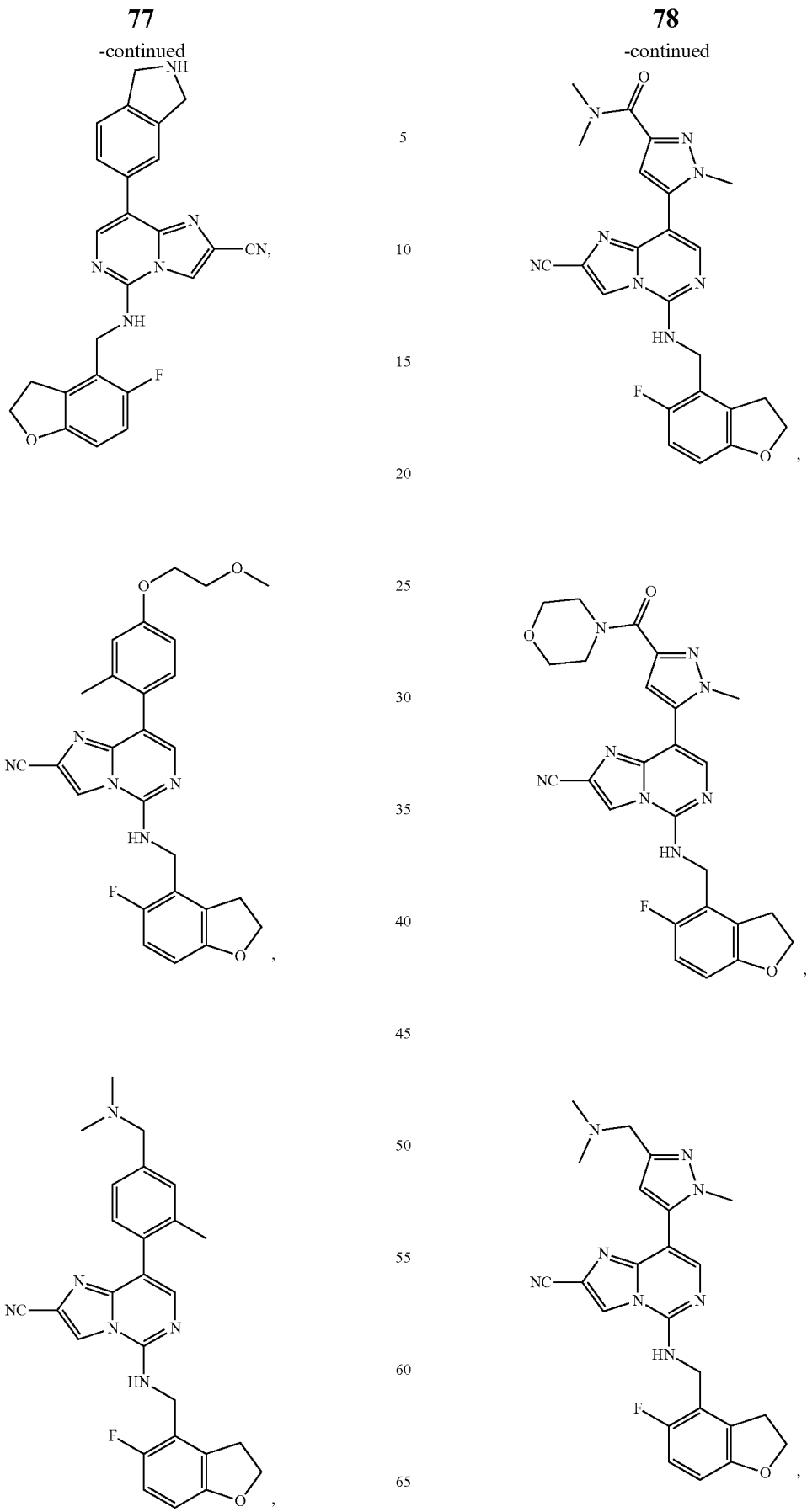

79
-continued
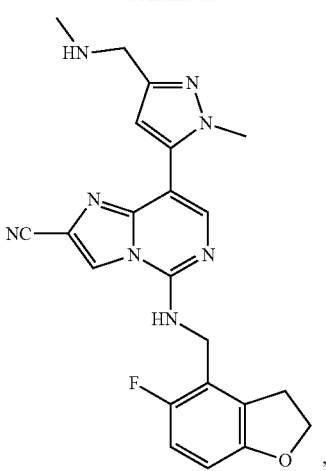
,
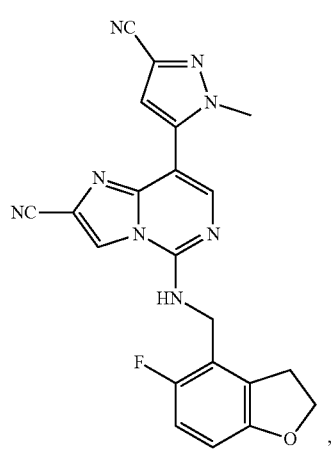
,
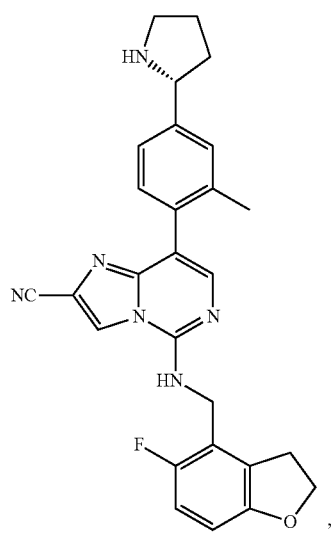
,
80
-continued
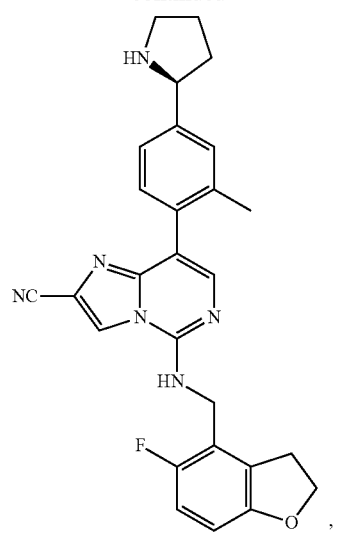
,
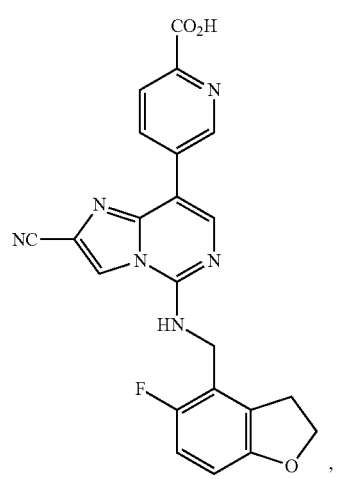
,
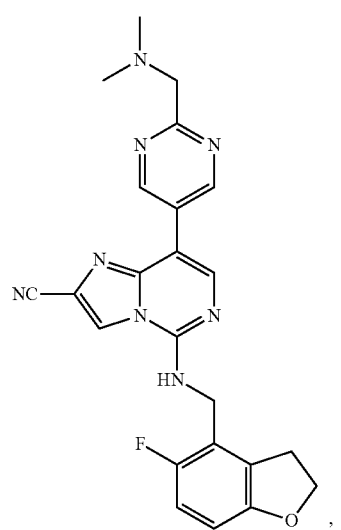
,

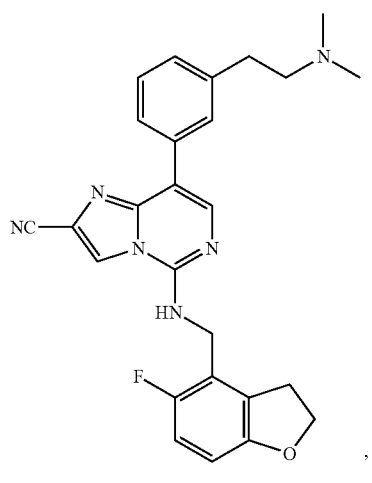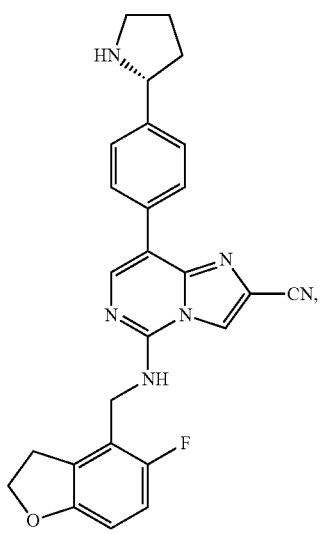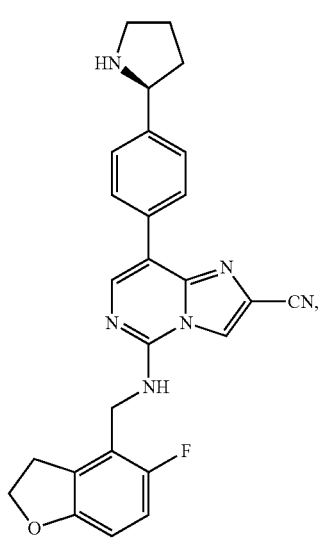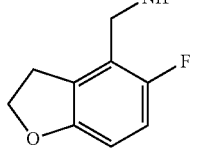

83
-continued
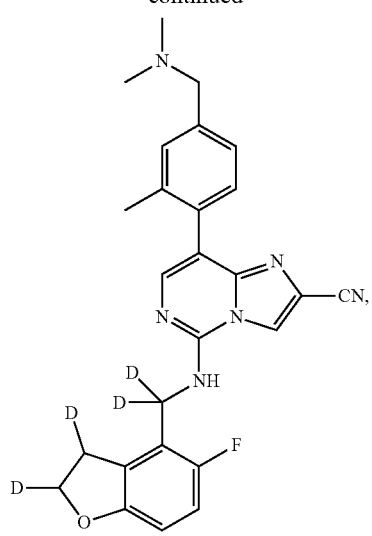
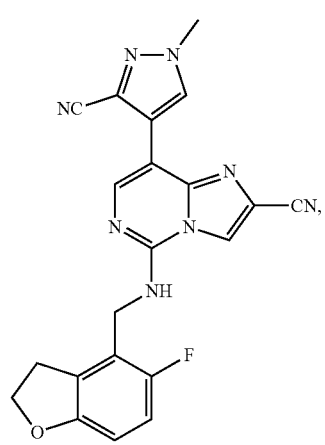
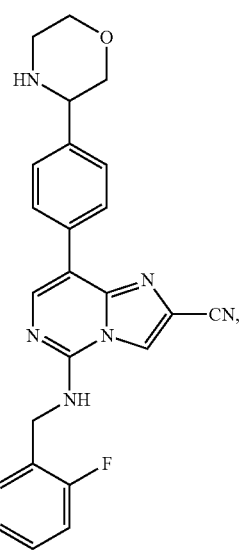
84
-continued
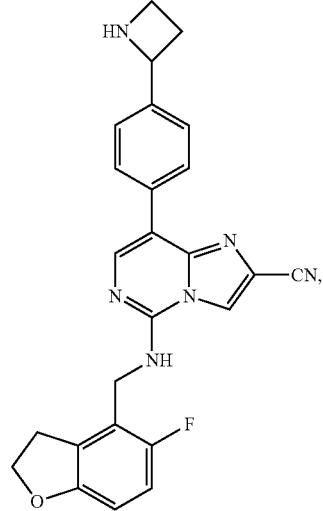
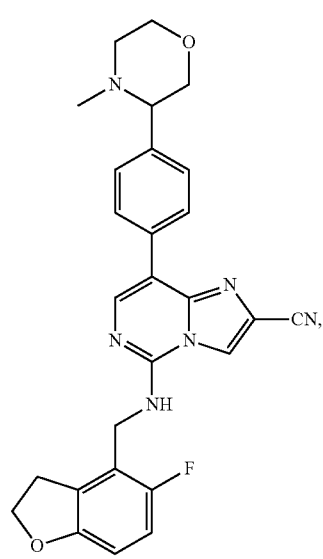
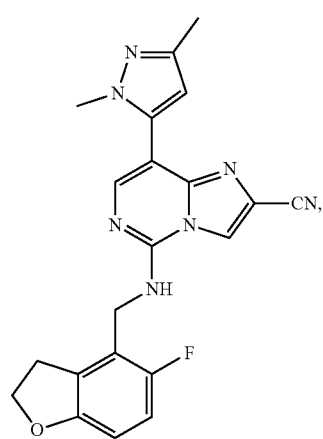

-continued

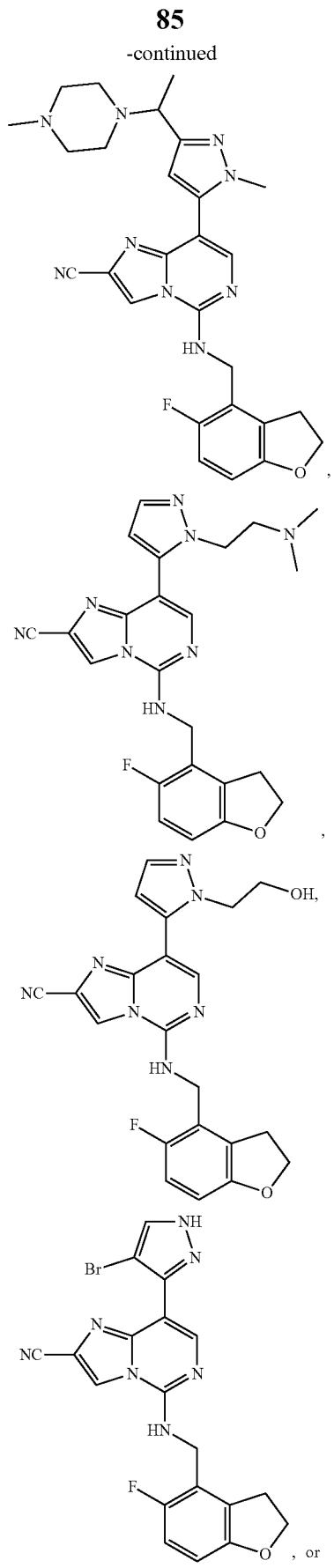
,

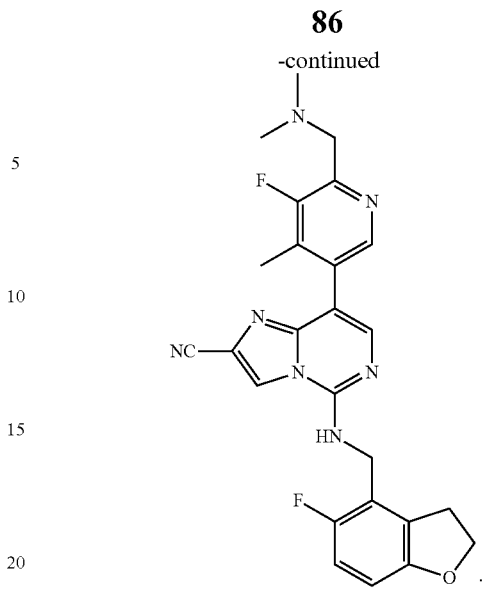
.

Pharmaceutical Compositions

In another aspect, the invention provides pharmaceutical compositions comprising a PRC2 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the preset invention may be used in the methods described herein.

Methods of Use

In yet another aspect, the invention provides for methods for inhibiting PRC2 activity in a cell, comprising contacting the cell in which inhibition of PRC2 activity is desired with a therapeutically effective amount of a compound of formula (I), pharmaceutically acceptable salts thereof or pharmaceutical compositions containing the compound or pharmaceutically acceptable salt thereof.

The compositions and methods provided herein are particularly deemed useful for inhibiting PRC2 activity in a cell. In one embodiment, a cell in which inhibition of PRC2 activity is desired is contacted with a therapeutically effective amount of a compound of formula (I) to negatively modulate the activity of PRC2. In other embodiments, a therapeutically effective amount of pharmaceutically acceptable salt or pharmaceutical compositions containing the compound of formula (I) may be used.

By negatively modulating the activity of PRC2, particularly in cases for cells overexpressing the EZH2 enzyme or somatic mutations that activate the EZH2 enzyme, the methods are designed to restore normal cellular transcription expression patterns, e.g., by altering methylation pattern of H3K27, to inhibition undesired cellular proliferation resulting from enhanced PRC2 activity within the cell. The cells may be contacted in a single dose or multiple doses in accordance with a particular treatment regimen to affect the desired negative modulation of PRC2. The degree of mono- and dimethylation of histone H3K27 may be monitored in the cell using well known methods, including those described in Example A below, to assess the effectiveness of treatment and dosages may be adjusted accordingly by the attending medical practitioner.

In another aspect, methods of treating cancer comprising administering to a patient having cancer a therapeutically effective amount of a compound of formula (I), pharmaceutically acceptable salts thereof or pharmaceutical compositions comprising the compound or pharmaceutically acceptable salts thereof are provided.

The compositions and methods provided herein may be used for the treatment of a wide variety of cancer including tumors such as prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromvxofibroma, osteoid osteoma and giant cell tumors; Nervous systent skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors. Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma. Kaposi's sarcoma, moles dysplastic nevi, lipoma, angioma, dermatofibroma, keloids, psoriasis; and Adrenal glands: neuroblastoma. In certain embodiments, the cancer is diffuse large B-cell lymphoma (DLBCL).

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively. The degree of mono- and dimethylation of histone H3K27 may be monitored in the patient using well known methods, including those described in Example A below, to access the effectiveness of treatment, along with other prognostic or biological factors, and dosages may be adjusted accordingly by the attending medical practitioner.

GENERAL REACTION SCHEME, INTERMEDIATES AND EXAMPLES

General Reaction Schemes

The compounds of the present invention may be prepared using commercially available reagents and intermediates in the synthetic methods and reaction schemes described herein, or may be prepared using other reagents and conventional methods well known to those skilled in the art.

For instance, intermediates for compounds and compounds of formula (I) of the present invention may be prepared according to General Reaction Schemes I or II:

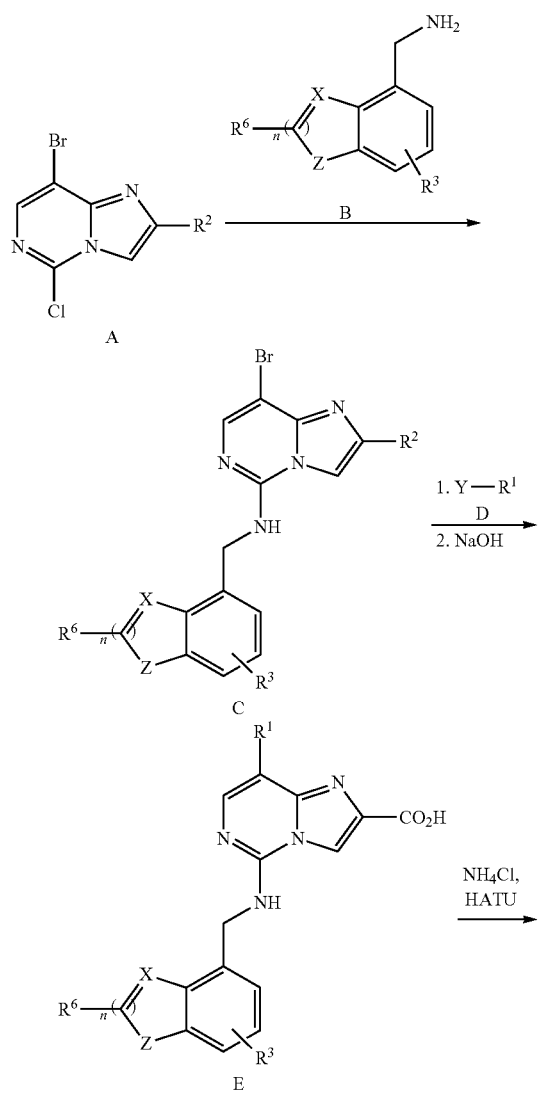

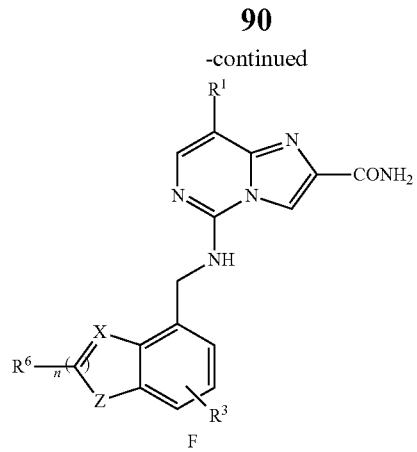

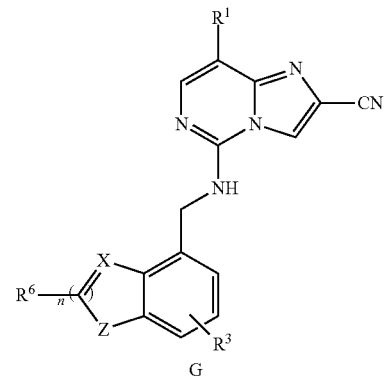

In General Reaction Scheme 1, $R^2$-ester substituted imidazol[1,2-c]pyrimidine A is coupled to $R^3$ optionally substituted intermediate amine B by nucleophilic substitution to yield Intermediate C. A boronic acid derivative (Y)—$R^1$ D is coupled via a Suzuki reaction with halogen substituted Intermediate C in the presence of a suitable base, e.g., sodium carbonate, and the $R^2$ ester is converted to the acid by saponification with NaOH to generate intermediate acid E. The acid is converted to the corresponding amide, which is dehydrated to form title compound nitrile G.

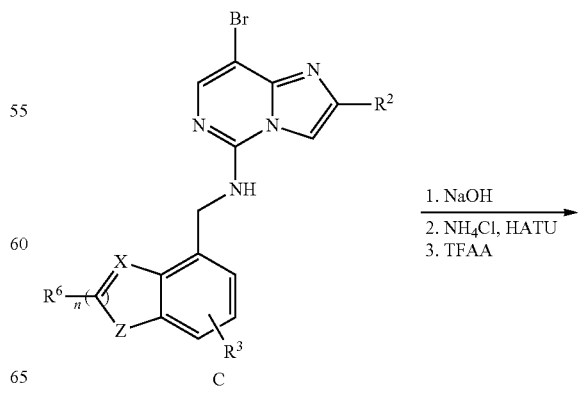

Intermediate A-1

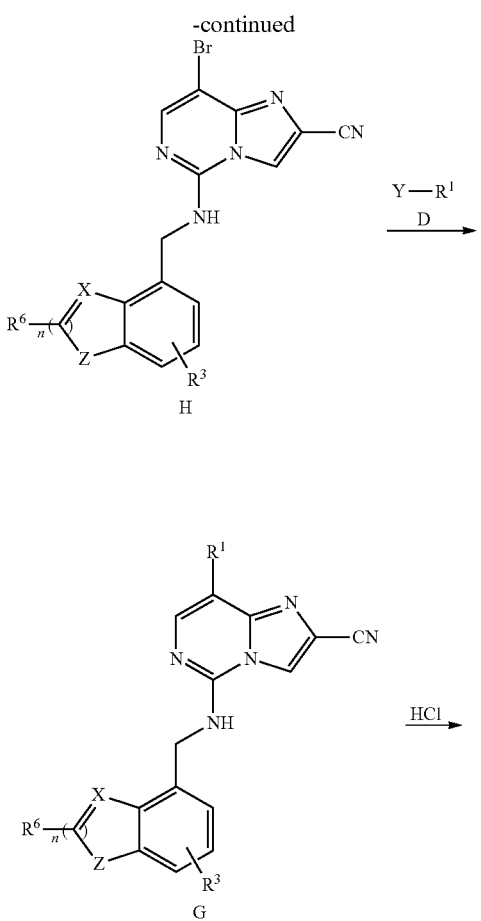

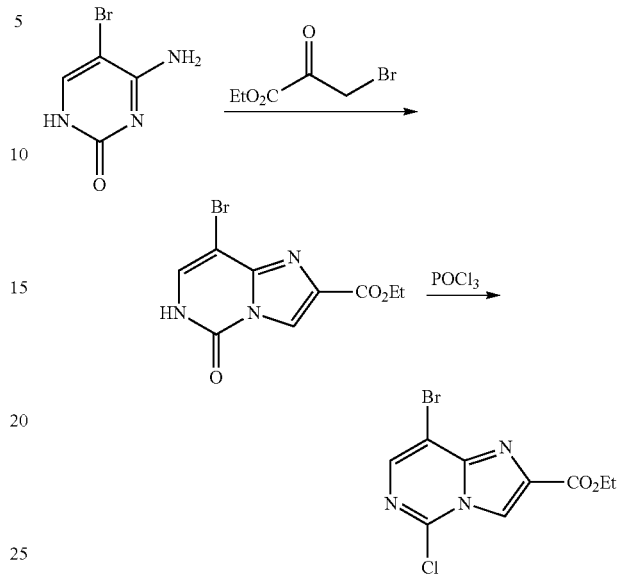

An exemplary Intermediate A, Intermediate A-1, may be used to synthesize compounds of formula (I). A mixture of 6-amino-5-bromo-1H-pyrimidin-2-one (2.00 g, 10.5 mmol, 1.00 equiv) and ethyl 3-bromo-2-oxo-propanoate (3.12 g, 16.0 mmol, 2.00 mL, 1.52 equiv) in DMF (20.0 mL) was stirred at 80° C. for 3 h. The mixture was concentrated in vacuo to give a residue. To the residue was added water (50.0 mL), the mixture was extracted with ethyl acetate (80.0 mL×3) and the organic layer was concentrated in vacuo. The crude material was heated in methanol (5.00 mL) and the solid was removed by filtration. The filtrate was concentrated under reduced pressure to provide ethyl 8-bromo-5-oxo-6H-imidazo[1,2-c]pyrimidine-2-carboxylate (1.00 g, 3.50 mmol, 33.2% yield) as a yellow solid.

$^1$H NMR (400 MHz, DMSO-$d_6$) δ=12.09 (br s, 1H), 8.32 (s, 1H), 7.73 (s, 1H), 4.30 (q, J=7.2 Hz, 2H), 1.31 (t, J=7.2 Hz, 3H).

A mixture of ethyl 8-bromo-5-oxo-6H-imidazol[1,2-c]pyrimidine-2-carboxylate (500 mg, 1.75 mmol, 1 equiv) and DIEA (564 mg, 4.37 mmol, 760 uL, 2.50 equiv) in POCl$_3$ (8.00 mL) was stirred for 15 h at 120° C. The mixture was concentrated in vacuo to afford the crude residue. The crude material was purified by column chromatography (petroleum ether/ethyl acetate, 10/1 to 1/1) to provide ethyl 8-bromo-5-chloro-imidazo[1,2-c]pyrimidine-2-carboxylate (380 mg, 1.25 mmol, 71.4% yield) as a yellow solid.

$^1$H NMR (400 MHz, CD$_3$OD) δ=8.61 (s, 1H), 8.20 (s, 1H), 4.46 (q, J=7.2 Hz, 2H), 1.43 (t, J=7.2 Hz, 3H).

Intermediate A-2

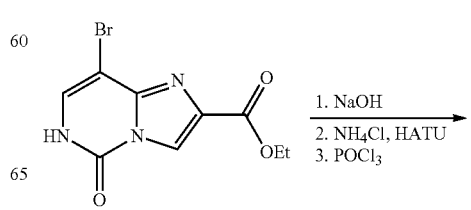

Halogenated Intermediate C containing a suitable R$^2$ reactant, e.g., an ester, in the presence of a suitable base is converted to acid intermediate by saponification, then treated with NH$_4$Cl in the presence of HATU to form the amide which is subsequently dehydrated to form nitrile Intermediate H. R$^1$ is coupled to Intermediate H via a Suzuki reaction using boronic acid derivative (Y) in the presence of base. The nitrile group of R$^1$-containing Intermediate G is hydrolyzed in the presence of acid and water to afford title compound amide F.

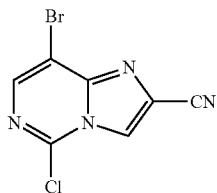

A second exemplary Intermediate A, Intermediate A-2, also may be used to synthesize compounds of formula (I). To a solution of ethyl 8-bromo-5-oxo-6H-imidazo[1,2-c]pyrimidine-2-carboxylate (3.00 g, 10.2 mmol, 1.00 equiv) in MeOH (60.0 mL) was added NaOH (1 M, 30.5 mL, 3.00 equiv). The resultant mixture was stirred at 60° C. for 1 h. Subsequently, the reaction mixture was concentrated and the pH was adjusted to 4 with 1M aq HCl at which time a precipitate formed. The solid was filtered and dried under vacuum to provide 8-bromo-5-oxo-6H-imidazo[1,2-c]pyrimidine-2-carboxylic acid (2.60 g, 10.1 mmol, 99.1% yield) as a brown solid.

To a solution of 8-bromo-5-oxo-6H-imidazo[1,2-c]pyrimidine-2-carboxylic acid (2.60 g, 10.1 mmol, 1.00 equiv) in DMF (60.0 mL) was added NH$_4$Cl (1.62 g, 30.2 mmol, 3.00 equiv), DIPEA (11.7 g, 90.7 mmol, 15.8 mL, 9.00 equiv) and HATU (5.75 g, 15.1 mmol, 1.50 equiv). The mixture was stirred at 15° C. for 12 h and was subsequently concentrated in vacuo. The resultant residue was triturated with MeOH (30 mL). The precipitate was washed with water 50 mL, filtered and the filtrate was concentrated in vacuo to afford 8-bromo-5-oxo-6H-imidazo[1,2-c]pyrimidine-2-carboxamide (1.78 g, 6.92 mmol, 68.7% yield) as a light-yellow solid. LC-MS [M+1]: 257.0.

To a solution of 8-brom-5-oxo-6H-imidazo[1,2-c]pyrimidine-2-carboxamide (1.70 g, 6.61 mmol, 1.00 equiv) in POCl$_3$ (20.0 mL) was added DIPEA (4.27 g, 33.1 mmol, 5.76 mL, 5.00 equiv) dropwise at 0° C. The mixture was stirred at 120° C. for 12 h. The reaction mixture was filtered and concentrated at reduced pressure to provide the crude material. The crude residue was purified by column chromatography (SiO$_2$, Petroleum ether/Ethyl acetate=10/1 to 4/1) to afford 8-bromo-5-chloro-imidazo[1,2-c]pyrimidine-2-carbonitrile (950 mg, 3.69 mmol, 55.8% yield) as a light-yellow solid. LC-MS [M+1]: 258.9.

Alternatively, Intermediate A-2 may be prepared on a large scale as follows:

To a solution of cytosine (300 g, 2.70 mol, 1.00 equiv) in DMF (1.5 L) was added NBS (480 g, 2.70 mol, 1.00 equiv). The mixture was stirred at 25° C. for 10 h at which time the crude $^1$H NMR spectrum indicated that the reaction was complete. The reaction mixture was filtered and the filter cake was washed with water (1 L×4). The solid was collected and dried under reduced pressure to afford 5-bromocytosine (480 g, 2.53 mol, 93.6% yield) as a white solid.

$^1$H NMR (400 MHz, DMSO-d$_6$) δ 10.80 (br s, 1H), 11.36-10.16 (m, 1H), 7.74 (s, 1H), 6.83 (br s, 2H).

A mixture of compound 5-bromocytosine (150 g, 789 mmol, 1.00 equiv) and ethyl 3-bromo-2-oxo-propanoate (385 g, 1.97 mol, 247 mL, 2.50 equiv) in AcOH (1.5 L) was stirred at 120° C. for 2 h. The crude $^1$H NMR spectrum indicated that the reaction was complete. Three batches were concentrated to provide a residue that was triturated with MTBE (3 L) and filtered. The filter cake was washed with water (1 L×4) and dried to afford ethyl 8-bromo-5-oxo-5,6-dihydroimidazo[1,2-c]pyrimidine-2-carboxylate (300 g, 1.05 mol, 44.3% yield) as a brown solid.

$^1$H NMR (400 MHz, DMSO-d$_6$) δ 12.47-11.64 (m, 1H), 8.33 (s, 1H), 8.06 (s, 2H), 7.73 (s, 1H), 4.31 (q, J=7.1 Hz, 2H), 1.32 (t, J=7.1 Hz, 3H).

To a solution of ethyl 8-bromo-5-oxo-5,6-dihydroimidazo[1,2-c]pyrimidine-2-carboxylate (150 g, 524 mmol, 1.00 equiv) in MeOH (1.5 L) was added NaOH (2 M, 786 mL, 3.00 equiv). The mixture was stirred at 65° C. for 2 h at which time the LCMS indicated that the reaction was complete. The reaction mixture was concentrated to give a residue that was acidified with HCl (2 M) to pH=2-3. The solid was filtered and the filter cake was washed with water (800 mL×4). The solid was collected and dried under vacuum to afford 8-bromo-5-oxo-5,6-dihydroimidazo[1,2-c]pyrimidine-2-carboxylic acid (140 g, 543 mmol, 51.7% yield) as a brown solid. LCMS (M+1): 257.9.

$^1$H NMR (400 MHz, DMSO-d$_6$) δ 12.86-11.28 (m, 1H), 8.27 (s, 1H), 7.73 (s, 1H).

To a suspension of 8-bromo-5-oxo-5,6-dihydroimidazo[1,2-c]pyrimidine-2-carboxylic acid (120 g, 465 mmol, 1.00 equiv) in SOCl$_2$ (787 g, 6.62 mol, 480 mL, 14.2 equiv) was added DMF (340 mg, 4.65 mmol, 358 µL, 0.01 equiv) and the mixture was stirred at 80° C. for 2 h. The solution was concentrated to give a residue that was dissolved in DCM (200 mL). The resulting mixture was added dropwise to conc. ammonium hydroxide (1.09 kg, 9.35 mol, 1.20 L, 20.1 equiv) at 0° C. and the mixture was subsequently stirred at 25° C. for 1 h. LCMS indicated that the reaction was complete. The mixture was filtered, the filter cake was washed with MeOH (200 mL), and the solid was dried under vacuum to afford 8-bromo-5-oxo-5,6-dihydroimidazo[1,2-c]pyrimidine-2-carboxamide (120 g, crude) as a brown solid. LCMS (M+1): 257.0/259.0.

$^1$H NMR (400 MHz, DMSO-d$_6$) δ 8.05 (s, 1H), 7.66 (s, 1H), 7.56 (br s, 1H), 7.41 (br s, 1H).

To a solution of 8-bromo-5-oxo-5,6-dihydroimidazo[1,2-c]pyrimidine-2-carboxamide (20.0 g, 77.8 mmol, 1.00 equiv) in POCl$_3$ (388 g, 2.53 mol, 235 mL, 32.5 equiv) was added DIEA (50.3 g, 389 mmol, 67.8 mL, 5.00 equiv) dropwise at 0° C. The mixture was stirred at 120° C. for 12 h. The reaction mixture (4 identical batches combined) was cooled to room temperature and was concentrated to afford a residue. The residue was purified by column chromatography (petroleum ether:ethyl acetate=20:1 to 5:1) to provide 8-bromo-5-chloroimidazo[1,2-c]pyrimidine-2-carbonitrile (19.9 g, 76.1 mmol, 24.5% yield, 98.6% purity) as an off-white solid. LCMS (M+1): 388.0/390.0.

$^1$H NMR (400 MHz, DMSO-d$_6$) δ 9.19 (s, 1H), 8.36 (s, 1H).

Intermediate B-1

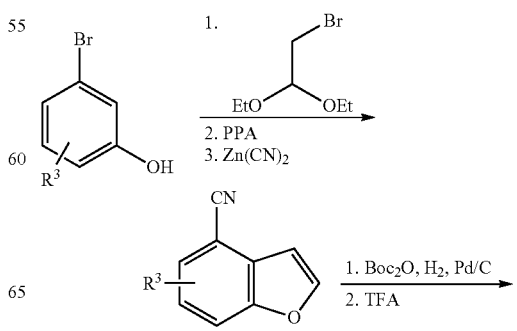

-continued

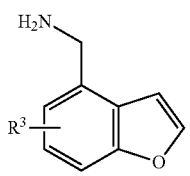

An exemplary Intermediate B, Intermediate B-1, may be used to synthesize compounds of formula I wherein Z is O, n is one, X is C(R$^5$)$_2$, and ===== is a single bond. A mixture of 3-bromophenol (10.0 g, 57.8 mmol, 1.00 equiv) and 2-bromo-1,1-diethoxy-ethane (13.7 g, 69.4 mmol, 10.4 mL, 1.20 equiv) in DMF (100 mL) was added potassium carbonate (24.0 g, 173 mmol, 3.00 equiv). The resultant mixture was stirred at 110° C. for 12 h under a nitrogen atmosphere. The reaction mixture was diluted with petroleum ether (100 mL) and washed with brine (50.0 mL×4), dried over anhydrous sodium sulfate, filtered and concentrated under reduced pressure to give a residue. The crude material was purified by column chromatography (petroleum ether) to afford 1-bromo-3-(2,2-diethoxyethoxy)benzene (17.0 g, 48.2 mmol, 83.4% yield, 82.0% purity) as a light yellow oil.

$^1$H NMR (400 MHz, CDCl$_3$) δ=7.17-7.07 (m, 3H), 6.88-6.84 (m, 1H), 4.82 (t, J=5.2 Hz, 1H), 3.99 (d, J=5.2 Hz, 2H), 3.80-3.74 (m, 1H), 3.80-3.73 (m, 2H), 3.68-3.61 (m, 2H), 1.25 (t, J=7.2 Hz, 6H).

To a solution of polyphosphoric acid (21.5 g, 63.6 mmol, 1.50 equiv) in toluene (80.0 mL) was added 1-bromo-3-(2,2-diethoxyethoxy)benzene (15.0 g, 42.5 mmol, 1.00 equiv) at 90° C. The mixture was stirred at 90° C. for 2 h and then concentrated under reduced pressure to give a residue. The crude material was purified by column chromatography (petroleum ether) to afford 4-bromobenzofuran (5.20 g, 13.2 mmol, 31.0% yield, 50.0% purity) as a yellow oil.

$^1$H NMR (400 MHz, CDCl3) δ=7.70 (s, 1H), 7.67 (d, J=2.0 Hz, 1H), 7.61 (d, J=2.4 Hz, 1H), 7.47 (d, J=8.4 Hz, 2H), 7.41 (d, J=8.0 Hz, 1H), 7.37 (dd, J=1.6, 8.4 Hz, 1H), 7.21-7.15 (m, 1H), 6.85-6.80 (m, 1H), 6.78-6.73 (m, 1H).

To a solution of 4-bromobenzofuran (5.20 g, 13.2 mmol, 1.00 equiv) in DMAC (50.0 mL) was added zinc cyanide (6.85 g, 58.3 mmol, 4.42 equiv) and Pd(PPh$_3$)$_4$ (1.52 g, 1.32 mmol, 0.100 equiv). The mixture was stirred at 140° C. for 12 h under a nitrogen atmosphere. The reaction mixture was diluted with ethyl acetate (80.0 mL), washed with brine (50.0 mL×3), dried over anhydrous sodium sulfate, filtered and concentrated under reduced pressure to give a residue. The crude material was purified by column chromatography (petroleum ether/ethyl acetate=50/1 to 0/1) to afford benzofuran-4-carbonitrile (1.60 g, 10.1 mmol, 76.2% yield, 90.0% purity) as a light-yellow oil.

$^1$H NMR (400 MHz, CDCl3) δ=7.80 (d, J=2.0 Hz, 1H), 7.75 (d, J=8.4 Hz, 1H), 7.60 (d, J=8.0 Hz, 1H), 7.38 (t, J=8.4 Hz, 1H), 7.03-7.00 (m, 1H).

To a solution of benzofuran-4-carbonitrile (750 mg, 4.72 mmol, 1.00 equiv) in methyl alcohol (10.0 mL) was added Boc$_2$O (3.09 g, 14.2 mmol, 3.00 equiv) and Pd/C (4.72 mmol, 10.0 w. %, 1.00 equiv). The mixture was stirred at 30° C. for 24 h under hydrogen (50.0 psi). The reaction mixture was filtered and concentrated under reduced pressure to give the crude material, which was purified by column chromatography (petroleum ether/ethyl acetate=1/0 to 50/1) to afford tert-butyl N-(2,3-dihydrobenzofuran-4-ylmethyl) carbamate (140 mg, 562 μmol, 11.9% yield) as a colorless oil.

$^1$H NMR (400 MHz, CDCl$_3$) δ=7.10 (t, J=8.0 Hz, 1H), 6.74 (dd, J=8.0, 14.0 Hz, 2H), 4.75 (br s, 1H), 4.59 (t, J=8.8 Hz, 2H), 4.28 (br d, J=5.6 Hz, 2H), 3.20 (t, J=8.8 Hz, 2H), 1.47 (s, 9H).

To a solution of tert-butyl N-(2,3-dihydrobenzofuran-4-ylmethyl) carbamate (140 mg, 562 μmol, 1.00 equiv) in DCM (2.00 mL) was added TFA (640 mg, 5.62 mmol, 416 μL, 10.0 equiv). The mixture was stirred at 25° C. for 1 h. The reaction mixture was diluted with DCM (10.0 mL) and was added to a saturated potassium carbonate aqueous solution (10.0 mL). The biphasic mixture was stirred at 25° C. for 0.5 h. The organic phase was separated, dried over sodium sulfate, concentrated in vacuo to afford 2,3-dihydrobenzofuran-4-ylmethanamine (80.0 mg, 483 μmol, 85.9% yield, 90.0% purity) as a yellow solid.

1H NMR (400 MHz, CDCl3)=7.13 (t, J=8.0 Hz, 1H), 6.84 (d, J=7.6 Hz, 1H), 6.72 (d, J=8.0 Hz, 1H), 4.60 (t, J=8.8 Hz, 2H), 3.82 (s, 2H), 3.20 (t, J=8.8 Hz, 2H).

Intermediate B-2

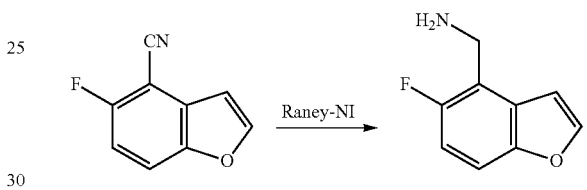

A second exemplary Intermediate B, Intermediate B-2, may be used to synthesize compounds of formula I wherein Z is O, n is one, X is CR$^5$, ===== is a double bond and one R$^3$ is fluorine. To a mixture of 5-fluorobenzofuran-4-carbonitrile (250 mg, 1.47 mmol, 1.00 equiv) and Raney-Ni (126 mg, 1.47 mmol, 1.00 equiv) in methyl alcohol (6.60 mL) was added ammonium hydroxide (1.60 mL). The mixture was purged with nitrogen and stirred at 25° C. for 12 h under a hydrogen atmosphere. The reaction mixture was filtered and concentrated under reduced pressure to afford (5-fluorobenzofuran-4-yl) methanamine (220 mg, 1.20 mmol, 81.3% yield, 90.0% purity) as a brown oil.

$^1$H NMR (400 MHz, CDCl$_3$) δ=7.67 (s, 1H), 7.33 (br d, J=5.6 Hz, 1H), 7.04 (br t, J=9.6 Hz, 1H), 6.90 (s, 1H), 4.54-3.78 (m, 2H).

Intermediate B-3

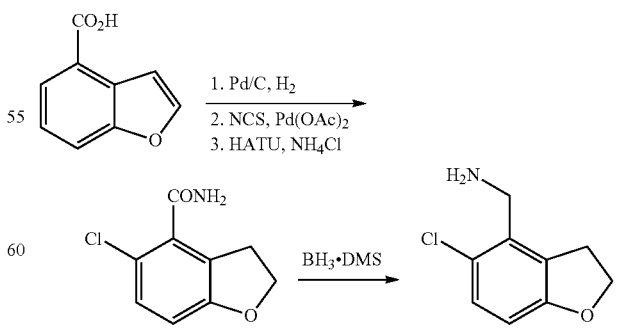

A third exemplary Intermediate B, Intermediate B-3, may be used to synthesize compounds of formula I wherein Z is O, n is one, X is C(R$^5$)$_2$, ===== is a single bond and one R$^3$ is chlorine. To a solution of benzofuran-4-carboxylic acid (900 mg, 5.55 mmol, 1 equiv) in MeOH (9.00 mL) was added palladium on activated carbon (20.0 mg, 555 μmol, 10.0 wt %, 0.10 equiv) under nitrogen. The vessel was evacuated and purged with hydrogen several times. The mixture was stirred at 25° C. for 12 h under hydrogen (50.0 psi). The reaction mixture was filtered and the filtrate was concentrated in vacuo to afford 2,3-dihydrobenzofuran-4-carboxylic acid (750 mg, 3.66 mmol, 65.9% yield, 80.0% purity) as a white solid.

$^1$H NMR (400 MHz, DMSO-$d_6$) δ=7.38 (d, J=8.0 Hz, 1H), 7.20 (t, J=8.0 Hz, 1H), 6.97 (d, J=8.0 Hz, 1H), 4.54 (t, J=8.8 Hz, 2H), 3.45 (br t, J=8.8 Hz, 2H).

To a solution of 2,3-dihydrobenzofuran-4-carboxylic acid (750 mg, 3.66 mmol, 1.00 equiv) in DMF (1.00 mL) was added Pd(OAc)$_2$ (82.1 mg, 366 μmol, 0.10 equiv) and NCS (586 mg, 4.39 mmol, 1.20 equiv). The reaction was stirred at 110° C. for 12 h under an atmosphere of nitrogen. The reaction mixture was filtered and concentrated in vacuo and the resultant residue was purified by silica gel chromatography (petroleum ether/ethyl acetate=5/1 to dichloromethane/methanol=10/1) to afford 5-chloro-2,3-dihydrobenzofuran-4-carboxylic acid (600 mg, crude) as a yellow oil. LC-MS. [M+1] 198.9.

To a solution of 5-chloro-2,3-dihydrobenzofuran-4-carboxylic acid (600 mg, 3.02 mmol, 1.00 equiv) in DMF (5.00 mL) was added ammonium chloride (242 mg, 4.53 mmol, 1.50 equiv), HATU (2.30 g, 6.04 mmol, 2.00 equiv), DIEA (1.17 g, 9.06 mmol, 1.58 mL, 3.00 equiv). The reaction mixture was stirred at 25° C. for 12 h and concentrated in vacuo to give the crude material, which was purified by silica gel chromatography (petroleum ether/ethyl acetate=10/1 to 1/1) to afford 5-chloro-2,3-dihydrobenzofuran-4-carboxamide (700 mg, 2.83 mmol, 93.8% yield, 80.0% purity) as a white solid.

$^1$H NMR (400 MHz, DMSO-$d_6$) δ=7.87 (br s, 1H), 7.63 (br s, 1H), 7.17 (d, J=8.4 Hz, 1H), 6.79 (d, J=8.4 Hz, 1H), 4.58 (t, J=8.8 Hz, 2H), 3.18 (t, J=8.8 Hz, 2H).

To a solution of 5-chloro-2,3-dihydrobenzofuran-4-carboxamide (300 mg, 1.21 mmol, 1.00 equiv) in THF (5.00 mL) was added dropwise BH$_3$-DMS (10.0, 607 μL, 5.00 equiv). The reaction was stirred at 70° C. for 2.5 h, quenched with MeOH (5.00 mL) and concentrated in vacuo to provide a residue. To the residue was added water (20.0 mL) and the mixture was extracted with DCM (20.0 mL×3). The combined organic phase was washed with brine (20.0 mL×2), dried over anhydrous sodium sulfate, filtered and concentrated to afford (5-chloro-2,3-dihydrobenzofuran-4-yl)methanamine (240 mg, crude) as a brown oil. LC-MS: [M−16] 167.1.

Intermediate B-4

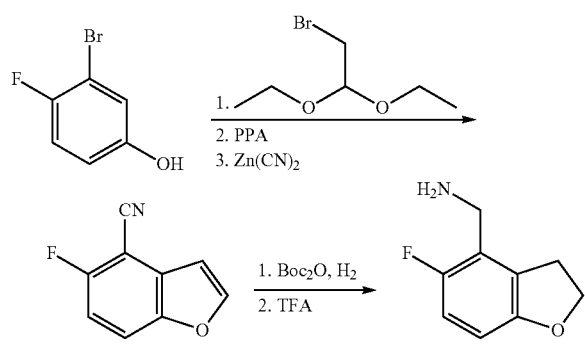

A fourth exemplary Intermediate B, Intermediate B-4, may be used to synthesize compounds of formula I wherein Z is O, n is one, X is C(R$^5$)$_2$, ===== is a single bond and one R$^3$ is fluorine. To a solution of 3-bromo-4-fluoro-phenol (100 g, 524 mmol, 1.00 equiv) and 2-bromo-1,1-diethoxy-ethane (124 g, 628 mmol, 94.5 mL, 1.20 equiv) in DMF (600 mL) was added potassium carbonate (217 g, 1.57 mol, 3.00 equiv). The mixture was stirred at 110° C. for 12 h under an atmosphere of nitrogen. The reaction mixture was diluted with ethyl acetate (500 mL), washed with brine (500 ml×5) and concentrated at reduced pressure to provide a residue. The residue was purified by column chromatography (petroleum ether/ethyl acetate=1/0 to 20/1) to afford 2-bromo-4-(2,2-diethoxyethoxy)-1-fluoro-benzene (171 g, 501 mmol, 95.7% yield, 90.0% purity) as a light-yellow oil.

$^1$H NMR (400 MHz, CDCl$_3$) δ=7.12 (dd, J=2.8, 5.6 Hz, 1H), 7.06-6.98 (m, 1H), 6.84 (td, J=3.2, 9.2 Hz, 1H), 4.81 (t, J=5.2 Hz, 1H), 3.96 (d, J=5.2 Hz, 2H), 3.81-3.72 (m, 2H), 3.68-3.59 (m, 2H), 1.25 (t, J=7.2 Hz, 6H).

To a solution of PPA (254 g, 752 mmol, 1.50 equiv) in toluene (1.30 L) was added 2-bromo-4-(2,2-diethoxy-ethoxy)-1-fluoro-benzene (171 g, 501 mmol, 1.00 equiv) at 90° C. The mixture was stirred at 95° C. for 2 h and concentrated at reduced pressure to provide a residue. The residue was purified by column chromatography (petroleum ether) to give 4-bromo-5-fluoro-benzofuran (87.3 g, 203 mmol, 40.5% yield, 50.0% purity) as a yellow oil. To a mixture of 4-bromo-5-fluoro-benzofuran (85.5 g, 398 mmol, 1.00 equiv) and 6-bromo-5-fluoro-benzofuran (85.5 g, 398 mmol, 1.00 equiv) in DMAC (1.50 L) was added zinc cyanide (31.1 g, 264 mmol, 0.67 equiv) and Pd(PPh$_3$)$_4$ (23.0 g, 19.9 mmol, 0.05 equiv). The mixture was stirred at 90° C. for 12 h under an atmosphere of nitrogen. The reaction mixture was diluted with ethyl acetate (1.00 L) and filtered. The filtrate was washed with brine (1.00 L x 3) and the organic layer was concentrated at reduced pressure to provide a residue. The residue was purified by column chromatography (petroleum ether/ethyl acetate=1/0 to 50/1) to afford 4-bromo-5-fluoro-benzofuran (78 g, crude) as a white solid.

To a solution of 4-bromo-5-fluoro-benzofuran (87.3 g, 203 mmol, 1.00 equiv) in DMAC (600 mL) was added zinc cyanide (94.6 g, 805 mmol, 3.97 equiv) and Pd(PPh$_3$)$_4$ (23.5 g, 20.3 mmol, 0.10 equiv). The mixture was stirred at 110° C. for 12 h under an atmosphere of nitrogen. The reaction mixture was diluted with ethyl acetate (500 mL), washed with brine (400 mL×5), dried over anhydrous sodium sulfate, filtered and concentrated at reduced pressure to provide a residue. The residue was purified by column chromatography (petroleum ether ethyl acetate=1/0 to 50/1) to afford 5-fluorobenzofuran-4-carbonitrile (20.0 g, 118 mmol, 58.1% yield, 95.0% purity) as a white solid.

$^1$H NMR (400 MHz, CDCl$_3$) δ=7.84 (d, J=2.0 Hz, 1H), 7.73-7.67 (m, 1H), 7.14 (t, J=9.2 Hz, 1H), 7.02-6.96 (m, 1H).

To a solution of 5-fluorobenzofuran-4-carbonitrile (19.6 g, 116 mmol, 1.00 equiv) in methyl alcohol (1.00 L) was added di-tert-butyl dicarbonate (75.7 g, 347 mmol, 300 equiv) and Pd/C 10 w. % (1.16 g). The mixture was stirred at 35° C. for 24 h under an atmosphere of hydrogen gas (50.0 psi). The reaction mixture was filtered and concentrated at reduced pressure to provide a residue. The residue was purified by column chromatography (petroleum ether/ethyl acetate=1/0 to 3/1) to afford tert-butyl N-[(5-fluoro-2,3-dihydrobenzofuran-4-yl)methyl]carbamate (22.0 g, 78.2 mmol, 67.7% yield, 95.0% purity) as a white solid.

¹H NMR (400 MHz, CDCl₃) δ=6.82-6.76 (m, 1H), 6.62 (dd, J=4.0, 8.8 Hz, 1H), 4.88 (br s, 1H), 4.60 (t, J=8.8 Hz, 2H), 4.30 (br d, J=6.0 Hz, 2H), 3.30 (br t, J=8.8 Hz, 2H), 1.44 (s, 9H).

To a solution of tert-butyl N-[(5-fluoro-2,3-dihydrobenzofuran-4-yl)methyl]carbamate (22.0 g, 78.2 mmol, 1.00 equiv) in DCM (200 mL) was added TFA (89.2 g, 782 mmol, 57.9 mL, 10.0 equiv). The mixture was stirred at 25° C. for 0.5 h and subsequently quenched with satd aq potassium carbonate (200 mL). The mixture was allowed to stir at 25° C. for 0.5 hour. The organic phase was separated and dried over sodium sulfate, concentrated in vacuo to afford (5-fluoro-2,3-dihydrobenzofuran-4-yl)methanamine (13.0 g, 73.9 mmol, 94.5% yield, 95.0% purity) as a light yellow oil.

¹H NMR (400 MHz, CDCl₃) δ=6.85-6.76 (m, 1H), 6.60 (dd, J=4.0, 8.8 Hz, 1H), 4.61 (t, J=8.8 Hz, 2H), 3.82 (s, 2H), 3.24 (t, J=8.8 Hz, 2H).

Alternatively, Intermediate A-2 may be prepared on a large scale as follows:

To a solution of 3-bromo-4-fluorophenol (1.00 kg, 5.24 mol, 1.00 equiv) and Cs₂CO₃ (3.41 kg, 10.5 mol, 2.00 equiv) in DMF (5.00 L) was added compound 2-bromo-1,1-diethoxyethane (1.24 kg, 6.28 mol, 1.20 equiv) in one portion. The suspension was stirred at 110° C. for 12 h. TLC (petroleum ether/ethyl acetate=10/1, $R_f$=0.50) indicated that the reaction was complete. The reaction mixture was filtered, diluted with water (15.0 L) and extracted with MTBE (5.00 L×2). The combined organic layers were washed with brine (3.00 L), dried over Na₂SO₄, filtered and concentrated under reduced pressure to give compound 2-bromo-4-(2,2-diethoxyethoxy)-1-fluorobenzene (1.61 kg, crude) as a yellow oil.

Two reactions were conducted in parallel on the same scale and combined during the workup. To a mixture of polyphosphoric acid (1.30 kg) in toluene (2.40 L) was added 2-bromo-4-(2,2-diethoxyethoxy)-1-fluorobenzene (800 g, 2.60 mol, 1.00 equiv) in one portion at 90° C. The mixture was stirred at 90° C. for 3 h. TLC (petroleum ether/EtOAc=10/1, $R_f$=0.6) indicated that the reaction was complete. The two reactions were combined prior to work up. The mixture was poured into water (6.00 L) and extracted with MTBE (6.00 L×2). The combined organic layer was washed with brine (5.00 L×2), dried over anhydrous Na₂SO₄, filtered and concentrated in vacuo. The residue was purified by silica gel chromatography (petroleum ether/EtOAc=1/0 to 100/1) to give a ~1:1 mixture of 4-bromo-5-fluorobenzofuran and 6-bromo-5-fluorobenzofuran (800 g, 3.72 mol, 71.4% yield) as a brown oil.

Two reactions were conducted in parallel on the same scale and combined during the workup. To a mixture of 4-bromo-5-fluorobenzofuran (150 g, 698 mmol, 1.00 equiv) and 6-bromo-5-fluorobenzofuran (150 g, 698 mmol, 1.0 equiv) in DMA (2.40 L) was added Zn(CN)₂ (49.2 g, 419 mmol, 0.60 equiv) and Pd(PPh₃)₄ (40.3 g, 34.9 mmol, 0.05 equiv) in one portion at 25° C. under N₂. The mixture was stirred at 90° C. for 12 h. TLC (petroleum ether/EtOAc=10/1) indicated the consumption of the undesired isomer (6-bromo-5-fluorobenzofuran). The two reactions were combined prior to work up. The mixture was diluted with EtOAc (5.00 L) and filtered. The filtrate was poured into water (8.00 L) and the mixture was extracted with EtOAc (3.00 L×2). The combined organic phase was washed with brine (4.00 L×2), dried over anhydrous Na₂SO₄, filtered and concentrated under reduced pressure. The residue was purified by silica gel chromatography (petroleum ether/EtOAc=1/0 to 5/1) to give compound 4-bromo-5-fluorobenzofuran (340 g) as a yellow oil.

Two reactions were conducted in parallel on the same scale and combined during the workup. To a mixture of compound 4-bromo-5-fluorobenzofuran (170 g, 791 mmol, 1.00 equiv) in DMA (1.30 L) was added Zn(CN)₂ (92.8 g, 791 mmol, 1.00 eq.) and Pd(PPh₃)₄ (91.4 g, 79.1 mmol, 0.10 equiv) in one portion at 25° C. under N₂. The resultant mixture was stirred at 120° C. for 12 h. TLC (petroleum ether/EtOAc=10/1) indicated that the reaction was complete. The two reactions were combined prior to work up and the mixture was poured into water (3.00 L) and EtOAc (4.00 L), filtered, and the filtrate was extracted with EtOAc (2.00 L×2). The combined organic layer was washed with brine (3.00 L×2), dried over anhydrous Na₂SO₄, filtered and concentrated in vacuo. The residue was purified by silica gel chromatography (petroleum ether/EtOAc=1/0 to 50/1) to afford compound 5-fluorobenzofuran-4-carbonitrile (120 g, 745 mmol, 47.1% yield) as a yellow oil.

¹H NMR (400 MHz, CD₃OD) δ 8.06 (d, J=2.0 Hz, 1H), 7.82-7.86 (m, 1H), 7.23-7.28 (m, 1H), 7.02 (d, J=2.0 Hz, 1H).

Two reactions were conducted in parallel on the same scale and combined during the workup. To a solution of compound 5-fluorobenzofuran-4-carbonitrile (60.0 g, 372 mmol, 1.00 equiv) in MeOH (1.50 L) was added Boc₂O (122 g, 559 mmol, 1.50 equiv) and Pd/C (12.0 g, 10 wt %) under N₂. The suspension was evacuated and purged with H₂ several times and the mixture was stirred under H₂ (50 psi) at 50° C. for 12 h. TLC (petroleum ether/EtOAc=10/1) indicated that the reaction was complete. The two reactions were combined prior to work up and filtered. The filtrate was concentrated to afford a residue that was triturated with petroleum ether (500 mL), filtered, and dried at 45° C. under vacuum to provide tert-butyl ((5-fluoro-2,3-dihydrobenzofuran-4-yl)methyl)carbamate (100 g, 374 mmol, 50.2% yield) as a white solid.

¹H NMR (400 MHz, CDCl₃) δ 6.76-6.81 (m, 1H), 6.60-6.63 (m, 1H), 4.60 (t, J=8.8 Hz, 2H), 4.29-4.31 (m, 2H), 3.30 (t, J=8.8 Hz, 2H), 1.44 (s, 9H).

Two reactions were conducted in parallel on the same scale and combined during the workup. To a mixture of tert-butyl ((5-fluoro-2,3-dihydrobenzofuran-4-yl)methyl)carbamate (50.0 g, 187 mmol, 1.00 equiv) in EtOAc (400 mL) was added HCL/EtOAc (300 mL, 4M) in one portion at 25° C. under N₂. The resultant mixture was stirred for 4 h at which time TLC (petroleum ether/EtOAc=5/1) indicated that the reaction was complete. The two reactions were combined prior to work up, filtered, and the filter cake was washed by MTBE (100 mL×2). The filter cake was dissolved in water (200 mL) and the pH was adjusted to 9 with sat. aq. K₂CO₃ at 0° C. prior to extraction with DCM (200 mL×4). The combined organic phase was washed with brine (200 mL×2), dried over anhdrous Na₂SO₄, filtered and concentrated in vacuo to afford (5-fluoro-2,3-dihydrobenzofuran-4-yl)methanamine (50.0 g, 299 mmol, 79.9% yield) as a brown oil.

¹H NMR (400 MHz, DMSO-d₆) δ 8.57 (br. s., 3H), 6.97 (m, 1H), 6.77-6.80 (m, 1H), 4.55-4.59 (m, 2H), 3.94 (s, 2H), 3.37-3.42 (m, 2H).

Intermediate B-5

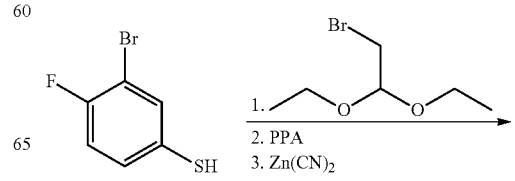

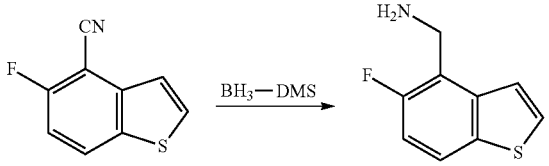

A fifth exemplary Intermediate B, Intermediate B-5, may be used to synthesize compounds of formula I wherein Z is S, n is one, X is C(R⁵)₂, ----- is a single bond and one R³ is fluorine. A mixture of 3-bromo-4-fluoro-benzenethiol (4.50 g, 21.7 mmol, 1.00 equiv), 2-bromo-1,1-diethoxy-ethane (4.71 g, 23.9 mmol, 3.60 mL, 1.10 equiv), and potassium carbonate (3.60 g, 26.1 mmol, 1.20 equiv) in DMF (50.0 mL) was purged with nitrogen. The mixture was stirred at 80° C. for 0.5 h under an atmosphere of nitrogen. The mixture was concentrated in vacuo to provide a residue, which was purified by column chromatography (petroleum ether/ethyl acetate, 20/1 to 5/1) to afford 2-bromo-4-(2,2-diethoxyethylsulfanyl)-1-fluoro-benzene (6.2 g, 19.2 mmol, 88.3% yield) as a colorless liquid.

$^1$H NMR (400 MHz, CDCl₃) δ=7.63 (dd, J=2.4, 6.4 Hz, 1H), 7.32 (ddd, J=2.4, 4.4, 8.8 Hz, 1H), 7.03 (t, J=8.4 Hz, 1H), 4.63 (t, J=5.6 Hz, 1H), 3.72-3.65 (m, 2H), 3.57-3.51 (m, 2H), 3.08 (d, J=5.6 Hz, 2H), 1.20 (t, J=7.2 Hz, 6H).

To a solution of polyphosphoric acid (39 g, 710 μL, 1.00 equiv) in chlorobenzene (70.0 mL) was added 2-bromo-4-(2,2-diethoxyethylsulfanyl)-1-fluoro-benzene (5.9 g, 18.3 mmol, 1.00 equiv) and the resultant mixture was stirred at 130° C. for 12 h. The mixture was concentrated in vacuo to provide a residue. The residue was purified by column chromatography (petroleum ether) to afford 4-bromo-5-fluoro-benzothiophene (2.50 g, 10.8 mmol, 29.8% yield, 50% purity) as a colorless liquid.

$^1$H NMR (400 MHz, CDCl₃) δ=7.75 (dd, J=4.4, 8.8 Hz, 1H), 7.61 (d, J=5.6 Hz, 1H), 7.49 (d, J=5.6 Hz, 1H), 7.17 (t, J=8.8 Hz, 1H).

To a solution of 4-bromo-5-fluoro-benzothiophene (1.25 g, 5.41 mmol, 1.00 equiv) in DMAC (12.0 mL) was added zinc cyanide (953 mg, 8.11 mmol, 515 μL, 1.50 equiv) and Pd(PPh₃)₄ (938 mg, 811 μmol, 0.150 equiv). The mixture was stirred at 100° C. for 12 h under an atmosphere of nitrogen. Water (50.0 mL) was added and the mixture was extracted with ethyl acetate (80.0 mL×3). The combined organic layer was concentrated in vacuo to provide a residue. The residue was purified by column chromatography (petroleum ether) to afford 5-fluorobenzothiophene-4-carbonitrile (530 mg, 2.99 mmol, 27.7% yield) as a white solid.

$^1$H NMR (400 MHz, CDCl₃) δ=8.05 (dd, J=4.4, 8.8 Hz, 1H), 7.80 (d, J=5.6 Hz, 1H), 7.57 (d, J=5.6 Hz, 1H), 7.23 (t, J=8.8 Hz, 1H).

To a mixture of 5-fluorobenzothiophene-4-carbonitrile (300 mg, 1.69 mmol, 1.0) equiv) in THF (2.00 mL) was added BH₃-Me₂S (10 M, 677 μL, 4.00 equiv) at 0° C. and the mixture was stirred for 6 h at 75° C. The mixture was cooled to room temperature and was quenched with ethanol (10.0 mL) and the pH was adjusted to 3 with aq HCl (2 M). The mixture was concentrated in vacuo to provide a residue to which water (20.0 mL) was added. The aqueous mixture was extracted with ethyl acetate (40.0 mL×4) and the combined organic layer was concentrated to afford (5-fluorobenzothiophen-4-yl)methanamine (150 mg, 828 μmol, 48.9% yield) as a yellow solid.

Intermediate B-6

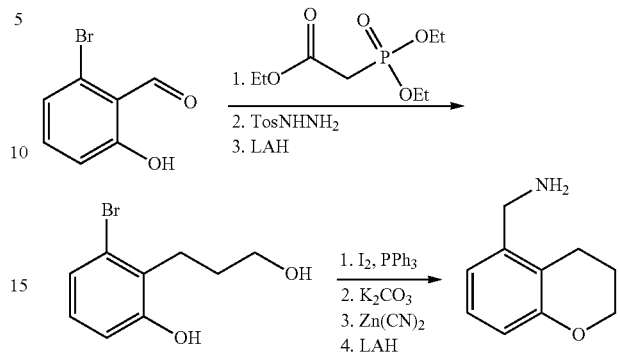

A sixth exemplary Intermediate B, Intermediate B-6, may be used to synthesize compounds of formula I wherein Z is O, n is two, X is C(R⁵)₂, ----- is a single bond and one R³ is fluorine.

To a solution of 2-bromo-6-hydroxy-benzaldehyde (0.30 g, 1.49 mmol, 1.00 eq.) and ethyl 2-diethoxyphosphorylac-etate (669 mg, 2.98 mmol, 592 μL, 2.00 eq.) in DMF (3.00 mL) was added NaH (119 mg, 2.98 mmol, 60% purity, 2.00 eq.) at rt under a nitrogen atmosphere. The resultant mixture was stirred at 40° C. for 12 h. The reaction mixture was diluted with ethyl acetate (50.0 mL) and quenched with water (10.0 mL). The combined organic phase was washed with brine (30.0 mL×3), dried over sodium sulfate, filtered and concentrated in vacuo. The crude residue was purified by column chromatography (SiO₂, Petroleum ether/Ethyl acetate=10/1 to 4/1) to afford ethyl (E)-3-(2-bromo-6-hydroxy-phenyl)prop-2-enoate (380 mg, 1.37 mmol, 92.0% yield, 98.0% purity) as a white solid.

$^1$H NMR (400 MHz, CD₃OD) δ=8.02 (d, J=16.0 Hz, 1H), 7.15 (dd, J=1.2, 8.0 Hz, 1H), 7.06 (t, J=8.0 Hz, 1H), 6.97 (d, J=16.0 Hz, 1H), 6.86 (d, J=8.0 Hz, 1H), 4.56 (s, 1H), 4.25 (q, J=7.2 Hz, 2H), 1.33 (t, J=7.2 Hz, 3H).

To a solution of ethyl (E)-3-(2-bromo-6-hydroxy-phenyl) prop-2-enoate (380 mg, 1.37 mmol, 1.00 eq.) in THF (5.00 mL) and water (5.00 mL) was added NaOAc (225 mg, 2.75 mmol, 2.00 eq.) and 4-methylbenzenesulfonohydrazide (512 mg, 2.75 mmol, 2.00 eq.). The mixture was stirred at 70° C. for 12 h. The mixture was cooled to rt and extracted with ethyl acetate (20.0 mL×2). The combined organic phase was washed with brine (30.0 mL×3), dried over sodium sulfate, filtered and concentrated in vacuo. The crude residue was purified by column chromatography (SiO₂, petroleum ether/ethyl acetate=20/1 to 10/1) to afford ethyl 3-(2-bromo-6-hydroxy-phenyl)propanoate (380 mg, 1.32 mmol, 96.2% yield, 95.0% purity) as a light-yellow oil.

$^1$H NMR (400 MHz, CDCl₃) δ=8.27 (s, 1H), 7.14 (dd, J=1.2, 8.0 Hz, 1H), 6.99 (t, J=8.0 Hz, 1H), 6.93-6.88 (m, 1H), 4.17 (q, J=7.2 Hz, 2H), 3.50 (s, 1H), 3.10-3.03 (m, 2H), 2.87-2.79 (m, 2H), 1.28-1.24 (m, 3H).

To a solution of ethyl 3-(2-bromo-6-hydroxy-phenyl) propanoate (0.10 g, 348 μmol, 1.00 eq.) in THF (2.00 mL) was added LAH (39.6 mg, 1.04 mmol, 3.00 eq.) at 0° C. The mixture was stirred at rt for 2 h. The reaction mixture was quenched with water (0.50 mL) and was diluted with DCM (30.0 mL). The mixture was dried over magnesium sulfate, filtered and concentrated in vacuo. The crude residue was purified by prep-TLC (SiO₂, PE:EA=2:1) to afford 3-bromo- 2-(3-hydroxypropyl)phenol (70.0 mg, 297 µmol, 85.4% yield, 98.0% purity) as a yellow oil.

$^1$H NMR (400 MHz, CDCl$_3$) δ=7.66 (br s, 1H), 7.14 (dd, J=1.2, 8.0 Hz, 1H), 6.97 (t, J=8.0 Hz, 1H), 6.84 (dd, J=1.2, 8.0 Hz, 1H), 3.64 (t, J=5.6 Hz, 2H), 3.03-2.94 (m, 2H), 2.01-1.90 (m, 2H).

Iodine (3.30 g, 13.0 mmol, 2.62 mL, 1.65 eq.) was added to a solution of imidazole (2.42 g, 35.5 mmol, 4.50 eq.) and PPh$_3$ (3.72 g, 14.2 mmol, 1.80 eq.) in DCM (40.0 mL) at 0° C. The reaction mixture was stirred for 15 min followed by the dropwise addition of a solution of 3-bromo-2-(3-hydroxypropyl)phenol (1.85 g, 7.89 mmol, 1.00 eq.) in DCM (10.0 mL). The reaction mixture was protected from light and stirred for 12 h at rt. The mixture was diluted with DCM (50.0 mL) and washed with brine (40.0 mL×2). The combined organic phase was dried over sodium sulfate, filtered and concentrated in vacuo. The crude material was purified by column chromatography (SiO$_2$, petroleum ether/ethyl acetate=1/0 to 20/1) to afford 3-bromo-2-(3-iodopropyl) phenol (2.10 g, 6.16 mmol, 78.1% yield) as a white solid.

To a solution of 3-bromo-2-(3-iodopropyl)phenol (2.10 g, 6.16 mmol, 1.00 eq.) in acetone (50.0 mL) was added K$_2$CO$_3$ (1.70 g, 12.3 mmol, 2.00 eq.). The mixture was stirred at 50° C. for 12 h. The reaction mixture was filtered and concentrated in vacuo. The crude material was purified by column chromatography (SiO$_2$, petroleum ether) to afford 5-bromochromane (1.20 g, 5.63 mmol, 91.5% yield, 100% purity) as a light-yellow oil.

A mixture of 5-bromochromane (0.10 g, 469 µmol, 1.00 eq.), Zn(CN)$_2$ (110 mg, 939 µmol, 2.00 eq.), Pd(PPh$_3$)$_4$ (81.4 mg, 70.4 µmol, 0.15 eq.) in DMAC (1.00 mL) was purged with nitrogen. The mixture was stirred at 100° C. for 8 h. The reaction mixture was diluted with ethyl acetate (20.0 mL) and washed with brine (15.0 mL×3). The combined organic phase was dried over sodium sulfate, filtered and concentrated in vacuo. The crude material was purified by prep-TLC (SiO$_2$, PE:EA=10:1) to afford chromane-5-carbonitrile (60.0 mg, 377 µmol, 80.3% yield) as a light-yellow oil.

$^1$H NMR (400 MHz, CDCl$_3$) δ=7.22-7.18 (m, 1H), 7.18-7.13 (m, 1H), 7.02 (dd, J=1.2, 8.0 Hz, 1H), 4.28-4.19 (m, 2H), 2.97 (t, J=6.4 Hz, 2H), 2.16-2.02 (m, 2H).

To a solution of chromane-5-carbonitrile (60.0 mg, 377 µmol, 1.00 eq.) in THF (3.00 mL) was added LAH (57.2 mg, 1.51 mmol, 4.00 eq.) at 0° C. The mixture was stirred at rt for 2 h. The reaction mixture was quenched with water (1.00 mL) and diluted with DCM (30 mL). The mixture was dried with magnesium sulfate and filtered. The filtrate was concentrated in vacuo to afford chroman-5-ylmethanamine (70.0 mg, crude) as a light-yellow oil.

Intermediate B-7

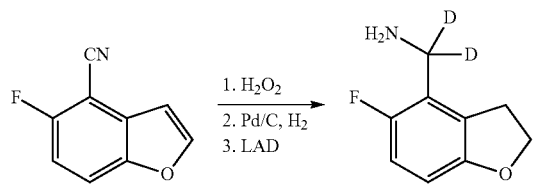 [SMILES: N#Cc1c(F)ccc2occc12 ; [2H]C([2H])(N)c1c(F)ccc2c1CCO2]

To a solution of 5-fluorobenzofuran-4-carbonitrile (2.00 g, 12.4 mmol, 1.00 equiv) in dimethyl sulfoxide (20.0 mL) was added hydrogen peroxide (7.04 g, 62.1 mmol, 5.96 mL, 30% purity, 5.00 equiv) and potassium carbonate (1.72 g, 12.4 mmol, 1.00 equiv) at 0° C. The mixture was stirred at 25° C. for 1 h. The residue was poured into ice-water (5.00 mL) and stirred for 10 min. The mixture was filtered and concentrated under vacuum to give 5-fluorobenzofuran-4-carboxamide (1.80 g, 10.1 mmol, 81.0% yield) as a white solid.

$^1$H NMR (400 MHz, DMSO-d$_6$) δ=8.11 (d, J=2.0 Hz, 1H), 7.81 (br s, 1H), 7.73 (dd, J=4.0, 8.8 Hz, 2H), 7.23 (dd, J=9.2, 10.4 Hz, 1H), 7.10 (d, J=1.2 Hz, 1H).

A solution of 5-fluorobenzofuran-4-carboxamide (1.80 g, 10.1 mmol, 1.00 equiv) in methyl alcohol (4.00 mL) was charged with hydrogen (50 psi) and Pd/C (500 mg, 50% purity). The mixture was stirred at 35° C. for 12 h. The mixture was filtered and concentrated under vacuum to give 5-fluoro-2,3-dihydrobenzofuran-4-carboxamide (1.60 g, 8.83 mmol, 87.9% yield) as a white solid. LCMS [M+1]: 182.2.

$^1$H NMR (400 MHz, DMSO-d$_6$) δ=7.82-7.55 (m, 2H), 6.96 (t, J=8.8 Hz, 1H), 6.79 (dd, J=4.0, 8.8 Hz, 1H), 4.54 (t, J=8.8 Hz, 2H), 3.25 (t, J=8.8 Hz, 2H).

To a solution of 5-fluoro-2,3-dihydrobenzofuran-4-carboxamide (1.60 g, 8.83 mmol, 1.00 equiv) in tetrahydrofuran (20.0 mL) was added lithium aluminumdeuteride (670 mg, 17.7 mmol, 911 µL, 2.00 equiv) at 0° C. The mixture was stirred at 60° C. for 12 h. The mixture was quenched with water (1.60 mL)(stirred for 15 min), followed by sodium hydroxide (1.50 mL, 15% aq.)(15 min) and water (4.80 mL)(30 min). The suspension was filtered and concentrated in vacuo to give a residue. The residue was purified by prep-HPLC (basic conditions) to afford (5-fluoro-2,3-dihydrobenzofuran-4-yl)methan-d2-amine (0.80 g, 4.56 mmol, 51.6% yield, 96.4% purity) as a red oil.

$^1$H NMR (400 MHz, CHLOROFORM-d) δ=6.82-6.76 (m, 1H), 6.59 (dd, J=4.0, 8.8 Hz, 1H), 4.59 (t, J=8.8 Hz, 2H), 3.23 (t, J=8.8 Hz, 2H).

Intermediate B-8

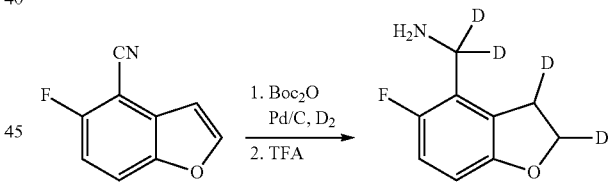

To a solution of 5-fluorobenzofuran-4-carbonitrile (100 mg, 620 µmol, 1.00 equiv) in methanol-d$_4$ (1.00 mL) was added di-tert-butyl dicarbonate (135 mg, 620 µmol, 143 µL, 1.00 equiv) and palladium on carbon (100 mg, 10.0 w %, 0.09 equiv). The mixture was stirred at 35° C. for 12 h under a deuterium gas atmosphere (15 psi). The reaction was filtered and concentrated at reduced pressure to give tert-butyl ((5-fluoro-2,3-dihydrobenzofuran-4-yl-2,3-d2)methyl-d2)carbamate (45.0 mg, 166 µmol, 26.7% yield) as a white solid.

$^1$H NMR (400 MHz, CDCl$_3$) δ=6.82-6.76 (m, 1H), 6.62 (dd, J=3.6, 8.4 Hz, 1H), 4.86 (br s, 1H), 4.57 (br d, J=10.0 Hz, 1H), 3.27 (br d, J=6.8 Hz, 1H), 1.46-1.41 (s, 9H).

To a solution of tert-butyl ((5-fluoro-2,3-dihydrobenzofuran-4-yl-2,3-d2)methyl-d2)carbamate (40.0 mg, 147 µmol, 1.00 equiv) in dichloromethane (2.00 mL) was added trifluoroacetic acid (109 µL, 1.47 mmol, 10.0 equiv). The mixture was stirred at 25° C. for 1 h. and subsequently was concentrated at reduced pressure to give a residue. The residue was added to saturated sodium bicarbonate (2.00 mL) and stirred for 5 min. The aqueous phase was extracted with ethyl acetate (2.00 mL×3). The combined organic phase was washed with brine (2.00 mL×3), dried with anhydrous sodium sulfate, filtered and concentrated at reduced pressure to afford dideuterio-(2,3-dideuterio-5-fluoro-2,3-dihydrobenzofuran-4-yl)methanamine (25.0 mg, crude) as a white solid, which was used without further purification.

Intermediate B-9

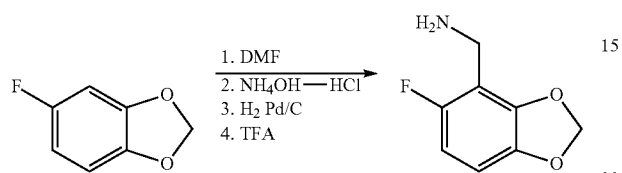

To a solution of 5-fluoro-1,3-benzodioxole (500 mg, 3.57 mmol, 1.00 equiv) in THF (5.00 mL) was added n-BuLi (2.50 M, 1.57 mL, 1.10 equiv) dropwise at −78° C. The mixture was stirred at −78° C. for 15 min followed by the dropwise addition of DMF (235 mg, 3.21 mmol, 247 µL, 0.90 equiv) and continued stirring at −78° C. for 0.5 h. The mixture was poured into saturated ammonium chloride aqueous solution (5.00 mL) and stirred for 15 min. The aqueous phase was extracted with ethyl acetate (6.00 mL×2). The combined organic phase was washed with brine (6.00 mL×3), dried with anhydrous sodium sulfate, filtered and concentrated under reduced pressure to give 5-fluoro-1,3-benzodioxole-4-carbaldehyde (370 mg, 2.20 mmol, 61.7% yield) as a white solid.

$^1$H NMR (400 MHz, DMSO-$d_6$) δ=10.07 (s, 1H), 7.12 (dd, J=4.4, 8.4 Hz, 1H), 6.72 (dd, J=8.8, 11.6 Hz, 1H), 6.17 (s, 2H).

To a solution of 5-fluoro-1,3-benzodioxole-4-carbaldehyde (200 mg, 1.19 mmol, 1.00 equiv) in ethyl alcohol (6.00 mL) was added hydroxylamine-hydrochloride (248 mg, 3.57 mmol, 3.00 equiv) and triethylamine (827 µL, 5.95 mmol, 5.00 equiv). The mixture was stirred at 15° C. for 0.5 h and the mixture was concentrated under reduced pressure to give a residue. The residue was triturated with water (3.00 mL×2) and filtered, the filter cake was collected and dried under reduced pressure to give 5-fluoro-1,3-benzodioxole-4-carbaldehyde oxime (200 mg, 1.09 mmol, 91.8% yield) as a white solid.

$^1$H NMR (400 MHz, DMSO-$d_6$) δ=11.68 (s, 1H), 8.08 (s, 1H), 6.91 (br dd, J=4.0, 8.4 Hz, 1H), 6.77-6.65 (m, 1H), 6.12 (s, 2H).

To a solution of 5-fluoro-1,3-benzodioxole-4-carbaldehyde oxime (280 mg, 2.07 mmol, 1.00 equiv) in methyl alcohol (3.00 mL) was added Pd/C (2.07 mmol, 10% purity, 1.00 equiv) and di-tert-butyl dicarbonate (906 mg, 4.15 mmol, 953 µL, 2.00 equiv). The mixture was stirred at 25° C. for 12 h under a hydrogen atmosphere (15 psi). The mixture was filtered and concentrated under reduced pressure to give a residue. The residue was purified by column chromatography (SiO$_2$, petroleum ether/ethyl acetate=1/0 to 2/1) to afford tert-butyl N-[(5-fluoro-1,3-benzodioxol-4-yl)methyl]carbamate (350 mg, 1.71 mmol, 82.3% yield) as a white solid. LCMS [M−55]: 214.1.

To a solution of tert-butyl ((5-fluorobenzo[d][1,3]dioxol-4-yl)methyl)carbamate (85.0 mg, 316 µmol, 1.00 equiv) in DCM (1.00 mL) was added TFA (0.30 mL). The mixture was stirred at 25° C. for 0.5 h. The reaction mixture was neutralized with saturated aq potassium carbonate (5.00 mL) and stirred for 30 min. The aqueous phase was extracted with DCM (5.00 mL×2). The combined organic phase was washed with brine (5.00 mL×2), dried with anhydrous sodium sulfate, filtered and concentrated under reduced pressure to give (5-fluorobenzo[d][1,3]dioxol-4-yl)methanamine (45.0 mg, 266 µmol, 84.3% yield) as a yellow oil.

$^1$H NMR (400 MHz, CDCl$_3$) δ=6.63 (dd, J=4.4, 8.4 Hz, 1H), 6.52 (dd, J=8.4, 10.4 Hz, 1H), 6.00 (s, 2H), 3.89 (s, 2H).

Intermediate C-1

An exemplary Intermediate C, Intermediate C-1, may be used to synthesize compounds of formula I wherein Z is O, n is one, X is C(R$^5$)$_2$, ===== is a single bond and one R$^3$ is fluorine. A mixture of ethyl 8-bromo-5-chloro-imidazo[1,2-c]pyrimidine-2-carboxylate (380 mg, 1.25 mmol, 1.00 equiv), (5-fluoro-2,3-dihydrobenzofuran-4-yl)methanamine (250.34 mg, 1.50 mmol, 1.20 equiv), DIEA (322 mg, 2.50 mmol, 434 uL, 2.00 equiv) in DMF (3.00 mL) was purged with nitrogen and was stirred at 85° C. for 0.5 h. To this mixture was added water (10.0 mL) and ethyl acetate (8.00 mL). The biphasic mixture was filtered to remove a solid impurity and the organic layer was concentrated in vacuo to provide ethyl 8-bromo-5-(((5-fluoro-2,3-dihydrobenzofuran-4-yl)methyl)amino)imidazo[1,2-c]pyrimidine-2-carboxylate (443 mg, 1.02 mmol, 81.5% yield) as a white solid.

$^1$H NMR (400 MHz, DMSO-$d_6$) δ=8.87 (s, 1H), 8.50 (t, J=4.8 Hz, 1H), 7.90 (s, 1H), 6.93 (t, J=9.6 Hz, 1H), 6.69 (dd, J=4.0, 8.8 Hz, 1H), 4.65 (d, J=4.8 Hz, 2H), 4.52 (t, J=8.8 Hz, 2H), 4.32 (q, J=7.2 Hz, 2H), 3.25 (t, J=8.8 Hz, 2H), 1.32 (t, J=7.2 Hz, 3H).

Intermediate C-2

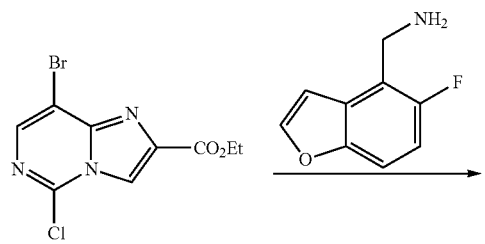

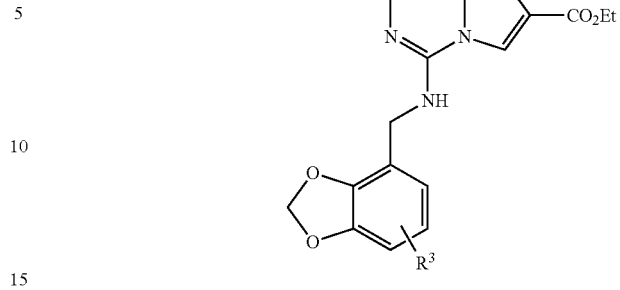

A second exemplary Intermediate C, Intermediate C-2, may be used to synthesize compounds of formula I wherein Z is O, n is one, X is $CR^5$, ===== is a double bond and one $R^3$ is fluorine. A mixture of 8-bromo-5-chloro-imidazo[1,2-c]pyrimidine-2-carboxylate (160 mg, 525 μmol, 1.00 equiv), (5-fluorobenzofuran-4-yl)methanamine (116 mg, 630 μmol, 1.20 equiv) and DIEA (136 mg, 1.05 mmol, 183 uL, 2.00 equiv) in DMF (2.00 mL) was stirred at 85° C. for 0.5 h under a nitrogen atmosphere. The reaction mixture was concentrated under reduced pressure to give a residue. The crude material was purified by column chromatography (petroleum ether/ethyl acetate, 0/1 to 2/1) to afford ethyl 8-bromo-5-(((5-fluorobenzofuran-4-yl)methyl)amino)imidazo[1,2-c]pyrimidine-2-carboxylate (180 mg, 78.2% yield) as a brown solid. LCMS [M+1]: 433.1.

$^1$H NMR (400 MHz, CD3OD) δ=8.63 (s, 1H), 7.92 (s, 1H), 7.80 (d, J=2.0 Hz, 1H), 7.45 (dd, J=3.6, 8.8 Hz, 1H), 7.13-7.07 (m, 1H), 7.06 (d, J=1.2 Hz, 1H), 5.04 (s, 2H), 4.38 (q, J=6.8 Hz, 2H), 1.38 (t, J=7.2 Hz, 3H).

Intermediate C-3

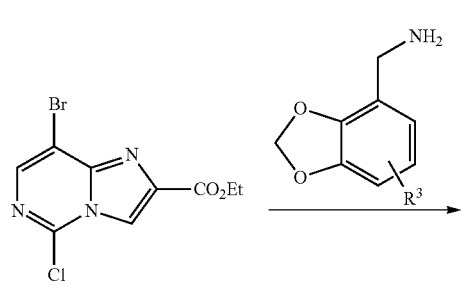

A third exemplary Intermediate C, Intermediate C-3, may be used to synthesize compounds of formula I wherein Z is O, n is one, X is O, and ===== is a single bond. To a solution of ethyl 8-bromo-5-chloro-imidazo[1,2-c]pyrimidine-2-carboxylate (103 mg, 328 μmol, 1.00 equiv), 1,3-benzodioxol-4-ylmethanamine (54.6 mg, 361 μmol, 1.10 equiv) in DMF (2.00 mL) was added DIEA (42.4 mg, 328 μmol, 57.2 uL, 1.00 equiv). The resultant mixture was stirred at 85° C. for 1 h and was subsequently concentrated to afford the crude material. The residue was washed with water (3.00 mL×2) to provide ethyl 5-((benzo[d][1,3]dioxol-4-ylmethyl)amino)-8-bromoimidazo[1,2-c]pyrimidine-2-carboxylate (120 mg, 286.24 μmol, 87.2% yield) as a brown solid. LCMS: [M+1] 421.2.

$^1$H NMR (400 MHz DMSO-$d_6$) δ=8.87 (s, 1H), 8.65 (br s, 1H), 7.88 (s, 1H), 6.90-6.77 (m, 3H), 6.03 (s, 2H), 4.66 (d, J=4.8 Hz, 2H), 4.36-4.31 (m, 2H), 1.33 (t, J=7.2 Hz, 3H).

Intermediate C-4

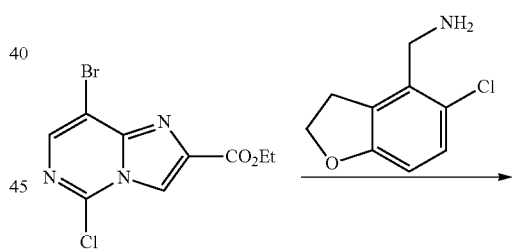

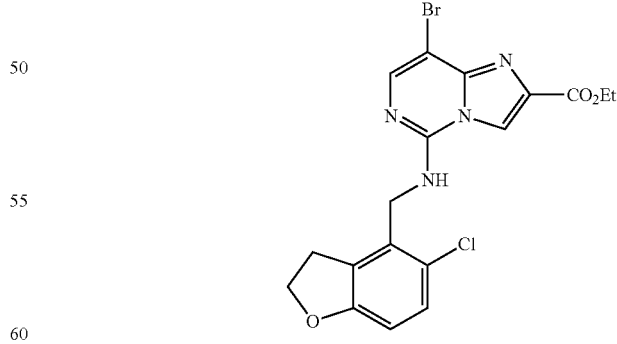

A fourth exemplary Intermediate C, Intermediate C-4, may be used to synthesize compounds of formula I wherein Z is O, n is one, X is $C(R^5)_2$, ===== is a single bond and one $R^3$ is chlorine. To a solution of ethyl 8-bromo-5-chloro-imidazo[1,2-c]pyrimidine-2-carboxylate (230 mg, 755 μmol, 1.00 equiv), (5-chloro-2,3-dihydrobenzofuran-4-yl)

methanamine (118 mg, 642 μmol, 0.850 equiv) in DMF (2.00 mL) was added DIEA (195 mg, 1.51 mmol, 263 μL, 2.00 equiv) and the reaction mixture was stirred at 85° C. for 1 h. The solution was concentrated in vacuo to give the crude material, which was purified by prep-TLC (petroleum ether/ethyl acetate=1/1) to afford ethyl 8-bromo-5-(((5-chloro-2,3-dihydrobenzofuran-4-yl)methyl)amino)imidazo[1,2-c]pyrimidine-2-carboxylate (320 mg) as a brown solid. LCMS: [M+3] 453.1.

Intermediate C-4A

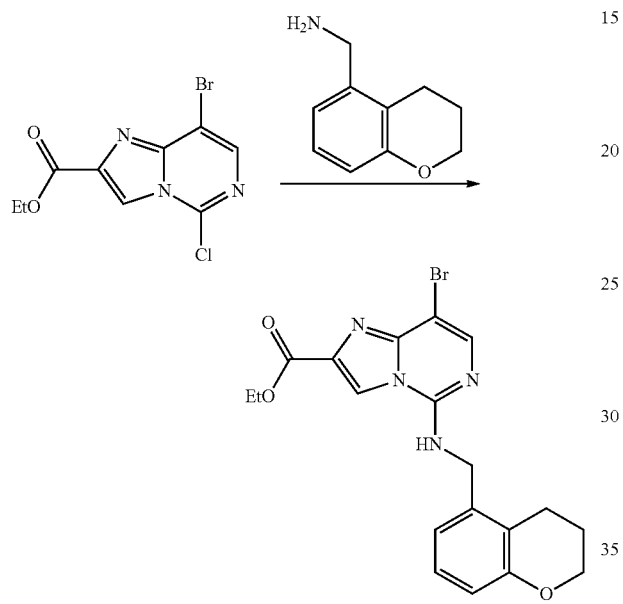

Another Intermediate C, Intermediate C-4A, may be used to synthesize compounds of formula I wherein Z is O, n is two, X is C(R⁵)₂, and $=====$ is a single bond. To a solution of ethyl 8-bromo-5-chloro-imidazo[1,2-c]pyrimidine-2-carboxylate (250 mg, 802 μmol, 1.00 eq.) in DMF (3.00 mL) was added DIPEA (207 mg, 1.60 mmol, 279 μL, 2.00 eq.) and chroman-5-ylmethanamine (170 mg, 1.04 mmol, 1.30 eq.). The mixture was stirred at 85° C. for 30 min. The reaction mixture was diluted with water (40 mL) and filtered. The solid was dried under vacuum to afford ethyl 8-bromo-5-((chroman-5-ylmethyl)amino)imidazo[1,2-c]pyrimidine-2-carboxylate (320 mg, 742 μmol, 92.5% yield) as a yellow solid. LC-MS: [M+1]433.3.

Intermediate C-4B

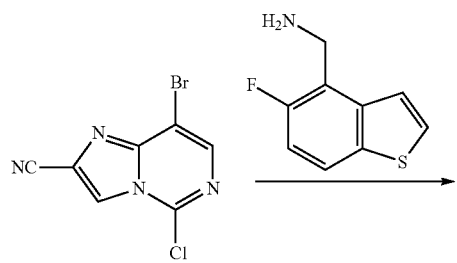

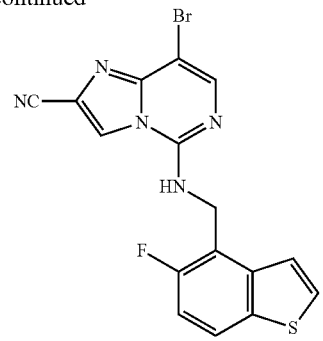

Yet another exemplary Intermediate C, Intermediate C-4B, may be used to synthesize compounds of formula I wherein Z is S, n is one, X is C(R⁵)₂, $=====$ is a single bond and one R³ is fluorine. To a solution of (5-fluorobenzothiophen-4-yl)methanamine (39.4 mg, 218 μmol, 1.40 eq.) and 8-bromo-5-chloro-imidazo[1,2-c]pyrimidine-2-carbonitrile (40.0 mg, 155 μmol, 1.00 eq.) in DMF (2.00 mL) was added DIEA (60.2 mg, 466 μmol, 81.2 μL, 3.00 eq.). The reaction mixture was stirred at 85° C. for 1 h. The mixture was diluted with ethyl acetate (10.0 mL), washed with brine (10.0 mL×2), dried with anhydrous sodium sulfate, filtered and concentrated in vacuo to afford the crude residue. The crude material was purified by prep-TLC (petroleum ether/ethyl acetate=1/1) to give 8-bromo-5-((5-fluorobenzo[b]thiophen-4-yl)amino)imidazo[1,2-c]pyrimidine-2-carbonitrile (35.0 mg, 87.0 μmol, 56.0% yield) as a brown solid. LCMS [M+1]: 404.0.

Intermediate C-5

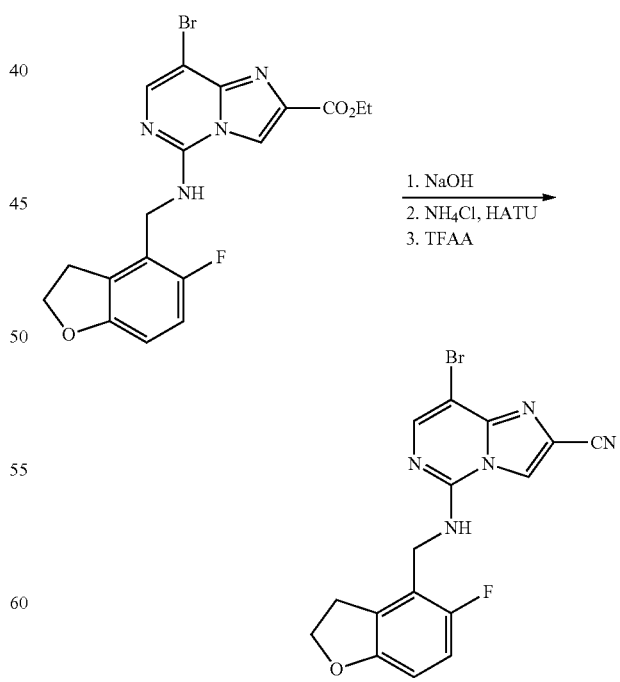

A fifth exemplary Intermediate C, Intermediate C-5, may be used to synthesize compounds of formula I wherein Z is O, n is one, X is C(R⁵)₂, $=====$ is a single bond and one R³ is fluorine. A mixture of ethyl 8-bromo-5-(((5-fluoro-2,3-dihydrobenzofuran-4-yl)methyl)amino)imidazo[1,2-c]pyrimidine-2-carboxylate (160 mg, 367 µmol, 1 equiv) and sodium hydroxide (1 M, 1.10 mL, 3 equiv) in methanol (3.30 mL) was stirred at 55° C. for 0.5 h under an atmosphere of nitrogen. The mixture was concentrated in vacuo and the residue was diluted with water (1.00 mL). The pH was adjusted to pH=2 with HCl (1 M) and the solid was collected by filtration. The resultant solid was dried under reduced pressure to afford 8-bromo-5-(((5-fluoro-2,3-dihydrobenzofuran-4-yl)methyl)amino)imidazo[1,2-c]pyrimidine-2-carboxylic acid (124 mg, 304 µmol, 82.8% yield) as a white solid. LC-MS: [M+1] 408.8.

A mixture of 8-bromo-5-(((5-fluoro-2,3-dihydrobenzofuran-4-yl)methyl)amino)imidazo[1,2-c]pyrimidine-2-carboxylic acid (124 mg, 304 µmol, 1.00 equiv), ammonium chloride (48.8 mg, 913 µmol, 3.00 equiv). HATU (173 mg, 1.50 equiv), DIEA (314 mg, 2.44 mmol, 424 uL, 8 equiv) in DMF (1.00 mL) was stirred at 30° C. for 1 h under an atmosphere of nitrogen. Subsequently, the mixture was concentrated in vacuo. To the crude material was added water (1.00 mL) and the resultant solid was collected by filtration. The solid was dried under reduced pressure to provide 8-bromo-5-(((5-fluoro-2,3-dihydrobenzofuran-4-yl)methyl)amino)imidazo[1,2-c]pyrimidine-2-carboxamide (100 mg) as a white solid, which was used without further purification.

To a mixture of 8-bromo-5-(((5-fluoro-2,3-dihydrobenzofuran-4-yl)methyl)amino)imidazo[1,2-c]pyrimidine-2-carboxamide (100 mg, 246 µmol, 1.00 equiv), TEA (484 mg, 4.79 mmol, 666 uL, 19.4 equiv) in THF (2.00 mL) was added TFAA (302 mg, 1.44 mmol, 200 uL, 5.84 equiv) at 0° C. Subsequently, the mixture was stirred at 0-30° C. for 40 min under an atmosphere of nitrogen. The mixture was concentrated to provide the crude residue, which was purified by column chromatography (petroleum ether/ethyl acetate, 5/1 to 0/1) to afford 8-bromo-5-(((5-fluoro-2,3-dihydrobenzofuran-4-yl)methyl)amino)imidazo[1,2-c]pyrimidine-2-carbonitrile (100 mg, 245 µmol, 99.7% yield) as a yellow solid. LC-MS: [M+1] 387.8.

Alternatively, Intermediate C-5 may be prepared as follows:

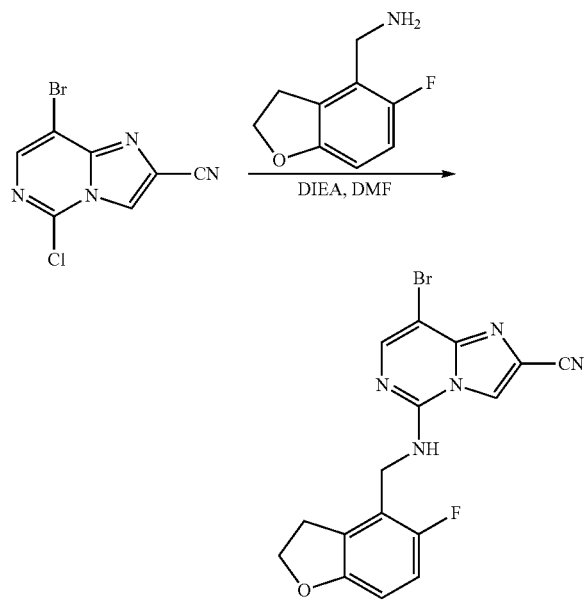

To a solution of 8-bromo-5-chloro-imidazo[1,2-c]pyrimidine-2-carbonitrile (3.00 g, 11.7 mmol, 1.00 equiv) and (5-fluoro-2,3-dihydrobenzofuran-4-yl) methanamine (2.14 g, 12.8 mmol, 1.10 equiv) in DMF (30.0 mL) was added DIEA (3.01 g, 23.3 mmol, 4.06 mL, 2.00 equiv). The resultant mixture was stirred at 85° C. for 1 h, cooled to rt, and poured into water (100 mL). The mixture was extracted with ethyl acetate (50.0 mL×3). The combined organic phase was washed with brine (50.0 mL×2), dried with anhydrous sodium sulfate, filtered and concentrated to give a residue. The residue was purified by silica gel chromatography (petroleum ether/ethyl acetate=10/1 to 1/1) to afford 8-bromo-5-(((5-fluoro-2,3-dihydrobenzofuran-4-yl)methyl)amino)imidazo[1,2-c]pyrimidine-2-carbonitrile (4.00 g, 10.3 mmol, 88.4% yield) as a yellow solid. LCMS [M+1]: 390.1.

Intermediate C-6

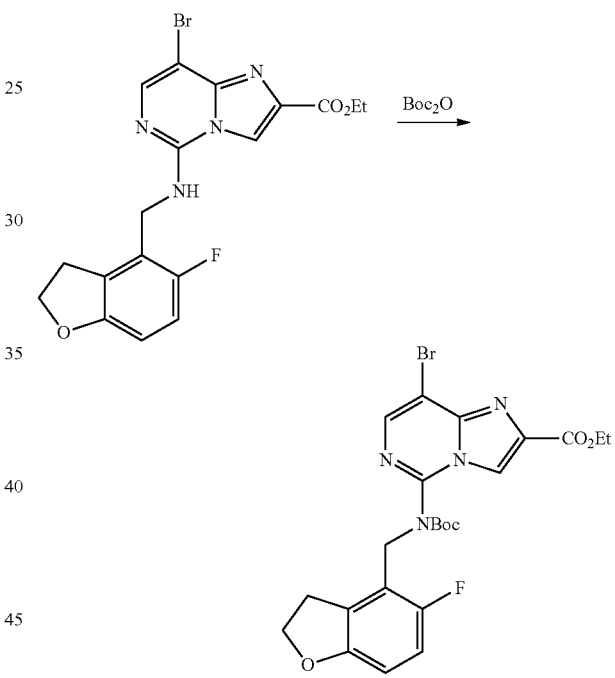

A sixth exemplary Intermediate C, Intermediate C-6 may be used to synthesize compounds of formula I wherein Z is O, n is one, X is C(R⁵)₂, ----- is a single bond and one R³ is fluorine. A mixture of ethyl 8-bromo-5-(((5-fluoro-2,3-dihydrobenzofuran-4-yl)methyl)amino)imidazo[1,2-c]pyrimidine-2-carboxylate (204 mg, 460 µmol, 1.00 equiv), di-tert-butyl dicarbonate (201 mg, 919 µmol, 2.00 equiv), 4-(dimethylamino)pyridine (561 ug, 4.60 µmol, 0.01 equiv) in tetrahydrofuran (2.00 mL) was purged with nitrogen and subsequently allowed to stir at 25° C. for 2 h under an atmosphere of nitrogen. The mixture was diluted with water (3.00 mL) and extracted with ethyl acetate (2.00 mL×3). The combined organic layers were washed with brine (2.00 mL×3), dried over anhydrous sodium sulfate, filtered and concentrated under reduced pressure to provide a residue. The crude material was purified by prep-TLC (SiO2, petroleum ether/ethyl acetate, 3/1) to afford ethyl 8-bromo-5-((tert-butoxycarbonyl)((5-fluoro-2,3-dihydrobenzofuran-4- yl)methyl)amino)imidazo[1,2-c]pyrimidine-2-carboxylate (160 mg, 198 μmol, 43.0% yield, 66.2% purity) as a white solid. LC-MS [M+1]: 537.2.

$^1$H NMR (400 MHz, CDCl$_3$) δ=8.11 (s, 1H), 7.93 (s, 1H), 6.67-6.61 (m, 1H), 6.59-6.54 (m, 1H), 5.08 (s, 2H), 4.58 (t, J=8.8 Hz, 2H), 4.47 (q, J=7.2 Hz, 2H), 3.32 (br t, J=8.8 Hz, 2H), 1.43 (t, J=7.2 Hz, 3H), 1.36 (s, 9H).

Intermediate C-7

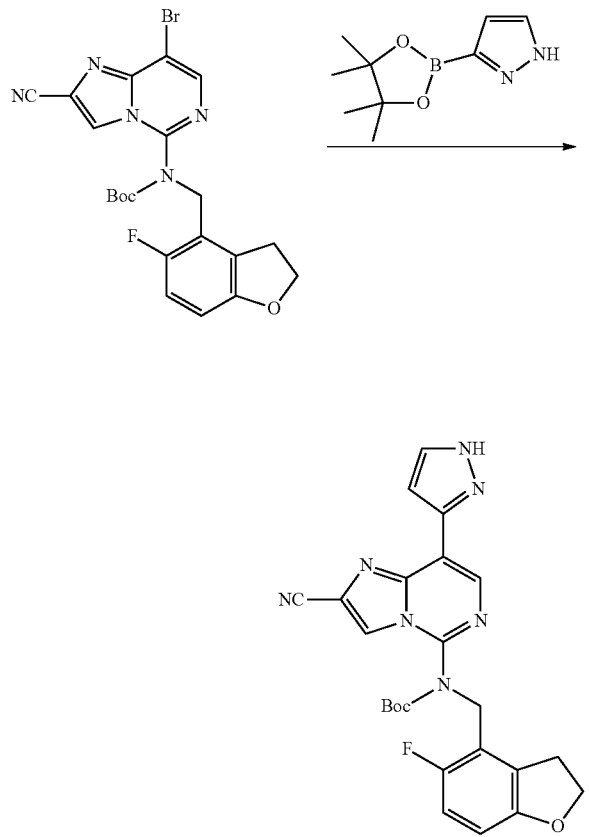

A seventh exemplary Intermediate C, Intermediate C-7, may be used to synthesize compounds of formula I wherein Z is O, n is one, X is C(R$^5$)$_2$, ===== is a single bond, one R$^3$ is fluorine and R$^1$ is heteroaryl which may then be further substituted with one or more R$^4$. To a solution of tert-butyl (8-bromo-2-cyanoimidazo[1,2-c]pyrimidin-5-yl)((5-fluoro-2,3-dihydrobenzofuran-4-yl)methyl)carbamate (500 mg, 1.01 mmol, 1.00 eq.), 3-(4,4,5,5-tetramethyl-1,3,2-dioxaborolan-2-yl)-1H-pyrazole (295 mg, 1.52 mmol, 1.50 eq.) and sodium bicarbonate (170 mg, 2.03 mmol, 2.00 eq.) in a mixture of dioxane (4.00 mL) and water (0.80 mL) was added Pd(dppf)Cl$_2$ (80.0 mg, 109 μmol, 0.01 eq). The mixture was purged with nitrogen and stirred at 105° C. for 2 h. The reaction mixture was cooled to rt and filtered through a pad of Celite. The filtrate was concentrated to give a residue. The residue was purified by prep-TLC (SiO$_2$, dichloromethane/methanol=10/1) to afford tert-butyl (2-cyano-8-(1H-pyrazol-3-yl)imidazol[1,2-c]pyrimidin-5-yl)((5-fluoro-2,3-dihydrobenzofuran-4-yl)methyl)carbamate (120 mg, 230 μmol, 22.7% yield, 91% purity) as a yellow solid.

Intermediate C-8

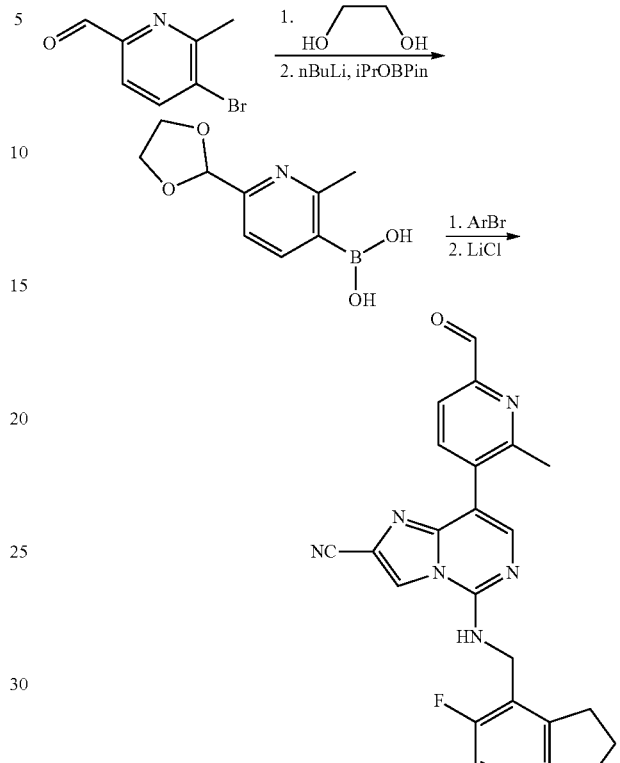

An eighth exemplary Intermediate C, Intermediate C-8, may be used to synthesize compounds of formula I wherein Z is O, n is one, X is C(R$^5$)$_2$, ===== is a single bond, one R$^3$ is fluorine and R$^1$ is heteroaryl which is substituted two R$^4$ groups, one of which serves as an intermediate to generate various R$^4$ groups, e.g., L-N(R$^5$)$_2$. To a solution of 5-bromo-6-methyl-pyridine-2-carbaldehyde (300 mg, 1.50 mmol, 1.00 eq.) in toluene (10.0 mL) was added TsOH.H$_2$O (28.5 mg, 150 μmol, 0.10 eq.) and ethylene glycol (186 mg, 3.00 mmol, 168 μL, 2.00 eq.). The mixture was stirred at 120° C. for 2 h. The reaction mixture was concentrated in vacuo. The residue was purified by prep-TLC (SiO$_2$ petroleum ether/ethyl acetate=1/1) to give compound 3-bromo-6-(1,3-dioxolan-2-yl)-2-methyl-pyridine (260 mg, 1.07 mmol, 71.0% yield) as a yellow oil.

To a solution of 3-bromo-6-(1,3-dioxolan-2-yl)-2-methyl-pyridine (0.30 g, 1.23 mmol, 1.00 eq.) in Et$_2$O (15.0 mL) was added n-BuLi (2.50 M, 737 μL, 1.50 eq.) dropwise at −78° C. The mixture was stirred at −78° C. for 30 min prior to the addition of 2-isopropoxy-4,4,5,5-tetramethyl-1,3,2-dioxaborolane (457 mg, 2.46 mmol, 501 μL, 2.00 eq.). The mixture was stirred at −78° C. for an additional hour. The reaction mixture was quenched with water (2.00 mL) and the resulting mixture was extracted with ethyl acetate (30.0 mL×2). The combined organic phase was dried over sodium sulfate, filtered and concentrated in vacuo. The residue was purified by prep-TLC (SiO$_2$, petroleum ether/ethyl acetate=1/1) to give [6-(1,3-dioxolan-2-yl)-2-methyl-3-pyridyl]boronic acid (160 mg, 766 μmol, 62.3% yield) as yellow oil. LC-MS [M+1]: 209.9.

A mixture of 8-bromo-5-(((5-fluoro-2,3-dihydrobenzofuran-4-yl)methyl)amino)imidazo[1,2-c]pyrimidine-2-carbonitrile (0.20 g, 515 µmol, 1.00 eq.), [6-(1,3-dioxolan-2-yl)-2-methyl-3-pyridyl]boronic acid (162 mg, 773 µmol, 1.50 eq.), sodium bicarbonate (130 mg, 1.55 mmol, 3.00 eq.) and Pd(dppf)Cl₂ (56.6 mg, 77.3 µmol, 0.15 eq.) in water (0.60 mL) and dioxane (1.80 mL) was purged with nitrogen and the resultant mixture was stirred at 100° C. for 2 h. The reaction mixture was filtered and concentrated in vacuo. The residue was purified by prep-TLC (SiO₂, dichloromethane:methanol=20:1) to give 8-(6-(1,3-dioxolan-2-yl)-2-methylpyridin-3-yl)-5-(((5-fluoro-2,3-dihydrobenzofuran-4-yl)methyl)amino)imidazo[12-c]pyrimidine-2-carbonitrile (150 mg, 317 µmol, 61.6% yield) as a yellow oil. LC-MS [M+1]: 473.3.

To a solution of 8-(6-(1,3-dioxolan-2-yl)-2-methylpyridin-3-yl)-5-(((5-fluoro-2,3-dihydrobenzofuran-4-yl)methyl)amino)imidazo[1,2-c]pyrimidine-2-carbonitrile (120 mg, 254 µmol, 1.00 eq.) in DMSO (3.00 mL) and water (0.30 mL) was added lithium chloride (53.8 mg, 1.27 mmol, 5.00 eq.) and the mixture was stirred at 130° C. for 3 h. The mixture was cooled to rt and diluted with water (15.0 mL). The mixture was extracted with ethyl acetate (20.0 mL×3) and the combined organic phase was washed with brine (20.0 mL×2), dried with anhydrous sodium sulfate, filtered and concentrated in vacuo to give 5-(((5-fluoro-2,3-dihydrobenzofuran-4-yl)methyl)amino)-8-(6-formyl-2-methylpyridin-3-yl)imidazo[1,2-c]pyrimidine-2-carbonitrile (100 mg, 233 µmol, 91.9% yield) as a brown solid. LC-MS [M+1]: 429.1.

Intermediate C-9

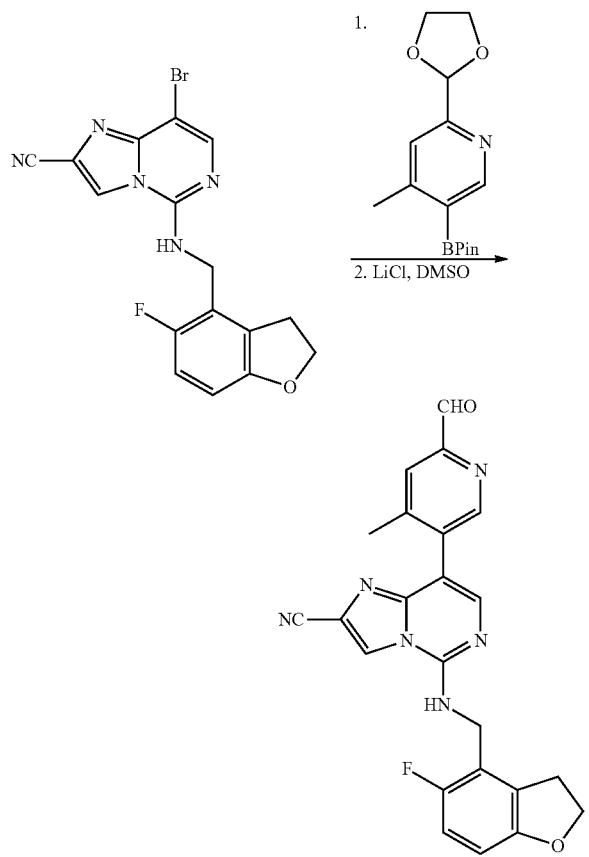

To a solution of 2-(1,3-dioxolan-2-yl)-4-methyl-5-(4,4,5,5-tetramethyl-1,3,2-dioxaborolan-2-yl)pyridine (45.0 mg, 155 µmol, 1.00 equiv), 8-bromo-5-(((5-fluoro-2,3-dihydrobenzofuran-4-yl)methyl)amino)imidazo[1,2-c]pyrimidine-2-carbonitrile (60.0 mg, 155 µmol, 1.00 equiv) in dioxane (1.00 mL) and water (0.30 mL) was added Pd(dppf)Cl₂ (11.3 mg, 15.5 µmol, 0.10 equiv) and sodium bicarbonate (26.0 mg, 309 µmol, 2.00 equiv) under a nitrogen atmosphere. The mixture was stirred at 100° C. for 1 h. The mixture was concentrated in vacuo to provide the crude residue. The residue was purified by prep-TLC (petroleum ether/ethyl acetate=0/1) to afford 5-(((5-fluoro-2,3-dihydrobenzofuran-4-yl)methyl)amino)-8-(6-formyl-4-methylpyridin-3-yl)imidazo[1,2-c]pyrimidine-2-carbonitrile (32.0 mg, 67.7 µmol, 43.8% yield) as a yellow solid. LCMS [M+1]: 473.2.

Intermediate C-10

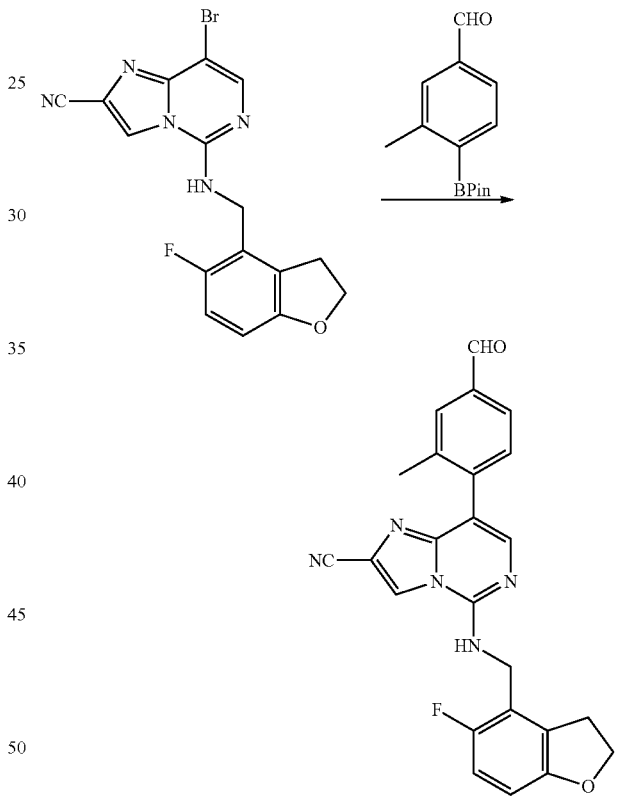

A mixture of (4-formyl-2-methyl-phenyl)boronic acid (80.0 mg, 488 µmol, 1.50 eq), 8-bromo-5-(((5-fluoro-2,3-dihydrobenzofuran-4-yl)methyl)amino)imidazo[1,2-c]pyrimidine-2-carbonitrile (126 mg, 325 µmol, 1.00 eq.), sodium bicarbonate (54.7 mg, 651 µmol, 2.00 eq.) and Pd(dppf)Cl₂ (23.8 mg, 32.5 µmol, 0.10 eq.) in dioxane (1.00 mL) and water (0.30 mL) was purged with nitrogen 3 times and subsequently stirred at 100° C. for 2 h under a nitrogen atmosphere. The reaction mixture was diluted with water (10.0 mL) and extracted with ethyl acetate (10.0 mL×3). The combined organic layer was washed with brine (20.0 mL), dried over anhydrous sodium sulfate, filtered and concentrated under reduced pressure to provide a residue. The residue was purified by prep-TLC (dichloromethane/methanol=10/1) to afford 5-(((5-fluoro-2,3-dihydrobenzofuran-4-yl)methyl)amino)-8-(4-formyl-2-methylphenyl)imidazo[1,2-c]pyrimidine-2-carbonitrile (74 mg, crude) as a yellow solid.

$^1$H NMR (400 MHz, DMSO-d6) δ10.04 (s, 1H), 8.93 (s, 1H), 8.55 (t, J=4.8 Hz, 1H), 7.85 (s, 1H), 7.82-7.77 (m, 2H), 7.54 (d, J=7.6 Hz, 1H), 7.01-6.90 (m, 1H), 6.71 (dd, J=4.0, 8.8 Hz, 1H), 4.73 (d, J=4.4 Hz, 2H), 4.55 (t, J=8.8 Hz, 2H), 3.38-3.32 (m, 2H), 2.27 (s, 3H).

Intermediate C-11

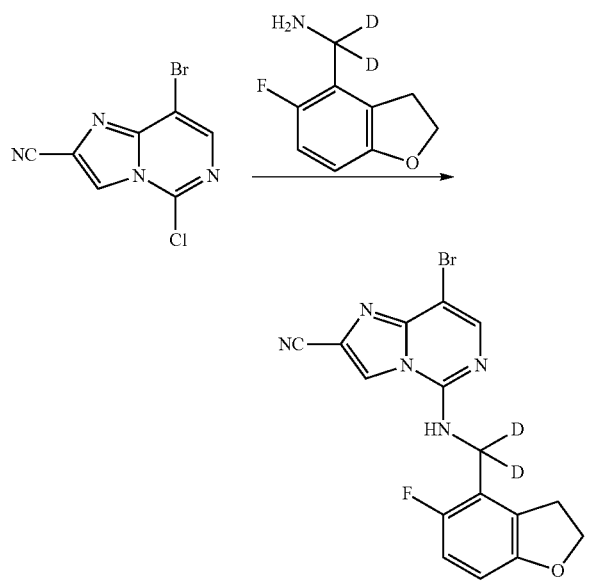

To a solution of (5-fluoro-2,3-dihydrobenzofuran-4-yl)methan-d2-amine (50.0 mg, 284 μmol, 1.00 equiv), 8-bromo-5-chloroimidazo[1,2-c]pyrimidine-2-carbonitrile (73.1 mg, 284 μmol, 1.00 equiv) in DMF (1.00 mL) was added DIEA (110 mg, 851 μmol, 148 μL, 3.00 equiv). The mixture was stirred at 85° C. for 1 h. The reaction mixture was diluted with water (1.00 mL) and extracted with ethyl acetate (1.00 mL×3). The combined organic layer was washed with brine (3.00 mL×2), dried over sodium sulfate, filtered and concentrated under reduced pressure to afford 8-bromo-5-(((5-fluoro-2,3-dihydrobenzofuran-4-yl)methyl-d2)amino)imidazo[1,2-c]pyrimidine-2-carbonitrile (20.0 mg, crude) as a white solid. LCMS [M+1]: 390.0.

Intermediate C-12

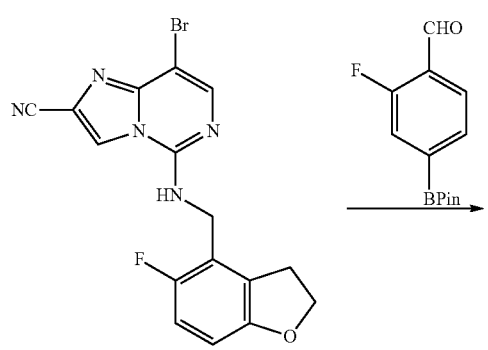

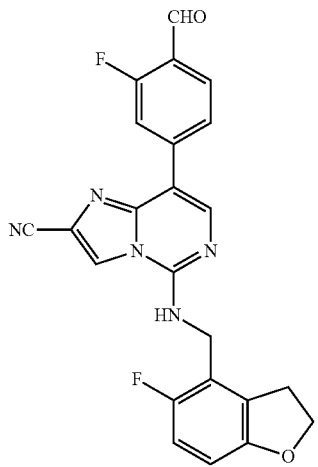

A mixture of (3-fluoro-4-formyl-phenyl)boronic acid (80.0 mg, 476 μmol, 1.50 equiv), 8-bromo-5-(((5-fluoro-2,3-dihydrobenzofuran-4-yl)methyl)amino)imidazo[1,2-c]pyrimidine-2-carbonitrile (123 mg, 318 μmol, 1.00 equiv), sodium bicarbonate (53.4 mg, 635 μmol, 2.00 equiv) and Pd(dppf)Cl$_2$ (23.2 mg, 31.8 μmol, 0.10 equiv) in dioxane (1.00 mL) and water (0.30 mL) was purged with nitrogen and subsequently allowed to stir at 100° C. for 2 h under a nitrogen atmosphere. The reaction mixture was diluted with water (10.0 mL) and extracted with ethyl acetate (10.0 mL×3). The combined organic layer was washed with brine (20.0 mL), dried over anhydrous sodium sulfate, filtered and concentrated under reduced pressure to provide a residue that was purified by prep-TLC (dichloromethane/methanol=10/1) to afford 5-[(5-fluoro-2,3-dihydrobenzofuran-4-yl) methylamino]-8-(3-fluoro-4-formyl-phenyl)imidazo[1,2-c]pyrimidine-2-carbonitrile (87.0 mg, crude) as a yellow solid.

$^1$H NMR (400 MHz, DMSO-d$_6$) δ=10.24 (s, 1H), 8.97 (s, 1H), 8.81 (t, J=5.2 Hz, 1H), 8.44 (s, 1H), 8.22-8.16 (m, 2H), 7.95-7.91 (m, 1H), 6.99-6.93 (m, 1H), 6.72 (dd, J=4.0, 8.8 Hz, 1H), 4.77 (d, J=4.8 Hz, 2H), 4.56 (t, J=8.8 Hz, 2H), 3.36-3.33 (m, 2H).

Intermediate C-13

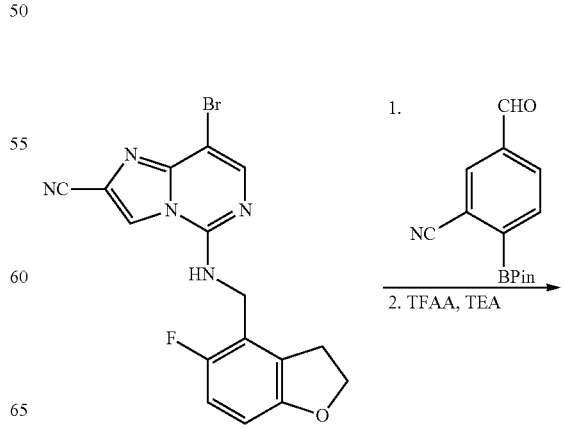

-continued

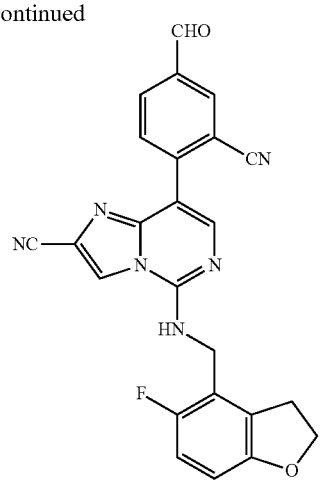

Intermediate C-14

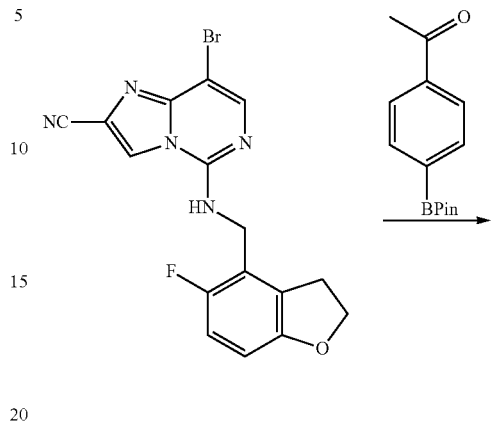

A mixture of 5-formyl-2-(4,4,5,5-tetramethyl-1,3,2-dioxaborolan-2-yl)benzonitrile (100 mg, 388 μmol, 1.00 equiv), 8-bromo-5-(((5-fluoro-2,3-dihydrobenzofuran-4-yl)methyl)amino)imidazo[1,2-c]pyrimidine-2-carbonitrile (31.7 mg, 81.7 μmol, 0.21 equiv), Pd(dppf)Cl$_2$ (28.5 mg, 38.9 μmol, 0.10 equiv) and sodium bicarbonate (98.0 mg, 1.17 mmol, 3.00 equiv) in dioxane (1.50 mL) and water (0.30 mL) was purged with nitrogen and subsequently stirred at 95° C. for 2 h. The reaction mixture was filtered and concentrated under reduced pressure to give a residue. The residue was purified by prep-TLC (petroleum ether/ethyl acetate=1/1) to afford 2-(2-cyano-5-(((5-fluoro-2,3-dihydrobenzofuran-4-yl)methyl)amino)imidazo[1,2-c]pyrimidin-8-yl)-5-formylbenzamide (70 mg, 31.5% yield, 80% purity) as a yellow solid. LCMS [M+1]: 457.2.

$^1$H NMR (400 MHz, DMSO-d$_6$) δ=10.09 (s, 1H), 8.92 (s, 1H), 8.60 (br s, 1H), 8.06 (s, 1H), 8.03 (br d, J=8.4 Hz, 1H), 7.93 (br s, 1H), 7.88-7.77 (m, 2H), 7.38 (br s, 1H), 6.95 (br t, J=9.2 Hz, 1H), 6.71 (dd, J=3.6, 8.4 Hz, 1H), 4.72 (br s, 2H), 4.55 (br t, J=8.8 Hz, 2H), 3.53-3.48 (m, 2H).

To a solution of 2-(2-cyano-5-(((5-fluoro-2,3-dihydrobenzofuran-4-yl)methyl)amino)imidazo[1,2-c]pyrimidin-8-yl)-5-formylbenzamide (70.0 mg, 123 μmol, 1.00 equiv) in THF (1.00 mL) was added TEA (248 mg, 2.45 mmol, 341 μL, 20.0 equiv) followed by TFAA (258 mg, 1.23 mmol, 171 μL, 10 equiv) dropwise at 0° C. The mixture was stirred at 25° C. for 2 h and was subsequently concentrated under reduced pressure. The resultant residue was diluted with dichloromethane (6 mL) and the combined organic layer was washed with brine (3 mL×2), dried over sodium sulfate, filtered and concentrated under reduced pressure to give a residue. The residue was purified by prep-TLC (ethyl acetate) to afford 8-(2-cyano-4-formylphenyl)-5-(((5-fluoro-2,3-dihydrobenzofuran-4-yl)methyl)amino)imidazo[1,2-c]pyrimidine-2-carbonitrile (30.0 mg, 50.2% yield, 90.0% purity) as a yellow solid.

$^1$H NMR (400 MHz, DMSO-d$_6$) δ=10.09 (s, 1H), 8.99 (s, 1H), 8.86 (br s, 1H), 8.50 (d, J=1.2 Hz, 1H), 8.26 (dd, J=1.6, 8.0 Hz, 1H), 8.14 (s, 1H), 8.07 (d, J=8.0 Hz, 1H), 6.96 (t, J=9.6 Hz, 1H), 6.72 (dd, J=4.0, 8.8 Hz, 1H), 4.77 (br s, 2H), 4.55 (t, J=8.8 Hz, 2H), 3.39-3.35 (m, 2H).

To a solution of 1-[4-(4,4,5,5-tetramethyl-1,3,2-dioxaborolan-2-yl) phenyl]ethanone (41.2 mg, 167 μmol, 1.30 equiv) and 8-bromo-5-(((5-fluoro-2,3-dihydrobenzofuran-4-yl)methyl)amino)imidazo[1,2-c]pyrimidine-2-carbonitrile (50.0 mg, 129 μmol, 1.00 equiv) in dioxane (1.00 mL) and water (0.20 mL) was added Pd(dppf)Cl$_2$ (9.42 mg, 12.9 μmol, 0.10 equiv) and sodium bicarbonate (21.6 mg, 258 μmol, 2.00 equiv). The mixture was purged with nitrogen and subsequently stirred at 100° C. for 1 h. The mixture was concentrated in vacuo to give a residue. The residue was purified by prep-TLC (petroleum ether/ethylacetate=1/1) to afford 8-(4-acetylphenyl)-5-(((5-fluoro-2,3-dihydrobenzofuran-4-yl)methyl)amino)imidazo[1,2-c]pyrimidine-2-carbonitrile (30.0 mg, 54.5% yield) as a yellow solid. LCMS [M+1]: 428.0.

$^1$H NMR (400 MHz, DMSO-d$_6$) δ=8.96 (s, 1H), 8.24 (s, 1H), 8.19 (d, J=8.4 Hz, 2H), 8.02 (d, J=8.8 Hz, 2H), 6.93 (t, J=9.2 Hz, 1H), 6.68 (dd, J=3.6, 8.4 Hz, 1H), 4.74 (s, 2H), 4.53 (t, J=8.4 Hz, 2H), 3.31-3.28 (m, 2H), 2.60 (s, 3H).

Intermediate C-15

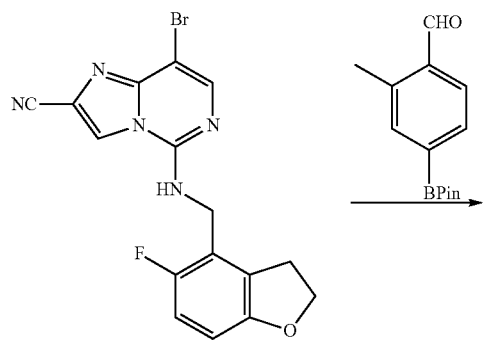

A mixture of 8-bromo-5-(((5-fluoro-2,3-dihydrobenzofuran-4-yl)methyl)amino)imidazo[1,2-c]pyrimidine-2-carbonitrile (50.0 mg, 129 µmol, 1.00 equiv), (4-formyl-3-methyl-phenyl)boronic acid (31.7 mg, 193 µmol, 1.50 equiv), sodium bicarbonate (21.6 mg, 258 µmol, 2.00 eq) and Pd(dppf)Cl$_2$·CH$_2$Cl$_2$ (10.5 mg, 12.9 µmol, 0.10 equiv) and in dioxane (1 mL) and water (0.30 mL) was purged with nitrogen and then stirred at 95° C. for 2 h. The reaction mixture was diluted with water (10.0 mL) and extracted with ethyl acetate (10.0 mL×3). The combined organic layer was washed with brine (20.0 mL), dried over anhydrous sodium sulfate, filtered and concentrated under reduced pressure to give a residue. The residue was purified by prep-TLC (petroleum ether/ethyl acetate=1/1) to afford 5-(((5-fluoro-2,3-dihydrobenzofuran-4-yl)methyl)amino)-8-(4-formyl-3-methylphenyl)imidazo[1,2-c]pyrimidine-2-carbonitrile (25.0 mg, 58.5 µmol, 45.4% yield) as a yellow solid.

$^1$H NMR (400 MHz, DMSO-d$_6$) δ=10.25 (s, 1H), 8.96 (s, 1H), 8.69 (br t, J=4.8 Hz, 1H), 8.29 (s, 1H), 8.12 (dd, J=1.2, 8.4 Hz, 1H), 8.01 (s, 1H), 7.91 (d, J=8.4 Hz, 1H), 6.96 (t, J=9.2 Hz, 1H), 6.71 (dd, J=4.0, 8.4 Hz, 1H), 4.76 (br d, J=4.8 Hz, 2H), 4.56 (t, 1=8.8 Hz, 2H), 3.31-3.29 (m, 2H), 2.70 (s, 3H).

Intermediate C-16

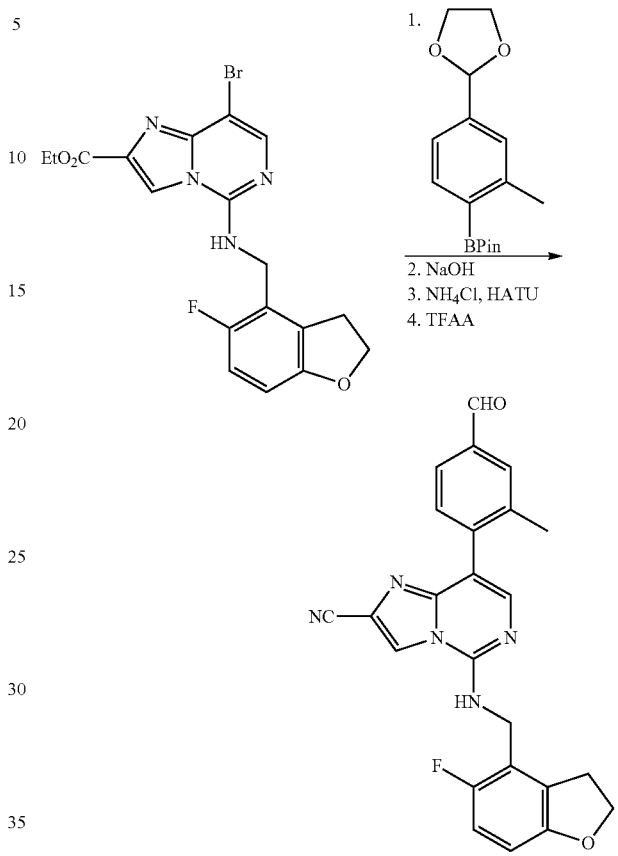

A mixture of ethyl 8-bromo-5-(((5-fluoro-2,3-dihydrobenzofuran-4-yl)methyl)amino)imidazo[1,2-c]pyrimidine-2-carboxylate (3.00 g, 6.89 mmol, 1.00 equiv), 2-[4-(1,3-dioxolan-2-yl)-2-methyl-phenyl]-4,4,5,5-tetramethyl-1,3,2-dioxaborolane (2.60 g, 8.96 mmol, 1.3 equiv), NaHCO$_3$ (1.74 g, 20.7 mmol, 3.00 equiv), Pd(dppf)Cl$_2$·CH$_2$Cl$_2$ (338 mg, 414 µmol, 0.06 equiv) in dioxane (35.0 mL) and H$_2$O (7.00 mL) was purged with N$_2$ and then stirred at 100° C. for 4 h. The reaction mixture was filtered and concentrated in vacuo. The residue was purified column chromatography (SiO$_2$, dichloromethane/methyl alcohol=100/1 to 30/1) to afford ethyl 8-(4-(1,3-dioxolan-2-yl)-2-methylphenyl)-5-(((5-fluoro-2,3-dihydrobenzofuran-4-yl)methyl)amino)imidazo[1,2-c]pyrimidine-2-carboxylate (1.70 g, 3.28 mmol, 47.6% yield) as a yellow solid. LCMS [M+1]: 519.2.

To a solution of ethyl 8-(4-(1,3-dioxolan-2-yl)-2-methylphenyl)-5-(((5-fluoro-2,3-dihydrobenzofuran-4-yl)methyl)amino)imidazo[1,2-c]pyrimidine-2-carboxylate (1.60 g, 3.09 mmol, 1.00 equiv) in methanol (16.0 mL) was added NaOH (1 M in water, 9.28 mL, 3.01 equiv) until the solution was adjusted to pH>12. The mixture was stirred at 50° C. for 2 h and was subsequently acidified to pH=6 with 1 M HC. The formed precipitate was filtered and dried under vacuum to give the crude product 8-(4-(1,3-dioxolan-2-yl)-2-methylphenyl)-5-(((5-fluoro-2,3-dihydrobenzofuran-4-yl)methyl)amino)imidazo[1,2-c]pyrimidine-2-carboxylic acid (1.55 g). LCMS [M+1]: 491.0.

To a solution of 8-(4-(1,3-dioxolan-2-yl)-2-methylphenyl)-5-(((5-fluoro-2,3-dihydrobenzofuran-4-yl)methyl)

amino)imidazo[1,2-c]pyrimidine-2-carboxylic acid (1.53 g, 3.12 mmol, 1.00 equiv) and ammonium chloride (536 mg, 10.0 mmol, 3.21 equiv) in DMF (15 mL) was added HATU (1.77 g, 4.67 mmol, 1.50 equiv) and DIEA (1.21 g, 9.35 mmol, 1.63 mL, 3.00 equiv). The mixture was stirred at 25° C. for 1 h and was subsequently diluted with water (20.0 mL). The suspension was filtered and the solid was dried under reduced pressure to give the crude product. The crude product diluted with water (60.0 mL) and extracted with ethyl acetate (60.0 mL×2). The combined organic layer was washed with brine (80.0 mL), dried over anhydrous sodium sulfate and concentrated under reduced pressure to afford 8-(4-(1,3-dioxolan-2-yl)-2-methylphenyl)-5-(((5-fluoro-2,3-dihydrobenzofuran-4-yl)methyl)amino)imidazo[1,2-c]pyrimidine-2-carboxamide (1.1 g, crude) as a yellow solid. LCMS [M+1]: 490.3.

To a solution of 8-(4-(1,3-dioxolan-2-yl)-2-methylphenyl)-5-(((5-fluoro-2,3-dihydrobenzofuran-4-yl)methyl)amino)imidazo[1,2-c]pyrimidine-2-carboxamide (500 mg, 1.02 mmol, 1.00 equiv) and triethylamine (2.07 g, 20.4 mmol, 2.84 mL, 20.0 equiv) in THF (2.00 mL) was added dropwise TFAA (1.82 g, 8.68 mmol, 1.21 mL, 8.50 equiv) at 0° C. The mixture was warmed to room temperature and stirred for 2 h and was subsequently concentrated under reduced pressure to give a residue. The residue was purified by column chromatography (SiO$_2$, petroleum ether/ethyl acetate=5/1 to 1/1) to provide the crude product. The crude product was triturated with methanol (5.00 mL) and the solid was collected by filtration to afford 5-(((5-fluoro-2,3-dihydrobenzofuran-4-yl)methyl)amino)-8-(4-formyl-2-methylphenyl)imidazo[1,2-c]pyrimidine-2-carbonitrile (740 mg, 1.73 mmol, 84.8% yield) as a light yellow solid.

$^1$H NMR (400 MHz, DMSO-d$_6$) δ=10.04 (s, 1H), 8.93 (s, 1H), 8.55 (t, J=4.8 Hz, 1H), 7.86 (s, 1H), 7.86 (s, 1H), 7.55 (d, J=7.6 Hz, 1H), 7.03-6.88 (m, 1H), 6.72 (dd, J=4.0, 8.8 Hz, 1H), 4.73 (d, J=4.8 Hz, 2H), 4.56 (t, J=8.8 Hz, 2H), 3.30-3.28 (m, 2H), 2.27 (s, 3H).

Intermediate C-17

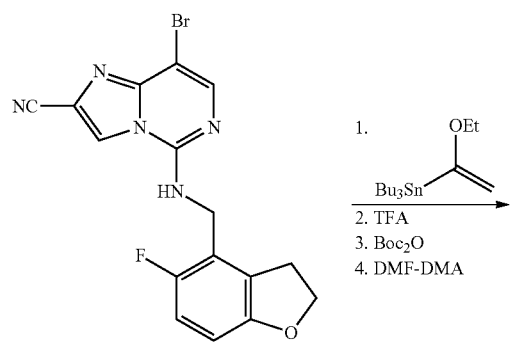

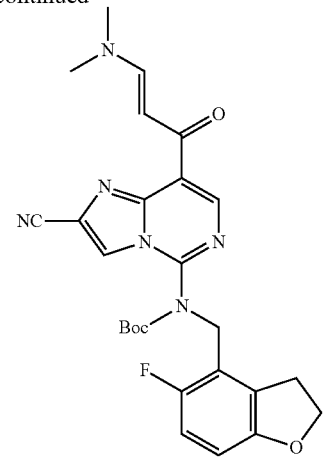

To a solution of 8-bromo-5-(((5-fluoro-2,3-dihydrobenzofuran-4-yl)methyl)amino)imidazo[1,2-c]pyrimidine-2-carbonitrile (300 mg, 773 μmol, 1.00 equiv) and tributyl(1-ethoxyvinyl)stannane (279 mg, 773 μmol, 261 μL, 1.00 equiv) in dioxane (5.00 mL) was added Pd(PPh$_3$)$_2$Cl$_2$(54.2 mg, 77.3 μmol, 0.10 equiv). The reaction was stirred at 100° C. for 2 h under nitrogen. The reaction was quenched with saturated aqueous potassium fluoride (20.0 mL) and extracted with ethyl acetate (20.0 mL×2). The combined organic phase was washed with brine (20.0 mL×2), dried over anhydrous sodium sulfate, filtered and concentrated under vacuum to provide a residue. The residue was purified by silica gel chromatography (petroleum ether/ethylacetate=10/1 to 3/1) to afford 8-(1-ethoxyvinyl)-5-(((5-fluoro-2,3-dihydrobenzofuran-4-yl)methyl)amino)imidazo[1,2-c]pyrimidine-2-carbonitrile (100 mg, 264 μmol, 34.1% yield) as a brown solid.

$^1$H NMR (400 MHz, CDCl$_3$) δ=8.21 (s, 1H), 7.88 (s, 1H), 6.87-6.80 (m, 1H), 6.66 (dd, J=4.0, 8.4 Hz, 1H), 5.80 (d, J=2.4 Hz, 1H), 5.55 (br t, J=5.6 Hz, 1H), 4.81 (d, J=5.6 Hz, 2H), 4.63 (t, J=8.8 Hz, 2H), 4.59 (d, J=2.4 Hz, 1H), 4.03-3.95 (m, 2H), 3.41 (t, J=8.8 Hz, 2H), 1.44 (t, J=6.8 Hz, 3H).

To a solution of 8-(1-ethoxyvinyl)-5-(((5-fluoro-2,3-dihydrobenzofuran-4-yl)methyl)amino)imidazo[1,2-c]pyrimidine-2-carbonitrile (100 mg, 264 μmol, 1.0 (equiv) in DCM (1.00 mL) was added TFA (1.00 mL). The reaction was stirred at 25° C. for 1 h. The reaction was concentrated under vacuum to give 8-acetyl-5-(((5-fluoro-2,3-dihydrobenzofuran-4-yl)methyl)amino)imidazo[1,2-c]pyrimidine-2-carbonitrile (90.0 mg, 256 μmol, 97.2% yield) as a brown solid.

$^1$H NMR (400 MHz, DMSO-d$_6$) δ=9.16 (br s, 1H), 8.95 (s, 1H), 8.44 (s, 2H), 6.98-6.91 (m, 1H), 6.71 (dd, J=4.4, 8.8 Hz, 1H), 4.78 (s, 2H), 4.54 (t, J=8.8 Hz, 2H), 3.28 (t, J=8.8 Hz, 2H), 2.72 (s, 3H).

To a solution of 8-acetyl-5-(((5-fluoro-2,3-dihydrobenzofuran-4-yl)methyl)amino)imidazo[1,2-c]pyrimidine-2-carbonitrile (50.0 mg, 142 μmol, 1.00 equiv) in THF (2.00 mL) was added di-tert-butyl dicarbonate (62.1 mg, 285 μmol, 2.00 equiv) and DMAP (1.74 mg, 14.2 μmol, 0.10 equiv). The reaction was stirred at 80° C. for 1 h. The reaction was concentrated under vacuum to give a residue. The residue was purified by prep-TLC (petroleum ether/ethyl acetate=3/1) to afford tert-butyl (8-acetyl-2-cyanoimidazo[1,2-c]pyrimidin-5-yl)((5-fluoro-2,3-dihydrobenzofuran-4-yl)methyl)carbamate (40.0 mg, 88.6 μmol, 62.3% yield) as a white solid.

$^1$H NMR (400 MHz, DMSO-d$_6$)=8.87 (s, 1H), 8.60 (s, 1H), 6.83-6.77 (m, 1H), 6.64 (dd, J=3.6, 8.4 Hz, 1H), 5.09 (s, 2H), 4.54 (t, J=8.8 Hz, 2H), 3.30-3.25 (m, 2H), 2.86 (s, 3H), 1.33 (s, 9H).

A solution of tert-butyl (8-acetyl-2-cyanoimidazo[1,2-c]pyrimidin-5-yl)((5-fluoro-2,3-dihydrobenzofuran-4-yl)methyl)carbamate (30.0 mg, 66.5 μmol, 1.00 equiv) in DMF-DMA (209 mg, 1.76 mmol, 233 μL, 26.5 equiv) was stirred at 100° C. for 1 h. The reaction was concentrated under vacuum to give a residue. The residue was purified by prep-TLC (petroleum ether/ethylacetate=1/1) to give tert-butyl(E)-(2-cyano-8-(3-(dimethylamino)acryloyl)imidazo[1,2-c]pyrimidin-5-yl)((5-fluoro-2,3-dihydrobenzofuran-4-yl)methyl)carbamate (20.0 mg, 39.5 μmol, 59.4% yield) as a yellow solid.

$^1$H NMR (400 MHz, CDCl$_3$) δ=8.71 (s, 1H), 8.01 (br d, J=12.8 Hz, 1H), 7.81 (s, 1H), 6.76 (br d, J=12.0 Hz, 1H), 6.70-6.63 (m, 1H), 6.56 (dd, J=4.0, 8.8 Hz, 1H), 5.12 (s, 2H), 4.56 (t, J=8.8 Hz, 3H), 3.28 (t, J=8.4 Hz, 2H), 3.23 (s, 3H), 3.06 (s, 3H), 1.38 (s, 9H).

Intermediate C-18

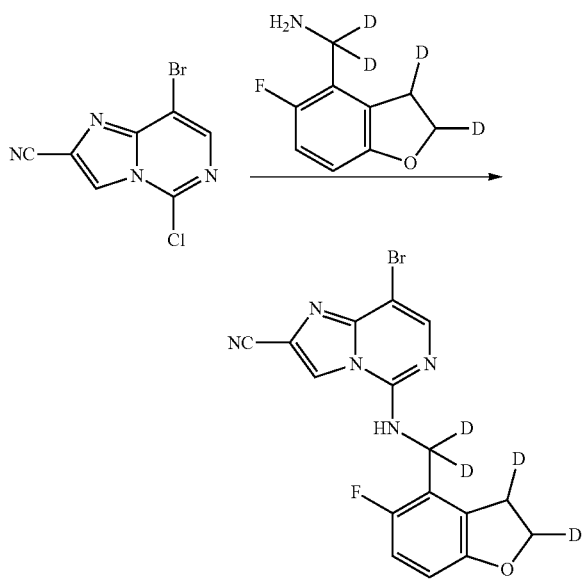

To a solution of dideuterio-(2,3-dideuterio-5-fluoro-2,3-dihydrobenzofuran-4-yl)methanamine (31.9 mg, 186 μmol, 1.20 equiv) and 8-bromo-5-chloroimidazo[1,2-c]pyrimidine-2-carbonitrile (40.0 mg, 155 μmol, 1.00 equiv) in DMF (1.00 mL) was added DIEA (108 uL, 621 μmol, 4.00 equiv) and the mixture was stirred at 85° C. for 0.5 h. The mixture was concentrated at reduced pressure to give a residue, which was poured into water (3.00 mL) and stirred for 5 min. The aqueous phase was extracted with ethyl acetate (3.00 mL×3). The combined organic phase was washed with brine (3.00 mL×2), dried with anhydrous sodium sulfate, filtered and concentrated under reduced pressure to afford 8-bromo-5-(((5-fluoro-2,3-dihydrobenzofuran-4-yl-2,3-d)methyl-d)amino)imidazo[1,2-c]pyrimidine-2-carbonitrile (25.0 mg, 63.7 μmol, 41.0% yield) as a white solid.

$^1$H NMR (400 MHz, CDCl$_3$) δ=8.30 (s, 1H), 7.94 (s, 1H), 7.93 (s, 1H), 6.83-6.76 (m, 1H), 6.64 (dd, J=4.0, 8.8 Hz, 1H), 4.59 (br d, J=10.0 Hz, 1H), 3.33 (br d, J=8.4 Hz, 1H).

Intermediate C-19

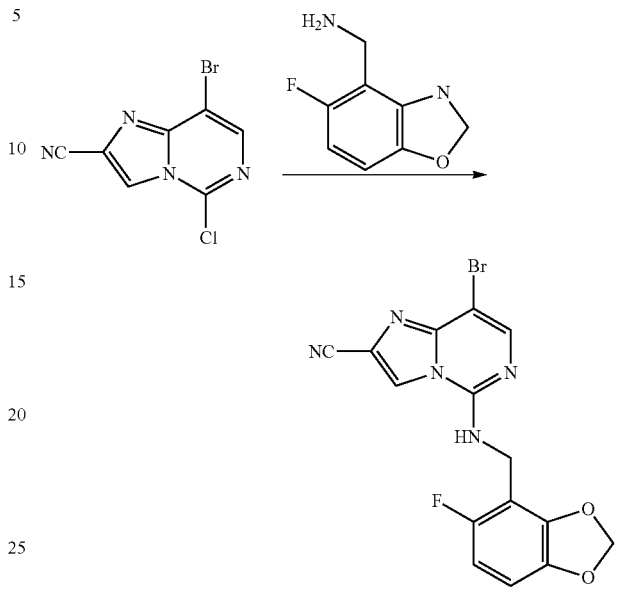

To a solution of 8-bromo-5-chloroimidazo[1,2-c]pyrimidine-2-carbonitrile (40.0 mg, 155 μmol, 1.00 equiv) and (5-fluorobenzo[d][1,3]dioxol-4-yl)methanamine (31.5 mg, 186 μmol, 1.20 equiv) in DMF (0.50 mL) was added DIEA (54.1 μL, 310 μmol, 2.00 equiv). The mixture was stirred at 85° C. for 0.5 h under a nitrogen atmosphere. The mixture was poured into water (3.00 mL) and stirred for 5 min. The aqueous phase was extracted with ethyl acetate (3.00 mL×2). The combined organic phase was washed with brine (3.00 mL×2), dried with anhydrous sodium sulfate, filtered and concentrated under reduced pressure to afford 8-bromo-5-(((5-fluorobenzo[d][1,3]dioxol-4-yl)methyl)amino)imidazo[1,2-c]pyrimidine-2-carbonitrile (50.0 mg, 128 μmol, 82.5% yield) as a yellow solid.

$^1$H NMR (400 MHz, DMSO-d$_6$) δ=8.92 (s, 1H), 8.567 (br s, 1H), 7.95 (s, 1H), 6.88 (dd, J=4.4, 8.4 Hz, 1H), 6.69 (dd, J=8.8, 10.4 Hz, 1H), 6.04 (s, 2H), 4.67 (br d, J=2.0 Hz, 2H).

Intermediate D-1

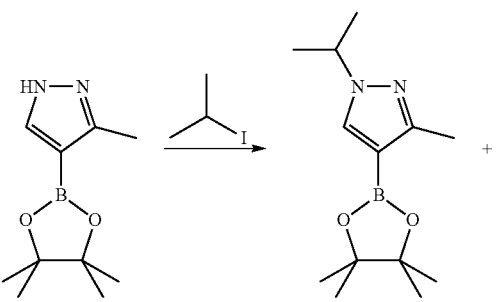

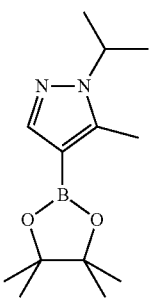

An exemplary Intermediate D, Intermediate D-1, may be used to synthesize compounds of formula I wherein $R^1$ is a disubstituted heteroaryl. A mixture of 3-methyl-4-(4,4,5,5-tetramethyl-1,3,2-dioxaborolan-2-yl)-1H-pyrazole (370 mg, 1.78 mmol, 1.00 equiv), 2-iodopropane (907 mg, 5.33 mmol, 533 uL, 3.00 equiv) and cesium carbonate (2.32 g, 7.11 mmol, 4.00 equiv) in acetonitrile (7.00 mL) was purged with nitrogen and subsequently stirred at 90° C. for 4 h. The reaction mixture was filtered and concentrated under reduced pressure to provide a residue. The crude material was purified by column chromatography (petroleum ether/ethyl acetate, 1/0 to 3/1) to afford a mixture of 1-isopropyl-3-methyl-4-(4,4,5,5-tetramethyl-1,3,2-dioxaborolan-2-yl)pyrazole (170 mg, 34.4% yield, 90.0% purity) and 1-isopropyl-5-methyl-4-(4,4,5,5-tetramethyl-1,3,2-dioxaborolan-2-yl)pyrazole (170 mg, 34.4% yield, 90.0% purity) as a light yellow oil. LCMS [M+1]: 251.4.

$^1$H NMR (400 MHz, CDCl$_3$) δ=7.73 (s, 0.6H), 7.65 (s, 1H), 4.50-4.36 (m, 2H), 2.45 (s, 2H), 2.40 (s, 3H), 1.50-1.44 (m, 12H), 1.31 (s, 22H).

Intermediate D-2

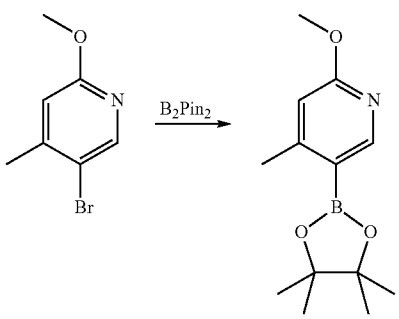

A second exemplary Intermediate D, Intermediate D-2, may be used to synthesize compounds of formula I, wherein $R^1$ is heteroaryl substituted with two $R^4$ substituents. A mixture of 5-bromo-2-methoxy-4-methyl-pyridine (350 mg, 1.73 mmol, 1.00 equiv), bis(pinacolato)diboron (2.20 g, 8.66 mmol, 5.00 equiv), potassium acetate (527 mg, 5.37 mmol, 3.10 equiv), Pd(dppf)Cl$_2$ (127 mg, 173 μmol, 0.10 equiv) in dioxane (5.00 mL) was purged with nitrogen and stirred at 90° C. for 3 h. The residue was diluted with ethyl acetate (3.00 mL) and extracted with ethyl acetate (2.00 mL×3). The combined organic layers were washed with brine (2.00 mL×3), dried over anhydrous sodium sulfate, filtered and concentrated under reduced pressure to give a residue. The crude material was purified by column chromatography (petroleum ether/ethyl acetate, 100/1 to 20/1) to afford 2-methoxy-4-methyl-5-(4,4,5,5-tetramethyl-1,3,2-dioxaborolan-2-yl)pyridine (150 mg, 546 μmol, 31.5% yield, 90.6% purity) as a white solid.

$^1$H NMR (400 MHz, CDCl$_3$) δ=8.47 (s, 1H), 6.51 (s, 1H), 3.93 (s, 3H), 2.45 (s, 3H), 1.33 (s, 12H).

Intermediate D-3

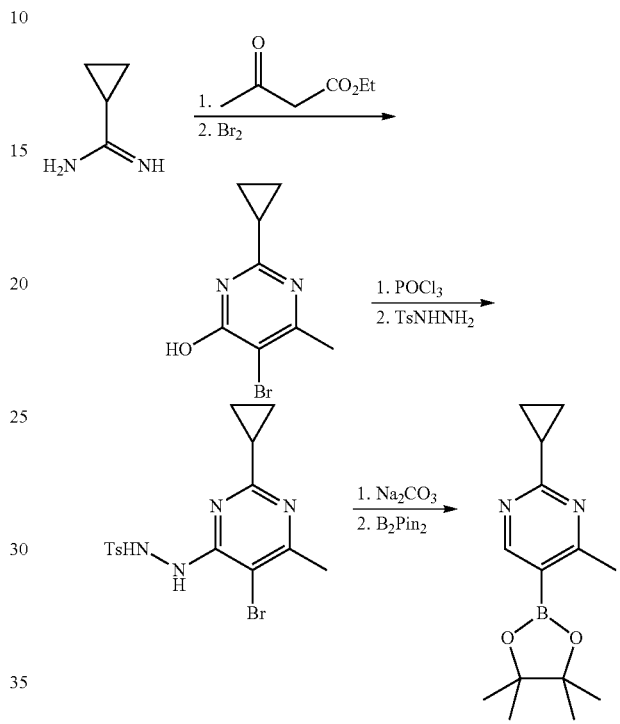

A third exemplary Intermediate D, Intermediate D-3, may be used to synthesize compounds of formula I or formula II wherein $R^1$ is heteroaryl substituted with two $R^4$ substituents. A mixture of cyclopropanecarboxamidine-HCl (5.00 g, 59.4 mmol, 1.00 equiv), ethyl 3-oxobutanoate (7.74 g, 59.4 mmol, 7.51 mL, 1.00 equiv), sodium ethoxide (8.09 g, 119 mmol, 2.00 equiv) in ethanol (500 mL) was purged with nitrogen and subsequently stirred at 25° C. for 12 h. The residue was dissolved in water (25.0 mL) and the pH was adjusted to ~4 with HCl (1M). After cooling to 5° C., the solid was collected and dried under reduced pressure to give 2-cyclo propy-6-methyl-pyrimidin-4-ol (4.00 g, 26.6 mmol, 44.8% yield, 100% purity) as a white solid. LC-MS [M+1]: 151.3.

$^1$H NMR (400 MHz, DMSO-d$_6$) δ=12.45 (s, 1H), 5.93 (s, 1H), 2.07 (s, 3H), 1.90-1.85 (m, 1H), 1.00-0.97 (m, 4H).

A mixture of 2-cyclopropyl-6-methyl-pyrimidin-4-ol (4.00 g, 26.6 mmol, 1.00 equiv), bromine (4.34 g, 27.2 mmol, 1.40 mL, 1.00 equiv), potassium hydroxide (1.49 g, 26.6 mmol, 1.00 equiv) in water (32.6 mL) was stirred at 25° C. for 2 h under a nitrogen atmosphere. The solid was filtered to give 5-bromo-2-cyclo propy-6-methyl-pyrimidin-4-ol (2.76 g, 9.31 mmol, 35.0% yield, 77.3% purity) as a white solid. LC-MS [M+3]: 231.0.

A mixture of 5-bromo-2-cyclopropyl-6-methyl-pyrimidin-4-ol (2.50 g, 8.44 mmol, 1.00 equiv) and dimethyl formamide (1.54 g, 21.1 mmol, 1.62 mL, 2.50 equiv) in toluene (36.9 mL) was added dropwise a solution of phosphorus oxychloride (1.57 g, 10.2 mmol, 951 uL, 1.21 equiv)

in toluene (9.20 mL) at 0° C. The mixture was subsequently stirred at 25° C. for 3 h under a nitrogen atmosphere. The mixture was poured into sodium carbonate (1.00 M, 55.2 mL) and extracted with ethyl acetate (10.0 mL, 3). The combined organic phase was concentrated to afford compound 5-bromo-4-chloro-2-cyclopropyl-6-methyl-pyrimidine (2.31 g, 4.51 mmol, 53.5% yield, 48.4% purity) as a yellow oil. LC-MS [M+3]: 249.1.

A mixture of 5-bromo-4-chloro-2-cyclopropyl-6-methyl-pyrimidine (2.31 g, 9.33 mmol, 1.00 equiv), 4-methylbenzenesulfonohydrazide (5.91 g, 31.7 mmol, 3.40 equiv) in chloroform (4.30 mL) was stirred at 90° C. for 16 h under a nitrogen atmosphere. The solid was filtered and rinsed with dichloromethane (20.0 mL) to afford M-(5-bromo-2-cyclopropyl-6-methyl-pyrimidin-4-yl)-4-methyl-benzenesulfonohydrazide (1.60 g, 4.02 mmol, 43.1% yield, 99.8% purity) as a white solid. LC-MS [M+3]: 399.2.

$^1$H NMR (400 MHz, DMSO-$d_6$) δ=10.08 (br s, 1H), 7.64 (d, J=8.4 Hz, 2H), 7.34 (d, J=8.0 Hz, 2H), 2.44 (br s, 3H), 2.37 (s, 3H), 2.05-1.83 (m, 1H), 1.05-0.90 (m, 2H), 0.87-0.75 (m, 2H).

A mixture of N-(5-bromo-2-cyclopropyl-6-methyl-pyrimidin-4-yl) 4-methyl-benzenesulfonohydrazide (0.60 g, 4.02 mmol, 1.00 equiv) and aqueous sodium carbonate (0.57 M, 90.6 mL, 12.8 equiv) was stirred at 90° C. for 1 h under a nitrogen atmosphere. The mixture was diluted with ethyl acetate (50.0 mL) and the organic phase was separated and concentrated to afford 5-bromo-2-cyclopropyl-4-methyl-pyrimidine (620 mg, 2.59 mmol, 64.6% yield, 89.2% purity) as a brown oil. LC-MS [M+1]: 213.2.

$^1$H NMR (400 MHz, CDCl$_3$) δ=8.49 (s, 1H), 2.56 (s, 3H), 2.25-2.08 (m, 1H), 1.19-0.99 (m, 4H).

A mixture of 5-bromo-2-cyclopropyl-4-methyl-pyrimidine (580 mg, 2.43 mmol, 1.00 equiv), 4,4,5,5-tetramethyl-2-(4,4,5,5-tetramethyl-1,3,2-dioxaborolan-2-yl)-1,3,2-dioxaborolane (863 mg, 3.40 mmol, 1.40 equiv), potassium acetate (715 mg, 7.28 mmol, 3.00 equiv), and Pd(dppf)Cl$_2$ (88.8 mg, 121 μmol, 0.05 equiv) in dioxane (5.00 mL) was purged with nitrogen and was subsequently stirred at 90° C. for 4 h under a nitrogen atmosphere. The residue was diluted with water (3.00 mL) and extracted with ethyl acetate (2.00 mL×3). The combined organic layers were washed with brine (2.00 mL×3), dried over anhydrous sodium sulfate, filtered and concentrated under reduced pressure to give a residue. The crude material was purified by column chromatography (petroleum ether/ethyl acetate, 100/1 to 10/1) to afford 2-cyclopropyl-4-methyl-5-(4,4,5,5-tetramethyl-1,3,2-dioxaborolan-2-yl)pyrimidine (1.00 g, 1.92 mmol, 79.2% yield, 50.0% purity) as a yellow oil.

$^1$H NMR (400 MHz, CDCl$_3$) δ=8.73 (s, 1H), 2.62 (s, 3H), 2.27-2.14 (m, 1H), 1.34 (s, 12H), 1.18-1.13 (m, 2H), 1.07-1.01 (m, 2H).

Intermediate D-4

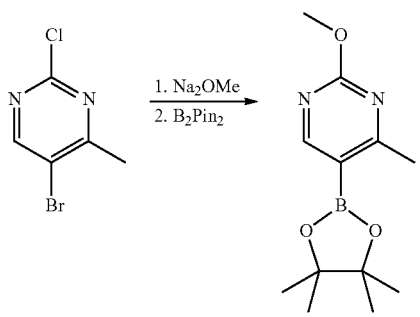

A fourth exemplary Intermediate D, Intermediate D-4, may be used to synthesize compounds of formula I, wherein $R^1$ is heteroaryl substituted with two $R^4$ substituents. A mixture of sodium (111 mg, 4.82 mmol, 1.00 equiv) in methanol (772 mg, 24.1 mmol, 975 μL, 5.00 equiv) was stirred at 25° C. for 0.5 h. To this solution was added 5-bromo-2-chloro-4-methyl-pyrimidine (1.00 g, 4.82 mmol, 1.00 equiv) and the mixture was stirred at 25° C. for 2 h. The reaction was quenched upon the addition of water (5 mL). The aqueous phase was extracted with ethyl acetate (10.0 mL×3) and the combined organic phase was washed with brine (10.0 mL×3), dried over anhydrous Na$_2$SO$_4$, filtered and concentrated in vacuo to afford 5-bromo-2-methoxy-4-methyl-pyrimidine (500 mg, 2.46 mmol, 51.1% yield) as a red oil. LCMS: [M+1] 203.1.

To a solution of 5-bromo-2-methoxy-4-methyl-pyrimidine (500 mg, 2.46 mmol, 1.00 equiv), 4,4,5,5-tetramethyl-2-(4,4,5,5-tetramethyl-1,3,2-dioxaborolan-2-yl)-1,3,2-dioxaborolane (813 mg, 3.20 mmol, 1.30 equiv) and potassium acetate (483 mg, 4.93 mmol, 2.00 equiv) in dioxane (5.00 mL) was added Pd(dppf)Cl$_2$ (180 mg, 246 μmol, 0.10 equiv) under nitrogen. The resultant mixture was stirred at 105° C. for 2 h. The mixture was concentrated in vacuo to give the crude material, which was purified by column chromatography (petroleum ether/ethyl acetate, 1/0 to 1:1) to afford 2-methoxy-4-methyl-5-(4,4,5,5-tetramethyl-1,3,2-dioxaborolan-2-yl)pyrimidine (150 mg, 539 μmol, 21.9% yield, 90.0% purity) as a red oil.

$^1$H NMR (400 MHz, MeOD) δ=8.69 (s, 1H), 4.03 (s, 3H), 2.65 (s, 3H), 1.38 (s, 12H).

Intermediate D-5

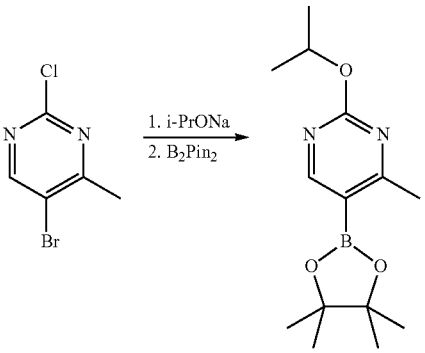

A fifth exemplary Intermediate D, Intermediate D-5, may be used to synthesize compounds of formula I, wherein $R^1$ is heteroaryl substituted with two $R^4$ substituents. To a solution of isopropanol (869 mg, 14.5 mmol, 1.11 mL, 3.00 equiv) in THF (10.0 mL) was added portionwise NaH (578 mg, 14.5 mmol, 60.0% purity, 3.00 equiv) at 0° C. The mixture was stirred at 0° C. for 0.5 h. Subsequent to the addition of 5-bromo-2-chloro-4-methyl-pyrimidine (1.00 g, 4.82 mmol, 1.00 equiv) the mixture was allowed to stir at 25° C. for 3 h. The mixture was poured into water (20.00 mL) and the aqueous phase was extracted with ethyl acetate (20.0 mL×3). The combined organic phase was washed with brine (20.0 mL×3), dried over anhydrous $Na_2SO_4$, filtered and concentrated to provide 5-bromo-2-isopropoxy-4-methyl-pyrimidine (600 mg, 2.60 mmol, 53.9% yield) as a yellow oil.

To a solution of 5-bromo-2-isopropoxy-4-methyl-pyrimidine (300 mg, 1.30 mmol, 1.00 equiv), 4,4,5,5-tetramethyl-2-(4,4,5,5-tetramethyl-1,3,2-dioxaborolan-2-yl)-1,3,2-dioxaborolane (429 mg, 1.69 mmol, 1.30 equiv) and potassium acetate (255 mg, 2.60 mmol, 2.00 equiv) in dioxane (5.00 mL) was added Pd(dppf)Cl$_2$ (95.0 mg, 130 μmol, 0.10 equiv).

The mixture was stirred at 105° C. for 2 h under an atmosphere of nitrogen. The mixture was concentrated in vacuo to provide the crude material, which was purified by column chromatography (petroleum ether/ethyl acetate, 1/1 to dichloromethane:methanol, 10/1) to afford 2-isopropoxy-4-methyl-5-(4,4,5,5-tetramethyl-1,3,2-dioxaborolan-2-yl)pyrimidine (60.0 mg, 216 μmol, 16.6% yield) as a white oil. LCMS: [M+1] 279.3.

Intermediate D-6 concentrated under reduced pressure to afford 1-bromo-2-methyl-4-methylsulfanyl-benzene (900 mg, crude) as a light yellow oil.

$^1$H NMR (400 MHz, MeOD) δ=7.42 (d, J=8.4 Hz, 1H), 7.17 (d, J=2.0 Hz, 1H), 6.97 (dd, J=2.0, 8.4 Hz, 1H), 2.45 (s, 3H), 2.35 (s, 3H).

To a solution of 1-bromo-2-methyl-4-methylsulfanyl-benzene (900 mg, 4.15 mmol, 1.00 equiv) in DCM (9.00 mL) was added m-CPBA (1.43 g, 8.29 mmol, 2.00 equiv) at 0° C. The reaction mixture was stirred at 25° C. for 2 h. The reaction mixture was diluted with DCM (20.0 mL), washed with said aq potassium carbonate (20.0 mL×3), brine (20.0 mL×2), and the organic phase was concentrated under reduced pressure to give a residue. The crude material was purified by column chromatography (petroleum ether/ethyl acetate, 1/0 to 3/1) to afford 1-bromo-2-methyl-4-methylsulfonyl-benzene (370 mg, 1.41 mmol, 34.0% yield, 95.0% purity) as a white solid.

$^1$H NMR (400 MHz, MeOD) δ=7.87 (d, J=1.6 Hz, 1H), 7.82 (d, J=8.4 Hz, 1H), 7.66 (dd, J=2.0, 8.4 Hz, 1H), 3.12 (s, 3H), 2.50 (s, 3H).

A mixture of 1-bromo-2-methyl-4-methylsulfonyl-benzene (170 mg, 648 μmol, 1.00 equiv), potassium acetate (127 mg, 1.30 mmol, 2.00 equiv), Pd(dppf)Cl$_2$ (47.4 mg, 64.8 μmol, 0.100 equiv) and 4,4,5,5-tetramethyl-2-(4,4,5,5-tetramethyl-1,3,2-dioxaborolan-2-yl)-1,3,2-dioxaborolane (247 mg, 972 μmol, 1.50 equiv) in dioxane (3.00 mL) was purged with nitrogen. The resultant reaction mixture was stirred at 105° C. for 1 h. The mixture was filtered and concentrated under reduced pressure to give a residue. The crude material was purified by prep-TLC (petroleum ether/ethyl acetate, 5/1) to afford 4,4,5,5-tetramethyl-2-(2-methyl-4-methylsulfonyl-phenyl)-1,3,2-dioxaborolane (110 mg, 338 μmol, 52.1% yield, 90.9% purity) as a colorless oil. LCMS [M+1]: 296.9.

Intermediate D-7

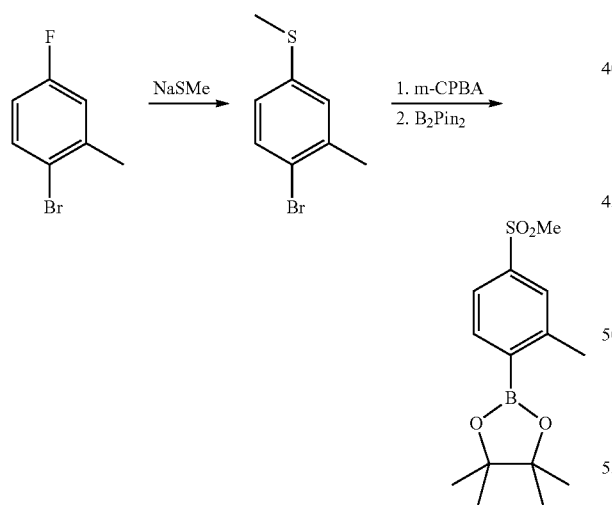

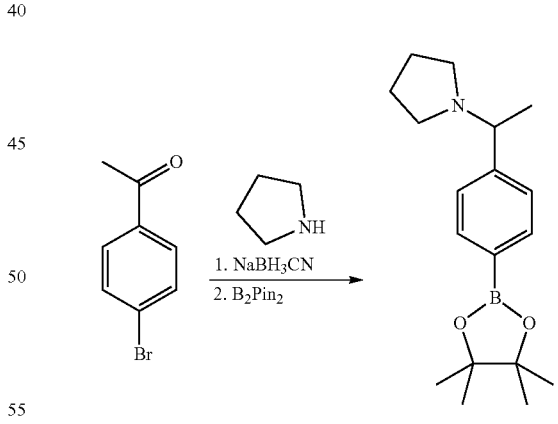

A sixth exemplary Intermediate D, Intermediate D-6, may be used to synthesize compounds of formula I, wherein $R^1$ is aryl substituted with two $R^4$ substituents. To a solution of 1-bromo-4-fluoro-2-methyl-benzene (1.00 g, 5.29 mmol, 1.00 equiv) in DMF (10.0 mL) was added NaSMe (869 mg, 5.29 mmol, 1.00 equiv). The mixture was stirred at 50° C. for 12 h. The reaction mixture was diluted with ethyl acetate (50.0 mL) and the organic layer was washed with brine (40.0 mL×3), dried over anhydrous sodium sulfate, filtered and A seventh exemplary Intermediate D, Intermediate D-7, may be used to synthesize compounds of formula I, wherein $R^1$ is aryl substituted with an $R^4$ substituent. To a solution of 1-(4-bromophenyl)ethanone (1.00 g, 5.02 mmol, 1.00 equiv), pyrrolidine (1.79 g, 25.1 mmol, 2.10 mL, 5.00 equiv) in methanol (16.0 mL) was added NaBH$_3$CN (347 mg, 5.53 mmol, 1.10 equiv). The mixture was stirred at 20° C. for 24 h. To the mixture was added water (4.00 mL) and the aqueous phase was extracted with ethyl acetate (5.00 mL). The combined organic phase was washed with brine (2.00 mL), dried over anhydrous Na$_2$SO$_4$, filtered and concentrated to afford 1-[1-(4-bromophenyl)ethyl]pyrrolidine (1.00 g, 3.93 mmol, 78.3% yield) as a yellow oil.

To a solution of 1-[1-(4-bromophenyl)ethyl]pyrrolidine (400 mg, 1.57 mmol, 1.00 equiv), 4,4,5,5-tetramethyl-2-(4,4,5,5-tetramethyl-1,3,2-dioxaborolan-2-yl)-1,3,2-dioxaborolane (799 mg, 3.15 mmol, 2.00 equiv) and potassium acetate (308 mg, 3.15 mmol, 2.00 equiv) in dioxane (2.00 mL) was added Pd(dppf)Cl$_2$(115 mg, 157 μmol, 0.100 equiv). The reaction mixture was stirred at 105° C. for 2 h under an atmosphere of nitrogen. The mixture was concentrated in vacuo to give a residue. The crude material was purified by column chromatography (petroleum ether/ethyl acetate, 1/0 to 1/1) to afford 1-[1-[4-(4,4,5,5-tetramethyl-1,3,2-dioxaborolan-2-yl)phenyl]ethyl]pyrrolidine (110 mg) as a red oil.

Intermediate D-8

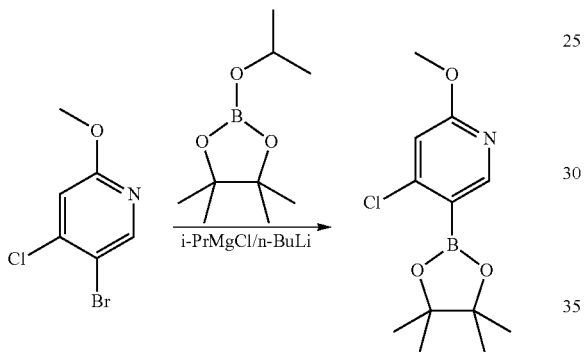

An eighth exemplary Intermediate D, Intermediate D-8, may be used to synthesize compounds of formula I, wherein $R^1$ is heteroaryl substituted with two $R^4$ substituents. To a solution of n-butyllithium (2.50 M, 1.80 mL, 1.00 equiv) was added dropwise over one min to i-PrMgCl (2.00 M, 1.12 mL, 0.500 equiv) in THF (12 mL) at 0° C. under a nitrogen atmosphere. The mixture was stirred at 0° C. for 5 min followed by the addition of 5-bromo-4-chloro-2-methoxy-pyridine (1.00 g, 4.50 mmol, 1.00 equiv) after which the mixture was stirred at 0° C. for 45 min. To this solution was added 2-isopropoxy-4,4,5,5-tetramethyl-1,3,2-dioxaborolane (836 mg, 4.50 mmol, 917 uL, 1.00 equiv) and the mixture stirred for an additional 15 min prior to stirring at 20° C. for 3 h. The reaction mixture was quenched by the addition of satd aq ammonium chloride (20.0 mL) at 20° C. and was extracted with ethyl acetate (20.0 mL×3). The combined organic layers were washed with brine (10.0 mL), dried over anhydrous sodium sulfate, filtered and concentrated under reduced pressure to afford 4-chloro-2-methoxy-5-(4,4,5,5-tetramethyl-1,3,2-dioxaborolan-2-yl)pyridine (1.00 g, 3.71 mmol, 82.5% yield) as a gray solid, which used for the next step without further purification.

$^1$H NMR (400 MHz, CDCl$_3$) δ=8.47 (s, 1H), 6.77 (s, 1H), 3.97 (s, 3H), 1.38 (s, 12H).

Intermediate D-9

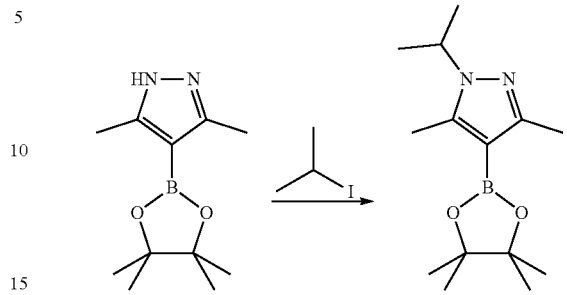

A ninth exemplary Intermediate D, Intermediate D-9 may be used to synthesize compounds of formula I, wherein $R^1$ is heteroaryl substituted with three $R^4$ substituents. A mixture of 3,5-dimethyl-4-(4,4,5,5-tetramethyl-1,3,2-dioxaborolan-2-yl)-1H-pyrazole (100 mg, 450 μmol, 1.00 equiv), isopropyl iodide (306 mg, 1.80 mmol, 180 uL, 4.00 equiv) and cesium carbonate (587 mg, 1.80 mmol, 4.00 equiv) in acetonitrile (3.00 mL) was purged with nitrogen and subsequently stirred at 65° C. for 4 h. The mixture was filtered and the solvent was removed in vacuo to afford 1-isopropyl-3,5-dimethyl-4-(4,4,5,5-tetramethyl-1,3,2-dioxaborolan-2-yl)pyrazole (100 mg, 368 μmol, 81.8% yield, 97.3% purity) as a green oil. LC-MS [M+1]: 265.

Intermediate D-10

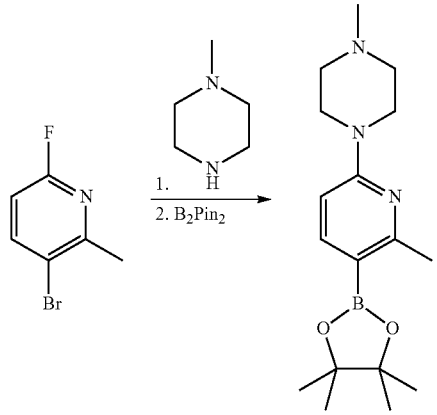

A tenth exemplary Intermediate D, Intermediate D-10, may be used to synthesize compounds of formula I, wherein $R^1$ is heteroaryl substituted with two $R^4$ substituents. A mixture of 3-bromo-6-fluoro-2-methyl-pyridine (1.00 g, 5.26 mmol, 1.00 equiv) and N-methylpiperazine (685 mg, 6.84 mmol, 759 μL, 1.30 equiv) was stirred at 110° C. for 12 h. The mixture was diluted with ethyl acetate (50.0 mL), washed with brine (20.0 mL×3), dried over anhydrous Na$_2$SO$_4$, filtered and concentrated to provide 1-(5-bromo-6-methyl-2-pyridyl)-4-methyl-piperazine (1.10 g, 4.07 mmol, 77.4% yield) as a yellow solid. LCMS [M+1]: 272.1.

To a solution of 1-(5-bromo-6-methyl-2-pyridyl)-4-methyl-piperazine (400 mg, 1.48 mmol, 1.00 equiv), 4,4,5,5-tetramethyl-2-(4,4,5,5-tetramethyl-1,3,2-dioxaborolan-2-yl)-1,3,2-dioxaborolane (752 mg, 2.96 mmol, 2.00 equiv)

and potassium acetate (291 mg, 2.96 mmol, 2.00 equiv) in dioxane (2.00 mL) was added Pd(dppf)Cl$_2$ (108 mg, 148 µmol, 0.100 equiv). The reaction was stirred at 105° C. for 2 h under an atmosphere of nitrogen. The mixture was concentrated in vacuo to give a residue. The crude material was purified by prep-TLC (DCM/MeOH=10/1) to afford compound 1-methyl-4-(6-methyl-5-(4,4,5,5-tetramethyl-1,3,2-dioxaborolan-2-yl)pyridin-2-yl)piperazine (210 mg, 662 µmol, 44.7% yield) as a brown oil. LCMS [M+1]: 318.3.

Intermediate D-11

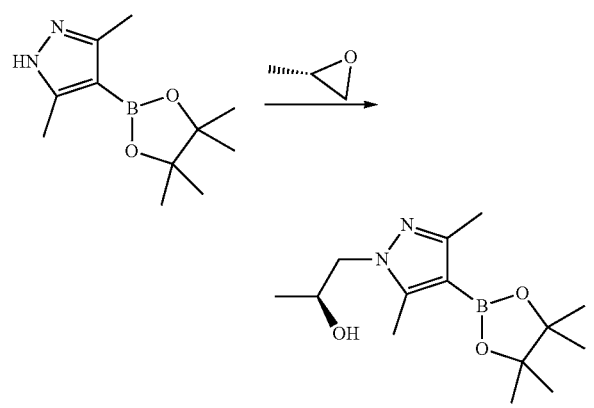

An eleventh exemplary Intermediate D, Intermediate D-11, may be used to synthesize compounds of formula I, wherein R$^1$ is heteroaryl substituted with three R$^4$ substituents. To a solution of 3,5-dimethyl-4-(4,4,5,5-tetramethyl-1,3,2-dioxaborolan-2-yl)-1H-pyrazole (100 mg, 450 µmol, 1.00 equiv), (2S)-2-methyloxirane (392 mg, 6.75 mmol, 473 µL, 15.0 equiv) was added cesium carbonate (29.3 mg, 90.1 µmol, 0.20 equiv). The reaction mixture was stirred at 50° C. for 16 h and was subsequently concentrated under vacuum to give a residue. The crude residue was purified by prep-TLC (SiO$_2$, petroleum ether:ethyl acetate=1:1) to afford (2S)-1-[3,5-dimethyl-4-(4,4,5,5-tetramethyl-1,3,2-dioxaborolan-2-yl)pyrazol-1-yl]propan-2-ol (56.0 mg, 44.4% yield) as a yellow oil. LCMS [M+1]: 281.3.

Intermediate D-12

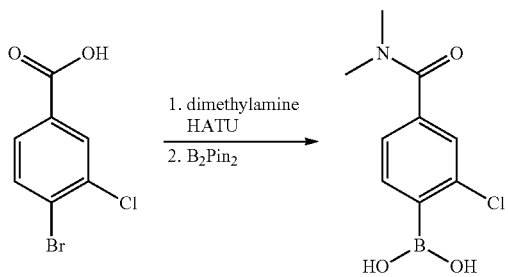

A twelfth exemplary Intermediate D, Intermediate D-12, may be used to synthesize compounds of formula I, wherein R$^1$ is aryl substituted with two R$^4$ substituents. To a solution of 4-bromo-3-chloro-benzoic acid (300 mg, 1.27 mmol, 1.00 equiv), DIEA (490 mg, 3.79 mmol, 660 µL, 3.00 equiv) and N,N-dimethylamine (2.00 M in THF 1.27 mL, 2.00 equiv) in DMF (3.00 mL) was added HATU (727 mg, 1.91 mmol, 1.50 equiv). The mixture was stirred at room temperature for 2 h and the reaction mixture was subsequently quenched upon the addition water (15.0 mL). The mixture was extracted with dichloromethane (20.0 mL×3). The combined organic layer was washed with water (30.0 mL) and concentrated to provide the crude mixture. The resultant residue was purified by column chromatography (SiO$_2$, petroleum ether/ethyl acetate=5/1 to 2/1) to afford 4-bromo-3-chloro-N,N-dimethyl-benzamide (430 mg, 983 µmol, 77.0% yield, 60.0% purity) as a white solid. LCMS [M+1]: 264.0.

$^1$H NMR (400 MHz, CDCl$_3$) δ=7.67 (d, J=8.2 Hz, 1H), 7.53 (d, J=1.6 Hz, 1H), 7.18 (dd, J=2.0, 8.4 Hz, 1H), 3.11 (s, 3H), 2.99 (s, 3H).

To a solution of 4-bromo-3-chloro-N,N-dimethyl-benzamide (150 mg, 343 µmol, 1.00 equiv), 4,4,5,5-tetramethyl-2-(4,4,5,5-tetramethyl-1,3,2-dioxaborolan-2-yl)-1,3,2-dioxaborolane (870 mg, 3.43 mmol, 10.0 equiv) and potassium acetate (67.0 mg, 683 µmol, 2.00 equiv) in dioxane (10.0 mL) was added Pd(PPh$_3$)$_2$Cl$_2$ (24.0 mg, 34.2 µmol, 0.10 equiv) The vessel was flushed with nitrogen and the mixture was stirred at 100° C. for 1 h. The reaction mixture was cooled to rt and filtered through a pad of Celite. Purification by prep-TLC (SiO$_2$, petroleum ether/ethyl acetate=2/1) afforded [2-chloro-4-(dimethylcarbamoyl)phenyl]boronic acid (200 mg) as a yellow solid. LCMS [M+1]: 228.0.

Intermediate D-13

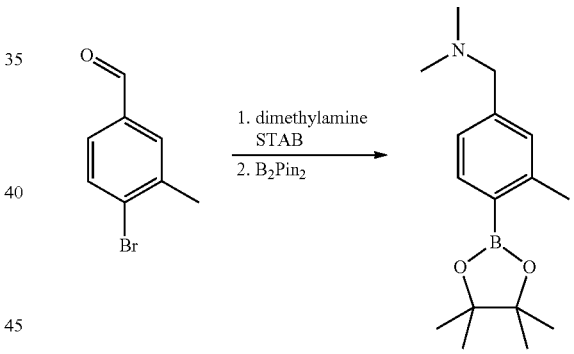

A thirteenth exemplary Intermediate D, Intermediate D-13, may be used to synthesize compounds of formula I, wherein R$^1$ is aryl substituted with two R$^4$ substituents. A mixture of 4-bromo-3-methyl-benzaldehyde (500 mg, 2.51 mmol, 1.00 equiv) and N,N-dimethylamine (2 M in THF, 6.3 mL, 12.6 mmol, 5.00 equiv) in methanol (10.0 mL) was stirred at 40° C. for 30 min. Subsequently, sodium triacetoxyborohydride (1.60 g, 7.54 mmol, 3.00 equiv) was added and the mixture was stirred for another 3 h. The solution was concentrated under reduced pressure to give a residue. The crude residue was purified by column chromatography (petroleum ether/ethyl acetate=1/0 to 0/1 then dichloromethane/methanol=20/1 to 10/1) to afford 1-(4-bromo-3-methyl-phenyl)-N,N-dimethyl-methanamine (570 mg) as a brown oil.

$^1$H NMR (400 MHz, CD$_3$OD) δ=7.61 (d, J=8.0 Hz, 1H), 7.38 (d, J=1.6 Hz, 1H), 7.16 (dd, J=1.6, 8.0 Hz, 1H), 3.96 (s, 2H), 2.63 (s, 6H), 2.42 (s, 3H).

A mixture of 1-(4-bromo-3-methyl-phenyl)-N,N-dimethyl-methanamine (470 mg, 2.06 mmol, 1.00 equiv), 4,4, 4',4',5,5,5',5'-octamethyl-2,2'-bi(1,3,2-dioxaborolane) (785 mg, 3.09 mmol, 1.50 equiv), potassium acetate (404 mg, 4.12 mmol, 2.00 equiv) and Pd(dppf)Cl₂(151 mg, 206 μmol, 0.100 equiv) in dioxane (8.00 mL) was purged with nitrogen and allowed to stir at 105° C. for 2 h. The mixture was concentrated under reduced pressure to give a residue. The residue was purified by column chromatography (dichloromethane/methanol=50/1 to 10/1) to afford N,N-dimethyl-1-[3-methyl-4-(4,4,5,5-tetramethyl-1,3,2-dioxaborolan-2-yl)phenyl]methanamine (70.0 mg, 185 μmol, 8.99% yield, 72.8% purity) as a brown oil. LCMS [M+]: 275.6.

Intermediate D-14

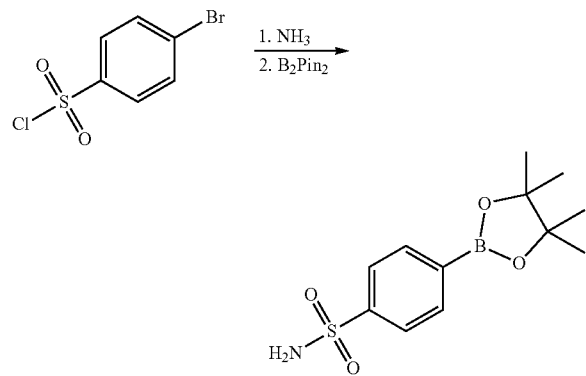

A fourteenth exemplary Intermediate D, Intermediate D-14, may be used to synthesize compounds of formula I, wherein $R^1$ is aryl substituted with one $R^4$ substituent. To a solution of 4-bromobenzenesulfonyl chloride (200 mg, 783 μmol, 1.00 equiv) in THF (2.00 mL) was added ammonia (7 N in MeOH, 224 μL, 1.57 mmol, 2.00 equiv). The reaction mixture was stirred at 25° C. for 30 min. The mixture was concentrated in vacuo to provide a residue that was poured into water (10.0 mL). The aqueous phase was extracted with ethyl acetate (10.0 mL×3) and the combined organic phase was washed with brine (3.00 mL×3), dried with anhydrous sodium sulfate, filtered and concentrated to give 4-bromobenzenesulfonamide (180 mg, 762 μmol, 97.4% yield) as a white solid.

¹H NMR (400 MHz, DMSO-d₆) δ=7.82-7.72 (m, 4H), 7.46 (s, 2H).

To a solution of 4-bromobenzenesulfonamide (100 mg, 424 μmol, 1.00 equiv) and 4,4,5,5-tetramethyl-2-(4,4,5,5-tetramethyl-1,3,2-dioxaborolan-2-yl)-1,3,2-dioxaborolane (129 mg, 508 μmol, 1.20 equiv) in DMSO (2.00 mL) was added potassium acetate (83.1 mg, 847 μmol, 2.00 equiv) and Pd(dppf)Cl₂ (31.0 mg, 42.4 μmol, 0.10 equiv) under an atmosphere of nitrogen. The mixture was stirred at 80° C. for 3 h and was subsequently concentrated under vacuum to give a residue. The residue was poured into water (10.0 mL) and the aqueous phase was extracted with ethyl acetate (10.0 mL×3). The combined organic phase was washed with brine (5.00 mL×3), dried with anhydrous sodium sulfate, filtered and concentrated to afford 4-(4,4,5,5-tetramethyl-1,3,2-dioxaborolan-2-yl)benzenesulfonamide (95.0 mg, 336 μmol, 79.2% yield) as a red solid.

¹H NMR (400 MHz, CDCl₃) δ=7.96-7.88 (m, 4H), 7.26 (s, 2H), 1.35 (s, 12H).

Intermediate D-15

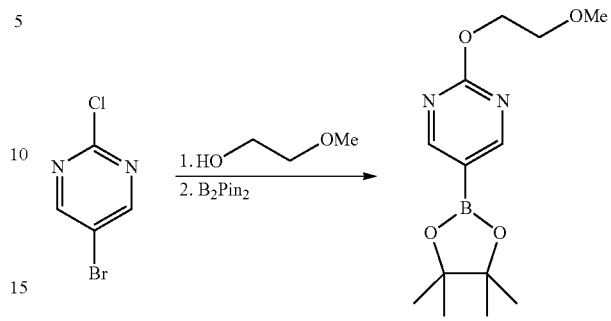

To a solution of 2-methoxyethanol (236 mg, 3.10 mmol, 245 μL, 1.50 equiv) in tetrahydrofuran (2.00 mL) was added portion wise sodium hydride (99.3 mg, 60.0%, 2.48 mmol, 1.20 equiv) at 0° C. The mixture was stirred at this temperature for 45 min followed by the dropwise addition of 5-bromo-2-chloro-pyrimidine (400 mg, 2.07 mmol, 1.00 equiv) at room temperature. The resulting mixture was stirred for an additional 4 h. The mixture was filtered and concentrated in vacuo to give a residue. The residue was purified by prep-TLC (petroleum ether/ethyl acetate=10/1) to afford 5-bromo-2-(2-methoxyethoxy)pyrimidine (150 mg, 644 μmol, 31.1% yield) as a white solid.

¹H NMR (400 MHz, CD₃OD) δ=8.54 (s, 2H), 4.42-4.37 (m, 2H), 3.68-3.62 (m, 2H), 3.30 (s, 3H).

A mixture of 5-bromo-2-(2-methoxyethoxy)pyrimidine (150 mg, 644 μmol, IA) equiv), 4,4,5,5-tetramethyl-2-(4,4,5,5-tetramethyl-1,3,2-dioxaborolan-2-yl)-1,3,2-dioxaborolane (327 mg 1.29 mmol, 2.00 equiv), potassium acetate (126 mg, 1.29 mmol, 2.00 equiv), Pd(dppf)Cl₂ (47.1 mg, 64.4 μmol, 0.10 equiv) in dioxane (1.00 mL) was purged with nitrogen stirred at 100° C. for 2 h. The reaction was filtered and concentrated in vacuo to give a residue. The residue was purified by prep-TLC (petroleum ether/ethyl acetate=1/1) to afford 2-(2-methoxyethoxy)-5-(4,4,5,5-tetramethyl-1,3,2-dioxaborolan-2-yl)pyrimidine (130 mg, 464 μmol, 72.1% yield) as a yellow oil.

¹H NMR (400 MHz, CDCl₃)=8.83-8.79 (m, 2H), 4.61-4.54 (m, 2H), 3.82-3.76 (m, 2H), 3.44 (s, 3H), 1.36 (s, 12H).

Intermediate D-16

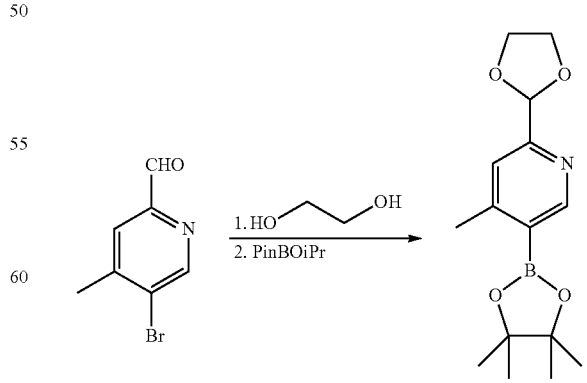

To a solution of ethylene glycol (310 mg, 5.00 mmol, 280 μL, 2.00 equiv), 5-bromo-4-methyl-pyridine-2-carbaldehyde (500 mg, 2.50 mmol, 1.00 equiv) in toluene (20.0 mL) was added p-toluenesulfonic acid (47.6 mg, 250 µmol, 0.10 equiv). The mixture was stirred at 110° C. for 12 h and was subsequently concentrated in vacuo to give a residue. The residue was purified by column chromatography (SiO$_2$, petroleum ether/ethyl acetate=1/0 to 5:1) to afford 5-bromo-2-(1,3-dioxolan-2-yl)-4-methylpyridine (320 mg, 1.24 mmol, 49.6% yield) as a colorless oil.

$^1$H NMR (400 MHz, CDCl$_3$) δ=8.64 (s, 1H), 7.42 (s, 1H), 5.80 (s, 1H), 4.19-4.14 (m, 2H), 4.10-4.05 (m, 2H), 2.42 (s, 3H).

To a solution of 5-bromo-2-(1,3-dioxolan-2-yl)-4-methylpyridine (300 mg, 1.23 mmol, 1.00 equiv) in diethyl ether (20.0 mL) was added n-butyllithium (2.5 M, 737 µL, 1.50 equiv) at −78° C. under a nitrogen atmosphere. The mixture was stirred at −78° C. for 0.5 h followed by the addition of 2-isopropoxy-4,4,5,5-tetramethyl-1,3,2-dioxaborolane (457 mg, 2.46 mmol, 501 µL, 2.00 equiv). The mixture was warmed to 0° C. and stirred for an additional 1.5 h. The mixture was quenched with water (15.0 mL) and the resulting mixture was extracted with ethyl acetate (20.0 mL×2). The combined organic phase was dried over sodium sulfate, filtered and concentrated under reduced pressure to afford 2-(1,3-dioxolan-2-yl)-4-methyl-5-(4,4,5,5-tetramethyl-1,3,2-dioxaborolan-2-yl)pyridine (150 mg, crude) as a yellow oil. LCMS [M+1]: 292.15.

Intermediate D-17

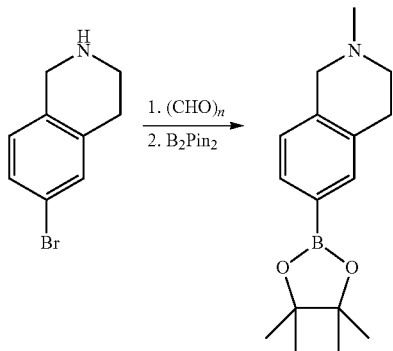 [SMILES: Brc1ccc2c(c1)CCNC2 ; CN1CCc2cc(B3OC(C)(C)C(C)(C)O3)ccc2C1]

A mixture of paraformaldehyde (350 mg, 3.63 mmol, 2.20 equiv) in methanol (1.00 mL) was stirred at 60° C. for 1 h and then cooled to 40° C. To the mixture was added AcOH (1 drop) and 6-bromo-1,2,3,4-tetrahydroisoquinoline (350 mg, 1.65 mmol, 1.00 equiv) followed by NaCNBH$_3$ (114 mg, 1.82 mmol, 1.1 equiv). The mixture was stirred at 40° C. for 1 h and was subsequently filtered and concentrated in vacuo to give a residue. The residue was purified by prep-TLC (petroleum ether/ethyl acetate=2/1) to afford 6-bromo-2-methyl-3,4-dihydro-1H-isoquinoline (360 mg, 1.59 mmol, 96.5% yield) as a yellow oil.

$^1$H NMR (400 MHz, CD$_3$OD) δ=7.32 (s, 1H), 7.28 (dd, J=2.0, 8.4 Hz, 1H), 7.00 (d, J=8.0 Hz, 1H), 3.57 (s, 2H), 2.94 (t, J=6.0 Hz, 2H), 2.75-2.72 (m, 2H), 2.46 (s, 3H).

A mixture of 6-bromo-2-methyl-3,4-dihydro-1H-isoquinoline (220 mg, 973 µmol, 1.00 equiv), 4,4,5,5-tetramethyl-2-(4,4,5,5-tetramethyl-1,3,2-dioxaborolan-2-yl)-1,3,2-dioxaborolane (494 mg, 1.95 mmol, 2.00 equiv), potassium acetate (191 mg, 1.95 mmol, 2.00 equiv), Pd(dppf)Cl$_2$ (71.2 mg, 97.3 µmol, 0.10 equiv) in dioxane (3.00 mL) was purged with nitrogen and subsequently stirred at 100° C. for 2 h. The mixture was filtered and concentrated in vacuo to give a residue. The residue was purified by prep-TLC (petroleum ether/ethyl acetate=2/1) to afford 2-methyl-6-(4,4,5,5-tetramethyl-1,3,2-dioxaborolan-2-yl)-3,4-dihydro-1H-isoquinoline (150 mg, crude) as a white solid.

Intermediate D-18

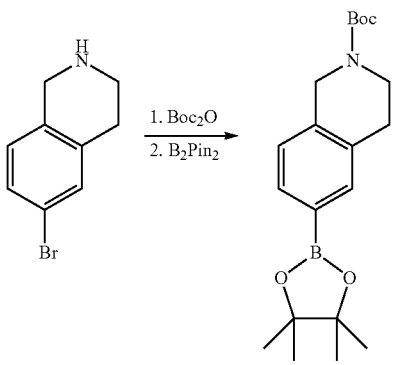 [SMILES: Brc1ccc2c(c1)CCNC2 ; CC(C)(C)OC(=O)N1CCc2cc(B3OC(C)(C)C(C)(C)O3)ccc2C1]

To a solution of 6-bromo-1,2,3,4-tetrahydroisoquinoline (400 mg, 1.89 mmol, 1.00 equiv) in tetrahydrofuran (2.00 mL) was added Boc$_2$O (617 mg, 2.83 mmol, 1.50 equiv) and dimethylaminopyridine (46.1 mg, 377 µmol, 0.20 equiv). The mixture was stirred at 25° C. for 3 h and was subsequently filtered and concentrated in vacuo to give a residue. The residue was purified by column chromatography (SiO$_2$, Petroleum ether/Ethyl acetate=20/1 to 3/1) to afford tert-butyl 6-bromo-3,4-dihydro-1H-isoquinoline-2-carboxylate (150 mg, 480 µmol, 25.5% yield) as a white solid.

$^1$H NMR (400 MHz, CD$_3$OD) δ=7.38-7.32 (m, 2H), 7.07 (d, J=8.0 Hz, 1H), 4.52 (br s, 2H), 3.64 (br t, J=6.0 Hz, 2H), 2.84 (t, J=6.0 Hz, 2H), 1.51 (s, 9H).

A mixture of tert-buty 6-bromo-3,4-dihydro-1H-isoquinoline-2-carboxylate (140 mg, 448 µmol, 1.00 equiv), 4,4,5,5-tetramethyl-2-(4,4,5,5-tetramethyl-1,3,2-dioxaborolan-2-yl)-1,3,2-dioxaborolane (228 mg, 897 µmol, 2.00 equi), Pd(dppf)Cl$_2$ (32.8 mg, 44.8 µmol, 0.10 equiv), potassium acetate (88.0 mg, 897 µmol, 2.00 equiv) in dioxane (1.00 mL) was purged with nitrogen and subsequently stirred at 100° C. for 2 h. The mixture was filtered and concentrated in vacuo to give a residue. The residue was purified by prep-TLC (petroleum ether/ethyl acetate=2/1) to afford tert-butyl 6-(4,4,5,5-tetramethyl-1,3,2-dioxaborolan-2-yl)-3,4-dihydro-1H-isoquinoline-2-carboxylate (100 mg, 278 µmol, 62.1% yield) as a yellow oil.

$^1$H NMR (400 MHz, CD$_3$OD) δ=7.58-7.54 (m, 2H), 7.13 (d, J=8.0 Hz, 1H), 4.58 (brs, 2H), 3.65 (brt, J=6.0 Hz, 2H), 2.84 (t, J=6.0 Hz, 2H), 1.35 (s, 12H), 1.19 (brs, 1H), 1.22 (s, 9H).

Intermediate D-19

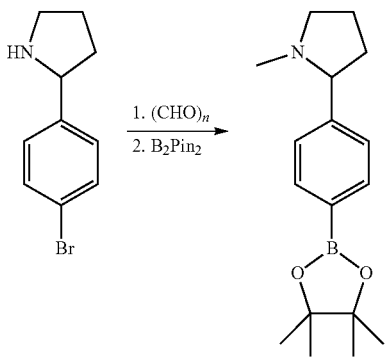

A mixture of paraformaldehyde (133 mg, 4.42 mmol, 122 μL, 10.0 equiv) and methyl alcohol (1.00 mL) was stirred at 60° C. for 1 h and then cooled to 0° C. To the mixture was added acetic acid (52.5 mg, 874 μmol, 0.05 mL, 1.98 equiv) and 2-(4-bromophenyl)pyrrolidine (100 mg, 442 μmol, 1.00 equiv). The mixture was allowed to stir for 1 h at room temperature prior to the addition of sodium cyanoborohydride (83.4 mg, 1.33 mmol, 3.00 equiv) and an additional hour of stirring. The mixture was filtered and concentrated under reduced pressure to give a residue. The residue was purified by prep-TLC (SiO$_2$, petroleum ether/ethyl acetate=3/1) to afford 2-(4-bromophenyl)-1-methyl-pyrrolidine (100 mg, 413 μmol, 93.3% yield, 99.1% purity) as a white solid. LC-MS [M+1]: 240.1.

$^1$H NMR (400 MHz, CDCl$_3$) δ=7.48-7.41 (m, 2H), 7.26-7.21 (m, 2H), 3.33-3.14 (m, 1H), 3.02 (t, J=8.4 Hz, 1H), 2.29 (q, J=9.2 Hz, 1H), 2.16 (s, 3H), 2.06-1.89 (m, 1H), 1.86-1.77 (m, 1H), 1.76-1.69 (m, 2H).

A mixture of 2-(4-bromophenyl)-1-methyl-pyrrolidine (48.0 mg, 200 μmol, 1.00 equiv), bis(pinacolato)diboron (76.1 mg, 300 μmol, 1.50 equiv), potassium acetate (58.9 mg 600 μmol, 3.00 equiv), Pd(dppf)Cl$_2$ (14.6 mg, 20.0 μmol, 0.10 equiv) in dioxane (0.00 mL) was purged with nitrogen and then stirred at 90° C. for 2 h. The mixture was filtered and concentrated under reduced pressure to provide a residue. The residue was purified by prep-TLC (SiO$_2$, petroleum ether/ethyl acetate=3/1) to afford 1-methyl-2-[4-(4,4,5,5-tetramethyl-1,3,2-dioxaborolan-2-yl)phenyl]pyrrolidine (23.0 mg, 73.3 μmol, 36.7% yield, 91.5% purity) as a white solid. LC-MS [M+1]: 288.0.

Intermediate D-20

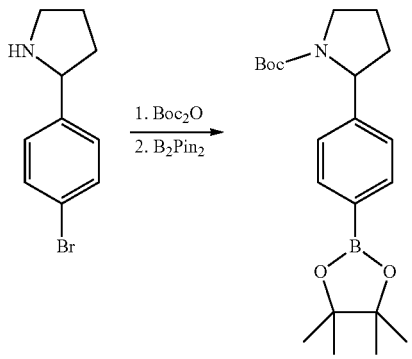 [SMILES: Brc1ccc(C2CCCN2)cc1 ; CC(C)(C)OC(=O)N1CCCC1c1ccc(B2OC(C)(C)C(C)(C)O2)cc1]

A mixture of 2-(4-bromophenyl)pyrrolidine (50.0 mg, 221 μmol, 1.00 equiv), di-tert-butyl dicarbonate (57.9 mg, 265 μmol, 1.20 equiv) and dimethylaminopyridine (2.70 mg, 22.1 μmol, 0.10 equiv) in tetrahydrofuran (1.00 mL) was purged with nitrogen and then was stirred at 25° C. for 2 h. The mixture was filtered and concentrated under reduced pressure. The resultant residue was purified by prep-TLC (SiO$_2$, petroleum ether/ethyl acetate=10/1) to afford tert-butyl 2-(4-bromophenyl)pyrrolidine-1-carboxylate (55.0 mg, 163 μmol, 73.6% yield, 96.5% purity) as a yellow oil. LC-MS [M−55]: 272.1.

A mixture of tert-butyl 2-(4-bromophenyl)pyrrolidine-1-carboxylate (46.6 mg, 138 μmol, 1.00 equiv), bis(pinacolato)diboron (52.5 mg, 207 μmol, 1.50 equiv), potassium acetate (40.6 mg, 414 μmol, 3.00 equiv) and Pd(dppf)Cl$_2$ (10.1 mg, 13.8 μmol, 0.10 equiv) in dioxane (1.00 mL) was purged with nitrogen and then stirred at 90° C. for 2 h. The mixture was filtered and concentrated under reduced pressure. The residue was purified by prep-TLC (SiO$_2$, petroleum ether/ethyl acetate=5/1) to afford tert-butyl 2-[4-(4,4,5,5-tetramethyl-1,3,2-dioxaborolan-2-yl)phenyl]pyrrolidine-1-carboxylate (45.0 mg, 102 μmol, 74.3% yield, 85.0% purity) as a yellow solid. LC-MS [M−55]: 318.2.

$^1$H NMR (400 MHz, CDCl$_3$) δ=7.75 (br d, J=7.6 Hz, 2H), 7.17 (br d, J=7.6 Hz, 2H), 4.80 (br s, 1H), 3.63 (br s, 2H), 2.32 (br s, 1H), 1.98-1.75 (m, 3H), 1.58 (s, 9H), 1.35 (br s, 12H).

Intermediate D-21

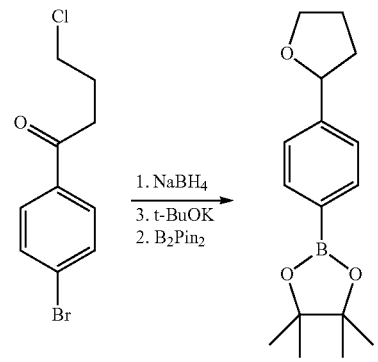

To a solution of a 1-(4-bromophenyl)-4-chloro-butan-1-one (1.00 g, 3.82 mmol, 1.00 equiv) in methanol (13.0 mL) was added portionwise NaBH$_4$ (300 mg, 7.93 mmol, 2.07 equiv) at room temperature. The mixture was allowed to stir at room temperature for 2 h and was subsequently quenched by the addition of water (10.0 mL). The mixture was diluted with dichloromethane (20 mL) and the organic layer was washed with water and brine, dried over anhydrous sodium sulfate, filtered and concentrated under reduced pressure to afford the crude product 1-(4-bromophenyl)-4-chloro-butan-1-ol (1.00 g, 3.79 mmol, 99.2% yield) as a light yellow oil.

$^1$H NMR (400 MHz, CDCl$_3$) δ=7.49 (d, J=8.4 Hz, 2H), 7.24 (d, J=8.4 Hz, 2H), 4.71 (br t, J=6.0 Hz, 1H), 3.54 (s, 2H), 2.01-1.72 (m, 4H).

A solution of 1-(4-bromophenyl)-4-chloro-butan-1-ol (500 mg, 1.90 mmol, 1.00 equiv) and t-BuOK (1.0 M in THF, 1.90 mL, 1.00 equiv) was stirred for 1 h at room temperature. The reaction was quenched with water and extracted with ether (2×20.0 ml). The combined organic phase was dried over anhydrous sodium sulfate, filtered and concentrated under reduced pressure to provide 2-(4-bromophenyl)tetrahydrofuran (420 mg, 1.85 mmol, 97.5% yield) as a white solid.

¹H NMR (400 MHz, CDCl₃) δ=7.49-7.42 (m, 2H), 7.24-7.18 (m, 2H), 4.85 (t, J=7.2 Hz, 1H), 4.13-4.05 (m, 1H), 3.97-3.90 (m, 1H), 2.38-2.27 (m, 1H), 2.06-1.95 (m, 2H), 1.80-1.70 (m, 1H).

To a mixture of 2-(4-bromophenyl)tetrahydrofuran (150 mg, 661 μmol, 1.00 equiv) and 4,4,5,5-tetramethyl-2-(4,4,5,5-tetramethyl-1,3,2-dioxaborolan-2-yl)-1,3,2-dioxaborolane (252 mg, 992 μmol, 1.50 equiv), potassium acetate (195 mg, 1.99 mmol, 3.01 equiv) in dioxane (5.00 mL) was added Pd(dppf)Cl₂ (48.3 mg, 66.0 μmol, 0.10 equiv). The mixture was stirred at 105° C. for 1 h, cooled to room temperature and filtered through a pad of Celite. The filtrate was concentrated to give a residue that was purified by prep-TLC (SiO₂, petroleum ether/ethyl acetate=2/1) to afford 4,4,5,5-tetramethyl-2-(4-tetrahydrofuran-2-ylphenyl)-1,3,2-dioxaborolane (240 mg, 639 μmol, 96.8% yield, 73% purity) as a colorless oil. LCMS [M+1]: 275.1.

¹H NMR (400 MHz, CDCl₃) δ=7.78 (d, J=8.4 Hz, 2H), 7.34 (d, J=7.6 Hz, 2H), 4.92 (t, J=7.2 Hz, 1H), 4.17-4.06 (m, 1H), 4.00-3.90 (m, 1H), 2.41-2.27 (m, 1H), 2.09-1.91 (m, 2H), 1.85-1.73 (m, 1H), 1.35 (s, 12H).

Intermediate D-22

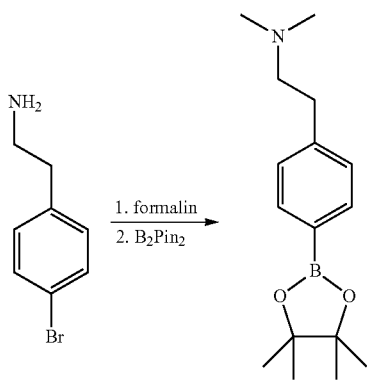

To a cooled solution of 2-(4-bromophenyl)ethanamine (200 mg, 1.0 mmol, 155 μL, 1.00 equiv) in formalin (300 mg, 9.99 mmol, 275 μL, 10.0 equiv) was added HCOOH (5.00 mL) and the solution was stirred at 110° C. for 16 h under nitrogen. The reaction mixture was concentrated to give a residue. To the residue was added HCl (3 N, 1.00 mL) and the mixture was washed with ethyl acetate (310 mL). The aqueous phase was basified to pH=14 with NaOH (10 N, 1.00 mL) and then extracted with ethyl acetate (3×15.0 mL). The combined organic phase was washed with brine (2×15.0 mL), dried over anhydrous sodium sulfate, and concentrated in vacuo to afford 2-(4-bromophenyl)-N,N-dimethyl-ethanamine (200 mg, 877 μmol, 87.7% yield) as a colorless oil.

¹H NMR (400 MHz, CDCl₃) δ=7.40 (d, J=8.4 Hz, 2H), 7.09 (d, J=8.4 Hz, 2H), 2.73 (d, J=8.4 Hz, 2H), 2.56-2.48 (m, 2H), 2.29 (s, 6H).

A mixture of 2-(4-bromophenyl)-N,N-dimethyl-ethanamine (160 mg, 701 μmol, 1.00 equiv), 4,4,5,5-tetramethyl-2-(4,4,5,5-tetramethyl-1,3,2-dioxaborolan-2-yl)-1,3,2-dioxaborolane (268 mg, 1.06 mmol, 1.50 equiv), Pd(dppf)Cl₂ (51.2 mg, 70.0 μmol, 0.10 equiv), potassium acetate (206 mg, 2.10 mmol, 3.00 equiv) in dioxane (8.00 mL) was purged with nitrogen and was stirred at 100° C. for 1 h. The mixture was concentrated to give a residue that was purified by prep-TLC (SiO₂, dichloromethane/methanol=10/1) to afford N,N-dimethyl-2-[4-(4,4,5,5-tetramethyl-1,3,2-dioxaborolan-2-yl)phenyl]ethanamine (350 mg, crude) as a black oil. LCMS [M+1]: 276.2.

Intermediate D-23

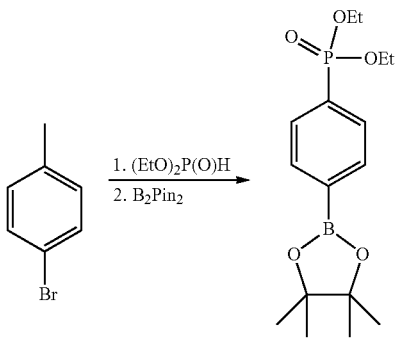

To a solution of 1-bromo-4-iodo-benzene (200 mg, 707 μmol, 1.00 equiv), diethyl phosphite (97.6 mg, 707 μmol, 91.2 μL, 1.00 equiv) in tetrahydrofuran (2.00 mL) was added Pd(OAc)₂ (4.76 mg, 21.2 μmol, 0.03 equiv), potassium acetate (9.02 mg, 91.9 μmol, 0.13 equiv), DPPF (23.5 mg, 42.4 μmol, 0.06 equiv) and triethylamine (107 mg, 1.06 mmol, 147 μL, 1.50 equiv). The vessel was flushed with nitrogen and stirred at 68° C. for 1 h. The mixture was concentrated in vacuo to give a residue. The residue was purified by prep-TLC (SiO₂, petroleum ether/ethyl acetate=1/1) to afford 1-bromo-4-diethoxyphosphoryl-benzene (110 mg, 341 μmol, 48.2% yield, 90.8% purity) as a red solid. LCMS [M+3]: 294.9.

¹H NMR (400 MHz, CDCl₃) δ=7.73-7.57 (m, 4H), 4.22-3.99 (m, 4H), 1.32 (t, J=7.2 Hz, 6H).

To a solution of 1-bromo-4-diethoxyphosphoryl-benzene (100 mg, 341 μmol, 1.00 equiv), 4,4,5,5-tetramethyl-2-(4,4,5,5-tetramethyl-1,3,2-dioxaborolan-2-yl)-1,3,2-dioxaborolane (104 mg, 409 μmol, 1.20 equiv) in dioxane (2.00 mL) was added Pd(dppf)Cl₂ (24.9 mg, 34.1 μmol, 0.10 equiv) and potassium acetate (67.0 mg, 682 umol, 2.00 equiv) under a nitrogen atmosphere. The mixture was stirred at 100° C. for 2 h and was subsequently concentrated in vacuo to give a residue. The residue was purified by prep-TLC (SiO₂, petroleum ether/ethyl acetate=1/1) to afford 2-(4-diethoxyphosphorylphenyl)-4,4,5,5-tetramethyl-1,3,2-dioxaborolane (55.0 mg, 162 μmol, 47.4% yield) as a red oil.

¹H NMR (400 MHz, CDCl₃) δ=7.93-7.87 (m, 2H), 7.85-7.76 (m, 2H), 4.21-4.01 (m, 4H), 1.36 (s, 12H), 1.32 (t, J=7.2 Hz, 6H).

Intermediate D-24

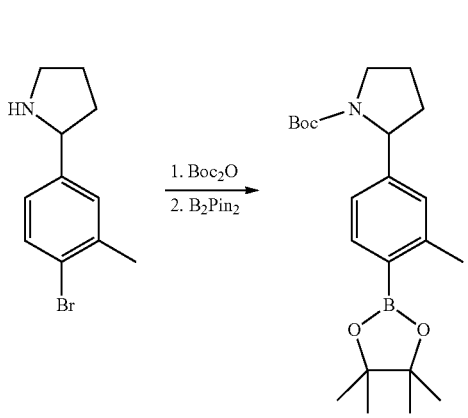 [SMILES: Cc1cc(C2CCCN2)ccc1Br ; Cc1cc(C2CCCN2C(=O)OC(C)(C)C)ccc1B1OC(C)(C)C(C)(C)O1]

To a solution of 2-(4-bromo-3-methyl-phenyl)pyrrolidine (500 mg, 2.08 mmol, 1.00 equiv) in dichloromethane (5.00 mL) was added Boc$_2$O (1.05 g, 4.79 mmol, 1.10 mL, 2.30 equiv) and dimethylaminopyridine (25.4 mg, 208 μmol, 0.10 equiv). The mixture was stirred at 25° C. for 1 h and was subsequently filtered and concentrated under reduced pressure to give a residue. The residue was purified by column chromatography (SiO$_2$, petroleum ether/ethyl acetate=30/1 to 20/1) to afford tert-butyl 2-(4-bromo-3-methyl-phenyl)pyrrolidine-1-carboxylate (600 mg, 84.7% yield) as a yellow oil.

$^1$H NMR (400 MHz, CD$_3$OD) δ=7.46 (br d, J=8.4 Hz, 1H), 7.10 (d, J=1.6 Hz, 1H), 6.92 (dd, J=1.6, 8.0 Hz, 1H), 4.73 (br s, 1H), 3.65-3.51 (m, 2H), 2.37 (s, 3H), 2.34-2.27 (m, 1H), 1.93-1.82 (m, 2H), 1.82-1.73 (m, 1H), 1.45 (br s, 3H), 1.24-1.13 (m, 6H).

A mixture of 4,4,5,5-tetramethyl-2-(4,4,5,5-tetramethyl-1,3,2-dioxaborolan-2-yl)-1,3,2-dioxaborolane (268 mg, 1.06 mmol, 1.20 equiv), tert-butyl 2-(4-bromo-3-methyl-phenyl)pyrrolidine-1-carboxylate (300 mg, 882 μmol, 1.00 equiv), Pd(dppf)Cl$_2$ (64.1 mg, 88.2 μmol, 0.10 equiv) and potassium acetate (173 mg, 1.76 mmol, 2.00 equiv) in dioxane (3.00 mL) was purged with nitrogen and then the mixture was stirred at 100° C. for 1.5 h. The reaction mixture was filtered and concentrated under reduced pressure to give a residue. The residue was purified by column chromatography (SiO$_2$, petroleum ether/ethyl acetate=20/1 to 10/1) to afford tert-butyl 2-[3-methyl-4-(4,4,5,5-tetramethyl-1,3,2-dioxaborolan-2-yl)phenyl]pyrrolidine-1-carboxylate (260 mg, 76.1% yield) as a white solid.

$^1$H NMR (400 MHz, CDCl$_3$) δ=7.68 (br d, J=7.6 Hz, 1H), 7.0-6.94 (m, 2H), 4.98-4.66 (m, 1H), 3.61 (br s, 2H), 2.52 (s, 3H), 2.36 (br s, 1H), 1.93-1.76 (m, 3H), 1.35 (s, 12H), 1.29-1.25 (m 3H), 1.21 (br s, 6H).

Intermediate D-25

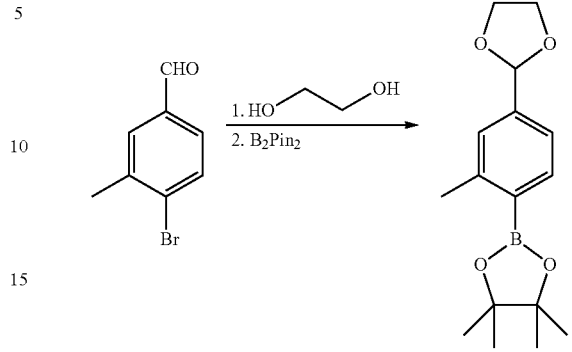

Toa solution of 4-bromo-3-methyl-benzaldehyde (2.00 g, 10.1 mmol, 1.00 equiv) in toluene (100 mL) was added TsOH—H$_2$O (191 mg, 1.00 mmol, 0.10 equiv) and ethylene glycol (1.25 g, 20.1 mmol, 1.12 mL, 2.00 equiv). The mixture was stirred at 130° C. for 12 h prior to cooling to room temperature. The pH was adjusted to 9 with DMAP and then concentrated in vacuo. The residue was purified by column chromatography (neutral Al$_2$O$_3$, petroleum ether/ethyl acetate=1/0 to 100/1) to afford 2-(4-bromo-3-methyl-phenyl)-1,3-dioxolane (2.30 g, 9.46 mmol, 94.2% yield) as a yellow oil.

$^1$H NMR (400 MHz, CDCl$_3$) δ=7.54 (d, J=8.4 Hz, 1H), 7.36 (d, J=1.6 Hz, 1H), 7.17 (dd, J=2.4, 8.0 Hz, 1H), 5.76 (s, 1H), 4.15-4.08 (m, 2H), 4.08-4.00 (m, 2H), 2.42 (s, 3H).

A mixture of 2-(4-bromo-3-methyl-phenyl)-1,3-dioxolane (2.50 g, 10.3 mmol, 1.00 equiv), Pin$_2$B$_2$ (3.39 g, 13.4 mmol, 1.30 equiv), KOAc (2.02 g, 20.6 mmol, 2.00 equiv) and Pd(dppf)Cl$_2$ (376 mg, 514 umol, 0.05 equiv) in dioxane (30.0 mL) was purged with N$_2$ and then stirred at 100° C. for 6 h. The mixture was filtered and concentrated in vacuo. The residue was purified by column chromatography (neutral Al$_2$O$_3$, petroleum ether/ethyl acetate=1/0 to 50/1) to afford 2-[4-(1,3-dioxolan-2-yl)-2-methyl-phenyl]-4,4,5,5-tetramethyl-1,3,2-dioxaborolane (2.60 g, 8.96 mmol, 87.1% yield) as a green oil.

$^1$H NMR (400 MHz, CDCl$_3$) δ=7.78 (d, J=7.6 Hz, 1H), 7.29-7.25 (m, 2H), 5.81 (s, 1H), 4.15-4.08 (m, 2H), 4.07-4.01 (m, 2H), 2.56 (s, 3H), 1.35 (s, 12H).

Intermediate D-26

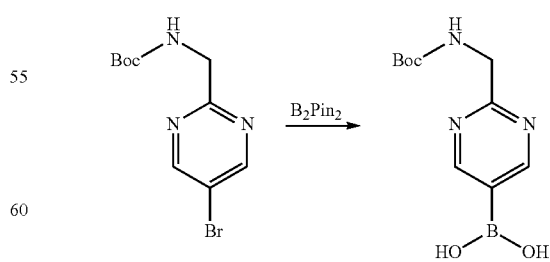

A mixture of tert-butyl N-[(5-bromopyrimidin-2-yl)methyl]carbamate (100 mg, 347 μmol, 1.00 equiv), Pin$_2$B$_2$ (176 mg, 694 μmol, 2.00 equiv), KOAc (68.1 mg, 694 μmol, 2.00 equiv) and Pd(dppf)Cl$_2$ (25.4 mg, 34.7 μmol, 0.10 equiv) in dioxane (2.00 mL) was purged with N₂ and then stirred at 100° C. for 2 h. The reaction mixture was filtered and concentrated in vacuo to afford [2-[(tert-butoxycarbonylamino)methyl]pyrimidin-5-yl]boronic acid (100 mg, crude) as a red oil. LCMS [M−55]: 198.1.

Intermediate D-27

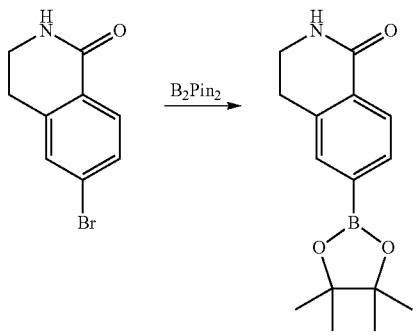 [SMILES: O=C1NCCc2cc(Br)ccc21 ; CC1(C)OB(c2ccc3c(c2)CCNC3=O)OC1(C)C]

A mixture of 6-bromo-3,4-dihydro-2H-isoquinolin-1-one (150 mg, 664 µmol, 1.00 equiv), 4,4,5,5-tetramethyl-2-(4,4,5,5-tetramethyl-1,3,2-dioxaborolan-2-yl)-1,3,2-dioxaborolane (253 mg, 996 µmol, 1.50 equiv), Pd(dppf)Cl₂ (48.55 mg, 66.35 µmol, 0.10 equiv), potassium acetate (195 mg, 1.99 mmol, 3.00 equiv) in dioxane (5.00 mL) was purged with nitrogen and then stirred at 95° C. for 2 h. The reaction mixture was cooled and filtered through a pad of Celite and the filtrate was concentrated to give a residue. The residue was purified by clout chromatography (SiO₂, petroleum ether/ethyl acetate=3/1 to 1/1) to afford 6-(4,4,5,5-tetramethyl-1,3,2-dioxaborolan-2-yl)-3,4-dihydro-2H-isoquinolin-1-one (180 mg, 659 µmol, 99.32% yield) as an off-white solid. LCMS [M+1]: 274.1.

¹H NMR (400 MHz, CDCl₃) δ=8.07 (d, J=8.0 Hz, 1H), 7.80 (d, J=7.6 Hz, 1H), 7.67 (s, 1H), 6.04 (s, 1H), 3.57 (dt, J=2.8, 6.4 Hz, 2H), 3.02 (t, J=6.4 Hz, 2H), 1.37 (s, 12H).

Intermediate D-28

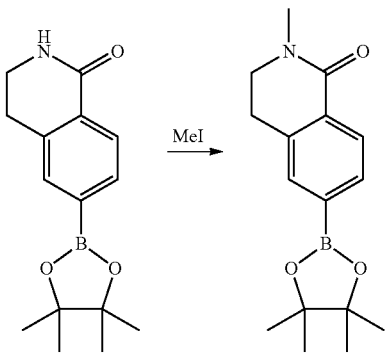 [SMILES: "MeI" ; CC1(C)OB(c2ccc3c(c2)CCNC3=O)OC1(C)C ; CN1CCc2cc(B3OC(C)(C)C(C)(C)O3)ccc2C1=O]

To a suspension of NaH (79.1 mg, 60%, 1.98 mmol, 2.00 equiv) in DMF (3.00 mL) at 0° C. was added dropwise a solution of 6-(4,4,5,5-tetramethyl-1,3,2-dioxaborolan-2-yl)-3,4-dihydro-2H-isoquinolin-1-one (270 mg, 989 µmol, 1.00 equiv) in DMF. The mixture was stirred at this temperature for an additional 30 min prior to the dropwise addition of CH₃I (1.40 g, 9.89 mmol, 615 µL, 10.0 equiv) at 0° C. The mixture was allowed to warm to room temperature and stirred for 3 h. The reaction was quenched upon the addition of 20.0 mL of water followed by extraction with diethyl ether (3×30.0 mL). The combined organic layer was washed with water (50.0 mL), dried over sodium sulfate, filtered and concentrated under reduced pressure to afford 2-methyl-6-(4,4,5,5-tetramethyl-1,32-dioxaborolan-2-yl)-3,4-dihydroisoquinolin-1-one (300 mg, crude) as a black oil. LCMS [M+1]: 288.1.

¹H NMR (400 MHz, CHCl₃-d) δ=8.07 (d, J=7.6 Hz, 1H), 7.77 (d, J=7.6 Hz, 1H), 7.63 (s, 1H), 3.56 (t, J=6.8 Hz, 2H), 3.16 (s, 3H), 3.01 (t, J=6.8 Hz, 2H), 1.36 (s, 12H).

Intermediate D-29

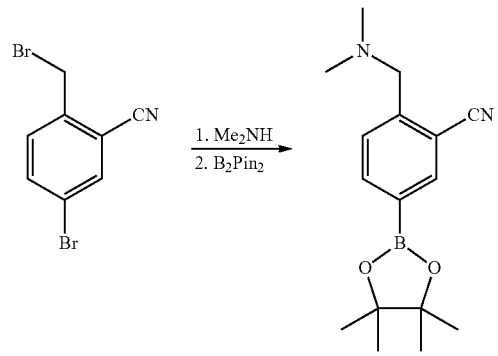 [SMILES: N#Cc1cc(Br)ccc1CBr ; "1. Me2NH" ; CN(C)Cc1ccc(B2OC(C)(C)C(C)(C)O2)cc1C#N]

A mixture of 5-bromo-2-(bromomethyl)benzonitrile (100 mg, 364 µmol, 1.00 equiv), diisopropylethylamine (141 mg, 1.09 mmol, 190 µL, 3.00 equiv) and dimethylamine (2.00 M, 1.82 mL, 10.0 equiv) in dimethyl formamide (2.00 mL) was stirred at room temperature for 3 h. The reaction mixture was diluted with water 5.00 mL and extracted with ethyl acetate (5.00 mL×3). The combined organic layer was washed with brine (3.00 mL-3), dried over sodium sulfate, filtered and concentrated under reduced pressure to give a residue. The residue was purified by prep-TLC (petroleum ether/ethyl acetate=3/1) to afford 5-bromo-2-[(dimethylamino)methyl] benzonitrile (50.0 mg, 209 µmol, 57.5% yield) as a yellow oil. LC-MS [M+1]: 239.2.

¹H NMR (400 MHz, CDCl₃) δ=7.77 (d, J=2.0 Hz, 1H), 7.69 (dd, J=2.0, 8.4 Hz, 1H), 7.46 (d, J=8.4 Hz, 1H), 3.59 (s, 2H), 1.59 (br s, 6H).

A mixture of 5-bromo-2-[(dimethylamino)methyl]benzonitrile (30.0 mg, 125 µmol, 1.00 equiv), bis(pinacolato) diboron (63.7 mg, 251 µmol, 2.00 equiv), potassium acetate (36.9 mg, 376 µmol, 3.00 equiv) and Pd(dppf)Cl₂.CH₂Cl₂ (3.07 mg, 3.76 µmol, 0.03 equiv) in dioxane (1.00 mL) was purged with nitrogen and then stirred at 90° C. for 4 h. The mixture was filtered and concentrated under reduced pressure to give the crude product 2-[(dimethylamino)methyl]-5-(4,4,5,5-tetramethyl-1,3,2-dioxaborolan-2-yl)benzonitrile (40.0 mg) as a black oil which was used in the next step without further purification.

Intermediate D-30

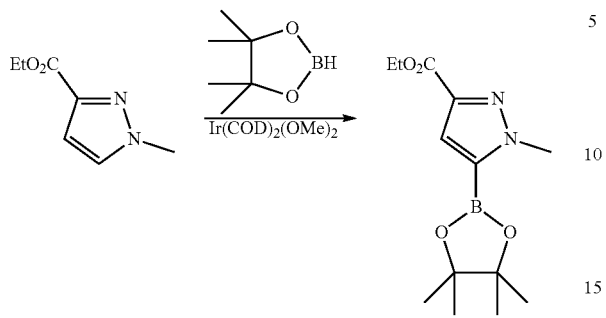

To a solution of Ir(COD)$_2$(OMe)$_2$(5.00 mg, 7.54 µmol, 0.02 equiv) and 4,4,5,5-tetramethyl-1,3,2-dioxaborolane (68.5 mg, 535 µmol, 77.7 µL, 1.50 equiv) in n-pentane (0.50 mL) was added 4-tert-buty-2-(4-tert-butyl-2-pyridyl)pyridine (5.00 mg, 18.6 µmol, 0.05 equiv) and the mixture was stirred at 25° C. for 20 minutes. To this mixture was added a solution of methyl 1-methylpyrazole-3-carboxylate (50.0 mg, 357 µmol, 1.00 equiv) in n-pentane (0.50 mL) and THF (0.50 mL) and the mixture was stirred at 25° C. for 24 h. The mixture was partitioned between ethyl acetate (10.0 mL) and water (10.0 mL). The organic phase was dried over anhydrous sodium sulfate and concentrated to afford the crude product methyl 1-methyl-5-(4,4,5,5-tetramethyl-1,3,2-dioxaborolan-2-yl)pyrazole-3-carboxylate (50.0 mg, 113 µmol, 31.6% yield, 60.0% purity) as a black oil.

$^1$H NMR (400 MHz, CDCl$_3$) δ=7.28 (s, 1H), 4.15 (s, 3H), 3.93 (s, 3H), 1.35 (s, 12H).

Intermediate D-31

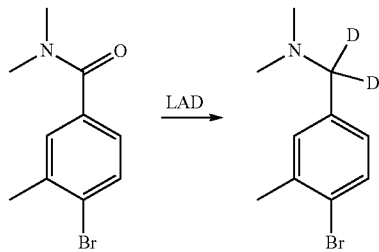

To a solution of 4-bromo-N,N,3-trimethyl-benzamide (500 mg, 2.07 mmol, 1.00 equiv) in THF (5.00 mL) was added lithium tetradeuterioalumanide (235 mg, 6.20 mmol, 3.00 equiv). The mixture was stirred at 0° C. for 1.5 h and subsequently was warmed to room temperature and allowed to stir for another hour. The reaction mixture was cooled to 0° C. and diluted with THF (10.0 mL). The reaction was quenched upon the dropwise addition of deuterium oxide (0.24 mL), 15% NaOD solution in deuterium oxide (0.24 mL) at 0° C., and finally deuterium oxide (0.72 mL). The mixture was stirred at room temperature for 10 min, dried over sodium sulfate, filtered and concentrated under reduced pressure to give a residue. The residue was purified by column chromatography (SiO$_2$, dichloromethane/methanol=50/1 to 20/1) to afford 1-(4-bromo-3-methy-phenyl)-1,1-dideuterio-N,N-dimethyl-methanamine (220 mg, crude) as a brown oil. LCMS [M+1]: 232.1.

Intermediate D-32

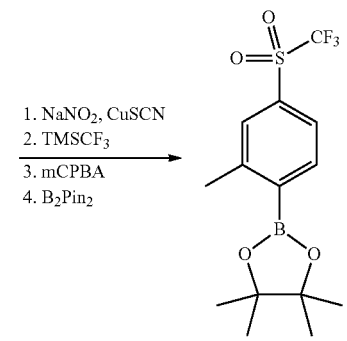

To a solution of 4-bromo-3-methyl-aniline (4.00 g, 21.5 mmol, 1.00 equiv) in concentrated sulfuric acid (40.0 mL) and water (40.0 mL) was added sodium nitrite (1.62 g, 23.4 mmol, 1.09 equiv) at 0° C. and the mixture was stirred for 90 min. Subsequently, potassium thiocyanate (2.82 g, 29.0 mmol, 2.82 mL, 1.35 equiv) in water (16.0 mL) and thiocyanatocopper (6.80 g, 55.9 mmol, 2.60 equiv) was then added to the suspension at 5° C. After stirring at 5° C. for 2 h, the mixture was allowed to stir at room temperature for 10 h. The mixture was filtered and concentrated under reduced pressure to give a residue. The residue was purified by column chromatography (SiO$_2$, petroleum ether) to afford (4-bromo-3-methyl-phenyl) thiocyanate (2.00 g, 8.77 mmol, 40.8% yield) as a yellow oil.

$^1$H NMR (400 MHz, CDCl$_3$)=7.52 (d, J=8.4 Hz, 1H), 7.33 (d, J=2.4 Hz, 1H), 7.14 (dd, J=2.4, 8.4 Hz, 1H), 2.36 (s, 3H).

A mixture of (4-bromo-3-methyl-phenyl) thiocyanate (500 mg, 2.19 mmol, 1.00 equiv), trimethyl(trifluoromethyl)silane(1.00 g, 7.04 mmol, 3.21 equiv) and tetrabutylammonium fluoride (1.00 M, 701 µL, 0.32 equiv) in tetrahydrofuran (1.00 mL) was stirred at room temperature for 4 h. The mixture was filtered and concentrated under reduced pressure. The residue was purified by column chromatography (SiO$_2$, petroleum ether) to afford 1-bromo-2-methyl-4-(trifluoromethylsulfanyl)benzene (450 mg, 1.66 mmol, 75.7% yield) as a colorless oil.

$^1$H NMR (400 MHz, CDCl$_3$) δ=7.59 (d, J=8.0 Hz, 1H), 7.52 (d, J=2.0 Hz, 1H), 7.34 (dd, J=2.4, 8.0 Hz, 1H), 2.44 (s, 3H).

A mixture of 1-bromo-2-methyl-4-(trifluoromethylsulfanyl)benzene (450 mg, 1.66 mmol, 1.00 equiv) and m-chloroperbenzoic acid (2.02 g, 85.0%, 9.96 mmol, 6.00 equiv) in chloroform (10.0 mL) was stirred at room temperature for 2 h. The mixture was heated to 60° C. and allowed to stir for an additional 10 h. The mixture was diluted with saturated sodium bicarbonate (15.0 mL) and extracted with dichloromethane (5.00 mL×3). The combined organic phase was washed with sodium sulfite (5.00 mL), brine (5.00 mL), dried over sodium sulfate, filtered and concentrated under pressure to give a residue. The residue was purified by column chromatography (SiO$_2$, petroleum ether) to afford 1-bromo-2-methyl-4-(trifluoromethylsulfonyl) benzene (400 mg, 1.32 mmol, 79.5% yield) as a white solid.

$^1$H NMR (400 MHz, CDCl$_3$) δ=7.88 (d, J=2.0 Hz, 1H), 7.86 (d, J=8.4 Hz 1H), 7.71 (dd, J=2.4, 8.4 Hz, 1H), 2.55 (s, 3H).

A mixture of 1-bromo-2-methyl-4-(trifluoromethylsulfonyl)benzene (100 mg, 330 µmol, 1.00 equiv), bis(pinacolato)diboron (168 mg, 660 µmol, 2.00 equiv), potassium acetate (97.1 mg, 990 µmol, 3.00 equiv) and Pd(dppf)Cl$_2$ (24.1 mg, 33.0 µmol, 0.10 equiv) in dioxane (2.00 mL) was purged with nitrogen and then stirred at 90° C. for 2 h. The mixture was filtered and concentrated under reduced pressure to afford 4,4,5,5-tetramethyl-2-[2-methyl-4-(trifluoromethyl-sulfonyl)phenyl]-1,3,2-dioxaborolane (200 mg, crude) as a black solid that was used into the next step without further purification.

Intermediate D-33

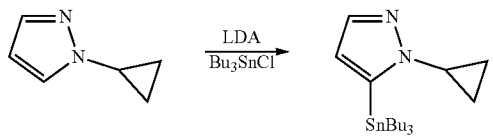

To a solution of diisopropylamine (243 mg, 2.40 mmol, 339 µL, 1.30 equiv) in THF (4.00 mL) was added dropwise n-BuLi (2.50 M, 961 uL, 1.30 equiv) at −78° C. and then the reaction was stirred at −78° C. for 30 mins. 1-cyclopropylpyrazole (200 mg, 1.85 mmol, 1.00 equiv) was added and the reaction was stirred at −78° C. for 1 h. Tributyl(chloro)stannane (602 mg, 1.85 mmol, 498 uL, 1.00 equiv) was added drop-wise and the reaction was stirred at −78° C. for another 30 min. The reaction mixture was partitioned between ethyl acetate (5.00 mL) and saturated ammonium chloride (5.00 mL). The organic phase was separated, washed with brine (5.00 mL), dried over sodium sulfate, filtered and concentrated under reduced pressure to give tributyl-(2-cyclopropylpyrazol-3-yl)stannane (1.00 g, crude) as a colorless oil which used for the next step without further purification.

$^1$H NMR (400 MHz, CDCl$_3$) δ=7.51 (d, J=1.6 Hz, 1H), 6.32 (d, J=1.6 Hz, 1H), 3.54-3.49 (m, 1H), 1.61-1.50 (m, 6H), 1.37-1.31 (m, 6H), 1.21-1.13 (m, 6H), 0.97-0.89 (m, 13H).

Intermediate D-34

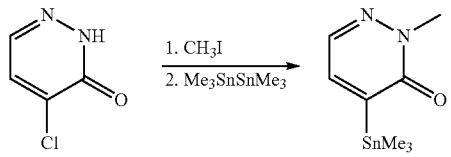

To a solution of 4-chloropyridazin-3-ol (300 mg, 2.30 mmol, 1.00 equiv) and methyl iodide (3.26 g, 23.0 mmol, 1.43 mL, 10.0 equiv) in dioxane (600 mL) was added silver oxide (533 mg, 2.30 mmol, 1.00 equiv). The mixture was stirred at 60° C. for 5 h. The mixture was filtered and concentrated in vacuo to provide a residue. The residue was purified by prep-TLC (SiO$_2$, petroleum ether/ethyl acetate=1/1) to afford 4-chloro-2-methyl-pyridazin-3-one (110 mg, 761 µmol, 33.1% yield) as a yellow solid.

$^1$H NMR (400 MHz, DMSO-d$_6$) δ=7.87 (d, J=4.4 Hz, 1H), 7.78 (d, J=4.4 Hz, 1H), 3.72 (s, 3H).

To a solution of 4-chloro-2-methyl-pyridazin-3-one (110 mg, 761 µmol, 1.00 equiv) and hexamethylditin (998 mg, 3.04 mmol, 631 µL, 4.00 equiv) in dioxane (2.00 mL) was added Pd(PPh$_3$)$_4$ (87.93 mg, 76.09 µmol, 0.10 equiv) under nitrogen. The mixture was stirred at 110° C. for 2 h and was subsequently filtered and concentrated in vacuo. The residue was purified by prep-TLC (SiO$_2$, petroleum ether/ethyl acetate=1/1) to afford 2-methyl-4-trimethylstannyl-pyridazin-3-one (130 mg, 476 µmol, 62.6% yield) as a white solid.

$^1$H NMR (400 MHz, CD$_3$OD) δ=7.79 (d, J=3.6 Hz, 1H), 7.51 (d, J=3.6 Hz, 1H), 3.73 (s, 3H), 0.32 (s, 9H).

Intermediate D-35

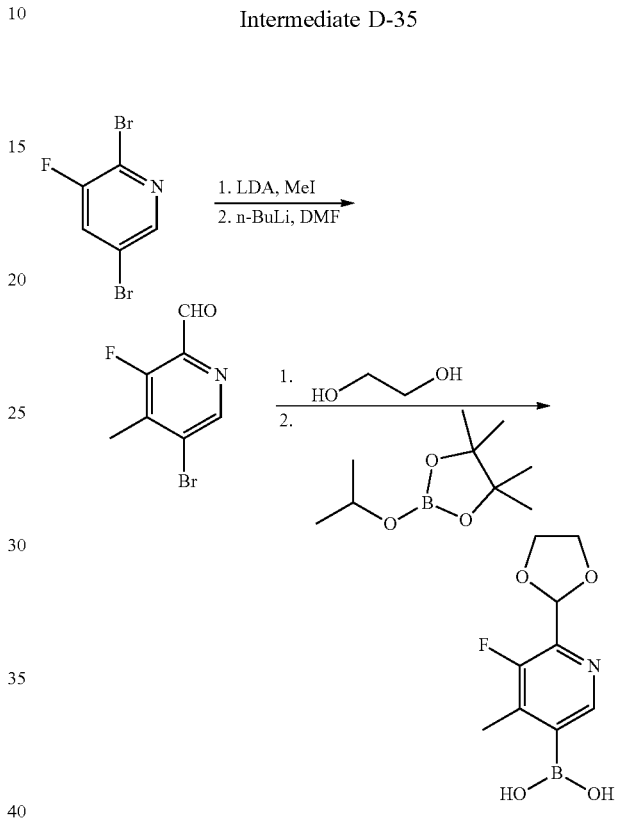

To a solution of 2,5-dibromo-3-fluoro-pyridine (0.50 g, 1.96 mmol, 1.00 equiv) in THF (10.0 mL) was added n-BuLi (2.50 M, 1.18 mL, 1.50 equiv) dropwise at −65° C. The mixture was stirred at −65° C. for 0.5 h followed by the addition of N-isopropylpropan-2-amine (397 mg, 3.92 mmol, 554 µL, 2.00 equiv) one portion and stirring at this temperature for an additional 30 min. To this mixture was added methyl iodide (334 mg, 2.35 mmol, 147 µL, 1.20 equiv) and the mixture was allowed to stir at −65° C. for 1 h. The reaction mixture was quenched by the addition of satd aq NH$_4$Cl (10.0 mL) and the resulting mixture was extracted with ethyl acetate (20.0 mL×3). The combined organic phase was washed with brine (30.0 mL×2), dried over anh sodium sulfate and concentrated under reduced pressure to give the crude residue. The residue was purified by prep-HPLC (acidic conditions) to afford 2,5-dibromo-3-fluoro-4-methyl-pyridine (3 mg, 1.12 mmol, 56.9% yield) as a yellow solid. LCMS [M+1]: 269.7.

To a solution of 2,5-dibromo-3-fluoro-4-methyl-pyridine (0.80 g, 2.97 mmol, 1.00 equiv) in THF (10.0 mL) was added n-BuLi (2.5 M, 1.19 mL, 1.00 equiv) at −65° C. and the resultant mixture was stirred for 0.5 h followed by the dropwise addition of DMF (326 mg, 4.46 mmol, 343 µL, 1.50 equiv). After an additional 30 min of stirring at −65° C. the reaction mixture was quenched with satd aq NH$_4$Cl (5.00 mL) and the resulting mixture was extracted with ethyl acetate (30.0 mL×2). The combined organic phase was washed with brine (30.0 mL×2), dried over anh sodium sulfate, filtered and concentrated under reduced pressure to give the crude residue. The residue was purified by column chromatography (SiO$_2$, petroleum ether/ethyl acetate=1/0 to 100/1) to afford 5-bromo-3-fluoro-4-methyl-pyridine-2-carbaldehyde (300 mg, 1.38 mmol, 46.3% yield) as a yellow solid.

$^1$H NMR (400 MHz, CDCl$_3$) δ=10.20 (d, J=0.8 Hz, 1H), 8.69 (s, 1H), 2.48 (d, J=2.4 Hz, 3H).

To a solution of 5-bromo-3-fluoro-4-methyl-pyridine-2-carbaldehyde (300 mg, 1.38 mmol, 1.00 equiv) in Tol. (10.0 mL) was added TsOH—H$_2$O (26.2 mg, 138 μmol, 0.10 equiv) and ethylene glycol (171 mg, 2.75 mmol, 14 μL, 2.00 equiv). The mixture was stirred at 120° C. for 2 h. The reaction mixture was concentrated under reduced pressure to provide a crude residue. The residue was purified by column chromatography (SiO$_2$, petroleum ether/ethyl acetate=1/0 to 100/1) to afford 5-bromo-2-(1,3-dioxolan-2-yl)-3-fluoro-4-methyl-pyridine (250 mg, 954 μmol, 69.3% yield) as a colorless oil.

$^1$H NMR (400 MHz, CDCl$_3$) δ=8.49 (s, 1H), 6.13 (s, 1H), 4.32-4.20 (m, 2H), 4.14-4.04 (m, 2H), 2.39 (d, J=2.4 Hz, 3H).

To a solution of 5-bromo-2-(1,3-dioxolan-2-yl)-3-fluoro-4-methyl-pyridine (450 mg, 1.72 mmol, 1.00 equiv) in Et$_2$O (10.0 mL) was added dropwise n-BuLi (2.5 M 756 μL, 1.10 equiv) at −70° C. The mixture was stirred for 0.5 h at −70° C. f and subsequently 2-isopropoxy-4,4,5,5-tetramethyl-1,3,2-dioxaborolane (639 mg, 3.43 mmol, 701 μL, 2.00 equiv) was added. The mixture was stirred at −70° C. for 1 h and was quenched with satd aq NH$_4$Cl (10 mL). The mixture was extracted with DCM (30 mL×3) and the combined organic phase was washed with brine (50.0 mL×2), dried over sodium sulfate, filtered and concentrated under reduced pressure to give a crude solid. The crude material was purified by prep-TLC (SiO$_2$, petroleum ether/ethyl acetate=1/1) to afford [6-(1,3-dioxolan-2-yl)-5-fluoro-4-methyl-3-pyridyl]boronic acid (220 mg, 940 μmol, 54.8% yield, 97.0% purity) as a light yellow oil. LCMS [M+1]: 228.0.

Intermediate D-36

To a solution of 3-phenylmorpholine (500 mg, 3.06 mmol, 1.00 equiv) in tetrahydrofuran (5.00 mL) was added triethylamine (512 μL, 3.68 mmol, 1.20 equiv) and di-tert-butyl dicarbonate (669 mg, 3.06 mmol, 704 μL, 1.00 eq.). The mixture was stirred at 20° C. for 1 h. The mixture was concentrated under reduced pressure to give a residue (1.30 g, crude) that was used in the next step directly.

To a solution of tert-butyl 3-phenylmorpholine-4-carboxylate (580 mg, 2.20 mmol, 1.00 equiv) in dichloromethane (6.00 mL) was added phenyl-λ$^3$-iodanediyl bis(2,2,2-trifluoroacetate)(1.04 g, 2.42 mmol, 1.10 equiv) and iodine (559 mg, 2.20 mmol, 444 uL, 1.00 equiv). The reaction mixture was stirred at 20° C. for 2 h. The mixture was diluted with sodium bicarbonate solution (20.0 mL) and extracted with dichloromethane (10.0 mL×3). The combined organic layer was washed with saturated sodium thiosulfate solution (20.0 mL), brine (20 mL), dried over anhydrous sodium sulfate, filtered and concentrated under reduced pressure to give a residue. The residue was purified by column chromatography (SiO$_2$, petroleum ether/ethyl acetate=1/0 to 10/1) to afford tert-butyl 3-(4-iodophenyl)morpholine-4-carboxylate (260 mg, 668 μmol, 30.3% yield) as a white oil.

$^1$H NMR (400 MHz, DMSO-d$_6$) δ=7.73 (br d, J=8.4 Hz, 2H), 7.16 (br d, J=8.0 Hz, 2H), 4.92 (br s, 1H), 4.20 (br d, J=12.0 Hz, 1H), 3.84-3.78 (m, 1H), 3.76-3.65 (m, 2H), 3.50-3.40 (m, 1H), 3.04-2.93 (m, 1H), 1.39 (s, 9H).

A mixture of tert-butyl 3-(4-iodophenyl)morpholine-4-carboxylate (260 mg, 668 μmol, 1.00 equiv), 4,4,5,5-tetramethyl-2-(4,4,5,5-tetramethyl-1,3,2-dioxaborolan-2-yl)-1,3,2-dioxaborolane (254 mg, 1.00 mmol, 1.50 equiv), potassium acetate (131 mg, 1.34 mmol, 2.00 equiv) and Pd(dppf)Cl$_2$ (48.9 mg, 66.8 μmol, 0.10 equiv) in dioxane (2.00 mL) was purged with and subsequently stirred at 100° C. for 2 h under a nitrogen atmosphere. The mixture was filtered and concentrated at reduced pressure to give a residue. The residue was purified by column chromatography (SiO$_2$, petroleum ether/ethyl acetate=1/0 to 10/1) to afford tert-butyl 3-[4-(4,4,5,5-tetramethyl-1,3,2-dioxaborolan-2-yl)phenyl]morpholine-4-carboxylate (100 mg, 257 umol, 38.5% yield) as white oil.

$^1$H NMR (400 MHz, DMSO-d$_6$) δ=7.67 (d, J=8.0 Hz, 2H), 7.37 (d, J=7.6 Hz, 2H), 4.98 (br s, 1H), 4.29-4.23 (m, 1H), 3.86-3.66 (m, 3H), 3.51-3.42 (m, 1H), 3.07-2.96 (m, 1H), 1.41-1.38 (m, 9H), 1.30 (s, 12H).

Intermediates D-37-D-38

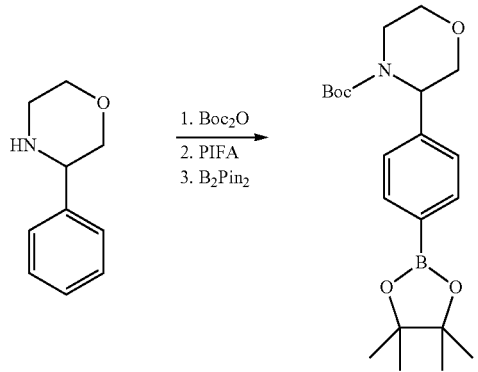 [SMILES: c1ccc(C2COCCN2)cc1 ; CC(C)(C)OC(=O)N1CCOCC1c1ccc(B2OC(C)(C)C(C)(C)O2)cc1]

| Characterization of Intermediates D36-D38 | | |
|---|---|---|
| Int. # | Structure | $^1$H NMR |
| D-37 | 5-((dimethylamino)methyl)-2-(4,4,5,5-tetramethyl-1,3,2-dioxaborolan-2-yl)benzonitrile | $^1$H NMR (400 MHz, CD$_3$OD) δ = 10.03 (s, 1H), 8.41 (s, 1H), 8.16-8.10 (m, 2H). |

Characterization of Intermediates D36-D38

| Int. # | Structure | ¹H NMR |
|---|---|---|
| D-38 | N,N-dimethyl-1-(4-(4,4,5,5-tetramethyl-1,3,2-dioxaborolan-2-yl)phenyl)cyclopropan-1-amine | ¹H NMR (400 MHz, DMSO-d$_6$) δ = 7.64 (d, J = 8.4 Hz, 2H), 7.27 (d, J = 7.6 Hz, 2H), 3.92 (s, 2H), 2.11 (s, 6H), 1.29 (s, 12H), 0.88-0.79 (m, 2H), 0.76-0.67 (m, 2H). LCMS [M + 1]: 288.2. |
| D-39 | 1-(4-(4,4,5,5-tetramethyl-1,3,2-dioxaborolan-2-yl)-1H-pyrazol-1-yl)propan-2-ol | ¹H NMR (400 MHz, methanol-d$_4$) δ = 7.84 (s, 1H), 7.68 (s, 1H), 4.16-4.04 (m, 3H), 1.31 (s, 12H), 1.16-1.12 (m, 3H). LCMS [M + 1]: 253.3. |
| D-40 | tert-butyl (S)-2-(4-(4,4,5,5-tetramethyl-1,3,2-dioxaborolan-2-yl)phenyl)pyrrolidine-1-carboxylate | ¹H NMR (400 MHz, CDCl$_3$) δ = 7.74 (br d, J = 7.6 Hz, 2H), 7.17 (br d, J = 7.6 Hz, 2H), 4.79 (br s, 1H), 3.63 (br s, 2H), 2.31 (br s, 1H), 1.94-1.73 (m, 3H), 1.35 (s, 12H), 1.19 (s, 9H). |
| D-41 | tert-butyl (R)-2-(4-(4,4,5,5-tetramethyl-1,3,2-dioxaborolan-2-yl)phenyl)pyrrolidine-1-carboxylate | LCMS [M − 55]: 318.2. |
| D-42 | 1-methyl-2-(4-(4,4,5,5-tetramethyl-1,3,2-dioxaborolan-2-yl)phenyl)azetidine | LCMS [M + 1]: 274.1. |
| D-43 | 4-(4-(4,4,5,5-tetramethyl-1,3,2-dioxaborolan-2-yl)phenyl)azetidin-2-one | LCMS [M + 1]: 274.1. |

Characterization of Intermediates D36-D38

| Int. # | Structure | ¹H NMR |
|---|---|---|
| D-44 | tert-butyl 3-(4-(4,4,5,5-tetramethyl-1,3,2-dioxaborolan-2-yl)phenyl)morpholine-4-carboxylate | ¹H NMR (400 MHz, DMSO-$d_6$) δ = 7.67 (d, J = 8.0 Hz, 2H), 7.37 (d, J = 7.6 Hz, 2H), 4.98 (br s, 1H), 4.29-4.23 (m, 1H), 3.86-3.66 (m, 3H), 3.51-3.42 (m, 1H), 3.07-2.96 (m, 1H), 1.41-1.38 (m, 9H), 1.30 (s, 12H). |

The following Examples are intended to illustrate further certain embodiments of the invention and are not intended to limit the scope of the invention.

Example 1

8-(1,3-dimethyl-1H-pyrazol-5-yl)-5-(((5-fluoro-2,3-dihydrobenzofuran-4-yl)methyl)amino)imidazo[1,2-c]pyrimidine-2-carboxylic acid

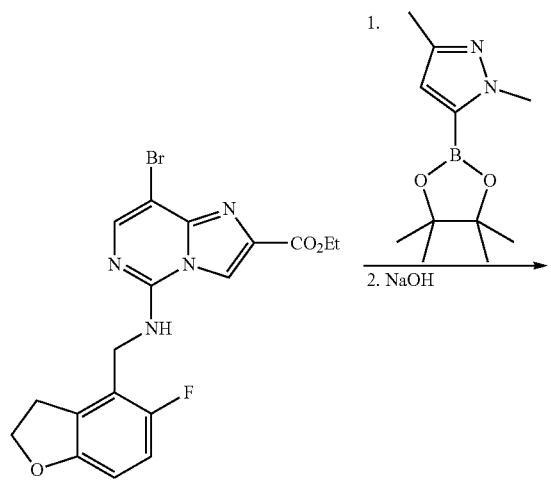

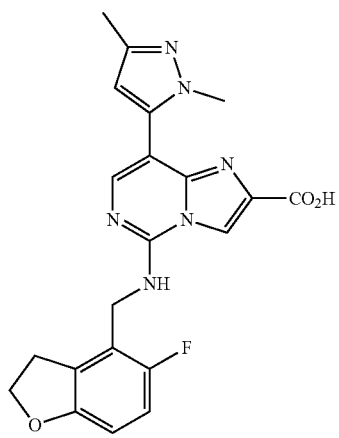

A mixture of ethyl 8-bromo-5-(((5-fluoro-2,3-dihydrobenzofuran-4-yl)methyl)amino)imidazo[1,2-c]pyrimidine-2-carboxylate (0.100 g, 230 μmol, 1.00 equiv), 1,3-dimethyl-5-(4,4,5,5-tetramethyl-1,3,2-dioxaborolan-2-yl)pyrazole (81.6 mg, 368 μmol, 1.60 equiv), sodium bicarbonate (77.2 mg, 919 μmol, 4.00 equiv), Pd(dppf)Cl$_2$ (16.8 mg, 23.0 μmol, 0.100 equiv) in dioxane (2.10 mL) and water (0.700 mL) was purged with nitrogen three times. Subsequently, the mixture was stirred at 105° C. for 1 h under a nitrogen atmosphere. The reaction mixture was filtered and concentrated in vacuo. The crude material was purified by prep-TLC (SiO$_2$, PE:EA=2:3) to afford ethyl 8-(1,3-dimethyl-1H-pyrazol-5-yl)-5-(((5-fluoro-2,3-dihydrobenzofuran-4-yl)methyl)amino)imidazo[1,2-c]pyrimidine-2-carboxylate (60.0 mg, 47.9% yield, 82.6% purity) as an orange solid. LC-MS: [M+1] 450.9.

To a solution of ethyl 8-(1,3-dimethyl-1H-pyrazol-5-yl)-5-(((5-fluoro-2,3-dihydrobenzofuran-4-yl)methyl)amino)imidazo[1,2-c]pyrimidine-2-carboxylate (55.0 mg, 101 μmol, 1.00 equiv) in methanol (2.00 mL) was added aq sodium hydroxide (1.00 M, 303 μL, 3.00 equiv). The resultant mixture was stirred at 60° C. for 0.5 h. The mixture was filtered and the majority of the methanol was removed in vacuo. The residue was adjusted to pH 4 with 2.00 M aq hydrochloric acid and the precipitate was filtered and dried under vacuum. The crude product was rinsed with methanol (2.00 mL) and dried under vacuum to afford 8-(1,3-dimethyl-1H-pyrazol-5-yl)-5-(((5-fluoro-2,3-dihydrobenzofuran-4-yl)methyl)amino)imidazo[1,2-c]pyrimidine-2-carboxylic acid (19.7 mg, 44.2% yield, 95.5% purity) as a yellow solid. LC-MS: [M+1]423.0.

¹H NMR (400 MHz, MeOD) δ=8.63 (s, 1H), 7.80 (s, 1H), 6.92-6.82 (m, 1H), 6.65 (dd, J=4.0, 8.8 Hz, 1H), 6.27 (s, 1H), 4.83 (s, 2H), 4.59 (t, J=8.8 Hz, 2H), 3.75 (s, 3H), 3.39 (t, J=8.8 Hz, 2H), 2.28 (s, 3H).

Example 2

5-(((5-fluoro-2,3-dihydrobenzofuran-4-yl)methyl)amino)-8-(2-methylpyridin-3-yl)imidazo[1,2-c]pyrimidine-2-carboxylic acid

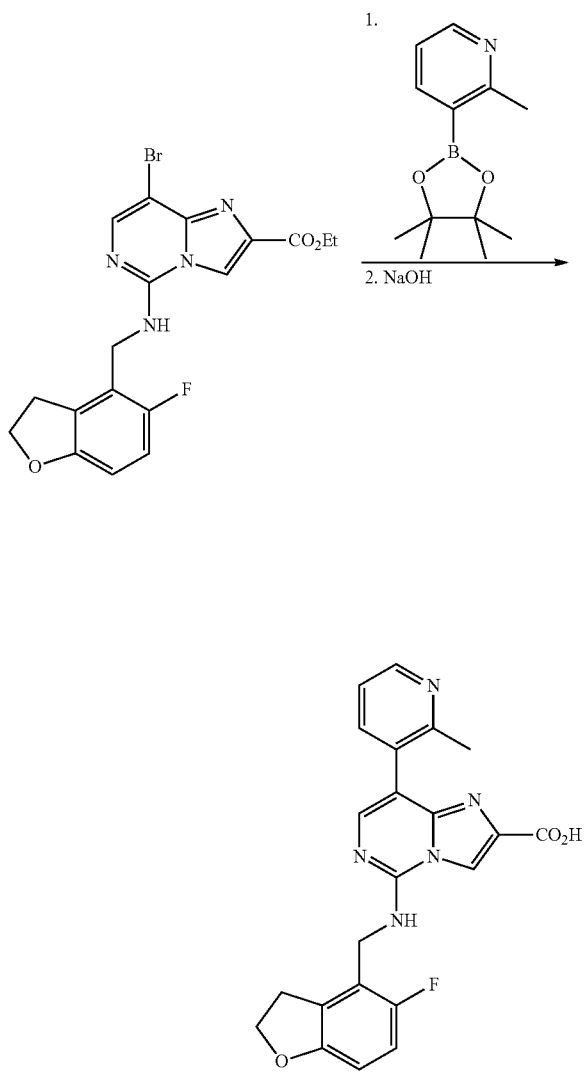

To a solution of ethyl 8-bromo-5-((((5-fluoro-2,3-dihydrobenzofuran-4-yl)methyl)amino)imidazo[1,2-c]pyrimidine-2-carboxylate (50.0 mg, 115 μmol, 1.00 equiv), 2-methyl-3-(4,4,5,5-tetramethyl-1,3,2-dioxaborolan-2-yl)pyridine (37.8 mg, 172 μmol, 1.50 equiv) in dioxane (3.00 mL) was added water (1.00 mL) followed by Pd(dppf)Cl$_2$ (8.41 mg, 11.5 μmol, 0.100 equiv) and sodium bicarbonate (29.0 mg, 345 μmol, 3.00 equiv). The reaction mixture was stirred at 105° C. for 1 h under nitrogen. The mixture was cooled to 25° C. and filtered. The filtrate was concentrated in vacuo to provide a residue. The crude material was purified by prep-TLC (dichloromethane/methanol=10/1) to afford ethyl 5-(((5-fluoro-2,3-dihydrobenzofuran-4-yl)methyl)amino)-8-(2-methylpyridin-3-yl)imidazo[1,2-c]pyrimidine-2-carboxylate (40.0 mg, 75.0% yield, 96.4% purity) as a brown solid.

To a solution of ethyl 5-(((5-fluoro-2,3-dihydrobenzofuran-4-yl)methyl)amino)-8-(2-methylpyridin-3-yl)imidazo[1,2-c]pyrimidine-2-carboxylate (40.0 mg, 86.2 μmol, 1.00 equiv) in methanol (4.00 mL) and water (1.00 mL) was added sodium hydroxide (10.3 mg, 258 μmol, 3.00 equiv). The reaction mixture was stirred at 55° C. for 20 min. The mixture was concentrated in vacuo to remove the majority of the methanol and the pH was adjusted to ~6 with aq hydrochloric acid (1.00 M, 0.500 mL). The resultant suspension was filtered and the filter cake was dried under vacuum to afford 5-(((5-fluoro-2,3-dihydrobenzofuran-4-yl)methyl)amino)-8-(2-methylpyridin-3-yl)imidazo[1,2-c]pyrimidine-2-carboxylic acid (18.1 mg, 48.0% yield, 95.7% purity) as a white solid. LCMS: [M+1]420.2.

1H NMR (400 MHz, CD$_3$OD) δ=8.74 (dd, J=1.2, 6.0 Hz, 1H), 8.68 (s, 1H), 8.50 (dd, J=1.2, 7.6 Hz, 1H), 7.93 (dd, J=6.4, 8.0 Hz, 1H), 7.88 (s, 1H), 6.91-6.83 (m, 1H), 6.66 (dd, J=4.0, 8.8 Hz, 1H), 4.86 (s, 2H), 4.60 (t, J=8.8 Hz, 2H), 3.43 (t, J=8.8 Hz, 2H), 2.68 (s, 3H).

Example 3

5-(((5-fluorobenzofuran-4-yl)methyl)amino)-8-(2-methylpyridin-3-yl)imidazol[1,2-c]pyrimidine-2-carboxylic acid

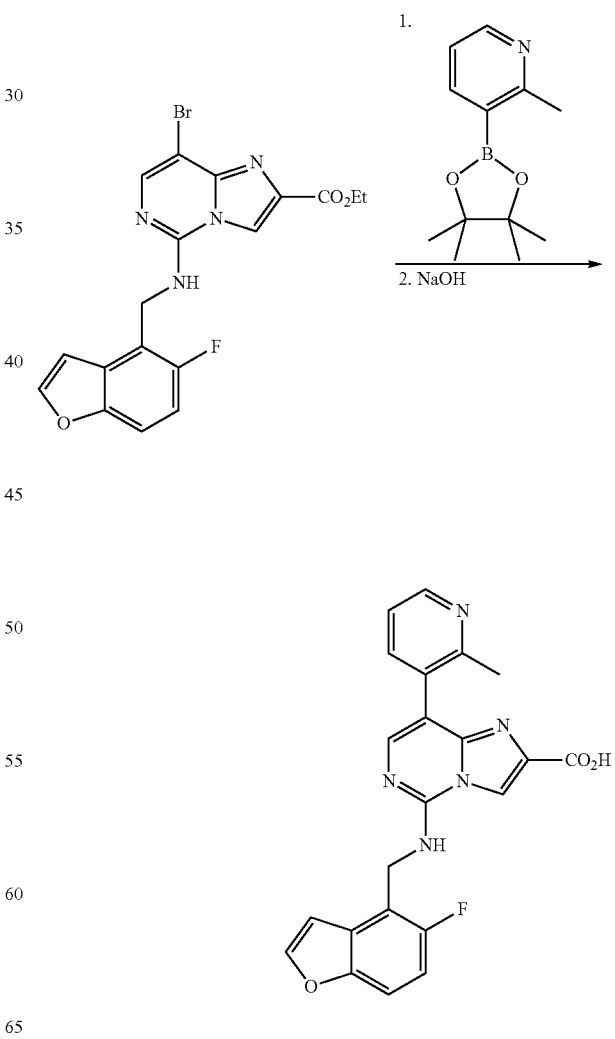

A mixture of ethyl 8-bromo-5-(((5-fluorobenzofuran-4-yl)methyl)amino)imidazo[1,2-c]pyrimidine-2-carboxylate (120 mg, 274 μmol, 1.00 equiv), 2-methyl-3-(4,4,5,5-tetramethyl-1,3,2-dioxaborolan-2-yl)pyridine (120 mg, 548 μmol, 2.00 equiv), sodium bicarbonate (69.0 mg, 822 μmol, 32.0 μL, 3.00 equiv) and Pd(dppf)Cl$_2$ (22.4 mg, 27.4 μmol, 0.100 equiv) in dioxane (3.00 mL) and water (0.600 mL) was purged with nitrogen and stirred at 105° C. for 1 h under a nitrogen atmosphere. The mixture was concentrated at reduced pressure to give a residue. The crude material was purified by prep-TLC (DCM/Methyl alcohol=20/1) to afford ethyl 5-(((5-fluorobenzofuran-4-yl)methyl)amino)-8-(2-methylpyridin-3-yl)imidazo[1,2-c]pyrimidine-2-carboxylate (100 mg, 78.9% yield, 96.3% purity) as a brown solid. LCMS [M+1]: 446.2.

To a solution of ethyl 5-(((5-fluorobenzofuran-4-yl)methyl)amino)-8-(2-methylpyridin-3-yl)imidazo[1,2-c]pyrimidine-2-carboxylate (100 mg, 216 μmol, 1.00 equiv) in methyl alcohol (4.00 mL) and water (1.00 mL) was added sodium hydroxide (17.3 mg, 432 μmol, 2.00 equiv). The resultant mixture was stirred at 25° C. for 0.5 h. The reaction mixture was concentrated at reduced pressure, water (2 ml) was added, and the pH was adjusted to 5 with aq hydrochloric acid (1.00 M). The precipitate was filtered to provide the crude material (80 mg) as a brown solid. The crude material was purified by prep-HPLC (column: Phenomenex Synergi C18 150×25×10 μm; mobile phase:[water (0.1% TFA)-ACN]:B %: 12%-42%, 10 min) to afford 5-(((5-fluorobenzofuran-4-yl)methyl)amino)-8-(2-methylpyridin-3-yl)imidazol[1,2-c]pyrimidine-2-carboxylic acid (10.0 mg, 99.7% purity) as a gray solid. LCMS [M+1]: 418.1.

$^1$H NMR (400 MHz, CD$_3$OD) δ=8.74 (dd, J=1.6, 5.6 Hz, 1H), 8.64 (s, 1H), 8.56 (dd, J=1.6, 8.0 Hz, 1H), 7.97 (dd, J=6.0, 7.6 Hz, 1H), 7.89 (s, 1H), 7.82 (d, J=2.4 Hz, 1H), 7.47 (dd, J=3.6, 8.8 Hz, 1H), 7.15-7.08 (m, 2H), 5.13 (s, 2H), 2.67 (s, 3H).

Example 4

5-(((5-fluoro-2,3-dihydrobenzofuran-4-yl)methyl) amino)-8-(4-methyl-1H-imidazol-1-yl)imidazo[1,2-c]pyrimidine-2-carboxylic acid

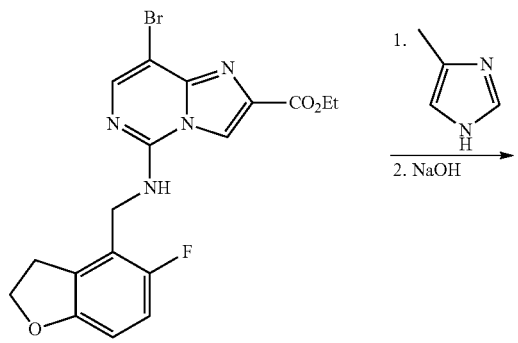

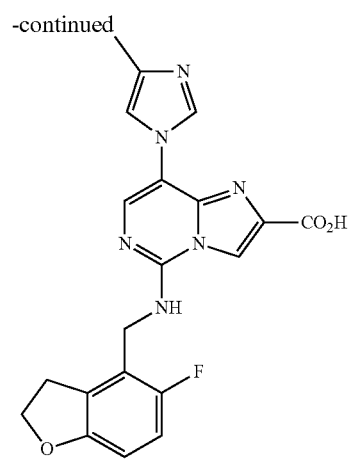

A mixture of 4-methyl-1H-imidazole (102 mg, 1.24 mmol, 4.40 equiv), ethyl 8-bromo-5-[tert-butoxycarbonyl-[(5-fluoro-2,3-dihydrobenzofuran-4-yl)methyl]amino]imidazo[1,2-c]pyrimidine-2-carboxylate (160 mg, 282 μmol, 1.00 equiv), Pd$_2$(dba)$_3$ (25.9 mg, 28.2 μmol, 0.10 equiv), ditert-butyl-[2,3,4,5-tetramethyl-6-(2,4,6-triisopropylphenyl)phenyl]phosphane (27.2 mg, 56.5 μmol, 0.20 equiv) and potassium phosphate (155 mg, 734 μmol, 2.60 equiv) in dioxane (5.00 mL) was purged with nitrogen. The resultant mixture was stirred at 120° C. for 2 h under a nitrogen atmosphere. The mixture was diluted with ethyl acetate (3 mL) and extracted with ethyl acetate (2.00 mL×3). The combined organic layers were washed with brine (2.00 mL×3), dried over anhydrous sodium sulfate, filtered and concentrated under reduced pressure to afford ethyl 5-(((5-fluoro-2,3-dihydrobenzofuran-4-yl)methyl)amino)-8-(4-methyl-1H-imidazol-1-yl)imidazo[1,2-c]pyrimidine-2-carboxylate (120 mg, crude) as a yellow oil.

A mixture of ethyl 5-(((5-fluoro-2,3-dihydrobenzofuran-4-yl)methyl)amino)-8-(4-methyl-1H-imidazol-1-yl)imidazo [1,2-c]pyrimidine-2-carboxylate (120 mg, 275 μmol, 1.00 equiv), sodium hydroxide (33.0 mg, 825 μmol, 3.00 equiv) in methyl alcohol (3.00 mL) and water (1.00 mL) was purged with nitrogen. The mixture was stirred at 60° C. for 1 h. The residue was diluted with ethyl acetate (3.00 mL) and extracted with ethyl acetate (2.00 mL×3). The combined organic layers were washed with brine (2.00 mL×3), dried over anhydrous sodium sulfate, filtered and concentrated under reduced pressure to provide a residue. The crude material was purified by prep-HPLC (basic conditions) to give 5-(((5-fluoro-2,3-dihydrobenzofuran-4-yl)methyl) amino)-8-(4-methyl-1H-imidazol-1-yl)imidazo[1,2-c]pyrimidine-2-carboxylic acid (37.1 mg, 90.0 μmol, 32.7% yield, 99.1% purity) as a bluish solid. LC-MS [M+1]: 409.3.

$^1$H NMR (400 MHz, DMSO-d$_h$) δ=8.68 (s, 1H), 8.54 (br s, 1H), 8.20 (s, 1H), 7.92 (s, 1H), 7.47 (s, 1H), 6.97-6.88 (m, 1H), 6.68 (dd, J=3.6, 8.8 Hz, 1H), 4.70 (br s, 2H), 4.53 (t, J=8.8 Hz, 2H), 3.31 (br d, J=8.8 Hz, 2H), 2.18 (s, 3H).

EXAMPLES 5-10 were prepared following the procedure set forth in Example 4 and using the general reactions schemes and intermediates described herein.

TABLE 1

Characterization of EXAMPLES 5-10

| Ex. # | Structure | $^1$H NMR |
|---|---|---|
| 5 | 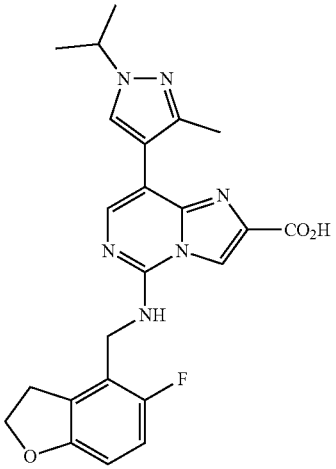<br>5-(((5-fluoro-2,3-dihydrobenzofuran-4-yl)methyl)amino)-8-(1-isopropyl-3-methyl-1H-pyrazol-4-yl)imidazo[1,2-c]pyrimidine-2-carboxylic acid | $^1$H NMR (400 MHz, CD$_3$OD) δ = 8.56 (s, 1H), 8.19 (s, 1H), 7.79 (s, 1H), 6.85 (t, J = 9.6 Hz, 1H), 6.63 (dd, J = 4.0, 8.8 Hz, 1H), 4.80 (s, 2H), 4.57 (t, J = 8.8 Hz, 2H), 4.53-4.46 (m, 1H), 3.38-3.34 (m, 2H), 2.37 (s, 3H), 1.54 (d, J = 6.8 Hz, 6H).<br>LCMS [M + 1]: 451.3. |
| 6 | 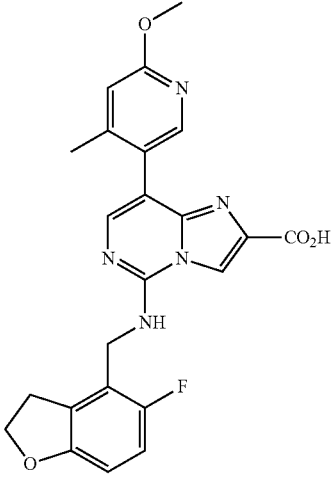<br>5-(((5-fluoro-2,3-dihydrobenzofuran-4-yl)methyl)amino)-8-(6-methoxy-4-methylpyridin-3-yl)imidazo[1,2-c]pyrimidine-2-carboxylic acid | $^1$H NMR (400 MHz, DMSO-d$_6$) δ = 8.78 (s, 1H), 8.43 (br s, 1H), 8.03 (s, 1H), 7.63 (s, 1H), 6.97-6.91 (m, 1H), 6.80 (s, 1H), 6.70 (dd, J = 4.0, 8.8 Hz, 1H), 4.70 (br d, J = 4.4 Hz, 2H), 4.55 (t, J = 8.8 Hz, 2H), 3.87 (s, 3H), 3.33-3.29 (m, 2H), 2.15 (s, 3H).<br>LC-MS [M + 1]: 450.1. |

TABLE 1-continued

Characterization of EXAMPLES 5-10

| Ex. # | Structure | ¹H NMR |
|---|---|---|
| 7 | 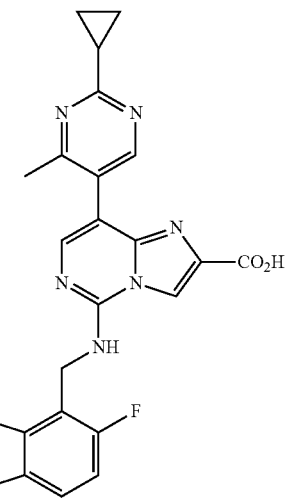<br>8-(2-cyclopropyl-4-methylpyrrolidin-5-yl)-5-(((5-fluoro-2,3-dihydrobenzofuran-4-yl)methyl)amino)imidazo[1,2-c]pyrimidine-2-carboxylic acid | ¹H NMR (400 MHz, DMSO-$d_6$) δ = 8.52-8.28 (m, 2H), 7.57 (s, 1H), 6.93 (br t, J = 9.6 Hz, 1H), 6.73-6.63 (m, 1H), 4.72 (br s, 2H), 4.52 (br d, J = 8.8 Hz, 2H), 3.30-3.24 (m, 2H), 2.34 (s, 3H), 2.25-2.17 (m, 1H), 1.17-0.91 (m, 4H).<br>LC-MS [M + 1]: 461.4. |
| 8 | 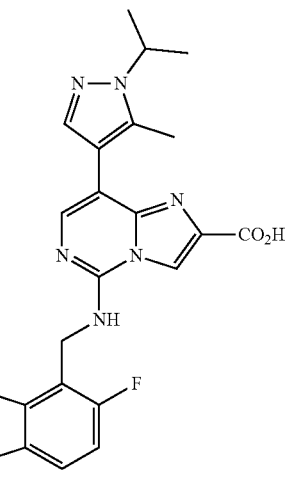<br>5-(((5-fluoro-2,3-dihydrobenzofuran-4-yl)methyl)amino)-8-(1-isopropyl-5-methyl-1H-pyrazol-4-yl)imidazo[1,2-c]pyrimidine-2-carboxylic acid | ¹H NMR (400 MHz, CD$_3$OD) δ = 8.71 (s, 1H), 7.92 (s, 1H), 7.67 (s, 1H), 6.90-6.82 (m, 1H), 6.65 (dd, J = 4.0, 8.8 Hz, 1H), 4.84 (br s, 2H), 4.68-4.62 (m, 1H), 4.58 (t, J = 8.8 Hz, 2H), 3.39 (t, J = 8.4 Hz, 2H), 2.28 (s, 3H), 1.52 (d, J = 6.4 Hz, 6H).<br>LCMS [M + 1]: 451.3. |

TABLE 1-continued

Characterization of EXAMPLES 5-10

| Ex. # | Structure | $^1$H NMR |
|---|---|---|
| 9 | 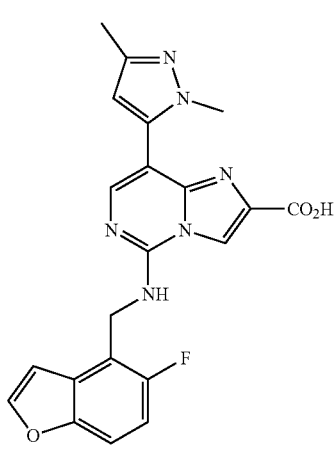<br>8-(1,3-dimethyl-1H-pyrazol-5-yl)-5-(((5-fluorobenzofuran-4-yl)methyl)amino)imidazo[1,2-c]pyrimidine-2-carboxylic acid | $^1$H NMR (400 MHz, DMSO-d$_6$) δ = 8.79 (s, 1H), 8.71 (t, J = 4.8 Hz, 1H), 8.06 (d, J = 2.0 Hz, 1H), 7.77 (s, 1H), 7.61 (dd, J = 3.6, 8.8 Hz, 1H), 7.25-7.18 (m, 2H), 6.23 (s, 1H), 5.01 (d, J = 4.8 Hz, 2H), 3.69 (s, 3H), 2.19 (s, 3H).<br>LCMS [M + 1]: 421.2. |
| 10 | 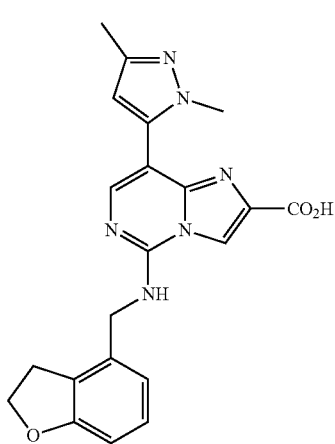<br>5-(((2,3-dihydrobenzofuran-4-yl)methyl)amino)-8-(1,3-dimethyl-1H-pyrazol-5-yl)imidazo[1,2-c]pyrimidine-2-carboxylic acid | $^1$H NMR (400 MHz, CD$_3$OD) δ = 8.17 (br s, 1H), 7.65 (s, 1H), 7.11-7.03 (m, 1H), 6.89 (d, J = 7.6 Hz, 1H), 6.66 (d, J = 8.0 Hz, 1H), 6.25 (br s, 1H), 4.78 (s, 2H), 4.56 (t, J = 8.8 Hz, 2H), 3.77 (br s, 3H), 3.29-3.26 (m, 2H), 2.25 (s, 3H).<br>LC-MS [M + 1]: 405.2. |

Example 11

8-(1,3-dimethyl-1H-pyrazol-5-yl)-5-(((5-fluoro-2,3-dihydrobenzofuran-4-yl)methyl)amino)imidazo[1,2-c]pyrimidine-2-carboxamide

Example 12

5-(((5-fluorobenzofuran-4-yl)methyl)amino)-8-(2-methylpyridin-3-yl)imidazo[1,2-c]pyrimidine-2-carboxamide

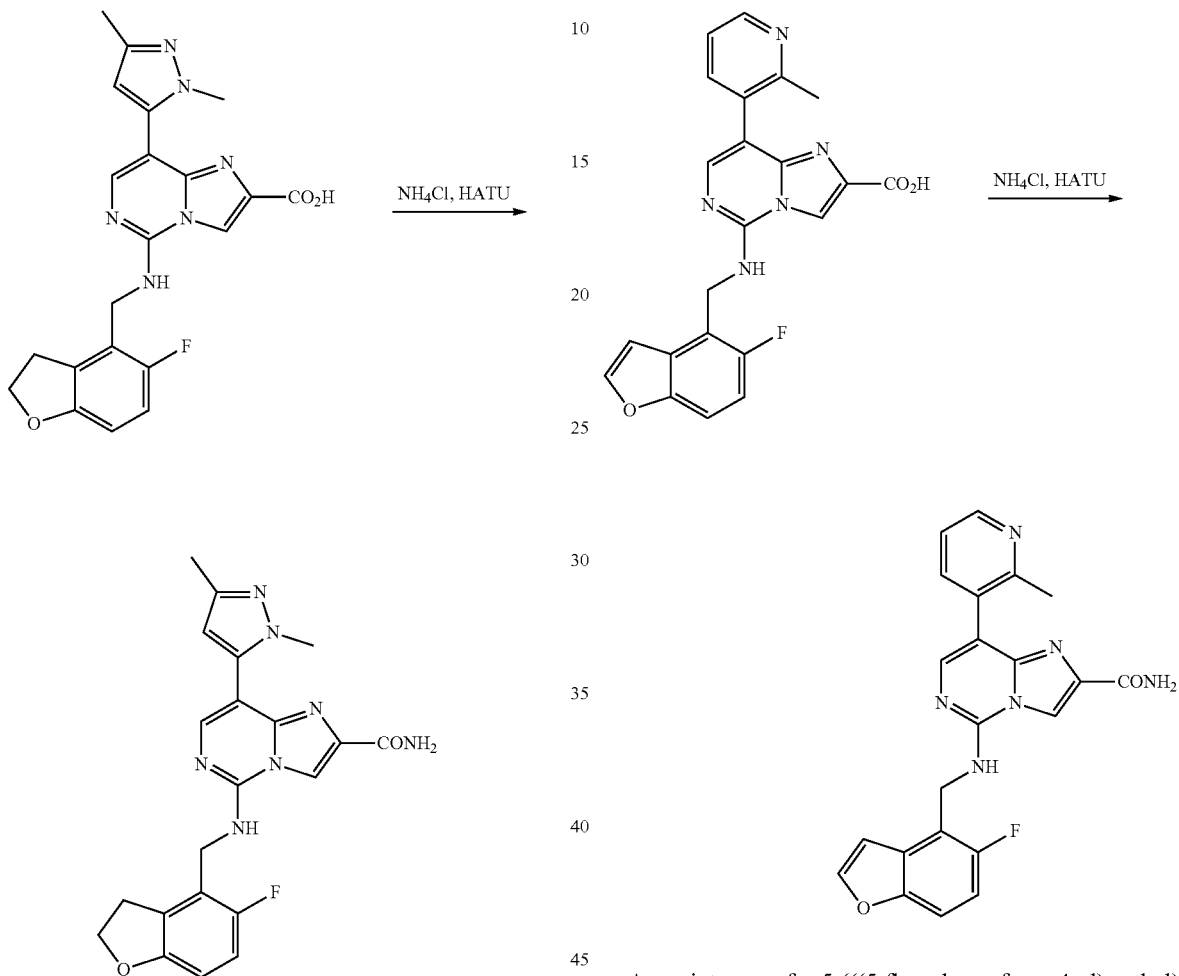

0415 To a solution of 8-(1,3-dimethyl-1H-pyrazol-5-yl)-5-(((5-fluoro-2,3-dihydrobenzofuran-4-yl)methyl)amino)imidazo[1,2-c]pyrimidine-2-carboxylic acid (24.9 mg, 52.7 µmol, 1.00 equiv) in DMF (1 mL) was added ammonium chloride (8.45 mg, 158 µmol, 3.00 equiv), DIPEA (47.7 mg, 369 µmol, 64.2 µL, 7.00 equiv) and HATU (40.1 mg, 105 µmol, 2.00 equi). The resultant mixture was stirred at 25° C. for 1 h. The mixture was diluted with water (10.0 mL) and filtered. The precipitate was washed with methanol (1.00 mL) and dried at reduced pressure to provide 8-(1,3-dimethyl-1H-pyrazol-5-yl)-5-(((5-fluoro-2,3-dihydrobenzofuran-4-yl)methyl)amino)imidazo[1,2-c]pyrimidine-2-carboxamide (12.3 mg, 53.8% yield, 97.5% purity) as a gray solid. LC-MS: [M+1] 1422.1.

$^1$H NMR (400 MHz, DMSO-d$_6$) δ=8.64 (s, 1H), 8.51 (brs, 1H), 7.74 (s, 1H), 7.62 (br s, 1H), 7.45 (br s, 1H), 6.93 (t, J=9.6 Hz, 1H), 6.69 (dd, J=4.0, 8.8 Hz, 1H), 6.25 (s, 1H), 4.71 (br d, J=4.4 Hz, 2H), 4.54 (br t, J=8.8 Hz, 2H), 3.72 (s, 3H), 3.31-3.27 (m, 2H), 2.18 (s, 3H).

A mixture of 5-(((5-fluorobenzofuran-4-yl)methyl)amino)-8-(2-methylpyridin-3-yl)imidazo[1,2-c]pyrimidine-2-carboxylic acid (80.0 mg, 192 µmol, 1.00 equiv), DIEA (74.3 mg, 575 µmol, 100 µL, 3.00 equiv) and ammonium chloride (30.8 mg, 575 µmol, 3 equiv) in DMF (3.00 mL) was cooled to 0° C. To this mixture was added HATU (109 mg, 287 µmol, 1.50 equiv) and the mixture was stirred at 25° C. for 1 h. The solution was diluted with water (10.0 mL), filtered, the filter cake was dried to afford 5-(((5-fluorobenzofuran-4-yl)methyl)amino)-8-(2-methylpyridin-3-yl)imidazo[1,2-c]pyrimidine-2-carboxamide (61.0 mg, 74.0% yield, 96.8% purity) as a white solid. LCMS [M+1]: 417.2.

$^1$H NMR (400 MHz, DMSO-d$_6$)=8.64 (s, 1H), 8.59 (t, J=5.2 Hz, 1H), 8.48 (dd, J=1.6, 4.8 Hz, 1H), 8.06 (d, J=2.0 Hz, 1H) 7.72 (dd, J=1.6, 7.6 Hz, 1H), 7.65 (s, 1H), 7.59 (dd, J=3.6, 9.0 Hz, 1H), 7.50 (brs, H), 7.39 (brs, 1H), 7.29 (dd, J=5.2, 7.6 Hz, 1H), 7.25-7.18 (m, 2H), 5.00 (d, J=5.2 Hz, 2H), 2.39 (s, 3H).

EXAMPLES 13-21 were prepared following the procedure set forth in Example 12 and using the general reactions schemes and intermediates described herein.

TABLE 2

Characterization of EXAMPLES 13-21

| Ex. # | Structure | ¹H NMR |
|---|---|---|
| 13 | 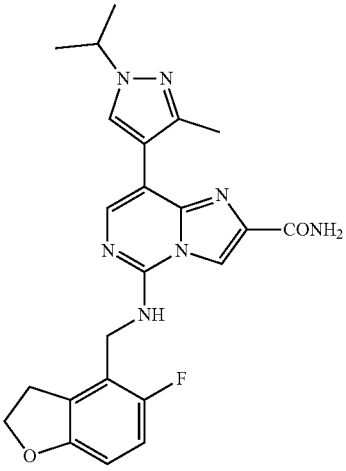<br>5-(((5-fluoro-2,3-dihydrobenzofuran-4-yl)methyl)amino)-8-(1-isopropyl-3-methyl-1H-pyrazol-4-yl)imidazo[1,2-c]pyrimidine-2-carboxamide | ¹H NMR (400 MHz, DMSO-$d_6$) δ = 8.58 (s, 1H), 8.54 (s, 1H), 8.18 (t, J = 5.2 Hz, 1H), 7.82 (br s, 1H), 7.79 (s, 1H), 7.51 (br s, 1H), 6.96-6.89 (m, 1H), 6.68 (dd, J = 4.0, 8.4 Hz, 1H), 4.69 (d, J = 4.8 Hz, 1H), , 4.57-4.47 (m, 3H), 3.30-3.25 (m, 2H), 2.36 (s, 3H), 1.44 (d, J = 6.8 Hz, 6H).<br>LCMS [M + 1]: 450.3. |
| 14 | 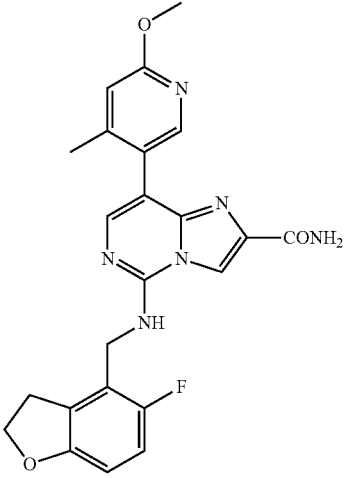<br>5-(((5-fluoro-2,3-dihydrobenzofuran-4-yl)methyl)amino)-8-(6-methoxy-4-methylpyridin-3-yl)imidazo[1,2-c]pyrimidine-2-carboxamide | ¹H NMR (400 MHz, DMSO-$d_6$) δ = 8.64 (s, 1H), 8.39 (br t, J = 4.4 Hz, 1H), 8.06 (s, 1H), 7.62 (s, 1H), 7.50 (s, 1H), 7.41 (s, 1H), 6.95 (br t, J = 9.6 Hz, 1H), 6.80 (s, 1H), 6.71 (dd, J = 4.0, 8.4 Hz, 1H), 4.72 (br d, J = 4.8 Hz, 2H), 4.56 (br t, J = 8.8 Hz, 2H), 3.88 (s, 3H), 3.34-3.28 (m, 2H), 2.19 (s, 3H).<br>LC-MS [M + 1]: 449.1. |

TABLE 2-continued

Characterization of EXAMPLES 13-21

| Ex. # | Structure | $^1$H NMR |
|---|---|---|
| 15 | 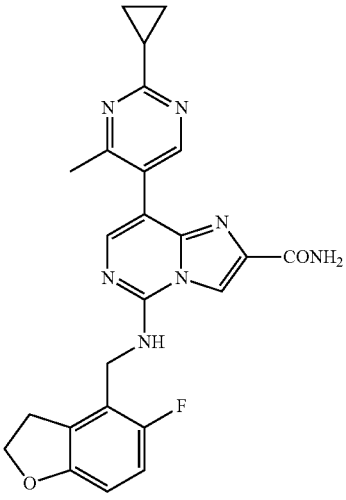<br>8-(2-cyclopropyl-4-methylpyrimidin-5-yl)-5-(((5-fluoro-2,3-dihydrobenzofuran-4-yl)methyl)amino)imidazo[1,2-c]pyrimidine-2-carboxamide | $^1$H NMR (400 MHz, DMSO-d$_6$) δ = 8.65 (s, 1H), 8.54-8.43 (m, 2H), 7.71 (s, 1H), 7.57 (br s, 1H), 7.40 (br s, 1H), 6.94 (t, J = 9.2 Hz, 1H), 6.70 (dd, J = 4.0, 8.4 Hz, 1H), 4.72 (br d, J = 4.8 Hz, 2H), 4.55 (t, J = 8.8 Hz, 2H), 3.32-3.29 (m, 2H), 2.36 (s, 3H), 2.26-2.17 (m, 1H), 1.14-0.98 (m, 4H)<br>LC-MS [M + 1]: 460.4. |
| 16 | 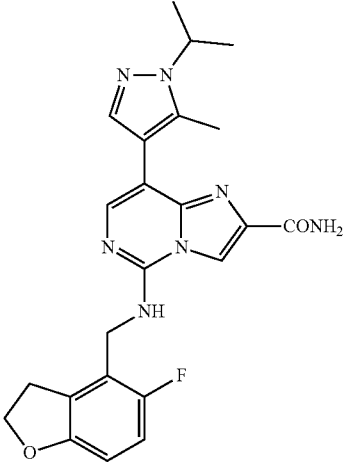<br>5-(((5-fluoro-2,3-dihydrobenzofuran-4-yl)methyl)amino)-8-(1-isopropyl-5-methyl-1H-pyrazol-4-yl)imidazo[1,2-c]pyrimidine-2-carboxamide | $^1$H NMR (400 MHz, CD$_3$OD) δ = 8.41 (s, 1H), 7.75 (s, 1H), 7.66 (s, 1H), 6.85 (br t, J = 9.2 Hz, 1H), 6.68-6.58 (m, 1H), 4.80 (s, 2H), 4.68-4.55 (m, 1H), 4.56 (br t, J = 8.8 Hz, 2H), 3.38-3.35 (m, 2H), 2.35 (s, 3H), 1.51 (br d, J = 6.4 Hz, 6H)<br>LCMS [M + 1]: 450.4. |

TABLE 2-continued

Characterization of EXAMPLES 13-21

| Ex. # | Structure | $^1$H NMR |
|---|---|---|
| 17 | 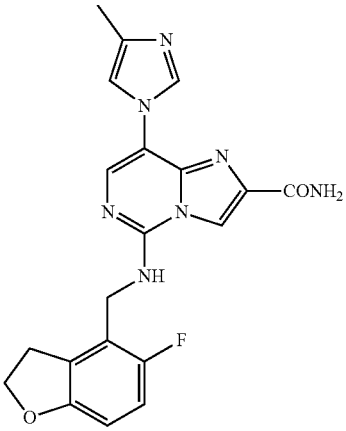<br>5-(((5-fluoro-2,3-dihydrofuran-4-yl)methyl)amino)-8-(4-methyl-1H-imidazol-1-yl)imidazo[1,2-c]pyrimidine-2-carboxamide | $^1$H NMR (400 MHz, CDCl$_3$) δ = 8.11 (s, 1H), 7.93 (s, 1H), 6.67-6.61 (m, 1H), 6.59-6.54 (m, 1H), 5.08 (s, 2H), 4.58 (t, J = 8.8 Hz, 2H), 4.47 (q, J = 7.2 Hz, 2H), 3.32 (br t, J = 8.8 Hz, 2H), 1.43 (t, J = 7.2 Hz, 3H), 1.36 (s, 9H) LC-MS [M + 3]: 537.2. |
| 18 | 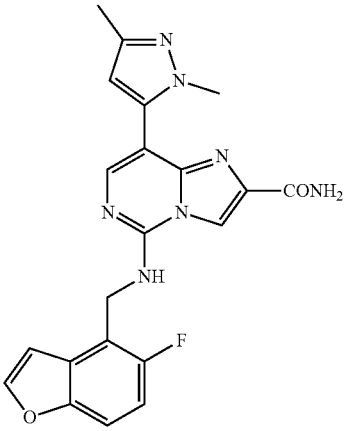<br>8-(1,3-dimethyl-1H-pyrazol-5-yl)-5-(((5-fluorobenzofuran-4-yl)methyl)amino)imidazo[1,2-c]pyrimidine-2-carboxamide | $^1$H NMR (400 MHz, DMSO-d$_6$) δ = 8.76-8.56 (m, 2H), 8.06 (br s, 1H), 7.75 (br s, 1H), 7.67-7.55 (m, 2H), 7.47 (br s, 1H), 7.28-7.16 (m, 2H), 6.25 (br s, 1H), 5.01 (br s, 2H), 3.72 (br s, 3H), 2.19 (br s, 3H). LCMS [M + 1] 420.2. |

TABLE 2-continued

Characterization of EXAMPLES 13-21

| Ex. # | Structure | ¹H NMR |
|---|---|---|
| 19 | 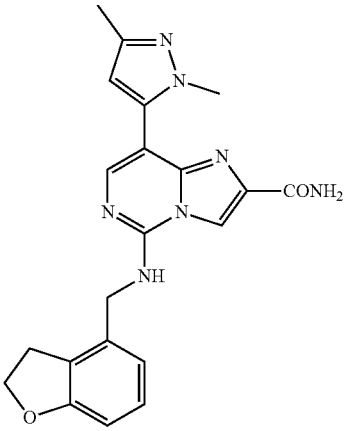<br>5-(((2,3-dihydrobenzofuran-4-yl)methyl)amino)-8-(1,3-dimethyl-1H-pyrazol-5-yl)imidazo[1,2-c]pyrimidine-2-carboxamide | ¹H NMR (400 MHz, DMSO-$d_6$) δ = 8.64 (br s, 2H), 7.71 (br s, 1H), 7.63 (br s, 1H), 7.46 (br s, 1H), 7.10-7.01 (m, 1H), 6.85 (br d, J = 7.6 Hz, 1H), 6.68 (br d, J = 8.0 Hz, 1H), 6.24 (br s, 1H), 4.70 (br s, 2H), 4.54 (br t, J = 8.4 Hz, 2H), 3.72 (br s, 3H), 3.26 (br d, J = 9.2 Hz, 2H), 2.18 (br s, 3H)<br>LC-MS [M + 1] 404.3. |
| 20 | 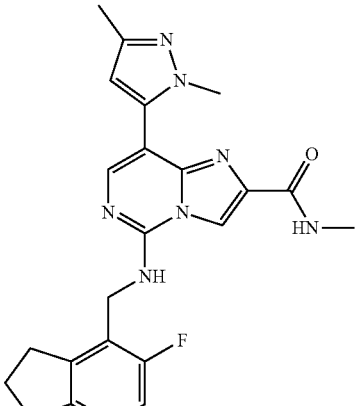<br>8-(1,3-dimethyl-1H-pyrazol-5-yl)-5-(((5-fluoro-2,3-dihydrobenzofuran-4-yl)methyl)amino)-N-methylimidazo[1,2-c]pyrimidine-2-carboxamide | ¹H NMR (400 MHz, DMSO-$d_6$) δ = 8.66 (br s, 1 H), 8.51 (br s, 1 H), 8.22 (br s, 1 H), 7.74 (br s, 1 H), 6.94 (br t, J = 8.8 Hz, 1 H), 6.71 (br s, 1 H), 6.24 (br s, 1 H), 4.72 (br s, 2 H), 4.55 (br t, J = 7.6 Hz, 2 H), 3.71 (s, 3 H), 3.28-3.31 (m, 2 H), 2.78 (s, 3 H), 2.19 (s, 3 H).<br>LCMS [M + 1]: 436.4. |

TABLE 2-continued

Characterization of EXAMPLES 13-21

| Ex. # | Structure | $^1$H NMR |
|---|---|---|
| 21 | 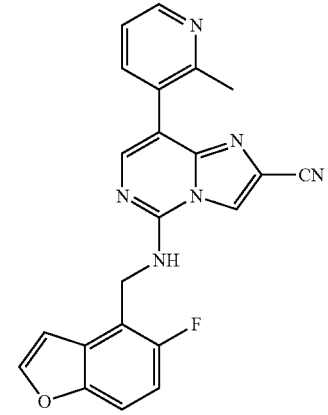<br>8-(1,3-dimethyl-1H-pyrazol-5-yl)-5-(((5-fluoro-2,3-dihydrobenzofuran-4-yl)methyl)amino)-N,N-dimethylimidazo[1,2-c]pyrimidine-2-carboxamide | $^1$H NMR (400 MHz, DMSO-d$_6$) δ = 8.59 (s, 1 H), 8.51 (br s, 1 H), 7.76 (s, 1 H), 6.94 (t, J = 9.2 Hz, 1 H), 6.70 (dd, J = 8.4, 3.6 Hz, 1 H), 6.23 (s, 1 H), 4.73 (d, J = 2.4 Hz, 2 H), 4.55 (br t, J = 8.8 Hz, 2 H), 3.72 (s, 3 H), 3.37 (br s, 3 H), 3.26-3.31 (m, 2 H), 2.99 (br s, 3 H), 2.18 (s, 3 H).<br>LCMS [M + 1]: 450.4. |

Example 22

5-(((5-fluorobenzofuran-4-yl)methyl)amino)-8-(2-methylpyridin-3-yl)imidazo[1,2-c]pyrimidine-2-carbonitrile

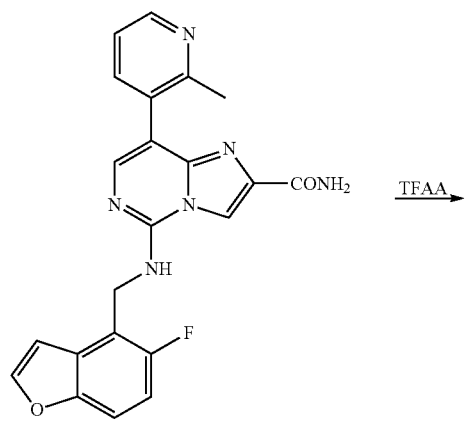

To a solution of 5-(((5-fluorobenzofuran-4-yl)methyl)amino)-8-(2-methylpyridin-3-yl)imidazo[1,2-c]pyrimidine-2-carboxamide (45.0 mg, 108 μmol, 1.00 equiv), TEA (219 mg, 2.16 mmol, 301 μL, 20.0 equiv) in THF (1.50 mL) was added TFAA (136 mg, 648 μmol, 90.2 μL, 6.00 equiv) at 0° C. The mixture was subsequently stirred at 25° C. for 1 h.

The reaction mixture was diluted with ethyl acetate (10.0 mL) and washed with water (10.0 mL×3). The organic layer was dried over anhydrous sodium sulfate, filtered and concentrated at reduced pressure to give a residue. The crude material was purified by prep-HPLC (column: Phenomenex Synergi C18 150×25×10 um; mobile phase: [A=water (0.1% TFA)–B=acetonitrile]; B %: 18%-48%, 12 min) to afford 5-(((5-fluorobenzofuran-4-yl)methyl)amino)-8-(2-methylpyridin-3-yl)imidazo[1,2-c]pyrimidine-2-carbonitrile (13.0 mg, 29.9% yield, 99.1% purity) as an off-white solid. LCMS [M+1]: 399.3.

$^1$H NMR (400 MHz, METHANOL-d$_4$) δ=8.75 (dd, J=1.6, 6.0 Hz, 1H), 8.65 (s, 1H), 8.54 (dd, J=1.6, 7.6 Hz, 1H), 8.0-7.95 (m, 2H), 7.83 (d, J=2.0 Hz, 1H), 7.53-7.44 (M 1H), 7.18-7.11 (m, 2H), 5.15 (d, J=0.4 Hz, 2H), 2.68 (s, 3H).

Example 23

5-(((5-fluoro-2,3-dihydrobenzofuran-4-yl)methyl)amino)-8-(1-isopropyl-3-methyl-1H-pyrazol-4-yl)imidazo[1,2-c]pyrimidine-2-carbonitrile

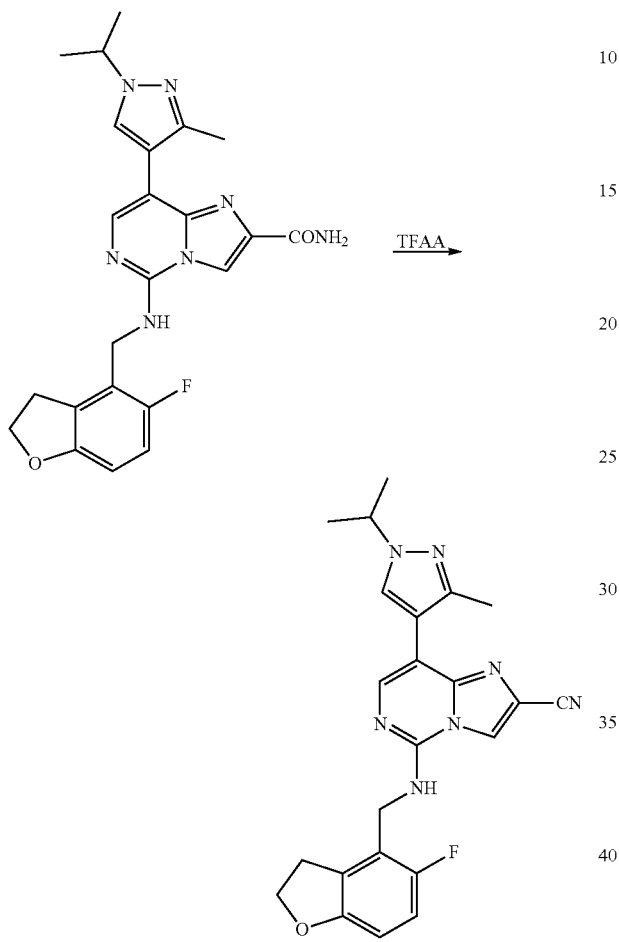

To a solution of 5-(((5-fluoro-2,3-dihydrobenzofuran-4-yl)methyl)amino)-8-(1-isopropyl-3-methyl-1H-pyrazol-4-yl)imidazo[1,2-c]pyrimidine-2-carboxamide (49.0 mg, 106 µmol, 1.00 equiv) and TEA (215 mg, 2.12 mmol, 296 µL, 20.0 equiv) in THF (1.00 mL) was added TFAA (134 mg, 637 µmol, 88.7 µL, 6.00 equiv) at 0° C. The mixture was subsequently stirred at 25° C. for 1 h. The reaction mixture was diluted with ethyl acetate (10.0 mL), the pH was adjusted to 7 with TFA, and the organic layer was washed with brine (5.00 mL×3). Concentration in vacuo provided the crude material. The crude residue was triturated with methyl alcohol (2.00 mL) and filtered to afford 5-(((5-fluoro-2,3-dihydrobenzofuran-4-yl)methyl)amino)-8-(I-isopropyl-3-methyl-1H-pyrazol-4-yl)imidazo[1,2-c]pyrimidine-2-carbonitrile (43.0 mg, 92.7% yield, 98.8% purity) as a white solid. LCMS [M+1]: 432.3.

$^1$H NMR (400 MHz, DMSO-$d_6$) δ=8.90 (s, 1H), 8.32 (brs, 1H), 8.16 (s, 1H), 7.84 (s, 1H), 6.94 (t, J=9.2 Hz, 1H), 6.70 (dd, J=3.6, 8.4 Hz, 1H), 4.70 (br s, 2H), 4.58-4.44 (m, 3H), 3.30-3.24 (m, 2H), 2.30 (s, 3H), 1.43 (d, J=6.8 Hz, 6H).

EXAMPLES 24-85 were prepared following the procedure set forth in Example 23 and using the general reactions schemes and intermediates described herein.

TABLE 3

Characterization of EXAMPLES 24-85

| Ex. # | Structure | ¹H NMR |
|---|---|---|
| 24 | 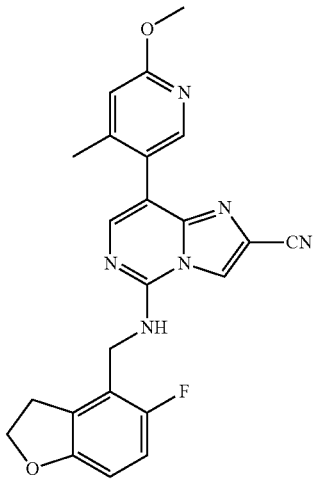<br>5-(((5-fluoro-2,3-dihydrobenzofuran-4-yl)methyl)amino)-8-(6-methoxy-4-methylpyridin-3-yl)imidazo[1,2-c]pyrimidine-2-carbonitrile | ¹H NMR (400 MHz, CD₃OD) δ = 8.63 (s, 1H), 8.01 (s, 1H), 7.74 (s, 1H), 6.91-6.85 (m, 1H), 6.81 (s, 1H), 6.67 (dd, J = 4.0, 8.4 Hz, 1H), 4.84 (s, 2H), 4.60 (t, J = 8.8 Hz, 2H), 3.96 (s, 3H), 3.41 (br t, J = 8.8 Hz, 2H), 2.20 (s, 3H).<br>LC-MS [M + 1]: 431.3. |
| 25 | 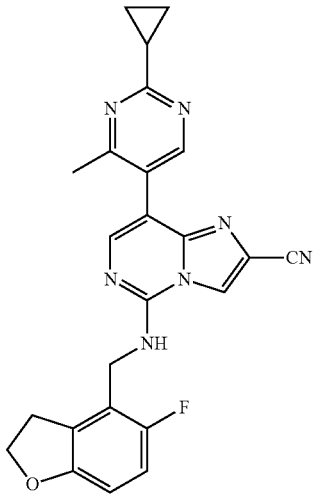<br>8-(2-cyclopropyl-4-methylpyrimidin-5-yl)-5-(((5-fluoro-2,3-dihydrobenzofuran-4-yl)methyl)amino)imidazo[1,2-c]pyrimidine-2-carbonitrile | ¹H NMR (400 MHz, DMSO-d₆) δ = 8.93 (s, 1H), 8.61 (br s, 1H), 8.48 (s, 1H), 7.83 (s, 1H), 6.96 (t, J = 9.2 Hz, 1H), 6.72 (dd, J = 4.0, 8.8 Hz, 1H), 4.73 (br d, J = 4.0 Hz, 2H), 4.56 (t, J = 8.8 Hz, 2H), 3.33 (br t, J = 8.8 Hz, 2H), 2.32 (s, 3H), 2.26-2.18 (m, 1H), 1.15-1.00 (m, 4H).<br>LC-MS [M + 1]: 442.4. |

TABLE 3-continued

Characterization of EXAMPLES 24-85

| Ex. # | Structure | ¹H NMR |
|---|---|---|
| 26 | 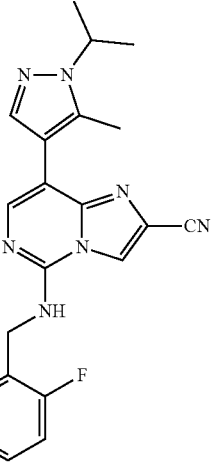<br>5-(((5-fluoro-2,3-dihydrobenzofuran-4-yl)methyl)amino)-8-(1-isopropyl-5-methyl-1H-pyrazol-4-yl)imidazo[1,2-c]pyrimidine-2-carbonitrile | ¹H NMR (400 MHz, CD₃OD) δ = 8.59 (s, 1H), 7.75 (s, 1H), 7.75 (s, 1H), 6.89-6.82 (m, 1H), 6.64 (dd, J = 4.0, 8.8 Hz, 1H), 4.80 (s, 2H), 4.72-4.63 (m, 1H), 4.57 (t, J = 8.8 Hz, 2H), 3.39-3.34 (m, 2H), 2.34 (s, 3H), 1.52 (d, J = 6.8 Hz, 6H).<br>LCMS [M + 1]: 432.4. |
| 27 | 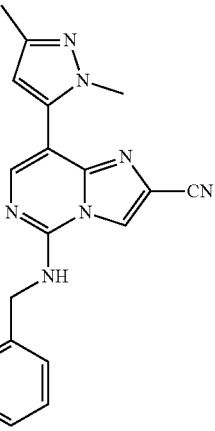<br>5-((benzo[d][1,3]dioxol-4-ylmethyl)amino)-8-(1,3-dimethyl-1H-pyrazol-5-yl)imidazo[1,2-c]pyrimidine-2-carbonitrile | ¹H NMR (400 MHz, DMSO-d₆) δ = 8.92 (s, 1H), 8.82 (br t, J = 5.2 Hz, 1H), 7.84 (s, 1H), 6.94-6.80 (m, 3H), 6.24 (s, 1H), 6.05 (s, 2H), 4.75 (d, J = 4.8 Hz, 2H), 3.74-3.72 (m, 3H), 2.19 (s, 3H).<br>LCMS [M + 1] 388.2. |

TABLE 3-continued

Characterization of EXAMPLES 24-85

| Ex. # | Structure | ¹H NMR |
|---|---|---|
| 28 | 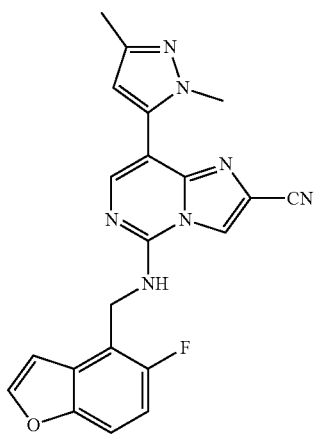<br>8-(1,3-dimethyl-1H-pyrazol-5-yl)-5-(((5-fluorobenzofuran-4-yl)methyl)amino)imidazo[1,2-c]pyrimidine-2-carbonitrile | ¹H NMR (400 MHz, CD$_3$OD) δ = 8.61 (s, 1H), 7.90 (s, 1H), 7.84 (d, J = 2.0 Hz, 1H), 7.50 (dd, J = 3.6, 8.8 Hz, 1H), 7.18-7.11 (m, 2H), 6.28 (s, 1H), 5.14 (s, 2H), 3.74 (s, 3H), 2.30 (s, 3H).<br>LCMS [M + 1] 402.2. |
| 29 | 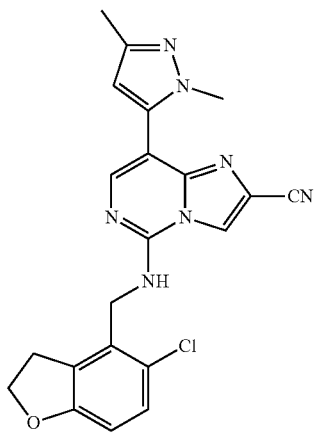 [SMILES: Cc1nc(-c2cnc(NCc3c(F)ccc4c3CCO4)n3cc(C#N)nc23)c(C)s1]<br>5-(((5-chloro-2,3-dihydrobenzofuran-4-yl)methyl)amino)-8-(1,3-dimethyl-1H-pyrazol-5-yl)imidazo[1,2-c]pyrimidine-2-carbonitrile | ¹H NMR (400 MHz, CD$_3$OD) δ = 8.67 (s, 1H), 7.91 (s, 1H), 7.19 (d, J = 8.4 Hz, 1H), 6.72 (d, J = 8.4 Hz, 1H), 6.33 (s, 1H), 4.89 (s, 2H), 4.62 (t, J = 8.8 Hz, 2H), 3.77 (s, 3H), 3.44 (t, J = 8.8 Hz, 2H), 2.32 (s, 3H).<br>LCMS [M + 1] 420.2. |

TABLE 3-continued

Characterization of EXAMPLES 24-85

| Ex. # | Structure | $^1$H NMR |
|---|---|---|
| 30 | 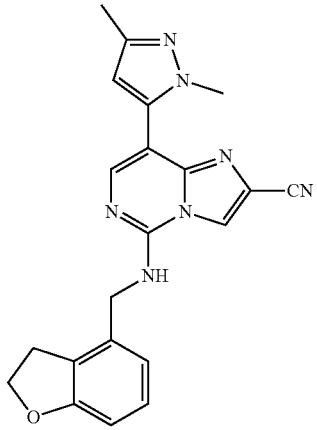<br>5-(((2,3-dihydrobenzofuran-4-yl)methyl)amino)-8-(1,3-dimethyl-1H-pyrazol-5-yl)imidazo[1,2-c]pyrimidine-2-carbonitrile | $^1$H NMR (400 MHz, CD$_3$OD) δ = 8.60 (s, 1H), 7.86 (s, 1H), 7.11-7.04 (m, 1H), 6.89 (d, J = 7.6 Hz, 1H), 6.67 (d, J = 8.0 Hz, 1H), 6.32 (s, 1H), 4.79 (s, 2H), 4.57 (t, J = 8.8 Hz, 2H), 3.76 (s, 3H), 3.30-3.25 (m, 2H), 2.30 (s, 3H).<br>LC-MS [M + 3] 386.0. |
| 31 | 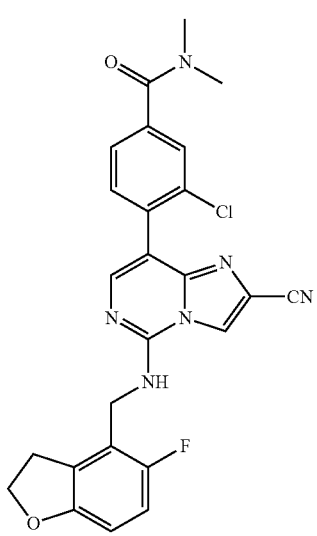<br>3-chloro-4-(2-cyano-5-(((5-fluoro-2,3-dihydrobenzofuran-4-yl)methyl)amino)imidazo[1,2-c]pyrimidin-8-yl)-N,N-dimethylbenzamide | $^1$H NMR (400 MHz, CD$_3$OD) δ = 8.62 (s, 1H), 7.84 (s, 1H), 7.63 (s, 1H), 7.58 (d, J = 8.0 Hz, 1H), 7.46 (d, J = 8.0 Hz, 1H), 6.86 (t, J = 9.2 Hz, 1H), 6.65 (dd, J = 4.0, 8.8 Hz, 1H), 4.83 (s, 2H), 4.58 (t, J = 8.8 Hz, 2H), 3.39 (t, J = 8.8 Hz, 2H), 3.13 (s, 3H), 3.08 (s, 3H).<br>LCMS [M + 1]: 491.2. |

TABLE 3-continued

Characterization of EXAMPLES 24-85

| Ex. # | Structure | ¹H NMR |
|---|---|---|
| 32 | 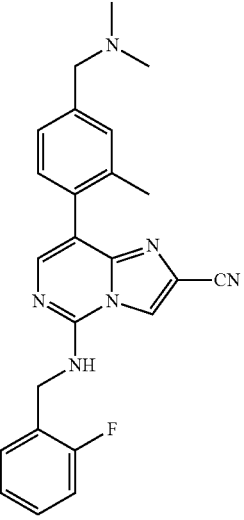<br>8-(4-((dimethylamino)methyl)-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.89 (br s, 1H), 8.94 (d, J = 2.0 Hz, 1H), 8.55 (br s, 1H), 7.73 (s, 1H), 7.45 (s, 1H), 7.43-7.35 (m, 2H), 6.96 (t, J = 9.6 Hz, 1H), 6.72 (dd, J = 4.0, 8.8 Hz, 1H), 4.72 (br d, J = 4.4 Hz, 2H), 4.56 (t, J = 8.8 Hz, 2H), 4.30 (br d, J = 4.4 Hz, 2H), 3.33 (br t, J = 8.8 Hz, 2H), 2.78 (br d, J = 4.0 Hz, 6H), 2.20 (s, 3H).<br>LCMS [M + 1]: 457.2. |
| 33 | 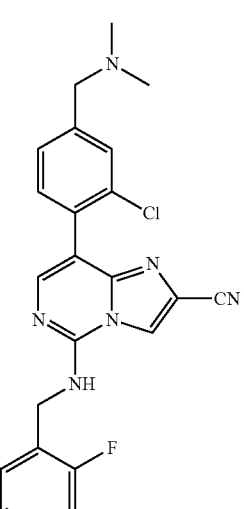<br>8-(2-chloro-4-((dimethylamino)methyl)phenyl)-5-(((5-fluoro-2,3-dihydrobenzofuran-4-yl)methyl)amino)imidazo[1,2-c]pyrimidine-2-carbonitrile | ¹H NMR (400 MHz, CD$_3$OD) δ = 8.63 (s, 1H), 7.84 (s, 1H), 7.74 (d, J = 1.6 Hz, 1H), 7.66-7.59 (d, J = 8.0 Hz, 1H), 7.53 (dd, J = 1.6, 7.6 Hz, 1H), 6.85 (t, J = 9.6 Hz, 1H), 6.66 (dd, J = 4.0, 8.4 Hz, 1H), 4.84 (s, 2H), 4.58 (t, J = 8.8 Hz, 2H), 4.39 (s, 2H), 3.38 (t, J = 8.4 Hz, 2H), 2.93 (s, 6H).<br>LCMS [M + 1]: 477.3. |

TABLE 3-continued

Characterization of EXAMPLES 24-85

| Ex. # | Structure | ¹H NMR |
|---|---|---|
| 34 | 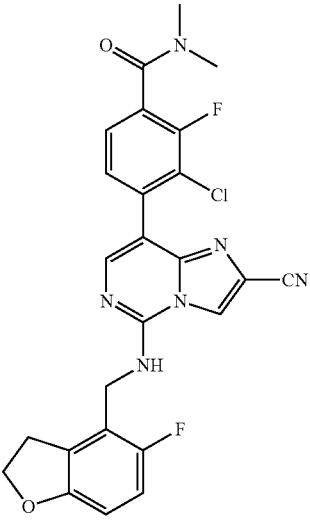<br>3-chloro-4-(2-cyano-5-(((5-fluoro-2,3-dihydrobenzofuran-4-yl)methyl)amino)imidazo[1,2-c]pyrimidin-8-yl)-2-fluoro-N,N-dimethylbenzamide | ¹H NMR (400 MHz, DMSO-d$_6$) δ = 8.94 (s, 1H), 8.68 (br s, 1H), 7.90 (s, 1H), 7.51-7.43 (m, 2H), 6.96 (t, J = 8.8 Hz, 1H), 6.72 (dd, J = 4.0, 8.8 Hz, 1H), 4.74 (br d, J = 4.4 Hz, 2H), 4.55 (t, J = 8.8 Hz, 2H), 3.33 (t, J = 8.8 Hz, 2H), 3.04 (s, 3H), 2.92 (s, 3H).<br>LCMS [M + 1]: 509.3. |
| 35 | 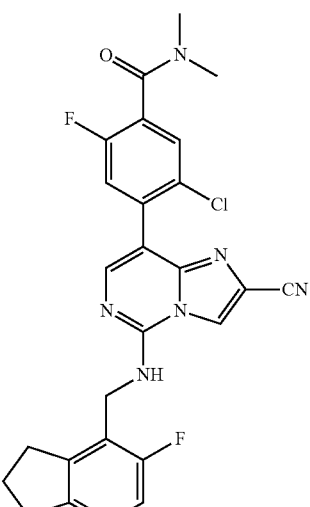<br>5-chloro-4-(2-cyano-5-(((5-fluoro-2,3-dihydrobenzofuran-4-yl)methyl)amino)imidazo[1,2-c]pyrimidin-8-yl)-2-fluoro-N,N-dimethylbenzamide | ¹H NMR (400 MHz, CD$_3$OD) δ = 8.63 (s, 1H), 7.88 (s, 1H), 7.59 (d, J = 6.0 Hz, 1H), 7.43 (d, J = 9.6 Hz, 1H), 6.86 (t, J = 9.2 Hz, 1H), 6.65 (dd, J = 4.0, 8.8 Hz, 1H), 4.83 (s, 2H), 4.59-4.56 (m, 2H), 3.38 (t, J = 8.8 Hz, 2H), 3.14 (s, 3H), 3.05 (s, 3H).<br>LCMS [M + 1]: 509.3. |

TABLE 3-continued

Characterization of EXAMPLES 24-85

| Ex. # | Structure | $^1$H NMR |
|---|---|---|
| 36 | 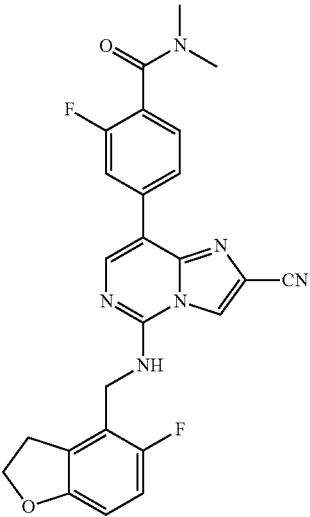<br>4-(2-cyano-5-(((5-fluoro-2,3-dihydrobenzofuran-4-yl)methyl)amino)imidazo[1,2-c]pyrimidin-8-yl)-2-fluoro-N,N-dimethylbenzamide | $^1$H NMR (400 MHz, DMSO-d$_6$) δ = 8.96 (s, 1H), 8.67 (br s, 1H), 8.29 (s, 1H), 8.04-7.96 (m, 2H), 7.47 (br t, J = 7.6 Hz, 1H), 6.95 (br t, J = 9.2 Hz, 1H), 6.71 (br dd, J = 3.6, 8.4 Hz, 1H), 4.75 (br d, J = 4.0 Hz, 2H), 4.55 (br t J = 8.4 Hz, 2H), 3.38-3.24 (m, 2H), 3.03 (s, 3H), 2.90 (s, 3H).<br>LCMS [M + 1]: 475.1. |
| 37 | 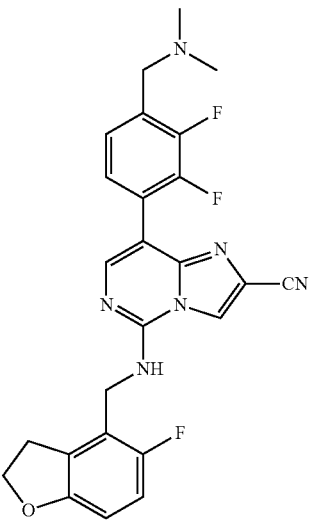<br>8-(4-((dimethylamino)methyl)-2,3-difluorophenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 9.98 (br s, 1H), 8.96 (s, 1H), 8.76 (br d, J = 4.4 Hz, 1H), 8.01 (s, 1H), 7.71 (br t, J = 7.2 Hz, 1H), 7.50 (br t, J = 7.2 Hz, 1H), 6.95 (t, J = 9.2 Hz, 1H), 6.71 (dd, J = 4.0, 8.8 Hz, 1H), 4.75 (br d, J = 4.8 Hz, 2H), 4.55 (t, J = 8.8 Hz, 2H), 4.45 (s, 2H), 3.33-3.29 (m, 2H), 2.84 (s, 6H).<br>LCMS [M + 1]: 479.1. |

TABLE 3-continued

Characterization of EXAMPLES 24-85

| Ex. # | Structure | ¹H NMR |
|---|---|---|
| 38 | 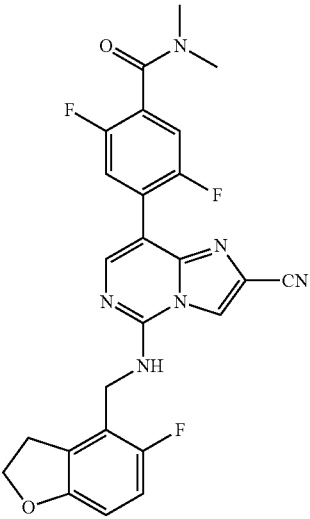<br>4-(2-cyano-5-(((5-fluoro-2,3-dihydrobenzofuran-4-yl)methyl)amino)imidazo[1,2-c]pyrimidin-8-yl)-2,5-difluoro-N,N-dimethylbenzamide | ¹H NMR (400 MHz, CD$_3$OD) δ = 8.63 (s, 1H), 8.06 (s, 1H), 7.74 (br dd, J = 5.6, 10.0 Hz, 1H), 7.32 (br dd, J = 6.0, 10.0 Hz, 1H), 6.88 (br t, J = 8.8 Hz, 1H), 6.72-6.63 (m, 1H), 4.86 (s, 2H), 4.60 (br t, J = 8.8 Hz, 2H), 3.42-3.38 (m, 2H), 3.16 (s, 3H), 3.06 (s, 3H).<br>LCMS [M + 1]: 493.2. |
| 39 | 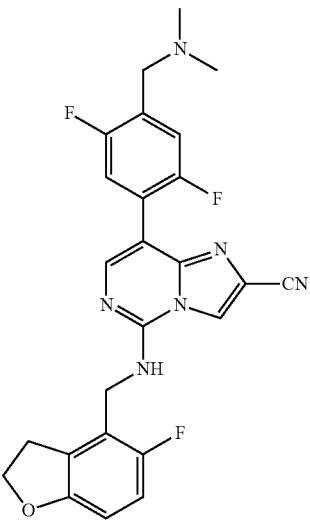<br>8-(4-((dimethylamino)methyl)-2,5-difluorophenyl)-5-(((5-fluoro-2,3-dihydrobenzofuran-4-yl)methyl)amino)imidazo[1,2-c]pyrimidine-2-carbonitrile | ¹H NMR (400 MHz, CD$_3$OD) δ = 8.66 (s, 1H), 8.06 (d, J = 1.6 Hz, 1H), 7.81 (dd, J = 6.0, 10.4 Hz, 1H), 7.51 (dd, J = 6.0, 10.0 Hz, 1H), 6.92-6.84 (m, 1H), 6.67 (dd, J = 4.0, 8.8 Hz, 1H), 4.86 (s, 2H), 4.60 (t, J = 8.8 Hz, 2H), 4.48 (s, 2H), 3.40 (t, J = 8.8 Hz, 2H), 2.98 (s, 6H).<br>LCMS [M + 1]: 479.3. |

TABLE 3-continued

Characterization of EXAMPLES 24-85

| Ex. # | Structure | ¹H NMR |
|---|---|---|
| 40 | 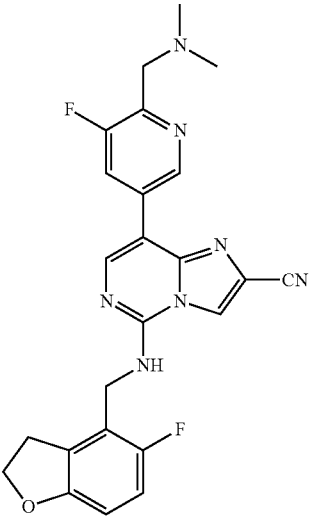<br>8-(6-((dimethylamino)methyl)-5-fluoropyridin-3-yl)-5-(((5-fluoro-2,3-dihydrobenzofuran-4-yl)methyl)amino)imidazo[1,2-c]pyrimidine-2-carbonitrile | ¹H NMR (400 MHz, CD$_3$OD) δ = 9.16 (t, J = 1.2 Hz, 1H), 8.67 (s, 1H), 8.42 (dd, J = 1.4, 10.8 Hz, 1H), 8.28 (s, 1H), 6.93-6.84 (m, 1H), 6.67 (dd, J = 4.0, 8.8 Hz, 1H), 4.87-4.86 (m, 2H), 4.66 (d, J = 1.6 Hz, 2H), 4.60 (t, J = 8.8 Hz, 2H), 3.41 (t, J = 8.8 Hz, 2H), 3.05 (s, 6H).<br>LCMS [M + 1]: 462.4. |
| 41 | 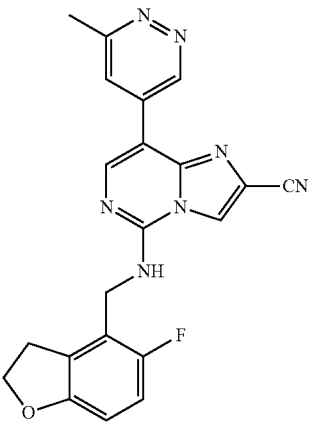<br>5-(((5-fluoro-2,3-dihydrobenzofuran-4-yl)methyl)amino)-8-(6-methylpyridazin-4-yl)imidazo[1,2-c]pyrimidine-2-carbonitrile | ¹H NMR (400 MHz, DMSO-d$_6$) δ = 9.81 (d, J = 2.0 Hz, 1H), 8.99 (s, 2H), 8.62 (s, 1H), 8.39 (d, J = 1.6 Hz, 1H), 6.95 (t, J = 8.8 Hz, 1H), 6.71 (dd, J = 4.0, 8.4 Hz, 1H), 4.77 (d, J = 4.8 Hz, 2H), 4.55 (t, J = 8.8 Hz, 2H), 3.32 (br t, J = 8.8 Hz, 2H), 2.70 (s, 3H).<br>LCMS [M + 1]: 402.2. |

TABLE 3-continued

Characterization of EXAMPLES 24-85

| Ex. # | Structure | ¹H NMR |
|---|---|---|
| 42 | 4-(2-cyano-5-(((5-fluoro-2,3-dihydrobenzofuran-4-yl)methyl)amino)imidazo[1,2-c]pyrimidin-8-yl)-2,3-difluoro-N,N-dimethylbenzamide | ¹H NMR (400 MHz, DMSO-d$_6$) δ = 8.97 (s, 1H), 8.76 (br t, J = 5.2 Hz, 1H), 8.01 (s, 1H), 7.65 (t, J = 6.4 Hz, 1H), 7.31 (t, J = 6.4 Hz, 1H), 6.95 (t, J = 9.6 Hz, 1H), 6.70 (dd, J = 4.0, 8.8 Hz, 1H), 4.74 (d, J = 4.8 Hz, 2H), 4.54 (t, J = 8.8 Hz, 2H), 3.32 (t, J = 8.8 Hz, 2H), 3.03 (s, 3H), 2.93 (s, 3H). LC-MS [M + 1]: 493.3. |
| 43 | 4-(2-cyano-5-(((5-fluoro-2,3-dihydrobenzofuran-4-yl)methyl)amino)imidazo[1,2-c]pyrimidin-8-yl)-2-fluoro-N,N,5-trimethylbenzamide | ¹H NMR (400 MHz, DMSO-d$_6$) δ = 8.93 (s, 1H), 8.55 (br t, J = 4.8 Hz, 1H), 7.79 (s, 1H), 7.32 (d, J = 7.2 Hz, 1H), 7.25 (d, J = 10.4 Hz, 1H), 6.96 (t, J = 9.2 Hz, 1H), 6.72 (dd, J = 4.0, 8.8 Hz, 1H), 4.72 (br d, J = 4.8 Hz, 2H), 4.56 (t, J = 8.8 Hz, 2H), 3.33 (br t, J = 8.4 Hz, 2H), 3.02 (s, 3H), 2.92 (s, 3H), 2.16 (s, 3H). LCMS [M + 1]: 489.4. |

TABLE 3-continued

Characterization of EXAMPLES 24-85

| Ex. # | Structure | ¹H NMR |
|---|---|---|
| 44 | 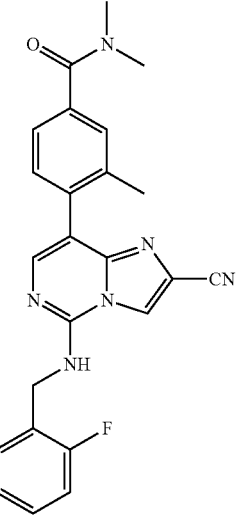<br>4-(2-cyano-5-(((5-fluoro-2,3-dihydrobenzofuran-4-yl)methyl)amino)imidazo[1,2-c]pyrimidin-8-yl)-N,N,3-trimethyl-benzamide | ¹H NMR (400 MHz, DMSO-d₆) δ = 8.92 (s, 1H), 8.51 (t, J = 4.8 Hz, 1H), 7.75 (s, 1H), 7.37-7.33 (m, 2H), 7.30-7.26 (m, 1H), 6.99-6.93 (m, 1H), 6.72 (dd, J = 3.6, 8.4 Hz, 1H), 4.72 (d, J = 4.8 Hz, 2H), 4.55 (t, J = 8.8 Hz, 2H), 3.33 (br t, J = 8.8 Hz, 2H), 2.99 (br d, J = 7.2 Hz, 6H), 2.19 (s, 3H).<br>LCMS [M + 1]: 471.2. |
| 45 | 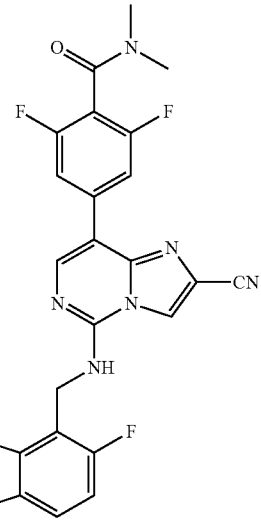<br>4-(2-cyano-5-(((5-fluoro-2,3-dihydrobenzofuran-4-yl)methyl)amino)imidazo[1,2-c]pyrimidin-8-yl)-2,6-difluoro-N,N-dimethylbenzamide | ¹H NMR (400 MHz, DMSO-d₆) δ = 8.97 (s, 1H), 8.80 (t, J = 4.8 Hz, 1H), 8.41 (s, 1H), 8.01 (d, J = 9.2 Hz, 2H), 6.96 (t, J = 8.8 Hz, 1H), 6.72 (dd, J = 4.0, 8.8 Hz, 1H), 4.75 (d, J = 4.4 Hz, 2H), 4.55 (t, J = 8.8 Hz, 2H), 3.34-3.30 (m, 2H), 3.05 (s, 3H), 2.93 (s, 3H).<br>LCMS [M + 1]: 493.3. |

TABLE 3-continued

Characterization of EXAMPLES 24-85

| Ex. # | Structure | ¹H NMR |
|---|---|---|
| 46 | 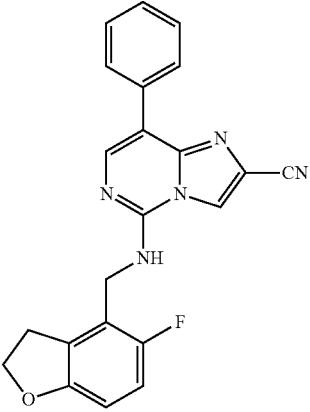 [SMILES: N#Cc1cn2c(NCc3c(F)ccc4c3CCO4)ncc(-c3ccccn3)c2n1]<br>5-(((5-fluoro-2,3-dihydrobenzofuran-4-yl)methyl)amino)-8-phenylimidazo[1,2-c]pyrimidine-2-carbonitrile | ¹H NMR (400 MHz, DMSO-d$_6$) δ = 8.94 (s, 1H), 8.50 (br s, 1H), 8.09 (s, 1H), 7.96 (br d, J = 7.6 Hz, 2H), 7.46 (br t, J = 7.6 Hz, 2H), 7.40-7.29 (m, 1H), 6.95 (br t, J = 9.6 Hz, 1H), 6.70 (dd, J = 4.0, 8.8 Hz, 1H), 4.74 (s, 2H), 4.54 (br t, J = 8.8 Hz, 2H), 3.33 (br s, 2H).<br>LC-MS [M + 1]: 386.0. |
| 47 | 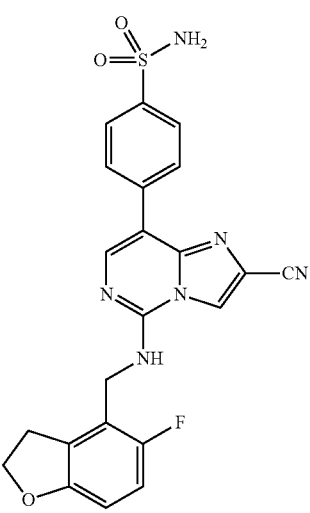<br>4-(2-cyano-5-(((5-fluoro-2,3-dihydrobenzofuran-4-yl)methyl)amino)imidazo[1,2-c]pyrimidin-8-yl)benzene-sulfonamide | ¹H NMR (400 MHz, DMSO-d$_6$) δ = 8.96 (s, 1H), 8.65 (t, J = 4.8 Hz, 1H), 8.24 (s, 1H), 8.20 (d, J = 8.8 Hz, 2H), 7.90 (d, J = 8.4 Hz, 2H), 7.38 (s, 2H), 6.96 (t, J = 9.2 Hz, 1H), 6.71 (dd, J = 4.0, 8.8 Hz, 1H), 4.76 (br d, J = 4.8 Hz, 2H), 4.56 (t, J = 8.8 Hz, 2H), 3.36-3.33 (m, 2H).<br>LCMS [M + 1]: 465.2. |

TABLE 3-continued

Characterization of EXAMPLES 24-85

| Ex. # | Structure | ¹H NMR |
|---|---|---|
| 48 | 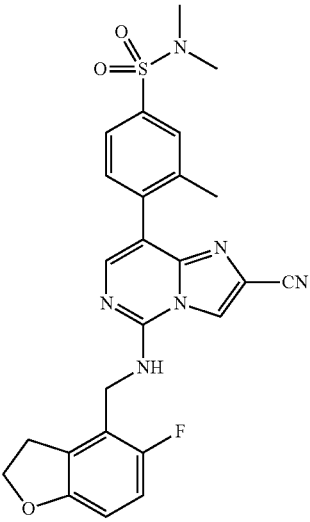<br>4-(2-cyano-5-(((5-fluoro-2,3-dihydrobenzofuran-4-yl)methyl)amino)imidazo[1,2-c]pyrimidin-8-yl)-N,N,3-trimethyl-benzenesulfonamide | ¹H NMR (400 MHz, DMSO-d6) δ = 8.94 (s, 1H), 8.57 (t, J = 4.0 Hz 1H), 7.81 (s, 1H), 7.71 (s, 1H), 7.66-7.61 (m, 1H), 7.61-7.55 (m, 1H), 6.96 (t, J = 8.8 Hz, 1H), 6.72 (dd, J = 4.0, 8.8 Hz, 1H), 4.73 (br d, J = 4.4 Hz, 2H), 4.56 (t, J = 8.8 Hz, 2H), 3.33 (t, J = 8.8 Hz, 2H), 2.69 (s, 6H), 2.29 (s, 3H).<br>LCMS [M + 1]: 507.1. |
| 49 | 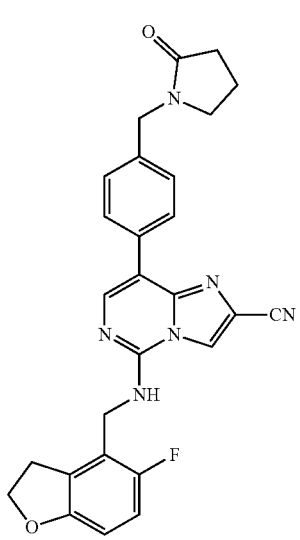<br>5-(((5-fluoro-2,3-dihydrobenzofuran-4-yl)methyl)amino)-8-(4-((2-oxopyrrolidin-1-yl)methyl)phenyl)imidazo[1,2-c]pyrimidine-2-carbonitrile | ¹H NMR (400 MHz, DMSO-d₆) δ = 8.94 (s, 1H), 8.50 (t, J = 4.8 Hz, 1H), 8.09 (s, 1H), 7.94 (d, J = 8.4 Hz, 2H), 7.32 (d, J = 8.0 Hz, 2H), 6.95 (t, J = 9.2 Hz, 1H), 6.71 (dd, J = 4.0, 8.8 Hz, 1H), 4.74 (d, J = 4.8 Hz, 2H), 4.55 (t, J = 8.8 Hz, 2H), 4.42 (s, 2H), 3.33-3.27 (m, 4H), 2.37-2.27 (m, 2H), 2.03-1.90 (m, 2H).<br>LC-MS [M + 1]: 483.0. |

TABLE 3-continued

Characterization of EXAMPLES 24-85

| Ex. # | Structure | $^1$H NMR |
|---|---|---|
| 50 | 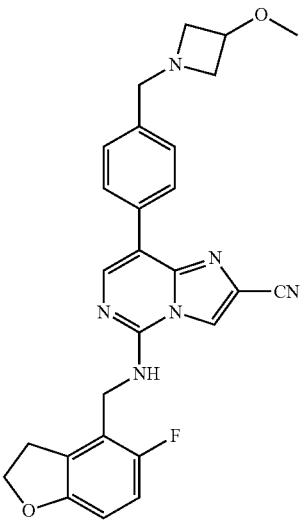 [SMILES: N#Cc1cn2c(NCc3c(F)ccc4c3CCO4)ncc(-c3ccc(CN4CC(O)C4)cc3)c2n1]<br>5-(((5-fluoro-2,3-dihydrobenzofuran-4-yl)methyl)amino)-8-(4-((3-methoxyazetidin-1-yl)methyl)phenyl)imidazo[1,2-c]pyrimidine-2-carbonitrile | $^1$H NMR (400 MHz, DMSO-d6) δ = 10.47 (s, 0.5H), 9.89 (s, 0.5H), 8.95 (s, 1H), 8.59 (br t, J = 5.2 Hz, 1H), 8.16 (s, 1H), 8.07 (d, J = 8.4 Hz, 2H), 7.62-7.53 (m, 2H), 6.95 (t, J = 9.2 Hz, 1H), 6.71 (dd, J = 4.0, 8.8 Hz, 1H), 4.74 (br d, J = 5.2 Hz, 2H), 4.55 (t, J = 8.8 Hz, 2H), 4.42 (br s, 2H), 4.35-4.22 (m, 3H), 4.01 (br. s, 2H), 3.32-3.28 (m, 2H), 3.26 (s, 3H). LCMS [M + 1]: 485.4. |
| 51 | 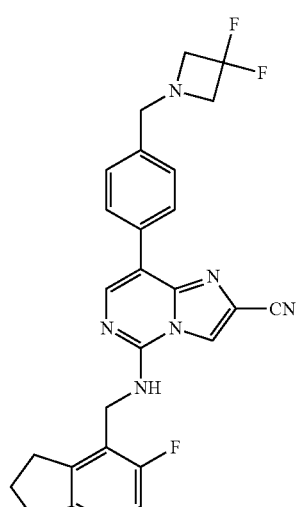<br>8-(4-((3,3-difluoroazetidin-1-yl)methyl)phenyl)-5-(((5-fluoro-2,3-dihydrobenzofuran-4-yl)methyl)amino)imidazo[1,2-c]pyrimidine-2-carbonitrile | $^1$H NMR (400 MHz, CD$_3$OD) δ = 8.62 (s, 1H), 8.05 (s, 1H), 8.00 (d, J = 8.0 Hz, 2H), 7.57 (d, J = 8.0 Hz, 2H), 6.89-6.82 (m, 1H), 6.65 (dd, J = 3.6, 8.4 Hz, 1H), 4.83 (s, 2H), 4.63-4.54 (m, 6H), 4.45 (s, 2H), 3.37 (t, J = 8.8 Hz, 2H). LCMS [M + 1]: 491.3. |

TABLE 3-continued

Characterization of EXAMPLES 24-85

| Ex. # | Structure | ¹H NMR |
|---|---|---|
| 52 | 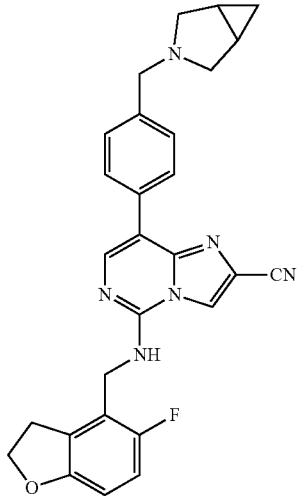<br>8-(4-((3-azabicyclo[3.1.0]hexan-3-yl)methyl)phenyl)-5-(((5-fluoro-2,3-dihydrobenzofuran-4-yl)methyl)amino)imidazo[1,2-c]pyrimidine-2-carbonitrile | ¹H NMR (400 MHz, methanol-d$_4$) δ = 8.63 (s, 1H), 8.06 (s, 1H), 8.01 (d, J = 8.4 Hz, 2H), 7.59 (d, J = 8.0 Hz, 2H), 6.86 (t, J = 8.8 Hz, 1H), 6.65 (dd, J = 4.0, 8.8 Hz, 1H), 4.83 (s, 2H), 4.58 (t, J = 8.8 Hz, 2H), 4.42 (s, 2H), 3.55 (s, 3H), 3.37 (t, J = 8.8 Hz, 2H), 3.34-3.33 (m, 1H), 1.89 (dd, J = 3.6, 8.0 Hz, 2H), 0.91-0.79 (m, 1H), 0.73-0.64 (m, 1H).<br>LCMS [M + 1]: 481.4. |
| 53 | 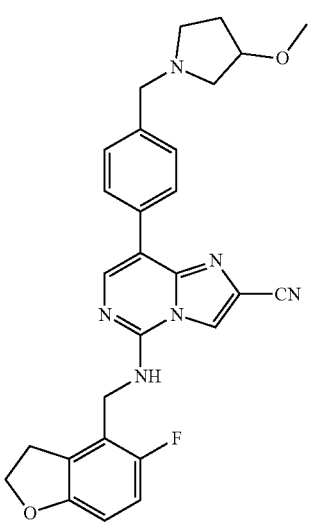<br>5-(((5-fluoro-2,3-dihydrobenzo-furan-4-yl)methyl)amino)-8-(4-((3-methoxypyrrolidin-1-yl)methyl)phenyl)imidazo[1,2-c]pyrimidine-2-carbonitrile | ¹H NMR (400 MHz, CD$_3$OD) δ = 8.62 (s, 1H), 8.05 (d, J = 2.0 Hz, 1H), 8.01 (d, J = 7.6 Hz, 2H), (d, J = 8.0 Hz, 2H), 6.85 (t, J = 9.2 Hz, 1H), 6.64 (dd, J = 3.6, 8.4 Hz, 1H), 4.82-4.79 (m, 2H), 4.58 (t, J = 8.8 Hz, 2H), 4.51-4.38 (m, 2H), 4.20 (br. s, 1H), 3.74-3.50 (m, 2H), 3.40-3.32 (m, 7H), 2.50-2.04 (m, 2H).<br>LCMS [M + 1]: 499.1. |

TABLE 3-continued

Characterization of EXAMPLES 24-85

| Ex. # | Structure | ¹H NMR |
|---|---|---|
| 54 | 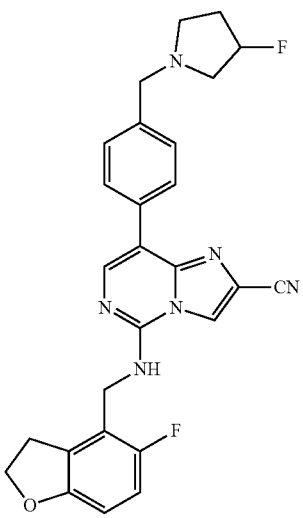 [SMILES: N#Cc1cn2c(NCc3c(F)ccc4c3CCO4)ncc(-c3ccc(CN4CCC(O)C4)cc3)c2n1]<br>5-(((5-fluoro-2,3-dihydrobenzo-furan-4-yl)methyl)amino)-8-(4-((3-fluoropyrrolidin-1-yl)methyl)phenyl)imidazo[1,2-c]pyrimidine-2-carbonitrile | ¹H NMR (400 MHz, DMSO-d6) δ = 10.52 (s, 0.5H), 10.16 (s, 0.3H), 8.95 (s, 1H), 8.60 (t, J = 5.2 Hz, 1H), 8.18 (s, 1H), 8.09 (br d, J = 8.0 Hz, 2H), 7.70-7.58 (m, 2H), 6.95 (t, J = 9.2 Hz, 1H), 6.71 (dd, J = 4.0, 8.8 Hz, 1H), 5.63-5.33 (m, 1H), 4.74 (d, J = 4.8 Hz, 2H), 4.55 (t, J = 8.8 Hz, 2H), 4.51-4.39 (m, 2H), 3.50-3.37 (m, 5H), 3.32 (t, J = 8.8 Hz, 2H), 2.25-2.05 (m, 1H).<br>LCMS [M + 1]: 487.2. |
| 55 | 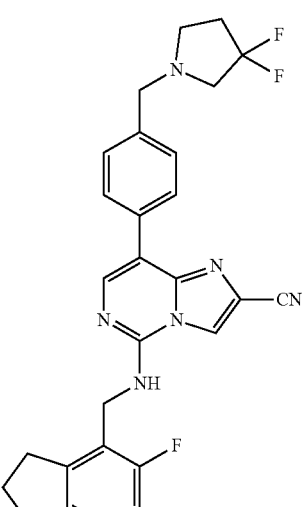<br>8-(4-((3,3-difluoropyrrolidin-1-yl)methyl)phenyl)-5-(((5-fluoro-2,3-dihydrobenzofuran-4-yl)methyl)amino)imidazo[1,2-c]pyrimidine-2-carbonitrile | ¹H NMR (400 MHz, DMSO-d₆) δ = 8.95 (s, 1H), 8.50 (t, J = 5.2 Hz, 1H), 8.10 (s, 1H), 7.94 (d, J = 8.0 Hz, 2H), 7.40 (d, J = 8.0 Hz, 2H), 6.99-6.91 (m, 1H), 6.71 (dd, J = 4.0, 8.8 Hz, 1H), 4.74 (d, J = 4.8 Hz, 2H), 4.55 (t, J = 8.4 Hz, 2H), 3.67 (s, 2H), 3.35-3.32 (m, 2H), 2.89 (t, J = 13.2 Hz, 2H), 2.73 (t, J = 6.8 Hz, 2H), 2.32-2.21 (m, 2H).<br>LCMS [M + 1]: 505.2. |

TABLE 3-continued

Characterization of EXAMPLES 24-85

| Ex. # | Structure | ¹H NMR |
|---|---|---|
| 56 | 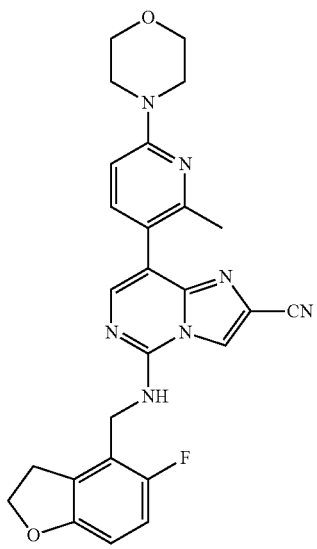<br>5-(((5-fluoro-2,3-dihydrobenzofuran-4-yl)methyl)amino)-8-(2-methyl-6-morpholinopyridin-3-yl)imidazo[1,2-c]pyrimidine-2-carbonitrile | ¹H NMR (400 MHz, DMSO-$d_6$) δ = 8.91 (s, 1H), 8.47 (br s, 1H), 7.72 (s, 1H), 7.61 (br d, J = 8.4 Hz, 1H), 6.99-6.91 (m, 1H), 6.87 (br d, J = 8.8 Hz, 1H), 6.71 (dd, J = 4.0, 8.8 Hz, 1H), 4.72 (br d, J = 4.8 Hz, 2H), 4.55 (t, J = 8.8 Hz, 2H), 3.77-3.67 (m, 4H), 3.59-3.51 (m, 4H), 3.32 (t, J = 8.4 Hz, 2H), 2.28 (s, 3H). LCMS [M + 1]: 496.4. |
| 57 | 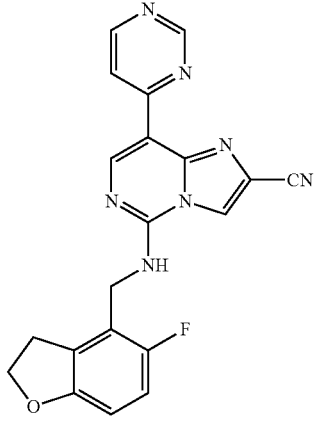<br>5-(((5-fluoro-2,3-dihydrobenzofuran-4-yl)methyl)amino)-8-(pyrimidin-4-yl)imidazo[1,2-c]pyrimidine-2-carbonitrile | ¹H NMR (400 MHz, DMSO-$d_6$) δ = 9.17 (d, J = 0.8 Hz, 1H), 8.98 (s, 2H), 8.95 (s, 1H), 8.86 (d, J = 5.6 Hz, 1H), 8.75 (dd, J = 1.2, 5.2 Hz, 1H), 6.99-6.92 (m, 1H), 6.71 (dd, J = 4.0, 8.8 Hz, 1H), 4.79 (s, 2H), 4.54 (t, J = 8.8 Hz, 2H), 3.36-3.28 (m, 2H). LCMS [M + 1]: 388.3. |

TABLE 3-continued

Characterization of EXAMPLES 24-85

| Ex. # | Structure | ¹H NMR |
|---|---|---|
| 58 | 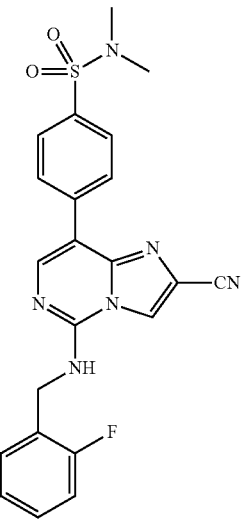<br>4-(2-cyano-5-(((5-fluoro-2,3-dihydrobenzofuran-4-yl)methyl)amino)imidazo[1,2-c]pyrimidin-8-yl)-N,N-dimethylbenzenesulfonamide | ¹H NMR (400 MHz, DMSO-d$_6$) δ = 8.97 (s, 1H), 8.69 (t, J = 4.8 Hz, 1H), 8.31 (d, J = 9.2 Hz, 2H), 8.29 (s, 1H), 7.84 (d, J = 8.8 Hz, 2H), 6.96 (t, J = 9.2 Hz, 1H), 6.72 (dd, J = 4.0, 8.8 Hz, 1H), 4.76 (d, J = 4.8 Hz, 2H), 4.56 (t, J = 8.8 Hz, 2H), 3.35-3.34 (m, 2H), 2.66 (s, 6H).<br>LCMS [M + 1]: 493.3. |
| 59 | 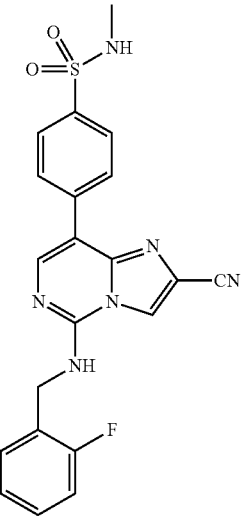<br>4-(2-cyano-5-(((5-fluoro-2,3-dihydrobenzofuran-4-yl)methyl)amino)imidazo[1,2-c]pyrimidin-8-yl)-N-methylbenzenesulfonamide | ¹H NMR (400 MHz, DMSO-d$_6$) δ = 8.97 (s, 1H), 8.67 (t, J = 4.8 Hz, 1H), 8.26 (s, 1H), 8.24 (d, J = 8.4 Hz, 2H), 7.86 (d, J = 8.4 Hz, 2H), 7.50-7.46 (m, 1H), 6.96 (t, J = 9.2 Hz, 1H), 6.72 (dd, J = 3.6, 8.4 Hz, 1H), 4.76 (d, J = 4.8 Hz, 2H), 4.56 (t, J = 8.8 Hz, 2H), 3.35-3.34 (m, 2H), 2.46 (d, J = 4.8 Hz, 3H).<br>LCMS [M + 1]: 479.2. |

TABLE 3-continued

Characterization of EXAMPLES 24-85

| Ex. # | Structure | $^1$H NMR |
|---|---|---|
| 60 | 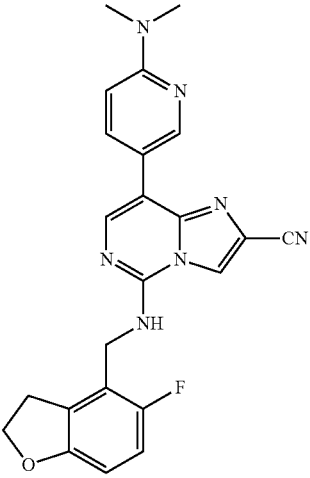<br>8-(6-(dimethylamino)pyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.95 (s, 1H), 8.83 (s, 1H), 8.60 (br s, 1H), 8.41 (br d, J = 7.6 Hz, 1H), 8.22 (s, 1H), 7.14 (br s, 1H), 6.99-6.92 (m, 1H), 6.71 (dd, J = 4.0, 8.8 Hz, 1H), 4.74 (d, J = 4.8 Hz, 2H), 4.55 (t, J = 8.8 Hz, 2H), 3.31 (br t, J = 8.8 Hz, 2H), 3.19 (s, 6H).<br>LCMS [M + 1]: 430.0. |
| 61 | 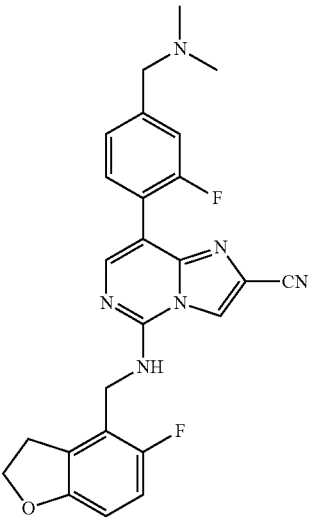<br>8-(4-((dimethylamino)methyl)-2-fluorophenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 9.73 (br s, 1H), 8.97 (s, 1H), 8.79-8.67 (m, 1H), 8.32 (s, 1H), 8.15-7.99 (m, 2H), 7.67 (t, J = 7.6 Hz, 1H), 7.01-6.91 (m, 1H), 6.72 (dd, J = 4.0, 8.8 Hz, 1H), 4.76 (d, J = 4.8 Hz, 2H), 4.56 (t, J = 8.8 Hz, 2H), 4.39 (br s, 2H), 3.30 (m, 2H), 2.81 (br s, 6H).<br>LC-MS [M + 1]: 461.2. |

TABLE 3-continued

Characterization of EXAMPLES 24-85

| Ex. # | Structure | ¹H NMR |
|---|---|---|
| 62 | 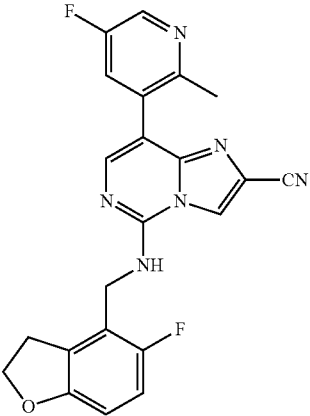<br>5-(((5-fluoro-2,3-dihydrobenzofuran-4-yl)methyl)amino)-8-(5-fluoro-2-methylpyridin-3-yl)imidazo[1,2-c]pyrimidine-2-carbonitrile | ¹H NMR (400 MHz, methanol-$d_4$) δ = 8.65 (s, 1H), 8.51 (d, J = 2.8 Hz, 1H), 7.86 (s, 1H), 7.79 (dd, J = 2.8, 8.8 Hz, 1H), 6.88 (t, J = 8.8 Hz, 1H), 6.67 (dd, J = 3.6, 8.8 Hz, 1H), 4.80-4.74 (m, 2H), 4.60 (t, J = 8.8 Hz, 2H), 3.41 (t, J = 8.8 Hz, 2H), 2.47 (s, 3H).<br>LCMS [M + 1]: 419.3. |
| 63 | 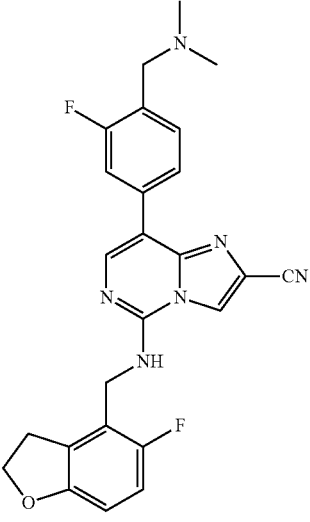<br>8-(4-((dimethylamino)methyl)-3-fluorophenyl)-5-(((5-fluoro-2,3-dihydrobenzofuran-4-yl)methyl)amino)imidazo[1,2-c]pyrimidine-2-carbonitrile | ¹H NMR (400 MHz, CDCl$_3$-d) δ = 8.05 (s, 1H), 8.01 (s, 1H), 7.92 (t, J = 7.6 Hz, 1H), 7.33 (d, J = 9.2 Hz, 2H), 6.84 (t, J = 9.2 Hz, 1H), 6.67 (dd, J = 4.0, 8.8 Hz, 1H), 6.03 (br s, 1H), 4.85 (br s, 2H), 4.64 (t, J = 8.8 Hz, 2H), 4.20 (s, 2H), 3.43 (t, J = 8.8 Hz, 2H), 2.84 (s, 6H).<br>LC-MS [M + 1]: 461. |

TABLE 3-continued

Characterization of EXAMPLES 24-85

| Ex. # | Structure | ¹H NMR |
|---|---|---|
| 64 | 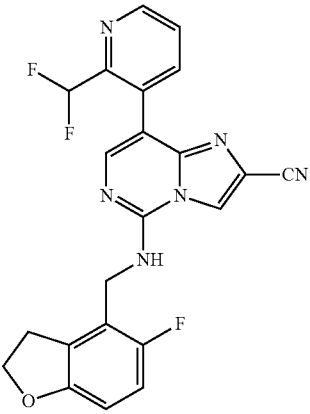<br>8-(2-(difluoromethyl)pyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.93 (s, 1H), 8.77 (dd, J = 1.6, 4.8 Hz, 1H), 8.62 (br s, 1H), 7.97 (d, J = 8.0 Hz, 1H), 7.76 (s, 1H), 7.68 (dd, J = 4.8, 8.0 Hz, 1H), 7.0, 6.86, 6.72 (m, 1H), 6.99-6.92 (m, 1H), 6.73-6.69 (dd, J = 4.0, 8.8 Hz, 1H), 4.73 (br d, J = 4.4 Hz, 2H), 4.56 (t, J = 8.8 Hz, 2H), 3.38-3.32 (m, 2H). LCMS [M + 1]: 437.1. |
| 65 | 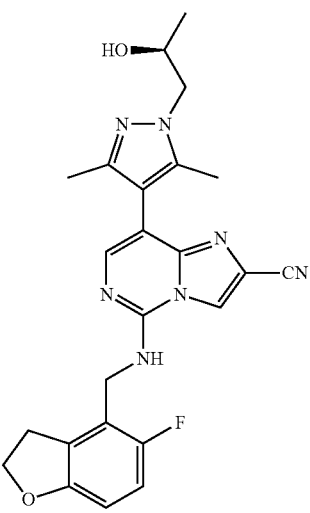<br>(S)-5-(((5-fluoro-2,3-dihydrobenzofuran-4-yl)methyl)amino)-8-(1-(2-hydroxypropyl)-3,5-dimethyl-1H-pyrazol-4-yl)imidazo[1,2-c]pyrimidine-2-carbonitrile | ¹H NMR (400 MHz, methanol-$d_4$) δ = 8.63 (s, 1H), 7.73 (s, 1H), 6.91-6.85 (m, 1H), 6.67 (dd, J = 4.0, 8.8 Hz, 1H), 4.83 (s, 2H), 4.60 (t, J = 8.8 Hz, 2H), 4.23-4.15 (m, 1H), 4.13-4.02 (m, 2H), 3.41 (t, J = 8.8 Hz, 2H), 2.23 (s, 3H), 2.19 (s, 3H), 1.28 (d, J = 6.4 Hz, 3H). LCMS [M + 1]: 462.1. |

TABLE 3-continued

Characterization of EXAMPLES 24-85

| Ex. # | Structure | $^1$H NMR |
|---|---|---|
| 66 | 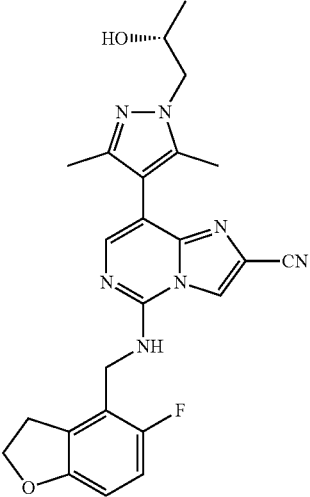<br>(R)-5-(((5-fluoro-2,3-dihydrobenzofuran-4-yl)methyl)amino)-8-(1-(2-hydroxypropyl)-3,5-dimethyl-1H-pyrazol-4-yl)imidazo[1,2-c]pyrimidine-2-carbonitrile | $^1$H NMR (400 MHz, methanol-d$_4$) δ = 8.51 (s, 1H), 7.59 (s, 1H), 6.76 (t, J = 9.2 Hz, 1H), 6.55 (dd, J = 4.0, 8.8 Hz, 1H), 4.71 (s, 2H), 4.48 (t, J = 8.8 Hz, 2H), 4.14-4.04 (m, 1H), 4.00-3.88 (m, 2H), 3.29 (t, J = 8.8 Hz, 3H), 2.09 (s, 3H), 2.04 (s, 3H), 1.16 (d, J = 6.4 Hz, 3H).<br>LCMS [M + 1]: 462.2. |
| 67 | 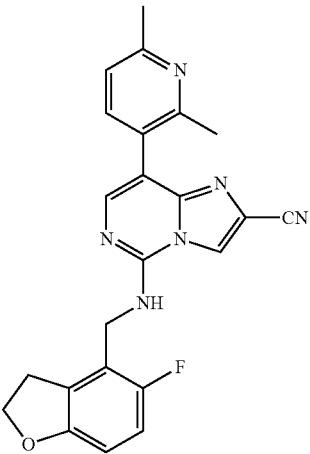<br>8-(2,6-dimethylpyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, methanol-d$_4$) δ = 8.66 (s, 1H), 8.38 (d, J = 8.0 Hz, 1H), 7.91 (s, 1H), 7.78 (d, J = 8.0 Hz, 1H), 6.86 (t, J = 8.8 Hz, 1H), 6.65 (dd, J = 3.6, 8.4 Hz, 1H), 4.84 (br s, 2H), 4.58 (t, J = 8.4 Hz, 2H), 3.40 (t, J = 8.8 Hz, 2H), 2.82 (s, 3H), 2.64 (s, 3H).<br>LCMS [M + 1]: 415.3. |

TABLE 3-continued

Characterization of EXAMPLES 24-85

| Ex. # | Structure | ¹H NMR |
|---|---|---|
| 68 | 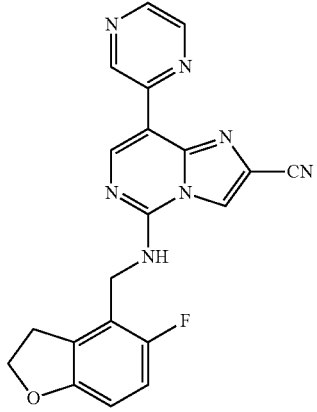<br>5-(((5-fluoro-2,3-dihydrobenzofuran-4-yl)methyl)amino)-8-(pyrazin-2-yl)imidazo[1,2-c]pyrimidine-2-carbonitrile | ¹H NMR (400 MHz, methanol-$d_4$) δ = 9.85 (d, J = 1.2 Hz, 1H), 8.77 (s, 1H), 8.68-8.65 (m, 1H), 8.63 (s, 1H), 8.50 (d, J = 2.4 Hz, 1H), 6.86 (t, J = 8.8 Hz, 1H), 6.65 (dd, J = 3.6, 8.8 Hz, 1H), 4.86 (s, 2H), 4.58 (t, J = 8.8 Hz, 2H), 3.38 (t, J = 8.8 Hz, 2H).<br>LCMS [M + 1]: 388.2. |
| 69 | 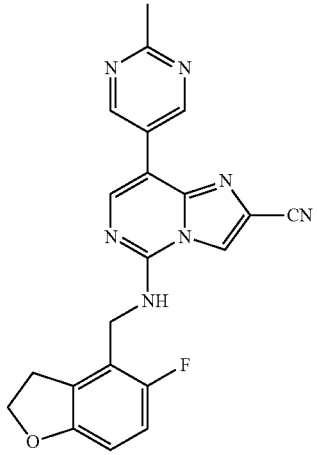<br>5-(((5-fluoro-2,3-dihydrobenzofuran-4-yl)methyl)amino)-8-(2-methylpyrimidin-5-yl)imidazo[1,2-c]pyrimidine-2-carbonitrile | ¹H NMR (400 MHz, CDCl₃) δ = 9.18 (s, 2H), 8.01 (s, 1H), 7.95 (s, 1H), 6.87 (t, J = 9.2 Hz, 1H), 6.69 (dd, J = 4.0, 8.8 Hz, 1H), 5.64 (s, 1H), 4.86 (br d, J = 4.0 Hz, 2H), 4.65 (br t, J = 8.4 Hz, 2H), 3.43 (br t, J = 8.4 Hz, 2H), 2.81 (s, 3H).<br>LCMS [M + 1]: 402.1. |

TABLE 3-continued

Characterization of EXAMPLES 24-85

| Ex. # | Structure | $^1$H NMR |
|---|---|---|
| 70 | 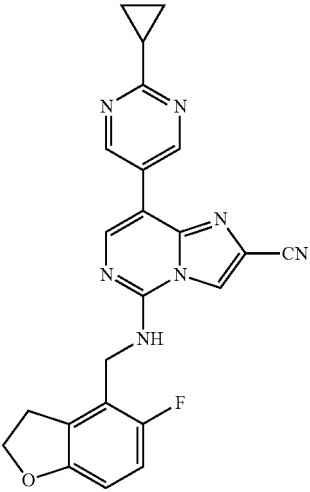<br>8-(2-cyclopropylpyrimidin-5-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d6) δ = 9.21 (s, 2H), 9.04 (s, 1H), 8.83 (s, 1H), 8.24 (s, 1H), 6.94 (t, J = 8.8 Hz, 1H), 6.69 (dd, J = 4.0, 8.4 Hz, 1H), 4.74 (br d, J = 4.0 Hz, 2H), 4.53 (br t, J = 8.8 Hz, 2H), 3.31 (br t, J = 8.4 Hz, 2H), 2.30-2.21 (m, 1H), 1.10-1.05 (m, 4H).<br>LCMS [M + 1]: 428.2. |
| 71 | 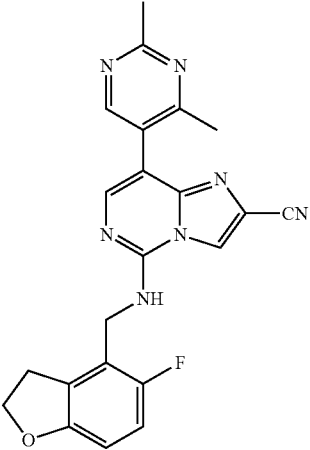<br>8-(2,4-dimethylpyrimidin-5-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.93 (s, 1H), 8.60 (t, J = 4.8 Hz, 1H), 8.54 (s, 1H), 7.84 (s, 1H), 7.00-6.90 (m, 1H), 6.71 (dd, J = 4.0, 8.8 Hz, 1H), 4.73 (d, J = 4.8 Hz, 2H), 4.55 (t, J = 8.8 Hz, 2H), 3.36-3.32 (m, 2H), 2.63 (s, 3H), 2.34 (s, 3H).<br>LCMS [M + 1]: 416.1. |

TABLE 3-continued

Characterization of EXAMPLES 24-85

| Ex. # | Structure | ¹H NMR |
|---|---|---|
| 72 | 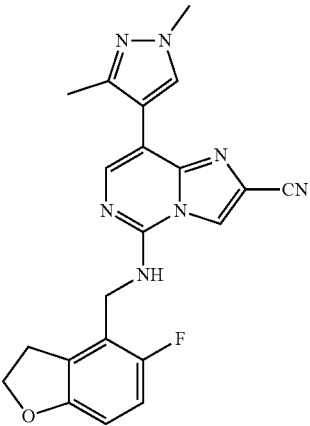<br>8-(1,3-dimethyl-1H-pyrazol-4-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.90 (s, 1H), 8.32 (br t, J = 5.2 Hz, 1H), 8.16 (s, 1H), 7.85 (s, 1H), 6.95 (t, J = 8.8 Hz, 1H), 6.71 (dd, J = 3.6, 8.4 Hz, 1H), 4.71 (d, J = 4.8 Hz, 2H), 4.55 (t, J = 8.8 Hz, 2H), 3.84 (s, 3H), 3.31-3.26 (m, 2H), 2.30 (s, 3H). LCMS [M + 1]: 404.3. |
| 73 | 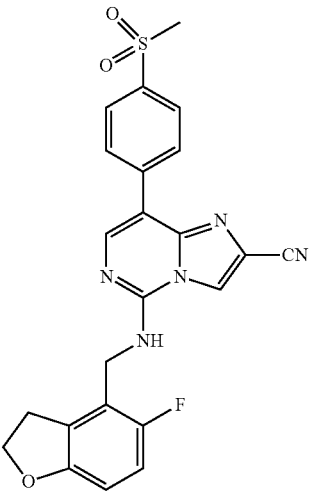<br>5-(((5-fluoro-2,3-dihydrobenzofuran-4-yl)methyl)amino)-8-(4-(methylsulfonyl)phenyl)imidazo[1,2-c]pyrimidine-2-carbonitrile | ¹H NMR (400 MHz, DMSO-$d_6$) δ = 9.03 (s, 1H), 8.79 (t, J = 5.2 Hz, 1H), 8.39-8.32 (m, 3H), 8.07 (d, J = 8.8 Hz, 2H), 7.02 (t, J = 8.8 Hz, 1H), 6.78 (dd, J = 4.0, 8.8 Hz, 1H), 4.82 (d, J = 4.8 Hz, 2H), 4.62 (t, J = 8.8 Hz, 2H), 3.38-3.35 (m, 2H), 3.32 (s, 3H). LCMS [M + 1]: 464.2. |

TABLE 3-continued

Characterization of EXAMPLES 24-85

| Ex. # | Structure | $^1$H NMR |
|---|---|---|
| 74 | 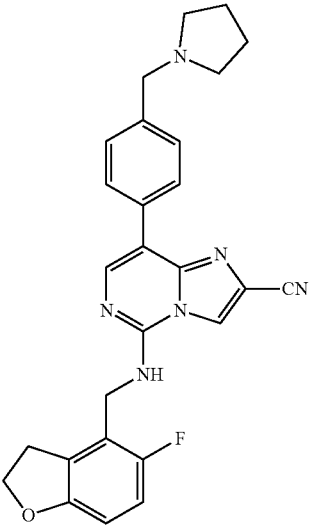<br>5-(((5-fluoro-2,3-dihydrobenzofuran-4-yl)methyl)amino)-8-(4-(pyrrolidin-1-ylmethyl)phenyl)imidazo[1,2-c]pyrimidine-2-carbonitrile | $^1$H NMR (400 MHz, DMSO-d$_6$) δ = 9.83 (br s, 1H), 8.96 (s, 1H), 8.61 (t, J = 5.6 Hz, 1H), 8.18 (s, 1H), 8.10 (d, J = 8.4 Hz, 2H), 7.61 (d, J = 8.4 Hz, 2H), 6.99-6.92 (m, 1H), 6.72 (dd, J = 3.6, 8.4 Hz, 1H), 4.75 (br d, J = 4.4 Hz, 2H), 4.56 (t, J = 8.8 Hz, 2H), 4.41 (br d, J = 5.2 Hz, 2H), 3.43-3.39 (m, 4H), 3.19-3.09 (m, 2H), 2.12-2.01 (m, 2H), 1.93-1.82 (m, 2H). LCMS [M + 1]: 469.2. |
| 75 | 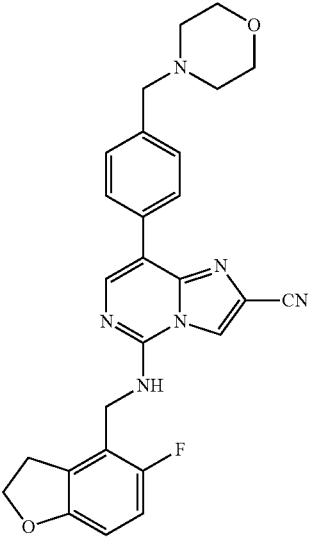<br>5-(((5-fluoro-2,3-dihydrobenzofuran-4-yl)methyl)amino)-8-(4-(morpholinomethyl)phenyl)imidazo[1,2-c]pyrimidine-2-carbonitrile | $^1$H NMR (400 MHz, DMSO-d$_6$) δ = 9.89 (br s, 1H), 8.96 (s, 1H), 8.62 (br s, 1H), 8.18 (s, 1H), 8.11 (br d, J = 7.2 Hz, 2H), 7.60 (br d, J = 7.2 Hz, 2H), 6.96 (t, J = 8.8 Hz, 1H), 6.72 (dd, J = 3.6, 8.4 Hz, 1H), 4.75 (d, J = 4.8 Hz, 2H), 4.56 (t, J = 8.8 Hz, 2H), 4.41 (br s, 2H), 3.99 (br d, J = 11.2 Hz, 2H), 3.64 (br t, J = 11.2 Hz, 2H), 3.35-3.30 (m, 4H), 3.22-3.08 (m, 2H). LCMS [M + 1]: 485.4. |

TABLE 3-continued

Characterization of EXAMPLES 24-85

| Ex. # | Structure | ¹H NMR |
|---|---|---|
| 76 | 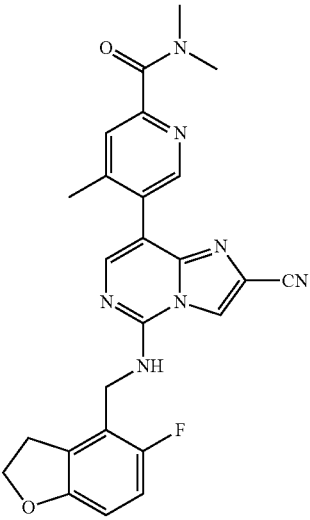<br>5-(2-cyano-5-(((5-fluoro-2,3-dihydrobenzofuran-4-yl)methyl)amino)imidazo[1,2-c]pyrimidin-8-yl)-N,N,4-trimethylpicolinamide | 1H NMR (400 MHz, DMSO-d6) δ = 8.94 (s, 1H), 8.59 (s, 1H), 8.45 (s, 1H), 7.85 (s, 1H), 7.53 (s, 1H), 6.96 (t, J = 8.8 Hz, 1H), 6.72 (dd, J = 4.0, 8.8 Hz, 1H), 4.73 (br d, J = 2.8 Hz, 2H), 4.56 (t, J = 8.8 Hz, 2H), 3.38-3.33 (m, 2H), 3.03 (s, 3H), 3.01 (s, 3H), 2.25 (s, 3H). LCMS [M + 1]: 472.2. |
| 77 | 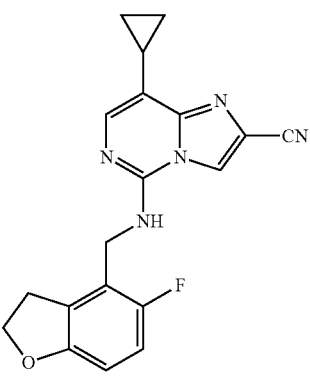<br>8-cyclopropyl-5-(((5-fluoro-2,3-dihydrobenzofuran-4-yl)methyl)amino)imidazo[1,2-c]pyrimidine-2-carbonitrile | ¹H NMR (400 MHz, DMSO-d₆) δ = 8.83 (s, 1H), 8.18 (br s, 1H), 7.51 (s, 1H), 6.93 (t, J = 8.8 Hz, 1 H), 6.69 (dd, J = 4.0, 8.8 Hz, 1H), 4.64 (s, 2H), 4.53 (t, J = 8.8 Hz, 2H), 3.27 (t, J = 8.8 Hz, 2H), 2.08-2.03 (m, 1H), 0.92-0.84 (m, 4H). LCMS [M + 1]: 350.2. |

TABLE 3-continued

Characterization of EXAMPLES 24-85

| Ex. # | Structure | ¹H NMR |
|---|---|---|
| 78 | 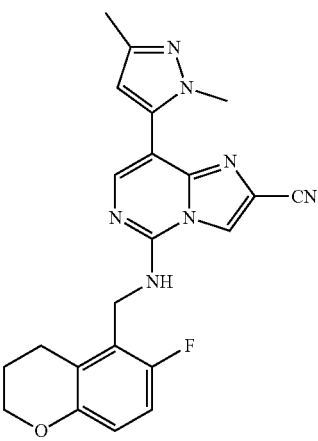<br>8-(1,3-dimethyl-1H-pyrazol-5-yl)-5-(((6-fluorochroman-5-yl)methyl)amino)imidazo[1,2-c]pyrimidine-2-carbonitrile | ¹H NMR (400 MHz, DMSO-$d_6$) δ = 8.96 (s, 1H), 8.66 (t, J = 5.2 Hz, 1H), 7.82 (s, 1H), 7.09-6.99 (m, 1H), 6.91 (d, J = 7.2 Hz, 1H), 6.70 (d, J = 7.6 Hz, 1H), 6.23 (s, 1H), 4.69 (d, J = 5.2 Hz, 2H), 4.16-4.05 (m, 2H), 3.68 (s, 3H), 2.77 (t, J = 6.4 Hz, 2H), 2.18 (s, 3H), 2.03-1.89 (m, 2H).<br>LC-MS [M + 1]: 400.3. |
| 79 | 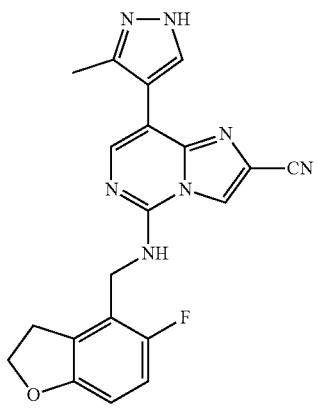<br>5-(((5-fluoro-2,3-dihydrobenzofuran-4-yl)methyl)amino)-8-(3-methyl-1H-pyrazol-4-yl)imidazo[1,2-c]pyrimidine-2-carbonitrile | ¹H NMR (400 MHz, DMSO-$d_6$) δ = 8.90 (s, 1H), 8.33 (t, J = 5.2 Hz, 1H), 7.98 (s, 1H), 7.82 (s, 1H), 7.00-6.91 (m, 1H), 6.71 (dd, J = 4.0, 8.8 Hz, 1H), 4.71 (d, J = 4.8 Hz, 2H), 4.55 (t, J = 8.8 Hz, 2H), 3.30 (br t, J = 8.8 Hz, 2H), 2.35 (s, 3H).<br>LCMS [M + 1]: 390.3. |

TABLE 3-continued

Characterization of EXAMPLES 24-85

| Ex. # | Structure | ¹H NMR |
|---|---|---|
| 80 | 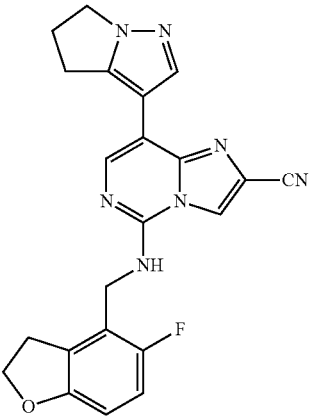<br>8-(5,6-dihydro-4H-pyrrolo[1,2-b]pyrazol-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.89 (s, 1H), 8.30 (br s, 1H), 8.12 (s, 1H), 7.88 (s, 1H), 6.94 (t, J = 9.2 Hz, 1H), 6.70 (dd, J = 4.0, 8.4 Hz, 1H), 4.70 (s, 2H), 4.53 (t, J = 8.8 Hz, 2H), 4.12 (t, J = 7.2 Hz, 2H), 3.28-3.23 (m, 2H), 3.12 (t, J = 6.8 Hz, 2H), 2.65-2.56 (m, 2H).<br>LCMS [M + 1]: 416.1. |
| 81 | 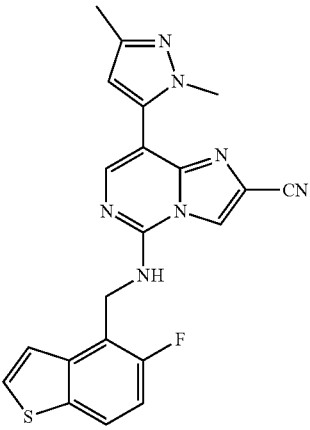<br>8-(1,3-dimethyl-1H-pyrazol-5-yl)-5-(((5-fluorobenzo[b]thiophen-4-yl)methyl)amino)imidazo[1,2-c]pyrimidine-2-carbonitrile | ¹H NMR (400 MHz, CD$_3$OD) δ = 8.60 (s, 1H), 7.96-7.89 (m, 2H), 7.75 (d, J = 5.6 Hz, 1H), 7.71 (dd, J = 0.8, 5.6 Hz, 1H), 7.24 (t, J = 9.6 Hz, 1H), 6.33 (s, 1H), 5.25 (d, J = 1.2 Hz, 2H), 3.77 (s, 3H), 2.32 (s, 3H).<br>LCMS [M + 1]: 418.2. |

TABLE 3-continued

Characterization of EXAMPLES 24-85

| Ex. # | Structure | ¹H NMR |
|---|---|---|
| 82 | 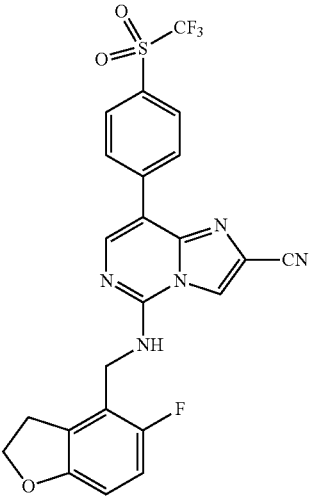<br>5-(((5-fluoro-2,3-dihydrobenzofuran-4-yl)methyl)amino)-8-(4-((trifluoromethyl)sulfonyl)phenyl)imidazo[1,2-c]pyrimidine-2-carbonitrile | ¹H NMR (400 MHz, DMSO-d$_6$) δ = 9.02 (s, 1H), 8.91 (t, J = 5.2 Hz, 1H), 8.54 (d, J = 8.8 Hz, 2H), 8.44 (s, 1H), 8.20 (d, J = 8.8 Hz, 2H), 6.99-6.92 (m, 1H), 6.72 (dd, J = 4.0, 8.8 Hz, 1H), 4.78 (d, J = 4.8 Hz, 2H), 4.56 (t, J = 8.8 Hz, 2H), 3.30-3.27 (m, 2H).<br>LC-MS [M + 1]: 518.3. |
| 83 | 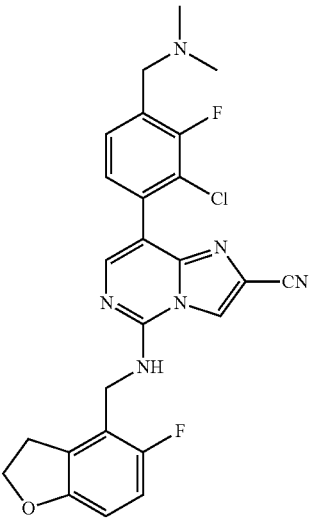<br>8-(2-chloro-4-((dimethylamino)methyl)-3-fluorophenyl)-5-(((5-fluoro-2,3-dihydrobenzofuran-4-yl)methyl)amino)imidazo[1,2-c]pyrimidine-2-carbonitrile | ¹H NMR (400 MHz, CD$_3$OD) δ = 8.64 (s, 1H), 7.87 (s, 1H), 7.61-7.55 (t, J = 7.2 Hz, 1H), 7.48 (d, J = 8.4 Hz, 1H), 6.87 (t, J = 9.6 Hz, 1H), 6.66 (dd, J = 4.0, 8.8 Hz, 1H), 4.84 (s, 2H), 4.58 (t, J = 8.8 Hz, 2H), 4.52 (s, 2H), 3.39 (t, J = 8.8 Hz, 2H), 2.97 (s, 6H).<br>LCMS [M + 1]: 495.3. |

TABLE 3-continued

Characterization of EXAMPLES 24-85

| Ex. # | Structure | ¹H NMR |
|---|---|---|
| 84 | 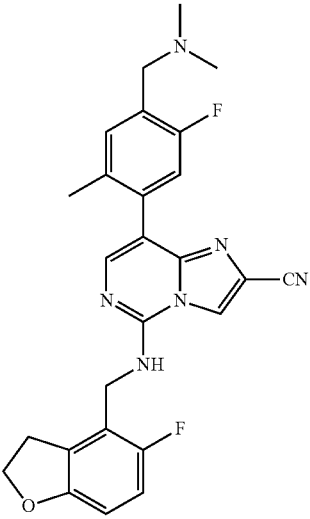<br>8-(4-((dimethylamino)methyl)-5-fluoro-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.82 (br s, 1H), 8.94 (s, 1H), 8.60 (br t, J = 4.4 Hz, 1H), 7.78 (s, 1H), 7.53 (d, J = 7.6 Hz, 1H), 7.33 (d, J = 10.8 Hz, 1H), 7.01-6.91 (m, 1H), 6.72 (dd, J = 4.0, 8.8 Hz, 1H), 4.73 (d, J = 4.8 Hz, 2H), 4.56 (t, J = 8.8 Hz, 2H), 4.37 (br s, 2H), 3.33 (t, J = 8.8 Hz, 2H), 2.83 (s, 6H), 2.18 (s, 3H).<br>LCMS [M + 1]: 475.4. |
| 85 | 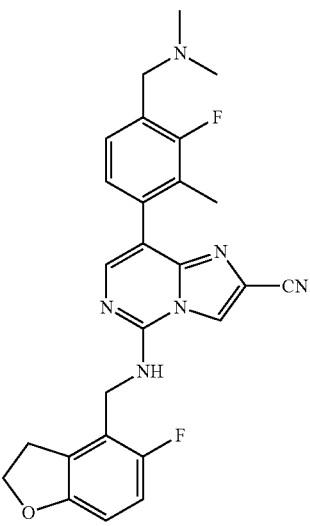<br>8-(4-((dimethylamino)methyl)-3-fluoro-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.80 (br s, 1H), 8.94 (s, 1H), 8.59 (t, J = 4.8 Hz, 1H), 7.76 (s, 1H), 7.47 (t, J = 7.6 Hz, 1H), 7.30 (d, J = 8.0 Hz, 1H), 6.99-6.91 (m, 1H), 6.71 (dd, J = 4.0, 8.8 Hz, 1H), 4.72 (d, J = 4.8 Hz, 2H), 4.55 (t, J = 8.8 Hz, 2H), 4.40 (br s, 2H), 3.32 (br t, J = 8.8 Hz, 2H), 2.82 (s, 6H), 2.11 (d, J = 2.0 Hz, 3H).<br>LC-MS [M + 1]: 475.3. |

Example 86

8-(1,3-dimethyl-1H-pyrazol-5-yl)-5-(((5-fluoro-2,3-dihydrobenzofuran-4-yl)methyl)amino)imidazo[1,2-c]pyrimidine-2-carbonitrile

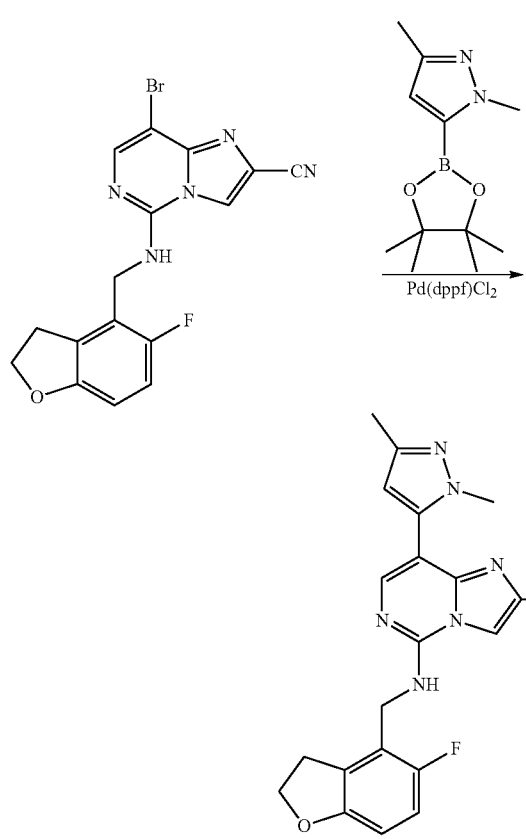

A mixture of 8-bromo-5-(((5-fluoro-2,3-dihydrobenzofuran-4-yl)methyl)amino)imidazo[1,2-c]pyrimidine-2-carbonitrile (90.0 mg, 231 μmol, 1.00 equiv), 1,3-dimethyl-5-(4,4,5,5-tetramethyl-1,3,2-dioxaborolan-2-yl)pyrazole (103 mg, 463 μmol, 2.00 equiv), Pd(dppf)Cl$_2$ (16.9 mg, 23.1 μmol, 0.100 equiv), sodium bicarbonate (58.4 mg, 695 μmol, 27.0 μL, 3 equiv) in dioxane (6.00 mL) and water (3.00 mL) was purged with nitrogen. The resultant mixture was stirred at 100° C. for 2 h under an atmosphere of nitrogen. Water (8.00 mL) was added and the mixture was extracted with ethyl acetate (8.00 mL×3). The combined organic layer was concentrated in vacuo to give a residue. The crude material was purified by Prep-HPLC (column: Phenomenex Synergi C18 150*25*10 μm; mobile phase: [water (0.1% TFA)-ACN]; B %: 33%-63%, 13 min) to 8-(1,3-dimethyl-1H-pyrazol-5-yl)-5-(((5-fluoro-2,3-dihydrobenzofuran-4-yl)methyl)amino)imidazo[1,2-c]pyrimidine-2-carbonitrile (51.0 mg, 120 μmol, 52.0% yield, 95.4% purity) as a white solid. LC-MS: [M+1] 404.

$^1$H NMR (400 MHz, DMSO-d$_6$) δ=8.92 (s, 1H), 8.64 (br t, J=4.8 Hz, 1H), 7.86 (s, 1H), 6.99-6.91 (m, 1H), 6.71 (dd, J=4.0, 8.8 Hz, 1H), 6.23 (s, 1H), 4.72 (br d, J=4.4 Hz, 2H), 4.55 (t, J=8.8 Hz, 2H), 3.67 (s, 3H), 3.31 (t, J=8.8 Hz, 2H), 2.18 (s, 3H).

Example 87

5-(((5-fluoro-2,3-dihydrobenzofuran-4-yl)methyl)amino)-8-(2-methyl-4-(methylsulfonyl)phenyl)imidazo[1,2-c]pyrimidine-2-carbonitrile

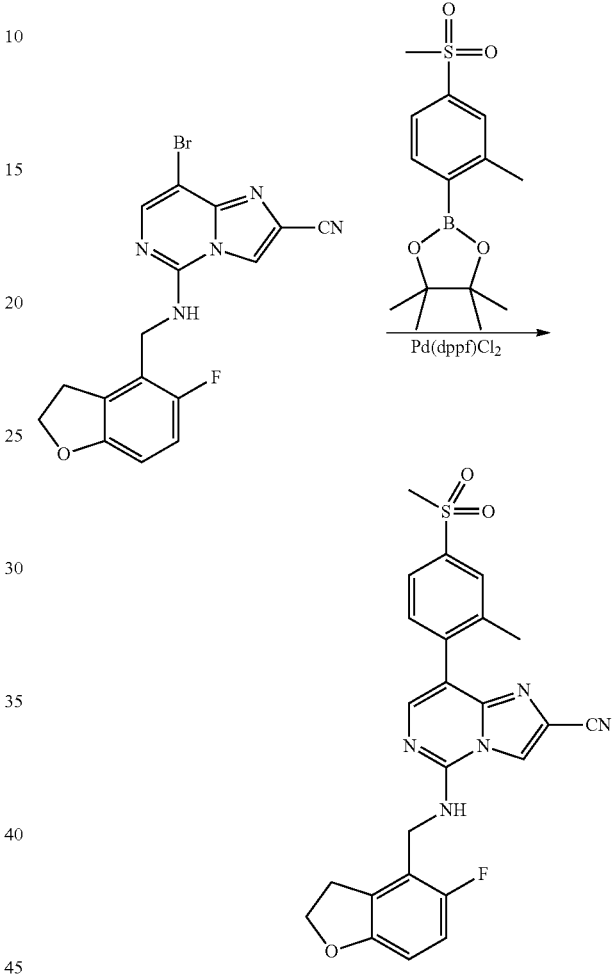

A mixture of 8-bromo-5-(((5-fluoro-2,3-dihydrobenzofuran-4-yl)methyl)amino)imidazo[1,2-c]pyrimidine-2-carbonitrile (90.0 mg, 231 μmol, 1.00 equiv), 1,3-dimethyl-5-(4,4,5,5-tetramethyl-1,3,2-dioxaborolan-2-yl)pyrazole (103 mg, 463 μmol, 2.00 equiv), Pd(dppf)Cl$_2$ (16.9 mg, 23.1 μmol, 0.100 equiv), sodium bicarbonate (58.4 mg, 695 μmol, 27.0 μL, 3 equiv) in dioxane (6.00 mL) and water (3.00 mL) was purged with nitrogen. The resultant mixture was stirred at 100° C. for 2 h under an atmosphere of nitrogen. Water (8.00 mL) was added and the mixture was extracted with ethyl acetate (8.00 mL×3). The combined organic layer was concentrated in vacuo to give a residue. The crude material was purified by Prep-HPLC (column: Phenomenex Synergi C18 150*25*10 μm; mobile phase: [water (0.1% TFA)-ACN]; B %:33%-63%, 13 min) to 8-(1,3-dimethyl-1H-pyrazol-5-yl)-5-(((5-fluoro-2,3-dihydrobenzofuran-4-yl)methyl)amino)imidazo[1,2-c]pyrimidine-2-carbonitrile (51.0 mg, 120 μmol, 52.0% yield, 95.4% purity) as a white solid. LC-MS: [M+1] 404.

$^1$H NMR (400 MHz, DMSO-d$_6$) δ=8.92 (s, 1H), 8.64 (br t, J=4.8 Hz, 1H), 7.86 (s 1H), 6.99-6.91 (m, 1H), 6.71 (dd,

J=4.0, 8.8 Hz, 1H), 6.23 (s, 1H), 4.72 (br d, J=4.4 Hz, 2H), 4.55 (t, J=8.8 Hz, 2H), 3.67 (s, 3H), 3.31 (t, J=8.8 Hz, 2H), 2.18 (s, 3H).

EXAMPLES 88-136 were prepared following the procedure set forth in Example 87 and using the general reactions schemes and intermediates described herein.

TABLE 4

Characterization of EXAMPLES 88-136

| Ex. # | Structure | ¹H NMR |
|---|---|---|
| 88 | 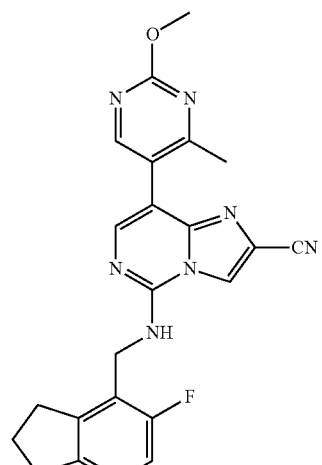 5-(((5-fluoro-2,3-dihydrobenzofuran-4-yl)methyl)amino)-8-(2-methoxy-4-methylpyrimidin-5-yl)imidazo[1,2-c]pyrimidine-2-carbonitrile | ¹H NMR (400 MHz, CDCl$_3$) δ = 8.45 (s, 1H), 8.00 (s, 1H), 7.74 (s, 1H), 6.86 (t, J = 9.2 Hz, 1H), 6.69 (dd, J = 4.0, 8.8 Hz, 1H), 5.76 (br s, 1H), 4.84 (s, 2H), 4.65 (t, J = 8.8 Hz, 2H), 4.09 (s, 4H), 3.43 (t, J = 8.8 Hz, 2H), 2.46 (s, 3H). LCMS: [M + 1] 432.2. |
| 89 | 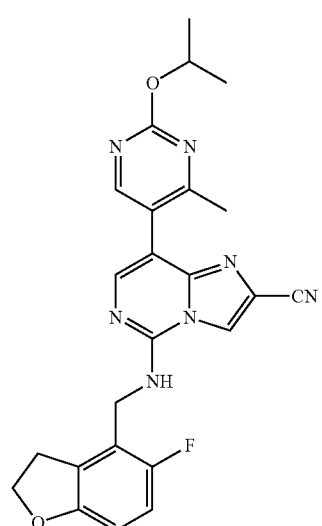 5-(((5-fluoro-2,3-dihydrobenzofuran-4-yl)methyl)amino)-8-(2-isopropoxy-4-methylpyrimidin-5-yl)imidazo[1,2-c]pyrimidine-2-carbonitrile | ¹H NMR (400 MHz, DMSO-d$_6$) δ = 8.93 (s, 1H), 8.57 (br t, J = 5.2 Hz, 1H), 8.43 (s, 1H), 7.82 (s, 1H), 6.96 (t, J = 9.2 Hz, 1H), 6.72 (dd, J = 4.0, 8.8 Hz, 1H), 5.29-5.23 (m, 1H), 4.73 (d, J = 4.8 Hz, 2H), 4.56 (t, J = 8.8 Hz, 2H), 3.38-3.35 (m, 2H), 2.30 (s, 3H), 1.35 (d, J = 6.4 Hz, 6H). LCMS: [M + 1] 460.4. |

TABLE 4-continued

Characterization of EXAMPLES 88-136

| Ex. # | Structure | $^1$H NMR |
|---|---|---|
| 90 | 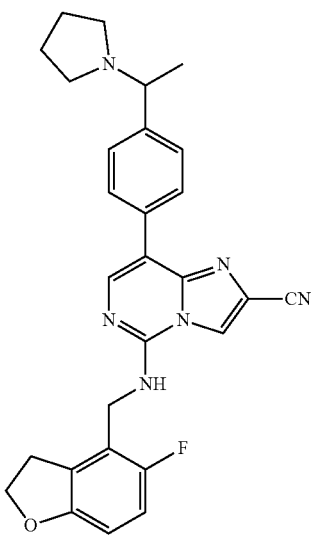<br>5-(((5-fluoro-2,3-dihydrobenzofuran-4-yl)methyl)amino)-8-(4-(1-(pyrrolidin-1-yl)ethyl)phenyl)imidazo[1,2-c]pyrimidine-2-carbonitrile | $^1$H NMR (400 MHz, METHANOL-d$_4$) δ = 8.65 (s, 1H), 8.07 (s, 1H), 8.03 (d, J = 8.4 Hz, 2H), 7.60 (d, J = 8.4 Hz, 2H), 6.91-6.84 (m, 1H), 6.67 (dd, J = 4.0, 8.8 Hz, 1H), 4.84 (s, 3H), 4.60 (t, J = 8.4 Hz, 2H), 4.45 (q, J = 6.8 Hz, 1H), 3.83 (m, 1H), 3.39 (t, J = 8.8 Hz, 2H), 3.20-3.02 (m, 2H), 2.28-1.91 (m, 5H), 1.80 (d, J = 6.8 Hz, 3H).<br>LCMS: [M + 1] 483.4. |
| 91 | 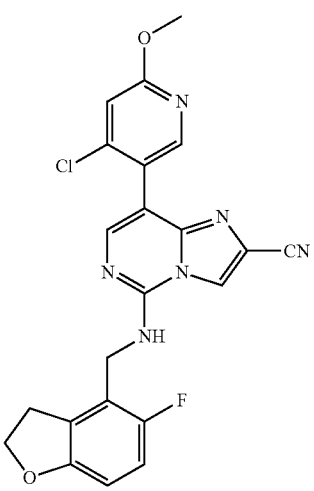<br>8-(4-chloro-6-methoxypyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, CDCl$_3$) δ = 8.17 (s, 1H), 7.83 (s, 1H), 7.74 (s, 1H), 6.87 (s, 1H), 6.79 (t, J = 9.6 Hz, 1H), 6.62 (dd, J = 4.0, 8.8 Hz, 1H), 5.43 (br s, 1H), 4.76 (s, 2H), 4.57 (t, J = 8.8 Hz, 2H), 3.91 (s, 3H), 3.36 (t, J = 8.8 Hz, 2H).<br>LCMS [M + 1]: 451. |

TABLE 4-continued

Characterization of EXAMPLES 88-136

| Ex. # | Structure | $^1$H NMR |
|---|---|---|
| 92 | 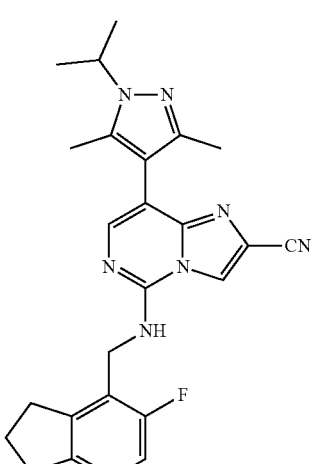<br>5-(((5-fluoro-2,3-dihydrobenzofuran-4-yl)methyl)amino)-8-(1-isopropyl-3,5-dimethyl-1H-pyrazol-4-yl)imidazo[1,2-c]pyrimidine-2-carbonitrile | $^1$H NMR (400 MHz, DMSO-d$_6$) δ = 8.88 (s, 1H), 8.34 (br t, J = 4.8 Hz, 1H), 7.63 (s, 1H), 6.95 (t, J = 9.6 Hz, 1H), 6.71 (dd, J = 3.6, 8.8 Hz, 1H), 4.70 (br d, J = 4.4 Hz, 2H), 4.61-4.36 (m, 3H), 3.32 (br t, J = 8.8 Hz, 2H), 2.13 (s, 3H), 2.05 (s, 3H), 1.39 (d, J = 6.8 Hz, 6H). LC-MS [M + 1]: 446. |
| 93 | 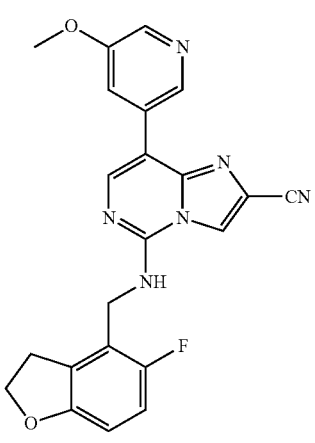<br>5-(((5-fluoro-2,3-dihydrobenzofuran-4-yl)methyl)amino)-8-(5-methoxypyridin-3-yl)imidazo[1,2-c]pyrimidine-2-carbonitrile | $^1$H NMR (400 MHz, DMSO-d$_6$) δ 8.96 (s, 1H), 8.81 (d, J = 1.6 Hz, 1H), 8.66 (br s, 1H), 8.29 (d, J = 2.8 Hz, 1H), 8.27 (s, 1H), 7.98-7.96 (m, 1H), 7.01-6.92 (m, 1H), 6.71 (dd, J = 4.0, 8.4 Hz, 1H), 4.75 (br s, 2H), 4.55 (t, J = 8.4 Hz, 2H), 3.90 (s, 3H), 3.30-3.28 (m, 2H). LCMS: [M + 1] 417.3. |

TABLE 4-continued

Characterization of EXAMPLES 88-136

| Ex. # | Structure | ¹H NMR |
|---|---|---|
| 94 | 5-(((5-fluoro-2,3-dihydrobenzofuran-4-yl)methyl)amino)-8-(6-methoxypyridin-3-yl)imidazo[1,2-c]pyrimidine-2-carbonitrile | ¹H NMR (400 MHz, DMSO-$d_6$) δ = 8.93 (s, 1H), 8.74 (d, J = 2.4 Hz, 1H), 8.53 (br s, 1H), 8.29 (dd, J = 2.4, 8.8 Hz, 1H), 8.11 (s, 1H), 7.01-6.89 (m, 2H), 6.71 (dd, J = 4.0, 8.8 Hz, 1H), 4.73 (br s, 2H), 4.55 (t, J = 8.8 Hz, 2H), 3.90 (s, 3H), 3.31-3.28 (m, 2H). LCMS: [M + 1] 417.3. |
| 95 | 8-(5-cyanopyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.52 (d, J = 2.4 Hz, 1H), 9.00-8.97 (m, 2H), 8.90 (t, J = 2.0 Hz, 1H), 8.81 (t, J = 4.8 Hz, 1H), 8.39 (s, 1H), 6.96 (t, J = 8.8 Hz, 1H), 6.72 (dd, J = 4.0, 8.8 Hz, 1H), 4.76 (d, J = 4.8 Hz, 2H), 4.56 (t, J = 8.8 Hz, 2H), 3.31 (br s, 2H). LCMS: [M + 1] 412.3. |
| 96 | 5-(((5-fluoro-2,3-dihydrobenzofuran-4-yl)methyl)amino)-8-(5-methylpyridin-3-yl)imidazo[1,2-c]pyrimidine-2-carbonitrile | ¹H NMR (400 MHz, DMSO-$d_6$) δ = 9.42 (s, 1H), 9.26-9.16 (m, 2H), 8.99 (s, 1H), 8.72 (s, 1H), 8.48 (s, 1H), 6.94 (t, J = 9.2 Hz, 1H), 6.70 (dd, J = 3.6, 8.4 Hz, 1H), 4.76 (br d, J = 4.4 Hz, 2H), 4.54 (t, J = 8.8 Hz, 2H), 3.34 (br t, J = 8.8 Hz, 2H), 2.54 (s, 3H). LCMS: [M + 1] 401.1. |

TABLE 4-continued

Characterization of EXAMPLES 88-136

| Ex. # | Structure | ¹H NMR |
|---|---|---|
| 97 | 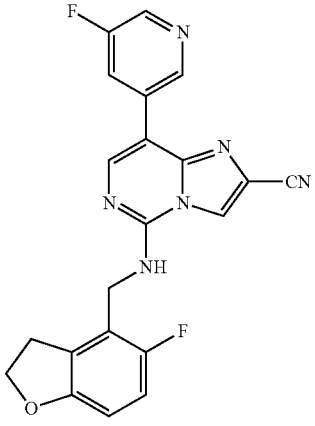<br>5-(((5-fluoro-2,3-dihydrobenzofuran-4-yl)methyl)amino)-8-(5-fluoropyridin-3-yl)imidazo[1,2-c]pyrimidine-2-carbonitrile | ¹H NMR (400 MHz, DMSO-$d_6$) δ = 9.13 (s, 1H), 9.04 (s, 1H), 8.86 (br t, J = 4.8 Hz, 1H), 8.56 (d, J = 2.4 Hz, 1H), 8.43-8.30 (m, 2H), 6.94 (t, J = 9.2 Hz, 1H), 6.70 (dd, J = 4.0, 8.4 Hz, 1H), 4.75 (br d, J = 4.8 Hz, 2H), 4.54 (t, J = 8.8 Hz, 2H), 3.32 (br t, J = 8.8 Hz, 2H). LCMS: [M + 1] 405.1. |
| 98 | 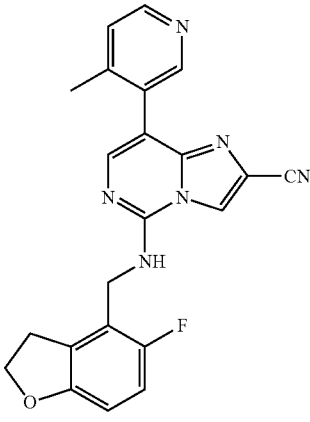<br>5-(((5-fluoro-2,3-dihydrobenzofuran-4-yl)methyl)amino)-8-(4-methylpyridin-3-yl)imidazo[1,2-c]pyrimidine-2-carbonitrile | ¹H NMR (400 MHz, DMSO-$d_6$) δ = 9.11 (s, 1H), 9.02 (br s, 1H), 8.86 (s, 1H), 8.81 (d, J = 5.6 Hz, 1H), 8.02 (d, J = 6.0 Hz, 1H), 7.96 (s, 1H), 6.95 (t, J = 8.8 Hz, 1H), 6.71 (dd, J = 3.6, 8.4 Hz, 1H), 4.74 (br d, J = 4.8 Hz, 2H), 4.55 (t, J = 8.8 Hz, 2H), 3.35 (br t, J = 8.4 Hz, 2H), 2.48 (br s, 3H). LCMS: [M + 1] 401.1. |

TABLE 4-continued

Characterization of EXAMPLES 88-136

| Ex. # | Structure | ¹H NMR |
|---|---|---|
| 99 | 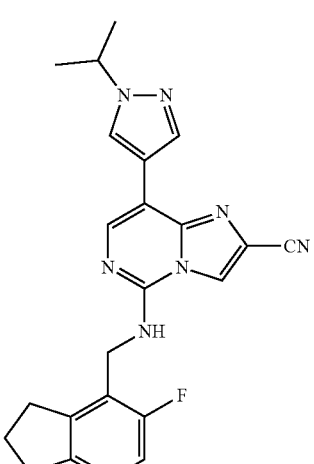<br>5-(((5-fluoro-2,3-dihydrobenzofuran-4-yl)methyl)amino)-8-(1-isopropyl-1H-pyrazol-4-yl)imidazo[1,2-c]pyrimidine-2-carbonitrile | ¹H NMR (400 MHz, DMSO-d6) δ = 8.91 (s, 1H), 8.41 (s, 1H), 8.39-8.35 (m, 1H), 8.17 (s, 1H), 8.11 (s, 1H), 6.94 (t, J = 9.2 Hz, 1H), 6.70 (dd, J = 3.6, 8.4 Hz, 1H), 4.70 (br d, J = 3.6 Hz, 2H), 4.64-4.57 (m, 1H), 4.54 (t, J = 8.8 Hz, 2H), 3.30 (br t, J = 8.8 Hz, 2H), 1.46 (d, J = 6.4 Hz, 6H).<br>LCMS: [M + 1] 418.3. |
| 100 | 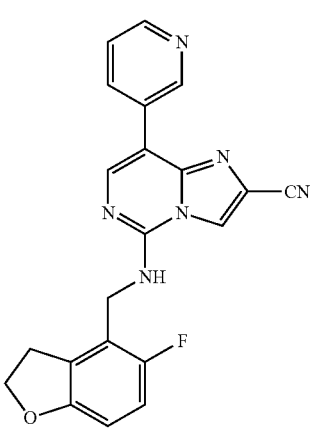<br>5-(((5-fluoro-2,3-dihydrobenzofuran-4-y)methyl)amino)-8-(pyridin-3-yl)imidazo[1,2-c]pyrimidine-2-carbonitrile | ¹H NMR (400 MHz, DMSO-d6) δ = 9.40 (d, J = 1.6 Hz, 1H), 9.11 (s, 1H), 9.02 (br t, J = 4.8 Hz, 1H), 8.87 (br d, J = 8.0 Hz, 1H), 8.72 (d, J = 5.2 Hz, 1H), 8.39 (s, 1H), 7.87 (dd, J = 5.6, 8.0 Hz, 1H), 6.94 (t, J = 9.2 Hz, 1H), 6.70 (dd, J = 3.6, 8.4 Hz, 1H), 4.76 (br d, J = 4.8 Hz, 2H), 4.54 (t, J = 8.4 Hz, 2H), 3.33 (br t, J = 8.8 Hz, 2H).<br>LCMS: [M + 1] 387.3. |

TABLE 4-continued

Characterization of EXAMPLES 88-136

| Ex. # | Structure | ¹H NMR |
|---|---|---|
| 101 | 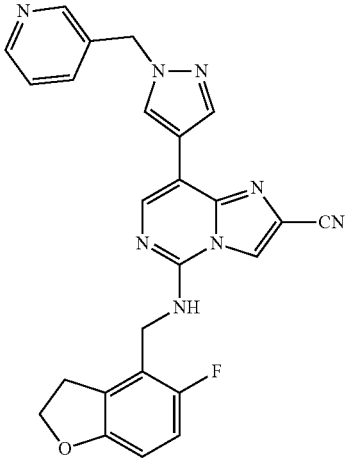<br>5-(((5-fluoro-2,3-dihydrobenzofuran-4-yl)methyl)amino)-8-(1-(pyridin-3-ylmethyl)-1H-pyrazol-4-yl)imidazo[1,2-c]pyrimidine-2-carbonitrile | ¹H NMR (400 MHz, DMSO-d6) δ = 8.92 (s, 1H), 8.69-8.60 (m, 3H), 8.39 (br t, J = 5.2 Hz, 1H), 8.21 (s, 1H), 8.18 (s, 1H), 7.91 (br d, J = 8.0 Hz, 1H), 7.63-7.54 (m, 1H), 6.99-6.88 (m, 1H), 6.70 (dd, J = 4.0, 8.8 Hz, 1H), 5.55 (s, 2H), 4.71 (br d, J = 4.4 Hz, 2H), 4.54 (t, J = 8.8 Hz, 2H), 3.29 (t, J = 8.8 Hz, 2H). LCMS: [M + 1] 467.3. |
| 102 | 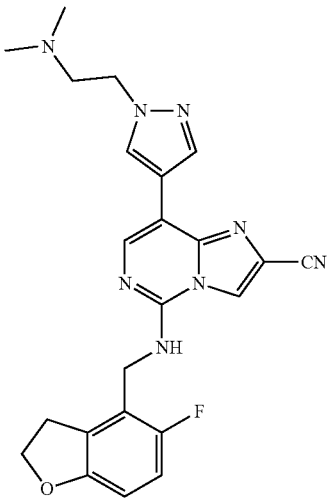<br>8-(1-(2-(dimethylamino)ethyl)-1H-pyrazol-4-yl)-5-(((5-fluoro-2,3-dihydrobenzofuran-4-yl)methyl)amino)imidazo[1,2-c]pyrimidine-2-carbonitrile | ¹H NMR (400 MHz, DMSO-d6) δ = 8.92 (s, 1H), 8.43 (s, 1H), 8.38 (t, J = 4.8 Hz, 1H), 8.18 (s, 1H), 8.10 (s, 1H), 6.94 (t, J = 9.2 Hz, 1H), 6.70 (dd, J = 3.6, 8.4 Hz, 1H), 4.70 (d, J = 4.8 Hz, 2H), 4.54 (t, J = 8.8 Hz, 2H), 4.29 (t, J = 6.4 Hz, 2H), 3.32-3.27 (m, 2H), 2.72 (br t, J = 6.0 Hz, 2H), 2.21 (s, 6H). LCMS: [M + 1] 447.3. |

TABLE 4-continued

Characterization of EXAMPLES 88-136

| Ex. # | Structure | ¹H NMR |
|---|---|---|
| 103 | 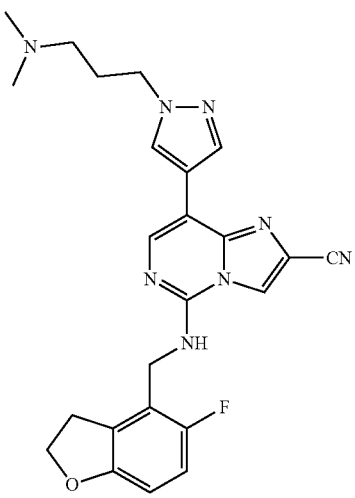<br>8-(1-(3-(dimethylamino)propyl)-1H-pyrazol-4-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.92 (s, 1H), 8.48 (s, 1H), 8.40 (t, J = 5.2 Hz, 1H), 8.21 (s, 1H), 8.17 (s, 1H), 6.99-6.91 (m, 1H), 6.71 (dd, J = 3.6, 8.8 Hz, 1H), 4.71 (d, J = 4.8 Hz, 2H), 4.55 (t, J = 8.8 Hz, 2H), 4.29 (t, J = 6.8 Hz, 2H), 3.30-3.27 (m, 2H), 3.08 (br s, 2H), 2.79 (s, 6H), 2.23-2.15 (m, 2H) LCMS: [M + 1] 461. |
| 104 | 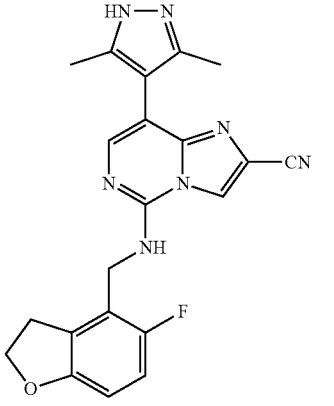<br>8-(3,5-dimethyl-1H-pyrazol-4-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 12.34 (br s, 1H), 8.95 (s, 1H), 8.45 (br s, 1H), 7.64 (s, 1H), 6.95 (t, J = 9.6 Hz, 1H), 6.71 (dd, J = 4.0, 8.8 Hz, 1H), 4.70 (br s, 2H), 4.55 (t, J = 8.8 Hz, 2H), 3.31 (br s, 2H), 2.31-1.94 (m, 6H). LCMS: [M + 1] 404. |

TABLE 4-continued

Characterization of EXAMPLES 88-136

| Ex. # | Structure | ¹H NMR |
|---|---|---|
| 105 | 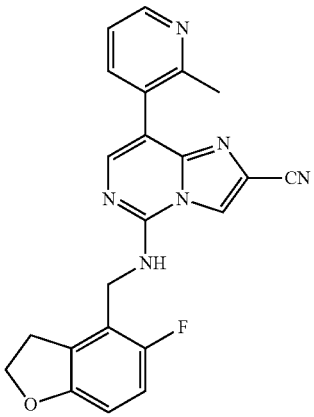<br>5-(((5-fluoro-2,3-dihydrobenzofuran-4-yl)methyl)amino)-8-(2-methylpyridin-3-yl)imidazo[1,2-c]pyrimidine-2-carbonitrile | ¹H NMR (400 MHz, DMSO-$d_6$) δ = 8.93 (s, 1H), 8.56-8.51 (m, 1H), 8.50 (dd, J = 1.6, 4.8 Hz, 1H), 7.79 (s, 1H), 7.70 (dd, J = 1.6, 7.6 Hz, 1H), 7.31 (dd, J = 4.8, 7.6 Hz, 1H), 6.96 (t, J = 9.6 Hz, 1H), 6.72 (dd, J = 4.0, 8.4 Hz, 1H) 4.73 (br d, J = 4.8 Hz, 2H), 4.56 (t, J = 8.8 Hz, 2H), 3.33-3.32 (m, 2H), 2.37 (s, 3H).<br>LC-MS: [M + 1] 400.9. |
| 106 | 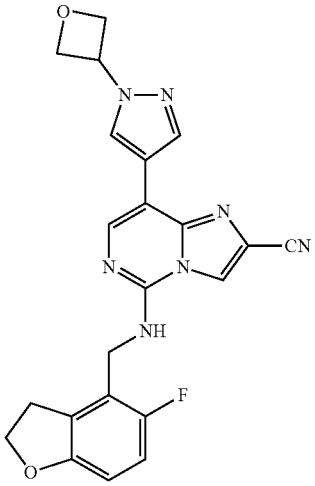<br>5-(((5-fluoro-2,3-dihydrobenzofuran-4-yl)methyl)amino)-8-(1-(oxetan-3-yl)-1H-pyrazol-4-yl)imidazo[1,2-c]pyrimidine-2-carbonitrile | ¹H NMR (400 MHz, DMSO-$d_6$) δ = 8.88 (s, 1H), 8.53 (s, 1H), 8.43 (br s, 1H), 8.26 (s, 1H), 8.20 (s, 1H), 6.94 (t, J = 9.6 Hz, 1H), 6.69 (dd, J = 3.7, 8.8 Hz, 1H), 5.72 (quin, J = 7.2 Hz, 1H), 4.94 (d, J = 7.2 Hz, 4H), 4.70 (s, 2H), 4.54 (t, J = 8.8 Hz, 2H), 3.31-3.26 (m, 2H).<br>LCMS: [M + 1] 432. |

TABLE 4-continued

Characterization of EXAMPLES 88-136

| Ex. # | Structure | ¹H NMR |
|---|---|---|
| 107 | 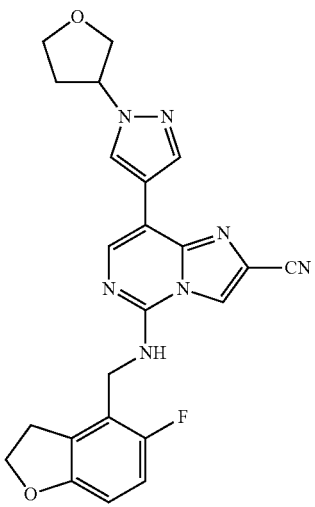<br>5-(((5-fluoro-2,3-dihydrobenzofuran-4-yl)methyl)amino)-8-(1-(tetrahydrofuran-3-yl)-1H-pyrazol-4-yl)imidazo[1,2-c]pyrimidine-2-carbonitrile | ¹H NMR (400 MHz, DMSO-$d_6$) δ = 8.91 (s, 1H), 8.46 (s, 1H), 8.38 (br t, J = 5.2 Hz, 1H), 8.20 (s, 1H), 8.15 (s, 1H), 6.95 (t, J = 9.2 Hz, 1H), 6.70 (dd, J = 4.0, 8.8 Hz, 1H), 5.18-5.10 (m, 1H), 4.70 (br d, J = 4.4 Hz, 2H), 4.54 (t, J = 8.8 Hz, 2H), 4.04-3.96 (m, 2H), 3.94-3.81 (m, 2H), 3.32-3.26 (m, 2H), 2.45-2.35 (m, 2H).<br>LCMS: [M + 1] 446.3. |
| 108 | 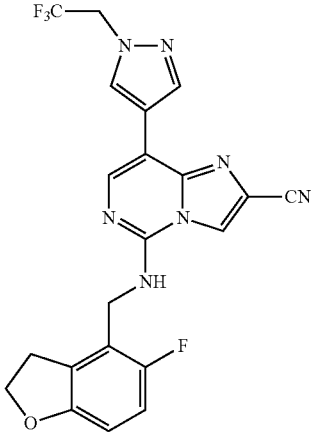<br>5-(((5-fluoro-2,3-dihydrobenzofuran-4-yl)methyl)amino)-8-(1-(2,2,2-trifluoroethyl)-1H-pyrazol-4-yl)imidazo[1,2-c]pyrimidine-2-carbonitrile | ¹H NMR (400 MHz, DMSO-$d_6$) δ = 8.91 (s, 1H), 8.61 (s, 1H), 8.43 (t, J = 5.2 Hz, 1H), 8.25 (s, 2H), 6.94 (t, J = 8.8 Hz, 1H), 6.70 (dd, J = 4.0, 8.8 Hz, 1H), 5.29-5.22 (m, 2H), 4.71 (d, J = 4.8 Hz, 2H), 4.53 (t, J = 8.8 Hz, 2H), 3.31-3.27 (m, 2H).<br>LCMS: [M + 1] 458.2. |

TABLE 4-continued

Characterization of EXAMPLES 88-136

| Ex. # | Structure | ¹H NMR |
|---|---|---|
| 109 | 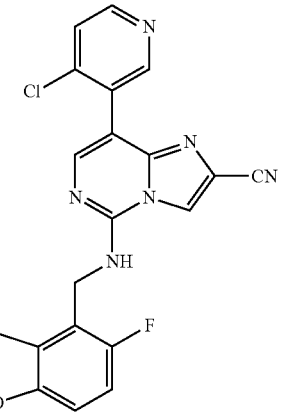<br>8-(4-chloropyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.94 (s, 1H), 8.66 (s, 2H), 8.59 (d, J = 5.6 Hz, 1H), 7.91 (s, 1H), 7.71 (d, J = 5.6 Hz, 1H), 6.96 (t, J = 9.6 Hz, 1H), 6.72 (dd, J = 3.6, 8.8 Hz, 1H), 4.74 (br s, 2H), 4.56 (t, J = 8.8 Hz, 2H), 3.35 (br s, 2H).<br>LCMS [M + 1]: 421/423. |
| 110 | 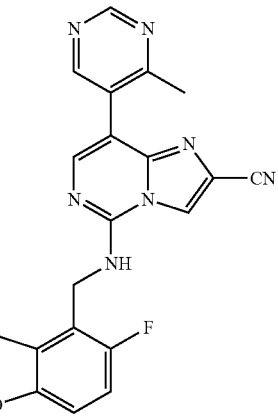<br>5-(((5-fluoro-2,3-dihydrobenzofuran-4-yl)methyl)amino)-8-(4-methylpyrimidin-5-yl)imidazo[1,2-c]pyrimidine-2-carbonitrile | ¹H NMR (400 MHz, CD$_3$OD) δ = 9.25 (s, 1H), 8.93 (s, 1H), 8.66 (s, 1H), 7.93 (s, 1H), 6.89-6.82 (m, 1H), 6.65 (dd, J = 4.0, 8.8 Hz, 1H), 4.85 (br s, 2H), 4.59 (t, J = 8.4 Hz, 2H), 3.41 (t, J = 8.8 Hz, 2H), 2.60 (s, 3H).<br>LCMS: [M + 1]: 402.1. |
| 111 | 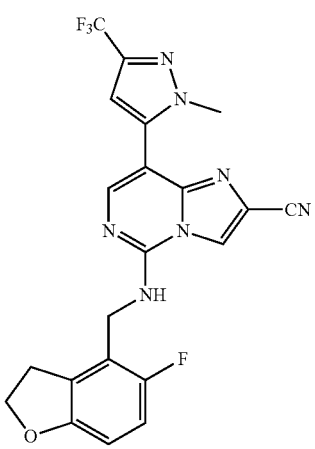<br>5-(((5-fluoro-2,3-dihydrobenzofuran-4-yl)methyl)amino)-8-(1-methyl-3-(trifluoromethyl)-1H-pyrazol-5-yl)imidazo[1,2-c]pyrimidine-2-carbonitrile | ¹H NMR (400 MHz, DMSO-$d_6$) δ = 8.96 (s, 1H), 8.79 (br t, J = 5.2 Hz, 1H), 8.00 (s, 1H), 7.00-6.93 (m, 2H), 6.72 (dd, J = 3.6, 8.8 Hz, 1H), 4.75 (d, J = 4.8 Hz, 2H), 4.56 (t, J = 8.8 Hz, 2H), 3.87 (s, 3H), 3.30-3.29 (m, 2H).<br>LCMS [M + 1]: 458. |

TABLE 4-continued

Characterization of EXAMPLES 88-136

| Ex. # | Structure | $^1$H NMR |
|---|---|---|
| 112 | 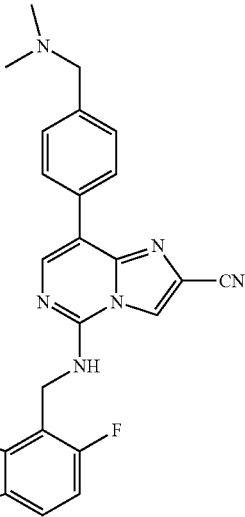<br>8-(4-(((dimethylamino)methyl)phenyl-5-(((5-fluoro-2,3-dihydrobenzofuran-4-yl)methyl)amino)imidazo[1,2-c]pyrimidine-2-carbonitrile | $^1$H NMR (400 MHz, DMSO-$d_6$) δ = 8.96 (s, 1H), 8.55 (t, J = 4.4 Hz, 1H), 8.10 (s, 1H), 7.93 (d, J = 8.0 Hz, 2H), 7.39 (d, J = 8.4 Hz, 2H), 6.95 (t, J = 9.2 Hz, 1H), 6.71 (dd, J = 8.8, 4.0 Hz, 1H), 4.73 (d, J = 4.8 Hz, 2H), 4.55 (t, J = 8.8 Hz, 2H), 3.47 (s, 1H), 3.33-3.28 (m, 4H), 2.20 (s, 6H).<br>LCMS [M + 1]: 443.1. |
| 113 | 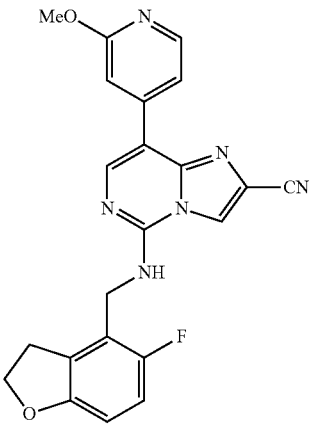<br>5-(((5-fluoro-2,3-dihydrobenzofuran-4-yl)methyl)amino)-8-(2-methoxypyridin-4-yl)imidazo[1,2-c]pyrimidine-2-carbonitrile | $^1$H NMR (400 MHz, CDCl$_3$) δ = 8.25 (d, J = 5.6 Hz, 1H), 8.10 (s, 1H), 7.91 (s, 1H), 7.45 (dd, J = 5.2, 1.2 Hz, 1H), 7.40 (s, 1H), 6.85 (t, J = 9.2 Hz, 1H), 6.68 (dd, J = 8.4, 4.0 Hz, 1H), 5.56 (t, J = 5.6 Hz, 1H), 4.84 (d, J = 5.6 Hz, 2H), 4.64 (t, J = 8.4 Hz, 2H), 3.99 (s, 3H), 3.42 (t, J = 8.8 Hz, 2H).<br>LCMS [M + 1]: 417.0. |

TABLE 4-continued

Characterization of EXAMPLES 88-136

| Ex. # | Structure | ¹H NMR |
|---|---|---|
| 114 | 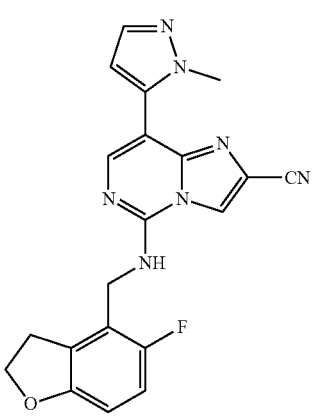<br>5-(((5-fluoro-2,3-dihydrobenzofuran-4-yl)methyl)amino)-8-(1-methyl-1H-pyrazol-5-yl)imidazo[1,2-c]pyrimidine-2-carbonitrile | ¹H NMR (400 MHz, CD₃OD) δ = 8.62 (s, 1H), 7.88 (s, 1H), 7.55 (s, 1H), 6.85 (br t, J = 8.8 Hz, 1H), 6.69-6.60 (m, 1H), 6.47 (s, 1H), 4.58 (br t, J = 8.8 Hz, 2H), 3.81 (s, 3H), 3.40-3.35 (m, 2H).<br>LCMS [M + 1] 390.2. |
| 115 | 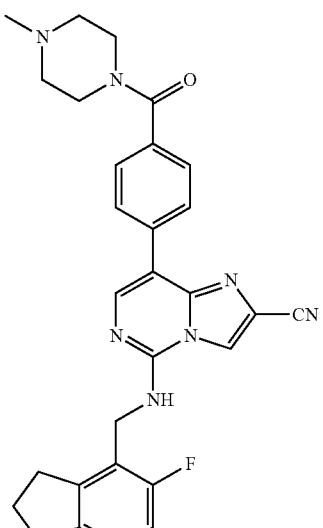<br>5-(((5-fluoro-2,3-dihydrobenzofuran-4-yl)methyl)amino)-8-(4-(4-methylpiperazine-1-carbonyl)phenyl)imidazo[1,2-c]pyrimidine-2-carbonitrile | ¹H NMR (400 MHz, CD₃OD) δ = 8.65 (s, 1H), 8.08 (s, 1H), 8.04 (d, J = 8.4 Hz, 2H), 7.61 (d, J = 8.0 Hz, 2H), 6.91-6.83 (m, 1H), 6.66 (dd, J = 4.0, 8.8 Hz, 1H), 4.84 (s, 2H), 4.59 (t, J = 8.8 Hz, 2H), 3.67-3.34 (m, 8H), 3.28-3.16 (m, 2H), 2.99 (s, 3H).<br>LCMS [M + 1]: 512.4. |

TABLE 4-continued

Characterization of EXAMPLES 88-136

| Ex. # | Structure | $^1$H NMR |
|---|---|---|
| 116 | 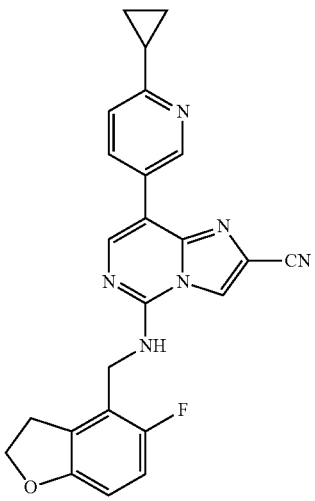<br>8-(6-cyclopropylpyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, CDCl$_3$) δ = 8.82 (d, J = 2.0 Hz, 1H), 8.18 (dd, J = 8.0, 2.4 Hz, 1H), 7.96 (s, 1H), 7.91 (s, 1H), 7.25 (d, J = 8.4 Hz, 1H), 6.82-6.90 (m, 1H), 6.69 (dd, J = 8.8, 4.0 Hz, 1H), 5.47 (t, J = 6.0 Hz 1H), 4.83 (d, J = 5.2 Hz, 2H), 4.65 (t, J = 8.4 Hz, 2H), 3.43 (d, J = 8.8 Hz, 2H), 2.10 (m, 1H), 1.06 (m, 4H).<br>LCMS [M + 1]: 427.1. |
| 117 | 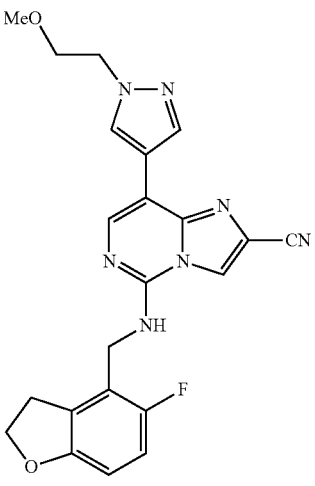<br>5-(((5-fluoro-2,3-dihydrobenzofuran-4-yl)methyl)amino)-8-(1-(2-methoxyethyl)-1H-pyrazol-4-yl)imidazo[1,2-c]pyrimidine-2-carbonitrile | $^1$H NMR (400 MHz, DMSO-d$_6$) δ ppm 8.93 (s, 1H), 8.43-8.38 (m, 2H), 8.17 (s, 1H), 8.11 (s, 1H), 6.97-6.89 (m, 1H), 6.69 (dd, J = 8.4, 4.0 Hz, 1H), 4.70 (d, J = 5.2 Hz, 2H), 4.53 (t, J = 8.8 Hz, 2H), 4.33 (t, J = 5.26 Hz, 2H), 3.71 (t, J = 5.2 Hz, 2H), 3.29 (t, J = 8.8 Hz, 2H), 3.23 (s, 3H).<br>LCMS [M + 1]: 434.0. |

TABLE 4-continued

Characterization of EXAMPLES 88-136

| Ex. # | Structure | ¹H NMR |
|---|---|---|
| 118 | 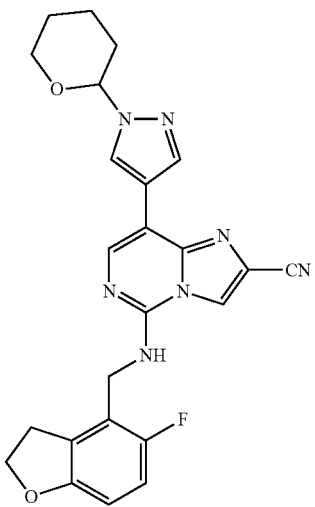<br>5-(((5-fluoro-2,3-dihydrobenzofuran-4-yl)methyl)amino)-8-(1-(tetrahydro-2H-pyran-2-yl)-1H-pyrazol-4-yl)imidazo[1,2-c]pyrimidine-2-carbonitrile | ¹H NMR (400 MHz, CDCl₃) δ ppm = 8.50 (s, 1H), 7.98 (s, 1H), 7.92 (br s, 1H), 7.77 (s, 1H), 6.82-6.74 (m, 1H), 6.61 (dd, J = 8.8, 4.0 Hz, 1H), 5.41 (dd, J = 9.6, 2.4 Hz, 1H), 4.71 (s, 2H), 4.57 (t, J = 8.8 Hz, 2H), 4.12-3.98 (m, 1H), 3.78-3.61 (m, 1H), 3.35 (t, J = 8.8 Hz, 2H), 2.25-1.88 (m, 3H), 1.77-1.47 (m, 3H).<br>LCMS [M + 1]: 460.4. |
| 119 | 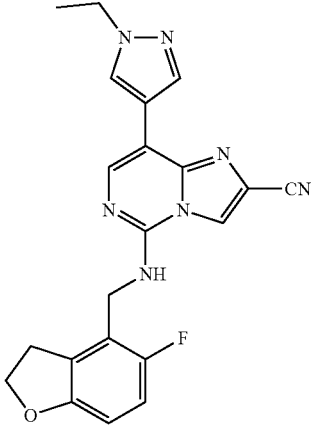<br>8-(1-ethyl-1H-pyrazol-4-yl)-5-(((5-fluoro-2,3-dihydrobenzofuran-4-yl)methyl)amino)imidazo[1,2-c]pyrimidine-2-carbonitrile | ¹H NMR (400 MHz, DMSO-d6) δ = 8.91 (s, 1H), 8.42 (s, 1H), 8.36 (t, J = 5.2 Hz, 1H), 8.17 (s, 1H), 8.10 (s, 1H), 6.98-6.92 (m, 1H), 6.70 (dd, J = 4.0, 8.8 Hz, 1H), 4.70 (d, J = 4.8 Hz, 2H), 4.54 (t, J = 8.8 Hz, 2H), 4.24-4.19 (m, 2H), 3.30 (t, J = 8.8 Hz, 2H), 1.41 (t, J = 7.6 Hz, 3H).<br>LCMS [M + 1]: 404.2. |

TABLE 4-continued

Characterization of EXAMPLES 88-136

| Ex. # | Structure | ¹H NMR |
|---|---|---|
| 120 | 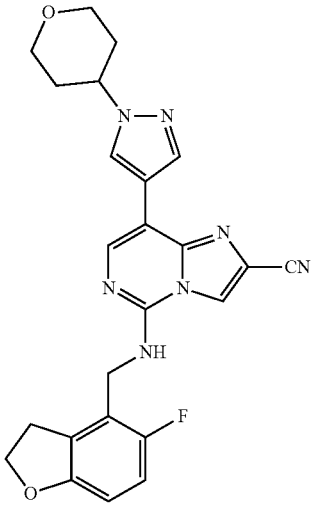<br>5-(((5-fluoro-2,3-dihydrobenzofuran-4-yl)methyl)amino)-8-(1-(tetrahydro-2H-pyran-4-yl)-1H-pyrazol-4-yl)imidazo[1,2-c]pyrimidine-2-carbonitrile | $^1$H NMR (400 MHz, DMSO-$d_6$) δ = 8.91 (s, 1H), 8.46 (s, 1H), 8.37 (t, J = 4.8 Hz, 1H), 8.18 (s, 1H), 8.14 (s, 1H), 6.92-6.98 (m, 1H), 6.70 (dd, J = 8.4, 3.6 Hz, 1H), 4.73-5.66 (m, 1H), 4.71 (d, J = 5.2 Hz, 2H), 4.48-4.57 (m, 3H), 4.02-3.94 (m, 2H), 3.46-3.69 (m, 2H), 3.30 (t, J = 8.8 Hz, 2H), 1.96-2.04 (m, 4H).<br>LCMS: [M + 1]: 460.3. |
| 121 | 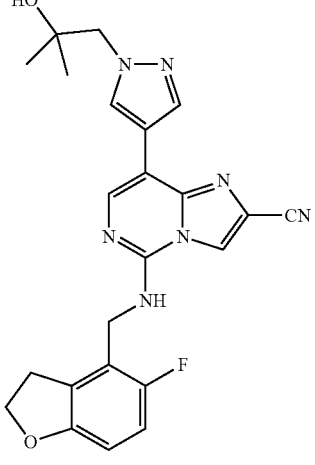<br>5-(((5-fluoro-2,3-dihydrobenzofuran-4-yl)methyl)amino)-8-(1-(2-hydroxy-2-methylpropyl)-1H-pyrazol-4-yl)imidazo[1,2-c]pyrimidine-2-carbonitrile | $^1$H NMR (400 MHz, DMSO-$d_6$) δ = 8.90 (s, 1H), 8.43 (s, 1H), 8.35 (br s, 1H), 8.19 (s, 1H), 8.09 (s, 1H), 6.98-6.90 (m, 1H), 6.69 (dd, J = 4.0, 8.8 Hz, 1H), 4.73 (s, 1H), 4.70 (br s, 2H), 4.53 (t, J = 8.8 Hz, 2H), 4.08 (s, 2H), 3.31-3.26 (m, 2H), 1.08 (s, 6H).<br>LCMS [M + 1]: 448.2. |

TABLE 4-continued

Characterization of EXAMPLES 88-136

| Ex. # | Structure | $^1$H NMR |
|---|---|---|
| 122 | 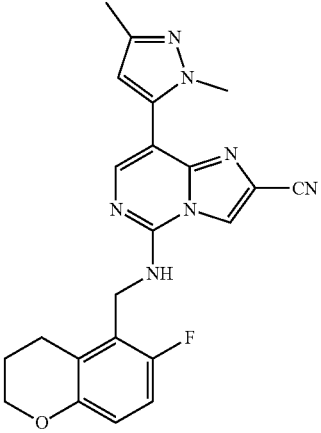<br>8-(1,3-dimethyl-1H-pyrazol-5-yl)-5-(((6-fluorochroman-5-yl)methyl)amino)imidazo[1,2-c]pyrimidine-2-carbonitrile | $^1$H NMR (400 MHz, DMSO-d$_6$) δ = 8.96 (s, 1H), 8.66 (t, J = 5.2 Hz, 1H), 7.82 (s, 1H), 7.09-6.99 (m, 1H), 6.91 (d, J = 7.2 Hz, 1H), 6.70 (d, J = 7.6 Hz, 1H), 6.23 (s, 1H), 4.69 (d, J = 5.2, Hz, 2H), 4.16-4.05 (m, 2H), 3.68 (s, 3H), 2.77 (t, J = 6.4 Hz, 2H), 2.18 (s, 3H), 2.03-1.89 (m, 2H).<br>LC-MS: [M + 1] 400.3. |
| 123 | 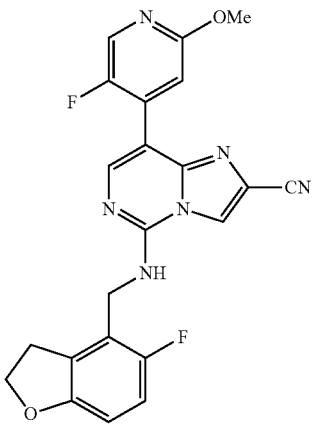<br>5-(((5-fluoro-2,3-dihydrobenzofuran-4-yl)methyl)amino)-8-(5-fluoro-2-methoxypyridin-4-yl)imidazo[1,2-c]pyrimidine-2-carbonitrile | $^1$H NMR (400 MHz, DMSO-d$_6$) δ = 8.94 (s, 1H), 8.80 (br s, 1H), 8.24 (d, J = 2.4 Hz, 1H), 8.11 (d, J = 0.8 Hz, 1H), 7.38 (d, J = 5.2 Hz, 1H), 6.95 (t, J = 9.2 Hz, 1H), 6.71 (dd, J = 4.0, 8.8 Hz, 1H), 4.74 (s, 2H), 4.54 (t, J = 8.8 Hz, 2H), 3.88 (s, 3H), 3.29-3.20 (m, 2H).<br>LCMS [M + 1]: 435.4. |
| 124 | 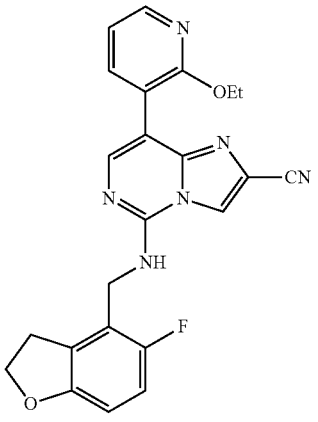<br>8-(2-ethoxypyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.91 (s, 1H), 8.52 (t, J = 4.8 Hz, 1H), 8.17 (dd, J = 2.0, 5.2 Hz, 1H), 8.04 (dd, J = 2.0, 7.6 Hz, 1H), 8.02 (s, 1H), 7.09 (dd, J = 4.8, 7.2 Hz, 1H), 6.96 (t, J = 8.8 Hz, 1H), 6.71 (dd, J = 4.0, 8.8 Hz, 1H), 4.72 (d, J = 4.4 Hz, 2H), 4.55 (t, J = 8.8 Hz, 2H), 4.37-4.32 (m, 2H), 3.32 (t, J = 8.8 Hz, 2H), 1.24 (t, J = 7.2 Hz, 3H).<br>LCMS [M + 1]: 431.4. |

TABLE 4-continued

Characterization of EXAMPLES 88-136

| Ex. # | Structure | $^1$H NMR |
|---|---|---|
| 125 | 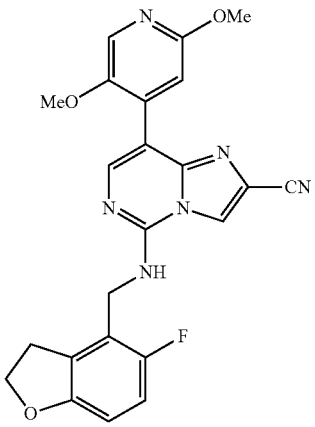<br>8-(2,5-dimethoxypyridin-4-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.91 (s, 1H), 8.63 (t, J = 4.8 Hz, 1H), 8.03 (s, 1H), 7.99 (s, 1H), 7.15 (s, 1H), 6.98-6.92 (m, 1H), 6.71 (dd, J = 4.0, 8.8 Hz, 1H), 4.72 (d, J = 4.4 Hz, 2H), 4.55 (t, J = 8.8 Hz, 2H), 3.84 (s, 3H), 3.79 (s, 3H), 3.32-3.27 (m, 2H). LCMS [M + 1]: 447.3. |
| 126 | 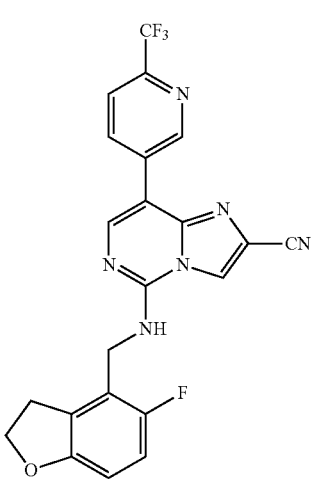<br>5-(((5-fluoro-2,3-dihydrobenzofuran-4-yl)methyl)amino)-8-(6-(trifluoromethyl)pyridin-3-yl)imidazo[1,2-c]pyrimidine-2-carbonitrile | $^1$H NMR (400 MHz, DMSO-d$_6$) δ = 9.35 (d, J = 1.6 Hz, 1H), 8.96 (s, 1H), 8.80 (br s, 1H), 8.75 (dd, J = 2.0, 8.8 Hz, 1H), 8.39 (s, 1H), 8.00 (d, J = 8.0 Hz, 1H), 6.95 (t, J = 8.8 Hz, 1H), 6.70 (dd, J = 4.0, 8.8 Hz, 1H), 4.76 (s, 2H), 4.55 (t, J = 8.8 Hz, 2H), 3.37-3.32 (m, 2H). LCMS [M + 1]: 455.3. |

TABLE 4-continued

Characterization of EXAMPLES 88-136

| Ex. # | Structure | ¹H NMR |
|---|---|---|
| 127 | 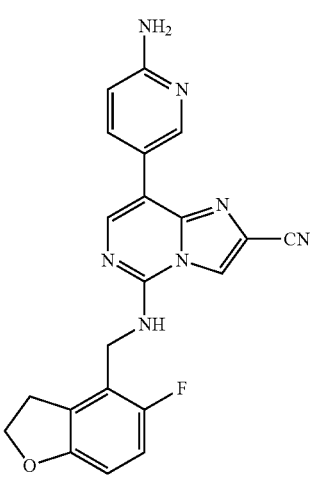<br>8-(6-aminopyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.97 (s, 1H), 8.72 (d, J = 2.0 Hz, 1H), 8.68 (br t, J = 4.0 Hz, 1H), 8.49 (dd, J = 1.6, 9.2 Hz, 1H), 8.21 (s, 1H), 7.98 (br s, 2H), 7.04 (d, J = 9.2 Hz, 1H), 6.99-6.89 (m, 1H), 6.71 (dd, J = 8.8, 4.0 Hz, 1H), 4.74 (d, J = 4.8 Hz, 2H), 4.55 (t, J = 8.4 Hz, 2H), 3.31 (t, J = 8.8 Hz, 2H). LCMS [M + 1]: 402.3. |
| 128 | 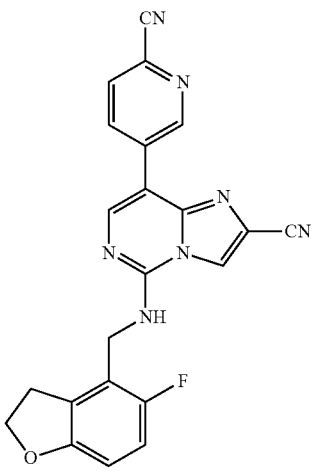<br>8-(6-cyanopyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.42 (d, J = 1.6 Hz, 1H), 8.98 (s, 1H), 8.86 (br s, 1H), 8.76 (dd, J = 8.4, 2.4 Hz, 1H), 8.46 (s, 1H), 8.14 (d, J = 8.4 Hz, 1H), 6.89-7.06 (m, 1H), 6.72 (dd, J = 8.4, 3.6 Hz, 1H), 4.77 (br d, J = 4.0 Hz, 2H), 4.55 (t, J = 8.8 Hz, 2H), 3.32-3.30 (m, 2H). LCMS [M + 1]: 412.3. |

TABLE 4-continued

Characterization of EXAMPLES 88-136

| Ex. # | Structure | ¹H NMR |
|---|---|---|
| 129 | 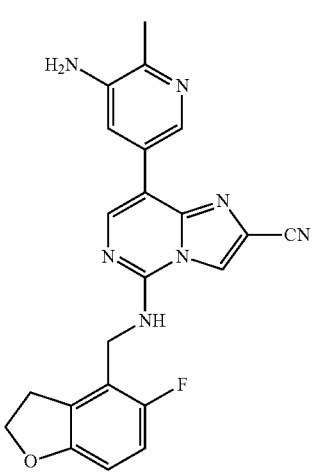<br>8-(5-amino-6-methylpyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.99 (s, 1H), 8.83 (t, J = 4.4 Hz, 1H), 8.44 (s, 1H), 8.27 (s, 1H), 8.22 (s, 1H), 6.96 (t, J = 8.8 Hz, 1H), 6.72 (dd, J = 8.8, 4.0 Hz, 1H), 6.35 (br s, 2H), 4.76 (br d, J = 4.8 Hz, 2H), 4.56 (t, J = 8.8 Hz, 2H), 3.32 (br t, J = 8.8 Hz, 2H), 2.48 (br s, 3H).<br>LCMS [M + 1]: 416.3. |
| 130 | 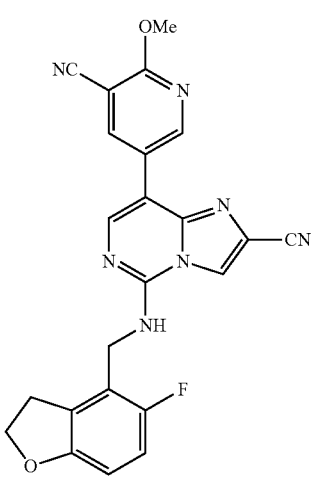<br>8-(5-cyano-6-methoxypyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.11 (d, J = 2.4 Hz, 1H), 8.98 (s, 1H), 8.82 (d, J = 2.8 Hz, 1H), 8.72 (br s, 1H), 8.24 (s, 1H), 6.95 (t, J = 9.2 Hz, 1H), 6.71 (dd, J = 8.0, 3.6 Hz, 1H), 4.74 (s, 2H), 4.55 (t, J = 8.8 Hz, 2H), 4.06 (s, 3H), 3.30-3.29 (m, 2H).<br>LCMS [M + 1]: 442.3. |

TABLE 4-continued

Characterization of EXAMPLES 88-136

| Ex. # | Structure | ¹H NMR |
|---|---|---|
| 131 | 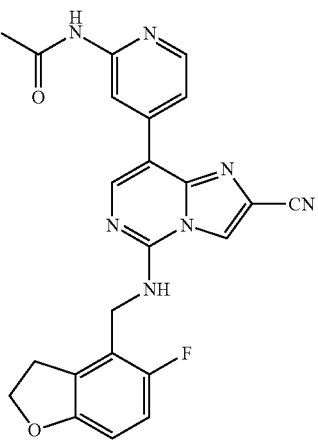<br>N-(4-(2-cyano-5-(((5-fluoro-2,3-dihydrobenzofuran-4-yl)methyl)amino)imidazo[1,2-c]pyrimidin-8-yl)pyridin-2-yl)acetamide | ¹H NMR (400 MHz, DMSO) δ = 10.95 (s, 1H), 8.98 (s, 1H), 8.88 (br s, 1H), 8.70 (s, 1H), 8.37-8.33 (m, 2H), 7.83 (br d, J = 5.6 Hz, 1H), 6.99-6.93 (m, 1H), 6.72 (dd, J = 4.0, 8.4 Hz, 1H), 4.77 (br d, J = 4.8 Hz, 2H), 4.55 (t, J = 8.4 Hz, 2H), 3.32 (t, J = 8.8 Hz, 2H), 2.17 (s, 3H).<br>LCMS [M + 1]: 444.2. |
| 132 | 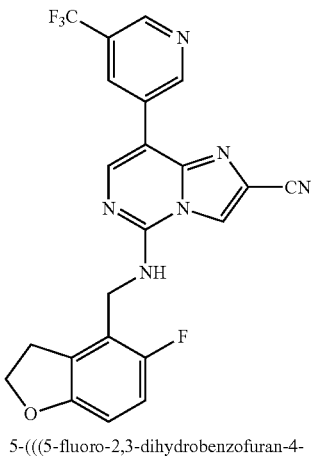<br>5-(((5-fluoro-2,3-dihydrobenzofuran-4-yl)methyl)amino)-8-(5-(trifluoromethyl)pyridin-3-yl)imidazo[1,2-c]pyrimidine-2-carbonitrile | ¹H NMR (400 MHz, DMSO-d6) δ = 9.51 (s, 1H), 8.98 (s, 1H), 8.95 (s, 1H), 8.85 (s, 1H), 8.79 (br t, J = 4.8 Hz, 1H), 8.43 (s, 1H), 6.96 (t, J = 9.2 Hz, 1H), 6.72 (dd, J = 3.6, 8.8 Hz, 1H), 4.76 (br d, J = 4.8 Hz, 2H), 4.56 (t, J = 8.8 Hz, 2H), 3.33 (br t, J = 8.8 Hz, 2H).<br>LCMS [M + 1]: 455.3. |

TABLE 4-continued

Characterization of EXAMPLES 88-136

| Ex. # | Structure | ¹H NMR |
| --- | --- | --- |
| 133 | 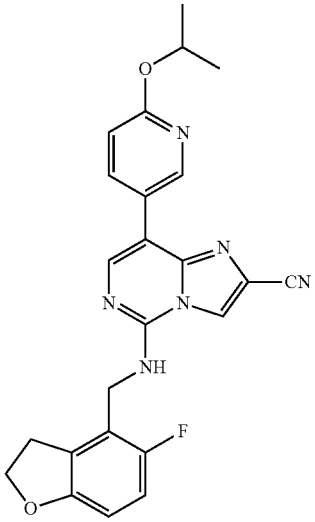<br>5-(((5-fluoro-2,3-dihydrobenzofuran-4-yl)methyl)amino)-8-(6-isopropoxypyridin-3-yl)imidazo[1,2-c]pyrimidine-2-carbonitrile | ¹H NMR (400 MHz, DMSO-d$_6$) δ = 8.94 (s, 1H), 8.72 (d, J = 2.4 Hz, 1H), 8.53 (t, J = 4.8 Hz, 1H), 8.27 (dd, J = 8.8, 2.4 Hz, 1H), 8.10 (s, 1H), 6.92-6.99 (m, 1H), 6.86 (d, J = 8.8 Hz, 1H), 6.71 (dd, J = 8.8, 4.0 Hz, 1H), 5.30 (m, 1H), 4.73 (d, J = 4.8 Hz, 2H), 4.55 (t, J = 8.8 Hz, 2H), 3.31 (t, J = 8.4 Hz, 2H), 1.33 (d, J = 6.0 Hz, 6H).<br>LCMS [M + 1]: 445.3. |
| 134 | 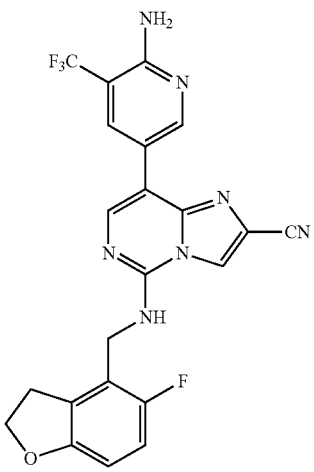<br>8-(6-amino-5-(trifluoromethyl)pyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-d$_6$) δ = 8.93 (s, 1H), 8.78 (d, J = 1.6 Hz, 1H), 8.52 (t, J = 4.8 Hz, 1H), 8.41 (d, J = 2.0 Hz, 1H), 8.14 (s, 1H), 6.91-6.98 (m, 1H), 6.71 (m, 3H), 4.72 (d, J = 4.8 Hz, 2H), 4.55 (t, J = 8.8 Hz, 2H), 3.32 (t, J = 8.8 Hz, 2H).<br>LCMS: [M + 1]: 470.3. |

TABLE 4-continued

Characterization of EXAMPLES 88-136

| Ex. # | Structure | ¹H NMR |
|---|---|---|
| 135 | 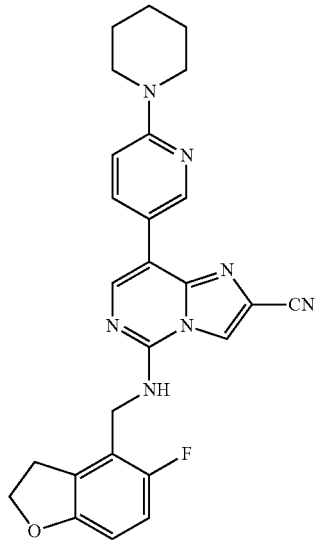<br>5-(((5-fluoro-2,3-dihydrobenzofuran-4-yl)methyl)amino)-8-(6-(piperidin-1-yl)pyridin-3-yl)imidazo[1,2-c]pyrimidine-2-carbonitrile | ¹H NMR (400 MHz, DMSO-$d_6$) δ = 8.95 (s, 1H), 8.80 (d, J = 1.6 Hz, 1H), 8.62 (br s, 1H), 8.40 (br d, J = 9.6 Hz, 1H), 8.22 (s, 1H), 7.30 (br d, J = 9.2 Hz, 1H), 6.95 (t, J = 9.2 Hz, 1H), 6.71 (dd, J = 4.0, 8.8 Hz, 1H), 4.73 (br d, J = 4.8 Hz, 2H), 4.55 (t, J = 8.8 Hz, 1H), 3.66 (br s, 4H), 3.31 (br t, J = 8.8 Hz, 2H), 1.65 (br s, 6H).<br>LCMS [M + 1]: 470.4. |
| 136 | 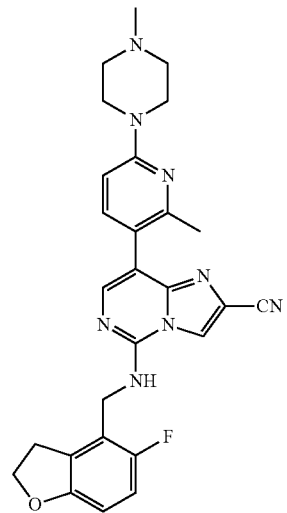<br>5-(((5-fluoro-2,3-dihydrobenzofuran-4-yl)methyl)amino)-8-(2-methyl-6-(4-methylpiperazin-1-yl)pyridin-3-yl)imidazo[1,2-c]pyrimidine-2-carbonitrile | ¹H NMR (400 MHz, CD$_3$OD) δ = 8.62 (s, 1H), δ = 7.74 (s, 1H), 7.71 (d, J = 8.8 Hz, 1H), 6.97 (d, J = 8.8 Hz, 1H), 6.86 (t, J = 8.8 Hz, 1H), 6.65 (dd, J = 4.0, 8.8 Hz, 1H), 4.81 (s, 2H), 4.58 (t, J = 8.8 Hz, 2H), 3.57-3.34 (m, 7H), 2.99 (s, 3H), 2.35 (s, 3H).<br>LCMS: [M + 1]: 499.4. |

Example 137

5-(((5-fluoro-2,3-dihydrobenzofuran-4-yl)methyl)amino)-8-(2-methylpyridin-3-yl)imidazo[1,2-c]pyrimidine-2-carboxamide

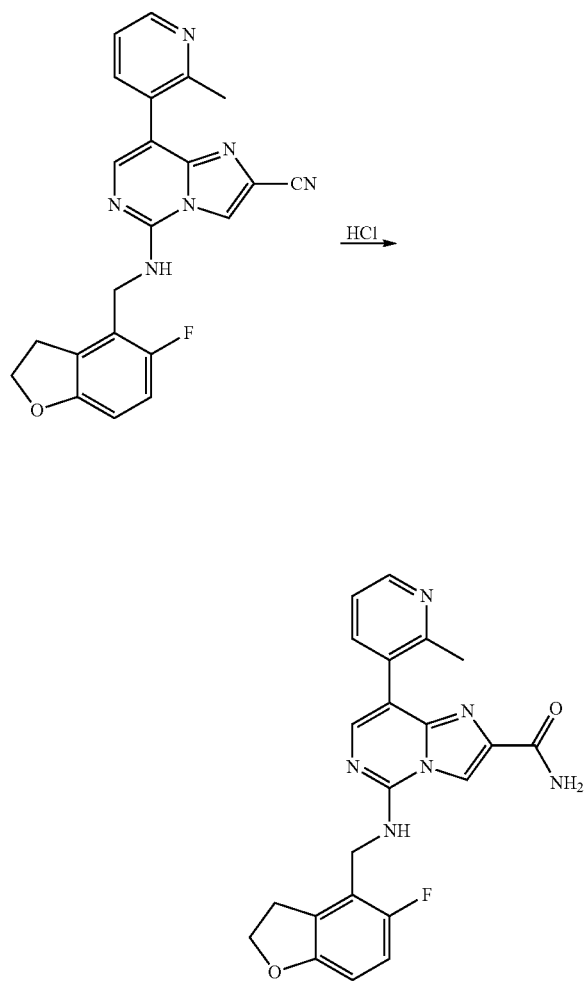

A mixture of 5-((((5-fluoro-2,3-dihydrobenzofuran-4-yl)methyl)amino)-8-(2-methylpyridin-3-yl)imidazo[1,2-c]pyrimidine-2-carbonitrile (38.0 mg, 92.5 µmol, 1.00 equiv) in conc. hydrochloric acid (1.00 mL) was stirred at 26° C. for 4 h. The reaction mixture was adjusted to pH 7 with satd aq sodium bicarbonate aqueous solution at which time a precipitate formed. The precipitate was filtered and dried at reduced pressure. The crude product was washed with methanol (2.00 mL) and filtered to afford 5-(((5-fluoro-2,3-dihydrobenzofuran-4-yl)methyl)amino)-8-(2-methylpyridin-3-yl)imidazo[1,2-c]pyrimidine-2-carboxamide (24.0 mg, 60.4% yield, 97.4% purity) as an off-white solid. LC-MS: [M+1] 419.1.

$^1$H NMR (400 MHz, DMSO-$d_6$) δ=8.65 (s, 1H), 8.48 (m, 1H), 8.42 (br t, J=4.8 Hz, 1H), 7.72 (m, 1H), 7.65 (s, 1H), 7.50 (br s, 1H), 7.40 (br s, 1H), 7.30 (dd, J=4.8, 7.6 Hz, 1H), 6.94 (t, J=9.6 Hz, 1H), 6.70 (dd, J=4.0, 8.8 Hz, 1H), 4.72 (br d, J=4.4 Hz, 2H), 4.55 (t, J=8.8 Hz, 2H), 3.33-3.29 (m, 2H), 2.40 (s, 3H).

Example 138

5-(((5-fluoro-2,3-dihydrobenzofuran-4-yl)methyl)amino)-8-(2-methyl-6-(4-methylpiperazin-1-yl)pyridin-3-yl)imidazol[1,2-c]pyrimidine-2-carboxamide

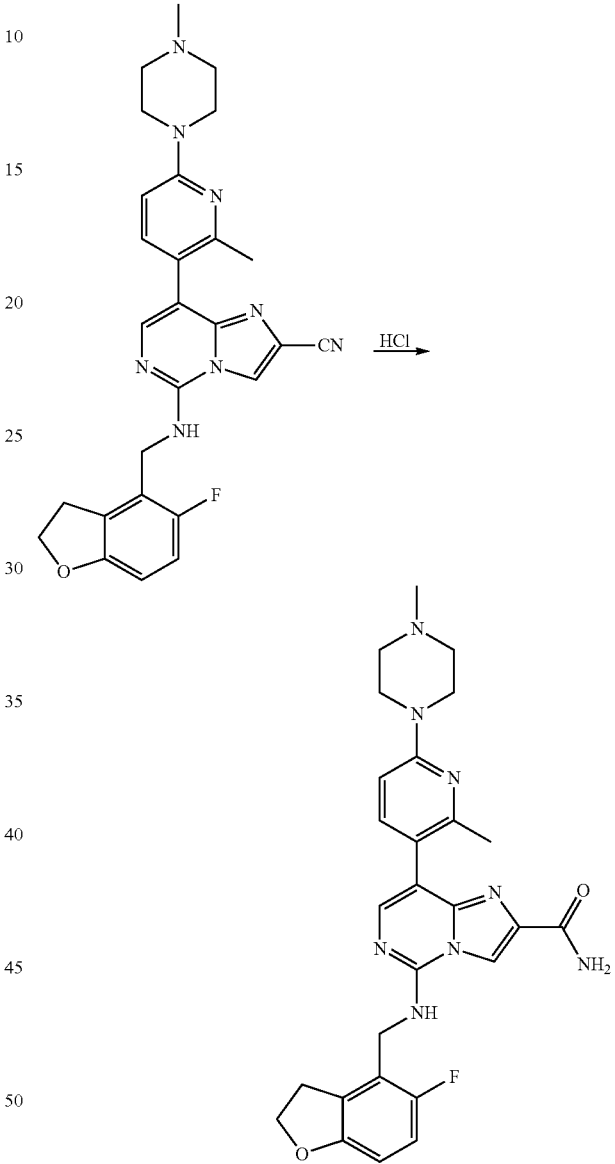

5-(((5-fluoro-2,3-dihydrobenzofuran-4-yl)methyl)amino)-8-(2-methyl-6-(4-methylpiperazin-1-yl)pyridin-3-yl)imidazo[1,2-c]pyrimidine-2-carbonitrile (25.0 mg, 49.8 µmol, 1.00 equiv) in HCl (0.500 mL) was stirred at 25° C. for 0.5 h. The pH was adjusted to 8 with saturated aqueous NaHCO$_3$ and filtered. The precipitate was triturated with MeOH (2.00 mL) to afford 5-(((5-fluoro-2,3-dihydrobenzofuran-4-yl)methyl)amino)-8-(2-methyl-6-(4-methylpiperazin-1-yl)pyridin-3-yl)imidazo[1,2-c]pyrimidine-2-carboxamide (6.00 mg, 11.2 µmol, 22.4% yield, 96.0% purity) as a brown solid. LCMS [M+1]: 517.5.

$^1$H NMR (400 MHz, DMSO-$d_6$) δ=8.62 (s, 1H), 8.30 (br s, 1H), 7.56 (s, 1H), 7.51-7.45 (m, 2H), 7.39 (br s, 1H), 6.94

(br t, J=9.2 Hz, 1H), 6.75-6.67 (m, 2H), 4.71 (br d, J=4.4 Hz, 2H), 4.55 (br t, J=8.4 Hz, 2H), 3.53 (br s, 4H), 3.32-3.25 (m, 6H), 2.25 (s, 6H).

Example 139

5-(((5-fluoro-2,3-dihydrobenzofuran-4-yl)methyl)amino)-8-(4-methyl-1H-imidazol-1-yl)imidazo[1,2-c]pyrimidine-2-carbonitrile

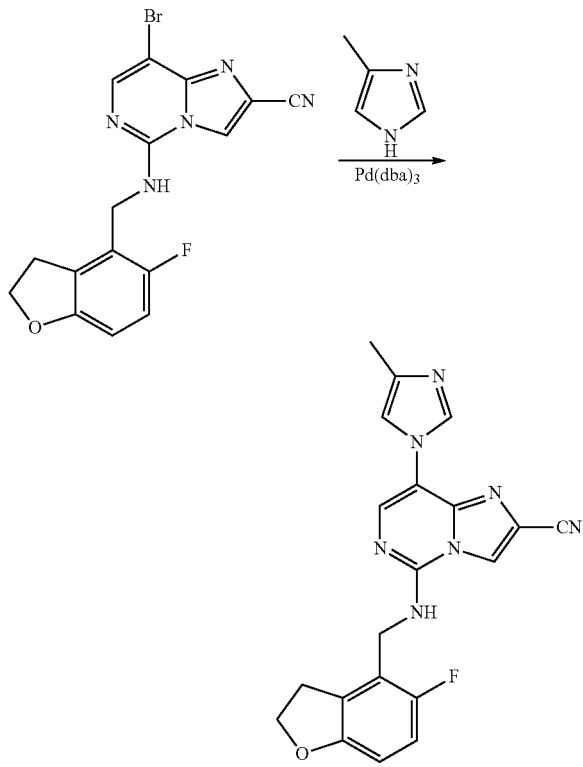

A mixture of tert-butyl (8-bromo-2-cyanoimidazo[1,2-c]pyrimidin-5-yl)((5-fluoro-2,3-dihydrobenzofuran-4-yl)methyl)carbamate (70.0 mg, 139 umol, 1.00 equiv), 4-methyl-1H-imidazole (50.2 mg, 612 umol, 4.40 equiv), Pd₂(dba)₃ (12.7 mg, 13.9 μmol, 0.100 equiv), ditert-butyl-[2,3,4,5-tetramethyl-6-(2,4,6-triisopropylphenyl)phenyl]phosphane (13.4 mg, 27.8 μmol, 0.20 eq.) and potassium phosphate (76.7 mg, 362 μmol, 2.60 equiv) in dioxane (0.50 mL) was purged with nitrogen. The mixture was stirred at 120° C. for 12 h under an atmosphere of nitrogen. The mixture was filtered and concentrated in vacuo to provide the crude residue. The residue was triturated with methanol (2.00 mL) and filtered to afford 5-(((5-fluoro-2,3-dihydrobenzofuran-4-yl)methyl)amino)-8-(4-methyl-1H-imidazol-1-yl)imidazo[1,2-c]pyrimidine-2-carbonitrile (9.89 mg, 24.8 μmol, 17.8% yield, 97.6% purity) as a yellow solid. LC-MS [M+1]: 390.4.

¹H NMR (400 MHz, DMSO-d₆) δ=8.97 (s, 1H), 8.63 (br t, J=4.8 Hz, 1H), 8.13-8.06 (m, 2H), 7.42 (s, 1H), 6.95 (t, J=9.2 Hz, 1H), 6.71 (dd, J=4.0, 8.8 Hz, 1H), 4.71 (br d, J=4.8 Hz, 2H), 4.55 (t, J=8.8 Hz, 2H), 3.31-3.23 (m, 2H), 2.18 (s, 3H).

Example 140

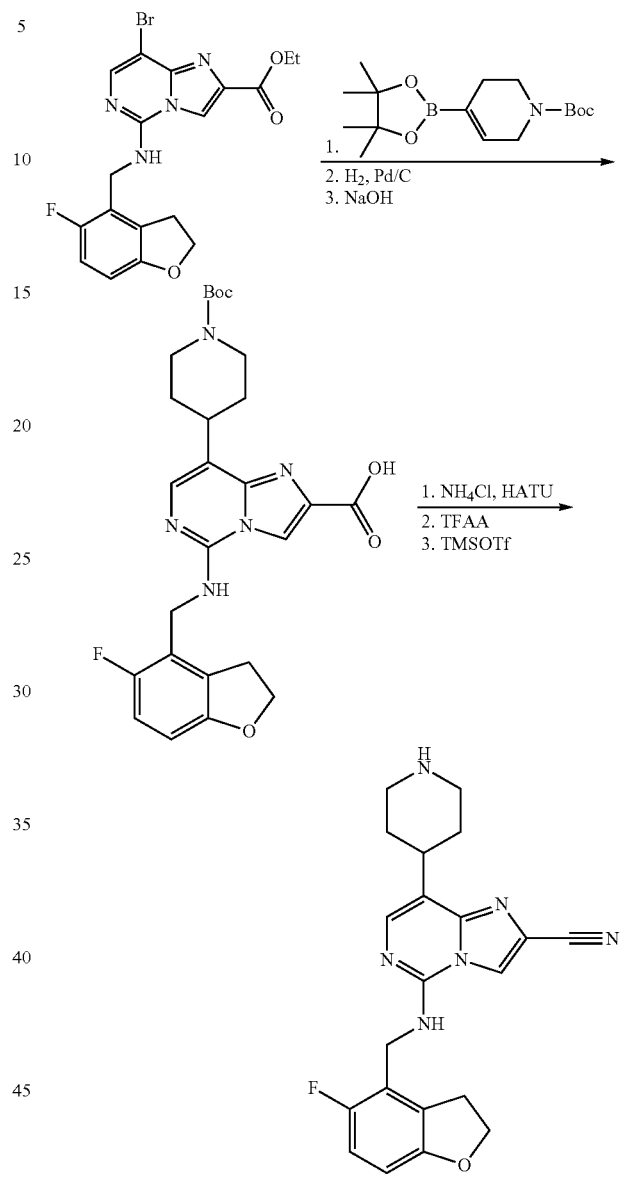

A mixture of ethyl 8-bromo-5-(((5-fluoro-2,3-dihydrobenzofuran-4-yl)methyl)amino)imidazo[1,2-c]pyrimidine-2-carboxylate (0.20 g, 460 μmol, 1.00 equiv), tert-butyl4-(4,4,5,5-tetramethyl-1,3,2-dioxaborolan-2-yl)-3,6-dihydro-2H-pyridine-1-carboxylate (227 mg, 735 μmol, 1.60 equiv), NaHCO₃ (116 mg, 1.38 mmol, 3.00 equiv), Pd(dppf)Cl₂ (33.6 mg, 46.0 μmol, 0.100 equiv) in dioxane (2.10 mL) and water (0.700 mL) was purged with nitrogen. The mixture was stirred at 105° C. for 1 h under nitrogen atmosphere. The reaction mixture was filtered and concentrated in vacuo. The residue was purified by prep-TLC (SiO₂, DCM/MeOH, 20/1) to provide ethyl 8-(1-(tert-butoxycarbonyl)-1,2,3,6-tetrahydropyridin-4-yl)-5-(((5-fluoro-2,3-dihydrobenzofuran-4-yl)methyl)amino)imidazo[1,2-c]pyrimidine-2-carboxylate (230 mg, 89.8% yield, 96.4% purity) as a yellow oil. LC-MS [M+1]: 538.3.

A mixture of ethyl 8-(1-(tert-butoxycarbonyl)-1,2,3,6-tetrahydropyridin-4-yl)-5-(((5-fluoro-2,3-dihydrobenzofuran-4-yl)methyl)amino)imidazo[1,2-c]pyrimidine-2-carboxylate (220 mg, 395 μmol, 1.00 equiv) and Pd/C 10 w. % (100 mg) in methanol (5.00 mL) was stirred at 25° C. for 12 h under an atmosphere of hydrogen gas (15.0 psi). The reaction mixture was filtered and concentrated in vacuo to provide ethyl 8-(1-(tert-butoxycarbonyl)piperidin-4-yl)-5-(((5-fluoro-2,3-dihydrobenzofuran-4-yl)methyl)amino)imidazo[1,2-c]pyrimidine-2-carboxylate (230 mg) as a yellow oil. LC-MS[M+1]: 540.2.

To a solution of ethyl 8-(1-(tert-butoxycarbonyl)piperidin-4-yl)-5-(((5-fluoro-2,3-dihydrobenzofuran-4-yl)methyl)amino)imidazo[1,2-c]pyrimidine-2-carboxylate (260 mg, 476 μmol, 1.00 equiv) in methanol (5.00 mL) was added aq sodium hydroxide (1.00 M, 1.43 mL, 3.00 equiv). The mixture was stirred at 25° C. for 3 h and subsequently concentrated in vacuo. The mixture was adjusted to pH=6 with acetic acid and the resultant precipitate was filtered. The solid was dried at reduced pressure to provide 8-(1-(tert-butoxycarbonyl)piperidin-4-yl)-5-(((5-fluoro-2,3-dihydrobenzofuran-4-yl)methyl)amino)imidazo[1,2-c]pyrimidine-2-carboxylic acid (230 mg, 450 μmol, 94.5% yield) as a light yellow solid. LC-MS[M+1]: 512.3.

To a solution of 8-(1-(tert-butoxycarbonyl)piperidin-4-yl)-5-(((5-fluoro-2,3-dihydrobenzofuran-4-yl)methyl)amino)imidazo[1,2-c]pyrimidine-2-carboxylic acid (0.220 g, 430 μmol, 1.00 equiv) in DMF (3.00 mL) was added ammonium chloride (184 mg, 3.44 mmol, 8.00 equiv), DIEA (1.00 g, 7.74 mmol, 1.35 mL, 18.0 equiv) and HATU (327 mg, 860 μmol, 2.00 equiv). The mixture was stirred at 25° C. for 1 h and subsequently diluted with water 10.0 mL. The formed precipitate was filtered and dried at reduced pressure to provide tert-butyl 4-(2-carbamoyl-5-(((5-fluoro-2,3-dihydrobenzofuran-4-yl)methyl)amino)imidazo[1,2-c]pyrimidin-8-yl)piperidine-1-carboxylate (210 mg, 95.6% yield) as a white solid. LC-MS: [M+1] 511.2.

To a solution of tert-butyl 4-(2-carbamoyl-5-(((5-fluoro-2,3-dihydrobenzofuran-4-yl)methyl)amino)imidazo[1,2-c]pyrimidin-8-yl)piperidine-1-carboxylate (150 mg, 294 μmol, 1.00 equiv) in THF (3.00 mL) was added triethylamine (595 mg, 5.88 mmol, 818 μL, 20.0 equiv) followed by TFAA (370 mg, 1.76 mmol, 245 μL, 6.00 equiv) at 0° C. The mixture was stirred at 25° C. for 1 h and subsequently diluted with DCM 30 mL. The organic layer was washed with brine (20 mL×2) and the organic phase was dried over sodium sulfate, filtered and concentrated in vacuo. The resultant residue was purified by prep-TLC (SiO$_2$, PE/EA, 1/1) to afford tert-butyl 4-(2-cyano-5-(((5-fluoro-2,3-dihydrobenzofuran-4-yl)methyl)amino)imidazo[1,2-c]pyrimidin-8-yl)piperidine-1-carboxylate (130 mg, 263 μmol, 89.4% yield, 99.5% purity) as a yellow solid. LC-MS: [M+Na$^+$] 515.3.

To a solution of tert-butyl 4-(2-cyano-5-(((5-fluoro-2,3-dihydrobenzofuran-4-yl)methyl)amino)imidazo[1,2-c]pyrimidin-8-yl)piperidine-1-carboxylate (100 mg, 202 μmol, 1.00 equiv) in DCM (3.00 mL) was added 2,6-lutidine (173 mg, 1.62 mmol, 188 μL, 8.00 equiv) followed by TMSOTf (112 mg, 505 μmol, 91.3 uL, 2.50 equiv) at 0° C. The mixture was stirred at 25° C. for 48 h and subsequently diluted with DCM (10 mL) and water (10 mL). The resultant mixture was filtered and the precipitate was dried at reduced pressure. The crude material was triturated with hot methanol (2 mL) and filtered. The solid was dried at reduced pressure to afford 5-(((5-fluoro-2,3-dihydrobenzofuran-4-yl)methyl)amino)-8-(piperidin-4-yl)imidazo[1,2-c]pyrimidine-2-carbonitrile (44.4 mg, 111 μmol, 55.1% yield, 98.5% purity) as an off-white solid. LC-MS: [M+1] 393.3.

$^1$H NMR (400 MHz, DMSO-d$_h$) δ=8.94 (s, 1H), 8.44 (br s, 1H), 7.60 (br s, 1H), 6.93 (br t, J=9.6 Hz, 1H), 6.69 (br d, J=4.8 Hz, 1H), 4.65 (br s, 2H), 4.54 (br t, J=8.0 Hz, 2H), 3.21-3.06 (m, 4H), 2.99 (br s, 3H), 2.01 (br s, 4H).

Example 141

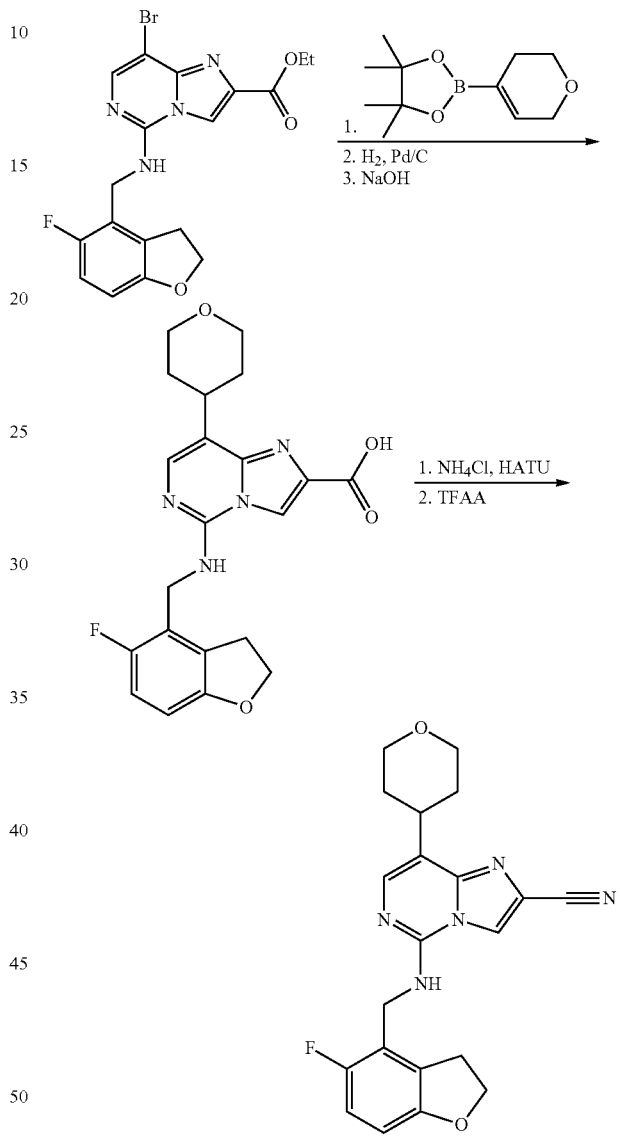

To a solution of ethyl 8-bromo-5-(((5-fluoro-2,3-dihydrobenzofuran-4-yl)methyl)amino)imidazo[1,2-c]pyrimidine-2-carboxylate (100 mg, 230 μmol, 1.00 equiv), 2-(3,6-dihydro-2H-pyran-4-yl)-4,4,5,5-tetramethyl-1,3,2-dioxaborolane (48.3 mg, 230 μmol, 1.00 equiv) and cesium carbonate (150 mg, 460 μmol, 2.00 equiv) in dioxane (1.00 mL) and water (0.300 mL) was added Pd(dppf)Cl$_2$ (16.8 mg, 23.0 μmol, 0.100 equiv). The vessel was purged with nitrogen, stirred at 105° C. for 1 h and subsequently concentrated in vacuo to provide a residue. The residue was purified by Prep-TLC (SiO$_2$, petroleum ether/ethyl acetate, 1/1) to afford ethyl 8-(3,6-dihydro-2H-pyran-4-yl)-5-(((5-fluoro-2,3-dihydrobenzofuran-4-yl)methyl)amino)imidazo[1,2-c]pyrimidine-2-carboxylate (81.0 mg, 77.7% yield, 96.6% purity) as a white solid. LCMS [M+1]: 439.2.

To a solution of ethyl 8-(3,6-dihydro-2H-pyran-4-yl)-5-(((5-fluoro-2,3-dihydrobenzofuran-4-yl)methyl)amino)imidazo[1,2-c]pyrimidine-2-carboxylate (70.0 mg, 160 µmol, 1.00 equiv) in methanol (5.00 mL) and THF (5.00 mL) was added palladium on carbon 10 w. % (172 mg, 0.1 equiv) at 25° C. The mixture was purged with hydrogen and allowed to stir for 1 h at 25° C. under an atmosphere of hydrogen gas (15.0 psi). The mixture was filtered and concentrated under reduced pressure to provide a residue. The residue was rinsed with 5 mL petroleum ether/ethyl acetate (2/1) to afford ethyl 5-(((5-fluoro-2,3-dihydrobenzofuran-4-yl)methyl)amino)-8-(tetrahydro-2H-pyran-4-yl)imidazo[1,2-c]pyrimidine-2-carboxylate (50.0 mg, 64.6 yield, 90.9% purity) as a white solid.

To a solution of ethyl 5-(((5-fluoro-2,3-dihydrobenzofuran-4-yl)methyl)amino)-8-(tetrahydro-2H-pyran-4-yl)imidazo[1,2-c]pyrimidine-2-carboxylate (50.0 mg, 103 µmol, 1.00 equiv) in THF (6.0 mL) and water (3.0 mL) was added sodium hydroxide (4.13 mg, 103 µmol, 1.00 equiv). The mixture was stirred at 25° C. for 1 h and subsequently concentrated in vacuo to remove the majority of the THF. The aqueous solution was adjusted to pH=6 with aq hydrochloric acid (1.0 M, 0.5 mL) and the resultant precipitate was filtered. The solid was triturated with 3 mL petroleum ether/ethyl acetate (2:1) and dried at reduced pressure to afford 5-(((5-fluoro-2,3-dihydrobenzofuran-4-yl)methyl)amino)-8-(tetrahydro-2H-pyran-4-yl)imidazo[1,2-c]pyrimidine-2-carboxylic acid (41.0 mg, 95.0% yield, 98.6% purity) as a white solid. LCMS [M+1]: 413.2.

$^1$H NMR (400 MHz, CD$_3$OD) δ=8.08 (s, 1H), 7.50 (s, 1H), 6.85 (t, J=9.2 Hz, 1H), 6.64 (dd, J=4.0, 8.8 Hz, 1H), 4.76 (s, 2H), 4.56 (t, J=8.8 Hz, 2H), 4.06 (dd, J=3.2, 11.2 Hz, 2H), 3.73-3.64 (m, 2H), 3.44-3.37 (m, 1H), 3.32-3.28 (m, 2H), 2.00 (dd, J=2.0, 12.8 Hz, 2H), 1.91-1.77 (m, 2H).

A mixture of 5-(((5-fluoro-2,3-dihydrobenzofuran-4-yl)methyl)amino)-8-(tetrahydro-2H-pyran-4-yl)imidazo[1,2-c]pyrimidine-2-carboxylic acid (34.0 mg, 81.3 µmol, 1.00 equiv), HATU (46.4 mg, 122 µmol, 1.50 equiv), DIEA (84.1 mg, 650 umol, 113 µL, 8.00 equiv) and ammonium chloride (13.0 mg, 244 µmol, 3.00 equiv) in DMF (2.00 mL) was purged with nitrogen. The mixture was stirred at 30° C. for 1 h and was subsequently concentrated in vacuo to provide the crude solid. The solid was rinsed with water (1.00 mL), filtered and dried at reduced pressure. The solid was triturated with 2 mL petroleum ether/ethyl acetate (2:1) to afford 5-(((5-fluoro-2,3-dihydrobenzofuran-4-yl)methyl)amino)-8-(tetrahydro-2H-pyran-4-yl)imidazo[1,2-c]pyrimidine-2-carboxamide (20.0 mg, 46.6 µmol, 57.3% yield, 95.8% purity) as a white solid. LCMS [M+1]: 412.17.

$^1$H NMR (400 MHz, DMSO-d$_6$) δ=8.54 (s, 1H), 8.11 (br t, J=4.8 Hz, 1H), 7.57 (br s, 1H), 7.52 (s, 1H), 7.47 (br s, 1H), 6.92 (t, J=9.2 Hz, 1H), 6.68 (dd, J=3.6, 8.8 Hz, 1H), 4.65 (br d, J=4.8 Hz, 2H), 4.53 (t, J=8.8 Hz, 2H), 3.97 (br d, J=10.8 Hz, 2H), 3.53-3.40 (M, 3H), 3.30-3.24 (m, 2H), 3.18-3.10 (m, 1H), 1.93-1.82 (m, 4H).

To a mixture of 5-(((5-fluoro-2,3-dihydrobenzofuran-4-yl)methyl)amino)-8-(tetrahydro-2H-pyran-4-yl)imidazo[1,2-c]pyrimidine-2-carboxamide (28.0 mg, 68.1 µmol, 1 equiv), triethylamine (138 mg, 1.36 mmol, 189 µL, 20.0 equiv) in THF (4.00 mL) was added TFAA (42.9 mg, 204 µmol, 28.4 µL, 3.00 equiv) at 0° C. The resultant mixture was stirred at 0-30° C. for 1 h and was subsequently filtered and concentrated to provide the crude residue. The residue was purified by prep-HPLC (column: Gemini 150×25 5 u; mobile phase: [water (0.04% NH$_3$H$_2$O)-ACN]; B %: 35.0%-65.0%, 10 min) to afford 5-(((5-fluoro-2,3-dihydrobenzofuran-4-yl)methyl)amino)-8-(tetrahydro-2H-pyran-4-yl)imidazo[1,2-c]pyrimidine-2-carbonitrile (26.0 mg, 63.1 µmol, 92.7% yield, 95.5% purity) as a yellow solid.

$^1$H NMR (400 MHz, DMSO-d$_6$) δ=8.84 (s, 1H), 8.24 (br s, 1H), 7.63 (s, 1H), 6.93 (t, J=9.6 Hz, 1H), 6.69 (dd, J=3.6, 8.4 Hz, 1H), 4.65 (br d, J=3.2 Hz, 2H), 4.54 (br t, J=8.8 Hz, 2H), 4.01-3.90 (m, 2H), 3.53-3.42 (m, 1H), 3.29-3.27 (m, 3H), 3.16-3.05 (m, 1H), 1.94-1.74 (m, 4H). LCMS: [M+1] 394.1.

Example 142

5-(((5-fluoro-2,3-dihydrobenzofuran-4-yl)methyl)amino)-8-(pyridazin-3-yl)imidazo[1,2-c]pyrimidine-2-carbonitrile

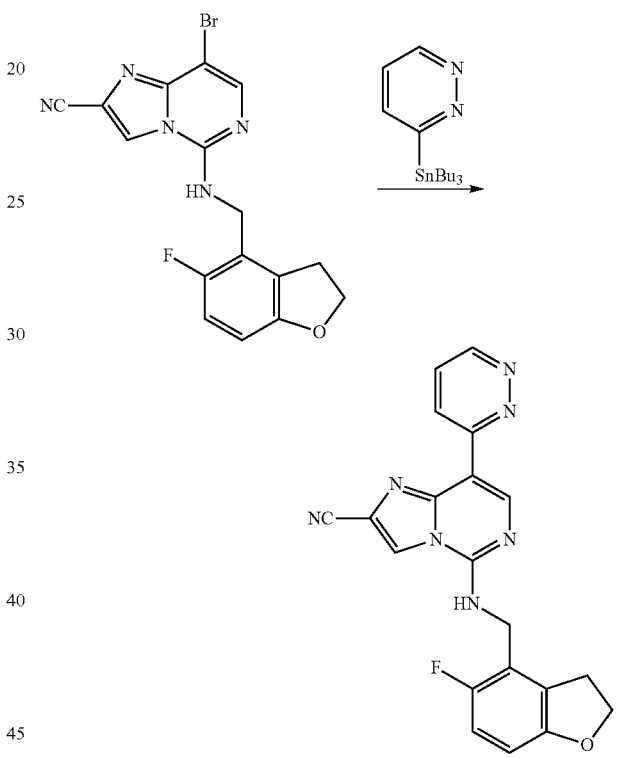

A mixture of tributyl(pyridazin-3-yl)stannane (90.7 mg, 246 µmol, 1.20 eq.), 8-bromo-5-(((5-fluoro-2,3-dihydrobenzofuran-4-yl)methyl)amino)imidazo[1,2-c]pyrimidine-2-carbonitrile (80.0 mg, 205 µmol, 1.00 eq.) and Pd(PPh$_3$)$_4$ (23.7 mg, 20.5 µmol, 0.10 eq.) in toluene (1.00 mL) was purged with nitrogen and was subsequently stirred at 110° C. for 2 h.

The reaction mixture was cooled to rt and quenched with sat aq potassium fluoride (2.00 mL). The mixture was extracted with ethyl acetate (2.00 mL×3) and the combined organic layer was washed with brine (2.00 mL×2), dried over sodium sulfate, filtered and concentrated under reduced pressure to give a residue. The residue was purified by prep-HPLC and lyophilized to provide title compound 5-1 (5-fluoro-2,3-dihydrobenzofuran-4-yl)methylamino-8-pyridazin-3-yl-imidazo[1,2-c]pyrimidine-2-carbonitrile (6.84 mg, 8.51% yield, 98.6% purity) as a yellow solid. LCMS [M+1]: 388.3.

$^1$H NMR (400 MHz, DMSO-d$_6$) δ=9.95 (dd, J=0.8, 2.0 Hz, 1H), 9.26 (dd, J=0.8, 5.6 Hz, 1H), 8.99 (s, 1H), 8.95 (br t, J=5.2 Hz, 1H), 8.62 (s, 1H), 8.46 (dd, J=2.4, 5.6 Hz, 1H), 7.01-6.91 (m, 1H), 6.72 (dd, J=4.0, 8.8 Hz, 1H), 4.78 (d, J=5.2 Hz, 2H), 4.55 (t, J=8.8 Hz, 2H), 3.32-3.28 (m, 2H).

EXAMPLES 143-146 were prepared following the procedure set forth in Example 142 and using the general reactions schemes and intermediates described herein.

TABLE 5

Characterization of EXAMPLES 143-146

| Ex. # | Structure | $^1$H NMR |
|---|---|---|
| 143 | 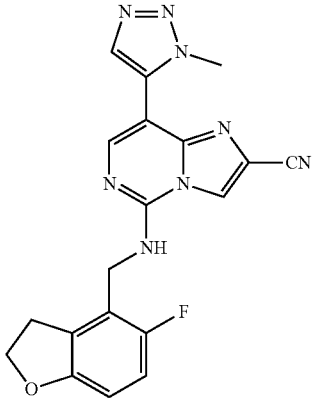<br>5-(((5-fluoro-2,3-dihydrobenzofuran-4-yl)methyl)amino)-8-(1-methyl-1H-1,2,3-triazol-5-yl)imidazo[1,2-c]pyrimidine-2-carbonitrile | $^1$H NMR (400 MHz, DMSO-d$_6$) δ = 8.81 (br s, 2H), 7.93 (s, 1H), 7,90 (s, 1H), 6.93 (br t, J = 9.2 Hz, 1H), 6.68 (dd, J = 4.0, 9.2 Hz, 1H), 4,71 (br s, 2H), 4.53 (br t, J = 8.8 Hz, 2H), 4,02 (s, 3H). LCMS [M + 1]: 391.0. |
| 144 | 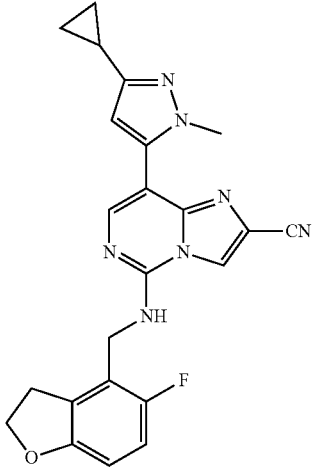<br>8-(3-cyclopropyl-1-methyl-1H-pyrazol-5-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d6) δ = 8.93 (s, 1H), 8.64 (br t, J = 4.8 Hz, 1H), 7.85 (s, 1H), 6.96 (t, J = 9.2 Hz, 1H), 6.72 (dd, J = 4.0, 8.8 Hz, 1H), 6.17 (s, 1H), 4.73 (d, J = 4.8 Hz, 2H), 4.56 (t, J = 8.8 Hz, 2H), 3.66 (s, 3H), 3.32 (t, J = 8.8 Hz, 2H), 1.94-1.81 (m, 1H), 0.95-0.81 (in, 2H), 0.75-0.62 (m, 2H). LCMS [M + 1]: 430.1. |

TABLE 5-continued

Characterization of EXAMPLES 143-146

| Ex. # | Structure | ¹H NMR |
|---|---|---|
| 145 | 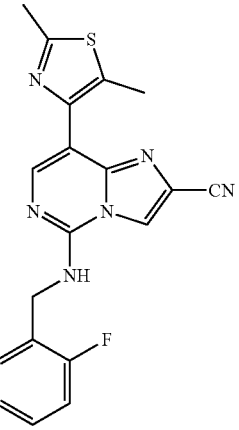<br>8-(2,5-dimethylthiazol-1-yl)-5-(((5-fluoro-2,3-dihydrobenzofuran-4-yl)methyl)amino)imidazol[1,2-c]pyrimidine-2-carbontrile | ¹H NMR (400 MHz, CD$_3$OD) δ = 8.61 (s, 1H), 7.88 (s, 1H), 6.85 (t, J= 9.6 Hz, 1H), 6.64 (dd, J = 4.0, 8.8 Hz, 1H), 4.82 (s, 2H), 4.57 (t, J = 8.8 Hz, 2H), 3.37 (br t, J = 8.8 Hz, 2H), 2.68 (s, 3H), 2.37 (s, 3H).<br>LC-MS [M + 1]: 421.1. |
| 146 | 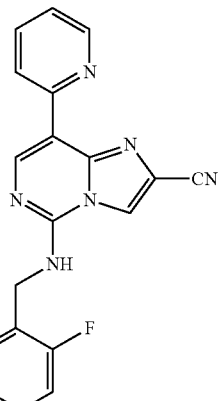<br>5-(((5-fluoro-2,3-dihydrobenzofuran-4-yl)methyl)amino)-8-(pyridin-2-yl)imidazo[1,2-c]pyrimidine-2-carbonitrile | ¹H NMR (400 MHz, DMSO-d$_6$) δ = 8.99 (s, 1H), 8.83 (t, J = 4.8 Hz 1H), 8.77(s, 1H), 8,74-8.65 (m, 2H), 8.02 (br t, J = 7.6 Hz, 1H), 7.45-7.41 (m, 1H), 6.99-6.92 (m, 1H), 6.71 (dd, J = 4.0, 8.8 Hz, 1H), 4.77 (d, J = 4.8 Hz, 2H), 4.55 (t, J = 8.4 Hz, 2H), 3.32 (t, J = 8.8 Hz, 2H).<br>LCMS [M + 1]: 387.3. |

Example 147

5-(((5-fluoro-2,3-dihydrobenzofuran-4-yl)methyl)amino)-8-(6-(hydroxymethyl)pyridin-3-yl)imidazo[1,2-c]pyrimidine-2-carbonitrile

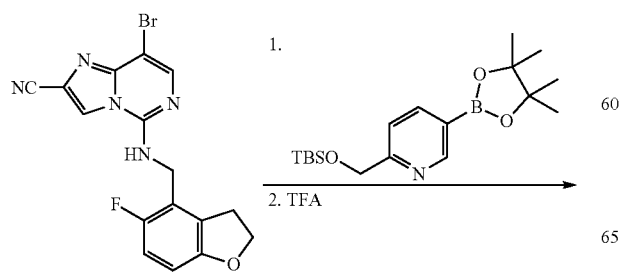

-continued

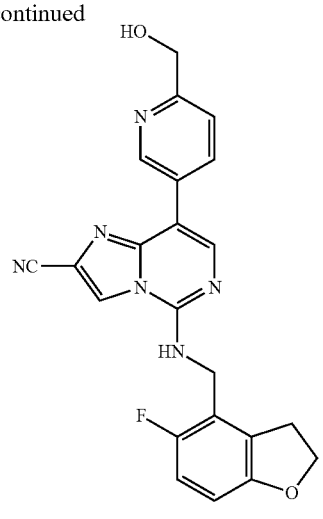

A solution of 8-bromo-5-(((5-fluoro-2,3-dihydrobenzofuran-4-yl)methyl)amino)imidazo[1,2-c]pyrimidine-2-carbonitrile (100 mg, 252 μmol, 1.00 eq.), tert-butyl-dimethyl-[[5-(4,4,5,5-tetramethyl-1,3,2-dioxaborolan-2-yl)-2-pyridyl]methoxy]silane (200 mg, 458 μmol, 1.82 eq.), sodium bicarbonate (65.0 mg, 774 μmol, 3.10 eq.) and Pd(dppf)Cl$_2$(19 mg, 26 μmol, 0.1 eq.) in dioxane (1.70 mL) and water (0.30 mL) was flushed with nitrogen. The mixture was stirred at 95° C. for 1 h. The mixture was cooled to rt, filtered and concentrated to provide the crude material. The residue was purified by prep-TLC (SiO$_2$, dichloromethane/MeOH=20/1) to afford 8-[6-[[tert-butyl(dimethyl)silyl]-oxymethyl]-3-pyridyl]-5-[(5-fluoro-2,3-dihydrobenzofuran-4-yl)methylamino]imidazo[1,2-c]pyrimidine-2-carbonitrile (140 mg, 224 μmol, 89.1% yield, 85.0% purity) as a yellow oil. LCMS [M+1]: 531.2.

$^1$H NMR (400 MHz, DMSO-d6) δ=9.05 (d, J=2.0 Hz, 1H), 8.95 (s, 1H), 8.59 (t, J=5.2 Hz, 1H), 8.41 (dd, J=2.0, 8.0 Hz, 1H), 8.20 (s, 1H), 7.53 (d, J=8.4 Hz, 1H), 7.01-6.89 (m, 1H), 6.71 (dd, J=4.0, 8.4 Hz, 1H), 4.80 (s, 2H), 4.74 (br d, J=4.4 Hz, 2H), 4.54 (t, J=8.8 Hz, 2H), 3.34-3.29 (m, 2H), 0.94 (s, 9H), 0.13 (s, 6H).

A solution of 8-[6-[[tert-butyl(dimethyl)silyl]oxymethyl]-3-pyridyl]-5-[(5-fluoro-2,3-dihydrobenzofuran-4-yl)methylamino]imidazo[1,2-c]pyrimidine-2-carbonitrile (90.0 mg, 144 μmol, 1.00 eq.) in dichloromethane (1.00 mL) and TFA (2.00 mL) was stirred at rt for 1 h. The reaction mixture was concentrated under reduced pressure to give a residue. The residue was purified by prep-TLC (SiO$_2$ dichloromethane/methanol=10/1) to provide the crude product. The solid was triturated with methanol (7.00 mL) and collected by filtration to afford title compound 5-[(5-fluoro-2,3-dihydrobenzofuran-4-yl)methylamino]-8-[6-(hydroxymethyl)-3-pyridyl]imidazo[1,2-c]pyrimidine-2-carbonitrile (45.0 mg, 106 μmol, 73.5% yield, 98.0% purity) as an off-white solid. LCMS [M+1]: 417.0.

$^1$H NMR (400 MHz, DMSO-d6) δ=9.04 (s, 1H), 8.94 (s, 1H), 8.59 (t, J=4.8 Hz, 1H), 8.37 (dd, J=2.0, 8.0 Hz, 1H), 8.18 (s, 1H), 7.56 (d, J=8.0 Hz, 1H), 6.95 (t, J=9.2 Hz, 1H), 6.71 (dd, J=4.0, 8.8 Hz, 1H), 5.44 (t, J=6.0 Hz, 1H), 4.74 (br d, J=4.8 Hz, 2H), 4.61 (d, J=5.6 Hz, 2H), 4.55 (t, J=8.8 Hz, 2H), 3.29-3.33 (m, 2H).

Example 148

5-(((5-fluoro-2,3-dihydrobenzofuran-4-yl)methyl)amino)-8-(2-(hydroxymethyl)pyridin-3-yl)imidazo[1,2-c]pyrimidine-2-carbonitrile

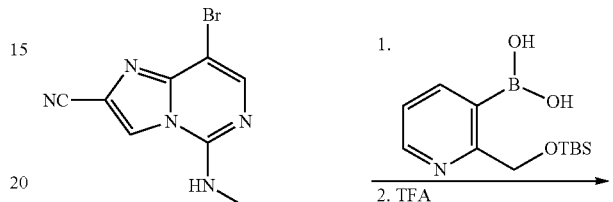

A solution of 8-bromo-5-(((5-fluoro-2,3-dihydrobenzofuran-4-yl)methyl)amino)imidazo[1,2-c]pyrimidine-2-carbonitrile (30.0 mg, 75.0 μmol, 1.00 eq.), [2-[[tert-butyl(dimethyl)silyl]oxymethyl]-3-pyridyl]boronic acid (20.0 mg, 74.9 μmol, 0.10 eq.), sodium bicarbonate (18.9 mg, 225 μmol, 3.00 eq.) and Pd(dppf)Cl$_2$ (5.50 mg, 7.50 umol, 0.10 eq.) in dioxane (1.00 mL) and water (0.20 mL) was purged with nitrogen and stirred at 95° C. for 1 h. The mixture was filtered and concentrated under reduced pressure. The residue was purified by prep-HPLC to afford 8-(2-(((tert-butyldimethylsilyl)oxy)methyl)pyridin-3-yl)-5-(((5-fluoro-2,3-dihydrobenzofuran-4-yl)methyl)amino)imidazo[1,2-c]pyrimidine-2-carbonitrile (30.0 mg, 41.8 μmol, 55.8% yield, 74.0% purity) as a white solid.

A mixture of 8-(2-(((tert-butyldimethylsilyl)oxy)methyl)pyridin-3-yl)-5-(((5-fluoro-2,3-dihydrobenzofuran-4-yl)methyl)amino)imidazo[1,2-c]pyrimidine-2-carbonitrile (15.0 mg, 20.9 μmol, 1.00 eq.) and trifluoroacetic acid (1.11 mL, 15.0 mmol, 717 eq.) in dichloromethane (1.00 mL) was stirred at rt for 1 h. The mixture was filtered and concentrated under reduced pressure to provide the crude residue. The residue was purified by prep-HPLC to afford title compound 5-(((5-fluoro-2,3-dihydrobenzofuran-4-yl)methyl)amino)-8-(2-(hydroxymethyl)pyridin-3-yl)imidazo[1,2-c]pyrimidine-2-carbonitrile (3.05 mg, 7.05 μmol, 33.7% yield, 96.3% purity) as a yellow oil. LC-MS [M+1]: 417.3.

$^1$H NMR (400 MHz, DMSO-d$_6$) δ=8.95 (s, 1H), 8.65 (d, J=4.0 Hz, 1H), 8.61 (br s, 1H), 8.00 (br d, J=7.6 Hz, 1H), 7.89 (s, 1H), 7.60-7.54 (m, 1H), 7.00-6.92 (m, 1H), 6.72 (dd, J=4.0, 8.8 Hz, 1H), 4.74 (d, J=4.4 Hz, 2H), 4.59-4.52 (m, 4H), 3.34-3.32 (m, 2H).

Example 149

8-(4-((dimethylamino)methyl)-3,5-difluorophenyl)-5-(((5-fluoro-2,3-dihydrobenzofuran-4-yl)methyl)amino)imidazo[1,2-c]pyrimidine-2-carbonitrile

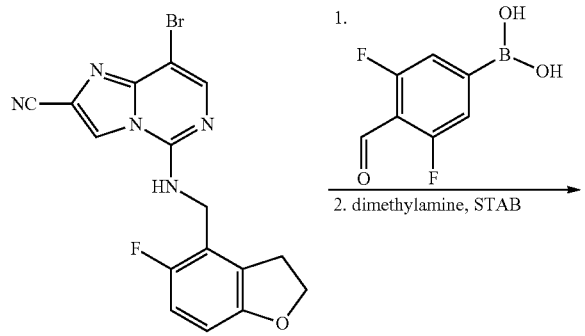

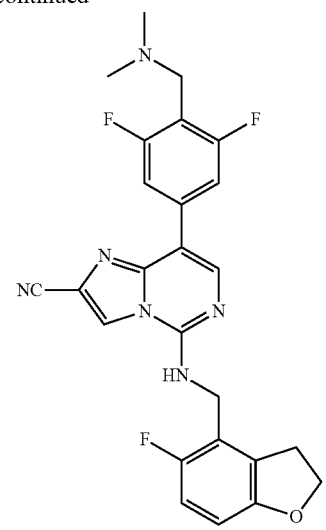

To a solution of 8-bromo-5-(((5-fluoro-2,3-dihydrobenzofuran-4-yl)methyl)amino)imidazo[1,2-c]pyrimidine-2-carbonitrile (50.0 mg, 129 μmol, 1.00 eq.), (3,5-difluoro-4-formyl-phenyl)boronic acid (28.7 mg, 155 μmol, 1.20 eq.) in dioxane (1.00 mL) and water (0.20 mL) was added Pd(dppf)Cl$_2$ (9.42 mg, 12.9 μmol, 0.10 eq.) and sodium bicarbonate (21.6 mg, 257 μmol, 2.00 eq.) under a nitrogen atmosphere. The mixture was stirred at 100° C. for 1 h and subsequently concentrated in vacuo to give a residue. The residue was purified by prep-TLC (SiO$_2$, petroleum ether/ethyl acetate=1/1) to give 8-(3,5-difluoro-4-formylphenyl)-5-(((5-fluoro-2,3-dihydrobenzofuran-4-yl)methyl)amino)imidazo[1,2-c]pyrimidine-2-carbonitrile (30.0 mg, 66.8 μmol, 51.8% yield) as a white solid.

To a solution of 8-(3,5-difluoro-4-forrmlphenyl)-5-(((5-fluoro-2,3-dihydrobenzofuran-4-yl)methyl)amino)imidazo[1,2-c]pyrimidine-2-carbonitrile (30.0 mg, 66.8 μmol, 1.00 eq.), N-methylmethanamine (2M in THF, 67.6 μL, 133 μmol, 2.00 eq.) in methanol (2.00 mL) was added sodium triacetoxyborohydride (28.3 mg, 134 μmol, 2.00 eq.). The mixture was stirred at 40° C. for 30 min. The mixture was concentrated in vacuo to give a residue. The residue was purified by prep-HPLC (TFA condition) to give 5-(((5-fluoro-2,3-dihydrobenzofuran-4-yl)methyl)amino)-8-(2-(hydroxymethyl)pyridin-3-yl)imidazo[1,2-c]pyrimidine-2-carbonitrile (11.0 mg, 17.8 μmol, 26.7% yield, 96.0% purity, TFA salt) as a white solid. LCMS [M+1]: 479.4.

$^1$H NMR (400 MHz, DMSO-d$_5$)$_{5=9.96}$ (br s, 1H), 8.99 (s, 1H), 8.85 (t, J=4.8 Hz, 1H), 8.44 (s, 1H), 8.08 (d, J=9.6 Hz, 2H), 7.00-6.92 (m, 1H), 6.72 (dd, J=4.0, 8.8 Hz, 1H), 4.76 (d, J=4.8 Hz, 2H), 4.56 (t, J=8.4 Hz, 2H), 4.40 (br s, 2H), 3.33-3.29 (m, 2H), 2.84 (s, 6H).

EXAMPLES 150-152 were prepared following the procedure set forth in Example 149 and using the general reactions schemes and intermediates described herein.

TABLE 6

Characterization of EXAMPLES 150-152

| Ex. # | Structure | $^1$H NMR |
|---|---|---|
| 150 | 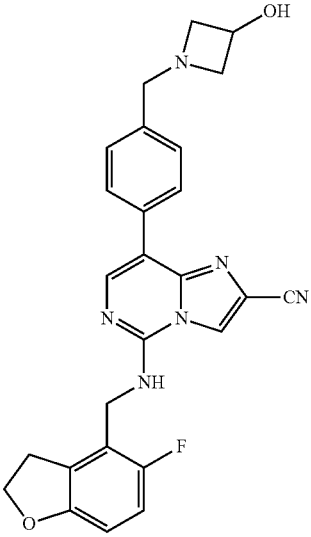<br>5-(((5-fluoro-2,3-dihydrobenzofuran-4-yl)methyl)amino)-8-(4-((3-hydroxyazetidin-1-yl)methylphenyl)imidazo[1,2-c]pyrimidine-2-carbonitrile | 1H NMR (400 MHz, methanol-d$_4$) δ = 8.62 (s, 1H), 8.05 (s, 1H), 8.01 (d, J = 8.4 Hz, 2H), 7.55 (d, J = 8.0 Hz, 2H), 6.86 (t, J = 9.2, 1H), 6.65 (dd, J = 3.6, 8,8 Hz, 1H), 4.83-4.83 (m, 2H), 4.58 (t, J = 8.4 Hz, 2H), 4.44 (br s, 2H), 4.35 (br dd, J = 6.4 Hz, 11.2 Hz, 2H), 3.99 (br dd, J = 5.6, 11.6 Hz, 2H), 3.37 (t, J = 8.4 Hz, 2H), 3.36-3.34 (m, 1H).<br>LCMS [M + 1]: 471.4. |
| 151 | 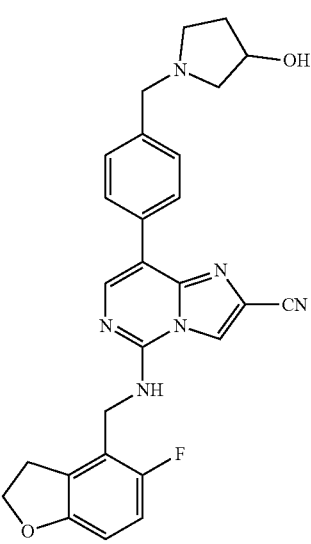<br>5-(((5-fluoro-2,3-dihydrobenzofuran-4-yl)methyl)amino)-8-(4-((3-hydroxypyrrolidin-1-yl)methyl)phenyl)imidazo[1,2-c]pyrimidine-2-carbonitrile | $^1$H NMR (400 MHz, DMSO-d$_6$) δ = 10.33-9.90 (m, 1H), 8.96 (s, 1H), 8.60 (br t, J = 4.8 Hz, 1H), 8.18 (s, 1H), 8.09 (br d, J = 8.0 Hz, 2H), 7.62 (br d, J = 8.4 Hz, 2H), 7.01-6.92 (m, 1H), 6.72 (dd, J = 4.0, 8.8 Hz, 1H), 5.58-5.39 (m, 1H), 4.75 (br d, J = 4.8 Hz, 2H), 4.56 (t, J = 8.8 Hz, 2H), 4.51-4.26 (m, 3H), 3.60-3.45 (m 1H), 3.38-3.34 (m, 2H), 3.29-2.99 (m, 3H), 2.08-1.93 (m, 1H), 1.90-1.75 (m, 1H).<br>LCMS [M + 1]: 485.4. |

TABLE 6-continued

Characterization of EXAMPLES 150-152

| Ex. # | Structure | $^1$H NMR |
|---|---|---|
| 152 | 8-(6-((methylamino)methyl)-2-methylpyridin-3-yl)-5-(((5-fluoro-2,3-dihydrobenzofuran-4-yl)methyl)amino)imidazo[1,2-c]pyrimidine-2-carbonitrile | $^1$H NMR (400 MHz, CD$_3$OD) δ = 8.66 (s, 1H), 7.86-7.76 (m, 2H), 7.41 (d, J = 7.6 Hz, 1H), 6.91-6.84 (m, 1H), 6.67 (dd, J = 4.0, 8.8 Hz, 1H), 4.85 (s, 2H), 4.60 (t, J = 8.8 Hz, 2H), 4.51 (s, 2H), 3.41 (t, J = 8.8 Hz, 2H), 3,01 (s, 6H), 2.49 (s, 3H). LC-MS [M + 1]: 458.1. |

Example 153

5-(((5-fluoro-2,3-dihydrobenzofuran-4-yl)methyl)amino)-8-(1-((tetrahydrofuran-2-yl)methyl)-1H-pyrazol-3-yl)imidazo[1,2-c]pyrimidine-2-carbonitrile

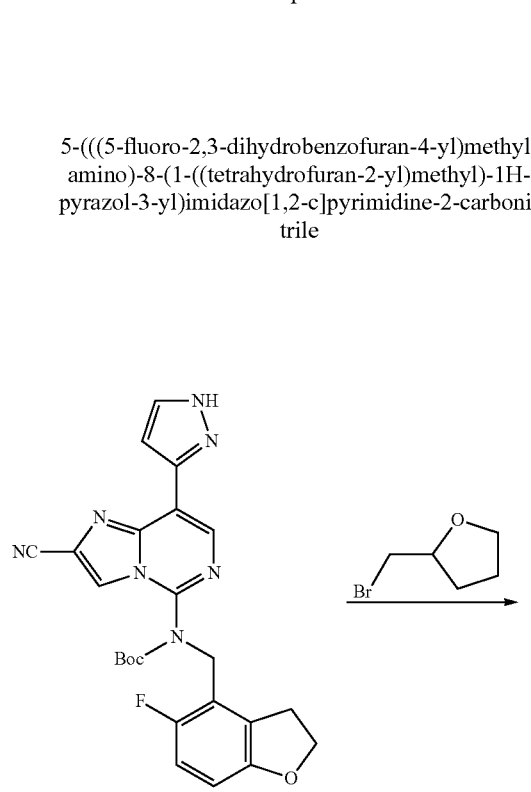

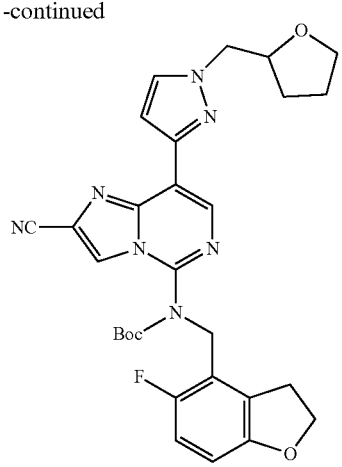

To a solution of tert-butyl (2-cyano-8-(1H-pyrazol-3-yl)imidazo[1,2-c]pyrimidin-5-yl)((5-fluoro-2,3-dihydrobenzofuran-4-yl)methyl)carbamate (30.0 mg, 57.4 μmol, 1.00 eq.) in DMF (1.00 mL) was added sodium hydride (4.59 mg, 115 μmol, 60.0% purity, 2.00 eq.) at 0° C. The mixture was stirred at 0° C. for 30 min prior to the dropwise addition of 2-(bromomethyl)tetrahydrofuran (1 1.5 mg, 69.7 μmol, 1.21 eq.). The mixture was allowed to stir for 3 h and was quenched with water (10.0 mL) and extracted with ethyl acetate (20.0 mL×2). The combined organic layer was washed with water (20.0 mL), dried over anhydrous sodium sulfate and concentrated under reduced pressure to give a residue. The residue was purified by prep-HPLC to give title compound 5-(((5-fluoro-2,3-dihydrobenzofuran-4-yl)methyl)amino)-8-(1-((tetrahydrofuran-2-yl)methyl)-1H-pyrazol-3-yl)imidazo[1,2-c]pyrimidine-2-carbonitrile (12.2 mg, 26.5 umol, 46.2% yield, 99.8% purity) as a white solid. LCMS [M+1]: 460.3.

¹H NMR (400 MHz, DMSO-d6) δ=8.92 (s, 1H), 8.48 (t, J=5.2 Hz, 1H), 8.30 (s, 1H), 7.77 (d, J=2.4 Hz, 1H), 7.06 (d, J=2.4 Hz, 1H), 6.99-6.91 (m, 1H), 6.71 (dd, J=3.6, 8.4 Hz, 1H), 4.73 (d, J=4.8 Hz, 2H), 4.55 (t, J=8.8 Hz, 2H), 4.24-4.18 (m, 3H), 3.80-3.72 (m, 1H), 3.68-3.60 (m, 1H), 3.30 (t, J=8.4 Hz, 2H), 2.01-1.88 (m, 1H), 1.84-1.70 (m, 2H), 1.69-1.57 (m, 1H).

EXAMPLE 154 was prepared following the procedure set forth in Example 153 and using the general reactions schemes and intermediates described herein.

TABLE 7

Characterization of EXAMPLE 154

| Ex. # | Structure | ¹H NMR |
|---|---|---|
| 154 | 5-(((5-fluoro-2,3-dihydrobenzofuran-4-yl)methyl)amino)-8-(1-((tetrahydrofuran-3-yl)methyl)-1H-pyrazol-4-yl)imidazo(1,2-c]pyrimidine-2-carbonitrile | ¹H NMR (400 MHz, DMSO-d₆) δ = 8.91 (s, 1H), 8.47 (t, J = 5.2 Hz, 1H), 8.29 (s, 1H), 7.84 (d, J = 2.0 Hz, 1H), 7.05 (d, J = 2.4 Hz, 1H), 6.99-6.89 (m, 1H), 6.70 (dd, J = 4,0, 8.8 Hz, 1H), 4.72 (d, J = 4.8 Hz, 2H), 4.54 (t, J = 8.8 Hz, 2H), 4.16 (d, J = 7.6 Hz, 2H), 3.80-3.75 (m, 1H), 3.70-3.60 (m, 2H), 3.54-3.49 (m, 1H), 3.79 (t, J = 8.8 Hz, 2H), 2.83-2.71 (m, 1H), 1.99-1.86 (m, 1H), 1.68-1.57 (m, 1H). LCMS [M + 1]: 460.3. |

Example 155

8-(1,3-dimethyl-1H-pyrazol-5-yl)-5-(((5-fluoro-3-hydroxy-2,3-dihydrobenzofuran-4-yl)methyl)amino)imidazo[1,2-c]pyrimidine-2-carbonitrile

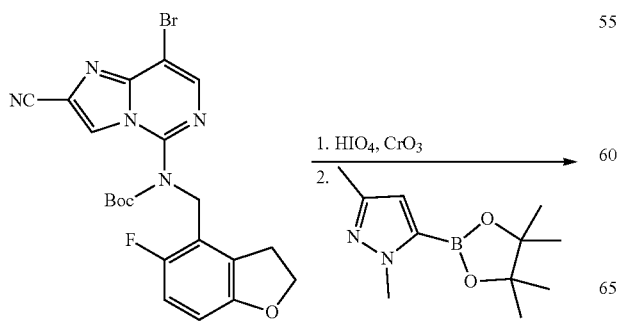

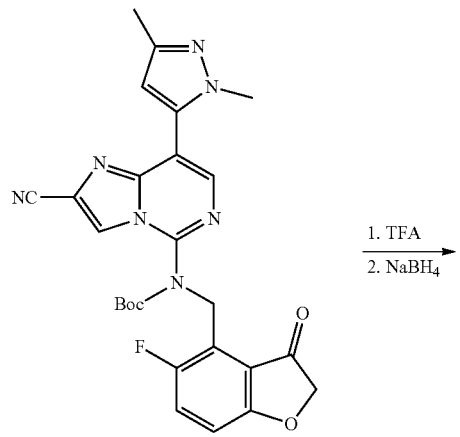

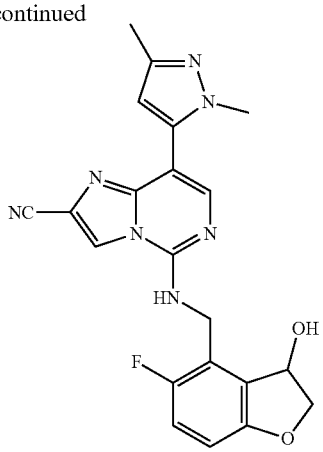

To a solution of tert-butyl (8-bromo-2-cyanoimidazo[1,2-c]pyrimidin-5-yl)((5-fluoro-2,3-dihydrobenzofuran-4-yl)methyl)carbamate (200 mg, 410 μmol, 1.00 eq.) in acetonitrile (4.50 mL) was added periodic acid (345 mg, 1.52 mmol, 345 μL, 3.70 eq.) and chromium trioxide (90.1 mg, 901 μmol, 2.20 eq.). The mixture was stirred at 15° C. for 3 h. The reaction mixture was filtered through a plug of Celite. The filtrate was diluted with water (3.00 mL) and extracted with ethyl acetate (5.00 mL×3). The combined organic phase was washed with aqueous sodium sulfite solution (2.00 mL), brine (2.00 mL), dried over anh sod sulfate, filtered and concentrated to provide the crude material. The residue was purified by column chromatography (SiO$_2$, petroleum ether/ethyl acetate=10/1 to 5:1) to give tert-butyl (8-bromo-2-cyanoimidazo[1,2-c]pyrimidin-5-yl)((5-fluoro-3-oxo-2,3-dihydrobenzofuran-4-yl)methyl)carbamate (114 mg, 227 μmol, 18.5% yield) as a colorless oil. LCMS [M+1]: 503.8.

$^1$H NMR (400 MHz, CDCl$_3$-d) δ=8.09 (s, 1H), 7.70 (s, 1H), 7.24 (t, J=9.4 Hz, 1H), 6.99 (dd, J=3.6, 9.2 Hz, 1H), 5.34 (s, 2H), 4.47 (s, 2H), 1.34 (s, 9H).

A mixture of tert-butyl (8-bromo-2-cyanoimidazo[1,2-c]pyrimidin-5-yl)((5-fluoro-3-oxo-2,3-dihydrobenzofuran-4-yl)methyl)carbamate (114 mg, 227 μmol, 1.00 eq.), 1,3-dimethyl-5-(4,4,5,5-tetramethyl-1,3,2-dioxaborolan-2-yl)pyrazole (101 mg, 454 μmol, 2.00 eq.), Pd(dppf)Cl$_2$ (16.6 mg, 22.7 μmol, 0.10 eq.) and sodium bicarbonate (38.1 mg, 454 μmol, 2.00 eq.) in dioxane (1.50 mL) and water (0.30 mL) was purged with nitrogen and subsequently stirred at 95° C. for 2 h. The reaction mixture was filtered and concentrated under reduced pressure. The residue was purified by prep-TLC (petroleum ether/ethyl acetate=3:1) to afford tert-butyl (2-cyano-8-(1,3-dimethyl-1H-pyrazol-5-yl)imidazo[1,2-c]pyrimidin-5-yl)((5-fluoro-3-oxo-2,3-dihydrobenzofuran-4-yl)methyl)carbamate (40.0 mg, 77.3 μmol, 34.1% yield) as a yellow oil. LCMS [M+1]: 518.4.

To a solution of tert-butyl (2-cyano-8-(1,3-dimethyl-1H-pyrazol-5-yl)imidazo[1,2-c]pyrimidin-5-yl)((5-fluoro-3-oxo-2,3-dihydrobenzofuran-4-yl)methyl)carbamate (40.0 mg, 77.3 μmol, 1.00 eq.) in dichloromethane (0.30 mL) was added trifluoroacetic acid (154 mg, 1.35 mmol, 0.10 mL, 17.5 eq.). The mixture was stirred at 15° C. for 30 min and was subsequently concentrated under reduced pressure. The residue was dissolved in ethyl acetate (2.00 mL) and washed with sat sodium bicarbonate (1.00 mL) and brine (1.00 mL).

The organic phase was dried, filtered and concentrated to give 8-(1,3-dimethyl-1H-pyrazol-5-yl)-5-(((5-fluoro-3-oxo-2,3-dihydrobenzofuran-4-yl)methyl)amino)imidazo[1,2-c]pyrimidine-2-carbonitrile (30.0 mg, 71.9 μmol, 93.0% yield) as a brown solid. LCMS [M+1]: 418.1.

To a solution of 8-(2,5-dimethylpyrazol-3-yl)-5-[(5-fluoro-3-oxo-benzofuran-4-yl)methylamino]imidazo[1,2-c]pyrimidine-2-carbonitrile (30.0 mg, 71.9 μmol, 1.00 eq.) in methanol (0.50 mL) was added sodium borohydride (5.44 mg, 144 μmol, 2.00 eq.) at 0° C. The mixture was stirred at 0° C. for 1 h prior to being quenched with water (0.10 mL). The mixture was purified by prep-HPLC to give title compound 8-(1,3-dimethyl-1H-pyrazol-5-yl)-5-(((5-fluoro-3-hydroxy-2,3-dihydrobenzofuran-4-yl)methyl)amino)imidazo[1,2-c]pyrimidine-2-carbonitrile (6.52 mg, 15.5 μmol, 21.6% yield, 99.7% purity) as an off-white solid. LCMS [M+1]: 420.2.

$^1$H NMR (400 MHz, MeOD-d$_4$) δ=8.59 (br s, 1H), 7.80 (s, 1H), 7.12-6.97 (m, 1H), 6.78 (dd, J=3.6, 8.8 Hz, 1H), 6.25 (s, 1H), 5.68 (br d, J=6.0 Hz, 1H), 5.05 (br d, J=14.6 Hz, 1H), 4.56 (br dd, J=6.0, 10.4 Hz, 2H), 4.44 (br d, J=10.4 Hz, 1H), 3.71 (s, 3H), 2.27 (s, 3H).

Example 156

5-(((5-fluoro-2,3-dihydrobenzofuran-4-yl)methyl)amino)-8-(1-methyl-2-oxo-1,2-dihydropyridin-3-yl)imidazo[1,2-c]pyrimidine-2-carbonitrile

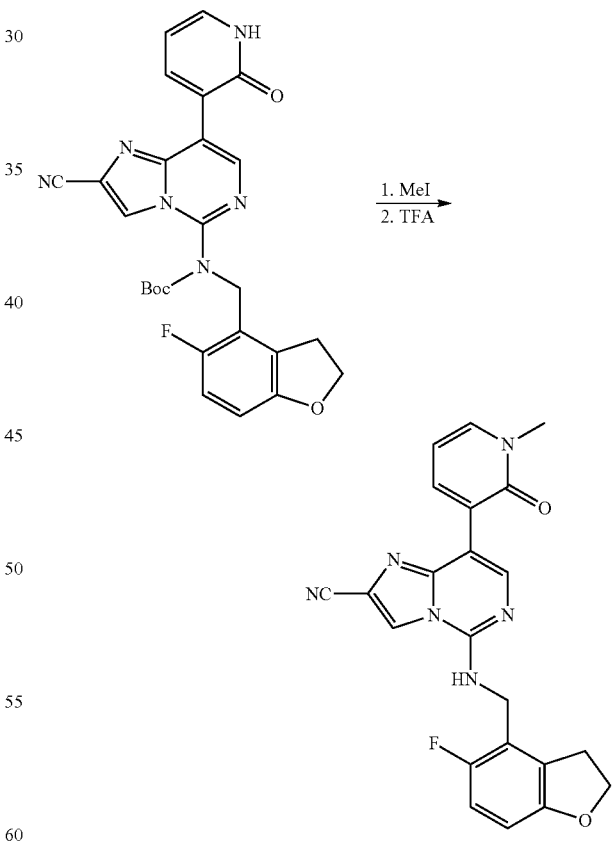

To a solution of tert-butyl tert-butyl (2-cyano-8-(2-oxo-1,2-dihydropyridin-3-yl)imidazo[1,2-c]pyrimidin-5-yl)((5-fluoro-2,3-dihydrobenzofuran-4-yl)methyl)carbamate (45.0 mg, 89.6 μmol, 1.00 eq.) in DMF (0.50 mL) was added potassium carbonate (24.8 mg 179 μmol, 2.00 eq.) at 0° C. The mixture was stirred at 0° C. for 30 min prior to the dropwise addition of methyl iodide (15.3 mg, 107 μmol, 6.69 μL, 1.20 eq.). The mixture was stirred at 0° C. for 1 hour followed by being quenched with saturated ammonium chloride (1.50 mL). The mixture was extracted with ethyl acetate (2.00 mL×3) and the combined organic phase was washed with brine (2.00 mL×2), dried with anhydrous sodium sulfate, filtered and concentrated in vacuo to give tert-butyl (2-cyano-8-(1-methyl-2-oxo-, 2-dihydropyridin-3-yl)imidazo[1,2-c]pyrimidin-5-yl)((5-fluoro-2,3-dihydrobenzofuran-4-yl)methyl)carbamate (30.0 mg, 62.2% yield, 96.0% purity) as a yellow solid. LCMS[M+1]: 517.4.

To a solution of tert-butyl (2-cyano-8-(1-methyl-2-oxo-, 2-dihydropyridin-3-yl)imidazo[1,2-c]pyrimidin-5-yl)((5-fluoro-2,3-dihydrobenzofuran-4-yl)methyl)carbamate (30.0 mg, 55.8 μmol, 1.00 eq.) in dichloromethane (1.00 mL) was added trifluoroacetic acid (380 mg, 3.33 mmol, 247 μL, 59.8 eq.). The mixture was stirred at 25° C. for 1 h prior to being filtered and concentrated under reduced pressure to provide the crude residue. The crude material was purified by prep-HPLC to give title compound 5-(((5-fluoro-2,3-dihydrobenzofuran-4-yl)methyl)amino)-8-(1-methyl-2-oxo-1,2-dihydropyridin-3-yl)imidazo[1,2-c]pyrimidine-2-carbonitrile (16.8 mg, 71.3% yield, 98.5% purity) as a white solid. LCMS [M+1]: 417.3.

$^1$H NMR (400 MHz, DMSO-d6) δ=8.90 (s, 1H), 8.58 (s, 1H), 8.49 (t, J=5.2 Hz, 1H), 8.31 (dd, J=2.0, 7.2 Hz, 1H), 7.75 (dd, J=2.0, 6.4 Hz, 1H), 6.99-6.91 (m, 1H), 6.71 (dd, J=4.0, 8.8 Hz, 1H), 6.40 (t, J=6.8 Hz, 1H), 4.73 (d, J=5.2 Hz, 2H), 4.55 (t, J=8.8 Hz, 2H), 3.53 (s, 3H), 3.33-3.28 (m, 2H).

Examples 157-184

EXAMPLES 157-184 were prepared following the procedure set forth in EXAMPLE 87 and using the general reactions schemes and intermediates described herein.

TABLE 8

Characterization of EXAMPLES 157-184

| Ex. # | Structure | $^1$H NMR |
|---|---|---|
| 157 | 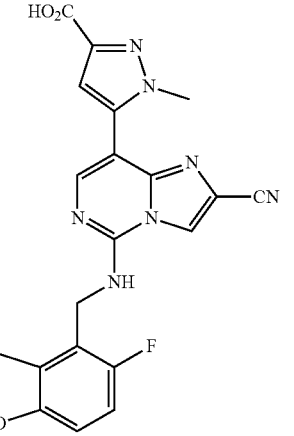<br>5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxylic acid | $^1$H NMR (400 MHz, CD$_3$OD) δ = 8.63 (s, 1H), 7.91 (s, 1H), 6.94-6.83 (m, 1H), 6.67 (dd, J = 4.0, 8.8 Hz, 1H), 6.48 (s, 1H), 4.60 (t, J = 8.8 Hz, 2H), 3.80 (s, 3H), 3.56 (s, 2H), 3.40 (br t, J = 8.8 Hz, 2H), 2.33 (s, 6H). LCMS [M + 1]: 447.2. |
| 158 | 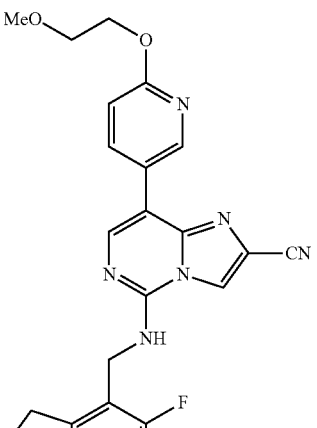<br>5-(((5-fluoro-2,3-dihydrobenzofuran-4-yl)methyl)amino)-8-(6-(2-methoxyethoxy)pyridin-3-yl)imidazo[1,2-c]pyrimidine-2-carbonitrile | $^1$H NMR (400 MHz, DMSO-d$_6$) δ = 8.99 (s, 1H), 8.73 (d, J = 2.4 Hz, 1H), 8.61 (br t, J = 4.8 Hz, 1H), 8.31 (dd, J = 2.4, 8.8 Hz, 1H), 8.11 (s, 1H), 6.99-6.91 (m, 2H), 6.70 (dd, J = 4.0, 8.8 Hz, 1H), 4.74 (br d, J = 4.4 Hz, 2H), 4.55 (t, J = 8.8 Hz, 2H), 4.47-4.40 (m, 2H), 3.73-3.65 (m, 2H), 3.36-3.27 (m, 5H). LC-MS [M + 1]: 461.2. |

TABLE 8-continued

Characterization of EXAMPLES 157-184

| Ex. # | Structure | ¹H NMR |
|---|---|---|
| 159 | 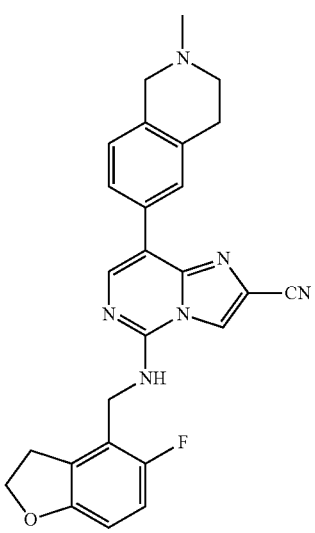 [SMILES: CN1CCc2cc(-c3cnc(NCc4c(F)ccc5c4CCO5)n4cc(C#N)nc34)ccc2C1]<br>5-(((5-fluoro-2,3-dihydrobenzofuran-4-yl)methyl)amino)-8-(2-methyl-1,2,3,4-tetrahydroisoquinolin-6-yl)imidazo[1,2-c]pyrimidine-2-carbonitrile | ¹H NMR (400 MHz, DMSO-d₆) δ = 8.93 (s, 1H), 8.50-8.40 (m, 1H), 8.05 (s, 1H), 7.76-7.66 (m, 2H), 7.14 (d, J = 8.8 Hz, 1H), 7.04-6.91 (m, 1H), 6.71 (dd, J = 4.0, 8.8 Hz, 1H), 4.73 (br d, J = 4. Hz, 2H), 4.55 (t, J = 8.8 Hz, 2H), 3.53 (s, 2H), 3.29 (br s, 2H), 2.89 (br t, J = 5.6 Hz, 2H), 2.63 (br t, J = 5.6 Hz, 2H), 2.37 (s, 3H).<br>LC-MS [M + 1]: 455.1. |
| 160 | 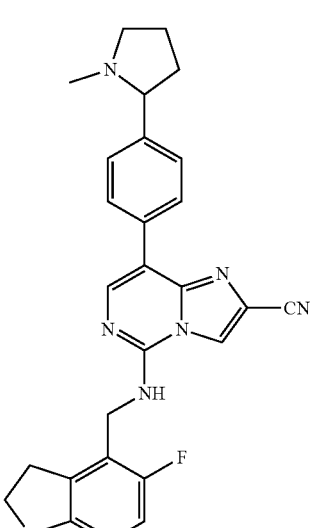<br>5-(((5-fluoro-2,3-dihydrobenzofuran-4-y)methyl)amino)-8-(4-(1-methylpyrrolidin-2-yl)phenyl)imidazo[1,2-c]pyrimidine-2-carbonitrile | ¹H NMR (400 MHz, DMSO-d₆) δ = 8.93 (s, 1H), 8.48 (br s, 1H), 8.07 (s, 1H), 7.89 (br d, J = 8.4 Hz, 2H), 7.41 (br d, J = 8.0 Hz, 2H), 6.98-6.93 (m, 1H), 6.71 (br dd, J = 4.0, 8.8 Hz, 1H), 4.74 (br d, J = 4.4 Hz, 2H), 4.55 (br t, J = 8.8 Hz, 2H), 3.18-3.12 (m, 2H), 3.08-2.96 (m, 2H), 2.30-2.24 (m, 1H), 2.17-2.08 (m, 3H) 1.86-1.76 (m, 2H), 1.68-1.55 (m, 2H).<br>LC-MS [M + 1]: 469.4. |

TABLE 8-continued

Characterization of EXAMPLES 157-184

| Ex. # | Structure | $^1$H NMR |
|---|---|---|
| 161 | 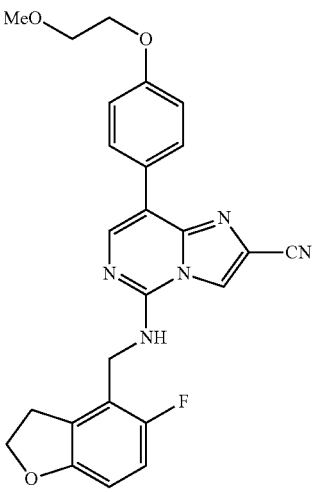 [SMILES: COCCOc1ccc(-c2cnc(NCc3c(F)ccc4c3CCO4)n3cc(C#N)nc23)cc1]<br>5-(((5-fluoro-2,3-dihydrobenzofuran-4-yl)methyl)amino)-8-(4-(2-methoxyethoxy)phenyl)imidazo[1,2-c]pyrimidine-2-carbonitrile | $^1$H NMR (400 MHz, DMSO-d$_6$) δ = 8.94 (s, 1H), 8.52-8.42 (m, 1H), 8.03 (s, 1H), 7.94-7.87 (m, 2H), 7.07-7.01 (m, 2H), 6.97-6.91 (m, 1H), 6.70 (dd, J = 4.0, 8.8 Hz, 1H), 4.72 (br d, J = 4.0 Hz, 2H) 4.54 (t, J = 8.8 Hz, 2H), 4.16-4.11 (m, 2H), 3.72-3.66 (m, 2H), 3.33 (s, 3H), 3.33-3.28 (m, 2H). LC-MS [M + 1]: 460.0. |
| 162 | 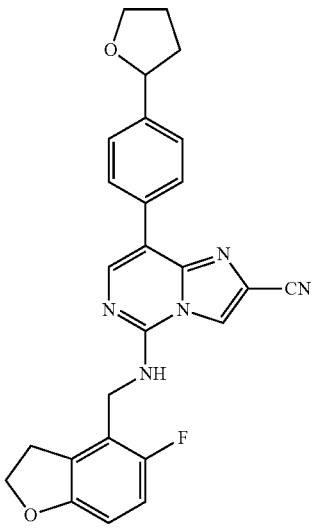 [SMILES: N#Cc1cn2c(NCc3c(F)ccc4c3CCO4)ncc(-c3ccc(C4CCCO4)cc3)c2n1]<br>5-(((5-fluoro-2,3-dihydrobenzofuran-4-yl)methyl)amino)-8-(4-(tetrahydrofuran-2-yl)phenyl)imidazo[1,2-c]pyrimidine-2-carbonitrile | $^1$H NMR (400 MHz, DMSO-d$_6$) δ = 8.93 (s, 1H), 8.50 (br s, 1H), 8.08 (s, 1H), 7.92 (d, J = 8.0 Hz, 2H), 7.40 (d, J = 8.0 Hz, 2H), 6.95 (t, J = 9.6 Hz, 1H), 6.71 (dd, J = 4.0, 8.8 Hz, 1H), 4.85 (t, J = 7.2 Hz, 1H), 4.74 (s, 2H), 4.55 (t, J = 8.8 Hz, 2H), 4.09-3.95 (m, 1H), 3.90-3.76 (m 1H), 3.31-3.26 (m, 2H), 2.36-2.26 (m, 1H), 2.01-1.90 (m, 2H), 1.77-1.64 (m, 1H). LCMS [M + 1]: 456.2. |

TABLE 8-continued

Characterization of EXAMPLES 157-184

| Ex. # | Structure | ¹H NMR |
|---|---|---|
| 163 | 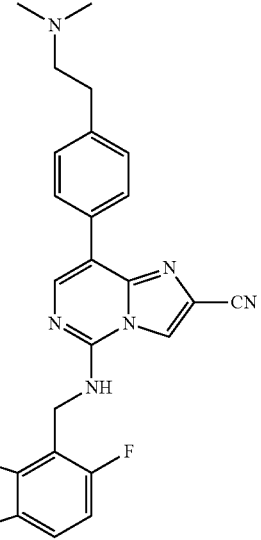<br>8-(4-(2-(dimethylamino)ethyl)phenyl)-5-(((5-fluoro-2,3-dihydrobenzofuran-4-yl)methyl)amino)imidazo[1,2-c]pyrimidine-2-carbonitrile | ¹H NMR (400 MHz, CD₃OD) δ = 8.59 (s, 1H), 7.96 (s, 1H), 7.79 (d, J = 8.4 Hz, 2H), 7.33 (d, J = 8.0 Hz, 2H), 6.90-6.82 (m, 1H), 6.64 (dd, J = 4.0, 8.8 Hz, 1H), 4.81 (s, 2H), 4.57 (br t, J = 8.8 Hz, 2H), 3.36 (s, 2H), 2.92-2.82 (m, 2H), 2.70-2.61 (m, 2H), 2.36 (s, 6H).<br>LCMS [M + 1]: 457.2. |
| 164 | 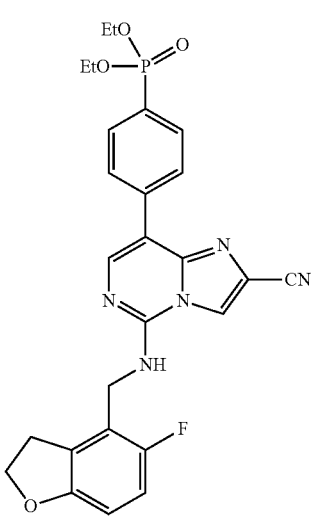 [SMILES: CCOP(=O)(OCC)c1ccc(-c2cnc(NCc3c(F)ccc4c3CCO4)n3cc(C#N)nc23)cc1]<br>diethyl (4-(2-cyano-5-(((5-fluoro-2,3-dihydrobenzofuran-4-yl)methyl)amino)imidazo[1,2-c]pyrimidin-8-yl)phenyl)phosphonate | ¹H NMR (400 MHz, DMSO-d₆) δ = 8.95 (s, 1H), 8.64 (br s, 1H), 8.22 (s, 1H), 8.17 (dd, J = 4.0, 8.4 Hz, 2H), 7.79 (dd, J = 8.4, 12.8 Hz, 2H), 6.98-6.90 (m, 1H), 6.71 (dd, J = 4.0, 8.8 Hz, 1H), 4.75 (br d, J = 3.6 Hz, 2H), 4.55 (t, J = 8.4 Hz, 2H), 4.09-3.96 (m, 4H), 3.29 (br s, 2H), 1.25 (t, J = 6.8 Hz, 6H).<br>LCMS [M + 1]: 522.0. |

TABLE 8-continued

Characterization of EXAMPLES 157-184

| Ex. # | Structure | ¹H NMR |
|---|---|---|
| 165 | 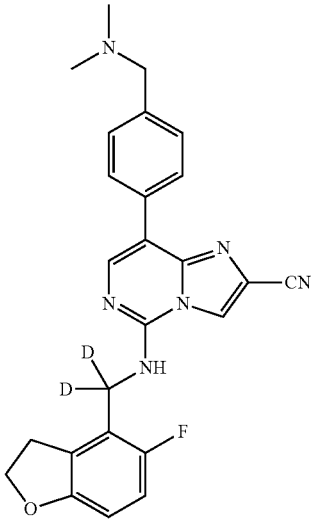<br>8-(4-((dimethylamino)methyl)phenyl)-5-(((5-fluoro-2,3-dihydrobenzofuran-4-yl)methyl-d₂)amino)imidazo[1,2-c]pyrimidine-2-carbonitrile | ¹H NMR (400 MHz, CD₃OD) δ = 8.77-8.66 (m, 1H), 8.04 (d, J = 13.6 Hz, 1H), 7.59-7.42 (m, 3H), 6.88 (t, J = 9.6 Hz, 1H), 6.68 (dd, J = 3.6, 8.4 Hz, 1H), 4.68-4.54 (m, 2H), 4.45-4.33 (m, 2H), 3.52-3.36 (m, 2H), 2.96-2.88 (m, 6H), 2.32-2.24 (m, 3H).<br>LCMS [M + 1]: 459.2. |
| 166 | 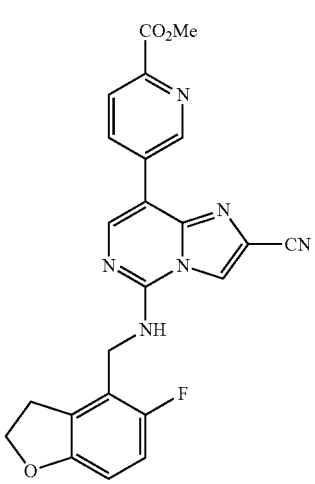 [SMILES: COC(=O)c1ccc(-c2cnc(NCc3c(F)ccc4c3CCO4)n3cc(C#N)nc23)cn1]<br>methyl 5-(2-cyano-5-(((5-fluoro-2,3-dihydrobenzofuran-4-yl)methyl)amino)imidazo[1,2-c]pyrimidin-8-yl)picolinate | ¹H NMR (400 MHz, DMSO-d₆) δ = 9.32 (d, J = 2.0 Hz, 1H), 8.97 (s, 1H), 8.78 (t, J = 5.2 Hz, 1H), 8.66 (dd, J = 2.4, 8.0 Hz, 1H), 8.38 (s, 1H), 8.15 (d, J = 8.4 Hz, 1H), 6.99-6.90 (m, 1H), 6.70 (dd, J = 4.0, 8.4 Hz, 1H), 4.76 (d, J = 4.8 Hz, 2H), 4.54 (t, J = 8.8 Hz, 2H), 3.90 (s, 3H), 3.29-3.29 (m, 2H).<br>LC-MS [M + 1]: 445.2. |

TABLE 8-continued

Characterization of EXAMPLES 157-184

| Ex. # | Structure | $^1$H NMR |
|---|---|---|
| 167 | 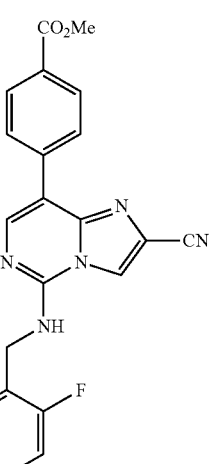<br>methyl 4-(2-cyano-5-(((5-fluoro-2,3-dihydrobenzofuran-4-yl)methyl)amino)imidazo[1,2-c]pyrimidin-8-yl)benzoate | $^1$H NMR (400 MHz, DMSO-$d_6$) δ = 8.97 (s, 1H), 8.68 (br t, J = 4.8 Hz, 1H), 8.26 (s, 1H), 8.19 (d, J = 8.8 Hz, 2H), 8.07-7.99 (m, 2H), 6.97-6.91 (m, 1H), 6.70 (dd, J = 4.0, 8.8 Hz, 1H), 4.75 (d, J= 4.8 Hz, 2H), 4.54 (t, J = 8.8 Hz, 2H), 3.87 (s, 3H), 3.37-3.35 (m, 2H). LC-MS [M + 1]: 443.9. |
| 168 | 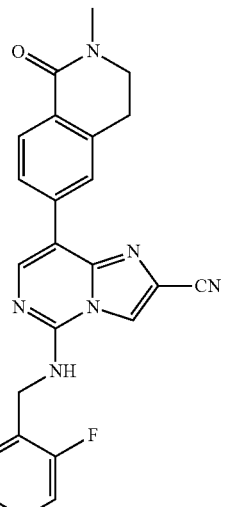<br>5-(((5-fluoro-2,3-dihydrobenzofuran-4-yl)methyl)amino)-8-(2-methyl-1-oxo-1,2,3,4-tetrahydroisoquinolin-6-yl)imidazo[1,2-c]pyrimidine-2-carbonitrile | $^1$H NMR (400 MHz, DMSO-$d_6$) δ = 8.98 (s, 1H), 8.65 (t, J = 5.2 Hz, 1H), 8.18 (s, 1H), 7.99-7.95 (m, 1H), 7.94-7.90 (m, 2H), 6.98-6.90 (m, 1H), 6.70 (dd, J = 4.0, 8.8 Hz, 1H), 4.74 (d, J = 4.8 Hz, 2H), 4.54 (t, J = 8.8 Hz, 2H), 3.58 (t, J = 6.8 Hz, 2H), 3.32 (br t, J = 8.8 Hz, 2H), 3.12-2.97 (m, 5H). LCMS [M + 1]: 469.3. |

TABLE 8-continued

Characterization of EXAMPLES 157-184

| Ex. # | Structure | $^1$H NMR |
|---|---|---|
| 169 | 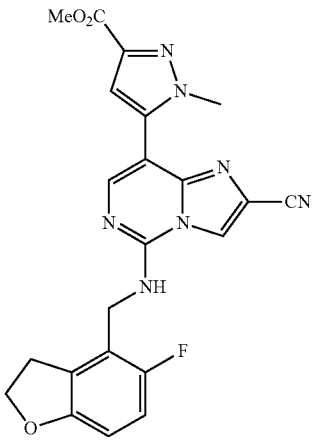<br>methyl 5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxylate | $^1$H NMR (400 MHz, CD$_3$OD) δ = 8.63 (s, 1H), 7.93 (s, 1H), 6.97 (s, 1H), 6.90-6.81 (m, 1H), 6.65 (dd, J = 4.0, 8.8 Hz, 1H), 4.83 (s, 2H), 4.58 (t, J = 8.8 Hz, 2H), 3.91 (s, 3H), 3.88 (s, 3H), 3.39 (t, J = 8.8 Hz, 2H).<br>LCMS [M + 1]: 448.2. |
| 170 | 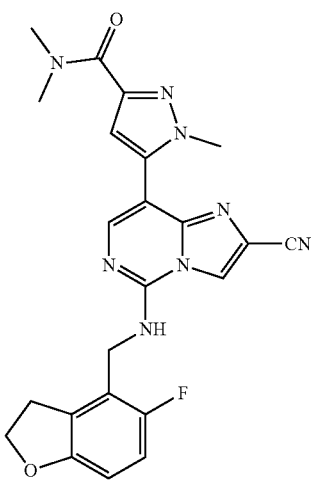 [SMILES: CN(C)C(=O)c1cc(-c2cnc(NCc3c(F)ccc4c3CCO4)n3cc(C#N)nc23)n(C)n1]<br>5-(2-cyano-5-(((5-fluoro-2,3-dihydrobenzofuran-4-yl)methyl)amino)imidazo[1,2-c]pyrimidin-8-yl)-N,N,1-trimethyl-1H-pyrazole-3-carboxamide | $^1$H NMR (400 MHz, DMSO-d$_6$) δ = 8.98 (s, 1H), 8.76 (t, J = 4.8 Hz, 1H), 7.95 (s, 1H), 6.99-6.91 (m, 1H), 6.74 (s, 1H), 6.71 (dd, J = 4.0, 8.8 Hz, 1H), 4.73 (d, J = 4.8 Hz, 2H), 4.55 (t, J = 8.8 Hz, 2H), 3.82 (s, 3H), 3.36-3.28 (m, 5H), 2.99 (s, 3H).<br>LC-MS [M + 1]: 461.3. |

TABLE 8-continued

Characterization of EXAMPLES 157-184

| Ex. # | Structure | ¹H NMR |
|---|---|---|
| 171 | 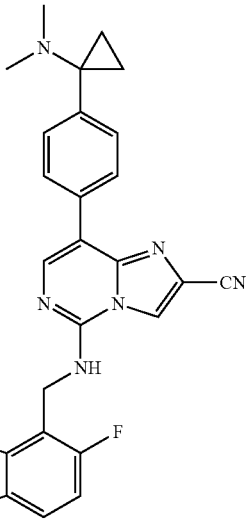<br>8-(4-(1-(dimethylamino)cyclopropyl)phenyl)-5-(((5-fluoro-2,3-dihydrobenzofuran-4-yl)methyl)amino)imidazo[1,2-c]pyrimidine-2-carbonitrile | ¹H NMR (400 MHz, CD₃OD) δ = 8.60 (s, 1H), 8.00 (s, 1H), 7.86 (d, J = 8.4 Hz, 2H), 7.45 (d, J = 8.4 Hz, 2H), 6.90-6.82 (m, 1H), 6.65 (dd, J = 4.0, 8.8 Hz, 1H), 4.83 (br s, 2H), 4.58 (t, J = 8.8 Hz, 2H), 3.37 (t, J = 8.4 Hz, 2H), 2.29 (s, 6H), 1.02-0.98 (m, 2H), 0.92-0.88 (m, 2H).<br>LCMS [M + 1]: 469.4. |
| 172 | 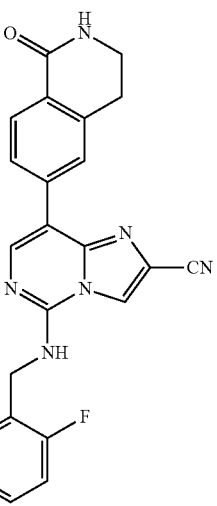<br>5-(((5-fluoro-2,3-dihydrobenzofuran-4-yl)methyl)amino)-8-(1-oxo-1,2,3,4-tetrahydroisoquinolin-6-yl)imidazo[1,2-c]pyrimidine-2-carbonitrile | ¹H NMR (400 MHz, CD₃OD) δ = 8.64 (s, 1H), 8.13 (s, 1H), 8.04 (d, J = 8.4 Hz, 1H), 7.93 (s, 1H), 7.89 (d, J = 8.0 Hz, 1H), 6.88 (t, J = 8.8 Hz, 1H), 6.67 (dd, J = 4.4, 8.4 Hz, 1H), 4.83-4.82 (m, 2H), 4.60 (t, J = 8.8 Hz, 2H), 3.58 (t, J = 6.8 Hz, 2H), 3.39-3.37 (m, 2H), 3.10 (br t, J = 6.8 Hz, 2H).<br>LCMS [M + 1]: 455.2. |

TABLE 8-continued

Characterization of EXAMPLES 157-184

| Ex. # | Structure | $^1$H NMR |
|---|---|---|
| 173 | 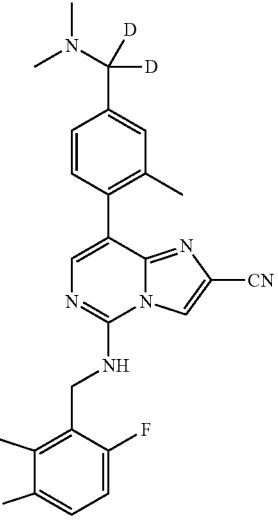<br>8-(4-((dimethylamino)methyl-d$_2$)-2-methylphenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 9.87 (br s, 1H), 8.94 (s, 1H), 8.54 (br t, J = 4.8 Hz, 1H), 7.73 (s, 1H), 7.45 (s, 1H), 7.42-7.36 (m, 2H), 6.99-6.90 (m, 1H), 6.71 (dd, J = 4.0, 8.4 Hz, 1H), 4.72 (br d, J = 4.8 Hz, 2H), 4.55 (t, J = 8.8 Hz, 2H), 3.33-3.29 (m, 2H), 2.78 (s, 6H), 2.20 (s, 3H).<br>LCMS [M + 1]: 459.3. |
| 174 | 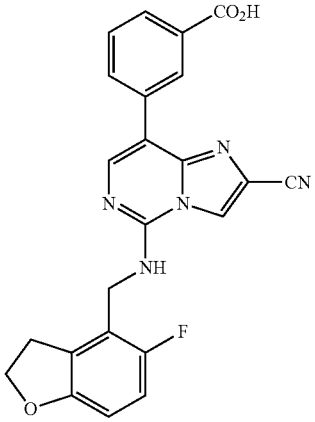 [SMILES: N#Cc1cn2c(NCc3c(F)ccc4c3CCO4)ncc(-c3cccc(C(=O)O)c3)c2n1]<br>3-(2-cyano-5-(((5-fluoro-2,3-dihydrobenzofuran-4-yl)methyl)amino)imidazo[1,2-c]pyrimidin-8-yl)benzoic acid | $^1$H NMR (400 MHz, DMSO-d$_6$) δ = 13.03 (s, 1H), 8.95 (s, 1H), 8.63-8.53 (m, 2H), 8.19-8.15 (m, 2H), 7.93 (d, J = 8.0 Hz, 1H), 7.59 (t, J = 8.0 Hz, 1H), 6.95 (t, J = 9.6 Hz, 1H), 6.70 (dd, J = 4.0, 8.8 Hz, 1H), 4.74 (d, J = 4.8 Hz, 2H), 4.55 (t, J = 8.8 Hz, 2H), 3.34-3.37 (m, 2H).<br>LCMS [M + 1]: 430.2. |

TABLE 8-continued

Characterization of EXAMPLES 157-184

| Ex. # | Structure | ¹H NMR |
|---|---|---|
| 175 | 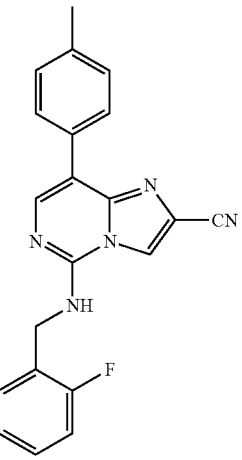<br>5-(((5-fluoro-2,3-dihydrobenzofuran-4-yl)methyl)amino)-8-(p-tolyl)imidazo[1,2-c]pyrimidine-2-carbonitrile | ¹H NMR (400 MHz, DMSO-$d_6$) δ = 8.92 (s, 1H), 8.45 (t, J = 5.2 Hz, 1H), 8.06 (s, 1H), 7.86 (d, J = 8.0 Hz, 2H), 7.27 (d, J = 8.0 Hz, 2H), 6.98-6.91 (m, 1H), 6.70 (dd, J = 4.0, 8.8 Hz, 1H), 4.73 (d, J = 4.8 Hz, 2H), 4.54 (t, J = 8.8 Hz, 2H), 3.31 (t, J = 8.8 Hz, 2H), 2.35 (s, 3H).<br>LC-MS [M + 1]: 400.0. |
| 176 | 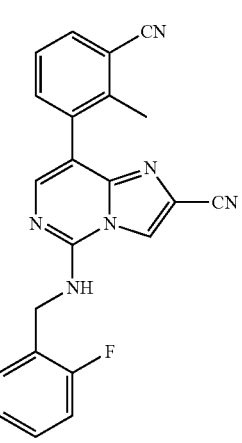<br>8-(3-cyano-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.93 (s, 1H), 8.56 (t, J = 4.8 Hz, 1H) 7.86 (dd, J = 1.2, 7.6 Hz, 1H), 7.78 (s, 1H), 7.66 (dd, J = 0.8, 7.6 Hz, 1H) 7.51-7.46 (m, 1H), 6.99-6.94 (m, 1H), 6.72 (dd, J = 4.0, 8.8 Hz, 1H), 4.74 (d, J = 4.8 Hz, 2H), 4.56 (t, J = 8.8 Hz, 2H), 3.50-3.48 (m, 2H), 2.35 (s, 3H).<br>LCMS [M + 1]: 425.0. |
| 177 | 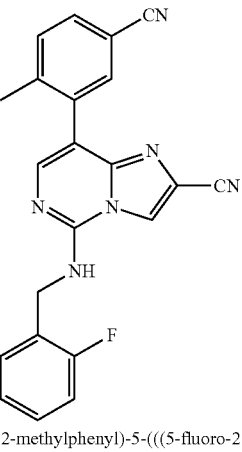<br>8-(5-cyano-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 8.99 (s, 1H), 8.63 (t, J = 5.2 Hz, 1H), 7.88-7.84 (m, 2H), 7.82 (d, J = 1.6 Hz, 1H), 7.61 (d, J = 8.0 Hz, 1H), 7.05-6.99 (m, 1H), 6.78 (dd, J = 4.0, 8.8 Hz, 1H), 4.79 (d, J = 4.8 Hz, 2H), 4.62 (t, J = 8.8 Hz, 2H), 3.47-3.45 (m, 2H), 2.31 (s, 3H).<br>LC-MS [M + 1]: 425.0. |

TABLE 8-continued

Characterization of EXAMPLES 157-184

| Ex. # | Structure | ¹H NMR |
|---|---|---|
| 178 | 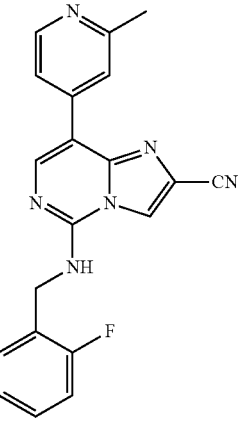<br>5-(((5-fluoro-2,3-dihydrobenzofuran-4-yl)methyl)amino)-8-(2-methylpyridin-4-yl)imidazo[1,2-c]pyrimidine-2-carbonitrile | ¹H NMR (400 MHz, DMSO-$d_6$) δ = 8.99-8.92 (m, 2H), 8.78 (d, J = 5.2 Hz, 1H), 8.73 (s, 1H), 8.59 (s, 1H), 8.56 (dd, J = 1.6, 5.2 Hz, 1H), 6.95 (t, J = 9.2 Hz, 1H), 6.71 (dd, J = 4.0, 8.8 Hz, 1H), 4.77 (br d, J = 4.0 Hz, 2H), 4.55 (t, J = 8.8 Hz, 2H), 3.28-3.21 (m, 2H).<br>LCMS [M + 1]: 411.9. |
| 179 | 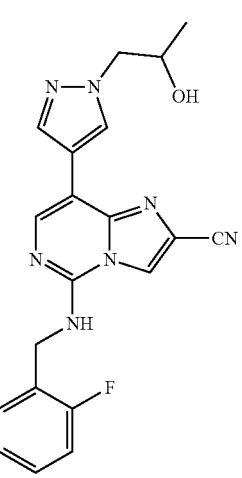<br>5-(((5-fluoro-2,3-dihydrobenzofuran-4-yl)methyl)amino)-8-(1-(2-hydroxypropyl)-1H-pyrazol-4-yl)imidazo[1,2-c]pyrimidine-2-carbonitrile | ¹H NMR (400 MHz, DMSO-$d_6$) δ = 8.90 (s, 1H), 8.41 (s, 1H), 8.35 (t, J = 5.2 Hz, 1H), 8.18 (s, 1H), 8.11 (s, 1H), 6.98-6.90 (m, 1H), 6.70 (dd, J = 3.6, 8.4 Hz, 1H), 4.89 (br s, 1H), 4.71 (d, J = 4.8 Hz, 2H), 4.54 (t, J = 8.8 Hz, 2H), 4.08 (dd, J = 3.2, 5.2 Hz, 2H), 4.04-3.96 (m, 1H), 3.29 (t, J = 8.8 Hz, 2H), 1.06 (d, J = 6.0 Hz, 3H).<br>LCMS [M + 1]: 434.3. |
| 180 | 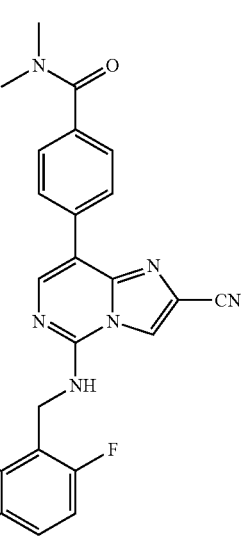 | ¹H NMR (DMSO-$d_6$, 400 MHz): δ = 8.95 (s, 1H), 8.55 (t, J = 5.2 Hz, 1H), 8.18 (s, 1H), 8.06 (d, J = 8.4 Hz, 2H), 7.49 (d, J = 8.4 Hz, 2H), 6.91-6.98 (m, 1H), 6.71 (dd, J = 8.8, 4.0 Hz, 1H), 4.74 (d, J = 4.8 Hz, 2H), 4.55 (t, J = 8.8 Hz, 2H), 3.31-3.27 (m, 2H), 2.99 (br s, 6H).<br>LC-MS [M + 1]: 456.7. |

TABLE 8-continued

Characterization of EXAMPLES 157-184

| Ex. # | Structure | ¹H NMR |
|---|---|---|
| | 4-(2-cyano-5-(((5-fluoro-2,3-dihydrobenzofuran-4-yl)methyl)amino)imidazo[1,2-c]pyrimidin-8-yl)-N,N-dimethylbenzamide | |
| 181 | 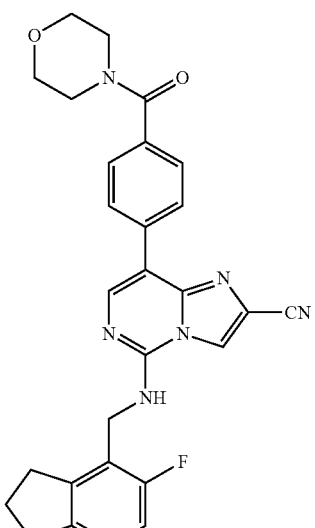<br>5-(((5-fluoro-2,3-dihydrobenzofuran-4-yl)methyl)amino)-8-(4-(morpholine-4-carbonyl)phenyl)imidazo[1,2-c]pyrimidine-2-carbonitrile | ¹H NMR (400 MHz, DMSO-d₆) δ = 8.94 (s, 1H), 8.56 (t, J = 5.2 Hz, 1H), 8.17 (s, 1H), 8.07 (d, J = 8.4 Hz, 2H), 7.50 (d, J = 8.4 Hz, 2H), 6.94 (t, J = 9.6 Hz, 1H), 6.70 (dd, J = 4.0, 8.8 Hz, 1H), 4.74 (d, J = 4.8 Hz, 2H), 4.54 (t, J = 8.8 Hz, 2H), 3.62 (br s, 5H), 3.55-3.33 (m, 5H).<br>LC-MS [M + 1]: 499.1. |
| 182 | 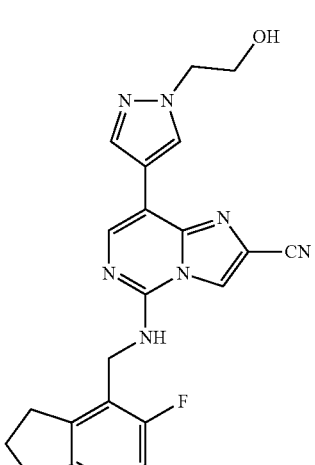<br>5-(((5-fluoro-2,3-dihydrobenzofuran-4-yl)methyl)amino)-8-(1-(2-hydroxyethyl)-1H-pyrazol-4-yl)imidazo[1,2-c]pyrimidine-2-carbonitrile | ¹H NMR (400 MHz, DMSO-d₆) δ = 8.91 (s, 1H), 8.42 (s, 1H), 8.35 (t, J = 5.2 Hz, 1H), 8.18 (s, 1H), 8.11 (s, 1H), 6.99-6.90 (m, 1H), 6.70 (dd, J = 3.6, 8.8 Hz, 1H), 4.71 (d, J = 4.8 Hz, 2H), 4.54 (t, J = 8.8 Hz, 2H), 4.22 (t, J = 5.6 Hz, 2H), 3.77 (t, J = 5.6 Hz, 2H), 3.29 (t, J = 8.4 Hz, 2H).<br>LC-MS [M + 1]: 420.3. |

TABLE 8-continued

Characterization of EXAMPLES 157-184

| Ex. # | Structure | $^1$H NMR |
|---|---|---|
| 183 | 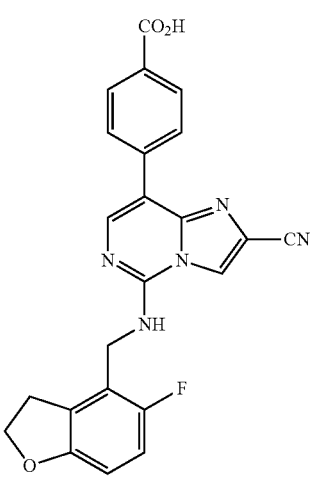 [SMILES: N#Cc1cn2c(NCc3c(F)ccc4c3CCO4)ncc(-c3ccc(C(=O)O)cc3)c2n1]<br>4-(2-cyano-5-(((5-fluoro-2,3-dihydrobenzofuran-4-yl)methyl)amino)imidazo[1,2-c]pyrimidin-8-yl)benzoic acid | $^1$H NMR (400 MHz, DMSO-d$_6$) δ = 8.98 (s, 1H), 8.22 (s, 1H), 8.11 (d, J = 8.0 Hz, 2H), 8.00 (d, J = 8.0 Hz, 2H), 6.96 (t, J = 8.8 Hz, 1H), 6.71 (dd, d, J = 3.6, 8.4 Hz, 1H), 4.76 (s, 2H), 4.55 (t, J = 8.4 Hz, 2H), 3.28-3.25 (m, 2H).<br>LC-MS [M + 1]: 430.3. |
| 184 | 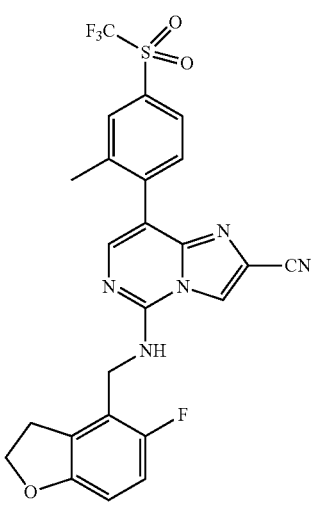 [SMILES: Cc1cc(S(=O)(=O)C(F)(F)F)ccc1-c1cnc(NCc2c(F)ccc3c2CCO3)n2cc(C#N)nc12]<br>5-(((5-fluoro-2,3-dihydrobenzofuran-4-yl)methyl)amino)-8-(2-methyl-4-((trifluoromethyl)sulfonyl)phenyl)imidazo[1,2-c]pyrimidine-2-carbonitrile | $^1$H NMR (400 MHz, DMSO-d$_6$) δ = 8.95 (s, 1H), 8.67 (br t, J = 4.8 Hz, 1H), 8.11 (s, 1H), 8.03 (d, J = 8.0 Hz, 1H), 7.90 (s, 1H), 7.82 (d, J = 8.0 Hz, 1H), 7.02-6.88 (m, 1H), 6.72 (dd, J = 4.0, 8.8 Hz, 1H), 4.74 (d, J = 4.4 Hz, 2H), 4.56 (t, J = 8.8 Hz, 2H), 3.34 (t, J = 8.8 Hz, 2H), 2.37 (s, 3H).<br>LC-MS [M + 1]: 532.0. |

TABLE 8-continued

Characterization of EXAMPLES 157-184

| Ex. # | Structure | ¹H NMR |
|---|---|---|
| 185 | 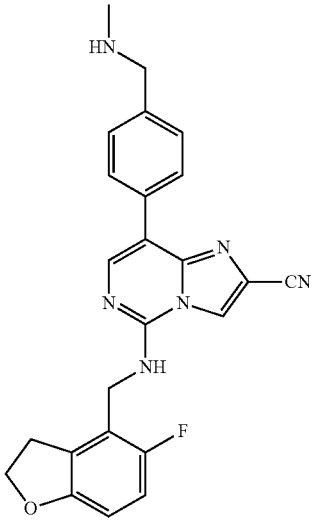 [SMILES: CNCc1ccc(-c2cnc(NCc3c(F)ccc4c3CCO4)n3cc(C#N)nc23)cc1]<br>5-(((5-fluoro-2,3-dihydrobenzofuran-4-yl)methyl)amino)-8-(4-((methylamino)methyl)phenyl)imidazo[1,2-c]pyrimidine-2-carbonitrile | ¹H NMR (400 MHz, DMSO-d6) δ 8.95 (s, 1H), 8.77 (s, 2H), 8.60 (t, J = 5.1 Hz, 1H), 8.16 (s, 1H), 8.11-8.01 (m, 2H), 7.59-7.49 (m, 2H), 6.94 (dd, J = 10.3, 8.7 Hz, 1H), 6.70 (dd, J = 8.6, 3.9 Hz, 1H), 4.73 (d, J = 4.9 Hz, 2H), 4.54 (t, J = 8.7 Hz, 2H), 4.17 (s, 2H), 3.29 (s, 1H), 2.59 (d, J = 4.8 Hz, 3H).<br>LCMS [M + 1]: 429.3. |
| 186 | 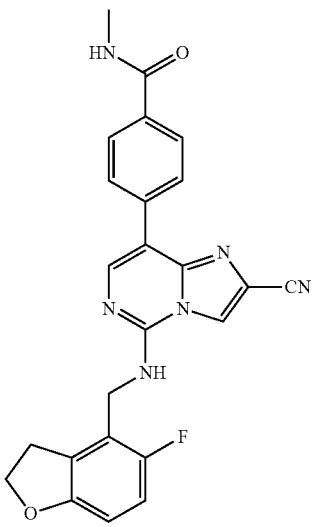 [SMILES: CNC(=O)c1ccc(-c2cnc(NCc3c(F)ccc4c3CCO4)n3cc(C#N)nc23)cc1]<br>4-(2-cyano-5-(((5-fluoro-2,3-dihydrobenzofuran-4-yl)methyl)amino)imidazo[1,2-c]pyrimidin-8-yl)-N-methylbenzamide | ¹H NMR (400 MHz, DMSO-d6) δ 8.96 (s, 1H), 8.59 (t, J = 5.2 Hz, 1H), 8.45 (d, J = 4.7 Hz, 1H), 8.21 (s, 1H), 8.14-8.05 (m, 2H), 7.92 (d, J = 8.5 Hz, 2H), 6.95 (dd, J = 10.3, 8.7 Hz, 1H), 6.71 (dd, J = 8.6, 3.9 Hz, 1H), 4.75 (d, J = 4.9 Hz, 2H), 4.55 (t, J = 8.7 Hz, 2H), 3.31 (d, J = 8.8 Hz, 2H), 2.82 (d, J = 4.5 Hz, 3H).<br>LCMS [M + 1]: 443.0. |

TABLE 8-continued

Characterization of EXAMPLES 157-184

| Ex. # | Structure | $^1$H NMR |
|---|---|---|
| 187 | 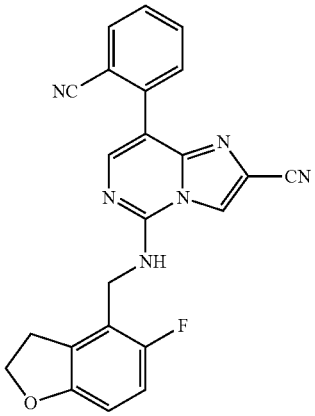 [SMILES: N#Cc1cn2c(NCc3c(F)ccc4c3CCO4)ncc(-c3ccccc3C#N)c2n1]<br>8-(2-cyanophenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d6) δ 8.97 (s, 1H), 8.71 (t, J = 5.1 Hz, 1H), 7.99 (d, J = 14.2 Hz, 2H), 7.86-7.75 (m, 2H), 7.62 (ddd, J = 7.8, 6.2, 2.6 Hz, 1H), 7.03-6.91 (m, 1H), 6.73 (dd, J = 8.6, 3.9 Hz, 1H), 4.76 (d, J = 4.8 Hz, 2H), 4.56 (t, J = 8.7 Hz, 2H), 3.33 (d, J = 8.7 Hz, 2H). LCMS [M + 1]: 411.0. |
| 188 | 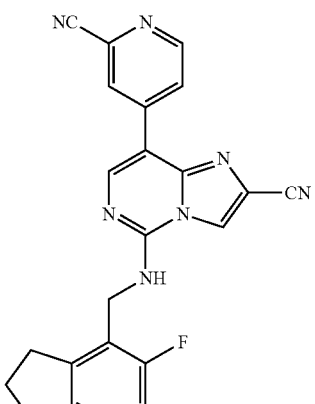<br>8-(2-cyanopyridin-4-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ 8.97 (d, J = 8.6 Hz, 2H), 8.77 (dd, J = 20.1, 3.6 Hz, 2H), 8.65-8.51 (m, 2H), 6.96 (t, J = 9.4 Hz, 1H), 6.72 (dd, J = 8.7, 3.9 Hz, 1H), 4.78 (d, J = 4.6 Hz, 2H), 4.56 (t, J = 8.7 Hz, 2H), 3.12 (m, 2H). LCMS [M + 1]: 411.9. |

TABLE 8-continued

Characterization of EXAMPLES 157-184

| Ex. # | Structure | $^1$H NMR |
|---|---|---|
| 189 | 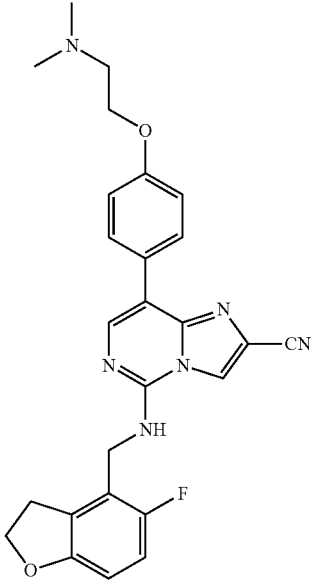 [SMILES: CN(C)CCOc1ccc(-c2cnc(NCc3c(F)ccc4c3CCO4)n3cc(C#N)nc23)cc1]<br>8-(4-(2-(dimethylamino)ethoxy)phenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d6) δ 8.80 (bs, 1H), 8.44 (bs, 1H), 7.98 (s, 1H), 7.89 (d, J = 8.7 Hz, 2H), 7.02 (d, J = 8.4 Hz, 2H), 6.92 (t, J = 9.4 Hz, 1H), 6.67 (d, J = 8.3 Hz, 1H), 4.69 (s, 2H), 4.53 (t, J = 8.7 Hz, 2H), 4.09 (t, J = 5.8 Hz, 2H), 3.29 (m, 2H), 2.65 (t, J = 5.8 Hz, 3H), 2.23 (s, 6H).<br>LCMS [M + 1]: 473.1. |
| 190 | 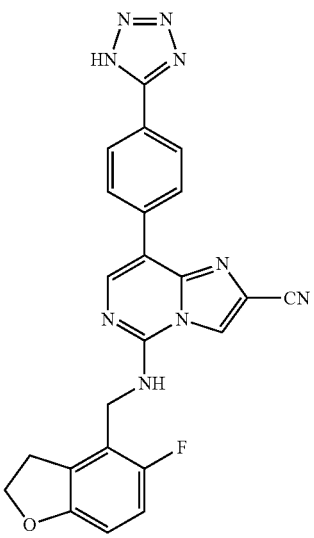 [SMILES: N#Cc1cn2c(NCc3c(F)ccc4c3CCO4)ncc(-c3ccc(-c4nnn[nH]4)cc3)c2n1]<br>8-(4-(1H-tetrazol-5-yl)phenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ 9.00 (s, 1H), 8.70 (t, J = 5.1 Hz, 1H), 8.28 (t, J = 4.3 Hz, 2H), 8.14 (d, J = 8.3 Hz, 2H), 7.02-6.87 (m, 1H), 6.71 (dd, J = 8.7, 3.9 Hz, 1H), 4.76 (d, J = 4.9 Hz, 2H), 4.56 (t, J = 8.7 Hz, 2H), 3.54-3.50 (m, 2H).<br>LCMS [M + 1]: 453.9. |

TABLE 8-continued

Characterization of EXAMPLES 157-184

| Ex. # | Structure | ¹H NMR |
|---|---|---|
| 191 | 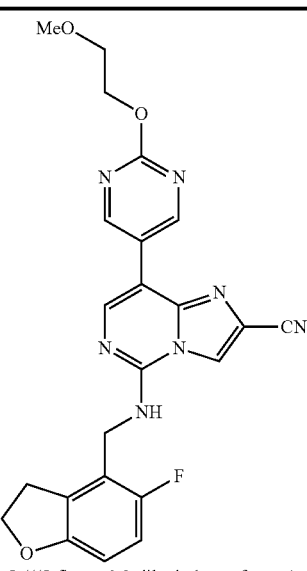<br>5-(((5-fluoro-2,3-dihydrobenzofuran-4-yl)methyl)amino)-8-(2-(2-methoxyethoxy)pyrimidin-5-yl)imidazo[1,2-c]pyrimidine-2-carbonitrile | ¹H NMR (400 MHz, DMSO-$d_6$) δ 9.17 (s, 2H), 8.96 (s, 1H), 8.66 (s, 1H), 8.22 (s, 1H), 6.95 (dd, J = 10.3, 8.7 Hz, 1H), 6.71 (dd, J = 8.7, 3.9 Hz, 1H), 4.74 (d, J = 4.9 Hz, 2H), 4.55 (t, J = 8.7 Hz, 2H), 4.51-4.45 (m, 2H), 3.74-3.67 (m, 2H), 3.38-3.28 (m, 5H).<br>LCMS [M + 1]: 462.0. |
| 192 | 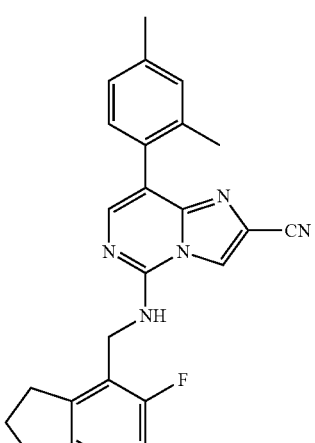<br>8-(2,4-dimethylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ 8.94 (d, J = 3.5 Hz, 1H), 8.49 (s, 1H), 7.65 (s, 1H), 7.18-7.12 (m, 2H), 7.06 (dd, J = 7.7, 1.9 Hz, 1H), 6.95 (dd, J = 10.3, 8.6 Hz, 1H), 6.71 (dd, J = 8.6, 3.9 Hz, 1H), 4.72 (d, J = 3.6 Hz, 2H), 4.55 (t, J = 8.7 Hz, 2H), 3.31 (m, 2H), 2.33 (s, 3H), 2.12 (s, 3H).<br>LCMS [M + 1]: 414.1. |

Examples 193 and 194

EXAMPLES 193 and 194 were prepared following the procedure set forth in EXAMPLE 142 and using the general reactions schemes and intermediates described herein.

TABLE 9

Characterization of EXAMPLES 193 and 194

| Ex. # | Structure | ¹H NMR |
|---|---|---|
| 193 | 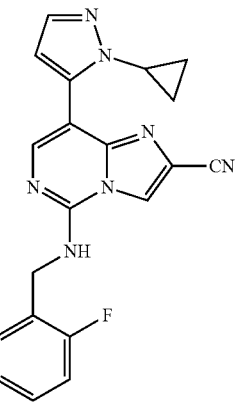<br>8-(1-cyclopropyl-1H-pyrazol-5-yl)-5-(((5-fluoro-2,3-dihydrobenzofuran-4-yl)methyl)amino)imidazo[1,2-c]pyrimidine-2-carbonitrile | ¹H NMR (400 MHz, d-DMSO) δ = 8.95 (s, 1H), 8.66 (br s, 1H), 8.02 (s, 1H), 7.47 (d, J = 1.6 Hz, 1H), 7.05-6.89 (m, 1H), 6.72 (dd, J = 4.0, 8.8 Hz, 1H), 6.53 (d, J = 1.6 Hz, 1H), 4.75 (s, 2H), 4.55 (t, J = 8.8 Hz, 2H), 3.74-3.68 (m, 1H), 3.32-3.28 (m, 2H), 0.98-0.91 (m, 2H), 0.86-0.78 (m, 2H).<br>LCMS [M + 1]: 416. |
| 194 | 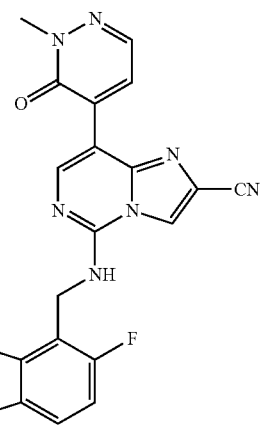<br>5-(((5-fluoro-2,3-dihydrobenzofuran-4-yl)methyl)amino)-8-(2-methyl-3-oxo-2,3-dihydropyridazin-4-yl)imidazo[1,2-c]pyrimidine-2-carbonitrile | ¹H NMR (400 MHz, DMSO-d₆) δ = 9.18 (s, 1H), 8.94 (s, 1H), 8.82 (t, J = 4.8 Hz, 1H), 8.60 (d, J = 4.4 Hz, 1H), 8.04 (d, J = 4.8 Hz, 1H), 6.98-6.91 (m, 1H), 6.70 (dd, J = 3.6, 8.4 Hz, 1H), 4.76 (d, J = 4.8 Hz, 2H), 4.54 (t, J = 8.4 Hz, 2H), 3.76 (s, 3H), 3.30-3.27 (m, 2H).<br>LC-MS [M + 1]: 418.2. |

Examples 195-202

EXAMPLES 195-202 were prepared following the procedure set forth in EXAMPLE 149 and using the general reactions schemes and intermediates described herein.

TABLE 10

Characterization of EXAMPLES 195-202

| Ex. # | Structure | ¹H NMR |
|---|---|---|
| 195 | 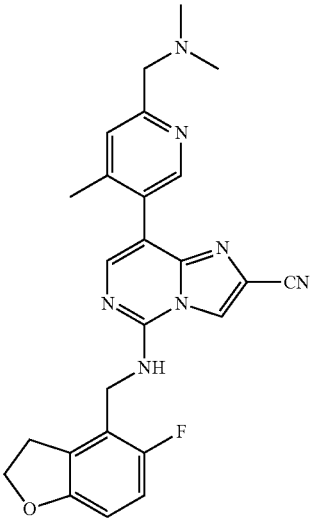 [SMILES: Cc1cc(CN(C)C)ncc1-c1cnc(NCc2c(F)ccc3c2CCO3)n2cc(C#N)nc12]<br>8-(6-((dimethylamino)methyl)-4-methylpyridin-3-yl)-5-(((5-fluoro-2,3-dihydrobenzofuran-4-yl)methyl)amino)imidazo[1,2-c]pyrimidine-2-carbonitrile | ¹H NMR (400 MHz, DMSO-$d_6$) δ = 9.03 (s, 1H), 8.64 (br s, 1H), 8.44 (s, 1H), 7.89 (s, 1H), 7.49 (s, 1H), 7.10-7.02 (m, 1H), 6.82 (dd, J = 4.0, 8.8 Hz, 1H), 4.83 (br s, 2H), 4.66 (t, J = 8.8 Hz, 2H), 3.63 (s, 2H), 2.34 (s, 6H), 2.31 (s, 3H).<br>LCMS [M + 1]: 458.3. |
| 196 | 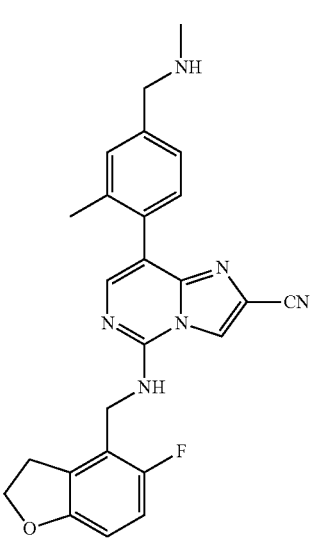 [SMILES: CNCc1ccc(-c2cnc(NCc3c(F)ccc4c3CCO4)n3cc(C#N)nc23)c(C)c1]<br>5-(((5-fluoro-2,3-dihydrobenzofuran-4-yl)methyl)amino)-8-(2-methyl-4-((methylamino)methyl)phenyl)imidazo[1,2-c]pyrimidine-2-carbonitrile | ¹H NMR (400 MHz, DMSO-$d_6$) δ = 9.33-9.12 (m, 2H), 9.06 (s, 1H), 8.76-8.51 (m, 1H), 7.71-7.62 (m, 1H), 7.46 (s, 1H), 7.42-7.35 (m, 2H), 6.94 (t, J = 9.6 Hz, 1H), 6.70 (dd, J = 3.6, 8.8 Hz, 1H), 4.72 (br d, J = 4.4 Hz, 2H), 4.55 (t, J = 8.8 Hz, 2H), 4.12 (br t, J = 5.6 Hz, 2H), 3.34 (br t, J = 8.4 Hz, 2H), 2.57 (t, J = 5.2 Hz, 3H), 2.23-2.16 (m, 3H).<br>LCMS [M + 1]: 443.0. |

TABLE 10-continued

Characterization of EXAMPLES 195-202

| Ex. # | Structure | $^1$H NMR |
|---|---|---|
| 197 | 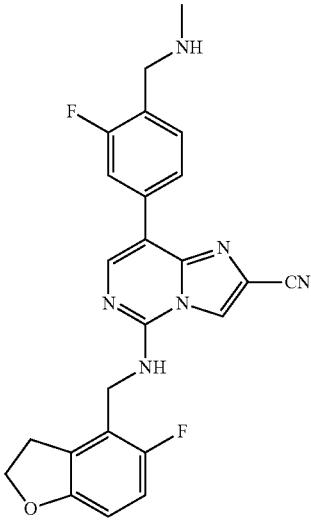 [SMILES: CNCc1ccc(-c2cnc(NCc3c(F)ccc4c3CCO4)n3cc(C#N)nc23)cc1F]<br>5-(((5-fluoro-2,3-dihydrobenzofuran-4-yl)methyl)amino)-8-(3-fluoro-4-((methylamino)methyl)phenyl)imidazo[1,2-c]pyrimidine-2-carbonitrile | $^1$H NMR (400 MHz, DMSO-d$_6$) δ = 9.26 (br s, 2H), 9.12 (s, 1H), 9.01-8.89 (m, 1H), 8.28 (s, 1H), 8.04 (br d, J = 12.0 Hz, 1H), 7.97 (d, J = 8.0 Hz, 1H), 7.71 (t, J = 8.4 Hz, 1H), 6.94 (t, J = 9.6 Hz, 1H), 6.69 (dd, J = 4.0, 8.8 Hz, 1H), 4.74 (br d, J = 4.4 Hz, 2H), 4.54 (t, J = 8.8 Hz, 2H), 4.20 (br t, J = 5.2 Hz, 2H), 3.32 (br t, J = 8.4 Hz, 2H), 2.60 (t, J = 5.2 Hz, 3H). LCMS [M + 1]: 447.0. |
| 198 | 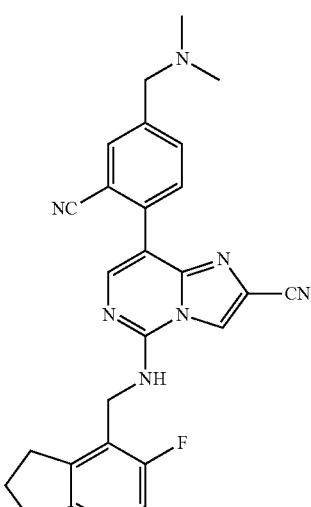<br>8-(2-cyano-4-((dimethylamino)methyl)phenyl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.96 (s, 1H), 8.69 (br s, 1H), 7.99 (s, 1H), 7.83 (s, 1H), 7.78-7.74 (m, 1H), 7.73-7.69 (m, 1H), 6.99-6.92 (m, 1H), 6.72 (dd, J = 4.0, 8.8 Hz, 1H), 4.75 (d, J = 3.6 Hz, 2H), 4.55 (t, J = 8.8 Hz, 2H), 3.50 (s, 2H), 3.35 (br s, 2H), 2.20 (s, 6H). LCMS [M + 1]: 468.2. |

TABLE 10-continued

Characterization of EXAMPLES 195-202

| Ex. # | Structure | ¹H NMR |
|---|---|---|
| 199 | 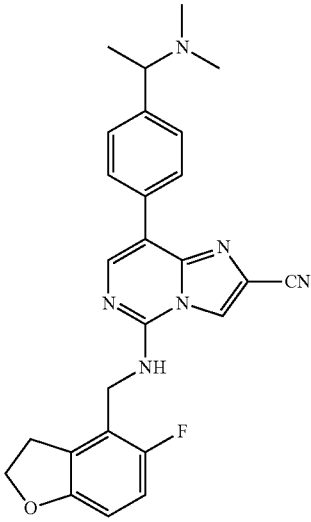 [SMILES: CC(c1ccc(-c2cnc(NCc3c(F)ccc4c3CCO4)n3cc(C#N)nc23)cc1)N(C)C]<br>8-(4-(1-(dimethylamino)ethyl)phenyl)-5-(((5-fluoro-2,3-dihydrobenzofuran-4-yl)methyl)amino)imidazo[1,2-c]pyrimidine-2-carbonitrile | ¹H NMR (400 MHz, CD$_3$OD) δ = 8.68-8.61 (m, 1H), 8.07-8.01 (m, 2H), 7.99 (d, J = 8.4 Hz, 1H), 7.69 (d, J = 8.0 Hz, 1H), 7.62 (d, J = 8.4 Hz, 1H), 6.92-6.80 (m, 1H), 6.70-6.61 (m, 1H), 4.88 (br s, 2H), 4.64-4.52 (m, 3H), 3.42-3.34 (m, 2H), 2.95-2.89 (m, 3H), 2.80-2.74 (m, 3H), 1.84-1.75 (m, 3H).<br>LCMS [M + 1]: 457.0. |
| 200 | 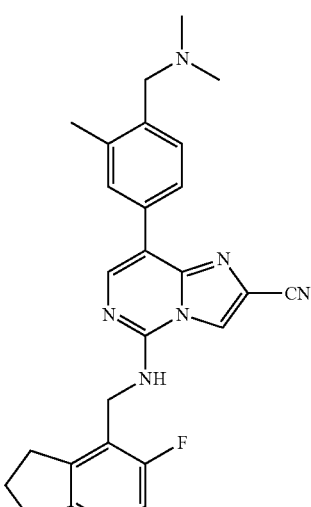<br>8-(4-((dimethylamino)methyl)-3-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-d$_6$) δ = 8.94 (s, 1H), 8.50 (br s, 1H), 8.06 (s, 1H), 7.76-7.72 (m, 2H), 7.29 (d, J = 8.0 Hz, 1H), 7.00-6.91 (m, 1H), 6.71 (dd, J = 3.6, 8.4 Hz, 1H), 4.73 (s, 2H), 4.55 (t, J = 8.8 Hz, 2H), 3.38-3.36 (m, 2H), 2.38 (s, 3H), 2.18 (s, 6H).<br>LCMS [M + 1]: 457.3. |

TABLE 10-continued

Characterization of EXAMPLES 195-202

| Ex. # | Structure | ¹H NMR |
|---|---|---|
| 201 | 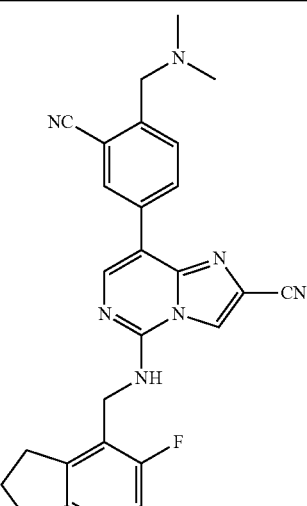 8-(3-cyano-4-((dimethylamino)methyl)phenyl)-5-(((5-fluoro-2,3-dihydrobenzofuran-4-yl)methyl)amino)imidazo[1,2-c]pyrimidine-2-carbonitrile | ¹H NMR (400 MHz, DMSO-d6) δ 8.96 (s, 2H), 8.65 (s, 2H), 8.44 (d, J = 1.9 Hz, 1H), 8.38-8.23 (m, 3H), 7.65 (d, J = 8.2 Hz, 2H), 7.02-6.88 (m, 2H), 6.71 (dd, J = 8.6, 3.9 Hz, 2H), 4.75 (d, J = 5.0 Hz, 3H), 4.56 (t, J = 8.7 Hz, 3H), 3.59 (s, 2H), 3.32-3.30 (m, 2H), 2.22 (s, 6H). LCMS [M + 1]: 468.0. |
| 202 | 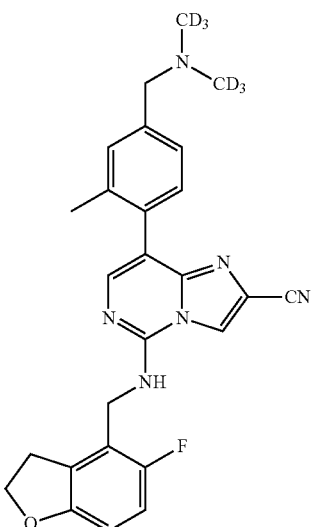 8-(4-((bis(methyl-d₃)amino)methyl)-2-methylphenyl)-5-(((5-fluoro-2,3-dihydrobenzofuran-4-yl)methyl)amino)imidazo[1,2-c]pyrimidine-2-carbonitrile | ¹H NMR (400 MHz, DMSO-d₆) δ 8.91 (s, 1H), 8.44 (s, 1H), 7.70 (s, 1H), 7.31-7.14 (m, 3H), 6.96 (dd, J = 10.3, 8.6 Hz, 1H), 6.72 (dd, J = 8.6, 3.9 Hz, 1H), 4.78-4.66 (m, 2H), 4.56 (t, J = 8.7 Hz, 2H), 3.40 (m, 2H), 3.31 (m, 2H), 2.15 (s, 3H). LCMS [M + 1]: 463.4. |

Example 203

5-(((5-fluoro-2,3-dihydrobenzofuran-4-yl)methyl)amino)-8-(1,2,3,4-tetrahydroisoquinolin-6-yl)imidazo[1,2-c]pyrimidine-2-carbonitrile

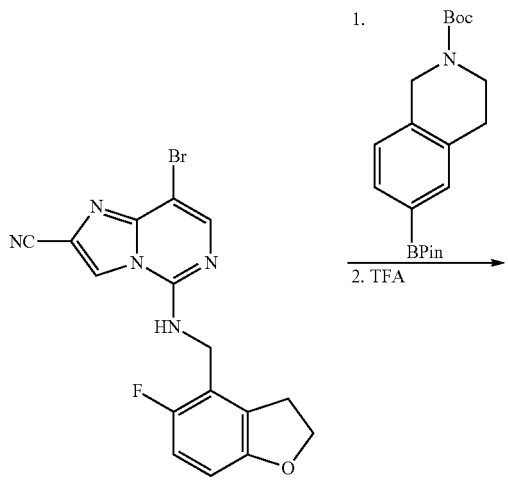

A mixture of 8-bromo-5-(((5-fluoro-2,3-dihydrobenzofuran-4-yl)methyl)amino)imidazo[1,2-c]pyrimidine-2-carbonitrile (70.0 mg, 180 μmol, 1.00 equiv), tert-butyl 6-(4,4,5,5-tetramethyl-1,3,2-dioxaborolan-2-yl)-3,4-dihydro-1H-isoquinoline-2-carboxylate (97.2 mg, 270 μmol, 1.50 equiv), sodium bicarbonate (30.3 mg, 361 μmol, 14.0 uL, 2.00 equiv), Pd(dppf)Cl₂ (13.2 mg, 18.0 μmol, 0.10 equiv) in dioxane (1.00 mL) and water (0.30 mL) was purged with nitrogen and then stirred at 100° C. for 2 h. The reaction was filtered and concentrated in vacuo to give a residue. The residue was purified by prep-TLC (petroleum ether/ethyl acetate=2/1) to afford tert-butyl 6-(2-cyano-5-(((5-fluoro-2,3-dihydrobenzofuran-4-yl)methyl)amino)imidazo[1,2-c]pyrimidin-8-yl)-3,4-dihydroisoquinoline-2(1H)-carboxylate (67.0 mg, 124 μmol, 68.7% yield) as a yellow solid.

$^1$H NMR (400 MHz, CD$_3$OD) δ=8.61 (s, 1H), 7.98 (s, 1H), 7.69 (s, 1H), 7.67 (br d, J=8.0 Hz, 1H), 7.24 (d, J=8.0 Hz, 1H), 6.87 (t, J=9.2 Hz, 1H), 6.66 (dd, J=4.0, 8.8 Hz, 1H), 4.83 (br s, 2H), 4.63-4.58 (m, 4H), 3.70 (br t, J=6.0 Hz, 2H), 3.38 (br t, J=8.8 Hz, 2H), 2.94 (br t, J=6.0 Hz, 2H), 1.53 (s, 9H).

To a solution of tert-butyl 6-(2-cyano-5-(((5-fluoro-2,3-dihydrobenzofuran-4-yl)methyl)amino)imidazo[1,2-c]pyrimidin-8-yl)-3,4-dihydroisoquinoline-2(1H)-carboxylate (50.0 mg, 92.5 μmol, 1.00 equiv) in dichloromethane (1.00 mL) was added trifluoroacetic acid (10.6 mg, 92.5 μmol, 6.85 μL, 1.00 equiv), the mixture was stirred at room temperature for 0.5 h. The mixture was filtered and concentrated in vacuo to give a residue. The residue was purified by prep-HPLC (hydrochloric acid conditions) to afford 5-(((5-fluoro-2,3-dihydrobenzofuran-4-yl)methyl)amino)-8-(1,2,3,4-tetrahydroisoquinolin-6-yl)imidazo[1,2-c]pyrimidine-2-carbonitrile hydrochloride salt (12.4 mg, 25.7 μmol, 27.8% yield, 98.6% purity) as a yellow solid. LC-MS [M+1]: 441.1.

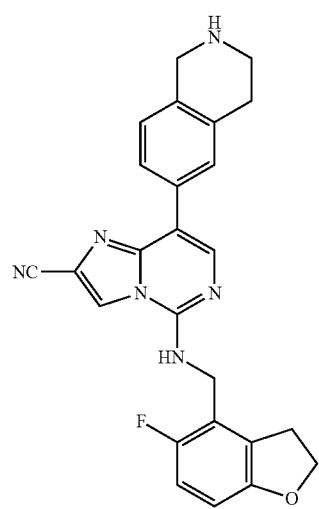

$^1$H NMR (400 MHz, DMSO-d$_6$) δ=9.43 (br s, 2H), 9.08 (s, 1H), 8.77 (br s, 1H), 8.10 (s, 1H), 7.86 (br d, J=8.4 Hz, 1H), 7.84 (br s, 1H), 7.31 (br d, J=7.6 Hz, 1H), 6.94 (br t, J=9.6 Hz, 1H), 6.70 (br dd, J=3.6, 8.4 Hz, 1H), 4.73 (br d, J=4.4 Hz, 2H), 4.54 (br t, J=8.8 Hz, 2H), 4.30 (br s, 2H), 3.30-3.27 (m, 2H), 3.26-3.19 (m, 2H), 3.09 (br d, J=5.2 Hz, 2H).

EXAMPLE 204 was prepared following the procedure set forth in EXAMPLE 193 and using the general reactions schemes and intermediates described herein.

TABLE 11

Characterization of EXAMPLE 194

| Ex. # | Structure | $^1$H NMR |
|---|---|---|
| 204 | 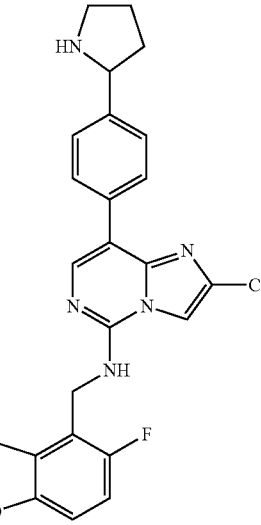<br>5-(((5-fluoro-2,3-dihydrobenzofuran-4-yl)methyl)amino)-8-(4-(pyrrolidin-2-yl)phenyl)imidazo[1,2-c]pyrimidine-2-carbonitrile | $^1$H NMR (400 MHz, DMSO-d$_6$) δ = 8.93 (s, 1H), 8.47 (br s, 1H), 8.07 (s, 1H), 7.88 (d, J = 8.0 Hz, 2H), 7.45 (d, J = 8.4 Hz, 2H), 6.99-6.92 (m, 1H), 6.71 (dd, J = 4.0, 8.8 Hz, 1H), 4.74 (br d, J = 4.0 Hz, 2H), 4.55 (t, J = 8.8 Hz, 2H), 4.08 (t, J = 7.6 Hz, 1H), 3.10-3.01 (m, 2H), 2.95-2.85 (m, 2H), 2.21-2.07 (m, 1H), 1.85-1.73 (m, 2H), 1.62-1.43 (m, 1H).<br>LC-MS [M + 1]: 455.3. |
| 205 | 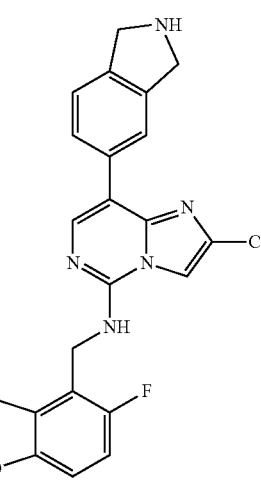<br>5-(((5-fluoro-2,3-dihydrobenzofuran-4-yl)methyl)amino)-8-(isoindolin-5-yl)imidazo[1,2-c]pyrimidine-2-carbonitrile | $^1$H NMR (400 MHz, Methanol-d4) δ 7.83 (s, 1H), 7.78-7.69 (m, 1H), 7.42 (d, J = 7.9 Hz, 1H), 6.93-6.80 (m, 1H), 6.66 (dd, J = 8.7, 3.9 Hz, 1H), 4.59 (t, J = 8.7 Hz, 2H), 4.34 (bs, 4H), 3.38 (t, J = 8.7 Hz, 2H).<br>LCMS [M + 1]: 427.2. |

Example 206

5-(((5-fluoro-2,3-dihydrobenzofuran-4-yl)methyl)amino)-8-(4-(2-methoxyethoxy)-2-methylphenyl)imidazo[1,2-c]pyrimidine-2-carbonitrile

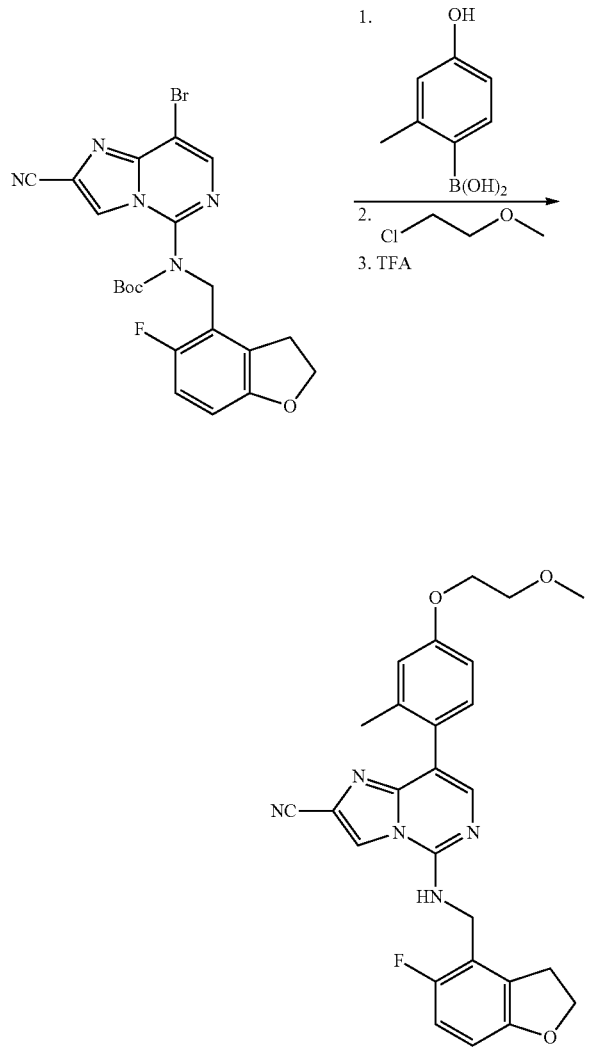

To a solution of (4-hydroxy-2-methyl-phenyl)boronic acid (30.5 mg, 201 μmol, 1.40 equiv), tert-butyl (8-bromo-2-cyanoimidazo[1,2-c]pyrimidin-5-yl)((5-fluoro-2,3-dihydrobenzofuran-4-yl)methyl)carbamate (70.0 mg, 143 μmol, 1.00 equiv) in dioxane (1.00 mL) and water (0.20 mL) were added Pd(dppf)Cl$_2$ (10.5 mg, 14.3 μmol, 0.10 equiv) and sodium bicarbonate (24.1 mg, 286 μmol, 2.00 equiv) under a nitrogen atmosphere. The mixture was stirred at 100° C. for 2 h and subsequently was concentrated in vacuo to give a residue. The residue was purified by prep-TLC (SiO$_2$, petroleum ether/ethyl acetate=1/1) to afford tert-butyl(2-cyano-8-(4-hydroxy-2-methylphenyl)imidazo[1,2-c]pyrimidin-5-yl)(5-fluoro-2,3-dihydrobenzofuran-4-yl)methyl)carbamate (70.0 mg, 136 μmol, 94.7% yield) as a yellow solid. LCMS [M+1]: 516.1.

$^1$H NMR (400 MHz, DMSO-d$_6$) δ=9.64 (s, 1H), 8.71 (s, 1H), 7.99 (s, 1H), 7.17 (d, J=8.0 Hz, 1H), 6.82-6.74 (m, 2H), 6.72 (dd, J=2.4, 8.4 Hz, 1H), 6.62 (dd, J=4.0, 8.8 Hz, 1H), 5.04 (s, 2H), 4.54 (t, J=8.8 Hz, 2H), 3.30-3.26 (m, 2H), 2.02 (s, 3H), 1.34 (s, 9H).

To a solution tert-butyl (2-cyano-8-(4-hydroxy-2-methylphenyl)imidazo[1,2-c]pyrimidin-5-yl)((5-fluoro-2,3-dihydrobenzofuran-4-yl)methyl)carbamate (70.0 mg, 135 μmol, 1.00 equiv), 1-chloro-2-methoxy-ethane (51.4 mg, 543 μmol, 49.4 μL, 4.00 equiv) in acetonitrile (1.00 mL) was added potassium carbonate (37.5 mg, 272 μmol, 2.00 equiv). The mixture was stirred at 85° C. for 12 h. The mixture was concentrated in vacuo to afford tert-butyl (2-cyano-8-(4-(2-methoxyethoxy)-2-methylphenyl)imidazo[1,2-c]pyrimidin-5-yl)((5-fluoro-2,3-dihydrobenzofuran-4-yl)methyl)carbamate (30.0 mg, crude) as a gray solid. LCMS [M+1]: 574.6.

To a solution of tert-butyl (2-cyano-8-(4-(2-methoxyethoxy)-2-methylphenyl)imidazo[1,2-c]pyrimidin-5-yl)((5-fluoro-2,3-dihydrobenzofuran-4-yl)methyl)carbamate (25.0 mg, 43.6 μmol, 1.00 equiv) in dichloromethane (1.00 mL) was added trifluoroacetic acid (0.30 mL). The mixture was stirred at room temperature for 1 h. The mixture was concentrated in vacuo to give a residue. The residue was purified by prep-HPLC (neutral conditions) to afford 5-[(5-fluoro-2,3-dihydrobenzofuran-4-yl)methylamino]-8-[4-(2-methoxyethoxy)-2-methyl-phenyl]imidazo[1,2-c]pyrimidine-2-carbonitrile (6.50 mg, 13.7 μmol, 31.5% yield, 99.9% purity) as a gray solid. LCMS [M+1]: 474.4.

$^1$H NMR (400 MHz, DMSO-d$_6$) δ=8.89 (s, 1H), 8.39 (br s, 1H), 7.65 (s, 1H), 7.18 (d, J=8.4 Hz, 1H), 6.99-6.92 (m, 1H), 6.90 (d, J=2.4 Hz, 1H), 6.83 (dd, J=2.8, 8.4 Hz, 1H), 6.71 (dd, J=4.0, 8.8 Hz, 1H), 4.71 (br d, J=3.6 Hz, 2H), 4.55 (t, J=8.8 Hz, 2H), 4.18-4.10 (m, 2H), 3.70-3.66 (m, 2H), 2.12 (s, 3H).

Example 207

8-(4-((dimethylamino)methyl)-2-methylphenyl)-5-(((5-fluoro-3-hydroxy-2,3-dihydrobenzofuran-4-yl)methyl)amino)imidazo[1,2-c]pyrimidine-2-carbonitrile

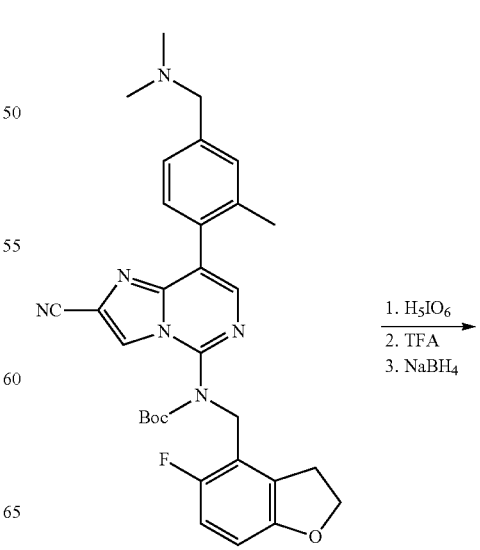

-continued

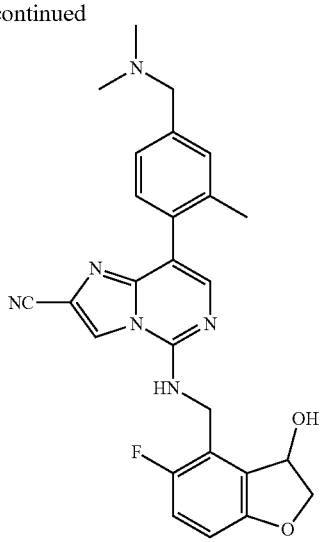

A mixture of tert-butyl (2-cyano-8-(4-((dimethylamino)methyl)-2-methylphenyl)imidazo[1,2-c]pyrimidin-5-yl)((5-fluoro-2,3-dihydrobenzofuran-4-yl)methyl)carbamate (200 mg, 359 μmol, 1.00 equiv), chromium trioxide (53.9 mg, 539 μmol, 20.0 μL, 1.50 equiv) and periodic acid (221 mg, 970 μmol, 221 μL, 2.70 equiv) in acetonitrile (1.00 mL) was stirred at room temperature for 2 h. The mixture was filtered and concentrated under reduced pressure to give a residue. The residue was purified by prep-HPLC (trifluoroacetic acid conditions) to afford tert-butyl (2-cyano-8-(4-((dimethylamino)methyl)-2-methylphenyl)imidazo[1,2-c]pyrimidin-5-yl)((5-fluoro-3-oxo-2,3-dihydrobenzofuran-4-yl)methyl)carbamate (30.0 mg, 48.9 μmol, 13.6% yield, 93.0% purity) as a white solid. LCMS [M+1]: 571.3.

A mixture of tert-butyl (2-cyano-8-(4-((dimethylamino)methyl)-2-methylphenyl)imidazo[1,2-c]pyrimidin-5-yl)((5-fluoro-3-oxo-2,3-dihydrobenzofuran-4-yl)methyl)carbamate (30.0 mg, 52.6 μmol, 1.00 equiv) and trifluoroacetic acid (1.54 g, 13.5 mmol, 1.00 mL, 257 equiv) in dichloromethane (3.00 mL) was stirred at room temperature for 1 h. The mixture was filtered and concentrated under reduced pressure to give a residue that was purified by prep-HPLC (trifluoroacetic acid conditions) to afford 8-(4-((dimethylamino)methyl)-2-methylphenyl)-5-(((5-fluoro-3-oxo-2,3-dihydrobenzofuran-4-yl)methyl)amino)imidazo[1,2-c]pyrimidine-2-carbonitrile (20.0 mg, 31.0 μmol, 59.0% yield, 90.6% purity, trifluoroacetic acid salt) as a purple solid. LC-MS [M+1]: 471.1.

$^1$H NMR (400 MHz, DMSO-d6) δ=9.64 (br s, 1H), 8.85 (s, 1H), 8.33 (t, J=4.4 Hz, 1H), 7.72 (s, 1H), 7.65 (t, J=9.2 Hz, 1H), 7.48-7.38 (m, 3H), 7.34 (dd, J=3.2, 8.8 Hz, 1H), 5.05 (d, J=4.4 Hz, 2H), 4.91 (s, 2H), 4.30 (br s, 2H), 2.79 (br s, 6H), 2.21 (s, 3H).

A mixture of 8-(4-((dimethylamino)methyl)-2-methylphenyl)-5-(((5-fluoro-3-oxo 2,3-dihydrobenzofuran-4-yl)methyl)amino)imidazo[1,2-c]pyrimidine-2-carbonitrile (10.0 mg, 21.3 μmol, 1.00 equiv) and sodium borohydride (1.61 mg, 42.5 μmol, 2.00 equiv) in methyl alcohol (1.00 mL) was stirred at 0° C. for 2.5 h. The mixture was concentrated under reduced pressure to give a residue. The mixture was purified by prep-HPLC (neutral conditions) to afford 8-(4-((dimethylamino)methyl)-2-methylphenyl)-5-(((5-fluoro-3-hydroxy-2,3-dihydrobenzofuran-4-yl)methyl) amino)imidazo[1,2-c]pyrimidine-2-carbonitrile (3.69 mg, 7.80 μmol, 36.7% yield, 99.9% purity) as an off-white solid. LC-MS [M+1]:473.4.

Example 208

5-(2-cyano-5-(((5-fluoro-2,3-dihydrobenzofuran-4-yl)methyl)amino)imidazo[1,2-c]pyrimidin-8-yl)-N,1-dimethyl-1H-pyrazole-3-carboxamide

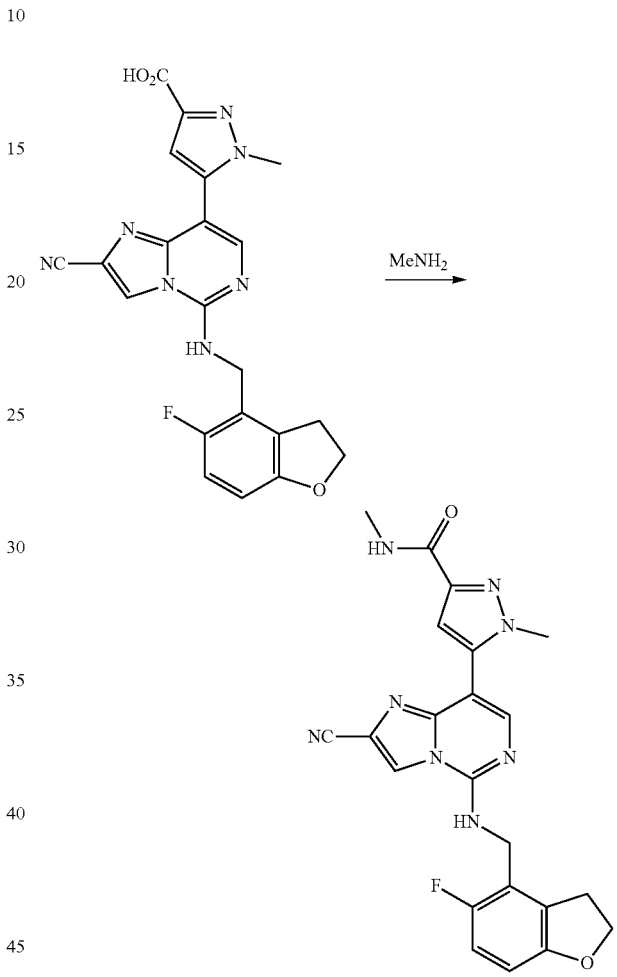

To a solution of 5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxylic acid (150 mg, 346 μmol, 1.00 equiv), DIEA (135 mg, 1.04 mmol, 182 μL, 3.02 equiv) and methylamine (2 M in THF, 519.16 μL, 3.00 equiv) in DMF (1.50 mL) was added HATU (200 mg, 526 μmol, 1.52 equiv). The mixture was stirred at room temperature for 1 h. The reaction mixture was quenched with water (5.00 mL) and filtered to afford the crude product. The crude product was triturated with methanol (5.00 mL) and collected by filtration to provide 5-(2-cyano-5-(((5-fluoro-2,3-dihydrobenzofuran-4-yl)methyl)amino)imidazo[1,2-c]pyrimidin-8-yl)-N,1-dimethyl-1H-pyrazole-3-carboxamide (130 mg, 256 μmol, 74.0% yield, 88.0% purity) as a yellow solid. A portion (40 mg) of the material was purified by prep-HPLC (neutral conditions) to give 5-(2-cyano-5-(((5-fluoro-2,3-dihydrobenzofuran-4-yl)methyl)amino)imidazo[1,2-c]pyrimidin-8-yl)-N,1-dimethyl-1H-pyrazole-3-carboxamide (8.4 mg, 17.5 μmol, 22.2% yield, 93.0% purity) as a white solid. LCMS [M+1]; 447.2.

369

$^1$H NMR (400 MHz, DMSO-d6) δ=8.92 (s, 1H), 8.12 (d, J=4.8 Hz, 1H), 7.94 (s, 1H), 6.95 (t, J=9.6 Hz, 1H), 6.81 (s, 1H), 6.71 (dd, J=4.0, 8.8 Hz, 1H), 4.73 (s, 2H), 4.55 (t, J=8.8 Hz, 2H), 3.83 (s, 3H), 3.30-3.32 (m, 2H), 2.76 (d, J=4.8 Hz, 3H).

Example 209

5-(((5-fluoro-2,3-dihydrobenzofuran-4-yl)methyl)amino)-8-(1-methyl-3-(morpholine-4-carbonyl)-1H-pyrazol-5-yl)imidazo[1,2-c]pyrimidine-2-carbonitrile

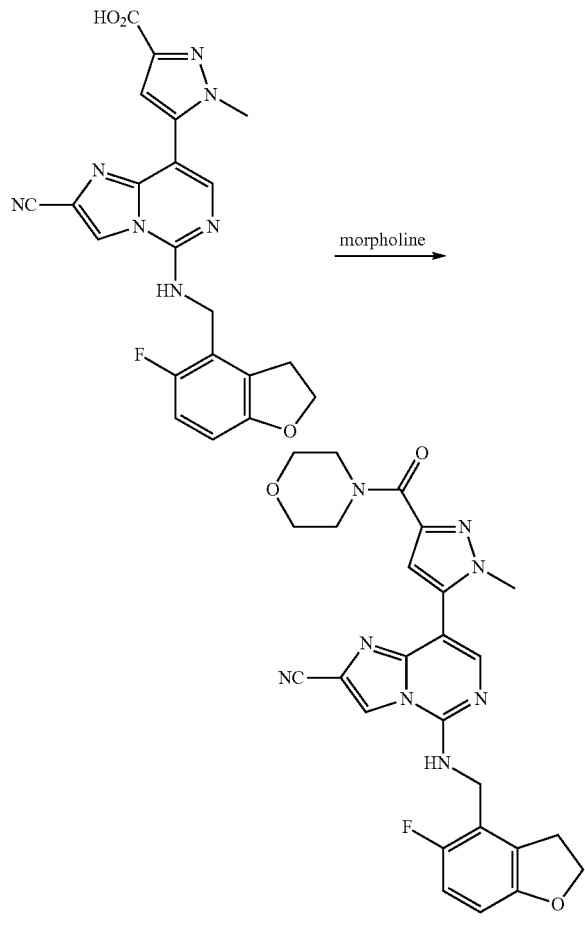

To a solution of 5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxylic acid (50.0 mg, 115 µmol, 1.00 equiv) and morpholine (20.00 mg, 229 µmol, 20.2 uL, 1.99 equiv) in DMF (1.00 mL) was added HATU (83.0 mg, 173 µmol, 1.50 equiv) and DIEA (45.0 mg, 348 µmol, 60.7 µL, 3.02 equiv). The mixture was stirred at room temperature for 1 h. The reaction mixture was quenched with water (15.0 mL) and extracted with dichloromethane (10.0 mL×3). The combined organic layer was washed with water (20.0 mL), dried over anhydrous sodium sulfate, filtered and concentrated under reduced pressure to give a residue. The residue was purified by prep-HPLC (neutral conditions) to afford 5-(((5-fluoro-2,3-dihydrobenzofuran-4-yl)methyl)amino)-8-(1-methyl-3-(morpholine-4-carbonyl)-1H-pyrazol-5-yl)imidazo[1,2-c]pyrimidine-2-carbonitrile (6.10 mg, 11.6 µmol, 10.0% yield, 95.3% purity) as a white solid. LCMS [M+1]: 503.2.

$^1$H NMR (400 MHz, DMSO-d6) δ=8.92 (s, 1H), 7.94 (s, 1H), 6.95 (t, J=9.6 Hz, 1H), 6.77 (s, 1H), 6.71 (dd, J=4.0, 8.8 Hz, 1H), 4.73 (s, 2H), 4.55 (t, J=8.8 Hz, 2H), 4.02 (s, 2H), 3.81 (s, 3H), 3.63 (s, 6H), 3.32-3.30 (m, 2H).

Example 210

8-(3-((dimethylamino)methyl)-1-methyl-1H-pyrazol-5-yl)-5-(((5-fluoro-2,3-dihydrobenzofuran-4-yl)methyl)amino)imidazo[1,2-c]pyrimidine-2-carbonitrile

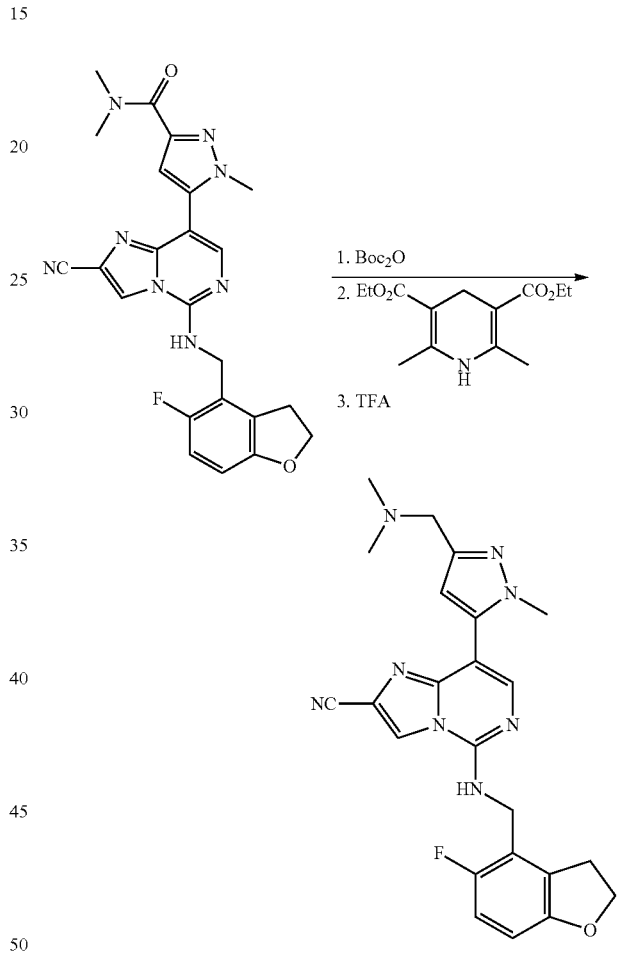

To a solution of 5-(2-cyano-5-(((5-fluoro-2,3-dihydrobenzofuran-4-yl)methyl)amino)imidazo[1,2-c]pyrimidin-8-yl)-N,N,1-trimethyl-1H-pyrazole-3-carboxamide (100 mg, 217 µmol, 1.00 equiv) in THF (1.00 mL) was added di-tert-butyl dicarbonate (56.9 mg, 261 µmol, 59.9 uL, 1.20 equiv) and DMAP (2.65 mg, 21.7 µmol, 0.10 equiv). The mixture was stirred at 60° C. for 4 h. The mixture was concentrated under reduced pressure to give a residue. The residue was purified by column chromatography (SiO$_2$, petroleum ether/ethyl acetate=3/1 to 1/1) to afford tert-butyl (2-cyano-8-(3-(dimethylcarbamoyl)-1-methyl-1H-pyrazol-5-yl)imidazo[1,2-c]pyrimidin-5-yl)((5-fluoro-2,3-dihydrobenzofuran-4-yl)methyl)carbamate (80.0 mg, 143 µmol, 65.7% yield) as an off-white solid. LCMS [M+1]: 561.6.

$^1$H NMR (400 MHz, CDCl$_3$) δ=8.07 (s, 1H), 7.84 (s, 1H), 7.00 (s, 1H), 6.74-6.65 (m, 1H), 6.64-6.56 (m, 1H), 5.14 (s,

2H), 4.60 (t, J=8.8 Hz, 2H), 3.95 (s, 3H), 3.42 (s, 3H), 3.34 (br t, J=8.8 Hz, 2H), 3.14 (s, 3H), 1.43 (s, 9H).

To aflame dried RBF charged with tert-butyl (2-cyano-8-(3-(dimethylcarbamoyl)-1-methyl-1H-pyrazol-5-yl)imidazo[1,2-c]pyrimidin-5-yl)((5-fluoro-2,3-dihydrobenzofuran-4-yl)methyl)carbamate (30.0 mg, 53.5 μmol, 00 equiv) was added dichloromethane (1.00 mL) followed by trifluoromethanesulfonic anhydride (30.2 mg, 107 μmol, 17.7 μL, 2.00 equiv). The resultant solution was stirred at room temperature under an atmosphere of nitrogen for 30 min followed by the addition diethyl 2,6-dimethyl-1,4-dihydropyridine-3,5-dicarboxylate (54.2 mg, 214 μmol, 4.00 equiv). The reaction mixture was stirred at room temperature for 2 h. The mixture was concentrated to give a residue. The residue was purified by prep-TLC (SiO₂ dichloromethane/methanol=10/1) to afford tert-butyl (2-cyano-8-(3-((dimethylamino)methyl)-1-methyl-1H-pyrazol-5-yl)imidazo[1,2-c]pyrimidin-5-yl)(5-fluoro-2,3-dihydrobenzofuran-4-yl)methyl)carbamate (30.0 mg) as a light yellow solid. LCMS [M+1]: 547.3.

A mixture of tert-butyl (2-cyano-8-(3-((dimethylamino)methyl)-1-methyl-1H-pyrazol-5-yl)imidazo[1,2-c]pyrimidin-5-yl)((5-fluoro-2,3-dihydrobenzofuran-4-yl)methyl)carbamate (30.0 mg, 54.9 μmol, 1.00 equiv) in trifluoroacetic acid (0.30 mL) and dichloromethane (1.00 mL) was stirred at room temperature for 1 h. The reaction mixture was concentrated to give a residue. The residue was purified by prep-HPLC (neutral conditions) to afford 8-(3-((dimethylamino)methyl)-1-methyl-1H-pyrazol-5-yl)-5-(((5-fluoro-2,3-dihydrobenzofuran-4-yl)methyl)amino)imidazo[1,2-c]pyrimidine-2-carbonitrile (2.50 mg, 5.46 μmol, 9.96% yield, 97.6% purity) as a yellow solid. LCMS [M+1]: 447.2.

¹H NMR (400 MHz, CD₃OD) δ=8.63 (s, 1H), 7.91 (s, 1H), 6.94-6.83 (m, 1H), 6.67 (dd, J=4.0, 8.8 Hz, 1H), 6.48 (s, 1H), 4.60 (t, J=8.8 Hz, 2H), 3.80 (s, 3H), 3.56 (s, 2H), 3.40 (br t, J=8.8 Hz, 2H), 2.33 (s, 6H).

Example 211

5-(((5-fluoro-2,3-dihydrobenzofuran-4-yl)methyl)amino)-8-(1-methyl-3-((methylamino)methyl)-1H-pyrazol-5-yl)imidazo[1,2-c]pyrimidine-2-carbonitrile

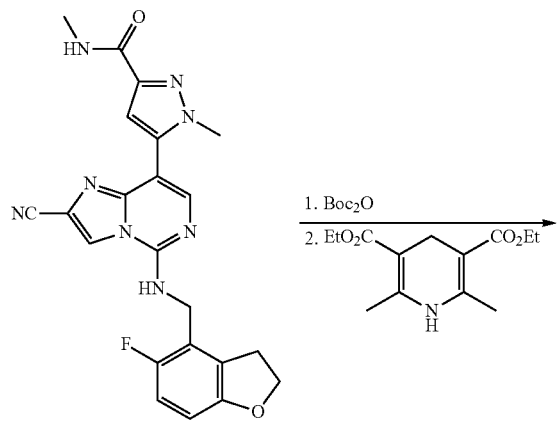

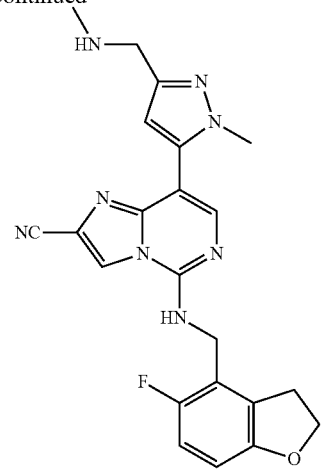

To a solution of 5-(2-cyano-5-(((5-fluoro-2,3-dihydrobenzofuran-4-yl)methyl)amino)imidazo[1,2-c]pyrimidin-8-yl)-N,1-dimethyl-1H-pyrazole-3-carboxamide (80.0 mg, 157 μmol, 1.00 equiv) in THF (1.50 mL) was added di-tert-butyl dicarbonate (41.3 mg, 189 μmol, 1.20 equiv) and DMAP (2.06 mg, 16.9 μmol, 0.10 equiv). The mixture was stirred at 60° C. for 4 h. The reaction mixture was concentrated under reduced pressure to give a residue. The residue was purified by column chromatography (SiO₂, petroleum ether/ethyl acetate=3/1 to 1/1) to afford tert-butyl (2-cyano-8-(1-methyl-3-(methylcarbamoyl)-1H-pyrazol-5-yl)imidazo[1,2-c]pyrimidin-5-yl)((5-fluoro-2,3-dihydrobenzofuran-4-yl)methyl)carbamate (50.0 mg, 91.5 μmol, 58.0% yield) as a yellow solid. LCMS [M+1]: 547.2.

To a flame-dried 10 mL round-bottom flask was added tert-butyl(2-cyano-8-(1-methyl-3-(methylcarbamoyl)-1H-pyrazol-5-yl)imidazo[1,2-c]pyrimidin-5-yl)((5-fluoro-2,3-dihydrobenzofuran-4-yl)methyl)carbamate (25.0 mg, 45.7 μmol, 1.00 equiv) followed by dichloromethane (1.80 mL) and 2-fluoropyridine (9.80 mg, 101 μmol, 8.67 μL, 2.21 equiv). The solution was then cooled to −78° C. and stirred for 10 min. To this solution was added dropwise Tf₂O (27.1 mg, 96.1 μmol, 15.9 μL, 2.10 equiv) and the reaction was stirred for an additional 10 min. The solution was warmed at 0° C. and the reaction was stirred for 10 min. To this solution was added dropwise Et₃SiH (11.7 mg, 101 μmol, 16.07 μL, 2.20 equiv) and the reaction was stirred for 10 min. The solution was allowed to warm to room temperature and was stirred for 5 h. To the mixture was added diethyl 1,4-dihydro-2,6-dimethyl-3,5-pyridinedicarboxylate (34.8 mg, 137.2 μmol, 3.00 equiv) and the yellow suspension was stirred for 12 h at room temperature. The reaction mixture was concentrated to give a residue. The residue was purified by prep-TLC (SiO₂, dichloromethane/methanol=10/1) to give partially pure material. This material was purified by prep-HPLC (HCl conditions) to afford 5-(((5-fluoro-2,3-dihydrobenzofuran-4-yl)methyl)amino)-8-(1-methyl-3-((methylamino)methyl)-1H-pyrazol-5-yl)imidazo[1,2-c]pyrimidine-2-carbonitrile hydrochloride salt (2.50 mg, 5.75 umol, 12.6% yield, 99.4% purity) as an off-white solid. LCMS [M+1]: 433.2.

¹H NMR (400 MHz, CD₃OD) δ=8.65 (s, 1H), 7.90 (s, 1H), 6.91-6.81 (m, 1H), 6.65 (dd, J=4.0, 8.8 Hz, 1H), 6.58 (s, 1H), 4.63-4.54 (m, 2H), 4.26-4.19 (m, 2H), 3.82 (s, 3H), 3.42-3.35 (m, 2H), 3.32 (s, 2H), 2.77 (s, 3H).

Example 212

8-(3-cyano-1-methyl-1H-pyrazol-5-yl)-5-(((5-fluoro-2,3-dihydrobenzofuran-4-yl)methyl)amino)imidazo[1,2-c]pyrimidine-2-carbonitrile

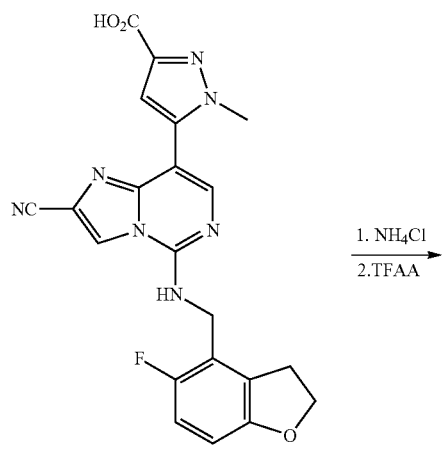

To a solution of 5-[2-cyano-5-[(5-fluoro-2,3-dihydrobenzofuran-4-yl)methylamino]imidazo[1,2-c]pyrimidin-8-yl]-1-methyl-pyrazole-3-carboxylic acid (100 mg, 185 μmol, 1.00 equiv) and ammonium chloride (30.0 mg, 561 μmol, 3.04 equiv) in DMF (2.00 mL) was added HATU (105 mg, 276 μmol, 1.50 equiv) and DIEA (72.0 mg 557 μmol, 97.0 μL, 3.02 equiv). The mixture was stirred at room temperature for 3 h. The mixture was diluted with water (20.0 mL) at which time a precipitate formed. The solid was filtered and dried under reduced pressure to give the crude product. The crude product was triturated with methanol (10.0 mL) and filtered to afford 5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxamide (44 mg) as a yellow solid that was used into the next step without further purification. LC-MS [M+1]: 433.1.

To a mixture of 5-(2-cyano-5-(((5-fluoro-2,3-dihydrobenzofuran-4-yl)methyl)amino)imidazo[1,2-c]pyrimidin-8-yl)-1-methyl-1H-pyrazole-3-carboxamide (44.0 mg, 102 μmol, 1.00 equiv), TEA (206 mg, 2.04 mmol, 283 μL, 20.0 equiv) in anhydrous THF (0.50 mL) was added TFAA (192 mg, 916 μmol, 127 μL, 9.00 equiv) at 0° C. with stirring. The resulting mixture was warmed to room temperature and stirred for 12 h. The reaction mixture was concentrated to give a residue. The residue was purified by prep-TLC (SiO$_2$, petroleum ether/ethyl acetate=1/1). The obtained material was purified again by prep-HPLC (hydrochloric acid conditions) to give 8-(3-cyano-1-methyl-1H-pyrazol-5-yl)-5-(((5-fluoro-2,3-dihydrobenzofuran-4-yl)methyl)amino)imidazo[1,2-c]pyrimidine-2-carbonitrile (6.10 mg, 14.6 μmol, 14.4% yield, 99.3% purity) as a white solid. LC-MS [M+1]: 415.2.

$^1$H NMR (400 MHz, CD$_3$OD) δ=8.63 (s, 1H), 7.93 (s, 1H), 7.34 (s, 1H), 6.97 (s, 1H), 6.85 (t, J=9.6 Hz, 1H), 6.65 (dd, J=3.6, 8.8 Hz, 1H), 4.76 (s, 2H), 4.58 (t, J=8.8 Hz, 2H), 3.89 (s, 3H), 3.39 (br t, J=8.8 Hz, 2H).

Examples 213 and 214

5-(((5-fluoro-2,3-dihydrobenzofuran-4-yl)methyl)amino)-8-(2-methyl-4-(pyrrolidin-2-yl)phenyl)imidazo[1,2-c]pyrimidine-2-carbonitrile

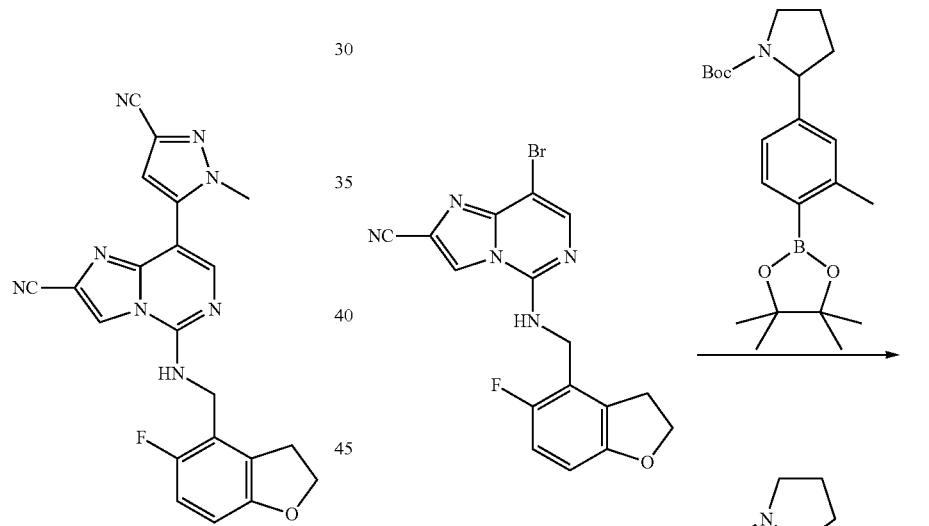

A mixture of 8-bromo-5-(((5-fluoro-2,3-dihydrobenzofuran-4-yl)methyl)amino)imidazo[1,2-c]pyrimidine-2-carbonitrile (255 mg, 657 μmol, 1.00 equiv), tert-butyl 2-[3-methyl-4-(4,4,5,5-tetramethyl-1,3,2-dioxaborolan-2-yl)phenyl]pyrrolidine-1-carboxylate (280 mg, 723 μmol, 1.10 equiv), Pd(dppf)Cl$_2$ (48.1 mg, 65.7 μmol, 0.10 equiv) and sodium bicarbonate (166 mg, 1.97 mmol, 76.7 μL, 3.00 equiv) in dioxane (3.00 mL) and water (0.60 mL) was purged with nitrogen and then stirred at 95° C. for 2 h. The mixture was filtered and concentrated under reduced pressure to give a residue. The residue was purified by prep-TLC (SiO$_2$, petroleum ether/ethylacetate=1/1) to afford tert-butyl 2-(4-(2-cyano-5-(((5-fluoro-2,3-dihydrobenzofuran-4-yl)methyl)amino)imidazo[1,2-c]pyrimidin-8-yl)-3-methylphenyl)pyrrolidine-1-carboxylate (160 mg, 38.7% yield, 90.4% purity) as a yellow solid.

$^1$H NMR (400 MHz, CD$_3$OD) δ=8.61 (s, 1H), 7.69 (s, 1H), 7.26 (br d, J=7.6 Hz, 1H), 7.15 (s, 1H), 7.10 (br d, J=7.6 Hz, 1H), 6.92-6.84 (m, 1H), 6.70-6.62 (m, 1H), 4.82-4.75 (m, 1H), 4.62-4.56 (m, 4H), 3.65-3.60 (m, 2H), 3.39 (t, J=8.8 Hz, 2H), 2.40 (br s, 1H), 2.20 (s, 3H), 2.0-1.80 (m, 3H), 1.49 (br s, 3H), 1.31-1.23 (m, 6H).

Chiral SFC separation of tert-butyl 2-(4-(2-cyano-5-(((5-fluoro-2,3-dihydrobenzofuran-4-yl)methyl)amino)imidazo[1,2-c]pyrimidin-8-yl)-3-methylphenyl)pyrrolidine-1-carboxylate provided enantiomerically pure intermediates A and B.

To a solution of A or B (60.0 mg, 105 μmol, 1.00 equiv) was added TFA (2.31 g, 20.3 mmol, 1.50 mL, 192 equiv). The mixture was stirred at room temperature for 0.5 h. The reaction mixture was filtered and concentrated under reduced pressure to give a residue. The residue was purified by prep-TLC (SiO$_2$, dichloromethane/methanol=10/1) to afford 5-(((5-fluoro-2,3-dihydrobenzofuran-4-yl)methyl)amino)-8-(2-methyl-4-(pyrrolidin-2-yl)phenyl)imidazo[1,2-c]pyrimidine-2-carbonitrile.

EXAMPLE 213: (18.06 mg, 34.6% yield, 94.6% purity), LCMS [M+1]; 469.1, (Amycoat 50×4.6 mm I.D., 3 μm; 30% MeOH (0.05% DEA) in CO$_2$: 3 ml/min; t$_r$=1.32 min).

$^1$H NMR (400 MHz, CD$_3$OD) δ=8.60 (s, 1H), 7.68 (s, 1H), 7.35 (s, 1H), 7.28 (s, 2H), 6.85 (t, J=9.2 Hz, 1H), 6.64 (dd, J=4.0, 8.8 Hz, 1H), 4.81 (s, 2H), 4.57 (t, J=8.8 Hz, 2H), 4.20 (dd, J=7.2, 8.8 Hz, 1H), 3.40-3.35 (m, 2H), 3.29-3.24 (m, 1H), 3.11-3.03 (m, 1H), 2.37-2.26 (m, 1H), 2.19 (s, 3H), 2.09-1.95 (m, 2H), 1.94-1.82 (m, 1H).

EXAMPLE 214: (18.1 mg, 35.7 μmol, 33.8% yield, 92.4% purity), LCMS [M+1]: 469.1, (Amycoat 50×4.6 mm I.D., 3 μm; 30% MeOH (0.05% DEA) in CO$_2$: 3 mL/min; t$_r$=3.22 min).

$^1$H NMR (400 MHz, CD$_3$OD) δ=8.61 (s, 1H), 7.69 (s, 1H), 7.38 (s, 1H), 7.32 (d, J=0.8 Hz, 2H), 6.89-6.82 (m, 1H), 6.64 (dd, J=4.0, 8.8 Hz, 1H), 4.81 (s, 2H), 4.58 (t, J=8.8 Hz, 2H), 4.42-4.36 (m, 1H), 3.40-3.35 (m, 2H), 3.27-3.20 (m, 1H), 2.45-2.35 (m, 1H), 2.21 (s, 3H), 2.19-2.12 (m, 1H), 2.11-1.98 (m, 2H).

Example 215

5-(2-cyano-5-(((5-fluoro-2,3-dihydrobenzofuran-4-yl)methyl)amino)imidazo[1,2-c]pyrimidin-8-yl)picolinic acid

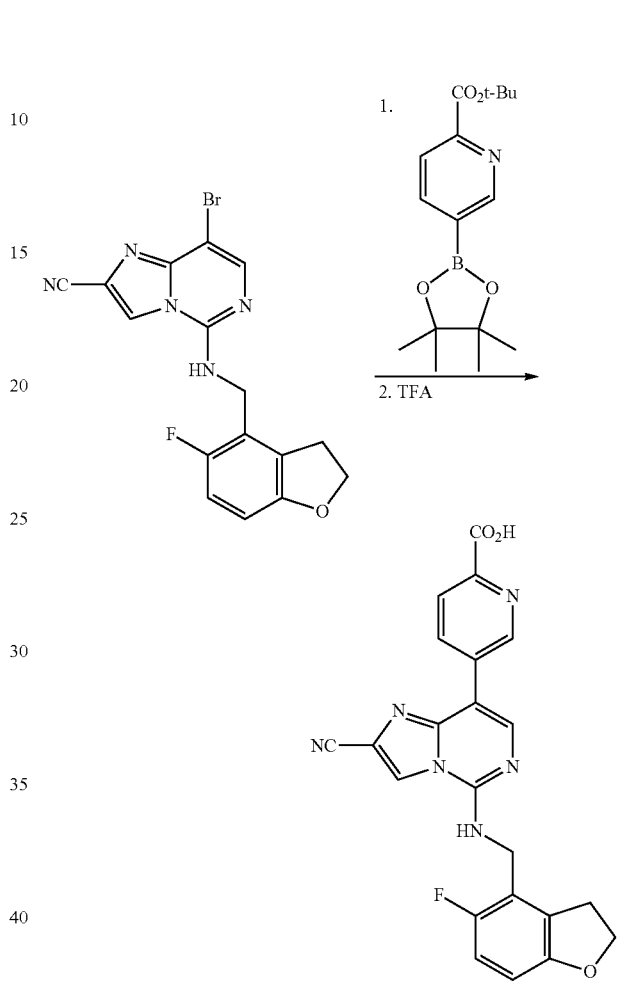

A mixture of 8-bromo-5-(((5-fluoro-2,3-dihydrobenzofuran-4-yl)methyl)amino)imidazo[1,2-c]pyrimidine-2-carbonitrile (39.0 mg, 100 μmol, 1.00 equiv), tert-butyl 5-(4,4,5,5-tetramethyl-1,3,2-dioxaborolan-2-yl)pyridine-2-carboxylate (73.6 mg, 121 μmol, 1.20 equiv), sodium bicarbonate (25.3 mg, 301 μmol, 3.00 equiv) and Pd(dppf)Cl$_2$ (7.35 mg, 10.1 μmol, 0.10 equiv) in dioxane (1.00 mL) and water (0.20 mL) was purged with nitrogen and stirred at 95° C. for 2 h. The mixture was filtered and concentrated under reduced pressure. The residue was purified by prep-TLC (SiO$_2$, dichloromethane/methyl alcohol=10/1) to afford tert-butyl 5-(2-cyano-5-(((5-fluoro-2,3-dihydrobenzofuran-4-yl)methyl)amino)imidazo[1,2-c]pyrimidin-8-yl)picolinate (50.0 mg, 60.0 μmol, 59.8% yield, 58.4% purity) as a yellow solid. LC-MS [M+1]: 487.4.

$^1$H NMR (400 MHz, DMSO-d$_h$) δ=9.30 (d, J=1.6 Hz, 1H), 8.97 (s, 1H), 8.77 (t, J=5.2 Hz, 1H), 8.63 (dd, J=2.4, 8.0 Hz, 1H), 8.68-8.59 (m, 1H), 8.36 (s, 1H), 8.09 (d, J=8.0 Hz, 1H), 6.99-6.92 (m, 1H), 6.71 (dd, J=4.0, 8.8 Hz, 1H), 4.77 (br d, J=4.4 Hz, 2H), 4.55 (br t, J=8.8 Hz, 2H), 3.31-3.29 (m, 2H), 1.59 (s, 9H).

A mixture of tert-butyl 5-(2-cyano-5-(((5-fluoro-2,3-dihydrobenzofuran-4-yl)methyl)amino)imidazo[1,2-c]pyrimidin-8-yl)picolinate (50.0 mg, 103 μmol, 1.00 equiv) and trifluoroacetic acid (3.85 g, 33.8 mmol, 2.50 mL, 329 equiv) in dichloromethane (0.50 mL) was stirred at 25° C. for 2 h. The mixture was filtered and concentrated under reduced pressure to give a residue. The residue was purified by prep-HPLC (basic conditions) to afford 5-(2-cyano-5-(((5-fluoro-2,3-dihydrobenzofuran-4-yl)methyl)amino)imidazo[1,2-c]pyrimidin-8-yl)picolinic acid (6.73 mg, 15.4 μmol, 15.0% yield, 98.4% purity) as a yellow solid. LC-MS [M+1]: 431.3.

$^{1}$H NMR (400 MHz, DMSO-$d_6$) δ=9.25 (br s, 1H), 8.98 (s, 1H), 8.48 (br d, J=9.6 Hz, 1H), 8.27 (br s, 1H), 8.05 (br d, J=8.4 Hz, 1H), 7.01-6.92 (m, 1H), 6.71 (dd, J=4.0, 8.8 Hz, 1H), 4.77 (s, 2H), 4.55 (t, J=8.8 Hz, 2H), 3.26-3.24 (m, 2H).

Example 216

8-(2-((dimethylamino)methyl)pyrimidin-5-yl)-5-(((5-fluoro-2,3-dihydrobenzofuran-4-yl)methyl)amino)imidazo[1,2-c]pyrimidine-2-carbonitrile

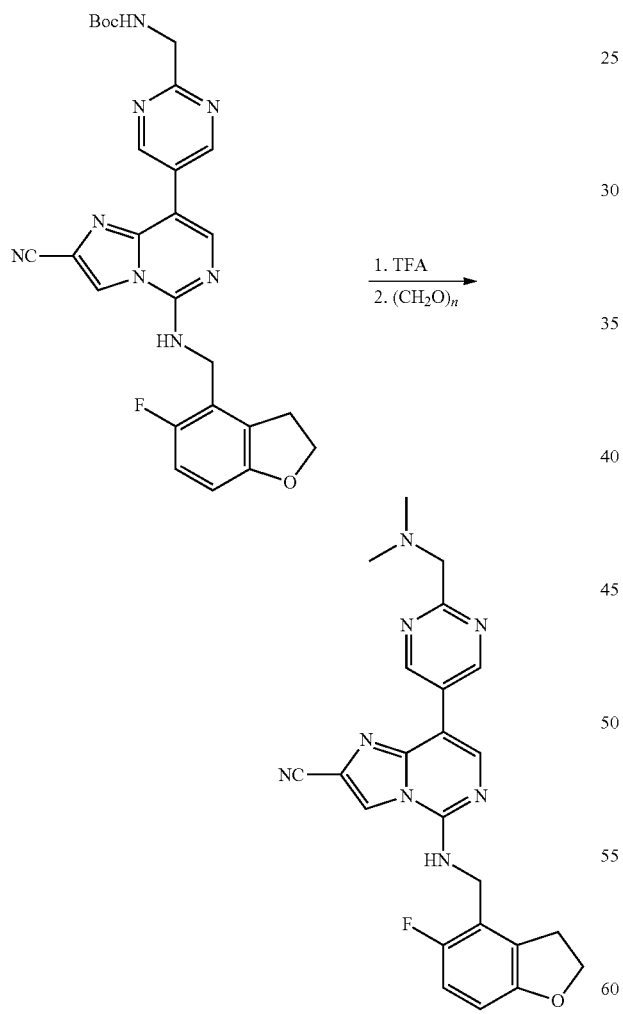

To a solution of tert-butyl ((5-(2-cyano-5-(((5-fluoro-2,3-dihydrobenzofuran-4-yl)methyl)amino)imidazo[1,2-c]pyrimidin-8-yl)pyrimidin-2-yl)methyl)carbamate (90.0 mg, 156 μmol, 1.00 equiv) in DCM (2.00 mL) was added TFA (890 mg, 7.81 mmol, 578 μL, 50.0 equiv). The mixture was stirred at room temperature for 1 h prior to concentration under reduced pressure. The residue was diluted with saturated sodium bicarbonate aqueous solution and subsequently filtered to provide 8-[2-(aminomethyl)pyrimidin-5-yl]-5-[(5-fluoro-2,3-dihydrobenzofuran-4-yl)methylamino]imidazo[1,2-c]pyrimidine-2-carbonitrile (75.0 mg, 147 μmol, 93.9% yield, 81.4% purity) as a purple solid. LCMS [M+1]: 417.0.

To a solution of 8-[2-(aminomethyl)pyrimidin-5-yl]-5-[(5-fluoro-2,3-dihydrobenzofuran-4-yl)methylamino]imidazo[1,2-c]pyrimidine-2-carbonitrile (65.0 mg, 127 μmol, 1 equiv) in MeOH (0.60 mL) was added paraformaldehyde (11.5 mg, 381 μmol, 10.5 μL, 3.00 equiv) and CH$_3$COOH (1 drop). The mixture was stirred at 60° C. for 1 h and then cooled to room temperature. To the resultant mixture was added NaBH$_3$CN (24.0 mg, 381 μmol, 3.00 equiv). After 1 h, the mixture was filtered and concentrated in vacuo to provide a residue. The residue was purified by prep-HPLC (basic conditions) to afford 8-(2-((dimethylamino)methyl)pyrimidin-5-yl)-5-(((5-fluoro-2,3-dihydrobenzofuran-4-yl)methyl)amino)imidazo[1,2-c]pyrimidine-2-carbonitrile (2.16 mg, 4.19 μmol, 3.3% yield, 86.3% purity) as a yellow gum. LCMS [M+1]: 445.1.

$^{1}$H NMR (400 MHz, DMSO-$d_6$) δ=9.36 (s, 2H), 8.97 (s, 1H), 8.75 (br s, 1H), 8.32 (s, 1H), 6.96 (t, J=8.8 Hz, 1H), 6.71 (dd, J=4.0, 8.8 Hz, 1H), 4.76 (br s, 2H), 4.55 (t, J=8.8 Hz, 2H), 3.70 (s, 2H), 3.31-3.28 (m, 2H), 2.28 (s, 6H).

Example 217

8-(3-(2-(dimethylamino)ethyl)phenyl)-5-(((5-fluoro-2,3-dihydrobenzofuran-4-yl)methyl)amino)imidazo[1,2-c]pyrimidine-2-carbonitrile

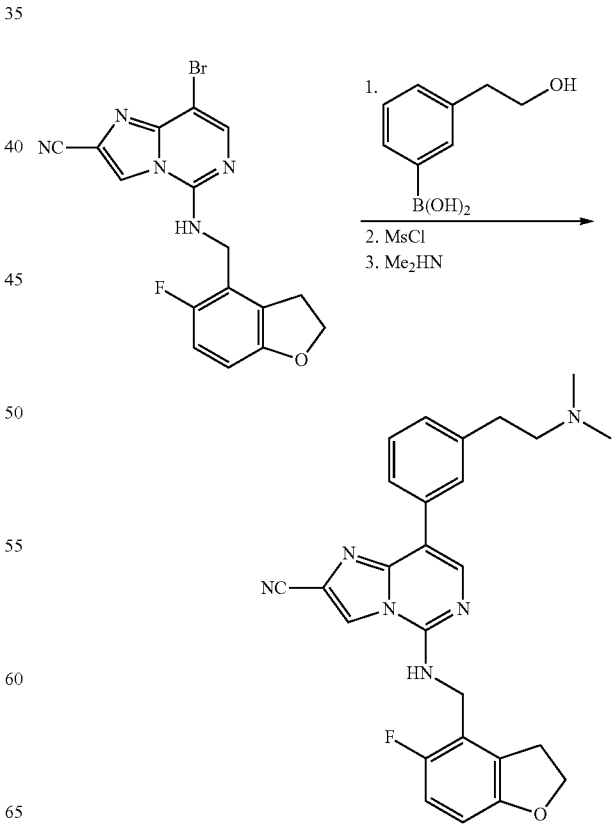

A mixture of 8-bromo-5-(((5-fluoro-2,3-dihydrobenzofuran-4-yl)methyl)amino)imidazo[1,2-c]pyrimidine-2-carbonitrile (50.0 mg, 129 μmol, 1.00 equiv), [3-(2-hydroxyethyl)phenyl]boronic acid (32.1 mg, 193 μmol, 1.50 equiv), sodium bicarbonate (32.5 mg, 386 μmol, 3.00 equiv) and Pd(dppf)Cl$_2$ (9.42 mg, 12.9 μmol, 0.10 equiv) in dioxane (2.00 mL) and water (0.40 mL) was purged with nitrogen and subsequently allowed to stir at 100° C. for 2 h. The mixture was filtered and concentrated under reduced pressure. The residue was purified by prep-TLC (dichloromethane/methanol=10/1) to afford 5-(((5-fluoro-2,3-dihydrobenzofuran-4-yl)methyl)amino)-8-(3-(2-hydroxyethyl)phenyl)imidazo[1,2-c]pyrimidine-2-carbonitrile (38.0 mg, 87.6 μmol, 68.0% yield, 99.0% purity) as a yellow solid. LC-MS [M+1]: 430.2.

$^1$H NMR (400 MHz, CDCl$_3$) δ=7.97 (s, 1H), 7.90 (s, 1H), 7.74 (br s, 2H), 7.44 (t, J=8.0 Hz, 1H), 7.30-7.28 (m, 1H), 6.87 (t, J=96 Hz, 1H), 6.69 (dd, J=4.0, 8.4 Hz, 1H), 5.43 (s, 1H), 4.84 (d, J=5.6 Hz, 2H), 4.65 (t, J=8.8 Hz, 2H), 3.94 (t, J=6.4 Hz, 2H), 3.44 (t, J=8.8 Hz, 2H), 2.97 (t, J=6.4 Hz, 2H).

A mixture of 5-(((5-fluoro-2,3-dihydrobenzofuran-4-yl)methyl)amino)-8-(3-(2-hydroxyethyl)phenyl)imidazo[1,2-c]pyrimidine-2-carbonitrile (30.0 mg, 69.9 μmol, 1.00 equiv), mesyl chloride (16.0 mg, 140 μmol, 10.8 μL, 2.00 equiv) and triethylamine (28.3 mg, 279 μmol, 38.9 μL, 4.00 equiv) in dichloromethane (1.00 mL) was stirred at 0° C. for h. The mixture was concentrated under reduced pressure to afford 3-(2-cyano-5-(((5-fluoro 2,3-dihydrobenzofuran-4-yl)methyl)amino)imidazo[1,2-c]pyrimidin-8-yl)phenethyl methanesulfonate (20.0 mg, 39.4 μmol) as a yellow oil that was used in the following step without purification. LC-MS [M+1]: 508.3.

A mixture of 3-(2-cyano-5-(((5-fluoro-2,3-dihydrobenzofuran-4-yl)methyl)amino)imidazo[1,2-c]pyrimidin-8-yl)phenethyl methanesulfonate (20.0 mg, 39.4 μmol, 1.00 equiv), dimethylamine (1.00 M in THF, 394 μL, 10.0 equiv) and diisopropylethylamine (15.3 mg, 118 μmol, 20.6 uL, 3.00 equiv) in dimethyl formamide (0.50 mL) was stirred at room temperature for 2 h prior to concentration in vacuo. The residue was purified by prep-HPLC (basic conditions) to afford 8-(3-(2-(dimethylamino)ethyl)phenyl)-5-(((5-fluoro-2,3-dihydrobenzofuran-4-yl)methyl)amino)imidazo[1,2-c]pyrimidine-2-carbonitrile (5.94 mg, 12.9 μmol, 32.8% yield, 99.2% purity) as a white solid. LC-MS [M+1]: 457.1.

$^1$H NMR (400 MHz, DMSO-d$_6$) δ=8.93 (s, 1H), 8.49 (t, J=5.6 Hz, 1H), 8.07 (s, 1H), 7.82-7.76 (m, 2H), 7.36 (t, J=7.6 Hz, 1H), 7.22 (d, J=8.0 Hz, 1H), 6.98-6.91 (m, 1H), 6.70 (dd, J=4.0, 8.8 Hz, 1H), 4.73 (d, J=4.4 Hz, 2H), 4.55 (t, J=8.8 Hz, 2H), 3.35-3.33 (m, 2H), 3.28 (br s, 2H), 2.78 (br t, J=7.6 Hz, 2H), 2.22 (br s, 6H).

Example 218

5-(((5-fluoro-2,3-dihydrobenzofuran-4-yl)methyl)amino)-8-(2-oxo-1,2-dihydropyridin-4-yl)imidazo[1,2-c]pyrimidine-2-carbonitrile

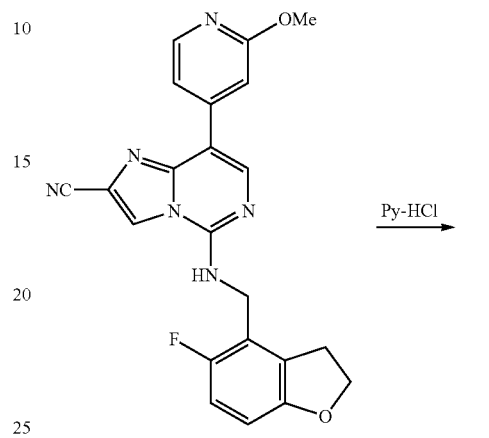

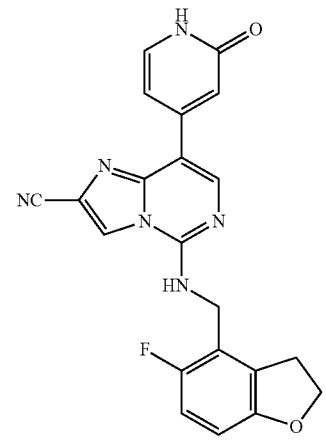

A mixture of 5-[(5-fluoro-2,3-dihydrobenzofuran-4-yl)methylamino]-8-(2-methoxy-4-pyridyl)imidazo[1,2-c]pyrimidine-2-carbonitrile (55.0 mg, 125 μmol, 1.00 equiv) and pyridine hydrochloride (71.5 mg, 619 μmol, 4.93 equiv) was heated at 130° C. for 0.5 h. The reaction mixture was diluted with water (10.0 mL) and extracted with ethyl acetate (10.0 mL×2). The combined organic layer was concentrated under reduced pressure to give a residue. The residue was triturated with methanol and filtered to afford 5-(((5-fluoro-2,3-dihydrobenzofuran-4-yl)methyl)amino)-8-(2-oxo-1,2-dihydropyridin-4-yl)imidazo[1,2-c]pyrimidine-2-carbonitrile (14.2 mg, 33.9 μmol, 27.0% yield, 96.1% purity) as an off-white solid. LCMS [M+1]: 403.1.

$^1$H NMR (400 MHz, DMSO-d6) δ=11.47 (s, 1H), 8.94 (s, 1H), 8.76 (s, 1H), 8.30 (s, 1H), 7.39 (d, J=6.8 Hz, 1H), 7.25 (d, J=1.6 Hz, 1H), 6.95 (t, J=9.6 Hz, 1H), 6.83 (dd, J=1.6, 7.2 Hz, 1H), 6.70 (dd, J=4.0, 8.8 Hz, 1H), 4.74 (s, 2H), 4.54 (t, J=8.8 Hz, 2H), 3.31-3.27 (m, 2H).

EXAMPLES 219-228 were prepared following the procedure set forth in Example 87 and using the general reactions schemes and intermediates described herein.

TABLE 12

| Ex. # | Structure | ¹H NMR |
|---|---|---|
| 219 | 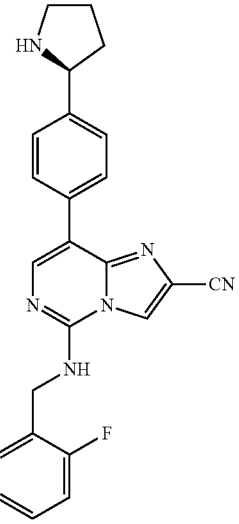<br>(S)-5-(((5-fluoro-2,3-dihydrobenzofuran-4-yl)methyl)amino)-8-(4-(pyrrolidin-2-yl)phenyl)imidazo[1,2-c]pyrimidine-2-carbonitrile | ¹H NMR (400 MHz, DMSO-$d_6$) δ = 8.93 (s, 1H), 8.54 (br s, 1H), 8.08-8.01 (m, 1H), 7.90-7.82 (m, 2H), 7.47-7.21 (m, 2H), 6.94 (t, J = 9.2 Hz, 1H), 6.70 (dd, J = 4.0, 8.8 Hz, 1H) 4.72 (s, 2H), 4.54 (t, J = 8.8 Hz, 2H), 4.05 (t, J = 8.0 Hz, 1H), 3.31-3.28 (m, 3H), 3.10-2.98 (m, 1H), 2.93-2.83 (m, 1H), 2.18-2.05 (m, 1H), 1.86-1.69 (m, 2H), 1.58-1.43 (m, 1H).<br>LCMS [M + 1]: 455.3. |
| 220 | 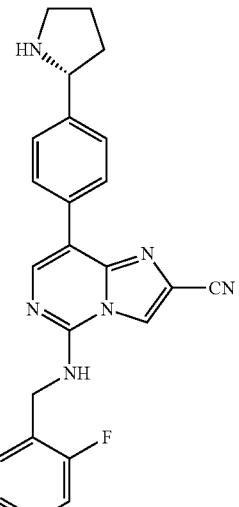<br>(R)-5-(((5-fluoro-2,3-dihydrobenzofuran-4-yl)methyl)amino)-8-(4-(pyrrolidin-2-yl)phenyl)imidazo[1,2-c]pyrimidine-2-carbonitrile | ¹H NMR (400 MHz, CD₃OD) δ ppm 8.62 (s, 1H), 8.02 (s, 1H) 7.90 (d, J = 8.4 Hz, 2H), 7.51 (d, J = 8.4 Hz, 2H), 6.91-6.83 (m, 1H), 6.66 (dd, J = 4.0, 8.8 Hz, 1H), 4.84 (s, 2H), 4.59 (t, J = 8.8 Hz, 2H), 4.28 (t, J = 8.4 Hz, 1H), 3.38 (t, J = 8.8 Hz, 2H), 3.31-3.27 (m, 1H), 3.16-3.08 (m, 1H), 2.42-2.30 (m, 1H), 2.16-2.00 (m, 2H), 1.99-1.86 (m, 1H).<br>LCMS [M + 1]: 455.3. |

TABLE 12-continued

| Ex. # | Structure | ¹H NMR |
|---|---|---|
| 221 | 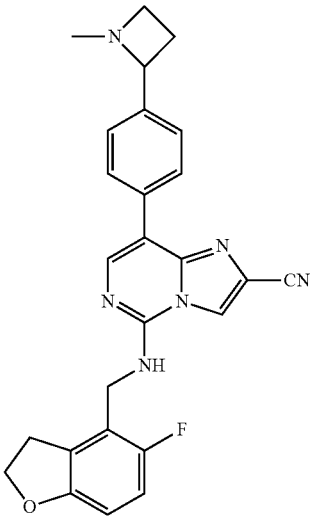 [SMILES: CN1CCC1c1ccc(-c2cnc(NCc3c(F)ccc4c3CCO4)n3cc(C#N)nc23)cc1]<br>5-(((5-fluoro-2,3-dihydrobenzofuran-4-yl)methyl)amino)-8-(4-(1-methylazetidin-2-yl)phenyl)imidazo[1,2-c]pyrimidine-2-carbonitrile | ¹H NMR (400 MHz, DMSO-$d_6$) δ = 8.94 (br s, 1H), 8.50 (br s, 1H), 8.07 (s, 1H), 7.91 (d, J = 8.0 Hz, 2H), 7.46 (d, J = 8.0 Hz, 2H), 6.95 (t, J = 10.0 Hz, 1H), 6.71 (dd, J = 4.0, 8.8 Hz, 1H), 4.74 (s, 2H), 4.55 (t, J = 8.8 Hz, 2H), 3.90 (t, J = 8.0 Hz, 1H), 3.31-3.30 (m, 2H), 2.86-2.76 (m, 1H), 2.53-2.52 (m, 1H), 2.32-2.26 (m, 1H), 2.25 (s, 3H), 2.03-1.92 (m, 1H).<br>LC-MS [M + 1]: 453.3. |
| 222 | 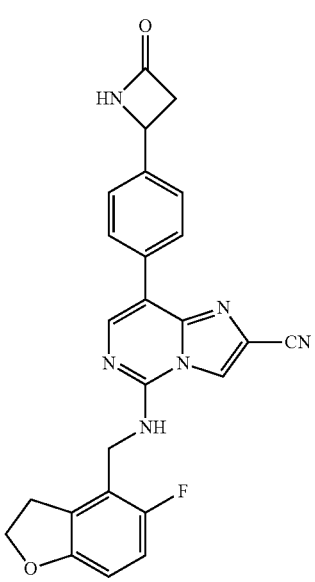 [SMILES: N#Cc1cn2c(NCc3c(F)ccc4c3CCO4)ncc(-c3ccc(C4CC(=O)N4)cc3)c2n1]<br>5-(((5-fluoro-2,3-dihydrobenzofuran-4-yl)methyl)amino)-8-(4-(4-oxoazetidin-2-yl)phenyl)imidazo[1,2-c]pyrimidine-2-carbonitrile | ¹H NMR (400 MHz, DMSO-$d_6$) δ = 8.94 (s, 1H), 8.51 (br s, 1H), 8.43 (s, 1H), 8.11 (s, 1H), 7.99 (d, J = 8.4 Hz, 2H), 7.46 (d, J = 8.4 Hz, 2H), 7.01-6.92 (m, 1H), 6.71 (dd, J = 4.0, 8.8 Hz, 1H), 4.74 (br s, 2H), 4.71 (dd, J = 2.4, 5.2 Hz, 1H), 4.55 (t, J = 8.8 Hz, 2H), 3.41-3.37 (m, 1H), 3.31-3.26 (m, 2H), 2.72 (dd, J = 1.6, 14.8 Hz, 1H).<br>LCMS [M + 1]: 455.2. |

TABLE 12-continued

| Ex. # | Structure | $^1$H NMR |
|---|---|---|
| 223 | 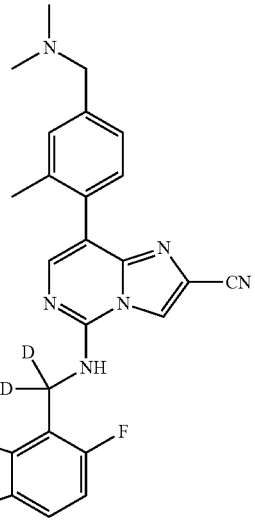<br>8-(4-((dimethylamino)methyl)-2-methylphenyl)-5-(((5-fluoro-2,3-dihydrobenzofuran-4-yl-2,3-d$_2$)methyl-d$_2$)amino)imidazo[1,2-c]pyrimidine-2-carbonitrile | $^1$H NMR (400 MHz, DMSO-d$_6$) δ = 8.92 (s, 1H), 8.43 (s, 1H), 7.69 (s, 1H), 7.26-7.19 (m, 2H), 7.16(d, J = 8.0 Hz, 1H), 7.00-6.91 (m, 1H), 6.71 (dd, J = 4.0, 8.8 Hz, 1H), 4.53 (d J = 10.0 Hz, 1H), 3.39 (s, 2H), 3.38-3.36 (m, 1H), 2.18 (s, 6H), 2.15 (s, 3H).<br>LCMS [M + 1]: 461.4. |
| 224 | 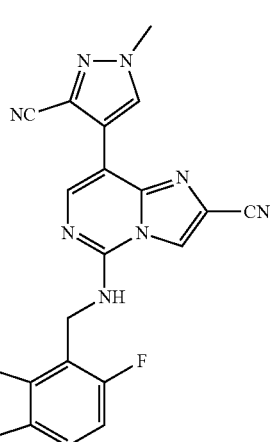<br>8-(3-cyano-1-methyl-1H-pyrazol-4-yl)-5-(((5-fluoro-2,3-dihydrobenzofuran-4-yl)methyl)amino)imidazo[1,2-c]pyrimidine-2-carbonitrile | $^1$H NMR (400 MHz, DMSO-d$_6$) δ = 8.93 (s, 1H), 8.64-8.56 (m, 2H), 8.20 (s, 1H), 6.94 (t, J = 9.2 Hz, 1H), 6.70 (dd, J = 3.6, 8.4 Hz, 1H), 4.73 (br s, 2H), 4.53 (t, J = 8.8 Hz, 2H), 4.03 (s, 3H), 3.29-3.24 (m, 2H).<br>LCMS [M + 1]: 414.9. |

TABLE 12-continued

| Ex. # | Structure | ¹H NMR |
|---|---|---|
| 225 | 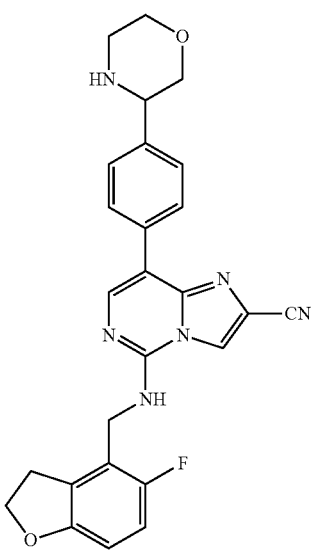 [SMILES: N#Cc1cn2c(NCc3c(F)ccc4c3CCO4)ncc(-c3ccc(C4COCCN4)cc3)c2n1]<br>5-(((5-fluoro-2,3-dihydrobenzofuran-4-yl)methyl)amino)-8-(4-(morpholin-3-yl)phenyl)imidazo[1,2-c]pyrimidine-2-carbonitrile | ¹H NMR (400 MHz, CD₃OD) δ = 8.63 (s, 1H), 8.12-7.99 (m, 3H), 7.59 (br d, J = 8.2 Hz, 2H), 6.87 (br t, J = 9.2 Hz, 1H), 6.66 (dd, J = 3.6, 8.4 Hz, 1H), 4.85-4.83 (m, 2H), 4.65-4.53 (m, 3H), 4.24-4.11 (m, 2H), 4.04-3.84 (m, 2H), 3.52-3.43 (m, 2H), 3.38 (br t, J = 8.8 Hz, 2H).<br>LCMS [M + 1]: 471.3. |
| 226 | 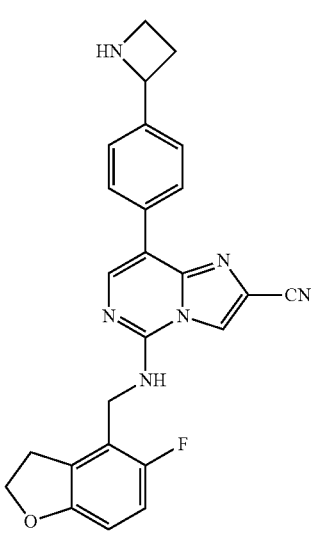 [SMILES: N#Cc1cn2c(NCc3c(F)ccc4c3CCO4)ncc(-c3ccc(C4CCN4)cc3)c2n1]<br>8-(4-(azetidin-2-yl)phenyl)-5-(((5-fluoro-2,3-dihydrobenzofuran-4-yl)methyl)amino)imidazo[1,2-c]pyrimidine-2-carbonitrile | ¹H NMR (400 MHz, CDCl₃) δ = 7.95 (s, 1H), 7.87 (s, 1H), 7.85-7.81 (m, 2H), 7.51-7.48 (m, 2H), 6.88-6.82 (m, 1H), 6.68 (dd, J = 8.7, 4.0 Hz, 1H), 5.48-5.40 (m, 1H), 5.03-4.98 (m, 1H), 4.85-4.79 (m, 2H), 4.67-4.60 (m, 2H), 3.81-3.73 (m, 1H), 3.46-3.39 (m, 3H), 2.65-2.56 (m, 1H), 2.47-2.35 (m, 1H).<br>LCMS [M + 1]: 439.3. |

TABLE 12-continued

| Ex. # | Structure | ¹H NMR |
|---|---|---|
| 227 | 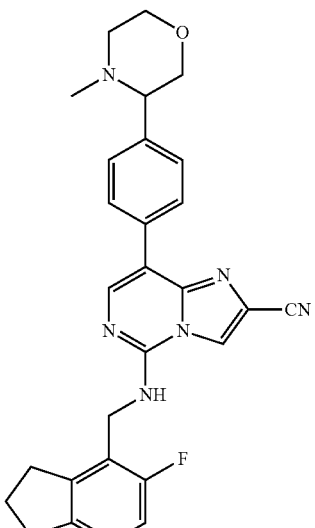<br>5-(((5-fluoro-2,3-dihydrobenzofuran-4-yl)methyl)amino)-8-(4-(4-methylmorpholin-3-yl)phenyl)imidazo[1,2-c]pyrimidine-2-carbonitrile | ¹H NMR (400 MHz, DMSO-d$_6$) δ = 8.94 (s, 1H), 8.50 (br s, 1H), 8.09 (s, 1H), 7.92 (d, J = 8.3 Hz, 2H), 7.44 (d, J = 8.2 Hz, 2H), 6.99-6.93 (m, 1H), 6.74-6.68 (m, 1H), 4.76-4.72 (m, 2H), 4.58-4.52 (m, 2H), 3.87-3.82 (m, 1H), 3.68-3.60 (m, 2H), 3.31-3.23 (m, 3H), 3.10-3.05 (m, 1H), 2.87-2.82 (m, 1H), 2.35-2.26 (m, 1H), 2.02 (s, 3H).<br>LCMS [M + 1]: 485.5 |
| 228 | 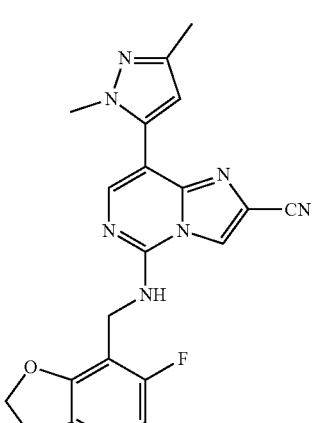<br>8-(1,3-dimethyl-1H-pyrazol-5-yl)-5-(((5-fluorobenzo[d][1,3]dioxol-4-yl)methyl)amino)imidazo[1,2-c]pyrimidine-2-carbonitrile | ¹H NMR (400 MHz, DMSO-d$_6$) δ = 8.81 (s, 1H), 7.81 (s, 1H), 6.91-6.85 (m, 1H), 6.72-6.65 (m, 1H), 6.21 (s, 1H), 6.06 (s, 2H), 4.71 (s, 2H), 3.67 (s, 3H), 2.18 (s, 3H).<br>LCMS [M + 1]: 406.3 |

Example 229

5-(((5-fluoro-2,3-dihydrobenzofuran-4-yl)methyl)amino)-8-(1-methyl-3-(4-methylpiperazine-1-carbonyl)-1H-pyrazol-5-yl)imidazo[1,2-c]pyrimidine-2-carbonitrile

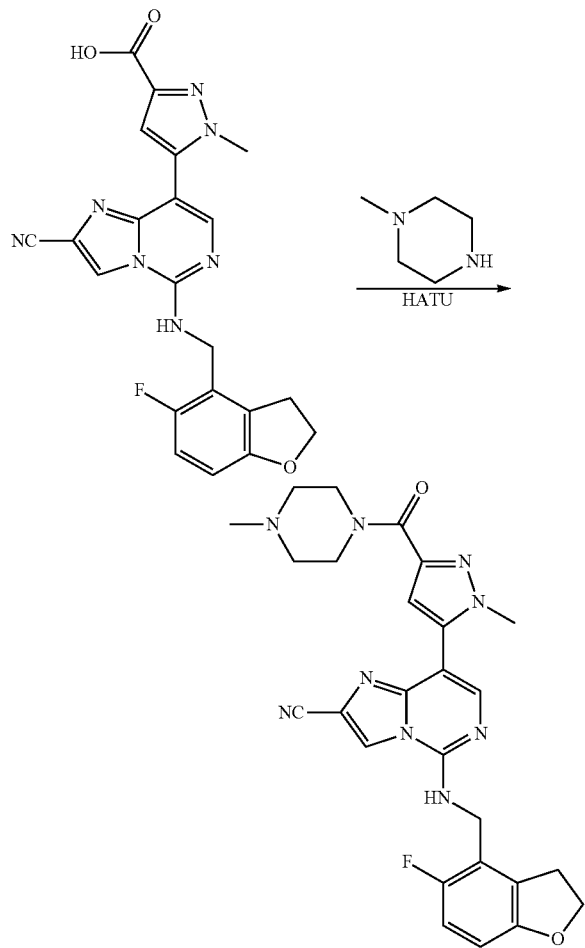

To a solution of 5-[2-cyano-5-[(5-fluoro-2,3-dihydrobenzofuran-4-yl) methylamino]imidazo[1,2-c]pyrimidin-8-yl]-1-methyl-pyrazole-3-carboxylic acid (40.0 mg, 92.3 μmol, 1.00 equiv) and 1-methylpiperazine (20.4 μL, 184 μmol, 1.99 equiv) in DMF (1.00 mL) was added HATU (66.4 mg, 139 μmol, 1.50 equiv) and DIEA (48.5 μL, 279 μmol, 3.02 equiv). The reaction was stirred at 25° C. for 1 h and was subsequently quenched by the addition of water (30.0 mL) at 25° C. The aqueous layer was diluted with ethyl acetate (50.0 mL), at which time a white precipitate formed. The solid was filtered off and dried at reduced pressure to afford 5-(((5-fluoro-2,3-dihydrobenzofuran-4-yl)methyl)amino)-8-(1-methyl-3-(4-methylpiperazine-1-carbonyl)-1H-pyrazol-5-yl)imidazo[1,2-c]pyrimidine-2-carbonitrile (24.5 mg, 45.8 μmol, 49.6% yield, 96.4% purity) as a white solid. LCMS [M+1]: 516.3.

$^1$H NMR (400 MHz, DMSO-$d_6$) δ=8.95 (s, 1H), 8.73 (t, J=5.2 Hz, 1H), 7.96 (s, 1H), 7.03-6.88 (m, 1H), 6.75 (s, 1H), 6.72 (dd, J=4.0, 8.8 Hz, 1H), 4.74 (d, J=4.8 Hz, 2H), 4.56 (t, J=8.8 Hz, 2H), 3.97 (s, 2H), 3.82 (s, 3H), 3.63 (s, 2H), 3.35-3.32 (m, 2H), 2.53-2.50 (m, 2H), 2.35-2.33 (m, 2H), 2.21 (s, 3H).

Example 230

8-(1-(2-(dimethylamino)ethyl)-1H-pyrazol-5-yl)-5-(((5-fluoro-2,3-dihydrobenzofuran-4-yl)methyl)amino)imidazo[1,2-c]pyrimidine-2-carbonitrile

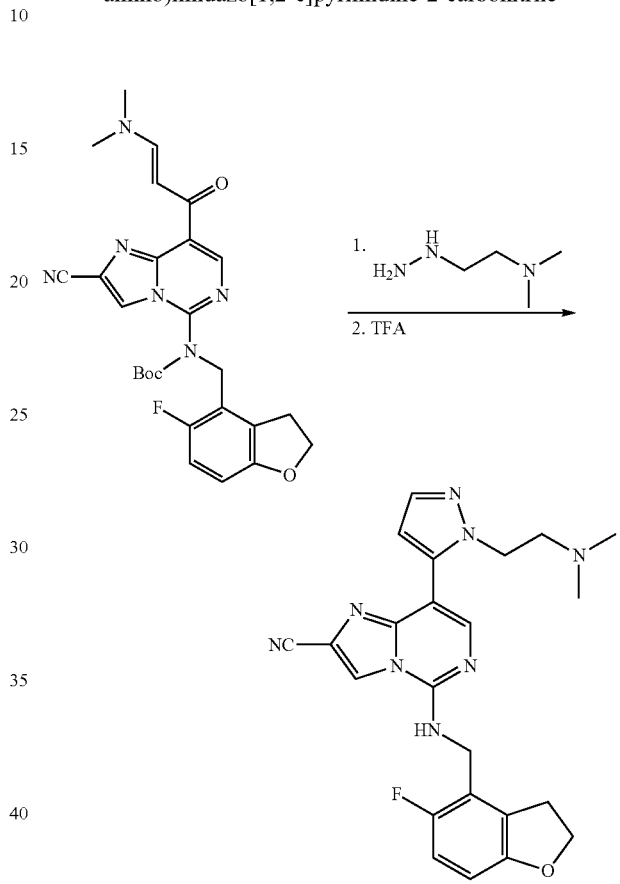

To a solution of tert-butyl (E)-(2-cyano-8-(3-(dimethylamino)acryloyl)imidazo[1,2-c]pyrimidin-5-yl)((5-fluoro-2,3-dihydrobenzofuran-4-yl)methyl)carbamate (13.0 mg, 25.0 μmol, 1.00 equiv) in ethanol (2.00 mL) was added 2-hydrazino-N,N-dimethyl-ethanamine-HCl (14.0 mg, 99.9 μmol, 4.00 equiv), the reaction was stirred at 80° C. for 1 h. The reaction was concentrated under reduced pressure to give tert-butyl N-[2-cyano-8-[2-[2-(dimethylamino)ethyl]pyrazol-3-yl]imidazo[1,2-c]pyrimidin-5-yl]-N-[(5-fluoro-2,3-dihydrobenzofuran-4-yl)methyl]carbamate (15.0 mg, crude) as brown oil. LCMS: [M+1]: 547.6.

A solution of tert-butyl(2-cyano-8-(1-(2-(dimethylamino)ethyl)-1H-pyrazol-5-yl)imidazo[1,2-c]pyrimidin-5-yl)((5-fluoro-2,3-dihydrobenzofuran-4-yl)methyl)carbamate (15.0 mg, 27.4 μmol, 1.00 equiv) in DCM (0.50 mL) was added TFA (0.50 mL) was stirred at 25° C. for 30 min. The reaction was concentrated under reduced pressure to give a residue. The residue was purified by prep-HPLC (neutral conditions) and lyophilization to afford 8-(1-(2-(dimethylamino)ethyl)-1H-pyrazol-5-yl)-5-(((5-fluoro-2,3-dihydrobenzofuran-4-yl)methyl)amino)imidazo[1,2-c]pyrimidine-2-carbonitrile (11.0 mg, 24.5 μmol, 89.2% yield, 99.4% purity) as a white solid. LCMS [M+1]: 447.4.

¹H NMR (400 MHz, CD₃OD) δ=8.62 (s, 1H), 7.89 (s, 1H), 7.60 (d, J=2.0 Hz, 1H), 6.90-6.80 (m, 1H), 6.64 (dd, J=4.0, 8.8 Hz, 1H), 6.43 (d, J=2.0 Hz, 1H), 4.83 (s, 2H), 4.58 (t, J=8.4 Hz, 2H), 4.22-4.15 (m, 2H), 3.38 (t, J=8.4 Hz, 2H), 2.81-2.76 (m, 2H), 2.14 (s, 6H).

Example 231

5-(((5-fluoro-2,3-dihydrobenzofuran-4-yl)methyl) amino)-8-(1-(2-hydroxyethyl)-1H-pyrazol-5-yl)imidazo[1,2-c]pyrimidine-2-carbonitrile

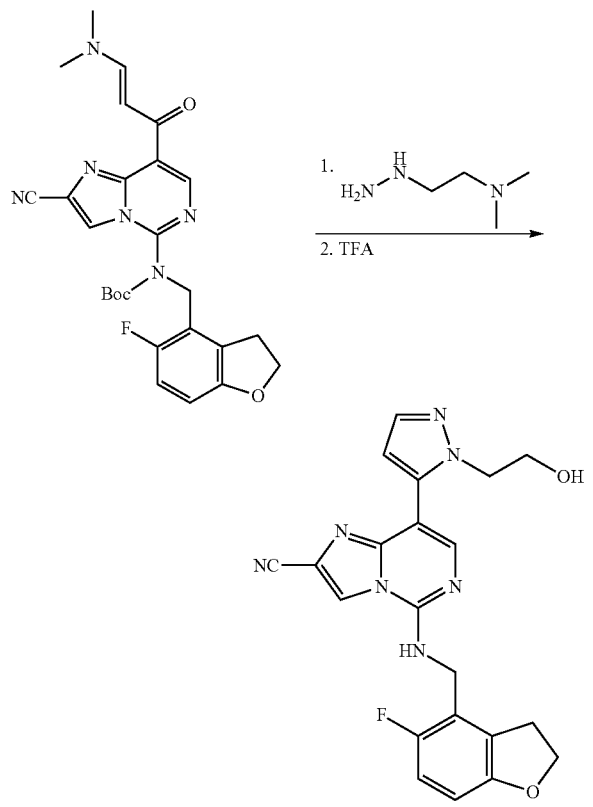

To a solution of tert-butyl (E)-(2-cyano-8-(3-(dimethylamino)acryloyl)imidazo[1,2-c]pyrimidin-5-yl)((5-fluoro-2,3-dihydrobenzofuran-4-yl)methyl)carbamate (16.0 mg, 31.6 µmol, 1.00 equiv) in ethanol (1.00 mL) was added 2-hydrazinoethanol (4.81 mg, 63.2 µmol, 4.29 µL, 2.00 equiv). The mixture was stirred at 80° C. for 1 h and subsequently concentrated under reduced pressure to provide a residue. The residue was purified by prep-TLC (dichloromethane/mehanol=20/1) to afford tert-butyl (2-cyano-8-(1-(2-hydroxyethyl)-1H-pyrazol-5-yl)imidazo[1,2-c]pyrimidin-5-yl)((5-fluoro-2,3-dihydrobenzofuran-4-yl)methyl)carbamate (13.0 mg, 22.3 µmol, 70.5% yield, 89.0% purity) as a brown solid.

To a solution of tert-butyl(2-cyano-8-(1-(2-hydroxyethyl)-1H-pyrazol-5-yl)imidazo[1,2-c]pyrimidin-5-yl)((5-fluoro-2,3-dihydrobenzofuran-4-yl)methyl)carbamate (13.0 mg, 22.3 µmol, 1.00 equiv) in DCM (1.00 mL) was added TFA (0.30 mL) and the resultant mixture was stirred at 25° C. for 1 h. The reaction was concentrated under reduced pressure to give a residue that was purified by prep-HPLC (neutral conditions) to afford 5-(((5-fluoro-2,3-dihydrobenzofuran-4-yl)methyl)amino)-8-(1-(2-hydroxyethyl)-1H-pyrazol-5-yl)imidazo[1,2-c]pyrimidine-2-carbonitrile (2.97 mg, 7.02 µmol, 31.5% yield, 99.2% purity) as a white solid. LCMS [M+1]: 420.2.

¹H NMR (400 MHz, CD₃OD) δ=8.64 (s, 1H), 7.95 (s, 1H), 7.64 (d, J=2.0 Hz, 1H), 6.92-6.84 (m, 1H), 6.66 (dd, J=4.0, 8.8 Hz, 1H), 6.47 (d, J=2.0 Hz, 1H), 4.84 (s, 2H), 4.63-4.56 (m, 2H), 4.22 (t, J=5.6 Hz, 2H), 3.85 (t, J=5.6 Hz, 2H), 3.40 (t, J=8.8 Hz, 2H).

Example 232

8-(4-bromo-1H-pyrazol-3-yl)-5-(((5-fluoro-2,3-dihydrobenzofuran-4-yl)methyl)amino)imidazo[1,2-c]pyrimidine-2-carbonitrile

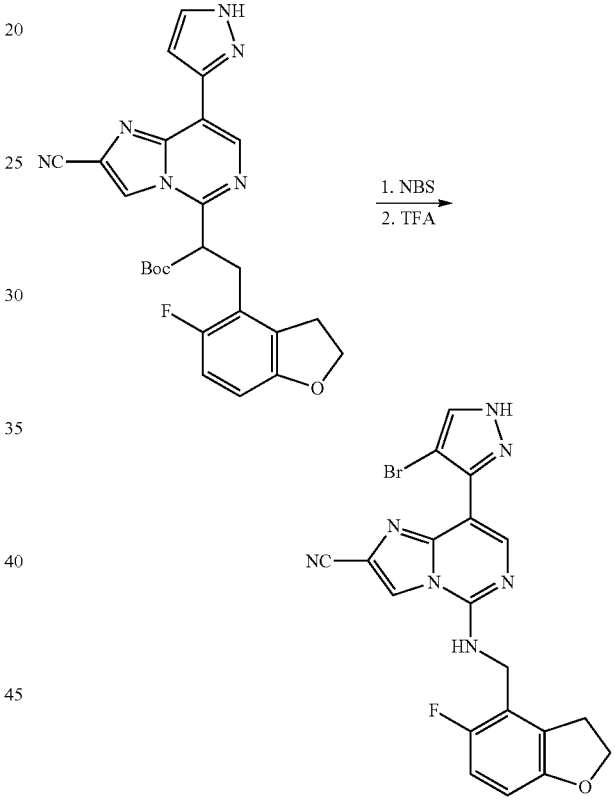

To a solution of tert-butyl (2-cyano-8-(1H-pyrazol-3-yl)imidazo[1,2-c]pyrimidin-5-yl)((5-fluoro-2,3-dihydrobenzofuran-4-yl)methyl)carbamate (95.0 mg, 200 µmol, 1.00 equiv) in dry chloroform (1.00 mL) was added portion wise NBS (53.5 mg, 300 µmol, 1.50 equiv). The mixture was stirred at 25° C. for 1 h. The reaction mixture was cooled to 0° C. and filtered through a pad of Celite. The filtrate was evaporated to give a residue. The residue was purified by prep-TLC (SiO₂, petroleum ether/ethyl acetate=2/1) to afford tert-butyl(8-(4-bromo-1H-pyrazol-3-yl)-2-cyanoimidazo[1,2-c]pyrimidin-5-yl)((5-fluoro-2,3-dihydrobenzofuran-4-yl)methyl)carbamate (20.0 mg, 27.4 µmol, 13.7% yield, 76% purity) as a white solid.

¹H NMR (400 MHz, CDCl₃) δ=9.23 (s, 1H), 7.83 (s, 1H), 7.73 (s, 1H), 6.72-6.64 (m, 1H), 6.59 (dd, J=4.0, 8.8 Hz, 1H), 5.13 (s, 2H), 4.60 (t, J=8.8 Hz, 2H), 3.34 (t, J=8.8 Hz, 2H), 1.41 (s, 9H).

A mixture of tert-butyl (8-(4-bromo-1H-pyrazol-3-yl)-2-cyanoimidazo[1,2-c]pyrimidin-5-yl)((5-fluoro-2,3-dihydrobenzofuran-4-yl)methyl)carbamate (20.0 mg, 36.1 µmol, 1.00 equiv) in TFA (0.40 mL) and DCM (2.00 mL) was stirred at 25° C. for 3 h. The reaction mixture was evaporated to give a residue. The residue was triturated with methanol and filtered to afford 8-(4-bromo-1H-pyrazol-3-yl)-5-(((5-fluoro-2,3-dihydrobenzofuran-4-yl)methyl)amino)imidazo[1,2c]pyrimidine-2-carbonitrile (3.10 mg, 5.98 µmol, 16.6% yield, 87.6% purity) as a gray solid. LCMS [M+1]: 456.1.

$^1$H NMR (400 MHz, DMSO-d$_6$) δ=13.38 (s, 1H), 8.96 (s, 0.5H), 8.91 (s, 0.5H), 8.75 (s, 0.5H), 8.55 (s, 0.5H), 8.14-8.06 (m, 1H), 7.84 (s, 0.5H), 7.69 (s, 0.5H), 7.01-6.90 (m, 1H), 6.75-6.67 (m, 1H), 4.74 (s, 2H), 4.55 (t, J=8.8 Hz, 2H), 3.31-3.29 (m, 2H).

Example 233

8-(6-((dimethylamino)methyl)-5-fluoro-4-methylpyridin-3-yl)-5-(((5-fluoro-2,3-dihydrobenzofuran-4-yl)methyl)amino)imidazo[1,2-c]pyrimidine-2-carbonitrile

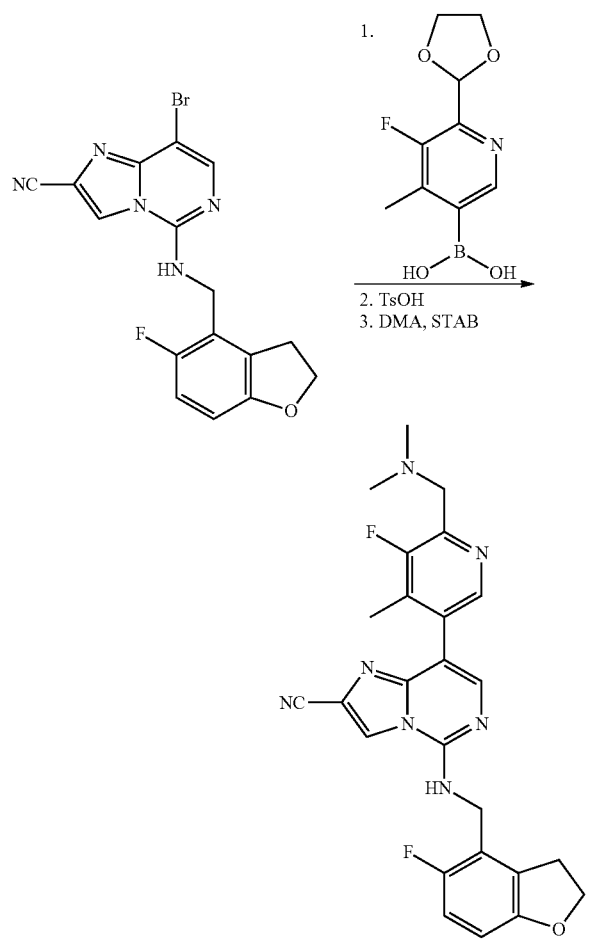 [SMILES: N#Cc1cn2c(NCc3c(F)ccc4c3CCO4)ncc(Br)c2n1 ; Cc1c(B(O)O)cnc(C2OCCO2)c1F ; Cc1c(-c2cnc(NCc3c(F)ccc4c3CCO4)n3cc(C#N)nc23)cnc(CN(C)C)c1F]

A mixture of 8-bromo-5-(((5-fluoro-2,3-dihydrobenzofuran-4-yl)methyl)amino)imidazo[1,2-c]pyrimidine-2-carbonitrile (300 mg, 773 µmol, 1.00 equiv), [6-(1,3-dioxolan-2-yl)-5-fluoro-4-methyl-3-pyridyl]boronic acid (217 mg, 927 µmol, 1.20 equiv), Pd(dppf)Cl$_2$ (56.6 mg, 77.3 µmol, 0.10 equiv), NaHCO$_3$(195 mg, 2.32 mmol, 90.2 µL, 3.00 equiv) in dioxane (3.00 mL) and water (1.00 mL) was purged with nitrogen and subsequently stirred at 100° C. for 2 h under an atmosphere of nitrogen. The reaction mixture was filtered and concentrated under reduced pressure to provide the crude residue. The residue was purified by prep-TLC (SiO$_2$, dichloromethane/methanol=20/1) to afford 8-(6-(1,3-dioxolan-2-yl)-5-fluoro-4-methylpyridin-3-yl)-5-(((5-fluoro-2,3-dihydrobenzofuran-4-yl)methyl)amino)imidazo[1,2-c]pyrimidine-2-carbonitrile (180 mg, 367 µmol, 47.5% yield) as a yellow solid. LCMS [M+1]: 491.2.

To a solution of 8-(6-(1,3-dioxolan-2-yl)-5-fluoro-4-methylpyridin-3-yl)-5-(((5-fluoro-2,3-dihydrobenzofuran-4-yl)methyl)amino)imidazo[1,2-c]pyrimidine-2-carbonitrile (100 mg, 204 µmol, 1.00 equiv) in acetone (3.00 mL) and water (1.50 mL) was added TsOH—H$_2$O (77.6 mg, 408 µmol, 2.00 equiv). The mixture was stirred at 60° C. for 12 h. The reaction mixture was diluted with DCM 20.0 mL and was neutralized with sodium bicarbonate. The organic phase was separated, dried and concentrated under reduced pressure to give the crude residue. The residue was purified by prep-TLC (SiO$_2$, dichloromethane/methanol=20/1) to give 5-(((5-fluoro-2,3-dihydrobenzofuran-4-yl)methyl)amino)-8-(5-fluoro-6-formyl-4-methylpyridin-3-yl)imidazo[1,2-c]pyrimidine-2-carbonitrile (60.0 mg, 134 µmol, 65.9% yield) as a yellow solid. LCMS [M+1]: 447.2.

A mixture of 5-(((5-fluoro-2,3-dihydrobenzofuran-4-yl)methyl)amino)-8-(5-fluoro-6-formyl-4-methylpyridin-3-yl)imidazo[1,2-c]pyrimidine-2-carbonitrile (90.0 mg, 202 µmol, 1.00 eq.), N-methylmethanamine (2 M, 302 µL, 3.00 equiv), AcOH (24.2 mg, 403 µmol, 23.1 µL, 2.00 equiv) and Ti(Oi-Pr)$_4$ (115 mg, 403 µmol, 119 uL, 2.00 equiv) in DCE (2.00 mL) was stirred at 45° C. for 1 h. To this mixture was added NaBH(OAc$_3$ (128 mg, 605 µmol, 3.00 equiv) was added and the mixture was allowed to stir at 25° C. for 1 h. The reaction was quenched with water (2 mL) and the resultant suspension was filtered. The filtrate was dried and concentrated under reduced pressure to provide the crude residue. The residue was purified by prep-HPLC (acidic conditions) followed by prep-HPLC (basic conditions) to afford 8-(6-((dimethylamino)methyl)-5-fluoro-4-methylpyridin-3-yl)-5-(((5-fluoro-2,3-dihydrobenzofuran-4-yl) methyl)amino)imidazo[1,2-c]pyrimidine-2-carbonitrile (10.3 mg, 21.7 µmol, 10.7% yield, 100% purity) as a white solid. LCMS [M+1]: 476.5.

$^1$H NMR (400 MHz, DMSO-d$_6$) δ=8.90 (s, 1H), 8.59 (s, 1H), 8.27 (s, 1H), 7.81 (s, 1H), 7.01-6.89 (m, 1H), 6.69 (dd, J=4.0, 8.8 Hz, 1H), 4.71 (s, 2H), 4.53 (t, J=8.8 Hz, 2H), 3.58 (d, J=2.4 Hz, 2H), 3.34-3.31 (m, 2H), 2.20 (s, 6H), 2.11 (d, J=2.4 Hz, 3H).

The compounds of the present invention may have one or more chiral center and, if so, are synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions, as well as methods described herein, e.g., EXAMPLES 213 and 214. Alternatively, compounds of the present invention may be synthesized using optically pure, chiral reagents and intermediates to prepare individual isomers or enantiomers.

Unless otherwise indicated, all chiral (enantiomeric and diastereomeric) and racemic forms are within the scope of the invention.

Also contemplated within the scope of the invention are variants of compounds of the present invention in which one or more hydrogen atoms have been replaced with deuterium. As exemplified herein. Intermediates C-11 and D-31 have one or more hydrogen atom replaced with deuterium and were used to generated EXAMPLE 165 and 173, respectively. Intermediates B-7, B-8, and C18 also contain deuteriums substituted as specifies location(s). In addition, EXAMPLE 202 illustrates deuterated compounds of the present invention wherein $R^7$ is deuterated. By substituting one or more hydrogen for deuterium on the Intermediates A-D exemplified herein, deuterated versions of the compounds of the present invention can be readily generated using methods well known in the art.

Example A

This Example illustrates that exemplary compounds of the present invention inhibit PRC2 enzymatic activity.

Ten-point dose-response curves for compounds of the present invention were determined using a Hot Spot HMT assay (Reaction Biology Corp; see Horiuchi et al., Assay Drug Dev Technol. (2013) 4: 227-236 doi: 10.1089/adt.2012.480). The assay uses purified human, His-tagged PRC2 complex, including N-terminal His-tagged EZH2 enzyme. N-terminal Flag-tagged embryonic ectoderm development protein (EED), N-terminal His-tagged suppressor of zeste 12 (SUZ12), N-terminal His-tagged AEBP2, and N-terminal His-tagged RbAp48. In this assay, the transfer of the tritiated methyl group from radiolabeled S-adenosyl methionine (SAM) to purified core histone protein by EZH2 is quantitated after filtration to determine the activity of the core PRC2 complex in the presence and absence of compound.

Briefly, compounds of the present invention were solubilized in DMSO and a series of 10, three-fold serial dilutions were made for each compound in 15% DMSO. The initial starting concentration for the serial dilutions of each compound was 1.0 µM. Control samples lacking compound, EZH2 enzyme or various reaction components also were prepared and processed in parallel with compound test samples. SAH (S-(5-adenosyl)-L-homocysteine) was used as a positive control for assay validation.

An aliquot of each serial dilution of test compound was added to deep 384 well plate using Acoustic Technology instrument (Echo 550, LabCyte) containing reaction buffer (50 mM Tris-HCl (pH 8)), 0.01% Brij35, 1 mM EDTA, 1 mM DTT, 1 mM PMSF and 1% DMSO), 10 nM purified PRC2 complex and 0.05 mg/ml core histone H3 in a 5 µl volume. The reaction was mixed gently and then pre-incubated for 20 min at 30° C. The enzymatic reaction was initiated by adding 1 uM S-Adenosyl-L-[methyl-$^3$H]methionine and incubated for 1 hr at 30° C. After 1 hr, the reaction product was detected using a filter binding method and the amount of tritiated H3 core histone was quantitated using a scintillation counter. The $IC_{50}$ value for each compound was determined from each 10-point dose-response curve using GraphPad Prism software and the results for exemplary compounds of Formula (I) are shown in Table 13. Key: A=<100 nM; B=>100 nM-<500 nM; and C=>500 nM.

TABLE 13

Inhibition of PRC2-mediated Enzymatic Activity by Exemplary Compounds of Formula (1)

| Example No. | $IC_{50}$ |
| --- | --- |
| 1 | A |
| 2 | A |
| 3 | B |
| 4 | A |
| 5 | A |
| 6 | B |
| 7 | A |
| 8 | A |
| 9 | A |
| 10 | A |
| 11 | A |
| 12 | A |
| 13 | A |
| 14 | B |
| 15 | B |
| 16 | A |
| 17 | B |
| 18 | A |
| 19 | A |
| 20 | A |
| 21 | C |
| 22 | B |
| 23 | B |
| 24 | B |
| 25 | B |
| 26 | B |
| 27 | C |
| 28 | A |
| 29 | C |
| 30 | B |
| 31 | A |
| 32 | B |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | B |
| 61 | A |
| 62 | A |
| 63 | A |
| 64 | A |
| 65 | B |
| 66 | B |
| 67 | A |
| 68 | A |
| 69 | A |
| 70 | A |
| 71 | A |
| 72 | A |
| 73 | A |
| 74 | A |
| 75 | A |

TABLE 13-continued

Inhibition of PRC2-mediated Enzymatic Activity by Exemplary Compounds of Formula (1)

| Example No. | IC$_{50}$ |
|---|---|
| 76 | A |
| 77 | B |
| 78 | C |
| 79 | A |
| 80 | A |
| 81 | C |
| 82 | B |
| 83 | A |
| 84 | B |
| 85 | A |
| 86 | A |
| 87 | A |
| 88 | A |
| 89 | A |
| 90 | A |
| 91 | B |
| 92 | B |
| 93 | B |
| 94 | A |
| 95 | A |
| 96 | A |
| 97 | A |
| 98 | A |
| 99 | A |
| 100 | A |
| 101 | B |
| 102 | B |
| 103 | B |
| 104 | C |
| 105 | A |
| 106 | B |
| 107 | B |
| 108 | A |
| 109 | A |
| 110 | A |
| 111 | A |
| 112 | A |
| 113 | A |
| 114 | A |
| 115 | A |
| 116 | A |
| 117 | B |
| 118 | A |
| 119 | B |
| 120 | C |
| 121 | A |
| 122 | C |
| 123 | A |
| 124 | A |
| 125 | A |
| 126 | B |
| 127 | A |
| 128 | A |
| 129 | A |
| 130 | B |
| 131 | A |
| 132 | C |
| 133 | A |
| 134 | B |
| 135 | A |
| 136 | B |
| 137 | A |
| 138 | A |
| 139 | A |
| 140 | C |
| 141 | C |
| 142 | A |
| 143 | A |
| 144 | A |
| 145 | B |
| 146 | B |
| 147 | B |
| 148 | A |
| 149 | B |
| 150 | A |
| 151 | A |
| 152 | B |
| 153 | B |
| 154 | B |
| 155 | A |
| 156 | B |
| 157 | A |
| 158 | B |
| 159 | B |
| 160 | A |
| 161 | A |
| 162 | A |
| 163 | A |
| 164 | A |
| 165 | A |
| 166 | A |
| 167 | B |
| 168 | A |
| 169 | A |
| 170 | A |
| 171 | A |
| 172 | A |
| 173 | A |
| 174 | A |
| 175 | B |
| 176 | A |
| 177 | B |
| 178 | B |
| 179 | A |
| 180 | A |
| 181 | A |
| 182 | B |
| 183 | A |
| 184 | B |
| 185 | A |
| 186 | A |
| 187 | A |
| 188 | B |
| 189 | B |
| 190 | A |
| 191 | B |
| 192 | C |
| 193 | A |
| 194 | B |
| 195 | A |
| 196 | B |
| 197 | A |
| 198 | A |
| 199 | A |
| 200 | B |
| 201 | A |
| 202 | A |
| 203 | B |
| 204 | B |
| 205 | B |
| 206 | B |
| 207 | A |
| 208 | A |
| 200 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | B |
| 221 | A |
| 222 | A |
| 223 | A |
| 224 | B |
| 225 | A |

TABLE 13-continued

Inhibition of PRC2-mediated Enzymatic Activity by Exemplary Compounds of Formula (1)

| Example No. | $IC_{50}$ |
|---|---|
| 226 | B |
| 227 | A |
| 228 | B |
| 229 | A |
| 230 | A |
| 231 | B |
| 232 | B |
| 233 | A |

Example B

This Example illustrates that exemplary compounds of the present invention inhibit the growth of tumor cells harboring PRC2 complexes containing EZH2 activating mutations.

The Pfeiffer cell line was established from a pleural infusion from a patient having metastatic diffuse large B-cell lymphoma (DLBCL). This cell line expresses a mutant form of the EZH2 enzyme (A677G) that results in enhanced EZH2 activity leading to increased methylation of histone H3 Lys27. Increased trimethylation of histone H3 Lys27 is believed to be implicated in tumorgenesis and poor clinical prognosis in lymphomas (McCabe et al., (2012) Nature 492:108-112).

Inhibition of PRC2-mediated histone H3 methylation by compounds of Formula (I) was measured by ELISA using a Tri-Methyl Histone H3 (Lys 27) Sandwich ELISA Kit (Cell Signaling Tech #7866C) in accordance with the manufacturer's instructions. Briefly, Pfeiffer cells were cultured in RPMI medium supplemented with 10% fetal bovine serum and 1% penicillin and 1% streptoncin in 96 well culture plates at 37° C. to a density of 8000 cells/90 µl/well and the cells were harvested. A series of 3-fold serial dilutions of each test compound of Formula (I) were prepared in RPMI medium and added to the cells at final concentrations ranging from 1 µM to 0.15 nM. The plates were incubated at 37° C. for 96 hours.

After incubation, the cells were pelleted by centrifugation in a pre-cooled 4° C. rotor at 1,100 rpm for 10 min and the supernatant was removed by aspiration. The cell pellet was resuspended in 55 µl of Lysis Buffer (0.4M HCl) and incubated on ice with periodic shaking for 30 minutes. The lysed cells were subjected to centrifugation at 4,200 rpm for 10 min at 4° C. and the supernatant containing acid-soluble proteins was collected and the remainder discarded. The acid-soluble proteins were brought to a neutral pH by the addition of 20 µl of Neutralization Buffer (1 M Sodium phosphate, dibasic (pH 12.5), 2.5 mM DTT and 1 mM PMSF) and the neutralized lysates were analyzed by ELISA.

A 65 µl aliquot of each cell lysate was added to a well of a microwell strip, the microwells were sealed using tape and incubated either at 37° C. for two hours or at 4° C. overnight. After incubation, the tape was removed at the microwells were washed four times using 200 µl of 1× Wash Buffer. To each washed microwell, a 100 µl aliquot of an anti-trimethyl histone H3 Lys27 Detection Antibody solution was added and the microwells were incubated at 37° C. for one hour. The Detection Antibody solution was removed by aspiration and the wells were washed four times each using 200 µl of 1× Wash Buffer.

A 100 µl aliquot of an HRP-linked secondary antibody was added to each well, the wells were sealed with tape and incubated at 37° C. for 30 min. The HRP-linked secondary antibody solution was removed by aspiration and the wells were washed four times using 200 µl of 1× Wash Buffer. A 100 µl aliquot of a TMB substrate was added to each well, the wells were sealed with tape and incubated at 37° C. for 10 min or 25° C. for 30 min. The reaction was stopped by the addition of 100 µl aliquot of a STOP solution and the plate was shaken briefly. The degree of histone H3 trimethylation was determined using a spectrophotometric readout by measuring the absorbance at 450 nm and then calculating the amount of trimethylated histone H3. The results are shown in Table 14. A=≤100 nM; B=>100 nM-≤500 nM; C=>500 nM and N.D.=not determined.

TABLE 14

Inhibition of EZH2-mediated Histone H3 Trimethylation by Exemplary Compounds of Formula (I)

| Example No. | $IC_{50}$ (nM) |
|---|---|
| 1 | C |
| 2 | C |
| 3 | C |
| 11 | A |
| 31 | A |
| 32 | A |
| 36 | A |
| 38 | A |
| 39 | A |
| 46 | B |
| 47 | A |
| 48 | B |
| 49 | B |
| 50 | B |
| 51 | A |
| 52 | A |
| 56 | B |
| 57 | B |
| 58 | B |
| 60 | C |
| 61 | A |
| 62 | B |
| 63 | A |
| 66 | B |
| 67 | A |
| 68 | B |
| 69 | B |
| 70 | A |
| 71 | B |
| 74 | A |
| 75 | B |
| 76 | A |
| 77 | C |
| 80 | B |
| 81 | C |
| 82 | C |
| 85 | A |
| 86 | A |
| 90 | A |
| 105 | A |
| 111 | A |
| 123 | A |
| 137 | B |
| 143 | A |
| 144 | B |
| 145 | B |
| 146 | B |
| 148 | B |
| 150 | A |
| 152 | B |
| 153 | B |
| 154 | B |
| 156 | C |
| 157 | A |
| 158 | B |
| 159 | A |

TABLE 14-continued

Inhibition of EZH2-mediated Histone H3 Trimethylation by Exemplary Compounds of Formula (I)

| Example No. | IC$_{50}$ (nM) |
|---|---|
| 160 | A |
| 161 | B |
| 162 | B |
| 163 | B |
| 164 | A |
| 165 | B |
| 166 | C |
| 167 | C |
| 168 | B |
| 169 | B |
| 170 | A |
| 171 | B |
| 172 | B |
| 173 | A |
| 174 | C |
| 175 | C |
| 176 | B |
| 177 | B |
| 178 | B |
| 179 | B |
| 180 | A |
| 181 | B |
| 182 | B |
| 183 | C |
| 184 | B |
| 185 | A |
| 186 | B |
| 187 | B |
| 188 | B |
| 189 | B |
| 190 | C |
| 191 | B |
| 192 | C |
| 193 | B |
| 194 | B |
| 195 | A |
| 196 | B |
| 197 | B |
| 198 | B |
| 199 | B |
| 200 | B |
| 201 | B |
| 202 | A |
| 203 | B |
| 204 | A |
| 205 | A |
| 206 | B |
| 207 | A |
| 208 | B |
| 209 | A |
| 210 | N.D. |
| 211 | N.D. |
| 212 | A |
| 213 | B |
| 214 | B |
| 215 | C |
| 216 | N.D. |
| 217 | B |
| 218 | B |
| 219 | B |
| 220 | B |
| 221 | B |
| 222 | A |
| 223 | B |
| 224 | B |
| 225 | N.D. |
| 226 | B |
| 227 | B |
| 228 | B |
| 229 | A |
| 230 | A |
| 231 | N.D. |
| 232 | N.D. |
| 233 | A |

Example C

This Example illustrates that exemplary compounds of the present invention exhibit a greater potency against DLBCL cell lines expressing an activating mutant form of EZH2 enzyme than wild type EZH2.

Karpas 422 cell line is a human B cell non-Hodgkin's lymphoma cell line established from a female patient having DLBCL. This EZH2 heterozygotic cell line expresses a mutant form of EZH2 enzyme (Y641N) that increases histone H3 methylation and this mutation has been implicated in the tumorgenesis of lymphomas, such as DLBCL.

Karpas 422 cells (PHE cat no., 06101702) were cultured in RPMI medium supplemented with 20% fetal bovine serum and 1% penicillin/1% streptomycin and plated at a density of 1000 cells/90 µl/well in 96 well white assay plates. A dose response curve for compounds of the present invention was determined by adding a 10 µl aliquot of stock solutions of varying concentrations of compounds to the same medium in each well, over a concentration range of 10 µM using 3-fold dilutions to a final concentration of 1.5 nM. The plates were incubated at 37° C. for predetermined time periods, Day 4, Day 7, or Day 11, and the viability of the cells was measured using a CTG assay kit (Cell Titre Glo; Promega cat. no G7573) on Day 4 and Day 7 in accordance with the manufacturer's instructions.

For the viability assay for the Day 11 plates, the plates were subjected to centrifugation at 1100 rpm for five minutes on Day 7 and the supernatant was removed by aspiration. The cells were resuspended in 90 µl aliquot of the appropriate growth medium lacking the compound followed by addition of 10 µl of a 10× stock of the same compound at the same concentration. The viability of the Day 11 cells was measured using the CTG assay kit described above in accordance with the manufacturer's instructions. The IC$_{50}$ values for each compound at each predetermined time point were calculated using Graph pad PRISM software and the results are shown in Table 15. A=≤250 nM; B=<250 nM-≤500 nM; and C=>500 nM.

TABLE 15

Enhanced Potency of Exemplary Compounds Inhibiting Proliferation of Cells Expressing an Activating Mutant Form of EZE2

| Example No. | IC$_{50}$ (nM) |
|---|---|
| 1 | C |
| 2 | C |
| 3 | C |
| 5 | C |
| 7 | C |
| 9 | C |
| 11 | A |
| 12 | C |
| 13 | B |
| 16 | B |
| 19 | B |

TABLE 15-continued

Enhanced Potency of Exemplary Compounds Inhibiting Proliferation of Cells Expressing an Activating Mutant Form of EZE2

| Example No. | IC$_{50}$ (nM) |
|---|---|
| 20 | A |
| 21 | A |
| 25 | B |
| 28 | B |
| 29 | C |
| 31 | A |
| 37 | A |
| 33 | A |
| 36 | A |
| 37 | A |
| 38 | A |
| 39 | A |
| 40 | A |
| 41 | A |
| 42 | A |
| 43 | A |
| 44 | A |
| 45 | A |
| 47 | A |
| 48 | A |
| 49 | A |
| 50 | A |
| 53 | A |
| 54 | A |
| 56 | A |
| 57 | A |
| 58 | A |
| 59 | B |
| 60 | B |
| 61 | A |
| 62 | A |
| 64 | B |
| 65 | C |
| 66 | A |
| 67 | A |
| 68 | A |
| 69 | A |
| 70 | A |
| 71 | A |
| 72 | C |
| 73 | A |
| 74 | A |
| 75 | A |
| 76 | A |
| 77 | C |
| 81 | C |
| 82 | B |
| 84 | A |
| 85 | A |
| 86 | A |
| 87 | A |
| 88 | A |
| 89 | A |
| 96 | B |
| 97 | A |
| 98 | A |
| 100 | A |
| 105 | A |
| 106 | C |
| 108 | A |
| 110 | A |
| 112 | A |
| 113 | C |
| 114 | A |
| 115 | A |
| 116 | A |
| 117 | A |
| 118 | C |
| 119 | A |
| 121 | B |
| 124 | C |
| 127 | B |
| 128 | C |
| 129 | A |
| 130 | C |
| 170 | B |
| 133 | C |
| 136 | A |
| 137 | A |
| 138 | A |
| 139 | A |
| 142 | A |
| 144 | A |
| 145 | A |
| 146 | A |
| 147 | A |
| 149 | A |
| 152 | A |
| 153 | B |
| 154 | B |
| 156 | C |
| 157 | A |
| 158 | B |
| 159 | A |
| 160 | A |
| 161 | A |
| 162 | B |
| 163 | A |
| 164 | A |
| 165 | A |
| 166 | B |
| 167 | A |
| 168 | A |
| 169 | A |
| 170 | A |
| 171 | A |
| 172 | B |
| 173 | A |
| 174 | C |
| 175 | B |
| 176 | B |
| 177 | N.D. |
| 178 | A |
| 179 | C |
| 180 | A |
| 181 | A |
| 182 | A |
| 183 | C |
| 184 | B |
| 185 | A |
| 186 | A |
| 187 | B |
| 188 | B |
| 189 | A |
| 190 | C |
| 191 | B |
| 192 | C |
| 193 | A |
| 194 | A |
| 195 | A |
| 196 | A |
| 197 | A |
| 198 | A |
| 199 | A |
| 200 | A |
| 201 | A |
| 202 | A |
| 203 | B |
| 204 | A |
| 205 | A |
| 206 | B |
| 207 | A |
| 208 | A |
| 209 | A |
| 210 | N.D. |
| 211 | N.D. |
| 212 | A |
| 213 | A |

TABLE 15-continued

Enhanced Potency of Exemplary Compounds
Inhibiting Proliferation of Cells Expressing an
Activating Mutant Form of EZE2

| Example No. | IC$_{50}$ (nM) |
|---|---|
| 214 | A |
| 215 | C |
| 216 | N.D. |
| 217 | A |
| 218 | B |
| 219 | A |
| 220 | A |
| 221 | A |
| 222 | A |
| 223 | A |
| 224 | N.D. |
| 225 | N.D. |
| 226 | A |
| 227 | A |
| 228 | A |
| 229 | A |
| 230 | A |
| 231 | N.D. |
| 232 | N.D. |
| 233 | A |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for treating cancer in a patient, comprising administering to the patient in need thereof a therapeutically effective amount of a compound selected from the group consisting of:

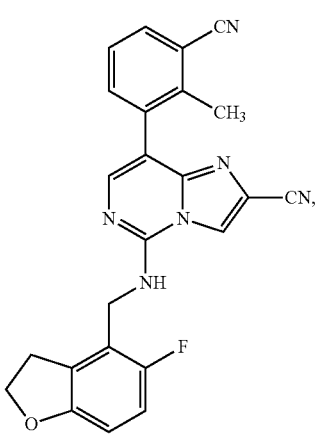 [SMILES: Cc1c(C#N)cccc1-c1cnc(NCc2c(F)ccc3c2CCO3)n2cc(C#N)nc12]

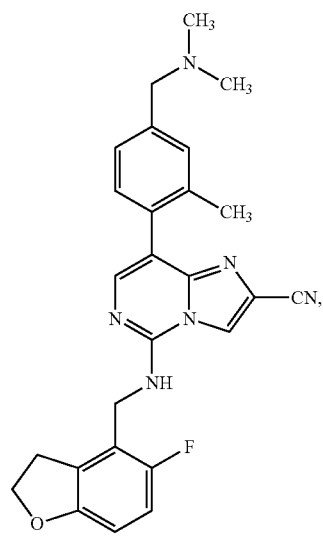 [SMILES: Cc1cc(CN(C)C)ccc1-c1cnc(NCc2c(F)ccc3c2CCO3)n2cc(C#N)nc12]

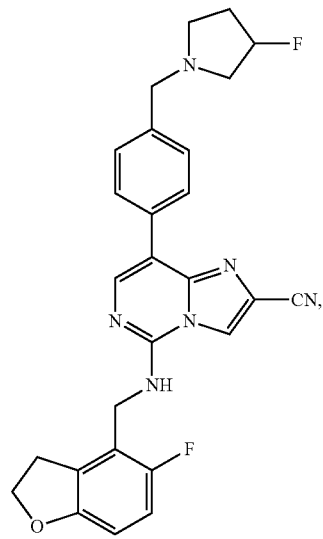

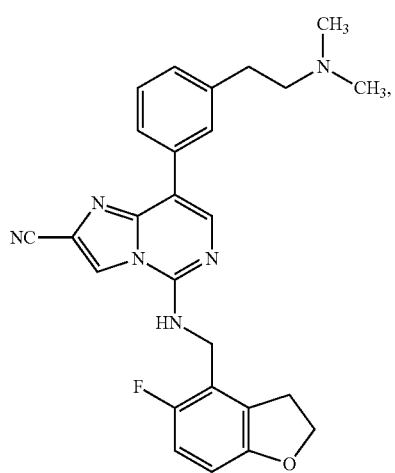

409
-continued
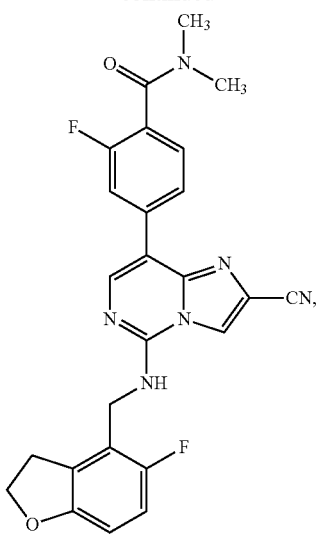
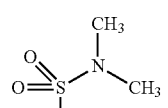
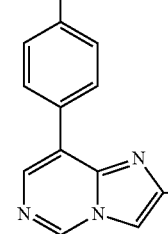
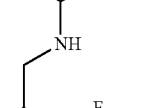
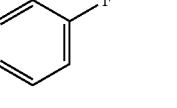
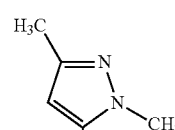
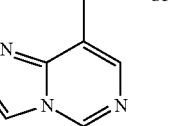
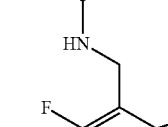
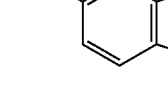
410
-continued
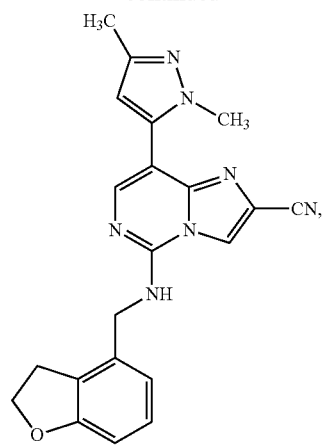
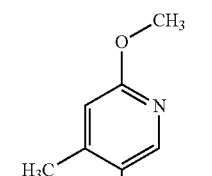
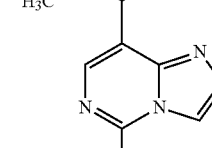
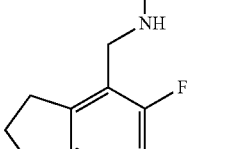
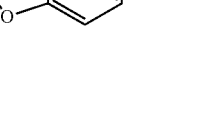
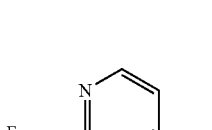
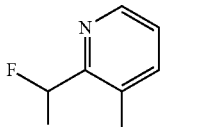
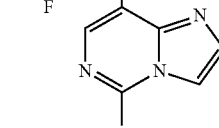
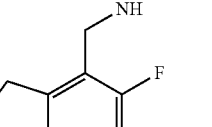
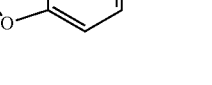

-continued

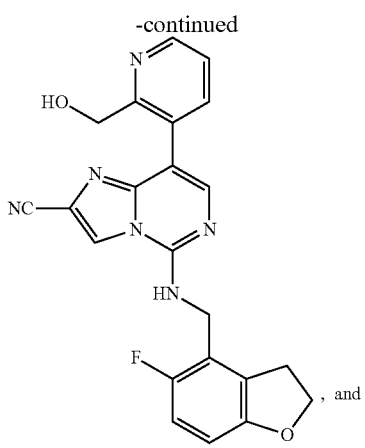

, and

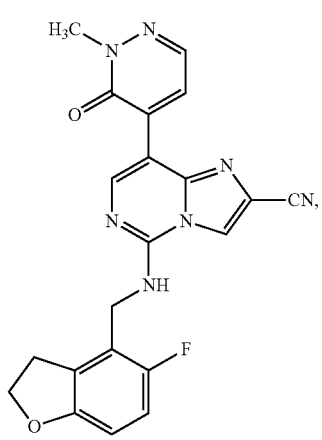

or a pharmaceutically acceptable salt thereof, wherein the cancer is a polycomb repressive complex 2-associated cancer selected from the group consisting of bladder cancer, breast cancer, head and neck cancer, liver cancer, pancreatic cancer, prostate cancer, skin cancer, lymphoma, sarcoma, lung cancer, and ovarian cancer.

2. The method according to claim 1, wherein the polycomb repressive complex 2-associated cancer is bladder cancer.

3. The method according to claim 1, wherein the poly comb repressive complex 2-associated cancer is breast cancer.

4. The method according to claim 1, wherein the polycomb repressive complex 2-associated cancer is head and neck cancer.

5. The method according to claim 1, wherein the polycomb repressive complex 2-associated cancer is liver cancer.

6. The method according to claim 1, wherein the poly comb repressive complex 2-associated cancer is pancreatic cancer.

7. The method according to claim 1, wherein the polycomb repressive complex 2-associated cancer is prostate cancer.

8. The method according to claim 1, wherein the polycomb repressive complex 2-associated cancer is skin cancer.

9. The method according to claim 1, wherein the polycomb repressive complex 2-associated cancer is lymphoma.

10. The method according to claim 1, wherein the polycomb repressive complex 2-associated cancer is sarcoma.

11. The method according to claim 1, wherein the polycomb repressive complex 2-associated cancer is lung cancer.

12. The method according to claim 1, wherein the polycomb repressive complex 2-associated cancer is ovarian cancer.

13. The method according to claim 1, wherein the compound is

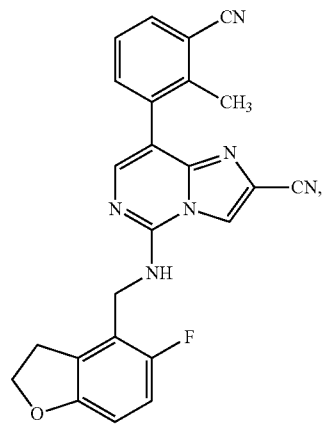

or a pharmaceutically acceptable salt thereof.

14. The method according to claim 1, wherein the compound is

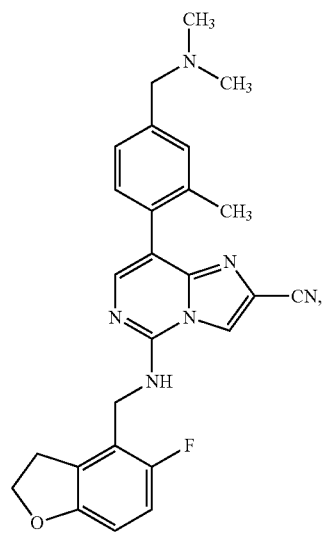

or a pharmaceutically acceptable salt thereof.

15. The method according to claim 1, wherein the compound is

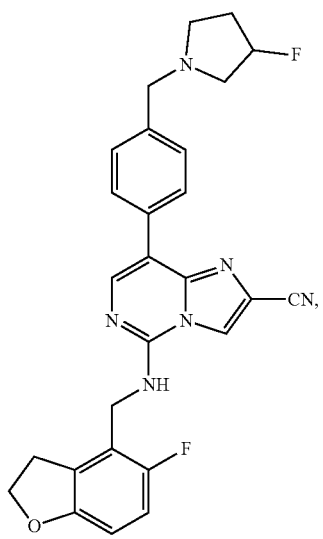 [SMILES: N#Cc1cn2c(NCc3c(F)ccc4c3CCO4)ncc(-c3ccc(CN4CCC(F)C4)cc3)c2n1]

or a pharmaceutically acceptable salt thereof.

16. The method according to claim 1, wherein the compound is

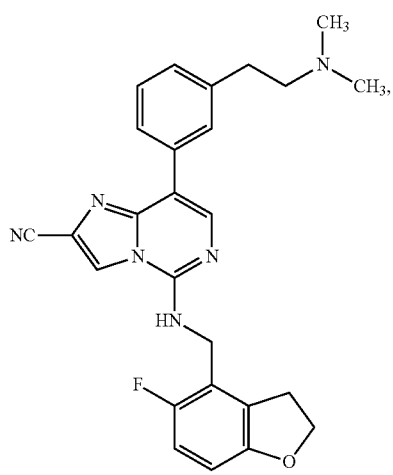 [SMILES: CN(C)CCc1cccc(-c2cnc(NCc3c(F)ccc4c3CCO4)n3cc(C#N)nc23)c1]

or a pharmaceutically acceptable salt thereof.

17. The method according to claim 1, wherein the compound is of a pharmaceutically acceptable salt thereof.

18. The method according to claim 1, wherein the compound is or a pharmaceutically acceptable salt thereof.

19. The method according to claim 1, wherein the compound is

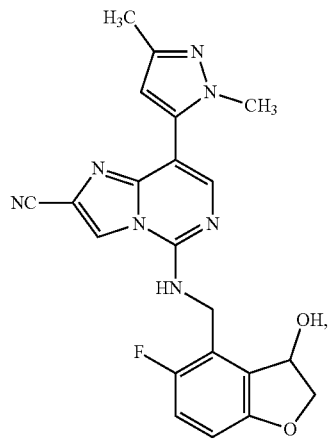 [SMILES: Cc1cc(-c2cnc(NCc3c(F)ccc4c3C(O)CO4)n3cc(C#N)nc23)n(C)n1]

or a pharmaceutically acceptable salt thereof.

20. The method according to claim 1, wherein the compound is

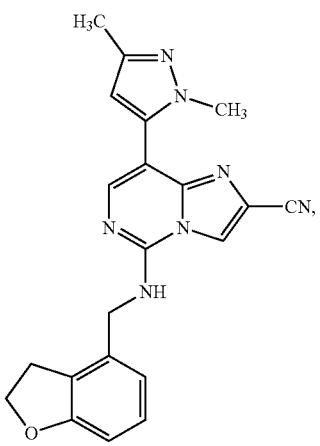 [SMILES: Cc1cc(-c2cnc(NCc3cccc4c3CCO4)n3cc(C#N)nc23)n(C)n1]

or a pharmaceutically acceptable salt thereof.

21. The method according to claim 1, wherein the compound is

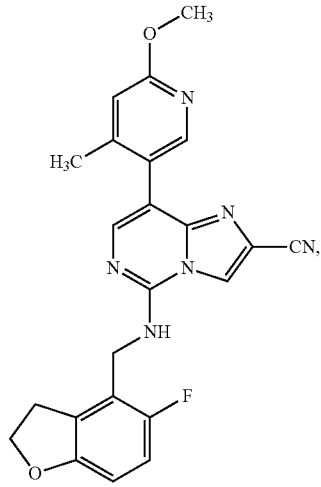 [SMILES: COc1cc(C)c(-c2cnc(NCc3c(F)ccc4c3CCO4)n3cc(C#N)nc23)cn1]

or a pharmaceutically acceptable salt thereof.

22. The method according to claim 1, wherein the compound is

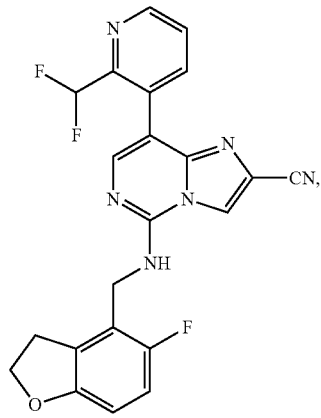 [SMILES: N#Cc1cn2c(NCc3c(F)ccc4c3CCO4)ncc(-c3cccnc3C(F)F)c2n1]

or a pharmaceutically acceptable salt thereof.

23. The method according to claim 1, wherein the compound is

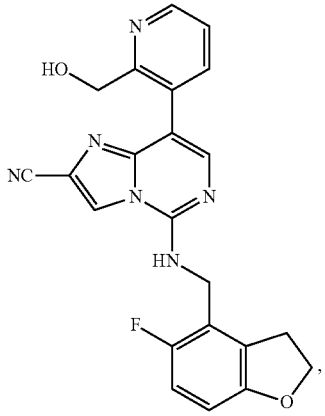 [SMILES: N#Cc1cn2c(NCc3c(F)ccc4c3CCO4)ncc(-c3cccnc3CO)c2n1]

or a pharmaceutically acceptable salt thereof.

24. The method according to claim 1, wherein the compound is
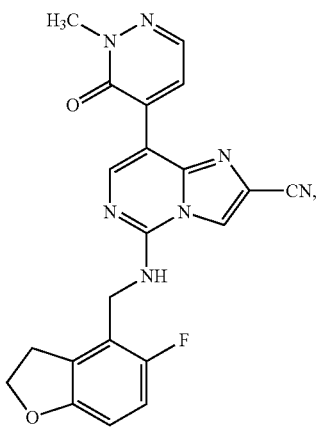 [SMILES: Cn1nccc(-c2cnc(NCc3c(F)ccc4c3CCO4)n3cc(C#N)nc23)c1=O]
or a pharmaceutically acceptable salt thereof.
25. A method for inhibiting poly comb repressive complex 2 activity in a patient, comprising administering to the patient in need thereof a therapeutically effective amount of a compound selected from the group consisting of:
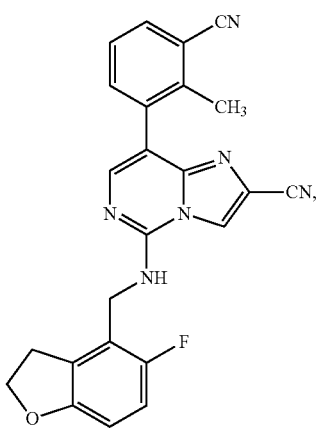
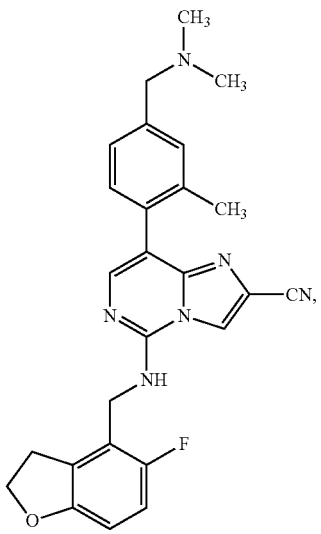
-continued
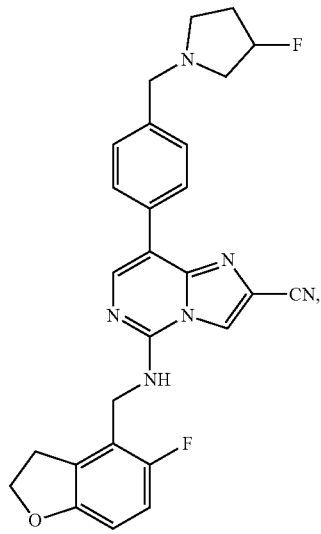
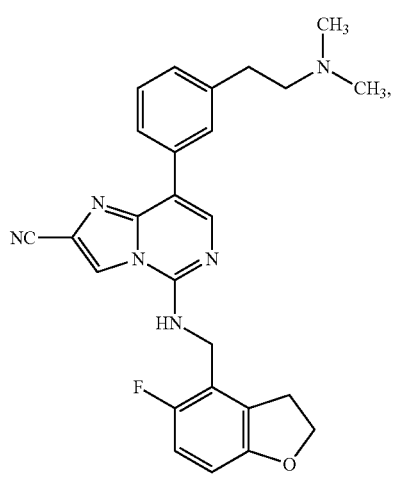
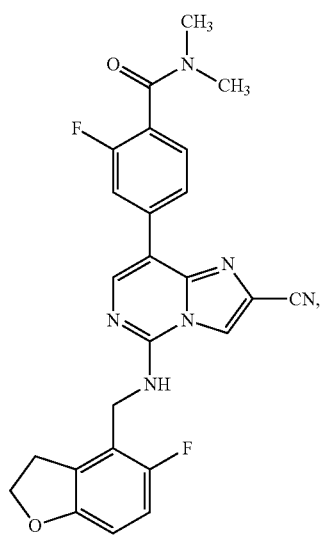

419
-continued

420
-continued

-continued

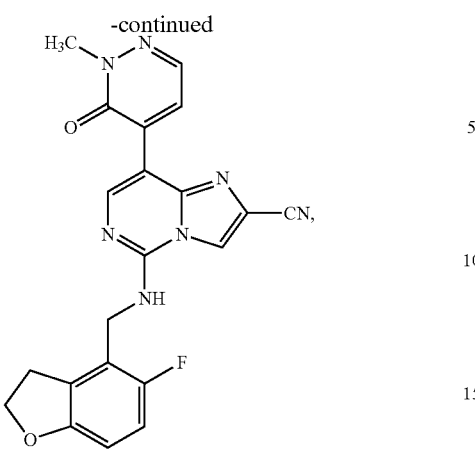

or a pharmaceutically acceptable salt thereof.

26. The method according to claim 25, wherein the patient has a polycomb repressive complex 2-associated cancer.

27. The method according to claim 26, wherein the polycomb repressive complex 2-associated cancer is selected from the group consisting of bladder cancer, breast cancer, head and neck cancer, liver cancer, pancreatic cancer, prostate cancer, skin cancer, lymphoma, sarcoma, lung cancer, and ovarian cancer.

* * * * *

UNITED STATES PATENT AND TRADEMARK OFFICE
CERTIFICATE OF CORRECTION

PATENT NO. : 11,220,509 B2  Page 1 of 1
APPLICATION NO. : 17/219379
DATED : January 11, 2022
INVENTOR(S) : Marx et al.

It is certified that error appears in the above-identified patent and that said Letters Patent is hereby corrected as shown below:

In the Claims

Column 411, Lines 53 and 54:
In Claim 3, replace "poly comb" with --polycomb--

Column 411, Lines 61 and 62:
In Claim 6, replace "poly comb" with --polycomb--

Column 417, Line 24:
In Claim 25, replace "poly comb" with --polycomb--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*